(12) United States Patent
Aehle et al.

(10) Patent No.: US 8,679,792 B2
(45) Date of Patent: *Mar. 25, 2014

(54) GLUCOAMYLASE VARIANTS WITH ALTERED PROPERTIES

(75) Inventors: Wolfgang Aehle, Delfgauw (NL); Richard R. Bott, Burlingame, CA (US); Martijn Scheffers, Leiden (NL); Piet Van Solingen, Naaldwijik (NL); Casper Vroemen, Oegstgeest (NL)

(73) Assignee: Danisco US Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/251,116

(22) Filed: Sep. 30, 2011

(65) Prior Publication Data

US 2012/0149087 A1  Jun. 14, 2012

Related U.S. Application Data

(63) Continuation of application No. 12/292,563, filed on Nov. 20, 2008, now Pat. No. 8,058,033.

(60) Provisional application No. 60/989,426, filed on Nov. 20, 2007.

(51) Int. Cl.
C12P 19/20 (2006.01)
C12N 9/34 (2006.01)
C12N 15/56 (2006.01)

(52) U.S. Cl.
USPC .......................... 435/96; 435/205; 536/23.2

(58) Field of Classification Search
None
See application file for complete search history.

(56) References Cited

U.S. PATENT DOCUMENTS

| | | | |
|---|---|---|---|
| 4,247,637 | A | 1/1981 | Tamura et al. |
| 4,514,496 | A | 4/1985 | Yoshizumi et al. |
| 4,618,579 | A | 10/1986 | Dwiggins et al. |
| 4,794,175 | A | 12/1988 | Nunberg et al. |
| 4,863,864 | A | 9/1989 | Ashikari et al. |
| 5,024,941 | A | 6/1991 | Maine et al. |
| 5,246,853 | A | 9/1993 | Clarkson et al. |
| 5,475,101 | A | 12/1995 | Ward et al. |
| 5,874,276 | A | 2/1999 | Fowler et al. |
| 6,022,725 | A | 2/2000 | Fowler et al. |
| 6,254,914 | B1 | 7/2001 | Singh et al. |
| 6,255,084 | B1 | 7/2001 | Nielsen et al. |
| 6,268,328 | B1 | 7/2001 | Mitchinson et al. |
| 6,352,851 | B1 | 3/2002 | Nielsen et al. |
| 6,537,792 | B1 | 3/2003 | Allen et al. |
| 6,582,914 | B1 | 6/2003 | Caldwell et al. |
| 6,620,924 | B2 | 9/2003 | Nielsen et al. |
| 6,777,589 | B1 | 8/2004 | Lundquist et al. |
| 6,803,499 | B1 | 10/2004 | Anderson et al. |
| 6,899,910 | B2 | 5/2005 | Johnston et al. |
| 7,037,704 | B2 | 5/2006 | Dunn-Coleman et al. |
| 7,413,887 | B2 | 8/2008 | Dunn-Coleman et al. |
| 7,563,607 | B2 | 7/2009 | Duan et al. |

FOREIGN PATENT DOCUMENTS

| | | |
|---|---|---|
| EP | 0 215 594 A2 | 3/1987 |
| EP | 0 238 023 A2 | 9/1987 |
| EP | 0 244 234 A2 | 11/1987 |
| WO | WO 88/09795 A1 | 12/1988 |
| WO | WO 92/06184 A1 | 4/1992 |
| WO | WO 92/06209 A1 | 4/1992 |
| WO | WO 96/00787 A1 | 1/1996 |
| WO | WO 02/14490 A2 | 2/2002 |
| WO | WO 03/049550 A2 | 6/2003 |
| WO | WO 2004/080923 A2 | 9/2004 |
| WO | WO 2004/081193 A2 | 9/2004 |
| WO | WO 2005/001036 A2 | 1/2005 |
| WO | WO 2005/052148 A2 | 6/2005 |
| WO | WO 2006/043178 A2 | 4/2006 |
| WO | WO 2006/060062 A2 | 6/2006 |

OTHER PUBLICATIONS

Aleshin, A.E. et al. "Refined crystal structures of glucoamylase from *Aspergillus awamori* var. X100." *Journal of Molecular Biology* 238(4): 575-591, May 13, 1994.

Altschul, S.F. et al. "Local alignment statistics." *Methods Enzymol* 266: 460-80, 1996.

Altschul, S.F. et al. "Basic local alignment search tool." *J. Mol. Biol.* 215(3): 403-410, 1990.

Anagnostopoulos, C. et al. "Requirements for Transformation in *Bacillus subtilis*." *Journal of Bacteriology* 81(5): 741-746, May 1961.

Ashikari, T. et al. "Direct fermentation of raw corn to ethanol by yeast transformants containing a modified *Rhizopus glucoamylase* gene." *Applied Microbiology and Biotechnology* 32(2): 129-133, Dec. 1, 1989.

Ashikari, T. et al. "Rhizopus raw-starch-degrading glucoamylase: its cloning and expression in yeast." *Agricultural and biological chemistry* 50(4): 957-964, 1986.

Bajar, A. et al. "Identification of a fungal cutinase promoter that is inducible by a plant signal via a phosphorylated trans-acting factor." *PNAS* 88(18): 8208-8212, 1991.

Bergès, T. et al. "Isolation of uridine auxotrophs from *Trichoderma reesei* and efficient transformation with the cloned ura3 and ura5 genes." *Current Genetics* 19(5): 359-365, May 1, 1991.

Berka, R.M. et al. "*Aspergillus niger* var. *awamori* as a host for the expression of heterologous genes." In *Applications of Enzyme Biotechnology*, edited by J.W. Kelly et al., pp. 273-292. New York: Plenum Press, 1991.

Boel, E. et al. "Two different types of intervening sequences in the glucoamylase gene from *Aspergillus niger*." *EMBO J.* 3(7): 1581-1585, Jul. 1984.

(Continued)

Primary Examiner — Rebecca Prouty
(74) Attorney, Agent, or Firm — Danisco US Inc.

(57) ABSTRACT

The present disclosure relates to variants of a parent glucoamylase having altered properties (e.g., improved thermostability and/or specific activity). In particular, the present disclosure provides compositions comprising the variant glucoamylases, including starch hydrolyzing compositions and cleaning compositions. The disclosure also relates to DNA constructs encoding the variants and methods of producing the glucoamylase variants in host cells.

19 Claims, 17 Drawing Sheets

(56) References Cited

OTHER PUBLICATIONS

Boel, E. et al. "Glucoamylases G1 and G2 from *Aspergillus niger* are synthesized from two different but closely related mRNAs." *The EMBO Journal* 3(5): 1097-1102, May 1984.

Brünger, A.T. "Free R value: a novel statistical quantity for assessing the accuracy of crystal structures." *Nature* 355(6359): 472-475, Jan. 30, 1992.

Campbell, E.I. et al. "Improved transformation efficiency of *Aspergillus niger* using the homologous niaD gene for nitrate reductase." *Current Genetics* 16(1): 53-56, Jul. 1, 1989.

Cao, Q.N. et al. "Penicillopepsin-JT2, a recombinant enzyme from *Penicillium janthinellum* and the contribution of a hydrogen bond in subsite S3 to k(cat)." *Protein Sci* 9(5): 991-1001, May 1, 2000.

Chen, H.-M. et al. "Identification and elimination by site-directed mutagenesis of thermolabile aspartyl bonds in *Aspergillus awamori* glucoamylase." *Protein Eng.* 8(6): 575-582, Jun. 1, 1995.

Chen, H.-M. et al. "Effect of replacing helical glycine residues with alanines on reversible and irreversible stability and production of *Aspergillus awamori* glucomylase." *Protein Eng.* 9(6): 499-505, Jun. 1, 1996.

Coutinho, P.M. et al. "Structural similarities in glucoamylases by hydrophobic cluster analysis." *Protein Eng.* 7(6): 749-760, 1994.

Coutinho, P.M. et al. "Structure-function relationships in the catalytic and starch binding domains of glucoamylase." *Protein Eng.* 7(3): 393-400, 1994.

Database UniProt. "Glucoamylase," retrieved from EBI accession No. UNIPROT:Q6DUY5, Aug. 16, 2004.

Devereux, P. et al. "A comprehensive set of sequence analysis programs for the VAX." *Nucl. Acids Res* 12: 387-395, 1984.

Elder, M.T. et al. "Glucoamylase activity in industrial enzyme preparations using colorimetric enzymatic method: collaborative study." *Journal of AOAC International* 78(2): 398-401, 1995.

Emsley, P. et al. "Coot: model-building tools for molecular graphics." *Acta Crystallographica. Section D, Biological Crystallography* 60(Pt 12 Pt 1): 2126-2132, Dec. 2004.

Feng, D.F. et al. "Progressive sequence alignment as a prerequisite to correct phylogenetic trees." *J. Mol. Evol* 25(4): 351-360, 1987.

Fierobe, H-P. et al. "Mutational Modulation of Substrate Bond-Type Specificity and Thermostability of Glucoamylase from Aspergillus awamori by Replacement with Short Homologue Active Site Sequences and Thiol/Disulfide Engineering." *Biochemistry* 35(26): 8696-8704, Jan. 1, 1996.

Finkelstein, D.B. "Transformation." In *Biotechnology of Filamentous Fungi: Technology and Products*, edited by D.B. Finkelstein et al., pp. 113-156. Boston, MA: Butterworth-Heinemann, 1992.

Fromm, M.E. et al. "Inheritance and Expression of Chimeric Genes in the Progeny of Transgenic Maize Plants." *Nat Biotech* 8(9): 833-839, 1990.

Goedegebuur, F. et al. "Cloning and relational analysis of 15 novel fungal endoglucanases from family 12 glycosyl hydrolase." *Current Genetics* 41(2): 89-98, May 1, 2002.

Goto, M. et al. "The Mechanism of Binding of Glucoamylase I from *Aspergillus awamori* var. *kawachi* to Cyclodextrins and Raw Starch." *Bioscience, biotechnology, and biochemistry* 58(1): 49-54, Jan. 23, 1994.

de Groot, M.J.A. et al. "*Agrobacterium tumefaciens*-mediated transformation of filamentous fungi." *Nat Biotech* 16(9): 839-842, 1998.

Guo, Haiwei H. et al., "Protein tolerance to random amino acid change," *PNAS*, 101(25):9205-9210 (2004).

Harkki, A. et al. "Genetic engineering of Trichoderma to produce strains with novel cellulase profiles." *Enzyme Microb. Technol* 13(3): 227-33, Mar. 1991.

Harkki, A. et al. "A Novel Fungal Expression System: Secretion of Active Calf Chymosin from the Filamentous Fungus Trichoderma Reesei." *Bio/Technology* 7(6): 596-603, Jun. 1989.

Hartingsveldt, Wim et al. "Development of a homologous transformation system for *Aspergillus niger* based on the pyrG gene." *Molecular and General Genetics MGG* 206(1): 71-75, Jan. 1, 1987.

Hayashida, S. et al. "Molecular cloning of the glucoamylase I gene of *Aspergillus awamori* var. *kawachi* for localization of the raw-starch-affinity site." Agricultural and Biological Chemistry 53(4): 923-929, 1989.

Higgins, D.G. et al. "Fast and sensitive multiple alignment sequence on a microcomputer." *CABIOS* 5: 151-153, 1989.

van den Hondel, C. et al. "Heterologous gene expression in filamentous fungi." In *More Gene Manipulations in Fungi*, edited by J.W. Bennett et al., pp. 396-428. San Diego, CA: Academic Press, 1991.

Houghton-Larsen, J. et al. "Cloning and characterisation of a glucoamylase gene (GlaM) from the dimorphic zygomycete Mucor circinelloides." *Applied Microbiology and Biotechnology* 62(2): 210-217, 2003.

Ilmen, M. et al. "Regulation of cellulase gene expression in the filamentous fungus *Trichoderma reesei*." *Appl. Environ. Microbiol.* 63(4): 1298-1306, Apr. 1, 1997.

Innis, M. A. et al. "Expression, Glycosylation, and Secretion of an *Aspergillus* Glucoamylase by *Saccharomyces cerevisiae*." *Science* 228(4695): 21-26, Apr. 5, 1985.

Jones, T.A. et al. "Improved methods for building protein models in electron density maps and the location of errors in these models." *Acta Crystallographica. Section A, Foundations of Crystallography* 47 ( Pt 2): 110-119, Mar. 1, 1991.

Karlin, S. et al. "Applications and statistics for multiple high-scoring segments in molecular sequences." *Proc. Natl. Acad. Sci. USA* 90(12): 5873-7, Jun. 15, 1993.

Kelly, J.M. et al. "Transformation of *Aspergillus niger* by the amdS gene of *Aspergillus nidulans*." *The EMBO Journal* 4(2): 475-479, Feb. 1985.

Li, Y. et al. "Effect of introducing proline residues on the stability of *Aspergillus awamori*." *Protein Eng.* 10(10): 1199-1204, Oct. 1, 1997.

Minshull, J. et al. "Engineered protein function by selective amino acid diversification." *Methods* 32(4): 416-427, Apr. 2004.

Murshudov, G.N. et al. "Refinement of macromolecular structures by the maximum-likelihood method." *Acta Crystallographica. Section D, Biological Crystallography* 53(Pt 3): 240-255, May 1, 1997.

Needleman, S.B. et al. "A general method applicable to the search for similarities in the amino acid sequence of two proteins." *J. Mol. Biol* 48(3): 443-53, Mar. 1970.

Nevalainen, K.M.H. et al. "The Molecular Biology of Trichoderma and its Application to the Expression of Both Homologous and Heterologous Genes." In *Molecular Industrial Mycology*, edited by S.A. Leong et al., pp. 129-148. New York: Marcel Dekker, 1991.

Nunberg, J.H. et al. "Molecular cloning and characterization of the glucoamylase gene of *Aspergillus awamori*." *Mol. Cell. Biol.* 4(11): 2306-2315, Nov. 1, 1984.

Pearson, W.R. et al. "Improved Tools for Biological Sequence Comparison." *Proc. Natl. Acad. Sci. USA* 85(8): 2444-2448, Apr. 15, 1988.

Penttilä, M. et al. "A versatile transformation system for the cellulolytic filamentous fungus *Trichoderma reesei*." *Gene* 61(2): 155-64, 1987.

Potrykus, I. et al. "Molecular and general genetics of a hybrid foreign gene introduced into tobacco by direct gene transfer." *Molecular and General Genetics MGG* 199(2): 169-177, May 1, 1985.

Pourquié, J. et al. "Scale up of cellulase production and utilization." In *Biochemistry and Genetics of Cellulose Degradation*, edited by J.P. Aubert et al., pp. 71-86. London: Academic Press, 1988.

Punt, P.J. et al. "Transformation of *Aspergillus* based on the hygromycin B resistance marker from *Escherichia coli*." *Gene* 56(1): 117-24, 1987.

Sheir-Neiss, G. et al. "Characterization of the secreted cellulases of *Trichoderma reesei* wild type and mutants during controlled fermentations." *Applied Microbiology and Biotechnology* 20(1): 46-53, Jul. 1, 1984.

Smith, T.F. et al. "Comparison of biosequences." *Adv. Appl. Math* 2: 482-489, 1981.

(56) References Cited

OTHER PUBLICATIONS

Svensson, B. et al. "The complete amino acid sequence of the glycoprotein, glucoamylase G1, from *Aspergillus niger*." *Carlsberg Research Communications* 48(6): 529-544, Nov. 1, 1983.

Timberlake, W.E. "Cloning and Analysis of Fungal Genes." In *More Gene Manipulations in Fungi*, edited by J.W. Bennett et al., pp. 70-76. San Diego, CA: Academic Press, 1991.

Ward, M. et al. "Use of *Aspergillus* overproducing mutants, cured for intergrated plasmid, to overproduce heterologous proteins." *Applied Microbiology and Biotechnology* 39(6): 738-743, 1993.

Yelton, M.M. et al. "Transformation of *Aspergillus nidulans* by using a trpC plasmid." *Proc. Natl. Acad. Sci. U.S.A* 81(5): 1470-4, Mar. 1984.

International Search Report for International Application No. PCT/US2008/012934 mailed Jun. 24, 2009.

TrGA Parent Protein (632 Amino Acids) (SEQ ID NO: 1)

```
  1  MHVLSTAVLL  GSVAVQKVLG  RPGSSGLSDV  TKRSVDDFIS  TETPIALNNL
 51  LCNVGPDGCR  AFGTSAGAVI  ASPSTIDPDY  YYMWTRDSAL  VFKNLIDRFT
101  ETYDAGLQRR  IEQYITAQVT  LQGLSNPSGS  LADGSGLGEP  KFELTLKPFT
151  GNWGRPQRDG  PALRAIALIG  YSKWLINNNY  QSTVSNVIWP  IVRNDLNYVA
201  QYWNQTGFDL  WEEVNGSSFF  TVANQHRALV  EGATLAATLG  QSGSAYSSVA
251  PQVLCFLQRF  WVSSGGYVDS  NINTNEGRTG  KDVNSVLTSI  HTFDPNLGCD
301  AGTFQPCSDK  ALSNLKVVVD  SFRSIYGVNK  GIPAGAAVAI  GRYAEDVYYN
351  GNPWYLATFA  AAEQLYDAIY  VWKKTGSITV  TATSLAFFQE  LVPGVTAGTY
401  SSSSSTFTNI  INAVSTYADG  FLSEAAKYVP  ADGSLAEQFD  RNSGTPLSAL
451  HLTWSYASFL  TATARRAGIV  PPSWANSSAS  TIPSTCSGAS  VVGSYSRPTA
501  TSFPPSQTPK  PGVPSGTPYT  PLPCATPTSV  AVTFHELVST  QFGQTVKVAG
551  NAAALGNWST  SAAVALDAVN  YADNHPLWIG  TVNLEAGDVV  EYKYINVGQD
601  GSVTWESDPN  HTYTVPAVAC  VTQVVKEDTW  QS
```

*FIG. 1A*

DNA Coding Sequence of TrGA (1899 bp) (SEQ ID NO: 4)

```
   1 ATGCACGTCC TGTCGACTGC GGTGCTGCTC GGCTCCGTTG CCGTTCAAAA
  51 GGTCCTGGGA AGACCAGGAT CAAGCGGTCT GTCCGACGTC ACCAAGAGGT
 101 CTGTTGACGA CTTCATCAGC ACCGAGACGC TATTGCACT GAACAATCTT
 151 CTTTGCAATG TTGGTCCTGA TGGATGCCGT GCATTCGGCA CATCAGCTGG
 201 TGCGGTGATT GCATCTCCCA GCACAATTGA CCCGGACTAC TATTACATGT
 251 GGACGCGAGA TAGCGCTCTT GTCTTCAAGA ACCTCATCGA CCGCTTCACC
 301 GAAACGTACG ATGCGGGCCT GCAGCGCCGC ATCGAGCAGT ACATTACTGC
 351 CCAGGTCACT CTCCAGGGCC TCTCTAACCC CTCGGGCTCC CTCGCGGACG
 401 GCTCTGGTCT CGGCGAGCCC AAGTTTGAGT TGACCCTGAA GCCTTTCACC
 451 GGCAACTGGG GTCGACCGCA GCGGGATGGC CCAGCTCTGC GAGCCATTGC
 501 CTTGATTGGA TACTCAAAGT GGCTCATCAA CAACAACTAT CAGTCGACTG
 551 TGTCCAACGT CATCTGGCCT ATTGTGCGCA ACGACCTCAA CTATGTTGCC
 601 CAGTACTGGA ACCAAACCGG CTTTGACCTC TGGGAAGAAG TCAATGGGAG
 651 CTCATTCTTT ACTGTTGCCA ACCAGCACCG AGCACTTGTC GAGGGCGCCA
 701 CTCTTGCTGC CACTCTTGGC CAGTCGGGAA GCGCTTATTC ATCTGTTGCT
 751 CCCCAGGTTT TGTGCTTTCT CCAACGATTC TGGGTGTCGT CTGGTGGATA
 801 CGTCGACTCC AACATCAACA CCAACGAGGG CAGGACTGGC AAGGATGTCA
 851 ACTCCGTCCT GACTTCCATC CACACCTTCG ATCCCAACCT TGGCTGTGAC
 901 GCAGGCACCT TCCAGCCATG CAGTGACAAA GCGCTCTCCA ACCTCAAGGT
 951 TGTTGTCGAC TCCTTCCGCT CCATCTACGG CGTGAACAAG GGCATTCCTG
1001 CCGGTGCTGC CGTCGCCATT GGCCGGTATG CAGAGGATGT GTACTACAAC
1051 GGCAACCCTT GGTATCTTGC TACATTTGCT GCTGCCGAGC AGCTGTACGA
1101 TGCCATCTAC GTCTGGAAGA AGACGGGCTC CATCACGGTG ACCGCCACCT
1151 CCCTGGCCTT CTTCCAGGAG CTTGTTCCTG GCGTGACGGC CGGGACCTAC
1201 TCCAGCAGCT CTTCGACCTT TACCAACATC ATCAACGCCG TCTCGACATA
1251 CGCCGATGGC TTCCTCAGCG AGGCTGCCAA GTACGTCCCC GCCGACGGTT
1301 CGCTGGCCGA GCAGTTTGAC CGCAACAGCG GCACTCCGCT GTCTGCGCTT
1351 CACCTGACGT GGTCGTACGC CTCGTTCTTG ACAGCCACGG CCCGTCGGGC
1401 TGGCATCGTG CCCCCCTCGT GGGCCAACAG CAGCGCTAGC ACGATCCCCT
1451 CGACGTGCTC CGGCGCGTCC GTGGTCGGAT CCTACTCGCG TCCCACCGCC
1501 ACGTCATTCC CTCCGTCGCA GACGCCCAAG CCTGGCGTGC CTTCCGGTAC
1551 TCCCTACACG CCCCTGCCCT GCGCGACCCC AACCTCCGTG GCCGTCACCT
1601 TCCACGAGCT CGTGTCGACA CAGTTTGGCC AGACGGTCAA GGTGGCGGGC
1651 AACGCCGCGG CCCTGGGCAA CTGGAGCACG AGCGCCGCCG TGGCTCTGGA
1701 CGCCGTCAAC TATGCCGATA ACCACCCCCT GTGGATTGGG ACGGTCAACC
1751 TCGAGGCTGG AGACGTCGTG GAGTACAAGT ACATCAATGT GGGCCAAGAT
1801 GGCTCCGTGA CCTGGGAGAG TGATCCCAAC CACACTTACA CGGTTCCTGC
1851 GGTGGCTTGT GTGACGCAGG TTGTCAAGGA GGACACCTGG CAGTCGTAA
```

*FIG. 1B*

```
AaGA    (1)    -ATLDSWLSNEATVARTAILNNIGADGAWVSGADSGIVVASPSTDNPDYF
AnGA    (1)    -ATLDSWLSNEATVARTAILNNIGADGAWVSGADSGIVVASPSTDNPDYF
AoGA    (1)    QSDLNAFIEAQTPIAKQGYLNNIGADGKLVEGAAAGIVYASPSKSNPDYF
HgGA    (1)    -AAVDTFINTEKPIAWNKLLANIGPNGKAAPGAAAGVVIASPSRTDPPYF
HvGA    (1)    --SVDDFINTQTPIALNNLLCNVGPDCRAFGTSAGAVIASPSTTDPDYY
TrGA    (1)    --SVDDFISTETPIALNNLLCNVGPDCRAFGTSAGAVIASPSTIDPDYY
                 *    *   *   *       *   * * ****    * *

AaGA   (50)    YTWTRDSGLVIKTLVDLFRNGDTD-LLSTIENYISSQAIVQGISNPSGDL
AnGA   (50)    YTWTRDSGLVLKTLVDLFRNGDTS-LLSTIENYISAQAIVQGISNPSGDL
AoGA   (51)    YTWTRDAGLTMEEYIEQFIGGDAT-LESTIQNYVDSQANEQAVSNPSGGL
HgGA   (50)    FTWTPDAALVLTGIIESLGHNYNT---------------TLQQVSNPSGTF
HvGA   (49)    YMWTRDSALVFKNIVDRFTQQYDAGLQRRIEQYISAQVTLQGISNPSGSL
TrGA   (49)    YMWTRDSALVFKNLIDRFTETYDAGLQRRIEQYITAQVTLQGLSNPSGSL
                ** *  *                             *  *****

AaGA   (99)    SSGG-LGEPKFNVDETAYTGSWGRPQRDGPALRATAMIGFRQWLLDNGYT
AnGA   (99)    SSGAGLGEPKFNVDETAYTGSWGRPQRDGPALRATAMIGFGQWLLDNGYT
AoGA  (100)    SDGSGLAEPKFYYNISQFTDSWGRPQRDGPALRASALIAYGNSLISSDKQ
HgGA   (86)    ADGSGLGEAKFNVDLTAFTGEWGRPQRDGPPLRAIALIQYAKWLIANGYK
HvGA   (99)    SDGSGLGEPKFELTLSQFTGNWGRPQRDGPALRAIALIGYSKWLINNYQ
TrGA   (99)    ADGSGLGEPKFELTLKPFTGNWGRPQRDGPALRAIALIGYSKWLINNNYQ
                 *  *  **     *    ********* *** * *          *

AaGA  (148)    SAATEIVWPLVRNDLSYVAQYWNQTGYDLWEEVNGSSFFTIAVQHRALVE
AnGA  (149)    STATDIVWPLVRNDLSYVAQYWNQTGYDLWEEVNGSSFFTIAVQHRALVE
AoGA  (150)    SVVKANIWPIYQNDLSYVGQYWNQTGFDLWEEVQGSSFFTVAVQHKALVE
HgGA  (136)    STAKSVVWPVVKNDLAYTAQYWNETGFDLWEEVPGSSFFTIASSHRALTE
HvGA  (149)    STVSNIIWPIVRNDLNYVAQYWNQTGFDLWEEVNGSSFFTVANQHRALVE
TrGA  (149)    STVSNVIWPIVRNDLNYVAQYWNQTGFDLWEEVNGSSFFTVANQHRALVE
                *    **   *** * **** ** ****** ****** *    ** *

AaGA  (198)    GSAFATAVGSSCSWCDSQAPQILCYLQSFWTG--EYILANFDSS---RSGK
AnGA  (199)    GSAFATAVGSSCSWCDSQAPEILCYLQSFWTG--SFILANFDSS---RSGK
AoGA  (200)    GDAFAKALGEECQACS-VAPQILCHLQDFWNG--SAVLSNLPTNG-RSGL
HgGA  (186)    GAYLAAQLDTECPPCTTVAPQVLCFQQAFWNSKGNYVVSTSTAGEYRSGK
HvGA  (199)    GATLAATLGQSGSTYSSVAPQILCFLQRFWVS-GGYIDSNINTNEGRTGK
TrGA  (199)    GATLAATLGQSGSAYSSVAPQVLCFLQRFWVSSGGYVDSNINTNEGRTGK
                 *  *              **  **   * **                * *

AaGA  (244)    DTNTLLGSIHTFDPEAGCDDSTFQPCSPRALANHKEVVDSFRSIYTLNDG
AnGA  (245)    DANTLLGSIHTFDPEAACDDSTFQPCSPRALANHKEVVDSFRSIYTLNDG
AoGA  (246)    DTNSLLGSIHTFDPAAACDDTTFQPCSSRALSNHKLVVDSFRSVYGINNG
HgGA  (236)    DANSILASIHNFDPEAGCDNLTFQPCSERALANHKAYVDSFRNLYAINKG
HvGA  (248)    DANSLLASIHTFDPSLGCDASTFQPCSDKALSNLKVVVDSFRSIYGVNKG
TrGA  (249)    DVNSVLTSIHTFDPNLGCDAGTFQPCSDKALSNLKVVVDSFRSIYGVNKG
               * *  *  ***  ***        ******      ** *  *****    *    *
```

*FIG. 4A*

```
AaGA  (294)  LSDSEAVAVGRYPKDSYYNGNPWFLCTLAAAEQLYDALYQWDKQGSLEIT
AnGA  (295)  LSDSEAVAVGRYPEDTYYNGNPWFLCTLAAAEQLYDALYQWDKQGSLEVT
AoGA  (296)  RGAGKAAAVGPYAEDTYQGGNPWYLTTLVAAELLYDALYQWDKQGQVNVT
HgGA  (286)  IAQGKAVAVGRYSEDVYYNGNPWYLANFAAAEQLYDAIYVWNKQGSITVT
HvGA  (298)  IPAGSAVAIGRYPEDVYFNGNPWYLATFAAAEQLYDSVYVWKKTGSITVT
TrGA  (299)  IPAGAAVAIGRYAEDVYYNGNPWYLATFAAAEQLYDAIYVWKKTGSITVT
              *  *  *   *  * * ****  *   *** ***    *   *      *

AaGA  (344)  DVSLDFFQALYSDAATGTYSSSSSTYSSIVDAVKTFADGFVSIVETHAAS
AnGA  (345)  DVSLDFFKALYSDAATGTYSSSSSTYSSIVDAVKTFADGFVSIVETHAAS
AoGA  (346)  ETSLPFFKDLSSNVTTGSYAKSSSAYESLTSAVKTYADGFISVVQEYTPD
HgGA  (336)  SVSLPFFRDLVSSVSTGTYSKSSSTFTNIVNAVKAYADGFIEVAAKYTPS
HvGA  (348)  STSSAFFQELVPGVAAGTYSSSQSTFTSIINAISTYADGFLSEAAKYVPA
TrGA  (349)  ATSLAFFQELVPGVTAGTYSSSSSTFTNIINAVSTYADGFLSEAAKYVPA
               * **   *       *  *   *      *       ****

AaGA  (394)  NGSLSEQYDKSDGDELSARDLTWSYAALLTANNRRNSVMPPSWGETSAS-
AnGA  (395)  NGSMSEQYDKSDGEQLSARDLTWSYAALLTANNRRNSVVPASWGETSAS-
AoGA  (396)  GGALAEQYSRDQGTPVSASDLTWSYAAFLSAVGRRNGTVPASWGSSTAN-
HgGA  (386)  NGALAEQYDRNTGKPDSAADLTWSYSAFLSAIDRRAGLVPPSWRASVAKS
HvGA  (398)  DGSLAEQFDRNTGTPLSAVHLTWSYASFLTAAARRAGVVPPSWASSGAN-
TrGA  (399)  DGSLAEQFDRNSGTPLSALHLTWSYASFLTATARRAGIVPPSWANSSAS-
                *  **     *   **  *****  *  *   **    * **       *

AaGA  (443)  SVPGTC
AnGA  (444)  SVPGTC
AoGA  (445)  AVPSQC
HgGA  (436)  QLPSTC
HvGA  (447)  TVPSSC
TrGA  (448)  TIPSTC
                * *
```

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| Trichoderma reesei | Position | 491 | 492 | 493 | 494 | 495 | 496 | 497 | 498 | 499 | 500 | 501 | 502 | 503 | 504 | 505 | 506 | 507 | 508 | 509 | 510 | 511 | 512 | 513 | 514 | 515 | 516 | 517 | 518 | 519 | 520 |
| | Amino Acid | C | A | T | P | T | S | V | A | V | T | F | H | E | L | V | S | T | Q | F | G | Q | T | V | K | V | A | G | N | A | A |
| Humicola grisea | Position | 493 | 494 | 495 | 496 | 497 | 498 | 499 | 500 | 501 | 502 | 503 | 504 | 505 | 506 | 507 | 508 | 509 | 510 | 511 | 512 | 513 | 514 | 515 | 516 | 517 | 518 | 519 | 520 | 521 | 522 |
| | Amino Acid | C | A | D | A | S | E | V | Y | V | T | F | N | E | R | V | S | T | A | W | G | E | T | I | K | V | V | G | N | V | P |
| Thielavia terrestris | Position | 489 | 490 | 491 | 492 | 493 | 494 | 495 | 496 | 497 | 498 | 499 | 500 | 501 | 502 | 503 | 504 | 505 | 506 | 507 | 508 | 509 | 510 | 511 | 512 | 513 | 514 | 515 | 516 | 517 | 518 |
| | Amino Acid | C | S | T | P | T | A | V | A | V | T | F | N | E | R | V | T | T | Q | W | G | Q | T | I | K | V | V | G | D | A | A |
| Thermomyces lanuginosus | Position | 475 | 476 | 477 | 478 | 479 | 480 | 481 | 482 | 483 | 484 | 485 | 486 | 487 | 488 | 489 | 490 | 491 | 492 | 493 | 494 | 495 | 496 | 497 | 498 | 499 | 500 | 501 | 502 | 503 | 504 |
| | Amino Acid | C | T | P | P | S | E | V | T | L | T | F | N | A | L | V | D | T | A | F | G | Q | N | Y | L | V | G | S | I | A |
| Talaromyces emersonii | Position | 482 | 483 | 484 | 485 | 486 | 487 | 488 | 489 | 490 | 491 | 492 | 493 | 494 | 495 | 496 | 497 | 498 | 499 | 500 | 501 | 502 | 503 | 504 | 505 | 506 | 507 | 508 | 509 | 510 | 511 |
| | Amino Acid | C | T | T | T | T | S | V | A | V | T | F | D | E | I | V | S | T | S | Y | G | E | T | I | Y | L | A | G | S | I | P |
| Aspergillus niger | Position | 509 | 510 | 511 | 512 | 513 | 514 | 515 | 516 | 517 | 518 | 519 | 520 | 521 | 522 | 523 | 524 | 525 | 526 | 527 | 528 | 529 | 530 | 531 | 532 | 533 | 534 | 535 | 536 | 537 | 538 |
| | Amino Acid | C | T | T | P | T | A | V | A | V | T | F | D | L | T | A | T | T | T | Y | G | E | N | I | Y | L | V | G | S | I | S |
| Aspergillus awamori | Position | 508 | 509 | 510 | 511 | 512 | 513 | 514 | 515 | 516 | 517 | 518 | 519 | 520 | 521 | 522 | 523 | 524 | 525 | 526 | 527 | 528 | 529 | 530 | 531 | 532 | 533 | 534 | 535 | 536 | 537 |
| | Amino Acid | C | T | T | P | T | A | V | A | V | T | F | D | L | T | A | T | T | T | Y | G | E | N | I | Y | L | V | G | S | I | S |

FIG. 4C-2

| Organism | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| Trichoderma reesei | Position | 521 | 522 | 523 | 524 | 525 | 526 | 527 | 528 | 529 | 530 | 531 | 532 | 533 | 534 | 535 | 536 | 537 | 538 | 539 | 540 | 541 | 542 | 543 | 544 | 545 | 546 | 547 | 548 | 549 | 550 |
| | Amino Acid | A | L | G | N | W | S | T | S | A | A | V | A | L | D | A | V | N | Y | A | D | N | H | P | L | W | I | G | T | V | N |
| Humicola grisea | Position | | | 523 | 524 | 525 | 526 | 527 | 528 | 529 | 530 | 531 | 532 | 533 | 534 | 535 | 536 | 537 | 538 | 539 | 540 | 541 | 542 | 543 | 544 | 545 | 546 | 547 | 548 | 549 | 550 | 551 | 552 |
| | Amino Acid | | | A | L | G | N | W | D | T | S | K | A | V | | S | A | S | G | Y | K | N | S | D | P | L | W | S | I | T | V | P |
| Thielavia terrestris | Position | 519 | 520 | 521 | 522 | 523 | 524 | 525 | 526 | 527 | 528 | 529 | 530 | 531 | 532 | 533 | 534 | 535 | 536 | 537 | 538 | 539 | 540 | 541 | 542 | 543 | 544 | 545 | 546 | 547 | 548 |
| | Amino Acid | A | L | G | G | W | D | T | S | K | A | V | P | L | S | A | A | G | Y | T | A | S | D | P | L | W | S | G | T | V | D |
| Thermomyces lanuginosus | Position | 505 | 506 | 507 | 508 | 509 | 510 | 511 | 512 | 513 | 514 | 515 | 516 | 517 | 518 | 519 | 520 | 521 | 522 | 523 | 524 | 525 | 526 | 527 | 528 | 529 | 530 | 531 | 532 | 533 | 534 |
| | Amino Acid | E | L | G | S | W | D | P | A | N | A | L | L | M | S | A | K | S | W | T | G | N | P | V | W | T | L | S | I | S |
| Talaromyces emersonii | Position | 512 | 513 | 514 | 515 | 516 | 517 | 518 | 519 | 520 | 521 | 522 | 523 | 524 | 525 | 526 | 527 | 528 | 529 | 530 | 531 | 532 | 533 | 534 | 535 | 536 | 537 | 538 | 539 | 540 | 541 |
| | Amino Acid | E | L | N | W | T | A | S | A | I | P | L | R | A | D | A | Y | T | N | S | N | P | L | W | Y | V | T | V | N |
| Aspergillus niger | Position | 539 | 540 | 541 | 542 | 543 | 544 | 545 | 546 | 547 | 548 | 549 | 550 | 551 | 552 | 553 | 554 | 555 | 556 | 557 | 558 | 559 | 560 | 561 | 562 | 563 | 564 | 565 | 566 | 567 | 568 |
| | Amino Acid | Q | L | D | W | E | T | S | D | G | I | A | L | S | A | D | K | Y | T | S | D | P | L | W | Y | V | T | V | T |
| Aspergillus awamori | Position | 538 | 539 | 540 | 541 | 542 | 543 | 544 | 545 | 546 | 547 | 548 | 549 | 550 | 551 | 552 | 553 | 554 | 555 | 556 | 557 | 558 | 559 | 560 | 561 | 562 | 563 | 564 | 565 | 566 | 567 |
| | Amino Acid | Q | L | D | W | E | T | S | D | G | I | A | L | S | A | D | K | Y | T | S | N | P | L | W | Y | V | T | V | T |

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Trichoderma reesei | Position | 551 | 552 | 553 | 554 | 555 | 556 | 557 | 558 | 559 | 560 | 561 | 562 | 563 | 564 | 565 | 566 | 567 | 568 | 569 | 570 | 571 | 572 | 573 | 574 | 575 | 576 | 577 | 578 |
| | Amino Acid | L | E | A | . | G | D | V | V | E | Y | K | I | N | V | G | Q | D | G | S | V | T | . | W | E | S | D | P | N | H |
| Humicola grisea | Position | 553 | 554 | 555 | 556 | 557 | 558 | 559 | 560 | 561 | 562 | 563 | 564 | 565 | 566 | 567 | 568 | 569 | 570 | 571 | 572 | 573 | 574 | 575 | 576 | 577 | 578 | 579 | 580 | 581 |
| | Amino Acid | I | K | A | T | G | S | A | V | Q | Y | K | I | K | V | G | T | N | G | K | I | T | . | W | E | S | D | P | N | R |
| Thielavia terrestris | Position | 549 | 550 | 551 | 552 | 553 | 554 | 555 | 556 | 557 | 558 | 559 | 560 | 561 | 562 | 563 | 564 | 565 | 566 | 567 | 568 | 569 | 570 | 571 | 572 | 573 | 574 | 575 | 576 |
| | Amino Acid | L | P | A | . | G | L | A | V | Q | Y | K | I | N | V | A | A | D | G | G | V | T | . | W | E | A | D | P | N | H |
| Thermomyces lanuginosus | Position | 535 | 536 | 537 | 538 | 539 | 540 | 541 | 542 | 543 | 544 | 545 | 546 | 547 | 548 | 549 | 550 | 551 | 552 | 553 | 554 | 555 | 556 | 557 | 558 | 559 | 560 | 561 | 562 | 563 |
| | Amino Acid | L | P | A | G | T | S | F | E | Y | K | F | I | R | K | D | D | S | G | G | V | V | . | W | E | S | D | P | N | R |
| Talaromyces emersonii | Position | 542 | 543 | 544 | 545 | 546 | 547 | 548 | 549 | 550 | 551 | 552 | 553 | 554 | 555 | 556 | 557 | 558 | 559 | 560 | 561 | 562 |  |  |  |  |  |  |  |  |
| | Amino Acid | L | P | P | G | T | S | F | E | Y | K | F | F | N | Q | T | D | G | T | I | V | . | W | E | D | D | P | N | R |  |
| Aspergillus niger | Position | 569 | 570 | 571 | 572 | 573 | 574 | 575 | 576 | 577 | 578 | 579 | 580 | 581 | 582 | 583 | 584 | 585 | 586 | 587 | 588 | 589 | 590 | 591 | 592 | 593 | 594 | 595 | 596 |  |
| | Amino Acid | L | P | A | G | E | S | F | E | Y | K | F | I | R | I | E | S | D | D | S | V | E | . | W | E | D | D | P | N | R |
| Aspergillus awamori | Position | 568 | 569 | 570 | 571 | 572 | 573 | 574 | 575 | 576 | 577 | 578 | 579 | 580 | 581 | 582 | 583 | 584 | 585 | 586 | 587 | 588 | 589 | 590 | 591 | 592 | 593 | 594 | 595 |  |
| | Amino Acid | L | P | A | G | E | S | F | E | Y | K | F | I | R | I | E | S | D | D | S | V | E | . | W | E | S | D | P | N | R |

FIG. 4D-2

| Organism | | 579 | 580 | 581 | 582 | 583 | | | | 584 | 585 | 586 | 587 | 588 | 589 | 590 | 591 | 592 | 593 | 594 | 595 | 596 | 597 | 598 | 599 |
|---|---|---|---|---|---|---|---|---|---|---|---|---|---|---|---|---|---|---|---|---|---|---|---|---|---|
| Trichoderma reesei | Position | 579 | 580 | 581 | 582 | 583 | | | | 584 | 585 | 586 | 587 | 588 | 589 | 590 | 591 | 592 | 593 | 594 | 595 | 596 | 597 | 598 | 599 |
| | Amino Acid | T | Y | T | V | P | . | . | . | A | V | A | C | V | T | Q | V | V | K | E | D | T | W | Q | S |
| Humicola grisea | Position | 582 | 583 | 584 | 585 | 586 | 587 | 588 | 589 | 590 | 591 | 592 | 593 | 594 | 595 | 596 | 597 | 598 | 599 | 600 | | 601 | 602 | 603 | 604 |
| | Amino Acid | S | I | T | L | Q | . | T | A | S | A | G | K | C | A | V | T | Q | V | N | . | D | S | W | R |
| Thielavia terrestris | Position | 577 | 578 | 579 | 580 | 581 | | | | 582 | 583 | 584 | 585 | 586 | 587 | 588 | 589 | 590 | 591 | 592 | 593 | 594 | 595 | 596 | |
| | Amino Acid | S | F | T | V | P | . | . | . | A | A | C | G | T | T | A | V | T | R | D | T | W | Q | . | |
| Thermomyces lanuginosus | Position | 564 | 565 | 566 | 567 | 568 | | | | 569 | 570 | 571 | 572 | 573 | 574 | 575 | 576 | 577 | 578 | 579 | 580 | 581 | 582 | 583 | |
| | Amino Acid | S | Y | N | V | P | . | . | . | K | D | C | G | A | N | T | A | T | V | N | S | W | W | R | . |
| Talaromyces emersonii | Position | 570 | 571 | 572 | 573 | 574 | | | | 575 | 576 | 577 | 578 | 579 | 580 | 581 | 582 | 583 | 584 | 585 | 586 | 587 | 588 | 589 | |
| | Amino Acid | S | Y | T | V | P | . | . | . | A | Y | C | G | Q | T | T | A | T | I | L | D | S | W | Q | . |
| Aspergillus niger | Position | 597 | 598 | 599 | 600 | 601 | | | | 602 | 603 | 604 | 605 | 606 | 607 | 608 | 609 | 610 | 611 | 612 | 613 | 614 | 615 | 616 | |
| | Amino Acid | E | Y | T | V | P | . | . | . | Q | A | C | G | T | S | T | A | T | V | D | T | W | R | . | |
| Aspergillus awamori | Position | 596 | 597 | 598 | 599 | 600 | | | | 601 | 602 | 603 | 604 | 605 | 606 | 607 | 608 | 609 | 610 | 611 | 612 | 613 | 614 | 615 | |
| | Amino Acid | E | Y | T | V | P | . | . | . | Q | A | C | G | E | S | T | A | T | V | . | T | W | R | . | |

SEQUENCE LISTING

<160> NUMBER OF SEQ ID NOS: 168

<210> SEQ ID NO 1
<211> LENGTH: 632
<212> TYPE: PRT
<213> ORGANISM: Trichoderma reesei

<400> SEQUENCE: 1

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Ala Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

-continued

```
Arg Asn Asp Leu Asn Tyr Val Ala Gln Tyr Trp Asn Gln Thr Gly Phe
    195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255

Leu Gln Arg Phe Trp Val Ser Ser Gly Gly Tyr Val Asp Ser Asn Ile
                260                 265                 270

Asn Thr Asn Glu Gly Arg Thr Gly Lys Asp Val Asn Ser Val Leu Thr
            275                 280                 285

Ser Ile His Thr Phe Asp Pro Asn Leu Gly Cys Asp Ala Gly Thr Phe
            290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
                340                 345                 350

Pro Trp Tyr Leu Ala Thr Phe Ala Ala Ala Glu Gln Leu Tyr Asp Ala
            355                 360                 365

Ile Tyr Val Trp Lys Lys Thr Gly Ser Ile Thr Val Thr Ala Thr Ser
            370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
                420                 425                 430

Gly Ser Leu Ala Glu Gln Phe Asp Arg Asn Ser Gly Thr Pro Leu Ser
            435                 440                 445

Ala Leu His Leu Thr Trp Ser Tyr Ala Ser Phe Leu Thr Ala Thr Ala
            450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
            500                 505                 510

Val Pro Ser Gly Thr Pro Tyr Thr Pro Leu Pro Cys Ala Thr Pro Thr
            515                 520                 525

Ser Val Ala Val Thr Phe His Glu Leu Val Ser Thr Gln Phe Gly Gln
530                 535                 540

Thr Val Lys Val Ala Gly Asn Ala Ala Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asn Leu Glu Ala Gly Asp Val Val Glu Tyr
            580                 585                 590

Lys Tyr Ile Asn Val Gly Gln Asp Gly Ser Val Thr Trp Glu Ser Asp
            595                 600                 605

Pro Asn His Thr Tyr Thr Val Pro Ala Val Ala Cys Val Thr Gln Val
            610                 615                 620
```

```
Val Lys Glu Asp Thr Trp Gln Ser
625                 630

<210> SEQ ID NO 2
<211> LENGTH: 599
<212> TYPE: PRT
<213> ORGANISM: Trichoderma reesei

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
    195                 200                 205

Ser Gly Ser Ala Tyr Ser Ser Val Ala Pro Gln Val Leu Cys Phe Leu
210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
    275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
    355                 360                 365
```

Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
            435                 440                 445

Ile Pro Ser Thr Cys Ser Gly Ala Ser Val Val Gly Ser Tyr Ser Arg
        450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
            500                 505                 510

Val Lys Val Ala Gly Asn Ala Ala Ala Leu Gly Asn Trp Ser Thr Ser
            515                 520                 525

Ala Ala Val Ala Leu Asp Ala Val Asn Tyr Ala Asp Asn His Pro Leu
        530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
        595

<210> SEQ ID NO 3
<211> LENGTH: 453
<212> TYPE: PRT
<213> ORGANISM: Trichoderma reesei

<400> SEQUENCE: 3

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65              70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

```
Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
            165                 170                 175

Leu Trp Glu Glu Val Asn Gly Ser Ser Phe Phe Thr Val Ala Asn Gln
        180                 185                 190

His Arg Ala Leu Val Glu Gly Ala Thr Leu Ala Thr Leu Gly Gln
    195                 200                 205

Ser Gly Ser Ala Tyr Ser Ser Val Ala Pro Gln Val Leu Cys Phe Leu
210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
                260                 265                 270

Pro Cys Ser Asp Lys Ala Leu Ser Asn Leu Lys Val Val Asp Ser
                275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
                340                 345                 350

Ala Phe Phe Gln Glu Leu Val Pro Gly Val Thr Ala Gly Thr Tyr Ser
                355                 360                 365

Ser Ser Ser Ser Thr Phe Thr Asn Ile Ile Asn Ala Val Ser Thr Tyr
370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
                420                 425                 430

Arg Ala Gly Ile Val Pro Pro Ser Trp Ala Asn Ser Ser Ala Ser Thr
                435                 440                 445

Ile Pro Ser Thr Cys
450

<210> SEQ ID NO 4
<211> LENGTH: 1899
<212> TYPE: DNA
<213> ORGANISM: Trichoderma reesei

<400> SEQUENCE: 4
atgcacgtcc tgtcgactgc ggtgctgctc ggctccgttg ccgttcaaaa ggtcctggga     60
agaccaggat caagcggtct gtccgacgtc accaagaggt ctgttgacga cttcatcagc   120
accgagacgc ctattgcact gaacaatctt ctttgcaatg ttggtcctga tggatgccgt   180
gcattcggca catcagctgg tcgggtgatt gcatctccca gcacaattga cccggactac   240
tattacatgt ggacgcgaga tagcgctctt gtcttcaaga acctcatcga ccgcttcacc   300
gaaacgtacg atgcgggcct gcagcgccgc atcgagcagt acattactgc ccaggtcact   360
```

```
ctccagggcc tctctaaccc ctcgggctcc ctcgcggacg gctctggtct cggcgagccc    420
aagtttgagt tgaccctgaa gcctttcacc ggcaactggg gtcgaccgca gcgggatggc    480
ccagctctgc gagccattgc cttgattgga tactcaaagt ggctcatcaa caacaactat    540
cagtcgactg tgtccaacgt catctggcct attgtgcgca acgacctcaa ctatgttgcc    600
cagtactgga accaaaccgg ctttgacctc tgggaagaag tcaatgggag ctcattcttt    660
actgttgcca accagcaccg agcacttgtc gagggcgcca ctcttgctgc cactcttggc    720
cagtcgggaa gcgcttattc atctgttgct ccccaggttt tgtgctttct ccaacgattc    780
tgggtgtcgt ctggtggata cgtcgactcc aacatcaaca ccaacgaggg caggactggc    840
aaggatgtca actccgtcct gacttccatc cacaccttcg atcccaacct tggctgtgac    900
gcaggcacct tccagccatg cagtgacaaa gcgctctcca acctcaaggt tgttgtcgac    960
tccttccgct ccatctacgg cgtgaacaag ggcattcctg ccggtgctgc cgtcgccatt   1020
ggccggtatg cagaggatgt gtactacaac ggcaaccctt ggtatcttgc tacatttgct   1080
gctgccgagc agctgtacga tgccatctac gtctggaaga gacgggctc catcacggtg   1140
accgccacct ccctggcctt cttccaggag cttgttcctg gcgtgacggc cgggacctac   1200
tccagcagct cttcgacctt taccaacatc atcaacgccg tctcgacata cgccgatggc   1260
ttcctcagcg aggctgccaa gtacgtcccc gccgacggtt cgctggccga gcagtttgac   1320
cgcaacagcg gcactccgct gtctgcgctt cacctgacgt ggtcgtacgc ctcgttcttg   1380
acagccacgg cccgtcgggc tggcatcgtg ccccccctcgt gggccaacag cagcgctagc   1440
acgatcccct cgacgtgctc cggcgcgtcc gtggtcggat cctactcgcg tcccaccgcc   1500
acgtcattcc ctccgtcgca gacgcccaag cctggcgtgc cttccggtac tccctacacg   1560
cccctgccct gcgcgacccc aacctccgtg gccgtcacct tccacgagct cgtgtcgaca   1620
cagtttggcc agacggtcaa ggtggcgggc aacgccgcgg ccctgggcaa ctggagcacg   1680
agcgccgccg tggctctgga cgccgtcaac tatgccgata accacccccct gtggattggg   1740
acggtcaacc tcgaggctgg agacgtcgtg gagtacaagt acatcaatgt gggccaagat   1800
ggctccgtga cctgggagag tgatcccaac cacacttaca cggttcctgc ggtggcttgt   1860
gtgacgcagg ttgtcaagga ggacacctgg cagtcgtaa                          1899
```

<210> SEQ ID NO 5
<211> LENGTH: 448
<212> TYPE: PRT
<213> ORGANISM: Aspergillus awamori

<400> SEQUENCE: 5

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
            20                  25                  30

Asp Ser Gly Ile Val Val Ala Ser Pro Ser Thr Asp Asn Pro Asp Tyr
        35                  40                  45

Phe Tyr Thr Trp Thr Arg Asp Ser Gly Leu Val Ile Lys Thr Leu Val
    50                  55                  60

Asp Leu Phe Arg Asn Gly Asp Thr Asp Leu Leu Ser Thr Ile Glu Asn
65                  70                  75                  80

Tyr Ile Ser Ser Gln Ala Ile Val Gln Gly Ile Ser Asn Pro Ser Gly
                85                  90                  95

Asp Leu Ser Ser Gly Gly Leu Gly Glu Pro Lys Phe Asn Val Asp Glu

```
                    100                 105                 110
Thr Ala Tyr Thr Gly Ser Trp Gly Arg Pro Gln Arg Asp Gly Pro Ala
                115                 120                 125
Leu Arg Ala Thr Ala Met Ile Gly Phe Arg Gln Trp Leu Leu Asp Asn
            130                 135                 140
Gly Tyr Thr Ser Ala Ala Thr Glu Ile Val Trp Pro Leu Val Arg Asn
145                 150                 155                 160
Asp Leu Ser Tyr Val Ala Gln Tyr Trp Asn Gln Thr Gly Tyr Asp Leu
                165                 170                 175
Trp Glu Glu Val Asn Gly Ser Ser Phe Phe Thr Ile Ala Val Gln His
            180                 185                 190
Arg Ala Leu Val Glu Gly Ser Ala Phe Ala Thr Ala Val Gly Ser Ser
        195                 200                 205
Cys Ser Trp Cys Asp Ser Gln Ala Pro Gln Ile Leu Cys Tyr Leu Gln
        210                 215                 220
Ser Phe Trp Thr Gly Glu Tyr Ile Leu Ala Asn Phe Asp Ser Ser Arg
225                 230                 235                 240
Ser Gly Lys Asp Thr Asn Thr Leu Leu Gly Ser Ile His Thr Phe Asp
                245                 250                 255
Pro Glu Ala Gly Cys Asp Asp Ser Thr Phe Gln Pro Cys Ser Pro Arg
            260                 265                 270
Ala Leu Ala Asn His Lys Glu Val Val Asp Ser Phe Arg Ser Ile Tyr
        275                 280                 285
Thr Leu Asn Asp Gly Leu Ser Asp Ser Glu Ala Val Ala Val Gly Arg
        290                 295                 300
Tyr Pro Lys Asp Ser Tyr Tyr Asn Gly Asn Pro Trp Phe Leu Cys Thr
305                 310                 315                 320
Leu Ala Ala Ala Glu Gln Leu Tyr Asp Ala Leu Tyr Gln Trp Asp Lys
                325                 330                 335
Gln Gly Ser Leu Glu Ile Thr Asp Val Ser Leu Asp Phe Phe Gln Ala
            340                 345                 350
Leu Tyr Ser Asp Ala Ala Thr Gly Thr Tyr Ser Ser Ser Ser Ser Thr
        355                 360                 365
Tyr Ser Ser Ile Val Asp Ala Val Lys Thr Phe Ala Asp Gly Phe Val
        370                 375                 380
Ser Ile Val Glu Thr His Ala Ala Ser Asn Gly Ser Leu Ser Glu Gln
385                 390                 395                 400
Tyr Asp Lys Ser Asp Gly Asp Glu Leu Ser Ala Arg Asp Leu Thr Trp
                405                 410                 415
Ser Tyr Ala Ala Leu Leu Thr Ala Asn Asn Arg Arg Asn Ser Val Met
            420                 425                 430
Pro Pro Ser Trp Gly Glu Thr Ser Ala Ser Ser Val Pro Gly Thr Cys
        435                 440                 445

<210> SEQ ID NO 6
<211> LENGTH: 449
<212> TYPE: PRT
<213> ORGANISM: Aspergillus niger

<400> SEQUENCE: 6

Ala Thr Leu Asp Ser Trp Leu Ser Asn Glu Ala Thr Val Ala Arg Thr
1               5                   10                  15
Ala Ile Leu Asn Asn Ile Gly Ala Asp Gly Ala Trp Val Ser Gly Ala
                20                  25                  30
Asp Ser Gly Ile Val Val Ala Ser Pro Ser Thr Asp Asn Pro Asp Tyr
```

-continued

```
             35                  40                  45
Phe Tyr Thr Trp Thr Arg Asp Ser Gly Leu Val Leu Lys Thr Leu Val
 50                  55                  60

Asp Leu Phe Arg Asn Gly Asp Thr Ser Leu Leu Ser Thr Ile Glu Asn
 65                  70                  75                  80

Tyr Ile Ser Ala Gln Ala Ile Val Gln Gly Ile Ser Asn Pro Ser Gly
                     85                  90                  95

Asp Leu Ser Ser Gly Ala Gly Leu Gly Glu Pro Lys Phe Asn Val Asp
                    100                 105                 110

Glu Thr Ala Tyr Thr Gly Ser Trp Gly Arg Pro Gln Arg Asp Gly Pro
                    115                 120                 125

Ala Leu Arg Ala Thr Ala Met Ile Gly Phe Gly Gln Trp Leu Leu Asp
                    130                 135                 140

Asn Gly Tyr Thr Ser Thr Ala Thr Asp Ile Val Trp Pro Leu Val Arg
145                 150                 155                 160

Asn Asp Leu Ser Tyr Val Ala Gln Tyr Trp Asn Gln Thr Gly Tyr Asp
                    165                 170                 175

Leu Trp Glu Glu Val Asn Gly Ser Ser Phe Phe Thr Ile Ala Val Gln
                    180                 185                 190

His Arg Ala Leu Val Glu Gly Ser Ala Phe Ala Thr Ala Val Gly Ser
                    195                 200                 205

Ser Cys Ser Trp Cys Asp Ser Gln Ala Pro Glu Ile Leu Cys Tyr Leu
                    210                 215                 220

Gln Ser Phe Trp Thr Gly Ser Phe Ile Leu Ala Asn Phe Asp Ser Ser
225                 230                 235                 240

Arg Ser Gly Lys Asp Ala Asn Thr Leu Leu Gly Ser Ile His Thr Phe
                    245                 250                 255

Asp Pro Glu Ala Ala Cys Asp Asp Ser Thr Phe Gln Pro Cys Ser Pro
                    260                 265                 270

Arg Ala Leu Ala Asn His Lys Glu Val Val Asp Ser Phe Arg Ser Ile
                    275                 280                 285

Tyr Thr Leu Asn Asp Gly Leu Ser Asp Ser Glu Ala Val Ala Val Gly
290                 295                 300

Arg Tyr Pro Glu Asp Thr Tyr Tyr Asn Gly Asn Pro Trp Phe Leu Cys
305                 310                 315                 320

Thr Leu Ala Ala Ala Glu Gln Leu Tyr Asp Ala Leu Tyr Gln Trp Asp
                    325                 330                 335

Lys Gln Gly Ser Leu Glu Val Thr Asp Val Ser Leu Ser Phe Phe Lys
                    340                 345                 350

Ala Leu Tyr Ser Asp Ala Ala Thr Gly Thr Tyr Ser Ser Ser Ser Ser
                    355                 360                 365

Thr Tyr Ser Ser Ile Val Asp Ala Val Lys Thr Phe Ala Asp Gly Phe
370                 375                 380

Val Ser Ile Val Glu Thr His Ala Ala Ser Asn Gly Ser Met Ser Glu
385                 390                 395                 400

Gln Tyr Asp Lys Ser Asp Gly Glu Gln Leu Ser Ala Arg Asp Leu Thr
                    405                 410                 415

Trp Ser Tyr Ala Ala Leu Leu Thr Ala Asn Asn Arg Arg Asn Ser Val
                    420                 425                 430

Val Pro Ala Ser Trp Gly Glu Thr Ser Ala Ser Ser Val Pro Gly Thr
                    435                 440                 445

Cys
```

<210> SEQ ID NO 7
<211> LENGTH: 450
<212> TYPE: PRT
<213> ORGANISM: Aspergillus orzyzae

<400> SEQUENCE: 7

Gln Ser Asp Leu Asn Ala Phe Ile Glu Ala Gln Thr Pro Ile Ala Lys
1               5                   10                  15

Gln Gly Tyr Leu Asn Asn Ile Gly Ala Asp Gly Lys Leu Val Glu Gly
            20                  25                  30

Ala Ala Ala Gly Ile Val Tyr Ala Ser Pro Ser Lys Ser Asn Pro Asp
        35                  40                  45

Tyr Phe Tyr Thr Trp Thr Arg Asp Ala Gly Leu Thr Met Glu Glu Tyr
    50                  55                  60

Ile Glu Gln Phe Ile Gly Gly Asp Ala Thr Leu Glu Ser Thr Ile Gln
65                  70                  75                  80

Asn Tyr Val Asp Ser Gln Ala Asn Glu Gln Ala Val Ser Asn Pro Ser
                85                  90                  95

Gly Gly Leu Ser Asp Gly Ser Gly Leu Ala Glu Pro Lys Phe Tyr Tyr
            100                 105                 110

Asn Ile Ser Gln Phe Thr Asp Ser Trp Gly Arg Pro Gln Arg Asp Gly
        115                 120                 125

Pro Ala Leu Arg Ala Ser Ala Leu Ile Ala Tyr Gly Asn Ser Leu Ile
130                 135                 140

Ser Ser Asp Lys Gln Ser Val Val Lys Ala Asn Ile Trp Pro Ile Tyr
145                 150                 155                 160

Gln Asn Asp Leu Ser Tyr Val Gly Gln Tyr Trp Asn Gln Thr Gly Phe
                165                 170                 175

Asp Leu Trp Glu Glu Val Gln Gly Ser Ser Phe Phe Thr Val Ala Val
            180                 185                 190

Gln His Lys Ala Leu Val Glu Gly Asp Ala Phe Ala Lys Ala Leu Gly
        195                 200                 205

Glu Glu Cys Gln Ala Cys Ser Val Ala Pro Gln Ile Leu Cys His Leu
210                 215                 220

Gln Asp Phe Trp Asn Gly Ser Ala Val Leu Ser Asn Leu Pro Thr Asn
225                 230                 235                 240

Gly Arg Ser Gly Leu Asp Thr Asn Ser Leu Leu Gly Ser Ile His Thr
                245                 250                 255

Phe Asp Pro Ala Ala Ala Cys Asp Asp Thr Thr Phe Gln Pro Cys Ser
            260                 265                 270

Ser Arg Ala Leu Ser Asn His Lys Leu Val Val Asp Ser Phe Arg Ser
        275                 280                 285

Val Tyr Gly Ile Asn Asn Gly Arg Gly Ala Gly Lys Ala Ala Ala Val
290                 295                 300

Gly Pro Tyr Ala Glu Asp Thr Tyr Gln Gly Gly Asn Pro Trp Tyr Leu
305                 310                 315                 320

Thr Thr Leu Val Ala Ala Glu Leu Leu Tyr Asp Ala Leu Tyr Gln Trp
                325                 330                 335

Asp Lys Gln Gly Gln Val Asn Val Thr Glu Thr Ser Leu Pro Phe Phe
            340                 345                 350

Lys Asp Leu Ser Ser Asn Val Thr Thr Gly Ser Tyr Ala Lys Ser Ser
        355                 360                 365

Ser Ala Tyr Glu Ser Leu Thr Ser Ala Val Lys Thr Tyr Ala Asp Gly
370                 375                 380

Phe Ile Ser Val Val Gln Glu Tyr Thr Pro Asp Gly Gly Ala Leu Ala

```
                385                 390                 395                 400
Glu Gln Tyr Ser Arg Asp Gln Gly Thr Pro Val Ser Ala Ser Asp Leu
                405                 410                 415

Thr Trp Ser Tyr Ala Ala Phe Leu Ser Ala Val Gly Arg Arg Asn Gly
            420                 425                 430

Thr Val Pro Ala Ser Trp Gly Ser Ser Thr Ala Asn Ala Val Pro Ser
        435                 440                 445

Gln Cys
    450

<210> SEQ ID NO 8
<211> LENGTH: 441
<212> TYPE: PRT
<213> ORGANISM: Humicola grisea

<400> SEQUENCE: 8

Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
            20                  25                  30

Ala Ala Gly Val Val Ile Ala Ser Pro Ser Arg Thr Asp Pro Pro Tyr
        35                  40                  45

Phe Phe Thr Trp Thr Pro Asp Ala Ala Leu Val Leu Thr Gly Ile Ile
    50                  55                  60

Glu Ser Leu Gly His Asn Tyr Asn Thr Thr Leu Gln Gln Val Ser Asn
65                  70                  75                  80

Pro Ser Gly Thr Phe Ala Asp Gly Ser Gly Leu Gly Glu Ala Lys Phe
                85                  90                  95

Asn Val Asp Leu Thr Ala Phe Thr Gly Glu Trp Gly Arg Pro Gln Arg
            100                 105                 110

Asp Gly Pro Pro Leu Arg Ala Ile Ala Leu Ile Gln Tyr Ala Lys Trp
        115                 120                 125

Leu Ile Ala Asn Gly Tyr Lys Ser Thr Ala Lys Ser Val Val Trp Pro
130                 135                 140

Val Val Lys Asn Asp Leu Ala Tyr Thr Ala Gln Tyr Trp Asn Glu Thr
145                 150                 155                 160

Gly Phe Asp Leu Trp Glu Glu Val Pro Gly Ser Ser Phe Phe Thr Ile
                165                 170                 175

Ala Ser Ser His Arg Ala Leu Thr Glu Gly Ala Tyr Leu Ala Ala Gln
            180                 185                 190

Leu Asp Thr Glu Cys Pro Pro Cys Thr Thr Val Ala Pro Gln Val Leu
        195                 200                 205

Cys Phe Gln Gln Ala Phe Trp Asn Ser Lys Gly Asn Tyr Val Val Ser
    210                 215                 220

Thr Ser Thr Ala Gly Glu Tyr Arg Ser Gly Lys Asp Ala Asn Ser Ile
225                 230                 235                 240

Leu Ala Ser Ile His Asn Phe Asp Pro Glu Ala Gly Cys Asp Asn Leu
                245                 250                 255

Thr Phe Gln Pro Cys Ser Glu Arg Ala Leu Ala Asn His Lys Ala Tyr
            260                 265                 270

Val Asp Ser Phe Arg Asn Leu Tyr Ala Ile Asn Lys Gly Ile Ala Gln
        275                 280                 285

Gly Lys Ala Val Ala Val Gly Arg Tyr Ser Glu Asp Val Tyr Tyr Asn
    290                 295                 300

Gly Asn Pro Trp Tyr Leu Ala Asn Phe Ala Ala Ala Glu Gln Leu Tyr
```

```
                    305                 310                 315                 320
Asp Ala Ile Tyr Val Trp Asn Lys Gln Gly Ser Ile Thr Val Thr Ser
                325                 330                 335

Val Ser Leu Pro Phe Phe Arg Asp Leu Val Ser Val Ser Thr Gly
        340                 345                 350

Thr Tyr Ser Lys Ser Ser Thr Phe Thr Asn Ile Val Asn Ala Val
            355                 360                 365

Lys Ala Tyr Ala Asp Gly Phe Ile Glu Val Ala Ala Lys Tyr Thr Pro
    370                 375                 380

Ser Asn Gly Ala Leu Ala Glu Gln Tyr Asp Arg Asn Thr Gly Lys Pro
385                 390                 395                 400

Asp Ser Ala Ala Asp Leu Thr Trp Ser Tyr Ser Ala Phe Leu Ser Ala
                405                 410                 415

Ile Asp Arg Arg Ala Gly Leu Val Pro Pro Ser Trp Arg Ala Ser Val
            420                 425                 430

Ala Lys Ser Gln Leu Pro Ser Thr Cys
        435                 440

<210> SEQ ID NO 9
<211> LENGTH: 452
<212> TYPE: PRT
<213> ORGANISM: Hypocrea vinosa

<400> SEQUENCE: 9

Ser Val Asp Asp Phe Ile Asn Thr Gln Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Thr Asp Pro Asp Tyr Tyr
            35                  40                  45

Tyr Met Trp Thr Arg Asp Ser Ala Leu Val Phe Lys Asn Ile Val Asp
    50                  55                  60

Arg Phe Thr Gln Gln Tyr Asp Ala Gly Leu Gln Arg Arg Ile Glu Gln
65                  70                  75                  80

Tyr Ile Ser Ala Gln Val Thr Leu Gln Gly Ile Ser Asn Pro Ser Gly
                85                  90                  95

Ser Leu Ser Asp Gly Ser Gly Leu Gly Glu Pro Lys Phe Glu Leu Thr
            100                 105                 110

Leu Ser Gln Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Ile Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Thr Tyr Ser Ser Val Ala Pro Gln Ile Leu Cys Phe Leu
    210                 215                 220

Gln Arg Phe Trp Val Ser Gly Gly Tyr Ile Asp Ser Asn Ile Asn Thr
225                 230                 235                 240

Asn Glu Gly Arg Thr Gly Lys Asp Ala Asn Ser Leu Leu Ala Ser Ile
```

```
                    245                 250                 255
His Thr Phe Asp Pro Ser Leu Gly Cys Asp Ala Ser Thr Phe Gln Pro
                260                 265                 270

Cys Ser Asp Lys Ala Leu Ser Asn Leu Lys Val Val Asp Ser Phe
            275                 280                 285

Arg Ser Ile Tyr Gly Val Asn Lys Gly Ile Pro Ala Gly Ser Ala Val
        290                 295                 300

Ala Ile Gly Arg Tyr Pro Glu Asp Val Tyr Phe Asn Gly Asn Pro Trp
305                 310                 315                 320

Tyr Leu Ala Thr Phe Ala Ala Ala Glu Gln Leu Tyr Asp Ser Val Tyr
                325                 330                 335

Val Trp Lys Lys Thr Gly Ser Ile Thr Val Thr Ser Thr Ser Ser Ala
                340                 345                 350

Phe Phe Gln Glu Leu Val Pro Gly Val Ala Ala Gly Thr Tyr Ser Ser
                355                 360                 365

Ser Gln Ser Thr Phe Thr Ser Ile Ile Asn Ala Ile Ser Thr Tyr Ala
            370                 375                 380

Asp Gly Phe Leu Ser Glu Ala Ala Lys Tyr Val Pro Ala Asp Gly Ser
385                 390                 395                 400

Leu Ala Glu Gln Phe Asp Arg Asn Thr Gly Thr Pro Leu Ser Ala Val
                    405                 410                 415

His Leu Thr Trp Ser Tyr Ala Ser Phe Leu Thr Ala Ala Arg Arg
                420                 425                 430

Ala Gly Val Val Pro Pro Ser Trp Ala Ser Ser Gly Ala Asn Thr Val
            435                 440                 445

Pro Ser Ser Cys
        450

<210> SEQ ID NO 10
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
tcgcgttaac gctagcatgg atctc                                           25

<210> SEQ ID NO 11
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (10)..(11)
<223> OTHER INFORMATION: a, c, g, t, unknown or other

<400> SEQUENCE: 11
tctgttgacn nsttcatcag caccgagacg c                                    31

<210> SEQ ID NO 12
<211> LENGTH: 34
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"
<220> FEATURE:
<221> NAME/KEY: modified_base
<222> LOCATION: (13)..(14)
<223> OTHER INFORMATION: a, c, g, t, unknown or other

<400> SEQUENCE: 12
tctgttgacg acnnsatcag caccgagacg ccta                                34

<210> SEQ ID NO 13
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 13
atcagcaccg agacgcctnn sgcactgaac aatcttcttt                           40

<210> SEQ ID NO 14
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 14
ctttgcaatg ttggtcctnn sggatgccgt gcattcggca                           40

<210> SEQ ID NO 15
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 15
cctgatggat gccgtgcann sggcacatca gctggtgcgg                           40

<210> SEQ ID NO 16
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 16
```
attgcatctc ccagcacann sgacccggac tactattaca                                40

<210> SEQ ID NO 17
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 17
gcatctccca gcacaattnn sccggactac tattacatgt                                40

<210> SEQ ID NO 18
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 18
tctcccagca caattgacnn sgactactat tacatgtgga                                40

<210> SEQ ID NO 19
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 19
cccagcacaa ttgacccgnn stactattac atgtggacgc                                40

<210> SEQ ID NO 20
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 20
agcacaattg acccggacnn stattacatg tggacgcgag                                40

<210> SEQ ID NO 21
<211> LENGTH: 40
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 21
attgacccgg actactatnn satgtggacg cgagatagcg                              40

<210> SEQ ID NO 22
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 22
ccggactact attacatgnn sacgcgagat agcgctcttg                              40

<210> SEQ ID NO 23
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 23
gaccgcttca ccgaaacgnn sgatgcgggc ctgcagcgcc                              40

<210> SEQ ID NO 24
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 24
acgtacgatg cgggcctgnn scgccgcatc gagcagtaca                              40

<210> SEQ ID NO 25
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other
```

```
<400> SEQUENCE: 25
tacgatgcgg gcctgcagnn scgcatcgag cagtacatta                              40

<210> SEQ ID NO 26
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 26
ctccagggcc tctctaacnn stcgggctcc ctcgcggacg                              40

<210> SEQ ID NO 27
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 27
ccctcgggct ccctcgcgnn sggctctggt ctcggcgagc                              40

<210> SEQ ID NO 28
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 28
aagtttgagt tgaccctgnn scctttcacc ggcaactggg                              40

<210> SEQ ID NO 29
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 29
gagttgaccc tgaagcctnn saccggcaac tggggtcgac                              40

<210> SEQ ID NO 30
<211> LENGTH: 40
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 30
ctgaagcctt tcaccggcnn stggggtcga ccgcagcggg                    40

<210> SEQ ID NO 31
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 31
ttcaccggca actggggtnn sccgcagcgg gatggcccag                    40

<210> SEQ ID NO 32
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 32
aactggggtc gaccgcagnn sgatggccca gctctgcgag                    40

<210> SEQ ID NO 33
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 33
aagtggctca tcaacaacnn statcagtcg actgtgtcca                    40

<210> SEQ ID NO 34
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
```

```
<222> LOCATION: (19)..(20)
<223> OTHER INFORMATION: a, c, g, t, unknown or other

<400> SEQUENCE: 34
ctcatcaaca acaactatnn stcgactgtg tccaacgtca                            40

<210> SEQ ID NO 35
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 35
ctcaactatg ttgcccagnn stggaaccaa accggctttg                            40

<210> SEQ ID NO 36
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 36
gttgcccagt actggaacnn saccggcttt gacctctggg                            40

<210> SEQ ID NO 37
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 37
tactggaacc aaaccggcnn sgacctctgg gaagaagtca                            40

<210> SEQ ID NO 38
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 38
caaaccggct ttgacctcnn sgaagaagtc aatgggagct                            40
```

```
<210> SEQ ID NO 39
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 39
ggctttgacc tctgggaann sgtcaatggg agctcattct                              40

<210> SEQ ID NO 40
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 40
tttgacctct gggaagaann saatgggagc tcattcttta                              40

<210> SEQ ID NO 41
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 41
cttgctgcca ctcttggcnn stcgggaagc gcttattcat                              40

<210> SEQ ID NO 42
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 42
actcttggcc agtcgggann sgcttattca tctgttgctc                              40

<210> SEQ ID NO 43
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<220> FEATURE:
<221> NAME/KEY: modified_base
<222> LOCATION: (19)..(20)
<223> OTHER INFORMATION: a, c, g, t, unknown or other

<400> SEQUENCE: 43
tgctttctcc aacgattcnn sgtgtcgtct ggtggatacg                              40

<210> SEQ ID NO 44
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 44
gactccaaca tcaacaccnn sgagggcagg actggcaagg                              40

<210> SEQ ID NO 45
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 45
tccaacatca acaccaacnn sggcaggact ggcaaggatg                              40

<210> SEQ ID NO 46
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 46
atcaacacca acgagggcnn sactggcaag gatgtcaact                              40

<210> SEQ ID NO 47
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 47
gtcgactcct tccgctccnn stacggcgtg aacaagggca                              40
```

```
<210> SEQ ID NO 48
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 48
tccttccgct ccatctacnn sgtgaacaag ggcattcctg                         40

<210> SEQ ID NO 49
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 49
tccatctacg gcgtgaacnn sggcattcct gccggtgctg                         40

<210> SEQ ID NO 50
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 50
gctgccgtcg ccattggcnn statgcagag gatgtgtact                         40

<210> SEQ ID NO 51
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 51
gccgtcgcca ttggccggnn sgcagaggat gtgtactaca                         40

<210> SEQ ID NO 52
<211> LENGTH: 40
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 52
attggccggt atgcagagnn sgtgtactac aacggcaacc                              40

<210> SEQ ID NO 53
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 53
ggccggtatg cagaggatnn stactacaac ggcaacccctt                             40

<210> SEQ ID NO 54
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 54
cggtatgcag aggatgtgnn stacaacggc aacccttggt                              40

<210> SEQ ID NO 55
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 55
tatgcagagg atgtgtacnn saacggcaac ccttggtatc                              40

<210> SEQ ID NO 56
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 56
```
gcagaggatg tgtactacnn sggcaaccct tggtatcttg                                40

<210> SEQ ID NO 57
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 57
tactacaacg gcaaccctnn statcttgct acatttgctg                                40

<210> SEQ ID NO 58
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 58
gatgccatct acgtctggnn saagacgggc tccatcacgg                                40

<210> SEQ ID NO 59
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 59
gccatctacg tctggaagnn sacgggctcc atcacggtga                                40

<210> SEQ ID NO 60
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 60
tccatcacgg tgaccgccnn stccctggcc ttcttccagg                                40

<210> SEQ ID NO 61
<211> LENGTH: 40
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 61
acctccctgg ccttcttcnn sgagcttgtt cctggcgtga                               40

<210> SEQ ID NO 62
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 62
gagcttgttc ctggcgtgnn sgccgggacc tactccagca                               40

<210> SEQ ID NO 63
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 63
gtgacggccg ggacctacnn sagcagctct tcgaccttta                               40

<210> SEQ ID NO 64
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 64
acggccggga cctactccnn sagctcttcg acctttacca                               40

<210> SEQ ID NO 65
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other
```

<400> SEQUENCE: 65
agctcttcga cctttaccnn satcatcaac gccgtctcga                              40

<210> SEQ ID NO 66
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 66
ctcagcgagg ctgccaagnn sgtccccgcc gacggttcgc                              40

<210> SEQ ID NO 67
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 67
gctgccaagt acgtccccnn sgacggttcg ctggccgagc                              40

<210> SEQ ID NO 68
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 68
tacgtccccg ccgacggtnn sctggccgag cagtttgacc                              40

<210> SEQ ID NO 69
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 69
ctggccgagc agtttgacnn saacagcggc actccgctgt                              40

<210> SEQ ID NO 70
<211> LENGTH: 40

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 70
gccgagcagt ttgaccgcnn sagcggcact ccgctgtctg                    40

<210> SEQ ID NO 71
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 71
tttgaccgca acagcggcnn sccgctgtct gcgcttcacc                    40

<210> SEQ ID NO 72
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 72
actccgctgt ctgcgcttnn sctgacgtgg tcgtacgcct                    40

<210> SEQ ID NO 73
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 73
tctgcgcttc acctgacgnn stcgtacgcc tcgttcttga                    40

<210> SEQ ID NO 74
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
```

```
<222> LOCATION: (19)..(20)
<223> OTHER INFORMATION: a, c, g, t, unknown or other

<400> SEQUENCE: 74
ttgacagcca cggcccgtnn sgctggcatc gtgccccct                    40

<210> SEQ ID NO 75
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 75
acggcccgtc gggctggcnn sgtgcccccc tcgtgggcca                   40

<210> SEQ ID NO 76
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, g, t, unknown or other

<400> SEQUENCE: 76
agcgctagca cgatccccnn sacgtgctcc ggcgcgtccg                   40

<210> SEQ ID NO 77
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
gtaacatcag agattttgag acac                                   24

<210> SEQ ID NO 78
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 78
gcgtctcggt gctgatgaas nngtcaacag a                           31

<210> SEQ ID NO 79
<211> LENGTH: 34
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 79
taggcgtctc ggtgctgats nngtcgtcaa caga                           34

<210> SEQ ID NO 80
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 80
aaagaagatt gttcagtgcs nnaggcgtct cggtgctgat                     40

<210> SEQ ID NO 81
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 81
tgccgaatgc acggcatccs nnaggaccaa cattgcaaag                     40

<210> SEQ ID NO 82
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 82
ccgcaccagc tgatgtgccs nntgcacggc atccatcagg                     40

<210> SEQ ID NO 83
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other
```

<400> SEQUENCE: 83
tgtaatagta gtccgggtcs nntgtgctgg gagatgcaat          40

<210> SEQ ID NO 84
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 84
acatgtaata gtagtccggs nnaattgtgc tgggagatgc          40

<210> SEQ ID NO 85
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 85
tccacatgta atagtagtcs nngtcaattg tgctgggaga          40

<210> SEQ ID NO 86
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 86
gcgtccacat gtaatagtas nncgggtcaa ttgtgctggg          40

<210> SEQ ID NO 87
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 87
ctcgcgtcca catgtaatas nngtccgggt caattgtgct          40

<210> SEQ ID NO 88
<211> LENGTH: 40

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 88
cgctatctcg cgtccacats nnatagtagt ccgggtcaat                    40

<210> SEQ ID NO 89
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 89
caagagcgct atctcgcgts nncatgtaat agtagtccgg                    40

<210> SEQ ID NO 90
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 90
ggcgctgcag gcccgcatcs nncgtttcgg tgaagcggtc                    40

<210> SEQ ID NO 91
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 91
tgtactgctc gatgcggcgs nncaggcccg catcgtacgt                    40

<210> SEQ ID NO 92
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
```

```
<222> LOCATION: (21)..(22)
<223> OTHER INFORMATION: a, c, g, t, unknown or other

<400> SEQUENCE: 92
taatgtactg ctcgatgcgs nnctgcaggc ccgcatcgta                              40

<210> SEQ ID NO 93
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 93
cgtccgcgag ggagcccgas nngttagaga ggccctggag                              40

<210> SEQ ID NO 94
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 94
gctcgccgag accagagccs nncgcgaggg agcccgaggg                              40

<210> SEQ ID NO 95
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 95
cccagttgcc ggtgaaaggs nncagggtca actcaaactt                              40

<210> SEQ ID NO 96
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 96
gtcgacccca gttgccggts nnaggcttca gggtcaactc                              40
```

```
<210> SEQ ID NO 97
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 97
cccgctgcgg tcgaccccas nngccggtga aaggcttcag                              40

<210> SEQ ID NO 98
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 98
ctgggccatc ccgctgcggs nnaccccagt tgccggtgaa                              40

<210> SEQ ID NO 99
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 99
ctcgcagagc tgggccatcs nnctgcggtc gaccccagtt                              40

<210> SEQ ID NO 100
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 100
tggacacagt cgactgatas nngttgttga tgagccactt                              40

<210> SEQ ID NO 101
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<220> FEATURE:
<221> NAME/KEY: modified_base
<222> LOCATION: (21)..(22)
<223> OTHER INFORMATION: a, c, g, t, unknown or other

<400> SEQUENCE: 101
tgacgttgga cacagtcgas nnatagttgt tgttgatgag                    40

<210> SEQ ID NO 102
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 102
caaagccggt ttggttccas nnctgggcaa catagttgag                    40

<210> SEQ ID NO 103
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 103
cccagaggtc aaagccggts nngttccagt actgggcaac                    40

<210> SEQ ID NO 104
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 104
tgacttcttc ccagaggtcs nngccggttt ggttccagta                    40

<210> SEQ ID NO 105
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 105
agctcccatt gacttcttcs nngaggtcaa agccggtttg                    40
```

```
<210> SEQ ID NO 106
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 106
agaatgagct cccattgacs nnttcccaga ggtcaaagcc                    40

<210> SEQ ID NO 107
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 107
taaagaatga gctcccatts nnttcttccc agaggtcaaa                    40

<210> SEQ ID NO 108
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 108
atgaataagc gcttcccgas nngccaagag tggcagcaag                    40

<210> SEQ ID NO 109
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 109
gagcaacaga tgaataagcs nntcccgact ggccaagagt                    40

<210> SEQ ID NO 110
<211> LENGTH: 40
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 110
cgtatccacc agacgacacs nngaatcgtt ggagaaagca                          40

<210> SEQ ID NO 111
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 111
ccttgccagt cctgccctcs nnggtgttga tgttggagtc                          40

<210> SEQ ID NO 112
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 112
catccttgcc agtcctgccs nngttggtgt tgatgttgga                          40

<210> SEQ ID NO 113
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 113
agttgacatc cttgccagts nngccctcgt tggtgttgat                          40

<210> SEQ ID NO 114
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 114
tgcccttgtt cacgccgtas nnggagcgga aggagtcgac         40

<210> SEQ ID NO 115
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 115
caggaatgcc cttgttcacs nngtagatgg agcggaagga         40

<210> SEQ ID NO 116
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 116
cagcaccggc aggaatgccs nngttcacgc cgtagatgga         40

<210> SEQ ID NO 117
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 117
agtacacatc ctctgcatas nngccaatgg cgacggcagc         40

<210> SEQ ID NO 118
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 118
tgtagtacac atcctctgcs nnccggccaa tggcgacggc         40

<210> SEQ ID NO 119
<211> LENGTH: 40
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 119
ggttgccgtt gtagtacacs nnctctgcat accggccaat                                40

<210> SEQ ID NO 120
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 120
aagggttgcc gttgtagtas nnatcctctg cataccggcc                                40

<210> SEQ ID NO 121
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 121
accaagggtt gccgttgtas nncacatcct ctgcataccg                                40

<210> SEQ ID NO 122
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 122
gataccaagg gttgccgtts nngtacacat cctctgcata                                40

<210> SEQ ID NO 123
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other
```

<400> SEQUENCE: 123
caagatacca agggttgccs nngtagtaca catcctctgc                              40

<210> SEQ ID NO 124
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 124
cagcaaatgt agcaagatas nnagggttgc cgttgtagta                              40

<210> SEQ ID NO 125
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 125
ccgtgatgga gcccgtctts nnccagacgt agatggcatc                              40

<210> SEQ ID NO 126
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 126
tcaccgtgat ggagcccgts nncttccaga cgtagatggc                              40

<210> SEQ ID NO 127
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 127
cctggaagaa ggccagggas nnggcggtca ccgtgatgga                              40

<210> SEQ ID NO 128
<211> LENGTH: 40

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 128
tcacgccagg aacaagctcs nngaagaagg ccagggaggt                            40

<210> SEQ ID NO 129
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 129
tgctggagta ggtcccggcs nncacgccag gaacaagctc                            40

<210> SEQ ID NO 130
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 130
taaaggtcga agagctgcts nngtaggtcc cggccgtcac                            40

<210> SEQ ID NO 131
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 131
tggtaaaggt cgaagagcts nnggagtagg tcccggccgt                            40

<210> SEQ ID NO 132
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
```

```
<222> LOCATION: (21)..(22)
<223> OTHER INFORMATION: a, c, g, t, unknown or other

<400> SEQUENCE: 132
tcgagacggc gttgatgats nnggtaaagg tcgaagagct                              40

<210> SEQ ID NO 133
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 133
gcgaaccgtc ggcggggacs nncttggcag cctcgctgag                              40

<210> SEQ ID NO 134
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 134
gctcggccag cgaaccgtcs nnggggacgt acttggcagc                              40

<210> SEQ ID NO 135
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 135
ggtcaaactg ctcggccags nnaccgtcgg cggggacgta                              40

<210> SEQ ID NO 136
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 136
acagcggagt gccgctgtts nngtcaaact gctcggccag                              40
```

```
<210> SEQ ID NO 137
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 137
cagacagcgg agtgccgcts nngcggtcaa actgctcggc                             40

<210> SEQ ID NO 138
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 138
ggtgaagcgc agacagcggs nngccgctgt tgcggtcaaa                             40

<210> SEQ ID NO 139
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 139
aggcgtacga ccacgtcags nnaagcgcag acagcggagt                             40

<210> SEQ ID NO 140
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 140
tcaagaacga ggcgtacgas nncgtcaggt gaagcgcaga                             40

<210> SEQ ID NO 141
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<220> FEATURE:
<221> NAME/KEY: modified_base
<222> LOCATION: (21)..(22)
<223> OTHER INFORMATION: a, c, g, t, unknown or other

<400> SEQUENCE: 141
aggggggcac gatgccagcs nnacgggccg tggctgtcaa                            40

<210> SEQ ID NO 142
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 142
tggcccacga gggggcacs nngccagccc gacgggccgt                             40

<210> SEQ ID NO 143
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(22)
<223> OTHER INFORMATION: a, c, g, t, unknown or other

<400> SEQUENCE: 143
cggacgcgcc ggagcacgts nnggggatcg tgctagcgct                            40

<210> SEQ ID NO 144
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 144
gcatctccca gcacacgaga cccggactac tat                                   33

<210> SEQ ID NO 145
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 145
gcatctccca gcacatacga cccggactac tat                                   33

<210> SEQ ID NO 146
<211> LENGTH: 33
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic primer"

<400> SEQUENCE: 146
gatgcgggcc tgcagctgcg catcgagcag tac                          33

<210> SEQ ID NO 147
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147
ctgaagcctt tcaccggcac ctggggtcga ccgcagcggg                   40

<210> SEQ ID NO 148
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 148
tgaagccttt caccggctac tggggtcgac cgcagcggg                    39

<210> SEQ ID NO 149
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 149
ctgaagcctt tcaccggcga ctggggtcga ccgcagcggg                   40

<210> SEQ ID NO 150
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 150
agtggctcat caacaacgas tatcagtcga ctgtgt                       36

<210> SEQ ID NO 151
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 151
agtggctcat caacaacacc tatcagtcga ctgtgt                       36

<210> SEQ ID NO 152
<211> LENGTH: 34

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 152
gtggctcatc aacaatggta tcagtcgact gtgt                                34

<210> SEQ ID NO 153
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 153
agtggctcat caacaacctg tatcagtcga ctgtgt                              36

<210> SEQ ID NO 154
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 154
agtggctcat caacaactcc tatcagtcga ctgtgt                              36

<210> SEQ ID NO 155
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 155
ttgcccagta ctggaacgas accggctttg acctctgg                            38

<210> SEQ ID NO 156
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 156
ttgcccagta ctggaacstg accggctttg acctctgg                            38

<210> SEQ ID NO 157
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 157
ttgcccagta ctggaacacc accggctttg acctctgg                            38
```

<210> SEQ ID NO 158
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 158
ttgcccagta ctggaaccga accggctttg acctctgg                                38

<210> SEQ ID NO 159
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 159
ttgcccagta ctggaactgc accggctttg acctctgg                                38

<210> SEQ ID NO 160
<211> LENGTH: 6
<212> TYPE: PRT
<213> ORGANISM: Trichoderma reesei

<400> SEQUENCE: 160

Ser Val Asp Asp Phe Ile
1               5

<210> SEQ ID NO 161
<211> LENGTH: 599
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Asn Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Phe Thr Val Ser Asn Val Ile Trp Pro Ile Val Arg

```
                                -continued
145                 150                 155                 160
Asn Asp Leu Asn Tyr Val Ala Gln Tyr Trp Asn Gln Thr Gly Phe Asp
                165                 170                 175
Leu Trp Glu Glu Val Asn Gly Ser Ser Phe Phe Thr Val Ala Asn Gln
                180                 185                 190
His Arg Ala Leu Val Glu Gly Ala Thr Leu Ala Ala Thr Leu Gly Gln
                195                 200                 205
Ser Gly Ser Ala Tyr Ser Ser Val Ala Pro Gln Val Leu Cys Phe Leu
            210                 215                 220
Gln Arg Phe Trp Val Ser Ser Gly Gly Tyr Val Asp Ser Asn Ile Asn
225                 230                 235                 240
Thr Asn Glu Gly Arg Thr Gly Lys Asp Val Asn Ser Val Leu Thr Ser
                245                 250                 255
Ile His Thr Phe Asp Pro Asn Leu Gly Cys Asp Ala Gly Thr Phe Gln
            260                 265                 270
Pro Cys Ser Asp Lys Ala Leu Ser Asn Leu Lys Val Val Asp Ser
            275                 280                 285
Phe Arg Ser Ile Tyr Gly Val Asn Lys Gly Ile Pro Ala Gly Ala Ala
290                 295                 300
Val Ala Ile Gly Arg Tyr Ala Glu Asp Val Tyr Tyr Asn Gly Asn Pro
305                 310                 315                 320
Trp Tyr Leu Ala Thr Phe Ala Ala Ala Glu Gln Leu Tyr Asp Ala Ile
                325                 330                 335
Tyr Val Trp Lys Lys Thr Gly Ser Ile Thr Val Thr Ala Thr Ser Leu
                340                 345                 350
Ala Phe Phe Gln Glu Leu Val Pro Gly Val Thr Ala Gly Thr Tyr Ser
                355                 360                 365
Ser Ser Ser Ser Thr Phe Thr Asn Ile Ile Asn Ala Val Ser Thr Tyr
            370                 375                 380
Ala Asp Gly Phe Leu Ser Glu Ala Ala Lys Tyr Val Pro Ala Asp Gly
385                 390                 395                 400
Ser Leu Ala Glu Gln Phe Asp Arg Asn Ser Gly Thr Pro Leu Ser Ala
                405                 410                 415
Leu His Leu Thr Trp Ser Tyr Ala Ser Phe Leu Thr Ala Thr Ala Arg
                420                 425                 430
Arg Ala Gly Ile Val Pro Pro Ser Trp Ala Asn Ser Ser Ala Ser Thr
            435                 440                 445
Ile Pro Ser Thr Cys Ser Gly Ala Ser Val Val Gly Ser Tyr Ser Arg
450                 455                 460
Pro Thr Ala Thr Ser Phe Pro Pro Ser Gln Thr Pro Lys Pro Gly Val
465                 470                 475                 480
Pro Ser Gly Thr Pro Tyr Thr Pro Leu Pro Cys Ala Thr Pro Thr Ser
                485                 490                 495
Val Ala Val Thr Phe His Glu Leu Val Ser Thr Gln Phe Gly Gln Thr
                500                 505                 510
Val Lys Val Ala Gly Asn Ala Ala Ala Leu Gly Asn Trp Ser Thr Ser
                515                 520                 525
Ala Ala Val Ala Leu Asp Ala Val Asn Tyr Ala Asp Asn His Pro Leu
            530                 535                 540
Trp Ile Ala Thr Val Asn Leu Glu Ala Gly Asp Val Val Glu Tyr Lys
545                 550                 555                 560
Tyr Ile Asn Val Gly Gln Asp Gly Ser Val Thr Trp Glu Ser Asp Pro
                565                 570                 575
```

Asn His Thr Tyr Thr Val Pro Ala Val Ala Cys Val Thr Gln Val Val
            580                 585                 590

Lys Glu Asp Thr Trp Gln Ser
        595

<210> SEQ ID NO 162
<211> LENGTH: 109
<212> TYPE: PRT
<213> ORGANISM: Trichoderma reesie

<400> SEQUENCE: 162

Cys Ala Thr Pro Thr Ser Val Ala Val Thr Phe His Glu Leu Val Ser
1               5                   10                  15

Thr Gln Phe Gly Gln Thr Val Lys Val Ala Gly Asn Ala Ala Ala Leu
            20                  25                  30

Gly Asn Trp Ser Thr Ser Ala Ala Val Ala Leu Asp Ala Val Asn Tyr
        35                  40                  45

Ala Asp Asn His Pro Leu Trp Ile Gly Thr Val Asn Leu Glu Ala Gly
    50                  55                  60

Asp Val Val Glu Tyr Lys Tyr Ile Asn Val Gly Gln Asp Gly Ser Val
65                  70                  75                  80

Thr Trp Glu Ser Asp Pro Asn His Thr Tyr Thr Val Pro Ala Val Ala
                85                  90                  95

Cys Val Thr Gln Val Val Lys Glu Asp Thr Trp Gln Ser
            100                 105

<210> SEQ ID NO 163
<211> LENGTH: 112
<212> TYPE: PRT
<213> ORGANISM: Humicola grisea

<400> SEQUENCE: 163

Cys Ala Asp Ala Ser Glu Val Tyr Val Thr Phe Asn Glu Arg Val Ser
1               5                   10                  15

Thr Ala Trp Gly Glu Thr Ile Lys Val Gly Asn Val Pro Ala Leu
            20                  25                  30

Gly Asn Trp Asp Thr Ser Lys Ala Val Thr Leu Ser Ala Ser Gly Tyr
        35                  40                  45

Lys Ser Asn Asp Pro Leu Trp Ser Ile Thr Val Pro Ile Lys Ala Thr
    50                  55                  60

Gly Ser Ala Val Gln Tyr Lys Tyr Ile Lys Val Gly Thr Asn Gly Lys
65                  70                  75                  80

Ile Thr Trp Glu Ser Asp Pro Asn Arg Ser Ile Thr Leu Gln Thr Ala
                85                  90                  95

Ser Ser Ala Gly Lys Cys Ala Ala Gln Thr Val Asn Asp Ser Trp Arg
            100                 105                 110

<210> SEQ ID NO 164
<211> LENGTH: 108
<212> TYPE: PRT
<213> ORGANISM: Thielavia terrestris

<400> SEQUENCE: 164

Cys Ser Thr Pro Thr Ala Val Ala Val Thr Phe Asn Glu Arg Val Thr
1               5                   10                  15

Thr Gln Trp Gly Gln Thr Ile Lys Val Val Gly Asp Ala Ala Ala Leu
            20                  25                  30

Gly Gly Trp Asp Thr Ser Lys Ala Val Pro Leu Ser Ala Ala Gly Tyr
        35                  40                  45

Thr Ala Ser Asp Pro Leu Trp Ser Gly Thr Val Asp Leu Pro Ala Gly
    50                  55                  60

Leu Ala Val Gln Tyr Lys Tyr Ile Asn Val Ala Ala Asp Gly Gly Val
65                  70                  75                  80

Thr Trp Glu Ala Asp Pro Asn His Ser Phe Thr Val Pro Ala Ala Cys
                85                  90                  95

Gly Thr Thr Ala Val Thr Arg Asp Asp Thr Trp Gln
            100                 105

<210> SEQ ID NO 165
<211> LENGTH: 109
<212> TYPE: PRT
<213> ORGANISM: Thermomyces lanuginosus

<400> SEQUENCE: 165

Cys Thr Pro Pro Ser Glu Val Thr Leu Thr Phe Asn Ala Leu Val Asp
1               5                   10                  15

Thr Ala Phe Gly Gln Asn Ile Tyr Leu Val Gly Ser Ile Pro Glu Leu
            20                  25                  30

Gly Ser Trp Asp Pro Ala Asn Ala Leu Leu Met Ser Ala Lys Ser Trp
        35                  40                  45

Thr Ser Gly Asn Pro Val Trp Thr Leu Ser Ile Ser Leu Pro Ala Gly
    50                  55                  60

Thr Ser Phe Glu Tyr Lys Phe Ile Arg Lys Asp Asp Gly Ser Ser Asp
65                  70                  75                  80

Val Val Trp Glu Ser Asp Pro Asn Arg Ser Tyr Asn Val Pro Lys Asp
                85                  90                  95

Cys Gly Ala Asn Thr Ala Thr Val Asn Ser Trp Trp Arg
            100                 105

<210> SEQ ID NO 166
<211> LENGTH: 108
<212> TYPE: PRT
<213> ORGANISM: Talaromyces emersonii

<400> SEQUENCE: 166

Cys Thr Thr Pro Thr Ser Val Ala Val Thr Phe Asp Glu Ile Val Ser
1               5                   10                  15

Thr Ser Tyr Gly Glu Thr Ile Tyr Leu Ala Gly Ser Ile Pro Glu Leu
            20                  25                  30

Gly Asn Trp Ser Thr Ala Ser Ala Ile Pro Leu Arg Ala Asp Ala Tyr
        35                  40                  45

Thr Asn Ser Asn Pro Leu Trp Tyr Val Thr Val Asn Leu Pro Pro Gly
    50                  55                  60

Thr Ser Phe Glu Tyr Lys Phe Phe Lys Asn Gln Thr Asp Gly Thr Ile
65                  70                  75                  80

Val Trp Glu Asp Asp Pro Asn Arg Ser Tyr Thr Val Pro Ala Tyr Cys
                85                  90                  95

Gly Gln Thr Thr Ala Ile Leu Asp Asp Ser Trp Gln
            100                 105

<210> SEQ ID NO 167
<211> LENGTH: 108
<212> TYPE: PRT
<213> ORGANISM: Aspergillus niger

<400> SEQUENCE: 167

Cys Thr Thr Pro Thr Ala Val Ala Val Thr Phe Asp Leu Thr Ala Thr

```
                1               5                       10                      15
        Thr Thr Tyr Gly Glu Asn Ile Tyr Leu Val Gly Ser Ile Ser Gln Leu
                        20                      25                      30

Gly Asp Trp Glu Thr Ser Asp Gly Ile Ala Leu Ser Ala Asp Lys Tyr
                    35                      40                      45

Thr Ser Ser Asp Pro Leu Trp Tyr Val Thr Val Thr Leu Pro Ala Gly
                50                      55                      60

Glu Ser Phe Glu Tyr Lys Phe Ile Arg Ile Glu Ser Asp Asp Ser Val
        65                      70                      75                      80

Glu Trp Glu Ser Asp Pro Asn Arg Glu Tyr Thr Val Pro Gln Ala Cys
                            85                      90                      95

Gly Thr Ser Thr Ala Thr Val Thr Asp Thr Trp Arg
                        100                     105

<210> SEQ ID NO 168
        <211> LENGTH: 108
        <212> TYPE: PRT
        <213> ORGANISM: Aspergillus awamori

<400> SEQUENCE: 168

Cys Thr Thr Pro Thr Ala Val Ala Val Thr Phe Asp Leu Thr Ala Thr
        1               5                       10                      15

Thr Thr Tyr Gly Glu Asn Ile Tyr Leu Val Gly Ser Ile Ser Gln Leu
                        20                      25                      30

Gly Asp Trp Asp Thr Ser Asp Gly Ile Ala Leu Ser Ala Asp Lys Tyr
                    35                      40                      45

Thr Ser Ser Asn Pro Leu Trp Tyr Val Thr Val Thr Leu Pro Ala Gly
                50                      55                      60

Glu Ser Phe Glu Tyr Lys Phe Ile Arg Ile Glu Ser Asp Asp Ser Val
        65                      70                      75                      80

Glu Trp Glu Ser Asp Pro Asn Arg Glu Tyr Thr Val Pro Gln Ala Cys
                            85                      90                      95

Gly Glu Ser Thr Ala Thr Val Thr Asp Thr Trp Arg
                        100                     105
```

US 8,679,792 B2

GLUCOAMYLASE VARIANTS WITH ALTERED PROPERTIES

CROSS REFERENCE TO RELATED APPLICATIONS

This application is a continuation of U.S. patent application Ser. No. 12/292,563, filed Nov. 20, 2008, now U.S. Pat. No. 8,058,033, which claims the benefit of U.S. Provisional Application No. 60/989,426, filed Nov. 20, 2007, which are herein incorporated in their entireties.

SEQUENCE LISTING

The sequence listing submitted via EFS, in compliance with 37 C.F.R. §1.52(e), is incorporated herein by reference. The sequence listing text file submitted via EFS contains the file "31060US-SEQLIST.txt" created on Feb. 14, 2012, which is 97,616 bytes in size.

FIELD OF THE INVENTION

Glucoamylase variants advantageously have altered properties (e.g., improved thermostability and/or specific activity). Compositions comprising the variant glucoamylases, DNA constructs encoding the variants, and methods of producing the glucoamylase variants in host cells are provided.

BACKGROUND

Glucoamylase enzymes (glucan 1,4-α-glucohydrolases, EC 3.2.1.3) are starch hydrolyzing exo-acting carbohydrases, which catalyze the removal of successive glucose units from the non-reducing ends of starch or related oligo and polysaccharide molecules. Glucoamylases can hydrolyze both the linear and branched glucosidic linkages of starch (e.g., amylose and amylopectin).

Glucoamylases are produced by numerous strains of bacteria, fungi, yeast and plants. Particularly interesting, and commercially important, glucoamylases are fungal enzymes that are extracellularly produced, for example from strains of *Aspergillus* (Svensson et al. (1983) *Carlsberg Res. Commun.* 48:529-544; Boel et al., (1984) *EMBO J.* 3:1097-1102; Hayashida et al., (1989) *Agric. Biol. Chem.* 53:923-929; U.S. Pat. No. 5,024,941; U.S. Pat. No. 4,794,175 and WO 88/09795); *Talaromyces* (U.S. Pat. No. 4,247,637; U.S. Pat. No. 6,255,084 and U.S. Pat. No. 6,620,924); *Rhizopus* (Ashikari et al., (1986) *Agric. Biol. Chem.* 50:957-964; Ashikari et al., (1989) *App. Microbiol. Biotech.* 32:129-133 and U.S. Pat. No. 4,863,864); *Humicola* (WO 05/052148 and U.S. Pat. No. 4,618,579) and *Mucor* (Houghton-Larsen et al., (2003) *Appl. Microbiol. Biotechnol.* 62:210-217). Many of the genes that code for these enzymes have been cloned and expressed in yeast, fungal and/or bacterial cells.

Commercially, glucoamylases are very important enzymes and have been used in a wide variety of applications that require the hydrolysis of starch (e.g., for producing glucose and other monosaccharides from starch). Glucoamylases are used to produce high fructose corn sweeteners, which comprise over 50% of the sweetener market in the United States. In general, glucoamylases may be, and commonly are, used with alpha amylases in starch hydrolyzing processes to hydrolyze starch to dextrins and then glucose. The glucose may then be converted to fructose by other enzymes (e.g., glucose isomerases); crystallized; or used in fermentations to produce numerous end products (e.g., ethanol, citric acid, lactic acid, succinate, ascorbic acid intermediates, glutamic acid, glycerol and 1,3-propanediol). Ethanol produced by using glucoamylases in the fermentation of starch and/or cellulose containing material may be used as a source of fuel or for alcoholic consumption.

Although glucoamylases have been used successfully in commercial applications for many years, a need still exists for new glucoamylases with altered properties, such as improved specific activity and increased thermostability.

Different mutations have been made in glucoamylases of *Aspergillus* that enhance thermal stability and specific activity. Reference is made to U.S. Pat. No. 6,537,792; U.S. Pat. No. 6,352,851; Chen et al. (1996) *Prot. Eng,* 9:499-505, Chen et al., (1995) *Prot Eng.* 8:575-582; Fierobe et al. (1996) *Biochem.* 35:8698-8704; and et al., (1997) *Prot. Eng.* 10:1199-1204. The need still exists for providing glucoamylase variants with altered properties relative to their parent.

SUMMARY

The present disclosure relates to glucoamylase variants of a parent glucoamylase. The glucoamylase variants contain amino acid substitutions with in the catalytic domain and/or the starch-binding domain. The variants display altered properties, such as improved thermostability and/or specific activity.

In one aspect, the present disclosure relates to a glucoamylase variant comprising two or more amino acid substitutions corresponding to position 61, 73, 417, 430, 431, 503, 511, 535, 539, or 563 of SEQ ID NO: 2, or an equivalent position in a parent glucoamylase. In another aspect, the present disclosure relates a glucoamylase variant having at least 80%, 85%, 90%, 95%, or 99.5% sequence identity with a parent glucoamylase of SEQ ID NO: 1, 2, 3, 5, 6, 7, 8, or 9. In one embodiment, the parent glucoamylase has a catalytic domain with at least 80% sequence identity with SEQ ID NO: 1, 2, 3, 5, 6, 7, 8, or 9, or a starch binding domain with at least 80% sequence identity with SEQ ID NO: 1 or 2. In other aspect, the parent glucoamylase is SEQ ID NO: 1 or 2. A further aspect of the present disclosure relates to glucoamylase variant further comprising one or more amino acid substitutions corresponding to position: 4, 5, 12, 24, 43, 44, 45, 46, 47, 49, 51, 70, 75, 6, 94, 100, 108, 114, 116, 119, 122, 124, 125, 137, 141, 143, 146, 148, 169, 171, 172, 175, 178, 180, 181, 208, 211, 228, 242, 243, 245, 292, 294, 197, 309, 310, 313, 314, 315, 316, 317, 321, 340, 341, 350, 353, 356, 363, 368, 369, 375, 376, 395, 398, 401, 408, 409, 412, 415, 418, 421, 433, 436 or 451 of SEQ ID NO: 2, or an equivalent position in the parent glucoamylase. In some aspects, the glucoamylase variant further comprises one or more amino acid substitutions corresponding to position: 4, 5, 24, 29, 43, 44, 49, 70, 75, 76, 100, 108, 119, 124, 137, 146, 148, 169, 171, 172, 175, 178, 181, 208, 211, 243, 292, 294, 297, 314, 316, 317, 340, 341, 350, 356, 363, 368, 369, 376, 395, 401, 412, 433, 436 or 451 of SEQ ID NO: 2, or an equivalent position in a parent glucoamylase. In some aspects, the glucoamylase further comprises one or more amino acid substitutions corresponding to position: 5, 24, 43, 44, 49, 70, 75, 76, 94, 119, 141, 146, 148, 172, 175, 178, 180, 181, 208, 211, 243, 294, 309, 314, 353, 369, 375, or 409 of SEQ ID NO: 2, or an equivalent position in a parent glucoamylase. In some aspects, the glucoamylase further comprises one or more amino acid substitutions corresponding to position: 43, 44, or 294 of SEQ ID NO: 2, or an equivalent position in a parent glucoamylase.

In further aspects of the invention, the glucoamylase variant comprises two or more amino acid substitutions corresponding to position: N61I, G73F, L417R/V, T430A/M, A431L/Q, E503A/V, Q511H, A535R, A539R, or N563I/K of SEQ ID NO: 2, or an equivalent position in a parent glucoamylase. In some aspects, the glucoamylase variant further comprises one or more of the following substitutions: D4L/ E/R/S/C/A/Q/W, F5C/M/N/R/S/T/V/W, I12L/R, D24E/L/Y/ T, F29L/I/D/C/S/V/W, I43F/R/D/Y/S/Q, D44E/H/K/S/N/Y/ F/R/C, Y47W, Y49N, Q70R/K/M/P/G/L/F, Q75R/K/A, R76L/M/K/T/P, P94L, D100W/I/Q/M/P/A/N, N119P/T/Y/ D/E, N146S/G/C/H/E/D/T/W/L/F/M, Q148V/Y/H/A/C/D/ G/M/R/S/T, Y169D/F, Q172C/A/D/R/E/F/H/V/L/M/N/S/T/ V, F175H/A/G/R/S/T/C/W/Y, W178A/C/D/E/F/G/H/K/N/R/ S/T/V/Y, E180A/C/G/H/I/L/N/P/Q/R/S/T/V/Y/, V181E/C/ D/G/H/I/P/T/Y/S/L/K/F/A, Q208L/A/C/E/N/F/H/T, S211C/ R/E/A/Y/W/M/H/L/I/R/Q/T, E243S/R/N/M/Y/A/L, R245A/ E/M/I/P/V, I292D/H/P/R/T/N/V/F/L, G294C/D/E/T/Q/I/A, K297F/L/P/T/M/D/N/Q/A/Y/H/S/R/W, R309A/C/G/H/I/N/ P/Q/S/T/W/Y/L, Y310E/G/L/P/S/W/R/Q, D313Q, V314A/ R/N/D/C/E/Q/G/H/I/L/K/M/F/P/S/T/W/Y, Y315F, Y316Q/ R, N317T/H, K340D/T, K341F/D/P/V/G/S, T350S/E/A/N, Q356H/D/E, T363L/R/C/H/W, S368W/D/F/L, S369F, N376Q/T/H/S/V, Y395Q/R/S, A398S/I/T, S401C/V, R408S, N409W/T/K, T412A/H/K/G, R433H/Q, I436A/T, or S451M/ T/H of SEQ ID NO: 2, or an equivalent position in a parent glucoamylase. In some aspects, the glucoamylase variant further comprises one or more of the following substitutions: I43F/R/D/Y/S/Q, D44E/H/K/S/N/Y/F/R/C, or G294C/D/E/ T/Q/I/A of SEQ ID NO: 2, or an equivalent position in a parent glucoamylase.

In one aspect, the present disclosure relates a variant glucoamylase comprises comprising amino acid substitutions corresponding to positions: I43Q/D44C, D44C/G294C, I43Q/G294C, or I43Q/D44C/G294 of SEQ ID NO: 2, or an equivalent position in a parent glucoamylase. The glucoamylase variant has at least 80%, 85%, 90%, 95%, or 99.5% sequence identity with SEQ ID NO: 1, 2, 3, 5, 6, 7, 8, or 9. In one embodiment, the parent glucoamylase has a catalytic domain with at least 80% sequence identity with SEQ ID NO: 1, 2, 3, 5, 6, 7, 8, or 9, or a starch binding domain with at least 80% sequence identity with SEQ ID NO: 1 or 2.

The parent glucoamylase can the enzyme obtained from any of: a *Trichoderma* spp., an *Aspergillus* spp., a *Humicola* spp., a *Penicillium* spp., a *Talaromycese* spp., or a *Schizosaccharmyces* Spp. In some aspects, the parent glucoamylase can be from a *Trichoderma* spp, or an *Aspergillus* spp.

In one aspect, the variant glucoamylase exhibits altered thermostability as compared to the parent glucoamylase. The altered thermostability can be increased thermostability. Alternatively, or in addition, the variant exhibits altered specific activity compared to the parent glucoamylase. The altered specific activity can be increased specific activity.

A further aspect of the disclosure is a polynucleotide encoding the variant described. A further aspect is a vector comprising the polynucleotide. A further aspect is a host cell containing the vector.

A further aspect of the disclosure is an enzyme composition including the glucoamylase variant. In one aspect, the enzyme composition is used in a starch conversion process or an alcohol fermentation process.

A further aspect of the invention is a method of producing a variant glucoamylase by culturing the host cell containing the polynucleotide under conditions suitable for the expression and production of the glucoamylase variant and producing the variant. The method may also include the step of recovering the glucoamylase variant from the culture.

BRIEF DESCRIPTION OF THE DRAWINGS

FIG. 1A depicts the *Trichoderma reesei* glucoamylase (TrGA) parent glucoamylase having 632 amino acids (SEQ ID NO: 1). The signal peptide is underlined, the catalytic region (SEQ ID NO: 3) starting with amino acid residues SVDDFI (SEQ ID NO: 160) and having 453 amino acid residues is in bold; the linker region is in italics; and the starch binding domain (SEQ ID NO: 161) is both italics and underlined. The mature protein, which includes the catalytic domain (SEQ ID NO: 3), linker region, and starch binding domain (SEQ ID NO: 161), is represented by SEQ ID NO: 2. FIG. 1B depicts the cDNA (SEQ ID NO: 4) that codes for the TrGA.

FIGS. 4A-4B depict an alignment comparison of the catalytic domains of parent glucoamylases including glucoamylase derived from *Aspergillus awamori* (AaGA) (SEQ ID NO: 5); *Aspergillus niger* (AnGA) (SEQ ID NO: 6); *Aspergillus orzyae* (AoGA) (SEQ ID NO: 7); *Trichoderma reesei* (TrGA) (SEQ ID NO: 3); *Humicola grisea* (HgGA) (SEQ ID NO: 8); and *Hypocrea vinosa* (HvGA) (SEQ ID NO: 9). Identical amino acids are indicated by an asterisk (*).

FIGS. 4C-4D depict an alignment comparing the Starch Binding Domain (SBD) of parent glucoamylases including *Trichoderma reesei* (TrGA) (SEQ ID NO: 161), *Humicola grisea* (HgGA) (SEQ ID NO: 162), *Thielavia terrestris* (TtGA) (SEQ ID NO: 163), *Thermomyces lanuginosus* (ThGA) (SEQ ID NO: 164), *Talaromyces emersonii* (TeGA) (SEQ ID NO: 165), *Aspergillus niger* (AnGA) (SEQ ID NO: 166), and *Aspergillus awamori* (AaGA) (SEQ ID NO: 167). Identical amino acids are indicated by a dot (.).

DETAILED DESCRIPTION

Figure 2:
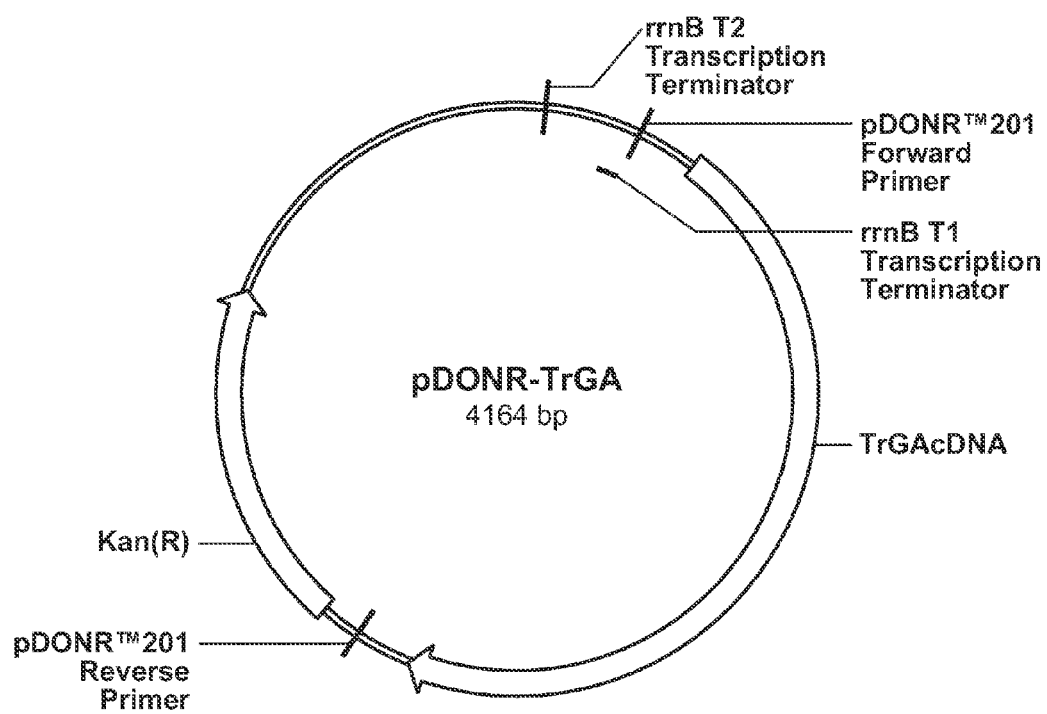
FIG. 2 depicts the plasmid pDONR-TrGA that includes the cDNA (SEQ ID NO: 4) of the parent TrGA.

Glucoamylases are commercially important enzymes in a wide variety of applications that require the hydrolysis of starch. Glucoamylases variants of described herein contains amino acid substitutions within the catalytic domain or the starch binding domain. The variants may display altered properties such as improved thermostability and/or specific activity. The variants with improved thermostability and/or specific activity may significantly improve the efficiency of glucose and fuel ethanol production from corn starch, for example.

1. DEFINITIONS

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Certain terms are defined below for the sake of clarity and ease of reference.

As used herein, the term "glucoamylase (EC 3.2.1.3)" refers to an enzyme that catalyzes the release of D-glucose from the non-reducing ends of starch and related oligo- and polysaccharides.

The term "parent" or "parent sequence" refers to a sequence that is native or naturally occurring in a host cell. Parent sequences include, but are not limited to, the glucoamylase sequences set forth in SEQ ID NOs: 1, 2, 3, 5, 6, 7, 8, and 9.

As used herein, an "equivalent position" means a position that is common to two parent sequences that is based on an alignment of the amino acid sequence of the parent glucoamylase in question as well as alignment of the three-dimensional structure of the parent glucoamylase in question with the TrGA reference glucoamylase amino acid sequence (SEQ ID NO: 2) and three-dimensional sequence.

The term "TrGA" refers to a parent *Trichoderma reesei* glucoamylase sequence having the mature protein sequence illustrated in SEQ ID NO: 2 that includes the catalytic domain having the sequence illustrated SEQ ID NO: 3. The isolation, cloning and expression of the TrGA are described in U.S. Pat. No. 7,413,887, which are incorporated herein by reference. In some embodiments, the parent sequence refers to a glucoamylase that is the starting point for protein engineering. The numbering of the glucoamylase amino acids herein is based on the sequence alignment of a glucoamylase with TrGA (SEQ ID NO: 2 and SEQ ID NO: 3).

The phrase "mature form of a protein or polypeptide" refers to the final functional form of the protein or polypeptide. To exemplify, a mature form of the TrGA includes the catalytic domain, linker region, and starch binding domain having the amino acid sequence of SEQ ID NO: 2.

As used herein, the terms "glucoamylase variant" and "variant" are used in reference to glucoamylases that have some degree of amino acid sequence identity to a parent glucoamylase sequence and that may retain the functional characteristics of a glucoamylase. A variant is similar to a parent sequence, but has at least one substitution, deletion or insertion in their amino acid sequence that makes them different in sequence from a parent glucoamylase. In some cases, variants have been manipulated and/or engineered to include at least one substitution, deletion, or insertion in their amino acid sequence that makes them different in sequence from a parent.

"Variants" may have at least 99.5%, at least 99%, at least 98%, at least 97%, at least 96%, at least 95%, at least 94%, at least 93%, at least 92%, at least 91%, at least 90%, at least 88%, at least 85%, at least 80%, at least 75%, at least 70%, at least 65%, at least 60%, at least 55%, at least 50%, or at least 45% sequence identity to a polypeptide sequence when optimally aligned for comparison. In some embodiments, the glucoamylase variant may have at least 99.5%, at least 99%, at least 98%, at least 97%, at least 96%, at least 95%, at least 94%, at least 93%, at least 92%, at least 91%, at least 90%, at least 88%, at least 85%, at least 80%, at least 75%, at least 70%, at least 65%, at least 60%, at least 55%, at least 50%, or at least 45% sequence identity to the catalytic domain of a parent glucoamylase. In some embodiments, the glucoamylase variant may have at least 99.5%, at least 99%, at least 98%, at least 97%, at least 96%, at least 95%, at least 94%, at least 93%, at least 92%, at least 91%, at least 90%, at least 88%, at least 85%, at least 80%, at least 75%, at least 70%, at least 65%, at least 60%, at least 55%, at least 50%, or at least 45% sequence identity to the starch binding domain of a parent glucoamylase. The sequence identity can be measured over the entire length of the parent or the variant sequence.

Sequence identity is determined using standard techniques known in the art (see e.g., Smith and Waterman, *Adv. Appl. Math.* 2: 482 (1981); Needleman and Wunsch, *J. Mol. Biol.* 48: 443 (1970); Pearson and Lipman, *Proc. Natl. Acad. Sci. USA* 85: 2444 (1988); programs such as GAP, BESTHT, FASTA, and TFASTA in the Wisconsin Genetics Software Package (Genetics Computer Group, Madison, Wis.); and Devereux el al., *Nucleic Acid Res.,* 12: 387-395 (1984)).

The "percent (%) nucleic acid sequence identity" or "percent (%) amino acid sequence identity" is defined as the percentage of nucleotide residues or amino acid residues in a candidate sequence that are identical with the nucleotide residues or amino acid residues of the starting sequence (e.g., TrGA). The sequence identity can be measured over the entire length of the starting sequence (e.g., SEQ ID NO: 2)

Sequence identity is determined by known methods of sequence alignment. A commonly used alignment method is BLAST described by Altschul et al., (Altschul et al., *J. Mol. Biol.* 215: 403-410 (1990); and Karlin et al., *Proc. Natl. Acad. Sci. USA* 90: 5873-5787 (1993)). A particularly useful BLAST program is the WU-BLAST-2 program (see Altschul et al, *Meth. Enzymol.* 266: 460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition attic particular sequence and composition attic particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Other methods find use in aligning sequences. One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, *J. Mol. Evol.* 35: 351-360 (1987)). The method is similar to that described by Higgins and Sharp (Higgins and Sharp, *CABIOS* 5: 151-153 (1989)). Useful PILEUP parameters including a default gap weight of 3.00, a default gap length weight of 0.10, and weighted end gaps.

The term "optimal alignment" refers to the alignment giving the highest percent identity score.

As used herein the term "catalytic domain" refers to a structural region of a polypeptide, which contains the active site for substrate hydrolysis.

The term "linker" refers to a short amino acid sequence generally having between 3 and 40 amino acids residues that covalently bind an amino acid sequence comprising a starch binding domain with an amino acid sequence comprising a catalytic domain.

The term "starch binding domain" refers to an amino acid sequence that binds preferentially to a starch substrate.

As used herein, the terms "mutant sequence" and "mutant gene" are used interchangeably and refer to a polynucleotide sequence that has an alteration in at least one codon occurring in a host cell's parent sequence. The expression product of the mutant sequence is a variant protein with an altered amino acid sequence relative to the parent. The expression product may have an altered functional capacity (e.g., enhanced enzymatic activity).

The term "property" or grammatical equivalents thereof in the context of a polypeptide, as used herein, refers to any characteristic or attribute of a polypeptide that can be selected or detected. These properties include, but are not limited to oxidative stability, substrate specificity, catalytic activity, thermal stability, pH activity profile, resistance to proteolytic degradation, $K_M$, $K_{CAT}$, $K_{CAT}/K_M$ ratio, protein folding, ability to bind a substrate and ability to be secreted.

The term "property" of grammatical equivalent thereof in the context of a nucleic acid, as used herein, refers to any characteristic or attribute of a nucleic acid that can be selected or detected. These properties include, but are not limited to, a property affecting gene transcription (e.g., promoter strength or promoter recognition), a property affecting RNA processing RNA splicing and RNA stability), a property affecting translation (e.g., regulation, binding of mRNA to ribosomal proteins).

The terms "thermally stable" and "thermostable" refer to glucoamylase variants of the present disclosure that retain a specified amount of enzymatic activity after exposure to a temperature over a given period of time under conditions prevailing during the hydrolysis of starch substrates, for example, while exposed to altered temperatures.

The term "enhanced stability" in the context of a property such as thermostability refers to a higher retained starch hydrolytic activity over time as compared to another reference (i.e., parent) glucoamylases.

The term "diminished stability" in the context of a property such as thermostability refers to a lower retained starch hydrolytic activity over time as compared to another reference glucoamylase.

The term "specific activity" is defined as the activity per mg of glucoamylase protein. In some embodiments, the activity for glucoamylase is determined by the ethanol assay described herein and expressed as the amount of glucose that is produced from the starch substrate. In some embodiments, the protein concentration can be determined using the Caliper assay described herein.

The terms "active" and "biologically active" refer to a biological activity associated with a particular protein. It follows that the biological activity of a given protein refers to any biological activity typically attributed to that protein by those skilled in the art. For example, an enzymatic activity associated with a glucoamylase is hydrolytic and, thus an active glucoamylase has hydrolytic activity.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases; or other natural, chemically, biochemically modified, non-natural or derivatized nucleotide bases.

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art. The DNA construct, transforming DNA or recombinant expression cassette can be incorporated into a plasmid, chromosome, mitochondrial DNA, plastid DNA, virus, or nucleic acid fragment. Typically, the recombinant expression cassette portion of an expression vector, DNA construct or transforming DNA includes, among other sequences, a nucleic acid sequence to be transcribed and a promoter. In some embodiments, expression vectors have the ability to incorporate and express heterologous DNA fragments in a host cell.

As used herein, the term "vector" refers to a polynucleotide construct designed to introduce nucleic acids into one or more cell types. Vectors include cloning vectors, expression vectors, shuttle vectors, plasmids, cassettes, and the like.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction.

As used herein, the terms "transformed" and "stably transformed" refers to a cell that has a non-native (heterologous) polynucleotide sequence integrated into its genome or as an episomal plasmid that is maintained for at least two generations.

As used herein, the terms "selectable marker" and "selective marker" refer to a nucleic acid (e.g., a gene) capable of expression in host cells that allows for ease of selection of those hosts containing the vector. Typically, selectable markers are genes that confer antimicrobial resistance or a metabolic advantage on the host cell to allow cells containing the exogenous DNA to be distinguished from cells that have not received any exogenous sequence during the transformation.

As used herein, the term "promoter" refers to a nucleic acid sequence that functions to direct transcription of a downstream gene. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide. Generally, "operably linked" means that the DNA sequences being linked are contiguous, and, in the case of a secretory leader, contiguous and in reading phase.

As used herein the term "gene" refers to a polynucleotide (e.g., a DNA segment), that encodes a polypeptide and includes regions preceding and following the coding regions, as well as intervening sequences (introns) between individual coding segments (exons).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature ($T_m$) of the nucleic acid binding complex or probe. For example, "maximum stringency" typically occurs at about $T_m$-5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous or homologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

In an embodiment of the disclosure, mutated DNA sequences are generated with site saturation mutagenesis in at least one codon. In another embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the parent sequence. In alternative embodiments, mutant DNA is generated in vivo using any known mutagenic procedure such as, for example, radiation, nitrosoguanidine, and the like. The desired DNA sequence is then isolated and used in the methods provided herein.

As used herein, "heterologous protein" refers to a protein or polypeptide that does not naturally occur in the host cell.

An enzyme is "over-expressed" in a host cell if the enzyme is expressed in the cell at a higher level than the level at which it is expressed in a corresponding wild-type cell.

The terms "protein" and "polypeptide" are used interchangeability herein. In the present disclosure and claims, the conventional one-letter and three-letter codes for amino acid residues are used. The 3-letter code for amino acids as defined in conformity with the IUPAC-IUB Joint Commission on Biochemical Nomenclature (JCBN). It is also understood that a polypeptide may be coded for by more than one nucleotide sequence due to the degeneracy of the genetic code.

Variants of the disclosure are described by the following nomenclature: [original amino acid residue/position/substituted amino acid residue]. For example, the substitution of leucine for arginine at position 76 is represented as R76L. When more than one amino acid is substituted at a given position, the substitution is represented as 1) Q172C, Q172D or Q172R; 2) Q172C, D, or R, or 3) Q172C/D/R. When a position suitable for substitution is identified herein without a specific amino acid suggested, it is to be understood that any amino acid residue may be substituted for the amino acid residue present in the position. Where a variant glucoamylase contains a deletion in comparison with other glucoamylases the deletion is indicated with "*". For example, a deletion at position R76 is represented as R76*. A deletion of two or more consecutive amino acids is indicated for example as (76-78)*.

A "prosequence" is an amino acid sequence between the signal sequence and mature protein that is necessary for the secretion of the protein. Cleavage of the pro sequence will result in a mature active protein.

The term "signal sequence" or "signal peptide" refers to any sequence of nucleotides and/or amino acids that may participate in the secretion of the mature or precursor forms of the protein. This definition of signal sequence is a functional one, meant to include all those amino acid sequences encoded by the N-terminal portion of the protein gene, which participate in the effectuation of the secretion of protein. They, are often, but not universally, bound to the N-terminal portion of a protein or to the N-terminal portion of a precursor protein. The signal sequence may be endogenous or exogenous. The signal sequence may be that normally associated with the protein (e.g., glucoamylase), or may be from a gene encoding another secreted protein.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Host strain" or "host cell" refers to a suitable host for an expression vector comprising DNA according to the present disclosure.

The terms "derived from" and "obtained from" refer to not only a glucoamylase produced or producible by a strain of the organism in question, but also a glucoamylase encoded by a DNA sequence isolated from such strain and produced in a host organism containing such DNA sequence. Additionally, the term refers to a glucoamylase that is encoded by a DNA sequence of synthetic and/or cDNA origin and that has the identifying characteristics of the glucoamylase in question.

A "derivative" within the scope of this definition generally retains the characteristic hydrolyzing activity observed in the wild-type, native or parent form to the extent that the derivative is useful for similar purposes as the wild-type, native or parent form. Functional derivatives of glucoamylases encompass naturally occurring, synthetically or recombinantly produced peptides or peptide fragments that have the general characteristics of the glucoamylases of the present disclosure.

The term "isolated" refers to a material that is removed from the natural environment if it is naturally occurring.

A "purified" protein refers to a protein that is at least partially purified to homogeneity. In some embodiments, a purified protein is more than 10% pure, optionally more than 20% pure, and optionally more than 30% pure, as determined by SDS-PAGE. Further aspects of the disclosure encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations that were not members of the predefined set of mutations. In some embodiments, the methods include those set forth in U.S. Pat. No. 6,582,914, hereby incorporated by reference. In alternative embodiments, combinatorial mutagenesis methods encompass commercially available kits (e.g., QuikChange® Multisite, Stratagene, San Diego, Calif.).

As used herein, the term "library of mutants" refers to a population of cells that are identical in most of their genome but include different homologues of one or more genes. Such libraries can be used, for example, to identify genes or operons with improved traits.

As used herein the term "dry solids content (DS or ds)" refers to the total solids of a slurry in % on a dry weight basis.

As used herein, the term "initial hit" refers to a variant that was identified by screening a combinatorial consensus mutagenesis library. In some embodiments, initial hits have improved performance characteristics, as compared to the starting gene.

As used herein, the term "improved hit" refers to a variant that was identified by screening an enhanced combinatorial consensus mutagenesis library.

As used herein, the term "target property" refers to the property of the starting gene that is to be altered. It is not intended that the present disclosure be limited to any particular target property. However, in some embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present disclosure. Other definitions of terms may appear throughout the specification.

Where a range of values is provided, it is understood that each intervening value, to the tenth of the unit of the tower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and tower limits of these smaller ranges my independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Before the exemplary embodiments are described in more detail, it is to be understood that this disclosure is not limited to particular embodiments described, as such may, of course, vary. Although any methods and materials similar or equivalent to those described herein can be used in the practice or testing of the present disclosure, exemplary methods and materials are now described.

As used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior invention.

2. PARENT GLUCOAMYLASES

In some embodiments, the present disclosure provides a glucoamylase variant. The glucoamylase variant is a variant of a parent glucoamylase, which may comprise both a catalytic domain and a starch binding domain. In some embodiments, the parent glucoamylase comprises a catalytic domain having an amino acid sequence as illustrated in SEQ ID NO: 1, 2, 3, 5, 6, 7, 8 or 9 or having an amino acid sequence displaying at least 80% sequence identity with one or more of the amino acid sequences illustrated in SEQ ID NO: 1, 2, 3, 5, 6, 7, 8, or 9. In yet other embodiments, the parent glucoamylase comprises a catalytic domain encoded by a DNA sequence that hybridizes under medium, high, or stringent conditions with a DNA encoding the catalytic domain of a glucoamylase having one of the amino acid sequences of SEQ ID NO: 1, 2 or 3.

In some embodiments, the parent glucoamylase comprises a starch binding domain having an amino acid sequence as illustrated in SEQ ID NO 1, 2, 161, 162, 163, 164, 165, 166, or 167, or having an amino acid sequence displaying at least 80% sequence identity with one or more of the amino acid sequence illustrated SEQ ID NO: 1, 2, 161, 162, 163, 164, 165, 166, or 167. In yet other embodiments, the parent glucoamylase comprises a starch binding domain encoded by a DNA sequence that hybridizes under medium, high, or stringent conditions with a DNA encoding the starch binding domain of a glucoamylase having one of the amino acid sequences of SEQ ID NO: it or 2.

Predicted structure and known sequences of glucoamylases are conserved among fungal species (Coutinho et al., 1994, *Protein Eng.*, 7:393-400 and Coutinho et al., 1994, *Protein Eng*, 7: 749-760). In some embodiments, the parent glucoamylase is a filamentous fungal glucoamylase. In some embodiments, the parent glucoamylase is obtained from a *Trichoderma* strain (e.g., *T. reesei, T. longibrachiatum, T. strictipilis, T. asperellum, T. konilangbra* and *T. hazianum*), an *Aspergillus* strain (e.g. *A. niger, A. nidulans, A. kawachi, A. awamori* and *A. orzyae*), a *Talaromyces* strain (e.g. *T. emersonii, T. thermophilus*, and *T. duponti*), a *Hypocrea* strain (e.g. *H. gelatinosa, H. orientalis, H. vinosa*, and *H. citrina*), a *Fusarium* strain (e.g., *F. oxysporum, F. roseum*, and *F. venenatum*), a *Neurospora* strain (e.g., *N. crassa*) and a *Humicola* strain (e.g., *H. grisea, H. insolens* and *H. lanuginose*), a *Penicillium* strain (e.g., *P. notatum* or *P. chrysogenum*), or a *Saccharomycopsis* strain (e.g., *S. fibuligera*).

In some embodiments, the parent glucoamylase may be a bacterial glucoamylase. For example, the polypeptide may be obtained from a gram-positive bacterial strain such as *Bacillus* (e.g., *B. alkalophilus, B. amyloliquefaciens, B. lentus, B. licheniformis, B. stearothermophilus, B. subtilis* and *B. thuringiensis*) or a *Streptomyces* strain (e.g., *S. lividans*).

In some embodiments, the parent glucoamylase will comprise a catalytic domain having at least 80% sequence identity, at least 85% sequence identity, at least 90% sequence identity, at least 95% sequence identity, at least 97% sequence identity and also at least 98% sequence identity with the catalytic domain of the TrGA amino acid sequence of SEQ ID NO: 3.

In other embodiments, the parent glucoamylase will comprise a catalytic domain having at least 90% sequence identity, at least 93% sequence identity, at least 95% sequence identity, at least 96% sequence identity, at least 97% sequence identity, at least 98% sequence identity and also at least 99% sequence identity with the catalytic domain of the *Aspergillus* parent glucoamylase of SEQ ID NO: 5 or SEQ ID NO: 6.

In yet other embodiments, the parent glucoamylase will comprise a catalytic domain having at least 90% sequence identity, at least 95% sequence identity, at least 97% sequence identity and also at least 99% sequence identity with the catalytic domain of the *Humicola grisea* (HgGA) parent glucoamylase of SEQ ID NO: 8.

In some embodiments, the parent glucoamylase will comprise a starch binding domain having at least 80% sequence identity, at least 85% sequence identity, at least 90% sequence identity, at least 95% sequence identity, at least 97% sequence identity and also at least 98% sequence identity with the starch binding domain of the TrGA amino acid sequence of SEQ ID NO: 1, 2, or 161.

In other embodiments, the parent glucoamylase will comprise a starch binding domain having at least 90% sequence identity, at least 95% sequence identity, at least 97% sequence identity and also at least 99% sequence identity with the catalytic domain of the *Humicola grisea* (HgGA) glucoamylase of SEQ ID NO: 162.

In other embodiments, the parent glucoamylase will comprise a starch binding domain having at least 90% sequence identity, at least 95% sequence identity, at least 97% sequence identity and also at least 99% sequence identity with the catalytic domain of the *Thielavia terrestris* (TtGA) glucoamylase of SEQ ID NO: 163.

In other embodiments, the parent glucoamylase will comprise a starch binding domain having at least 90% sequence identity, at least 95% sequence identity, at least 97% sequence identity and also at least 99% sequence identity with the catalytic domain of the *Thermomyces lanuginosus* (ThGA) glucoamylase of SEQ ID NO: 164.

In other embodiments, the parent glucoamylase will comprise a starch binding domain having at least 90% sequence identity, at least 95% sequence identity, at least 97% sequence identity and also at least 99% sequence identity with the catalytic domain of the *Talaromyces emersonii* (TeGA) glucoamylase of SEQ ID NO: 165.

In yet other embodiments, the parent glucoamylase will comprise a starch binding domain having at least 90% sequence identity, at least 93% sequence identity, at least 95% sequence identity, at least 96% sequence identity, at least 97% sequence identity, at least 98% sequence identity and also at least 99% sequence identity with the starch binding domain of the *Aspergillus* parent glucoamylase SEQ ID NO: 166 or 167.

In some embodiments, the parent glucoamylase will have at least 80% sequence identity, at least 85% sequence identity, at least 88% sequence identity, at least 90% sequence identity, at least 93% sequence identity, at least 95% sequence identity, at least 96% sequence identity, at least 97% sequence identity, at least 98% sequence identity and also at least 99% sequence identity with the TrGA amino acid sequence of SEQ ID NO: 2.

In further embodiments, a *Trichoderma* glucoamylase homologue will be obtained from a *Trichoderma* or *Hypocrea* strain. Some typical *Trichoderma* glucoamylase homologues are described in U.S. Pat. No. 7,413,887 and reference is made specifically to amino acid sequences set forth in SEQ ID NOs: 17-22 and 43-47 of the reference.

In some embodiments, the parent glucoamylase is TrGA comprising the amino acid sequence of SEQ ID NO: 2, or a *Trichoderma* glucoamylase homologue having at least 80%, at least 85%, at least 88%, at least 90%, at least 93%, at least 95%, at least 96%, at least 97%, at least 98%, at least 99% sequence identity to the TrGA sequence (SEQ ID NO: 2).

A parent glucoamylase can be isolated and/or identified using standard recombinant DNA techniques. Any standard techniques can be used that are known to the skilled artisan. For example, probes and/or primers specific for conserved regions of the glucoamylase can be used to identify homologous bacterial or fungal cells (the catalytic domain, the active site, etc.). Alternatively, degenerate PCR can be used to identify homologues in bacterial or fungal cells. In some cases, known sequences, such as in a database, can be analyzed for sequence and/or structural identity to one of the known glucoamylases, including SEQ ID NO: 2, or a known starch binding domains, including SEQ ID NO: 161. Functional assays can also be used to identify glucoamylase activity in a bacterial or fungal cell. Proteins having glucoamylase activity can be isolated and reverse sequenced to isolate the corresponding DNA sequence. Such methods are known to the skilled artisan.

3. GLUCOAMYLASE STRUCTURAL HOMOLOGY

The central dogma of molecular biology is that the sequence of DNA encoding a gene for a particular enzyme, determines the amino acid sequence of the protein, this sequence in turn determines the three-dimensional folding of the enzyme. This folding brings together disparate residues that create a catalytic center and substrate binding surface and this results in the high specificity and activity of the enzymes in question.

Figure 12:
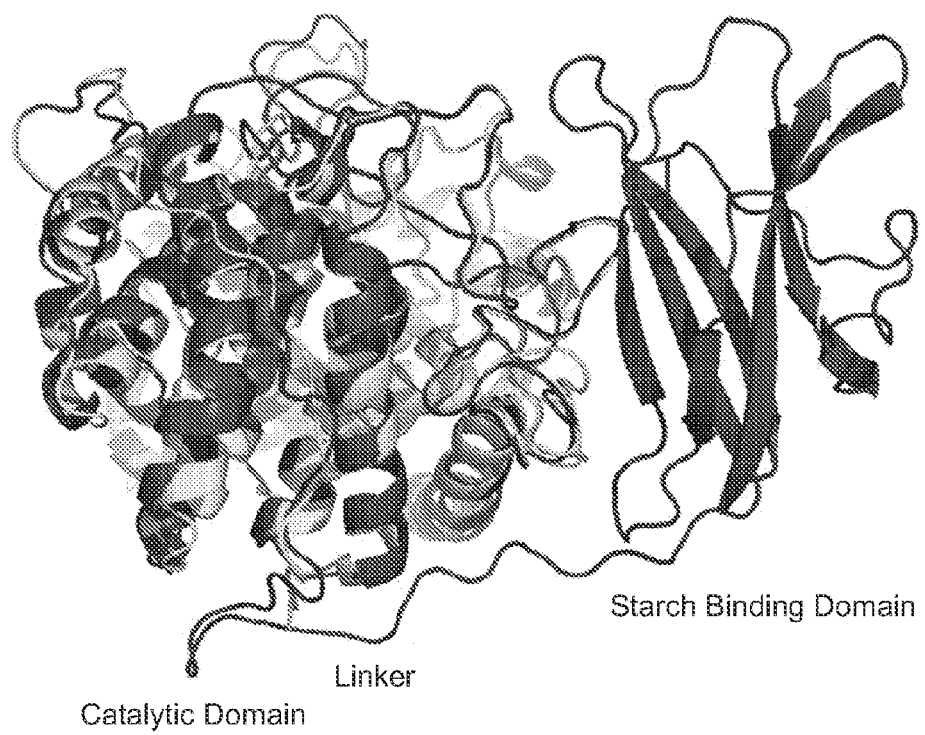
FIG. 12 depicts a comparison of the three dimensional structures of *Trichoderma reesei* glucoamylase (black) (SEQ ID NO: 2) and *Aspergillus awamori* glucoamylase (grey) viewed from the side.
Figure 13:
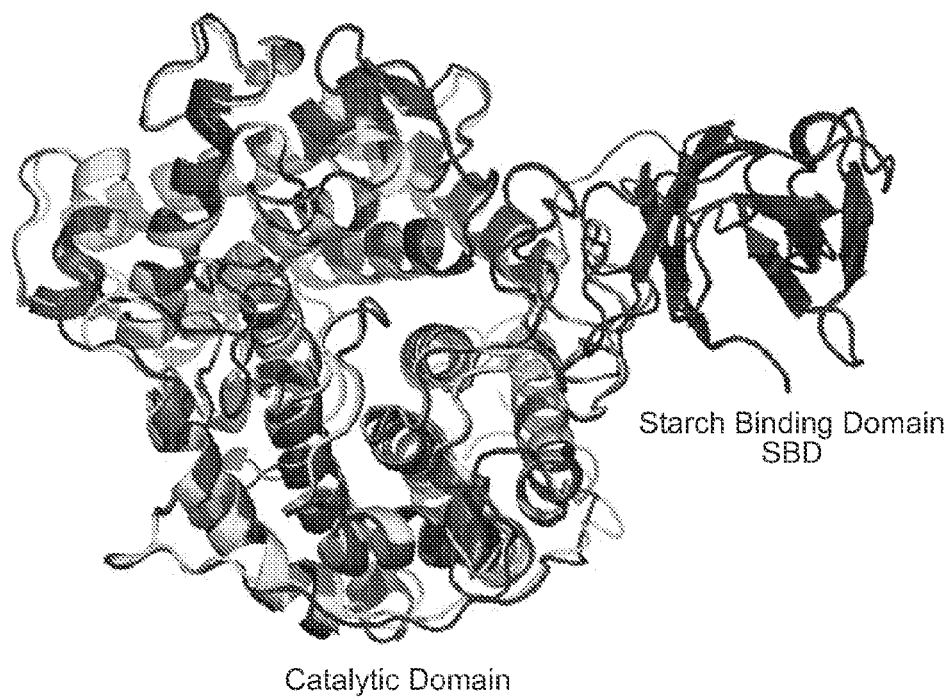
FIG. 13 depicts a comparison of the three dimensional structures of *Trichoderma reesei* glucoamylase (black and *Aspergillus awamori* glucoamylase (grey) viewed from the top.

Glucoamylases consist of as many as three distinct structural domains, a catalytic domain of approximately 450 residues that is structurally conserved in all glucoamylases, generally followed by a linker region consisting of between 30 and 80 residues that are connected to a starch binding domain of approximately 100 residues. The structure of the *Trichoderma reesei* glucoamylase with all three regions intact was determined to 1.8 Angstrom resolution herein (see Table 20 and Example 13). Using the coordinates (see Table 20) the structure was aligned with the coordinates of the catalytic domain from *Aspergillus awamori* strain X100 that was determined previously (Aleshin, A. E., Hoffman, C., Firsov, L. M., and Honzatko, R. B. 1994 Refined crystal structures of glucoamylase from *Aspergillus awamori* var. X100. J. Mol Biol 238: 575-591). The *Aspergillus awamori* crystal structure only included the catalytic domain. As seen in FIGS. 12 and 13, the structure of the catalytic domains overlap very closely and it is possible to identify equivalent residues based on this structural superposition. It is believed that all glucoamylases share the basic structure depicted in FIGS. 12 and 13.

FIG. 12 is a comparison of the three dimensional structures of the *Trichoderma* glucoamylase (black) of SEQ ID NO: 1 (see FIG. 1 for amino acid sequence) and of *Aspergillus awamori* (grey) viewed from the side. In this view the relationship between the catalytic domain and the linker region and the starch binding domain can be seen.

FIG. 13 is a comparison of the three dimensional structures of the *Trichoderma* glucoamylase (black) and of *Aspergillus awamori* (grey) viewed from the top. The glucoamylases shown here and indeed all known glucoamylases to date share this structural homology. The conservation of structure correlates with the conservation of activity and a conserved mechanism of action for all glucoamylases. Given this high homology, changes resulting from site specific variants of the *Trichoderma* glucoamylase resulting in altered function would also have similar structural and therefore functional consequences in other glucoamylases. Therefore, the teachings of which variants result in desirable benefits can be applied to other glucoamylases.

A further crystal structure was produced using the coordinates in Table 20 for the Starch Binding Domain (SBD). The SBD for TrGA was aligned with the SBD for *A. niger*. As shown in FIG. 13, the structure of the *A. niger* and TrGA SBDs overlaps very closely. It is believed that while all starch binding domains share at least some of the basic structure depicted in FIG. 13, some SBDs are more structurally similar than others. For example, the TrGA SBD can be classified as within the carbohydrate binding module 20 family within the CAZY database (cazy.org). The CAZY database describes the families of structurally-related catalytic and carbohydrate-binding modules (or functional domains) of enzymes that degrade, modify, or create glycosidic bonds. Given a high structural homology, site specific variants of the TrGA SBD resulting in altered function would also have similar structural and therefore functional consequences in other glucoamylases having SBDs with similar structure to that of the TrGA SBD, particularly those classified within the carbohydrate binding module 20 family. Thus, the teachings of which variants result in desirable benefits can be applied to other SBDs having structural similarity.

Thus, the amino acid position numbers discussed herein refer to those assigned to the mature *Trichoderma reesei* glucoamylase sequence presented in FIG. 1. The present disclosure, however, is not limited to the variants of *Trichoderma* glucoamylase, but extends to glucoamylases containing amino acid residues at positions that are "equivalent" to the particular identified residues in *Trichoderma reesei* glucoamylase (SEQ ID NO: 2). In a embodiment of the present disclosure, the parent glucoamylase is *Taleromyces glucoamylase* and the substitutions are made at the equivalent amino acid residue positions in *Taleromyces* glucoamylase as those described herein. In other embodiments, the parent glucoamylase is one of those listed in Table 1. In further embodiments, the parent glucoamylase is a *Penicillium* glucoamylase, such as *Penicillium chrysogenum*, Structural identity determines whether the amino acid residues are equivalent. Structural identity is a one-to-one topological equivalent when the two structures (three dimensional and amino acid structures) are aligned. A residue (amino acid) position of a glucoamylase is equivalent to a residue of *T. reesei* glucoamylase if it is either homologous (i.e., corresponding in position in either primary or tertiary structure) or analogous to a specific residue or portion of that residue in *T. reesei* glucoamylase (having the same or similar functional capacity to combine, react, or interact chemically).

In order to establish identity to the primary structure, the amino acid sequence of a glucoamylase can be directly compared to *Trichoderma reesei* glucoamylase primary sequence and particularly to a set of residues known to be invariant in glucoamylases for which sequence is known. For example, FIGS. 4A and 4B herein shows the conserved residues between glucoamylases, FIGS. 4C and 4D show an alignment of starch binding domains from various glucoamylases. After aligning the conserved residues, allowing for necessary insertions and deletions in order to maintain alignment (i.e. avoiding the elimination of conserved residues through arbitrary deletion and insertion), the residues equivalent to particular amino acids in the primary sequence of *Trichoderma reesei* glucoamylase are defined. Alignment of conserved residues typically should conserve 100% of such residues. However, alignment of greater than 75% or as little as 50% of conserved residues is also adequate to define equivalent residues. Further, the structural identity can be used in combination with the sequence identity to identify equivalent residues.

For example, in FIGS. 4A and 4B, the catalytic domains of glucoamylases from six organisms are aligned to provide the maximum amount of homology between amino acid sequences. A comparison of these sequences shows that there are a number of conserved residues contained in each sequence as designated by an asterisk. These conserved residues, thus, may be used to define the corresponding equivalent amino acid residues of *Trichoderma reesei* glucoamylase in other glucoamylases such as glucoamylase from *Aspergillus niger*. Similarly, FIGS. 4C and 4D show the starch binding domains of glucoamylases from seven organisms aligned to identify equivalent residues.

Structural identity involves the identification of equivalent residues between the two structures. "Equivalent residues" can be defined by determining homology at the level of tertiary structure (structural identity) for an enzyme whose tertiary structure has been determined by X-ray crystallography. Equivalent residues are defined as those for which the atomic coordinates of two or more of the main chain atoms of a particular amino acid residue of the *Trichoderma reesei* glucoamylase (N on N, CA on CA, C on C and O on O) are within 0.13 nm and optionally 0.1 nm after alignment. Alignment is achieved after the best model has been oriented and positioned to give the maximum overlap of atomic coordinates of non-hydrogen protein atoms of the glucoamylase in question to the *Trichoderma reesei* glucoamylase. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues that are functionally analogous to a specific residue of *Trichoderma reesei* glucoamylase are defined as those amino acids of the enzyme that may adopt a conformation such that they either alter, modify or contribute to protein structure, substrate binding or catalysis in a manner defined and attributed to a specific residue of the *Trichoderma reesei* glucoamylase. Further, they are those residues of the enzyme (for which a tertiary structure has been obtained by X-ray crystallography) that occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Trichoderma reesei* glucoamylase. The coordinates of the three dimensional structure of *Trichoderma reesei* glucoamylase are set forth in Table 15 and can be used as outlined above to determine equivalent residues on the level of tertiary structure.

Some of the residues identified for substitution are conserved residues whereas others are not. In the case of residues that are not conserved, the substitution of one or more amino acids is limited to substitutions that produce a variant that has an amino acid sequence that does not correspond to one found in nature. In the case of conserved residues, such substitutions should not result in a naturally-occurring sequence.

4. VARIANTS

The variants according to the disclosure include at least one substitution, deletion or insertion in the amino acid sequence of a parent glucoamylase that makes the variant different in sequence from the parent glucoamylase. In some embodiments, the variants of the disclosure will have at least 20%, at least 40%, at least 60%, at least 80%, at least 85%, at least 90%, at least 95%, or at least 100% of the glucoamylase activity of the TrGA activity of SEQ ID NO: 2.

In some embodiments, the variants according to the disclosure will comprise a substitution, deletion, or insertion in at least one amino acid position of the parent TrGA (SEQ ID NO: 2), or in an equivalent position in the sequence of another parent glucoamylase having at least 80% sequence identity to the TrGA sequence, including but not limited to, at least 90%, at least 93%, at least 95%, at least 97%, and at least 99% sequence identity.

In other embodiments, the variant according to the disclosure will comprise a substitution, deletion or insertion in at least one amino acid position of a fragment of the parent TrGA, wherein the fragment comprises the catalytic domain of the TrGA sequence (SEQ ID NO: 3) or in an equivalent position in a fragment comprising the catalytic domain of a parent glucoamylase having at least 80% sequence identity to the fragment of the TrGA sequence, including but not limited to, at least 90%, at least 95%, at least 97%, and at least 99%. In some embodiments, the fragment will comprise at least 400, 425, 450, and/or 500 amino acid residues.

In other embodiments, the variant according to the disclosure will comprise a substitution, deletion or insertion in at least one amino acid position of a fragment of the parent TrGA, wherein the fragment comprises the starch binding domain of the TrGA sequence (SEQ ID NO: 161) or in an equivalent position in a fragment comprising the starch binding domain of a parent glucoamylase having at least 80% sequence identity to the fragment of the TrGA sequence, including but not limited to, at least 90%, at least 95%, at least 97%, and at least 99%. In some embodiments, the fragment will comprise at least 40, 50, 60, 70, 80, 90, 100, and/or 109 amino acid residues of TrGA starch binding domain (SEQ ID NO: 161).

In some embodiments, when the parent glucoamylase includes a catalytic domain, a linker region, and a starch binding domain, the variant will comprise a substitution, deletion or insertion in at least one amino acid position of a fragment comprising part of the linker region. In some embodiments, the variant will comprise a substitution deletion, or insertion in the amino acid sequence of a fragment of the TrGA sequence (SEQ ID NO 2).

Structural identity with reference to an amino acid substitution means that the substitution occurs at the equivalent amino acid position in the homologous glucoamylase or parent glucoamylase. The term equivalent position means a position that is common to two parent sequences that is based on an alignment of the amino acid sequence of the parent glucoamylase in question as well as alignment of the three-dimensional structure of the parent glucoamylase in question with the TrGA reference glucoamylase amino acid sequence and three-dimensional sequence. For example, with reference to FIG. 5, position 24 in TrGA (SEQ ID NO: 2 or 3) is D24 and the equivalent position for *Aspergillus niger* (SEQ ID NO: 6) is position D25, and the equivalent position for *Aspergillus oryzea* (SEQ ID NO: 7) is position D26. See FIGS. 12 and 13 for an exemplary alignment of the three-dimensional sequence.

In some embodiments, the glucoamylase variant will include at least one substitution in the amino acid sequence of a parent. In further embodiments, the variant may have more than one substitution (e.g., two, three, or four substitutions).

Figure 5A:
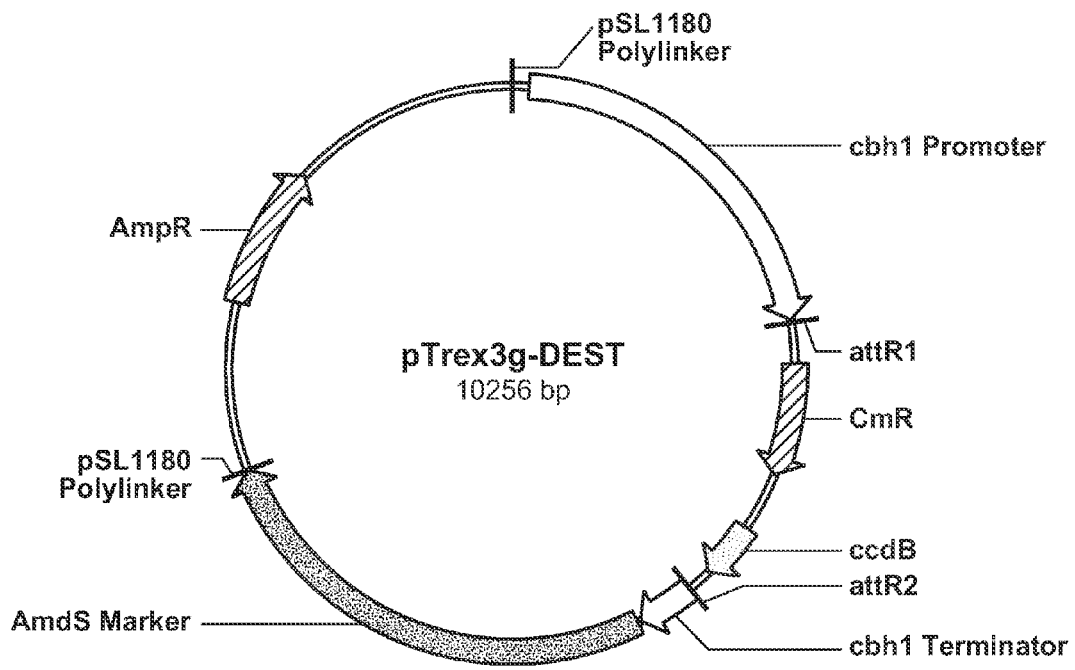
FIG. 5A depicts the plasmid pTrex3g-DEST.
Figure 5B:
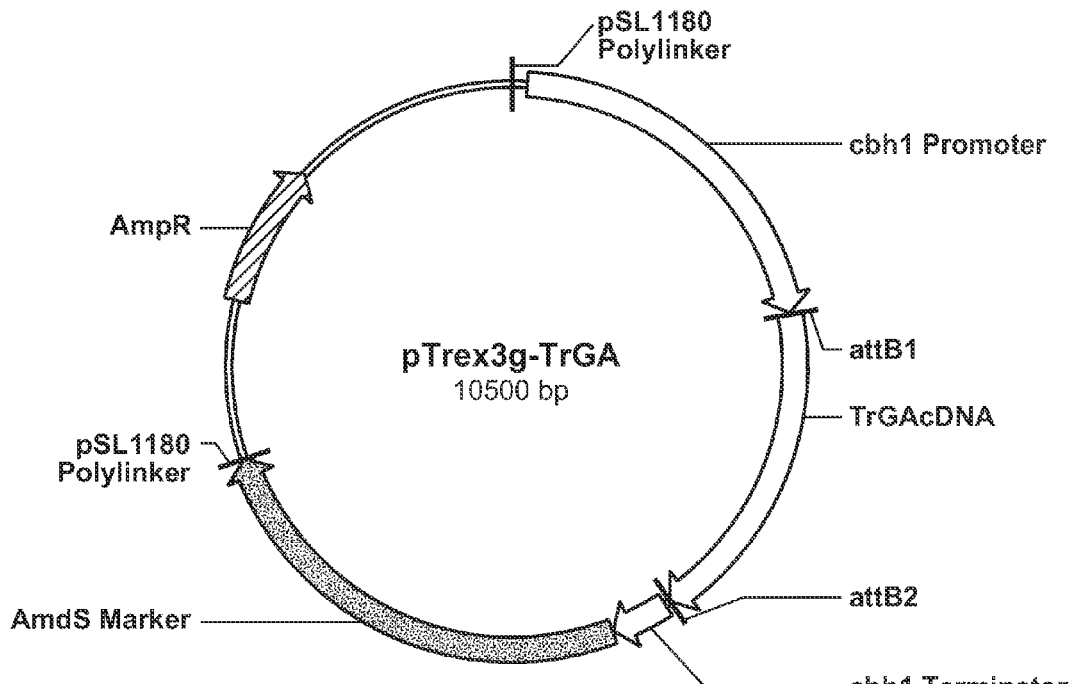
FIG. 5B depicts the plasmid pTrex3g-TrGA. The plasmids were used as expression vectors for expression and production of variant glucoamylases in a *Trichoderma reesei* host.

In some embodiments, a glucoamylase variant comprises a substitution, deletion or insertion, and typically a substitution in at least one amino acid position in a position corresponding to the regions of non-conserved amino acids as illustrated in FIG. 5 (e.g., amino acid positions corresponding to those positions that are not designated by "*" in FIG. 5).

While the variants can be in any position in the mature protein sequence (SEQ ID NO: 2), in one embodiment, a glucoamylase variant comprises one or more substitutions in the following positions in the amino acid sequence set forth in SEQ ID NO: 2: 4, 5, 12, 24, 29, 43, 44, 45, 46, 47, 49, 51, 61, 70, 73, 75, 76, 94, 100, 108, 114, 116, 119, 122, 124, 125, 137, 143, 146, 148, 169, 171, 172, 175, 178, 180, 181, 208, 211, 228, 242, 243, 245, 292, 294, 297, 309, 310, 313, 314, 315, 316, 317, 321, 340, 341, 350, 353, 356, 363, 368, 369, 375, 376, 395, 398, 401, 408, 409, 412, 415, 417, 418, 421, 430, 431, 433, 436, 451, 503, 511, 535, 539, or 563; or in an equivalent position in a parent glucoamylase. In some embodiments, the parent glucoamylase will have at least 90%, at least 95%, at least 96%, at least 97% at least 98%, and at least 99% identity with SEQ ID NO: 2. In other embodiments the parent glucoamylase will be a *Trichoderma* glucoamylase homologue.

In some embodiments, the glucoamylase variant comprises one or more substitutions in the following positions in the amino acid sequence set forth in SEQ ID NO: 2:
D4, F5, I12, D24, F29, I43, D44, P45, D46, Y47, Y49, W51, N61, Y70, G73, Q75, R76, P94, D100, K108, K114, F116, N119, R122, Q124, R125, G137, N146, Q148, Y169, N171, Q172, F175, W178, E180, V181, Q208, S211, W228, N242, E243, R245, I292, G294, K297, R309, Y310, D313, V314, Y315, Y316, N317, W321, K340, K341, T350, Q356, T363, S368, S369, N376, Y395, A398, S401, R408, N409, T412, L417, H418, W421, T430, A431, R433, I436, S451, E503, Q511, A535, A539, or N563; or an equivalent position in parent glucoamylase (e.g., a *Trichoderma* glucoamylase homologue).

In other embodiments, the variant of a glucoamylase parent comprises one or more substitutions in the following positions in the amino acid sequence set forth in SEQ ID NO:2: 4, 5, 24, 29, 43, 44, 49, 61, 70, 73, 75, 76, 100, 108, 119, 124, 137, 146, 148, 169, 171, 172, 175, 178, 181, 208, 211, 243, 292, 294, 297, 314, 316, 317, 340, 341, 350, 356, 363, 368, 369, 376, 395, 401, 409, 412, 417, 430, 431, 433, 436, 451, 503, 511, 535, 539, or 563; or an equivalent position in a parent glucoamylase (e.g., a *Trichoderma* glucoamylase homologue).

In further embodiments, the variant of a glucoamylase parent comprises at least one of the following substitutions in the following positions in an amino acid sequence set forth in SEQ ID NO: 2: D4L/E/R/S/C/A/Q/W, F5C/M/N/R/S/T/V/W, D24E/L/Y/T, F29L/I/D/C/S/V/W, I43F/R/D/Y/S/Q, D44E/H/K/S/N/Y/F/R/C, Y47W, Y49N, N61D/I/L/Q/V/W, Q70R/K/M/P/G/L/F, G73F/C/L/W, Q75R/K/A, R76L/M/K/T/P, P94L, D100W/I/Q/M/P/A/N, N119P/T/Y/D/E, N146S/G/C/H/E/D/T/W/L/F/M, Q148V/Y/H/A/C/D/G/M/R/S/T, Y169D/F, Q172C/A/D/R/E/F/H/V/L/M/N/S/T/V, F175H/A/G/R/S/T/C/W/Y, W178A/C/D/E/F/G/H/K/N/R/S/T/V/Y, E180A/C/G/H/I/L/N/P/Q/R/S/T/V/Y/, V181E/C/D/G/H/I/P/T/Y/S/L/K/F/A, Q208L/A/C/E/N/F/H/T, S211C/R/E/A/Y/W/M/H/L/I/R/Q/T, E243S/R/N/M/Y/A/L, R245A/E/M/I/P/V, I292D/H/P/R/T/N/V/F/L, G294C/D/E/T/Q/I/A, K297F/L/P/T/M/D/N/Q/A/Y/H/S/R/W, R309A/C/G/H/I/N/P/Q/S/T/W/Y/L, Y310E/G/L/P/S/W/R/Q, D313Q, V314A/R/N/D/C/E/Q/G/H/I/L/K/M/F/P/S/T/W/Y, Y315F, Y316Q/R, N317T/H, K340D/T, K341F/D/P/V/G/S, T350S/E/A/N, Q356H/D/E, T363L/R/C/H/W, S368W/D/F/L, S369F, N376Q/T/H/S/V, Y395Q/R/S, A398S/I/T, S401C/V, R408S, N409W/T/K, T412A/H/K/G, L417A/D/E/F/G/I/K/Q/R/S/T/V/W/Y, T430A/E/F/G/H/I/K/M/N/Q/R/V, A431C/E/H/I/L/M/Q/R/S/W/Y, R433H/Q, I436A/T, S451M/T/H, E503A/C/D/H/S/V/W, Q511C/G/H/I/K/T/V, A535E/F/G/K/L/N/P/R/S/T/V/W/Y, A539E/H/M/R/S/W, or N563A/C/E/I/K/L/Q/T/V; or a substitution in an equivalent position in a parent glucoamylase homologue.

In some embodiments, the glucoamylase variant comprises at least one substitution in a position corresponding to the amino acid residue position set forth in SEQ ID NO: 2: 5, 24, 43, 44, 49, 61, 70, 73, 75, 76, 94, 119, 146, 148, 172, 175, 178, 180, 181, 208, 211, 245, 294, 353, 315, 375, 409, 309, 314, 369, 412, 417, 430, 431, 503, 511, 535, 539, or 563; or an equivalent position in a homologous parent glucoamylase.

In some representative embodiments, the glucoamylase variant comprises at least one substitution selected from the group consisting of F5W, D24E, I43R, I43Y, I43Q, I43S, I43F, D44C, D44R, Y47V, Y49N, N61I, Q70K, G73F, Q75R, R76L, P94L, N119P/T/Y/D, N146S/D/T/E/W/L, Q148V N171D, Q172C/D/R/E/F/V/L/T, F175R/W/Y, W178K/N/Y, E180H/N/V/R, V181E/F/G/I/H, Q208A/T/N, S211H/M/L/R, R245E, R245M, G294C, R309W, V314F/G/H/K/P/R/Y, Y315F, S369F, T412K, L417R, L417V, T430A, T430M, A431L, A431Q, E503A, E503V, Q511H, A535R, A539R, N563I, and N563K corresponding to the position set forth in SEQ ID NO: 2, or an equivalent position in a homologous parent glucoamylase.

In further particular embodiments, the glucoamylase variant comprises at least one substitution of an amino acid residue selected from the positions corresponding to position 5, 43, 44, 61, 73, 75, 76, 94, 108, 119, 124, 146, 148, 171, 172, 175, 178, 180, 181, 208, 211, 294, 297, 314, 316, 412, 417, 430, 431, 503, 511, 535, 539 or 563 of SEQ ID NO: 2, or an equivalent position in a *Trichoderma* glucoamylase homologue. In some embodiments, the substitution is at a position corresponding to position number 43, 44, 61, 73, 148, 172, 175, 178, 180, 208, 211, 294, 297, 314, 412, 417, 430, 431, 503, 511, 535, 539, or 563 of SEQ ID NO: 2, or an equivalent position in a *Trichoderma* glucoamylase homologue.

In some representative embodiments, the substitution is at a position corresponding to position number 43, 44, 61, 73, 108, 124, 171, 172, 208, 211, 294, 314, 316, 417, 430, 431, 503, 511, 535, 539, or 563 of SEQ ID NO: 2, or a homologous parent glucoamylase (e.g., *Trichoderma* glucoamylase homologue).

In some embodiments, the glucoamylase variants comprise multiple substitutions. Some of the multiple substitutions will include a substitution at one or more of the positions equivalent to and including the positions 24, 43, 44, 108, 124, 171, 175, 181, 208, 243, 292, 294, 297, 310, 314, 363, 417, 430, 431, 503, 511, 535, 539, or 563 of SEQ ID NO: 2. Some typical multiple substitutions will include one or more of the positions equivalent to and corresponding to positions 43, 44, 61, 73, 08, 124, 171, 208, 211, 294, 314 417, 430, 431, 503, 511, 535, 539, or 563 of SEQ ID NO: 2.

Some examples of variants with multiple substitutions include substitutions at positions:
D24/I43/D44/F175/V181/V314/T363;
D24/Q208/I292/G294/K297/Y310;
V181/E243/I292/k297/N317/Y395;
D24/V181/Q208/G294/T363/N376/N409;
D24/V181/I292/G294/E243/N409;
I43R/E243/I292/G294/K297;
I43/D44/N61/L417/E503/Q511/A539;
I43/D44/L417/E503/Q511/A539;
I43/N61/L417/T430/Q511/A539;
I43/N61/L417/E503/Q511/A539;
I43/N61/T430/A431/Q511/A539;
I43/N61/T430/Q511;
I43/N61/T430/Q511/A539;
I43/N61/Q511;
I43/N61/Q511/A539;
I43/G73/T430;
I43/L417/E503/Q511/A539;
I43/L417/Q511;
I43/L417/T430/A431/Q511/A539;
I43/L417/T430/Q511;
I43/L417/T430/Q511/A539;
I43/L417/E503/A539;
I43/L417/E503/Q511/A539;
I43/T430;
I43/T430/A431/E503/Q511;
I43/T430/A431/Q511;
I43/T430/A431/Q511/A539;
I43/T430/E503/Q511;
I43/T430/Q511;
I43Q/17430/Q511/A539;
I43/A431/Q511;
I43/T430/E503/Q511/N563;
I43/T430/E503/A535/N563;
I43/E503/Q511/A539;
I43/Q511/A539;
D44/G73/L417/N563;
D44/G73/E503/Q511;
D44/G73/N563;
D44/L417/N563;
D44/T430/Q511/A535;
D44/E503/Q511/N563;

G73/T430/E503/Q511;
G73/T430/Q511;
G294/L417/A431;
G294/L417/A431;
G294/L417/A431/Q511;
L417/T430/A431/Q511/A535/A539/N563;
L417/A431/Q511;
L417/T430/Q511/A535/N563;
L417/7430/Q511/A539/N563; and
E503/N563;
of SEQ ID NO: 2, or equivalent positions in parent glucoamylases and particularly *Trichoderma* glucoamylase homologues.

Some variants with multiple substitutions may include the substitutions at positions:
Y47F/W, Y315F/W;
D24E, L/I43F,R/D44H, N/F175H/V181K,L/V314D,H,K/T363R;
D24L,W,Y/Q208F/I292F,N,V/G294A,I,Q/K297A/Y310F,Q,R;
V181F,K,L/E243A,N,M,R,Y/I292F,L,N,V/K297A,D,H,M,N,Q/N317H/Y395Q,R;
D24E,L,Y/V181F,K,L/Q208C,F/G294A,I,Q/T363R/N376Q/N409K,W;
D24E,L,Y/V181F,K,L/I292F,L,N,V/G294A,I,Q/E243A,M,N,R,Y/N409K,W;
I43R/E243A,M,N,R,Y/I292F,L,N,V/G294A/K297A,D,H,M,N,Q,S,R,W,Y;
I43Q/D44C/N61I/L417V/E503A/Q511H/A539R;
I43Q/D44C/L417V/E503A/Q511H/A539R;
I43Q/N61I/L417V/E503A/Q511H/A539R;
I43Q/N61I/L417V/T430M/Q511H/A539R;
I43R/N61I/L417R,V/E503A/Q511H/A539R;
I43Q/N61I/T430A/A431L511H/A539R;
I43Q/N61I/T430A/Q511H;
I43Q/N61I/T430A/Q511H/A539R;
I43Q/N61I/T430M/Q511H/A539R I43Q/N61I/Q511H;
I43Q/N61I/Q511H/A539R;
I43R/G73F/T430A;
I43Q/L417V/T430A/A431L/Q511H/A539R;
I43Q/L417V/T430A/Q511H;
I43Q/L417V/T430A/Q511H/A539R;
I43R/L417R/E503A/A539R;
I43R,Q/L417V/E503A/Q511H/A539R;
I43Q/L417V/Q511H;
I43R,Q/T430A;
I43Q/T430A/A431L/E503A/Q511H;
I43Q/T430A/A431L/Q511H;
I43Q/T430A/A431L/Q511H/A539R;
I43Q/T430A/E503A/Q511H;
I43Q/T430A/Q511H;
I43Q/T430A,M/Q511H/A539R;
I43R/T430A/E503A,V/Q511H/N563K;
I43Q/A431L/Q511H;
I43Q/E503A/Q511H/A539R;
I43Q/Q511H/A539R;
D44C/G73F/E503V/Q511H;
D44C/G73F/L417R/N563K;
D44C/G73F/N563K;
D44C/L417R/N563K;
D44R/E503A/Q511H/N563I;
D44R/T430A/Q511H/A535R;
G73F/T430A/E503V/Q511H;
G73F/T430A/Q511H;
G294C/L417R/A431L;
G294C/L417R/A431L,Q/Q511H;
G294C/L417V/A431Q;
L417R,V/A431L,Q/Q511H;
L417V/T430A/A431L,Q/Q511H/A535R/A539R/N563I;
L417V/T430A/Q511H/A535R/N563I;
L417V/T430A/Q511H/A539R/N563I; and
E503A/N563I
of SEQ ID NO: 2, or equivalent positions in parent glucoamylases and particularly *Trichoderma* glucoamylase homologue.

A number of parent glucoamylases have been aligned with the amino acid sequence of TrGA. FIGS. 4A and 4B include the catalytic domain of the following parent glucoamylases: *Aspergillus awamori* (AaGA) (SEQ ID NO: 5); *Aspergillus niger* (AnGA) (SEQ ID NO: 6); *Aspergillus orzyae* (AoGA) (SEQ ID NO: 7), *Humicola grisea* (HgGA) (SEQ ID NO: 8) and *Hypocrea vinosa* (HvGA) (SEQ ID NO: 9). The percent identity of the catalytic domains is represented in Table 1 below. FIGS. 4C and 4D include the starch binding domain of the following parent glucoamylases: *Trichoderma reesei* (TrGA) (SEQ ID NO: 161), *Humicola grisea* (HgGA) (SEQ ID NO: 162), *Thielavia terrestris* (TtGA) (SEQ ID NO: 163), *Thermomyces lanuginosus* (ThGA) (SEQ ID NO: 164), *Talaromyces emersonii* (TeGA) (SEQ ID NO: 165), *Aspergillus niger* (AnGA) (SEQ ID NO: 166), and *Aspergillus awamori* (AaGA) (SEQ ID NO: 167). In some embodiments, for example, the variant glucoamylase will be derived from a parent glucoamylase that is an *Aspergillus* glucoamylase and the variant will include at least one substitution in a position equivalent to a position set forth in SEQ ID NO: 2, and particularly in a position corresponding to D4, F5, I12, D24, F29, I43, D44, P45, D46, Y47, Y49, W51, N61, Y70, G73, Q75, R76, P94, D100, K108, K114, F116, N119, R122, Q124, R125, G137, N146, Q148, Y169, N171, Q172, F175, W178, E180, V181, Q208, S211, W228, N242, E243, R245, I292, G294, K297, R309, Y310, D313, V314, Y315, Y316, N317, W321, $K_{340}$, $K_{341}$, T350, Q356, T363, S368, S369, N376, Y395, A398, S401, R408, N409, T412, L417, H418, W421, T430, A431, R433, I436, S451, E503, Q511, A535, A539, or N563.

Endo-H removal of N-linked sugars in the *Trichoderma reesei* glucoamylase had a stabilizing effect (when looking at $T_m$). Thus, variants having an N171D substitution can have increased thermostability as compared to the wild-type parent. In some embodiments, variants having one or more substitutions at sites having N-linked sugars are provided, including N171 D in *Trichoderma reesei* (SEQ ID NO: 2).

TABLE 1

|  | AaGA | AnGA | AoGA | HgGA | HvGA | TrGA |
|---|---|---|---|---|---|---|
| AaGA | 100 | 95 | 58 | 53 | 57 | 56 |
| AnGA |  | 100 | 59 | 53 | 57 | 56 |
| AoGA |  |  | 100 | 55 | 56 | 56 |
| HgGA |  |  |  | 100 | 61 | 63 |
| HvGA |  |  |  |  | 100 | 91 |
| TrGA |  |  |  |  |  | 100 |

The present disclosure also provides glucoamylase variants having at least one altered property (e.g., improved property) as compared to a parent glucoamylase and particularly to the TrGA. In some embodiments, at least one altered property (e.g., improved property) is selected from the group consisting of acid stability, thermal and specific activity. Typically, the altered property is increased acid stability, increased thermal stability and/or increased specific activity. The increased thermal stability typically is at higher temperatures.

In one embodiment, the increased pH stability is at high pH. In a further embodiment, the increased pH stability is at low pH.

The glucoamylase variants of the disclosure may also provide higher rates of starch hydrolysis at low substrate concentrations as compared to the parent glucoamylase. The variant may have a higher $V_{max}$ or lower $K_m$ than a parent glucoamylase when tested under the same conditions. For example the variant glucoamylase may have a higher $V_{max}$ at a temperature range of 25° C. to 70° C. (e.g., at 25° C. to 3.5° C.; 30° C. to 3.5° C.; 40° C. to 50° C.; at 50° C. to 55° C. and at 55° C. to 62° C.). The Michaelis-Menten constant; $K_m$ and $V_{max}$ values can be easily determined using standard known procedures.

5. THERMAL STABILITY (THERMOSTABLE VARIANTS)

In one aspect, the disclosure relates to a variant glucoamylase having altered thermal stability at altered temperatures as compared to a parent or wild type. Altered temperatures include increased or decreased temperatures. In some embodiments, the glucoamylase variant will have improved thermostability such as retaining at least 50%, 60%, 70%, 75%, 80%, 85%, 90%, 92%, 95%, 96%, 97%, 98% or 99% enzymatic activity after exposure to altered temperatures over a given time period, for example, at least 60 minutes, 120 minutes, 180 minutes, 240 minutes, 300 minutes, etc. In some embodiments, the variant has increased thermal stability compared to the parent glucoamylase at selected temperatures in the range of 40 to 80° C., also in the range of 50 to 75° C. and in the range of 60 to 70° C., and typically at a pH range of 4.0 to 6.0. In some embodiments, the thermostability is determined as described in the Examples.

In some embodiments, particularly interesting variants in connection with an improvement in thermostability include one or more deletions, substitutions or insertions and particularly substitutions in the following positions in the amino acid sequence set forth in SEQ ID NO: 2: D4, F5, I12, D24, F29, I43, D44, P45, D46, Y47, Y49, W51, N61,Y70, G73, Q75, R76, P94, D100, K108, K114, F116, N119, R122, Q124, R125, G137, N146, Q148, Y169, N171, Q172, F175, W178, E180, V181, Q208, S211, W228, N242, E243, R245, I292, G294, K297, R309, Y310, D313, V314, Y315, Y316, N317, W321, K340, K341, T350, Q356, T363, S368, S369, N376, Y395, A398, S401, R408, N409, T412, L417, H418, W421, T430, A431, R433, I436, S451, E503, Q511, A535, A539, or N563; or an equivalent position in a parent glucoamylase. In some embodiments, the parent glucoamylase will be a *Trichoderma* glucoamylase homologue, and in typical embodiments, the parent glucoamylase will have at least 90%, at least 95%, or at least 98% sequence identity to SEQ ID NO: 2.

6. CHIMERIC GLUCOAMYLASES

Glucoamylase variants of the disclosure may also include chimeric or hybrid glucoamylases with, for example a starch binding domain (SBD) from one glucoamylase and a catalytic domain and linker from another. For example, a hybrid glucoamylase can be made by swapping the SBD from AnGA with the SBD from TrGA, making a hybrid with the AnGA SBD and the TrGA catalytic domain and linker. Alternatively, the SBD and linker from AnGA can be swapped for the SBD and linker of TrGA.

7. SPECIFIC ACTIVITY

In another aspect, the disclosure relates to a variant glucoamylase having altered specific activity as compared to a parent or wild-type glucoamylase.

In some embodiments, particularly interesting variants in connection with an improvement in specific activity include one or more deletions, substitutions or insertions and particularly substitutions in the following positions in the amino acid sequence set forth in SEQ ID NO: 2: D4, F5, I12, D24, F29, I43, D44, P45, D46, Y47, Y49, W51, N61, Y70, G73, Q75, R76, P94, D100, K108, K114, F116, N119, R122, Q124, R125, G137, N146, Q148, Y169, N171, Q172, F175, W178, E1180, V181, Q208, S211, W228, N242, E243, R245, I292, G294, K297, R309, Y310, D313, V314, Y315, Y316, N317, W321, K340, $K_{341}$, T350, Q356, T363, S368, S369, N376, Y395, A398, S401, R408, N409, T412, L417, T430, A431, H418, W421, R433, I436, S451, E503, Q511, A535, A539, or N563; or an equivalent position in a parent glucoamylase. In some embodiments, variants of the disclosure having improved specific activity include a substitution in the following positions in the amino acid sequence set forth in SEQ ID NO: 2: D4, D24, I43, D44, N61, Y70, G73, Q75, R76, D100, K108, N119, Q124, N146, Q148, N171, Q172, F175, V181, Q208, S211, E243, R245, I292, G294, K297, V314, Y316, N317, K340, K341, T350, Q356, T363, S368, N376, Y395, A398, S401, N409, T412, L417, T430, A431, I436, S451, E503, Q511, A535, A539, or N563; or an equivalent position in a parent glucoamylase. In some embodiments, the parent glucoamylase will comprise a sequence having at least 90% or 95% sequence identity to the sequence of SEQ ID NO: 2.

8. POLYNUCLEOTIDES

The present disclosure also relates to isolated polynucleotides encoding a variant glucoamylase of the disclosure. The polynucleotides encoding a variant glucoamylase may be prepared by established techniques known in the art. The polynucleotides may be prepared synthetically, such as by an automatic DNA synthesizer. The DNA sequence may be of mixed genomic (or cDNA) and synthetic origin prepared by ligating fragments together. The polynucleotides may also be prepared by polymerase chain reaction (PCR) using specific primers. In general, reference is made to Minshull J., et al., (2004), Engineered protein function by selective amino acid diversification, Methods 32(4):416-427. Also a number of companies now synthesize DNA such as Geneart AG, Regensburg, Germany.

The present disclosure also provides isolated polynucleotides comprising a nucleotide sequence (i) having at least 70% identity to SEQ ID NO: 4, or (ii) being capable of hybridizing to a probe derived from the nucleotide sequence set forth in SEQ ID NO: 4, under conditions of intermediate to high stringency, or (iii) being complementary to a nucleotide sequence having at least 90% sequence identity to the sequence set forth in SEQ ID NO: 4. Probes useful according to the disclosure may include at least 50, 100, 150, 200, 250, 300 or more contiguous nucleotides of SEQ ID NO: 4.

The present disclosure further provides isolated polynucleotides that encode variant glucoamylases that comprise an amino acid sequence comprising at least 80% amino acid sequence identity to SEQ ID NO: 2. In some embodiments, the variant glucoamylases have at least 80% amino acid sequence identity to SEQ ID NO: 2. In some embodiments, the variant glucoamylases have at least 90% amino acid sequence identity to SEQ ID NO: 2. In some embodiments, the variant glucoamylases have at least 93% amino acid sequence identity to SEQ ID NO: 2. In some embodiments, the variant glucoamylases have at least 95% amino acid sequence identity to SEQ ID NO: 2. In some embodiments, the variant glucoamylases have at least 97% amino acid sequence identity to SEQ ID NO: 2. In some embodiments, the variant glucoamylases have at least 98% amino acid sequence identity to SEQ ID NO: 2. In some embodiments, the variant glucoamylases have at least 99% amino acid sequence identity to SEQ ID NO: 2. The present disclosure also provides expression vectors comprising any of the polynucleotides provided above.

The present disclosure also provides fragments portions) of the DNA encoding the variant glucoamylases provided herein. These fragments find use in obtaining partial length DNA fragments capable of being used to isolate or identify polynucleotides encoding mature glucoamylase enzymes described herein from filamentous fungal cells (e.g., *Trichoderma*, *Aspergillus*, *Fusarium*, *Penicillium*, *Schizosaccharotnyces*, and *Humicola*), or a segment thereof having glucoamylase activity. In some embodiments, fragments of the DNA may comprise at least 50, 100, 150, 200, 250 300 or more contiguous nucleotides. In some embodiments, portions of the DNA provided in SEQ ID NO: 4 may be used in obtaining parent glucoamylase and particularly *Trichoderma* glucoamylase homologues from other species, such as filamentous fungi that encode a glucoamylase.

9. DNA CONSTRUCTS AND VECTORS

According to one embodiment of the disclosure, a DNA construct comprising a polynucleotide as described above encoding a variant glucoamylase encompassed by the disclosure and operably linked to a promoter sequence is assembled to transfer into a host cell.

The DNA construct may be introduced into a host cell using a vector. The vector may be any vector that when introduced into a host cell is typically integrated into the host cell genome and is replicated. Vectors include cloning vectors, expression vectors, shuttle vectors, plasmids, phage particles, cassettes and the like. In some embodiments, the vector is an expression vector that comprises regulatory sequences operably linked to the glucoamylase coding sequence.

Examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396-428 and U.S. Pat. No. 5,874,276, Fungal Genetics Stock Center Catalogue of Strains (FGSC, <www.fgsc.net>) also discloses useful vectors. Particularly useful vectors include vectors obtained from, for example, Invitrogen and Promega.

Specific vectors suitable for use in fungal host cells include vectors such as pFB6, pBR322, pUC18, pUC100, pDONR™201, pDONR™221, pENTR™, pGEM®3Z and pGEM®4Z. A general purpose expression vector useful in *Aspergillus* includes pRAX with a glaA promoter, and in *Hypocrea/Trichoderma* includes pTrex3g with a cbh1 promoter.

Suitable plasmids for use in bacterial cells include pBR322 and pUC19 permitting replication in *E. coli* and pE194 for example permitting replication in *Bacillus*.

In some embodiments, the promoter shows transcriptional activity in a bacterial or a fungal host cell and may be derived from genes encoding proteins either homologous or heterologous to the host cell. The promoter may be a mutant, a truncated and/or a hybrid promoter. The above-mentioned promoters are known in the art.

Examples of suitable promoters useful in fungal cells and particularly filamentous fungal cells such as *Trichoderma* or *Aspergillus* cells include such exemplary promoters as the *T. reesei* promoters cbh1, cbh2, egl1, egl2, eg5, xln1 and xln2. Other examples of useful promoters include promoters from *A. awamori* and *A. niger* glucoamylase genes (glaA) (see, Nunberg et al., (1984) *Mol. Cell Biol.* 4:2306-2315 and Boel et al., (1984) *EMBO J.* 3:1581-1585), *A. oryzae* TAKA amylase promoter, the TPI (triose phosphate isomerase) promoter from *S. cerevisiae*, the promoter from *Aspergillus nidulans* acetamidase genes and *Rhizomucor miehei* genes.

Examples of suitable promoters useful in bacterial cells include those obtained from the *E. coli* lac operon; *Bacillus licheniformis* alpha amylase gene (amyL), *B. stearothermophilus* amylase gene (amyM); *Bacillus subtilis* xylA and xylB genes, the beta-lactamase gene, and the tac promoter.

In one embodiment, the promoter is one that is native to the host cell. For example, when *T. reesei* is the host, the promoter is a native *T. reesei* promoter. In another embodiment, the promoter is one that is heterologous to the fungal host cell. In some embodiments the promoter will be the parent glucoamylase promoter such as the TrGA promoter.

In some embodiments, the DNA construct includes nucleic acids coding for a signal sequence that is an amino acid sequence linked to the amino terminus of the polypeptide that directs the encoded polypeptide into the cell's secretory pathway. The 5' end of the coding sequence of the nucleic acid sequence may naturally include a signal peptide coding region that is naturally linked in translation reading frame with the segment of the glucoamylase coding sequence that encodes the secreted glucoamylase or the 5' end of the coding sequence of the nucleic acid sequence may include a signal peptide that is foreign to the coding sequence. In some embodiments, the DNA construct includes a signal sequence that is naturally associated with a parent glucoamylase gene from that a variant glucoamylase has been obtained. In some embodiments the signal sequence will be the sequence depicted in SEQ ID NO: 1 or a sequence having at least 90%, at least 94% and at least 98% sequence identity thereto. Effective signal sequences may include the signal sequences obtained from glucoamylases of other filamentous fungal enzymes, such as from *Trichoderma* (*T. reesei* glucoamylase), *Humicola* (*H. insolens* cellulase or *H. grisea* glucoamylase), *Aspergillus* (*A. niger* glucoamylase and *A. oryzae* TAKA amylase), and *Rhizopus*.

In additional embodiments, a DNA construct or vector comprising a signal sequence and a promoter sequence to be introduced into a host cell are derived from the same source. In some embodiments, the native glucoamylase signal sequence of a *Trichoderma* glucoamylase homologue, such as a signal sequence from a *Hypocrea* strain may be used.

In some embodiments, the expression vector also includes a termination sequence. Any terminator sequence functional in the host cell may be used in the present disclosure. In one embodiment, the termination sequence and the promoter sequence are derived from the same source. In another embodiment, the termination sequence is homologous to the host cell. Useful terminator sequence include terminator sequences obtained from the genes of *Trichoderma reesei* cbh1; *A. niger* or *A. awamori* glucoamylase (Nunberg et al. (1984) supra, and Boel et al., (1984) supra), *Aspergillus nidulans* anthranilate synthase, *Aspergillus oryzae* TAKA amylase, or *A. nidulans* trpC (Punt et al., (1987) *Gene* 56:117-124).

In some embodiments, an expression vector includes a selectable marker. Examples of typical selectable markers include ones that confer antimicrobial resistance (e.g., hygromycin and phleomycin). Nutritional selective markers also find use in the present disclosure including those markers known in the art as amdS (acetamidase), argB (ornithine carbamoyltransferase) and pyrG (orotidine-5' phosphate decarboxylase). Markers useful in vector systems for transformation of *Trichoderma* are known in the art (see, e.g., Finkelstein, chapter 6 in BIOTECHNOLOGY OF FILAMENTOUS FUNGI, Finkelstein et al. Eds. Butterworth-Heinemann, Boston, Mass. (1992); Kinghorn et al. (1992) APPLIED MOLECULAR GENETICS OF FILAMENTOUS FUNGI, Mackie Academic and Professional, Chapman and Hall, London; Berges and Barreau (1991) *Curr. Genet.* 19:359-365; and van Hartingsveldt et al., (1987) *Mol. Gen. Genet,* 206:71-75). In a typical embodiment, the selective marker is the amdS gene, which encodes the enzyme acetamidase, allowing transformed cells to grow on acetamide as a nitrogen source. The use of *A. nidulans* amdS gene as a selective marker is described in Kelley et al., (1985) *EMBO J.* 4:475-479 and Penttilä et al.; (1987) *Gene* 61:155-164.

Methods used to ligate the DNA construct comprising a nucleic acid sequence encoding a variant glucoamylase, a promoter, a terminator and other sequences and to insert them into a suitable vector are well known in the art. Linking is generally accomplished by ligation at convenient restriction sites. If such sites do not exist, synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76). Additionally, vectors can be constructed using known recombination techniques (e.g., Invitrogen Life Technologies, Gateway Technology).

10. HOST CELLS

The present disclosure also relates to host cells comprising a polynucleotide encoding a variant glucoamylase of the disclosure, which are used to produce the glucoamylases of the disclosure. In some embodiments, the host cells are selected from bacterial, fungal, plant and yeast cells. The term host cell includes both the cells, progeny of the cells and protoplasts created from the cells that are used to produce a variant glucoamylase according to the disclosure.

In some embodiments, the host cells are fungal cells and typically filamentous fungal host cells. The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present disclosure are morphologically, physiologically, and genetically distinct from yeasts, Vegetative growth by filamentous fungi is by hyphal elongation and carbon catabolism is obligatory aerobic. In the present disclosure, the filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., (1984) Appl. Microbiol. Biotechnol 20:46-53; ATCC No. 56765 and ATCC No. 26921); *Penicillium* sp., *Humicola* sp. (e.g., *H. insolens, H. lanuginosa* and *H. grisea*); *Chrysosporium* sp, (e.g., *C. lucknowense*), *Gliocladium* sp., *Aspergillus* sp. (e.g., *A. oryzae, A. niger, A. sojae, A. japonicus, A. nidulans,* and *A. awamori*) (Ward et al., (1993) Appl, Microbiol. Biotechnol, 39:738-743 and Goedegebuur et al., (2002) Genet 41:89-98), *Fusarium* sp., (e.g., *F. roseum, F. graminum, F. eerealis, F. oxysporuim* and *F. venenatum*), *Neurospora* sp., (*N. crassa*), *Hypocrea* sp., *Mucor* sp., (*M. miehei*), *Rhizopus* sp. and *Emericella* sp. (see also, Innis et al., (1985) Sci. 228:21-26), The term "*Trichoderma*" or "*Trichoderma* sp." or "*Trichoderma* spp." refer to any fungal genus previously or currently classified as *Trichoderma*.

In some embodiments, the host cells will be gram-positive bacterial cells. Non-limiting examples include strains of *Streptomyces*, (e.g., *S. lividans, S. coelicolor* and *S. griseus*) and *Bacillus*. As used herein, "the genus *Bacillus*" includes all species within the genus "*Bacillus*," as known to those of skill in the art, including but not limited to *B. subtilis, B. lichenformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*."

In some embodiments the host cell is a gram-negative bacterial strain, such as *E. coli* or *Pseudomonas* sp. In other embodiments, the host cells may be yeast cells such as *Saccharomyces* sp., *Schizosaccharomyces* sp., *Pichia* sp., or *Candida* sp.

in other embodiments, the host cell will be a genetically engineered host cell wherein native genes have been inactivated, for example by deletion in bacterial or fungal cells. Where it is desired to obtain a fungal host cell having one or more inactivated genes known methods may be used (e.g. methods disclosed in U.S. Pat. No. 5,246,853, U.S. Pat. No. 5,475,101, and WO 92/06209). Gene inactivation may be accomplished by complete or partial deletion, by insertional inactivation or by any other means that renders a gene nonfunctional for its intended purpose (such that the gene is prevented from expression of a functional protein). In some embodiments, when the host cell is a *Trichoderma* cell and particularly a *T. reesei* host cell, the cbh1, cbh2, egl1 and egl2 genes will be inactivated and/or typically deleted. Typically, *Trichoderma reesei* host cells having quad-deleted proteins are set forth and described in U.S. Pat. No. 5,847,276 and WO 05/001036. In other embodiments, the host cell is a protease deficient or protease minus strain.

11. TRANSFORMATION OF HOST CELLS

Introduction of a DNA construct or vector into a host cell includes techniques such as transformation; electroporation; nuclear microinjection, transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al, (1987), supra, chapter 9; and Sambrook (1989) supra, and Campbell et al., (1989) *Curr. Genet.* 16:53-56).

Transformation methods for *Bacillus* are disclosed in numerous references including Anagnostopoulos C and J. Spizizen (1961) *J. Bacteriol* 81:741-746 and WO 02/14490.

Transformation methods for *Aspergillus* are described in Yelton et al (1984) Proc. Natl. Acad. Sci. USA 81:1470-1474; Berka et al., (1991) in Applications of Enzyme Biotechnology, Eds. Kelly and Baldwin, Plenum Press (NY); Cao et al., (2000) *Science* 9:991-1001; Campbell et al., (1989) *Curr. Genet.* 16:53-56 and EP 238 023. The expression of heterologous protein in *Trichoderma* is described in U.S. Pat. No. 6,022,725; U.S. Pat. No. 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its*

Application to the Expression of Both Homologous and Heterologous Genes", in MOLECULAR INDUSTRIAL MYCOLOGY, Eds. Leong and Berka, Marcel Dekker Inc., NY (1992) pp. 129-148). Reference is also made to WO96/00787 and Bajar et al., (1991) *Proc. Natl. Acad. Sci. USA* 88:8202-8212 for transformation of *Fusarium* strains.

In one specific embodiment, the preparation of *Trichoderma* sp. for transformation involves the preparation of protoplasts from fungal mycelia (See, Campbell et al., (1989) *Curr. Genet.* 16:53-56; Pentilla et al., (1987) *Gene* 61:155-164). *Agrobacterium tumefaciens*-mediated transformation of filamentous fungi is known (See, de Groot et al, (1998) *Nat. Biotechnol.* 16:839-842). Reference is also made to U.S. Pat. No. 6,022,725 and U.S. Pat. No. 6,268,328 for transformation procedures used with filamentous fungal hosts.

Typically, genetically stable transformants are constructed with vector systems whereby the nucleic acid encoding the variant glucoamylase is stably integrated into a host strain chromosome, Transformants are then purified by known techniques.

In some further embodiments, the host cells are plant cells, such as cells from a monocot plant (e.g. corn, wheat and sorghum) or cells from a dicot plant (e.g. soybean), Methods for making DNA constructs useful in transformation of plants and methods for plant transformation are known. Some of these methods include *Agrobacterium tumefaciens* mediate gene transfer; microprojectile bombardment, PEG mediated transformation of protoplasts, electroporation and the like. Reference is made to (U.S. Pat. No. 6,803,499, U.S. Pat. No. 6,777,589; Fromm et al (1990) *Biotechnol.* 8:833-839; Potrykus et al (1985) *Mol. Gen. Genet.* 199:169-177.

12. PRODUCTION OF PROTEINS

The present disclosure further relates to methods of producing the variant glucoamylases comprising transforming a host cell with an expression vector comprising a polynucleotide encoding a variant glucoamylase according to the disclosure, optionally culturing the host cell under conditions suitable for production of the variant glucoamylase and optionally recovering the glucoamylase.

In the expression and production methods of the present disclosure the host cells are cultured under suitable conditions in shake flask cultivation, small scale or large scale fermentations (including continuous, batch and fed batch fermentations) in laboratory or industrial fermentors, with suitable medium containing physiological salts and nutrients (see, e.g., Pourquie, et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth) find use in the present disclosure. Representative culture conditions for bacterial and filamentous fungal cells are known in the art and may be found in the scientific literature and/or from the source of the fungi such as the American Type Culture Collection and Fungal Genetics Stock Center. In cases where a glucoamylase coding sequence is under the control of an inducible promoter, the inducing agent (e.g., a sugar, metal salt or antimicrobial), is added to the medium at a concentration effective to induce glucoamylase expression.

In some embodiments, the present disclosure relates to methods of producing the variant glucoamylase comprising cultivating a plant or plant cell comprising a polynucleotide encoding a variant glucoamylase according to the disclosure under conditions suitable for the production of the variant and optionally recovering the glucoamylase.

In some embodiments, in order to evaluate the expression of a variant glucoamylase by a cell line that has been transformed with a polynucleotide encoding a variant glucoamylase encompassed by the disclosure, assays are carried out at the protein level, the RNA level and/or by use of functional bioassays particular to glucoamylase activity and/or production. Some of these assays include Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a variant glucoamylase may be measured in a sample directly, for example, by assays directly measuring reducing sugars such as glucose in the culture medium and by assays for measuring glucoamylase activity, expression and/or production. In particular, glucoamylase activity may be assayed by the 3,5-dinitrosalicylic acid (DNS) method (see, Goto et al., (1994) *Biosci. Biotechnol. Biochem.* 58:49-54). In additional embodiments, protein expression, is evaluated by immunological methods, such as immunohistochemical staining of cells, tissue sections or immunoassay of tissue culture medium, (e.g., by Western blot or ELISA), Such immunoassays can be used to qualitatively and quantitatively evaluate expression of a glucoamylase. The details of such methods are known to those of skill in the art and many reagents for practicing such methods are commercially available.

The glucoamylases of the present disclosure may be recovered or purified from culture media by a variety of procedures known in the art including centrifugation, filtration, extraction, precipitation and the like.

13. COMPOSITIONS

The variant glucoamylases may be used in enzyme compositions including but not limited to starch hydrolyzing and saccharifying compositions, cleaning and detergent compositions (e.g., laundry detergents, dish washing detergents, and hard surface cleaning compositions), alcohol fermentation compositions, and in animal feed compositions. Further the variant glucoamylases may be used in baking applications, such as bread and cake production, brewing, healthcare, textile, environmental waste conversion processes, biopulp processing, and biomass conversion applications.

In some embodiments, an enzyme composition including a variant glucoamylase encompassed by the disclosure obtained in culture media or recovered and purified from the culture medium will be optionally used in combination with any one or combination of the following enzymes—alpha amylases, proteases, pullulanases, isoamylases, cellulases, hemicellulases, xylanases, cyclodextrin glycotransferases, lipases, phytases, laccases, oxidases, esterases, cutinases, xylanases, granular starch hydrolyzing enzyme and other glucoamylases. In one embodiment, the proteases are acid fungal proteases (AFP). In a further embodiment, the acid fungal proteases are from *Trichoderma* (e.g., NSP-24, see also US 2006/0154353, published Jul. 13, 2006, incorporated herein by reference). In a further embodiment, the phytase is from *Buttiauxiella*.spp. (e.g., BP-17, see also variants disclosed in PCT patent publication WO 2006/043178).

In some representative compositions, the variant glucoamylases of the disclosure will be combined with an alpha amylase, such as fungal alpha amylases (e.g., *Aspergillus* sp.) or bacterial alpha amylases (e.g., *Bacillus* sp. such as *B.* stearothermophilus, B. amyloliquefaciens and B. licheniformis) and variants and hybrids thereof. In one embodiment the alpha amylase is an acid stable alpha amylase. In one embodiment, the alpha amylase is a granular starch hydrolyzing enzyme (GSHE). In one embodiment, the alpha amylase is Aspergillus kawachi alpha amylase (AKAA), see U.S. Pat. No. 7,037,704. Commercially available alpha amylases contemplated for use in the compositions of the disclosure are known and include GZYME G997, SPEZYME FRED, SPEZYME XTRA, STARGEN (Danisco US, Inc, Genencor Division), TERMAMYL 120-L and SUPRA (Novozymes, Biotech.) and VIRIDIUM (Diversa).

In other embodiments, the variant glucoamylases of the disclosure may be combined with other glucoamylases. In some embodiments, the glucoamylases of the disclosure will be combined with one or more glucoamylases derived from strains of *Aspergillus* or variants thereof, such as *A. oryzae, A. niger, A. kawachi*, and *A. awamori*; glucoamylases derived from strains of *Humicola* or variants thereof, particularly *H. grisea*, such as the glucoamylase having at least 90%, 93%, 95%, 96%, 97%, 98% and 99% sequence identity to SEQ ID NO: 3 disclosed in WO 05/052148; glucoamylases derived from strains of *Talaromyces* or variants thereof, particularly *T. emersonii*; glucoamylases derived from strains of *Athelia* and particularly *A. rolfsii*; glucoamylases derived from strains of *Penicillium*, particularly *P. chrysogenum*.

14. USES

In particular, the variant glucoamylases may be used for starch conversion processes, and particularly in the production of dextrose for fructose syrups, specialty sugars and in alcohol and other end-product (e.g., organic acid, ascorbic acid, and amino acids) production from fermentation of starch containing substrates (G. M. A van Beynum et al., Eds. (1985) STARCH CONVERSION TECHNOLOGY, Marcel Dekker Inc, NY). Dextrins produced using variant glucoamylase compositions of the disclosure may result in glucose yields of at least 80%, at least 85%, at least 90% and at least 95%. Production of alcohol from the fermentation of starch substrates using glucoamylases encompassed by the disclosure may include the production of fuel alcohol or portable alcohol. In some embodiments, the production of alcohol will be greater when the variant glucoamylase is used under the same conditions as the parent glucoamylase. In some embodiments, the production of alcohol will be between about 0.5% and 2.5% better, including but not limited to 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, and 2.4% more alcohol than the parent glucoamylase.

In one representative embodiment, the variant glucoamylases of the disclosure will find use in the hydrolysis of starch from various plant-based substrates, which are used for alcohol production. In some embodiments, the plant-based substrates will include corn, wheat, barley, rye, milo, rice, sugar cane, potatoes and combinations thereof. In some embodiments, the plant-based substrate will be fractionated plant material, for example a cereal grain such as corn, which is fractionated into components such as fiber, germ, protein and starch (endosperm) (U.S. Pat. No. 6,254,914 and U.S. Pat. No. 6,899,910). Methods of alcohol fermentations are described in THE ALCOHOL TEXTBOOK, A REFERENCE FOR THE BEVERAGE, FUEL AND INDUSTRIAL ALCOHOL INDUSTRIES, 3$^{rd}$ Ed., Eds K. A. Jacques et al., 1999, Nottingham University Press, UK. In certain embodiments, the alcohol will be ethanol. In particular, alcohol fermentation production processes are characterized as wet milling or dry milling processes. In some embodiments, the variant glucoamylase will be used in a wet milling fermentation process and in other embodiments the variant glucoamylase will find use in a dry milling process.

Dry grain milling involves a number of basic steps, which generally include: grinding, cooking, liquefaction, saccharification, fermentation and separation of liquid and solids to produce alcohol and other co-products. Plant material and particularly whole cereal grains, such as corn, wheat or rye are ground. In Some cases the grain may be first fractionated into component parts. The ground plant material may be milled to obtain a coarse or fine particle. The ground plant material is mixed with liquid (e.g., water and/or thin stillage) in a slurry tank. The slurry is subjected to high temperatures (e.g., 90° C. to 105° C. or higher) in a jet cooker along with liquefying enzymes (e.g., alpha amylases) to solubilize and hydrolyze the starch in the grain to dextrins. The mixture is cooled down and further treated with saccharifying enzymes, such as glucoamylases encompassed by the instant disclosure, to produce glucose. The mash containing glucose may then be fermented for approximately 24 to 1120 hours in the presence of fermentation microorganisms, such as ethanol producing microorganism and particularly yeast (*Saccharomyces* spp.). The solids in the mash are separated from the liquid phase and alcohol such as ethanol and useful co-products such as distillers' grains are obtained.

In some embodiments, the saccharification step and fermentation step are combined and the process is referred to as simultaneous saccharification and fermentation or simultaneous saccharification, yeast propagation and fermentation.

In other embodiments, the variant glucoamylase is used in a process for starch hydrolysis wherein the temperature of the process is carried out at a temperature of between 30° C. and 75° C. and also at a temperature of between 40° C. and 65° C. at a pH range of between pH 3.0 and pH 6.5. The fermentation processes in some embodiments include milling of a cereal grain or fractionated grain and combining the ground cereal grain with liquid to form a slurry that is then mixed in a single vessel with a variant glucoamylase according to the disclosure and optionally other enzymes such as but not limited to alpha amylases, other glucoamylases, phytases, proteases, pullulanases, isoamylases or other enzymes having granular starch hydrolyzing activity and yeast to produce ethanol and other co-products (U.S. Pat. No. 4,514,496, WO 04/081193 and WO 04/080923).

In some embodiments, the disclosure pertains to a method of saccharifying a liquid starch solution, which comprises an enzymatic saccharification step using a variant glucoamylase of the disclosure.

The present disclosure also provides an animal feed comprising at least one variant glucoamylase encompassed by the disclosure. Methods of using a glucoamylase enzyme in the production of feeds comprising starch are provided in WO 03/049550, filed Dec. 13, 2002 (herein incorporated by reference in its entirety). Briefly, the glucoamylase variant is admixed with a feed comprising starch. The glucoamylase is capable of degrading resistant starch for use by the animal.

Other objects and advantages of the present disclosure are apparent from the present Specification.

EXAMPLES

The following examples are provided in order to demonstrate and further illustrate certain representative embodiments and aspect of the present disclosure and are not to be construed as limiting the scope thereof.

In the disclosure and experimental section that follows, the following abbreviations apply: GA (glucoamylase); GAU (glucoamylase unit); wt %; (weight percent); ° C. (degrees Centigrade); rpm (revolutions per minute); H$_2$O (water); dH$_2$O (deionized water); dIH$_2$O (deionized water, Milli-Q filtration); aa or AA (amino acid); bp (base pair); kb (kilobase pair); kD (kilodaltons); g or gm (grams); µg (micrograms); mg (milligrams); µL (microliters); ml and mL (milliliters); mm (millimeters); µm (micrometer); M (molar); mM (millimolar); µM (micromolar); U (units); V (volts); MW (molecular weight); sec(s) or s(s) (second/seconds); min(s) or m(s) (minute/minutes); hr(s) or h(s) (hour/hours); DO (dissolved oxygen); ABS (Absorbance); EtOH (ethanol); PSS (physiological salt solution; m/v (mass/volume); and MTP (microtiter plate); N (Normal); DP1 (monosaccharides); DP2 (disaccharides); DP>3 (oligosaccharides, sugars having a degree of polymerization greater than 3); ppm (parts per million).

The methods used to provide variants are described below. However, it should be noted that different methods may be used to provide variants of a parent molecule and the disclosure is not limited to the methods used in the examples. It is intended that any suitable means for making variants and selection of variants may be used.

pNPG Glucoamylase Activity Assay for 96-Well Microtiter Plates:

The reagent solutions were: NaAc buffer: 200 mM sodium acetate buffer pH 4.5; Substrate: 50 mM p-nitrophenyl-α-D-glucopyranoside (Sigma N-1377) in NaAc buffer (0.3 g/20 ml) and stop solution: 800 mM glycine-NaOH buffer pH 10. 30 µl filtered supernatant was placed in a fresh 96-well flat bottom MTP. To each well 50 µl NaAc buffer and 120 µl substrate was added and incubated for 30 minutes at 50° C. (Thermolab systems iEMS Incubator/shaker HT). The reaction was terminated by adding 100 µl stop solution. The absorbance was measured at 405 nm in a MTP-reader (Molecular Devices Spectramax 384 plus) and the activity was calculated using a molar extinction coefficient of 0.011 µM/cm.

Thermal Stability Assay:

Crude supernatant (100 µl) was added to 100 µl 50 mM NaAc buffer pH 4.5. the sample was equally divided over 2 MTP. One MTP (initial plate) was incubated for 1 hr at 4° C. and the other MTP (residual plate) was incubated at 60° C. (Thermolab systems iEMS Incubator/Shaker HT) for 1 hr. The residual plate was chilled for 15 min on ice. Activity is measured on both plates using the ethanol application assay described below, with the following modification: the amount of sample taken for the thermostability assay is 25 µl and the amount of 30 mM NaAc buffer pH 4.0 is 35 µl.

Thermostability is calculated as % residual activity as follows:

$$\frac{ABS(340) residual - blank}{ABS(340) initial - blank} \times 100\%$$

The crude supernatant material is tested for remaining glucose in the culture medium after the growth period. If remaining glucose is found, the absorbance value is subtracted from the measured absorbance values of both the initial activity as the residual activity.

Bradford Assay for Protein Quantification in 96-Well Microtiter Plates:

The reagent solution was Bradford Quickstart work solution (BioRad cat#500-0205). 100 µl of 10 kD-filtered supernatant was placed in a fresh 96-well flat bottom plate. To each well 200 µl reagent was added and incubated for 5 minutes at room temperature. The absorbance was measured at 595 nm in a MTP-reader (Molecular Devices Spectramax 384 plus). Protein concentrations were calculated according to a Bovine Serum Albumin (BSA) (0-50 µg/ml) standard curve.

Hexokinase Activity Assay:

Hexokinase cocktail: 10-15 minutes prior to use, 90 ml water was added to a BoatIL container glucose HK R1 (IL test glucose (HK) kit, Instrument Laboratory #182507-40) and gently mixed. 85 µl of Hexokinase cocktail were added to 100 µl of dH$_2$O. 15 µl of sample were added to the mixtures and incubated for 5 mins in the dark at room temperature. Absorbance was read at 340 nm in a MTP-reader. Glucose concentrations were calculated according to a glucose (0-1 mg/ml) standard curve, Assay Conditions Ethanol Application:

To prepare the 8% stock solution, 8 g of soluble corn starch (Sigma #S4180) was suspended in 40 ml dH$_2$O at room temperature. Fifty milliliters of boiling dH$_2$O was added to the slurry in a 250 ml flask and cooked for 5 minutes. The starch solution was cooled to 25° C. and the volume adjusted to 100 ml with dH$_2$O. The 4% (m/v) soluble starch working solution was prepared by diluting (1:1) the stock solution with 100 mM sodium acetate buffer pH 3.7.

For the screening assay, 5 µl crude supernatant was diluted with 175 µl 50 mM NaAc buffer pH 4.5 in a flat bottom 96-well MTP. Sixty microliters of this dilution was added to 120 µl 4% soluble corn starch and incubated at 900 rpm for 2 hrs at 32° C. (Thermolab systems iEMS Incubator/Shaker HT). The reaction was stopped by adding 90 µl 4° C.-cold Stop Solution (800 mM Glycine-NaOH buffer, pH 10). The sample was placed on ice. Starch was spun down at 1118×g at 15° C. for 5 minutes (SIGMA 6K15) and 15 µl supernatant was used in the Hexokinase activity assay described above to determine the glucose content.

The crude supernatant material was tested for remaining glucose in the culture medium after the growth period. If remaining glucose was found, the amount of glucose produced by the glucoamylase was not calculated.

Assay Conditions Sweetener Application:

To prepare the 8% stock solution, 8 g of soluble starch (Sigma #S4180) was suspended in 40 ml water at room temperature. Then, 50 ml of boiling dH$_2$O was added to the slurry in a 250 ml flask and cooked for 5 mins. The starch solution was cooled to 25° C. and the volume adjusted to 100 ml with dH$_2$O. The 4% (m/v) soluble starch working solution was prepared by diluting stock solution 1:1 with 100 mM sodium acetate buffer pH 4.5.

Fifty microliters of 80 mM NaAc buffer pH 4.5 were placed in a fresh 96-well flat bottom plate. To each well, 120 µl 4% soluble cornstarch and 5 µl 10 kD-filtered supernatant was added and incubated for 1 hr at 60° C. The reaction was stopped by adding 90 µl 4° C. cold Stop Solution (800 mM Glycine-NaOH buffer, pH 10.0). The sample was placed on ice for 30 mins. Starch was spun down at 716 rpm at 15° C. for 5 minutes (Sigma 6K15, centrifuge) and 15 µl of the supernatant was used in the Hexokinase activity assay described herein to determine glucose content.

Example 1

Construction of the pREP3Y-TrGA Vector

Figure 3A:
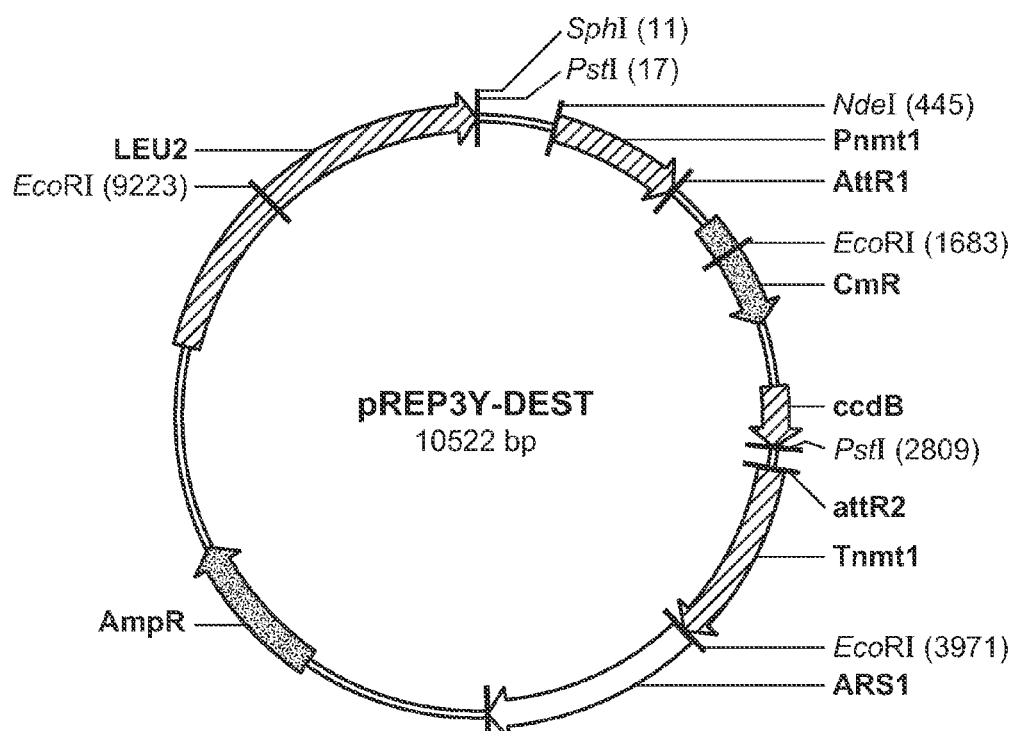
FIG. 3 depicts the plasmids pREP3Y-DEST (A) and pREP3Y-TrGA (B).
Figure 3B:
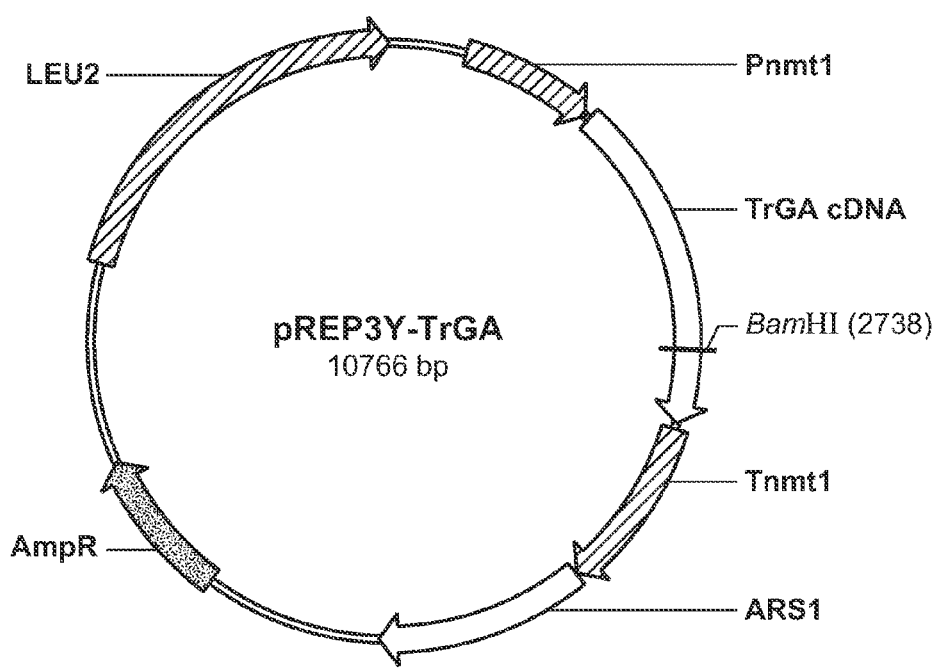

The TrGA expression cassette composed of the DNA sequence (SEQ ID NO: 4) encoding the TrGA signal peptide, the pro-sequence, and the mature protein, including the catalytic domain, linker region and starch binding domain, was cloned into pDONR™201, a Gateway® Entry vector (Invitrogen, Carlsbad, Calif., USA). The TrGA expression cassette was cloned into the Gateway compatible destination vector pREP3Y-DEST (FIG. 3) by the Gateway® LR recombination reaction.

The pRep3Y-TrGA expression vector (FIG. 3B) enabled the expression of the TrGA protein (SEQ ID NO: 2) in *Schizosaccharomyces pombe*.

Sixty-five TrGA site saturated mutagenesis (SSM) libraries were constructed using the pDONR-TrGA entry vector (FIG. 2) as a template and the primers listed in Table 2. The mutagenesis primers used in the experiments all contain the triple DNA sequence code NNS (N=A,C,T,G and S=C or O) at the position that corresponds with the codon of the TrGA sequence to be mutated (SEQ ID NO: 2) and initiated random incorporation of nucleotides at that position. Construction of each SSM library started with two PCR amplifications using the Gateway forward (pDONR201-FW) and a specific reverse mutagenesis primer (Table 3), and Gateway reversed (pDONR201-RV) primer and a specific forward mutagenesis primer (Table 2) (equal positions for the mutagenesis primers). Phusion high fidelity DNA polymerase (Finnzymes OY, Espoo, Finland) was used for PCR amplification (0.2 μM primers, 25 cycles) according to the protocol provided by Finnzymes. Briefly, 1 μl (SEQ ID NO: 1), DNA fragment of both specific PCR mixes, both targeted at the same codon were added to 48 μl of fresh PCR reaction solution together with primers Gateway FW and Gateway RV (Invitrogen) and mixed. This fusion PCR amplification (22 cycles) resulted in a linear expression cassette DNA fragment with a specific TrGA codon randomly mutated and unique Gateway recombination sites on both ends. Purification of this DNA fragment (ChargeSwitch® PCR clean-up, Invitrogen, Carlsbad USA) and a BP recombination reaction (Invitrogen, Carlsbad, USA) with pDONR201 (Invitrogen) generated a circular multimeric DNA (entry vector) that was subsequently transformed to *E. coli* Max efficiency DH5α (Invitrogen) and plated on 2×TY medium [Bacto Tryptone (Difco) 16 g/L, Bacto Yeast Extract (Difco) 10 g/L, NaCL 5 g/L] supplemented with 50 μg/mL, kanamycin.

TABLE 2

Forward primers used to generate TrGA SSM libraries

| Primers | DNA SEQUENCE 5' TO 3' | SEQ ID NO: |
|---|---|---|
| pDONR201-FW | TCGCGTTAACGCTAGCATGGATCTC | 10 |
| D4F | TCTGTTGACNNSTTCATCAGCACCGAGACGC | 11 |
| F5F | TCTGTTGACGACNNSATCAGCACCGAGACGCCTA | 12 |
| I12F | ATCAGCACCGAGACGCCTNNSGCACTGAACAATCTTCTTT | 13 |
| D24F | CTTTGCAATGTTGGTCCTNNSGGATGCCGTGCATTCGGCA | 14 |
| F29F | CCTGATGGATGCCGTGCANNSGGCACATCAGCTGGTGCGG | 15 |
| I43F | ATTGCATCTCCCAGCACANNSGACCCGGACTACTATTACA | 16 |
| D44F | GCATCTCCCAGCACAATTNNSCCGGACTACTATTACATGT | 17 |
| P45F | TCTCCCAGCACAATTGACNNSGACTACTATTACATGTGGA | 18 |
| D46F | CCCAGCACAATTGACCCGNNSTACTATTACATGTGGACGC | 19 |
| Y47F | AGCACAATTGACCCGGACNNSTATTACATGTGGACGCGAG | 20 |
| Y49F | ATTGACCCGGACTACTATNNSATGTGGACGCGAGATAGCG | 21 |
| W51F | CCGGACTACTATTACATGNNSACGCGAGATAGCGCTCTTG | 22 |
| Y70F | GACCGCTTCACCGAAACGNNSGATGCGGGCCTGCAGCGCC | 23 |
| Q75F | ACGTACGATGCGGGCCTGNNSCGCCGCATCGAGCAGTACA | 24 |
| R76F | TACGATGCGGGCCTGCAGNNSCGCATCGAGCAGTACATTA | 25 |
| P94F | CTCCAGGGCCTCTCTAACNNSTCGGGCTCCCTCGCGGACG | 26 |
| D100F | CCCTCGGGCTCCCTCGCGNNSGGCTCTGGTCTCGGCGAGC | 27 |
| K114F | AAGTTTGAGTTGACCCTGNNSCCTTTCACCGGCAACTGGG | 28 |
| F116F | GAGTTGACCCTGAAGCCTNNSACCGGCAACTGGGGTCGAC | 29 |
| N119F | CTGAAGCCTTTCACCGGCNNSTGGGGTCGACCGCAGCGGG | 30 |
| R122F | TTCACCGGCAACTGGGGTNNSCCGCAGCGGGATGGCCCAG | 31 |
| R125F | AACTGGGGTCGACCGCAGNNSGATGGCCCAGCTCTGCGAG | 32 |
| N146F | AAGTGGCTCATCAACAACNNSTATCAGTCGACTGTGTCCA | 33 |
| Q148E | CTCATCAACAACAACTATNNSTCGACTGTGTCCAACGTCA | 34 |

TABLE 2-continued

Forward primers used to generate TrGA SSM libraries

| Primers | DNA SEQUENCE 5' TO 3' | SEQ ID NO: |
|---|---|---|
| Y169F | CTCAACTATGTTGCCCAGNNSTGGAACCAAACCGGCTTTG | 35 |
| Q172F | GTTGCCCAGTACTGGAACNNSACCGGCTTTGACCTCTGGG | 36 |
| F175F | TACTGGAACCAAACCGGCNNSGACCTCTGGGAAGAAGTCA | 37 |
| W178F | CAAACCGGCTTTGACCTCNNSGAAGAAGTCAATGGGAGCT | 38 |
| E180F | GGCTTTGACCTCTGGGAANNSGTCAATGGGAGCTCATTCT | 39 |
| V181F | TTTGACCTCTGGGAAGAANNSAATGGGAGCTCATTCTTTA | 40 |
| Q208F | CTTGCTGCCACTCTTGGCNNSTCGGGAAGCGCTTATTCAT | 41 |
| S211F | ACTCTTGGCCAGTCGGGANNSGCTTATTCATCTGTTGCTC | 42 |
| W228F | TGCTTTCTCCAACGATTCNNSGTGTCGTCTGGTGGATACG | 43 |
| N242F | GACTCCAACATCAACACCNNSGAGGGCAGGACTGGCAAGG | 44 |
| E243F | TCCAACATCAACACCAACNNSGGCAGGACTGGCAAGGATG | 45 |
| R245F | ATCAACACCAACGAGGGCNNSACTGGCAAGGATGTCAACT | 46 |
| 1292F | GTCGACTCCTTCCGCTCCNNSTACGGCGTGAACAAGGGCA | 47 |
| G294F | TCCTTCCGCTCCATCTACNNSGTGAACAAGGGCATTCCTG | 48 |
| K297F | TCCATCTACGGCGTGAACNNSGGCATTCCTGCCGGTGCTG | 49 |
| R309F | GCTGCCGTCGCCATTGGCNNSTATGCAGAGGATGTGTACT | 50 |
| Y310F | GCCGTCGCCATTGGCCGGNNSGCAGAGGATGTGTACTACA | 51 |
| D313F | ATTGGCCGGTATGCAGAGNNSGTGTACTACAACGGCAACC | 52 |
| V314F | GGCCGGTATGCAGAGGATNNSTACTACAACGGCAACCCTT | 53 |
| Y315F | CGGTATGCAGAGGATGTGNNSTACAACGGCAACCCTTGGT | 54 |
| Y316F | TATGCAGAGGATGTGTACNNSAACGGCAACCCTTGGTATC | 35 |
| N317F | GCAGAGGATGTGTACTACNNSGGCAACCCTTGGTATCTTG | 56 |
| W321F | TACTACAACGGCAACCCTNNSTATCTTGCTACATTTGCTG | 37 |
| K340F | GATGCCATCTACGTCTGGNNSAAGACGGGCTCCATCACGG | 58 |
| K341F | GCCATCTACGTCTGGAAGNNSACGGGCJCCATCACGGTGA | 59 |
| T350F | TCCATCACGGTGACCGCCNNSTCCCTGGCCTTCTTCCAGG | 60 |
| Q356F | ACCTCCCTGGCCTTCTTCNNSGAGCTIUTTCCTGGCGTGA | 61 |
| T363F | GAGCTTGTTCCTGGCGTGNNSGCCGGGACCTACTCCAGCA | 62 |
| S368F | GTGACGGCCGGGACCTACNNSAGCAGCTCTTCGACCTTTA | 63 |
| 5369F | ACGGCCGGGACCTACTCCNNSAGCTCTTCGACCTTTACCA | 64 |
| N376F | AGCTCTTCGACCTTTACCNNSATCATCAACGCCGTCTCGA | 65 |
| Y395F | CTCAGCGAGGCTGCCAAGNNSGTCCCCGCCGACGGTTCGC | 60 |
| A398F | GCTGCCAAGTACGTCCCCNNSGACGGTTCGCTGGCCGAGC | 67 |
| S401F | TACGTCCCCGCCGACGGTNNSCTGGCCGAGCAGTTTGACC | 68 |
| R408F | CTGGCCGAGCAGTTTGACNNSAACAGCGGCACTCCGCTGT | 69 |
| N409F | GCCGAGCAGTTTGACCGCNNSAGCGGCACTCCGCTGTCTG | 70 |
| T412F | TTTGACCGCAACAGCGGCNNSCCGCTGTCTGCGCTTCACC | 71 |
| H418F | ACTCCGCTGTCTGCGCTTNNSCTGACGTGGTCGTACGCCT | 72 |

TABLE 2-continued

Forward primers used to generate TrGA SSM libraries

| Primers | DNA SEQUENCE 5' TO 3' | SEQ ID NO: |
|---|---|---|
| W421F | TCTGCGCTTCACCTGACGNNSTCGTACGCCTCGTTCTTGA | 73 |
| R433F | TTGACAGCCACGGCCCGTNNSGCTGGCATCGTGCCCCCCT | 74 |
| I436F | ACGGCCCGTCGGGCTGGCNNSGTGCCCCCCTCGTGGGCCA | 75 |
| S451F | AGCGCTAGCACGATCCCCNNSACGTGCTCCGGCGCGTCCG | 76 |

TABLE 3

Primers used to generate TrGA SSM libraries

| Primer | DNA sequence 5' to 3' | SEQ ID NO: |
|---|---|---|
| pDON201-RV | GTAACATCAGAGATTTTGAGACAC | 77 |
| D4R | CTCCTTCATCGGTGCTGATGAASNNGTCAACAGA | 78 |
| F5R | TAGGCGTCTCGGTGCTGATSNNGTCGTCAACAGA | 79 |
| I12R | AAAGAAGATTGTTCAGTGCSNNAGGCGTCTCGGTGCTGAT | 80 |
| D24R | TGCCGAATGCACGGCATCCSNNAGGACCAACATTGCAAAG | 81 |
| F29R | CCGCACCAGCTGATGTGCCSNNTGCACGGCATCCATCAGG | 82 |
| I43R | TGTAATAGTAGTCCGGGTCSNNTGTGCTGGGAGATGCAAT | 83 |
| D44R | ACATGTAATAGTAGTCCGGSNNAATTGTGCTGGGAGATGC | 84 |
| P45R | TCCACATGTAATAGTAGTCSNNGTCAATTGTGCTGGGAGA | 85 |
| D46R | GCGTCCACATGTAATAGTASNNCGGGTCAATTGTGCTGGG | 86 |
| Y47R | CTCGCGTCCACATGTAATASNNGTCCGGGTCAATTGTGCT | 87 |
| Y49R | CGCTATCTCGCGTCCACATSNNATAGTAGTCCGGGTCAAT | 88 |
| W51R | CAAGAGCGCTATCTCGCGTSNNCATGTAATAGTAGTCCGG | 89 |
| Y70R | GGCGCTGCAGGCCCGCATCSNNCGTTTCGGTGAAGCGGTC | 90 |
| Q75R | TGTACTGCTCGATGCGGCGSNNCAGGCCCGCATCGTACGT | 91 |
| R76R | TAATGTACTGCTCGATGCGSNNCTGCAGGCCCGCATCGTA | 92 |
| P94R | CGTCCGCGAGGGAGCCCGASNNGTTAGAGAGGCCCTGGAG | 93 |
| D100R | GCTCGCCGAGACCAGAGCCSNNCGCGAGGGAGCCCGAGGG | 94 |
| K114R | CCCAGTTGCCGGTGAAAGGSNNCAGGGTCAACTCAAACTT | 95 |
| F116R | GTCGACCCCAGTTGCCGGTSNNAGGCTTCAGGGTCAACTC | 96 |
| N119R | CCCGCTGCGGTCGACCCCASNNGCCGGTGAAAGGCTTCAG | 97 |
| R122R | CTGGGCCATCCCGCTGCGGSNNACCCCAGTTGCCGGTGAA | 98 |
| R125R | CTCGCAGAGCTGGGCCATCSNNCTGCGGTCGACCCCAGTT | 99 |
| N146R | TGGACACAGTCGACTGATASNNGTTGTTGATGAGCCACTT | 100 |
| Q148R | TGACGTTGGACACAGTCGASNNATAGTTGTTGTTGATGAG | 101 |
| Y169R | CAAAGCCGGTTTGGTTCCASNNCTGGGCAACATAGTTGAG | 102 |
| Q172R | CCCAGAGGTCAAAGCCGGTSNNGTTCCAGTACTGGGCAAC | 103 |
| F175R | TGACTTCTTCCCAGAGGTCSNNGCCGGTTTGGTTCCAGTA | 104 |
| W178R | AGCTCCCATTGACTTCTTCSNNGAGGTCAAAGCCGGTTTG | 105 |

TABLE 3-continued

Primers used to generate TrGA SSM libraries

| Primer | DNA sequence 5' to 3' | SEQ ID NO: |
| --- | --- | --- |
| E180R | AGAATGAGCTCCCATTGACSNNTTCCCAGAGGTCAAAGCC | 106 |
| V181R | TAAAGAATGAGCTCCCATTSNNTTCTTCCCAGAGGTCAAA | 107 |
| Q208R | ATGAATAAGCGCTTCCCGASNNGCCAAGAGTGGCAGCAAG | 108 |
| S211R | GAGCAACAGATGAATAAGCSNNTCCCGACTGGCCAAGAGT | 109 |
| NV228R | CGTATCCACCAGACGACACSNNGAATCGTTGGAGAAAGCA | 110 |
| N242R | CCTTGCCAGTCCTGCCCTCSNNGGTGTTGATGTTGGAGTC | 111 |
| E243R | CATCCTTGCCAGTCCTGCCSNNGTTGGTGTTGATGTTGGA | 112 |
| R245R | AGTTGACATCCTTGCCAGTSNNGCCCTCGTTGGTGTTGAT | 113 |
| I292R | TGCCCTTGTTCACGCCGTASNNGGAGCGGAAGGAGTCGAC | 114 |
| G294R | CAGGANTGCCCTTGTTCACSNNGTAGATGGAGCGGAAGGA | 115 |
| K297R | CAGCACCGGCAGGAATGCCSNNGTTCACGCCGTAGATGGA | 116 |
| R309R | AGTACACATCCTCTGCATASNNGCCAATGGCGACGGCAGC | 117 |
| Y310R | TGTAGTACACATCCTCTGCSNNCCGGCCAATGGCGACGGC | 118 |
| D313R | GGTTGCCGTTGTAGTACACSNNCTCTGCATACCGGCCAAT | 119 |
| V314R | AAGGGTTGCCGTTGTAGTASNNATCCTCTGCATACCGGCC | 120 |
| Y315R | ACCAAGGGTTGCCGTTGTASNNCACATCCTCTGCATACCG | 121 |
| Y316R | GATACCAAGGGTTGCCGTTSNNGTACACATCCTCTGCATA | 122 |
| N317R | CAAGATACCAAGGGTTGCCSNNGTAGTACACATCCTCTGC | 123 |
| W321R | CAGCAAATGTAGCAAGATASNNAGGGTTGCCGTTGTAGTA | 124 |
| K340R | CCGTGATGGAGCCCGTCTTSNNCCAGACGTAGATGGCATC | 125 |
| K341R | TCACCGTGATGGAGCCCGTSNNCTTCCAGACGTAGATGGC | 126 |
| T350R | CCTGGAAGAAGGCCAGGGASNNGGCGGTCACCGTGATGGA | 127 |
| Q356R | TCACGCCAGGAACAAGCTCSNNGAAGAAGGCCAGGGAGGT | 128 |
| T363R | TGCTGGAGTAGGTCCCGGCSNNCACGCCAGGAACAAGCTC | 129 |
| S368R | TAAAGGTCGAAGAGCTGCTSNNGTAGGTCCCGGCCGTCAC | 130 |
| S369R | TGGTAAAGGTCGAAGAGCTSNNGGAGTAGGTCCCGGCCGT | 131 |
| N376R | TCGAGACGGCGTTGATGATSNNGGTAAAGGTCGAAGAGCT | 132 |
| Y395R | GCGAACCGTCGGCGGGGACSNNCTTGGCAGCCTCGCTGAG | 133 |
| A398R | GCTCGGCCAGCGAACCGTCSNNGGGGACGTACTTGGCAGC | 134 |
| S401R | GGTCAAACTGCTCGGCCAGSNNACCGTCGGCGGGGACGTA | 133 |
| R408R | ACAGCGGAGTGCCGCTGTTSNNGTCAAACTGCTCGGCCAG | 136 |
| N409R | CAGACAGCGGAGTGCCGCTSNNGCGGTCANACTGCTCGGC | 137 |
| T412R | GGTGAAGCGCAGACAGCGGSNNCCGCTGTTGCGGTCAAA | 138 |
| H418R | AGGCGTACGACCACGTCAGSNNAAGCGCAGACAGCGGAGT | 139 |
| W421R | TCAAGAACGAGGCGTACGASNNCGTCAGGTGAAGCGCAGA | 140 |
| R433R | AGGGGGGCACGATGCCAGCSNNACGGGCCGTGGCTGTCAA | 141 |
| I436R | TGGCCCACGAGGGGGGCACSNNGCCAGCCCGACGGGCCGT | 142 |
| S451R | CGGACGCGCCGGAGCACGTSNNGGGGATCGTGCTAGCGCT | 143 |

For each library, after overnight incubation at 37° C. colonies were pooled by resuspension of the clones in PSS. From the pooled *E. coli* transformants, total plasmid was isolated (Qiagen) using standard techniques. Briefly 1 µl of the plasmid solution was added to 1 µl of pRep3Y destination vector (FIG. 1A) solution and added to the LR CLONASE™ II enzyme mix according to the protocol supplied by Invitrogen. A circular multimeric DNA was generated and transformed to *E. coli* Max EfficiencyDH5α as described by the supplier.

After overnight incubation at 37° C., 96 single colonies of each library were picked from 2×TY agar plates with 100 µg/ml ampicillin and grown for 24 hrs at 37° C. in a MTP containing 200 µL 2×TY medium with 100 µg/ml ampicillin. Cultures were used for sequence analyses (BaseClear B.V., Leiden, Netherlands).

The library numbers ranged from 1 to 65 with an addition referring to the codon of the TrGA sequence that is randomly mutated. After selection, each library included a maximum of 19 TrGA variants, These variants were individually transferred to *Schizosaccharomyces pombe* according to manufacturers instruction. (Zymo Research, Orange Calif. USA).

*S. pombe* transformations were plated on selective medium (EMM agar, Qbiogene, Irvine, USA Cat. No. 4110-232) and incubated at 28° C. for 4 days. Transformants were purified from the transformation plate by streaking the colonies on EMM agar.

Example 2

Description of the Growth Conditions and the Sample Pre-Treatment

*S. pombe* transformants were inoculated in 96 well microliter plates (MTP) containing selective medium (2×EMM-C) [64.4 g/L EMM Broth (Qbiogene Cat. No: 4110-032), 0.62 g/L Complete Supplement Mixture (CSM-HIS-LEU-TRP, Qbiogene, Cat. No. 4530-122)] and incubated overnight at 28° C. From the overnight incubated microliter plate, 200 µl of grown *S. pombe* culture was inoculated in 20 ml of 2×EMM-C liquid medium in a 100 ml shake flask and incubated for 4 days at 26° C. at 280 rpm in a Multitron shaking incubator (Infers AG, Bottmingen, Switzerland). From the grown culture, 2 ml of *S. pombe* culture was sampled and centrifuged for 5 min at 14,000 rpm (Sigma). The supernatant was transferred into a 10 kD Vivaspin 500 HT filter set-up (VivaScience AG, Hannover, Germany) and centrifuged for 25 min at 1000 g. The retentate was diluted back to the original start volume with 50 mM NaAc pH 4.5 supplemented with 0.015% Tween-80. This solution was used in the different assays.

Example 3

Construction of a Combinatorial Library of 4 Variants of TrGA (A) Experiments were conducted for the construction of TrGA-variants carrying combinations of the following single site mutations: Q172F; Q208N; S211R and V314H. A review of the variants is shown below:
a) Q172F; Q208N
b) Q172F; S211R
c) Q172F; V314H
d) Q208N; S211R
e) Q208N V314H
f) S211R; V314H
g) Q172F; Q208N; S211R
h) Q172F; Q208N; V314H
i) Q172F; S211R; V314H
j) Q208N; S211R; V314H
k) Q172F; Q208N; S211R; V314H The Quikchange® multi site-directed mutagenesis (QCMS) kit (Stratagene) was used to construct the library. The 5' phosphorylated (primers used to create the library are shown in Table 4. Optimal results in terms of incorporation of full length primers as well as significant reduction in primer-derived errors were obtained by the use of HPLC, PAGE or any other type of purified primers (Invitrogen).

TABLE 4

Primers used to construct selected combinatorial variants

| Primer | Sequence | SEQ ID NO: |
|---|---|---|
| I43R | GCATCTCCCAGCACACGAGACCCGGACTACTAT | 144 |
| I43Y | GCATCTCCCAGCACATACGACCCGGACTACTAT | 145 |
| R76L | GATGCGGGCCTGCAGCTGCGCATCGAGCAGTAC | 146 |
| N119T | CTGAAGCCTTTCACCGGCACCTGGGGTCGACCGCAGCGGG | 147 |
| N119Y | TGAAGCCTTTCACCGGCTACTGGGGTCGACCGCAGCGGG | 148 |
| N119D | CTGAAGCCTTTCACCGGCGACTGGGGTCGACCGCAGCGGG | 149 |
| N146 | AGTGGCTCATCAACAACGASTATCAGTCGACTGTGT | 150 |
| N146T | AGTGGCTCATCAACAACACCTATCAGTCGACTGTGT | 151 |
| N146W | GTGGCTCATCAACAATGGTATCAGTCGACTGTGT | 152 |
| N146L | AGTGGCTCATCAACAACCTGTATCAGTCGACTGTGT | 153 |
| N146S | AGTGGCTCATCAACAACTCCTATCAGTCGACTGTGT | 154 |
| Q172D/E | TTGCCCAGTACTGGAACGASACCGGCTTTGACCTCTGG | 155 |
| Q172V/L | TTGCCCAGTACTGGAACSTGACCGGCTTTGACCTCTGG | 156 |
| Q172T | TTGCCCAGTACTGGAACACCACCGGCTTTGACCTCTGG | 157 |
| Q172R | TTGCCCAGTACTGGAACCGAACCGGCTTTGACCTCTGG | 158 |
| Q172C | TTGCCCAGTACTGGAACTGCACCGGCTTTGACCTCTGG | 159 |

The template plasmid pDONR-TrGA (FIG. 2) was used to construct the combinatorial library using the QCMS kit of Stratagene. The library was constructed as described by the supplier with modified primer concentrations used in the reactions. Specifically, 4 µl pDONR-TrGA (25-50 ng) was mixed with 11 µl of sterile distilled water; 1.5 µl of dNTP; 2.5 µl of 10×QCMS-buffer; 1 µl of enzyme blend and 1 µl of each mutant primer mix giving a total of 100 ng of primers in each reaction. The PCR conditions were 95° C. for 1 min, followed by 30 cycles of 95° for 1 min, 55° C. for 1 min, and 65° C. for 6 min, in an MJ Research thermocycler using thin-walled 0.2 ml PCR tubes. The reaction product was digested with 1 µl of Dpn1 from the QCMS kit by incubating at 37° C. overnight. A PCR purification kit (Qiagen) was used for sample purification and a second round of digestion was carried out with Dpn1 (Stratagene) for 1 hour at 37° C.

The reaction mixture was transformed to into *E. coli* Max efficiency DH5α (Invitrogen) and plated on selective agar (2×TY supplemented with 50 µg kanamycin/ml). After overnight incubation at 37° C. 96 single colonies were picked for sequence analysis (BaseClear B.V., Leiden, Netherlands).

The combinatorial variants were cloned and expressed in a *T. reesei* host strain as described below and in WO 06/060062.

(B) A further six combinatorial libraries (Table 5) were synthetically made by Geneart (Regensburg, Germany) and were tested for thermal stability and in ethanol and sweetener application assays as described herein.

TABLE 5

Combinatorial libraries

| | |
|---|---|
| 1 | D24E,L/I43F,R/D44H,N/F175H/V181K,L/V314D,H,K/T363R |
| 2 | D24L,W,Y/Q208F/I292F,L,N,V/G294A,I,Q/K297A/Y310F,Q,R |
| 3 | V181F,K,L/E243A,N,M,R,Y/I292F,L,N,V/K297A,D,H,M,N,Q/N317H/Y395Q,R |
| 4 | D24E,L,Y/V181F,K,L/Q208C/F/G294A,I,Q/T363R/N376Q/N409K,W |
| 5 | D24E,L,Y/V181F,K,L/I292F,L,N,V/G294A,I,Q/E243A,M,N,R,Y/N409K,W |
| 6 | I43R/E243A,M,N,R,Y/I292F,L,N,V/G294A/K297A,D,H,M,N,Q,S,R,W,Y |

Example 4

Variants with Improved Thermal Stability

The parent TrGA molecule under the conditions described had a residual activity between 15 and 44% (day-to-day variation). The performance index was calculated based on the TrGA thermostability of the same batch. The performance indices are the quotients PI=(Variant residual activity)/(TrGA residual activity). A performance index >1 indicates an improved stability. Variants that have a thermal stability performance index of more than 1.0 are shown in the following Table 6.

TABLE 6

Thermostability screening

| Variant | PI Thermal Stability, 60° C., pH 4.5 | Variant | PI Thermal Stability, 60° C., pH 4.5 |
|---|---|---|---|
| D4P | 1.05 | D24W | 1.13 |
| I12E | 1.09 | D24Y | 1.03 |
| I12Y | 1.40 | I43R | 1.28 |
| D24L | 1.09 | D44N | 1.06 |
| D44Q | 1.10 | V181R | 1.07 |
| Q75N | 1.09 | Q208F | 1.06 |
| R76K | 1.03 | Q208T | 1.17 |
| N146D | 1.20 | Q208V | 1.15 |
| N146E | 1.24 | S211D | 1.10 |
| N146L | 1.10 | S211E | 1.02 |
| N146V | 1.28 | S211I | 1.31 |
| N146W | 1.17 | S211M | 1.90 |
| Q148D | 1.02 | E243A | 1.19 |
| F175I | 1.02 | E243H | 1.04 |
| F175Y | 1.06 | E243M | 1.53 |
| E180A | 1.41 | E243N | 1.35 |
| E180D | 1.02 | E243P | 1.06 |
| E180G | 1.13 | E243R | 1.21 |
| E180I | 1.41 | E243S | 1.09 |
| E180L | 1.38 | E243T | 1.48 |
| E180M | 1.10 | E243Y | 1.43 |
| E180N | 1.27 | I292F | 1.17 |
| E180Q | 1.72 | I292L | 1.10 |
| E180R | 1.59 | I292N | 1.31 |
| E180V | 1.08 | I292V | 1.02 |
| E180W | 1.30 | G294A | 1.30 |
| E180Y | 1.31 | G294C | 1.41 |
| V181I | 1.20 | G294D | 1.31 |
| V181K | 1.12 | G294E | 1.34 |
| V181L | 1.06 | G294H | 1.17 |

TABLE 6-continued

Thermostability screening

| Variant | PI Thermal Stability, 60° C., pH 4.5 | Variant | PI Thermal Stability, 60° C., pH 4.5 |
|---|---|---|---|
| V181Q | 1.09 | G294I | 2.15 |
| G294L | 2.01 | Y315E | 1.24 |
| G294P | 1.13 | Y315H | 1.48 |
| G294Q | 1.91 | Y315L | 1.35 |
| G294R | 1.34 | Y315N | 1.17 |
| G294V | 1.10 | Y315P | 1.19 |
| K297A | 1.47 | Y315Q | 1.43 |
| K297C | 1.10 | Y315T | 1.34 |
| K297D | 1.50 | Y316D | 1.06 |
| K297F | 1.24 | N317H | 1.26 |
| K297G | 1.25 | N317Q | 1.09 |
| K297H | 1.63 | K340H | 1.02 |
| K297L | 1.62 | K340R | 1.09 |
| K297M | 1.62 | K341I | 1.10 |
| K297N | 1.87 | K341V | 1.07 |
| K297Q | 1.82 | T350G | 1.08 |
| K297R | 1.29 | T350P | 1.08 |
| K297S | 1.22 | T350S | 1.33 |
| K297T | 1.33 | Q356L | 1.20 |
| K297V | 1.10 | T363N | 1.30 |
| K297W | 1.85 | S368C | 1.12 |
| K297Y | 1.71 | S368E | 1.07 |
| R309S | 1.08 | S368F | 1.16 |
| Y310C | 1.06 | 5368H | 1.26 |
| Y310F | 1.35 | S368I | 1.15 |
| Y310L | 1.11 | S368L | 1.33 |
| Y310Q | 1.40 | S368N | 1.21 |
| Y310R | 1.61 | S368P | 1.05 |
| S368Q | 1.10 | Y395C | 1.02 |
| S368R | 1.14 | Y395F | 1.03 |
| S368T | 1.15 | Y395G | 1.13 |
| S368W | 1.16 | Y395H | 1.10 |
| S369A | 1.22 | Y395L | 1.50 |
| S369D | 1.05 | Y395N | 1.20 |
| S369F | 1.20 | Y395Q | 1.18 |
| S369G | 1.05 | Y395R | 1.14 |
| S369K | 1.12 | Y395S | 1.13 |
| S369L | 1.49 | Y395T | 1.04 |
| S369M | 1.36 | A398C | 1.10 |
| S369N | 1.25 | A398D | 1.39 |
| S369P | 1.16 | A398F | 1.05 |
| S369R | 1.12 | A398G | 1.17 |
| S369T | 1.25 | A398H | 1.33 |
| N376F | 1.12 | A398I | 1.41 |
| N376G | 1.26 | A398K | 1.47 |
| N376H | 1.21 | A398L | 1.44 |
| N376K | 1.40 | A398N | 1.23 |
| N376L | 1.34 | A398P | 1.38 |
| N376P | 1.05 | A398Q | 1.43 |
| N376Q | 1.11 | A398R | 1.59 |
| N376S | 1.09 | A398S | 1.14 |
| N376V | 1.19 | A398T | 1.25 |
| N376W | 1.12 | A398V | 1.29 |
| N376Y | 1.05 | A398W | 1.45 |
| Y395A | 1.05 | A398Y | 1.38 |
| S401A | 1.12 | N409A | 1.25 |
| S401E | 1.08 | N409C | 1.18 |
| S401I | 1.05 | N409D | 1.21 |
| S401N | 1.12 | N409E | 1.27 |
| S401P | 1.15 | N409F | 1.32 |
| S401R | 1.25 | N409G | 1.14 |
| S401T | 1.26 | N409H | 1.29 |
| S401V | 1.18 | N409I | 1.56 |
| R408A | 1.14 | N409K | 1.44 |
| R408E | 1.41 | N409L | 1.57 |
| R408G | 1.15 | N409M | 1.17 |
| R408H | 1.12 | N409Q | 1.03 |
| R408I | 1.19 | N409R | 1.29 |
| R408K | 1.80 | N409V | 1.11 |
| R408L | 1.55 | N409W | 1.58 |
| R408N | 1.09 | T412L | 1.10 |
| R408Q | 1.23 | S451R | 1.01 |
| R408S | 1.17 | | |

Example 5

High Performing Variants from an Ethanol Screening Assay

Variants were tested in an ethanol screening assay using the assays described above. Table 7 shows the results of the screening assay for variants with a Performance Index (PI) >1.0 compared to the parent TrGA PI. The PI is a measure of specific activity (activity/mg enzyme). The PI of the specific activity is the quotient "Variant-specific activity/WT-specific activity." The PI of the specific activity is 1.0 and a variant with a PI>1.0 has a specific activity that is greater than the parent TrGA. The specific activity is the activity measured by the ethanol screening assay divided by the results obtained in the Bradford assay described above.

TABLE 7

Ethanol Screening

| Variant | P.I. 32° C., pH 4 | Variant | P.I. 32° C., pH 4 |
|---|---|---|---|
| D4A | 1.07 | D44F | 1.07 |
| D4C | 1.08 | D44G | 1.03 |
| D4E | 1.23 | D44H | 1.11 |
| D4L | 1.34 | D44K | 1.09 |
| D4R | 1.18 | D44N | 1.07 |
| D4S | 1.17 | D44S | 1.08 |
| F5C | 1.35 | D44Y | 1.07 |
| I12L | 1.19 | Y70E | 1.02 |
| I12R | 1.13 | Y70G | 1.06 |
| D24E | 1.60 | Y70K | 1.01 |
| D24L | 1.19 | Y70M | 1.36 |
| D24W | 1.03 | Y70P | 1.15 |
| D24Y | 1.14 | Y70R | 1.40 |
| F29A | 1.05 | Y70S | 1.04 |
| F29C | 1.12 | Q75A | 1.10 |
| F29D | 1.20 | Q75K | 1.77 |
| F29E | 1.05 | R76K | 1.06 |
| F29I | 1.26 | R76L | 1.11 |
| F29L | 1.42 | R76M | 1.13 |
| F29Q | 1.01 | R76N | 1.02 |
| F29S | 1.07 | R76T | 1.04 |
| F29V | 1.06 | R76V | 1.05 |
| I43D | 1.14 | R76W | 1.02 |
| I43F | 1.33 | R76Y | 1.05 |
| I43R | 1.21 | D100A | 1.08 |
| I43Y | 1.05 | D100I | 1.14 |
| D44E | 1.37 | D100L | 1.03 |
| D100M | 1.12 | F175Y | 1.05 |
| D100N | 1.06 | V181F | 1.28 |
| D100P | 1.09 | V181K | 1.35 |
| D100Q | 1.14 | V181L | 1.37 |
| D100T | 1.06 | V181R | 1.01 |
| D100W | 1.19 | Q208A | 1.22 |
| D100Y | 1.05 | Q208C | 1.17 |
| N119E | 1.02 | Q208F | 1.12 |
| N119F | 1.03 | Q208H | 1.02 |
| N119Y | 1.28 | Q208I | 1.02 |
| N146C | 1.11 | Q208L | 1.32 |
| N146E | 1.02 | S211A | 1.30 |
| N146G | 1.11 | S211E | 1.30 |
| N146H | 1.07 | S211G | 1.05 |
| N146K | 1.06 | S211L | 1.04 |
| Q148H | 1.10 | S211M | 1.05 |
| Q148N | 1.05 | S211R | 1.34 |
| Q148V | 1.18 | S211W | 1.07 |
| Q148W | 1.05 | S211Y | 1.08 |
| Q148Y | 1.16 | E243A | 1.23 |
| Y169D | 1.18 | E243L | 1.20 |
| Y169F | 1.10 | E243M | 1.26 |
| Y169H | 1.05 | E243N | 1.28 |
| Y169R | 1.02 | E243R | 1.31 |
| Q172E | 1.08 | E243Y | 1.25 |
| Q172G | 1.05 | I292F | 1.23 |
| Q172R | 1.22 | I292H | 1.04 |
| Q172S | 1.03 | I292L | 1.21 |

TABLE 7-continued

Ethanol Screening

| Variant | P.I. 32° C., pH 4 | Variant | P.I. 32° C., pH 4 |
|---|---|---|---|
| F175C | 1.18 | I292N | 1.27 |
| F175H | 1.26 | I292R | 1.02 |
| F175T | 1.28 | I292V | 1.24 |
| F175W | 1.16 | G294A | 1.91 |
| G294I | 1.92 | K341F | 1.64 |
| G294Q | 1.99 | K341G | 1.64 |
| K297A | 1.82 | K341L | 1.04 |
| K297D | 1.87 | K341N | 1.05 |
| K297H | 1.79 | K341S | 1.06 |
| K297M | 1.91 | T350A | 1.56 |
| K297N | 1.87 | T350D | 1.04 |
| K297Q | 1.85 | T350E | 1.59 |
| K297R | 1.71 | T350H | 1.03 |
| K297S | 1.72 | T350N | 1.06 |
| K297W | 1.70 | T350Q | 1.05 |
| K297Y | 1.80 | T350R | 1.02 |
| R309L | 1.43 | Q356D | 1.69 |
| Y310F | 1.05 | Q356E | 1.07 |
| Y310Q | 1.16 | Q356H | 1.03 |
| Y310R | 1.24 | Q356K | 1.03 |
| V314D | 1.10 | T363A | 1.04 |
| V314F | 1.04 | T363C | 1.54 |
| V314H | 1.31 | T363G | 1.02 |
| V314K | 1.08 | T363H | 1.09 |
| V314L | 1.02 | T363N | 1.02 |
| V314N | 1.05 | T363R | 1.61 |
| V314R | 1.06 | T363V | 1.05 |
| Y316R | 1.42 | T363W | 1.08 |
| Y316W | 1.05 | S368D | 1.11 |
| N317H | 1.14 | S368F | 1.08 |
| N317K | 1.02 | S368H | 1.04 |
| N317S | 1.03 | S368L | 1.07 |
| N317T | 1.23 | S368M | 1.03 |
| K340D | 1.33 | S368N | 1.02 |
| K340T | 1.16 | S368W | 1.24 |
| K341D | 1.04 | S369F | 1.68 |
| S369M | 1.04 | S401G | 1.04 |
| S369T | 1.05 | S401N | 1.02 |
| N376G | 1.05 | S401V | 1.06 |
| N376H | 1.10 | N409K | 1.30 |
| N376Q | 1.16 | N409L | 1.04 |
| N376S | 1.06 | N409W | 1.31 |
| N376T | 1.12 | T412A | 1.04 |
| N376V | 1.64 | T412G | 1.06 |
| Y395A | 1.02 | T412K | 1.05 |
| Y395C | 1.05 | R433Q | 1.16 |
| Y395G | 1.02 | I436A | 1.32 |
| Y395Q | 1.63 | I436H | 1.02 |
| Y395R | 1.20 | I436T | 1.03 |
| Y395S | 1.09 | S451A | 1.03 |
| A398D | 1.05 | S451M | 1.28 |
| A398P | 1.03 | S451T | 1.09 |
| S401A | 1.04 | S451Y | 1.03 |
| S401D | 1.01 | | |

Example 6

High Performing Variants from a Sweetener Screening Assay

Variants were tested in a sweetener screening assay as described hereinabove. Table 8 shows the results of the screening assay wherein variants with a Performance Index (PI)>1.00 compared to the parent TrGA PI are shown. The PI is a measure of specific activity (activity/mg enzyme). The PI of the specific activity is the quotient "Variant-specific activity/WT-specific activity." The PI of the specific activity is 1.0 and a variant with a PI>1.0 has a specific activity that is greater than the parent TrGA.

TABLE 8

Sweetener screening

| Variant | P.I. 60° C., pH 4.5 | Variant | P.I. 60° C., pH 4.5 |
|---|---|---|---|
| D4E | 1.09 | F175Y | 1.11 |
| D4L | 1.03 | V181A | 1.10 |
| D4S | 1.07 | V181F | 1.01 |
| D24E | 1.45 | V181K | 1.43 |
| D24L | 1.31 | V181L | 1.42 |
| D24Y | 1.01 | Q208C | 1.08 |
| I43D | 1.05 | Q208F | 1.20 |
| I43F | 1.31 | Q208H | 1.11 |
| I43R | 1.28 | Q208L | 1.03 |
| D44E | 1.09 | Q208N | 1.03 |
| D44H | 1.12 | Q208S | 1.06 |
| D44N | 1.31 | Q208T | 1.12 |
| Y70F | 1.26 | S211H | 1.16 |
| Y70L | 1.22 | S211M | 1.16 |
| Q75K | 1.12 | S211R | 1.34 |
| R76K | 1.11 | S211W | 1.09 |
| R76M | 1.03 | E243A | 1.06 |
| R76P | 1.13 | E243F | 1.01 |
| R76T | 1.11 | E243N | 1.05 |
| R76W | 1.07 | E243R | 1.14 |
| D100Y | 1.04 | E243S | 1.09 |
| N119E | 1.12 | E243Y | 1.07 |
| N119Y | 1.01 | R245A | 1.01 |
| N146D | 1.05 | I292N | 1.04 |
| N146E | 1.11 | I292V | 1.12 |
| Q148D | 1.02 | G294A | 1.06 |
| Q148W | 1.05 | G294Q | 1.02 |
| Q172H | 1.05 | K297A | 1.04 |
| Q172Y | 1.03 | K297D | 1.10 |
| F175H | 1.42 | K297Q | 1.07 |
| V314D | 1.22 | T363N | 1.02 |
| V314H | 1.85 | T363R | 1.50 |
| V314K | 1.34 | S368G | 1.04 |
| V314L | 1.13 | S368M | 1.03 |
| V314N | 1.08 | N376G | 1.02 |
| V314R | 1.20 | N376Q | 1.07 |
| V314Y | 1.05 | Y395Q | 1.01 |
| Y316R | 1.20 | A398H | 1.03 |
| N317H | 1.25 | A398S | 1.03 |
| N317K | 1.03 | S401A | 1.01 |
| K340D | 1.21 | N409K | 1.19 |
| K340E | 1.05 | N409T | 1.02 |
| K341D | 1.08 | N409W | 1.01 |
| K341G | 1.22 | T412G | 1.06 |
| K341L | 1.08 | T412S | 1.03 |
| K341N | 1.08 | I436D | 1.02 |
| K341S | 1.12 | I436Q | 1.06 |
| T350H | 1.03 | I436T | 1.16 |
| T350L | 1.04 | S451D | 1.01 |
| Q356D | 1.31 | S451E | 1.09 |
| Q356E | 1.04 | S451F | 1.02 |
| Q356K | 1.05 | S451H | 1.11 |
| T363C | 1.08 | S451T | 1.11 |
| T363G | 1.04 | | |

Example 7

Construction of Vectors and Transformation into *Trichoderma reesei* Host Cells

A. Construction of Expression Vectors Comprising a Polynucleotide Encoding a Variant GA.

The TrGA expression cassette comprising the DNA sequence SEQ ID NO: 4 was cloned into pDONR™ 201, a Gateway® Entry vector (Invitrogen, Carlsbad, Calif.). The TrGA expression cassette was cloned into the Gateway compatible destination vector pTrex3g-DEST (FIG. 5), which is also described in WO 06/060062, by the Gateway® LR recombination reaction. The pTrex3g-TrGA expression vector (FIG. 5) enabled the expression of the TrGA protein (SEQ ID NO: 2) in a *Trichoderma reesei* host. Vectors were constructed, which included modified TrGA cDNA coding at least the following variants (1) V314H; (2) S211R; (3) Q208N and (4) Q172F.

B. Transformation.

An expression vector containing a variant GA was transformed into a *T. reesei* host strain derived from RL-P37 (IA52) and having various gene deletions (Δ cbh1, Δcbh2, Δegl1, Δegl2) using particle bombardment by the PDS-1000/Helium System (BioRad Cat. No, 165-02257). The protocol is outlined below, and reference is also made to examples 6 and 11 of WO 05/001036.

A suspension of spores (approximately $5 \times 10^8$ spores/ml) from the strain of *T. reesei* was prepared. One hundred to two hundred microliters of spore suspension were spread onto the center of plates of Minimal Medium (MM) acetamide medium. The MM acetamide medium had the following composition: 0.6 g/L acetamide; 1.68 g/L CsCl; 20 g/L glucose; 20 g/L $KH_2PO_4$; 0.6 g/L $CaCl_2.2H_2O$; 1 ml/L 1000× trace elements solution: 20 g/L agar; and pH 5.5; 1 ml/L 400× trace element salt solution; citric acid 175 g/L, $FeSO_4.7H_2O$ 200 g/L, $ZnSO_4.7H_2O$ 16 g/L, $CuSO_4.5H_2O$ 3.2 g/L, $MnSO_4.H_2O$ 1.4 g/L, $H_3BO_3$ 0.8 g/L. The spore suspension was allowed to dry on the surface of the MM acetamide medium.

Transformation followed the manufacturers instruction. Briefly, 60 mg of M10 tungsten particles were placed in a microcentrifuge tube. 1 mL of ethanol was added and allowed to stand for 15 minutes. The particles were centrifuged at 15,000 rpm for 15 seconds. The ethanol was removed and the particles were washed three times with sterile $dH_2O$ before 1 mL of 50% (v/v) sterile glycerol was added. 25 µl of tungsten particle suspension was placed into a microcentrifuge tube. While continuously vortexing, the following were added: 0.5-5 µl (100-200 ng/µl) of plasmid DNA, 25 µl of 2.5 M $CaCl_2$ and 10 µl of 0.1 M spermidine. The particles were centrifuged for 3 seconds. The supernatant was removed and the particles were washed with 200 µl of 70% (v/v) ethanol and centrifuged for 3 seconds. The supernatant was removed and 24 µl 100% ethanol was added, mixed by pipetting, and the tube was placed in an ultrasonic bath, 8 µl aliquots of particles were removed and placed onto the center of macrocarrier disks that were held in a desiccator. Once the tungsten/DNA suspension had dried the microcarrier disk was placed in the bombardment chamber along with the plate of MM acetamide with spores and the bombardment process was performed according to the manufacturers instructions. After bombardment of the plated spores with the tungsten/DNA particles, the plates were incubated at 28° C. Transformed colonies were picked to fresh plates of MM acetamide after 4 days (Pentillä et al. (1987) *Gene* 61: 155-164), C. Demonstration of GA Activity from the Expressed Variant TrGA in Transformed Cells.

After 5 days growth on MM acetamide plates transformants displaying stable morphology were inoculated into 250 ml shake flasks containing 30 ml of Proflo medium, Proflo medium contained: 30 g/L α-lactose; 6.5 g/L $(NH_4)_2SO_4$; 2 g/L $KH_2PO_4$; 0.3 g/L $MgSO_4.7H_2O$; 0.2 g/L $CaCl_2.2H_2O$; 1 ml/L 400× trace element salt solution: citric acid 175 g/L, $FeSO_4.7H_2O$ 200 g/L, $ZnSO_4.7H_2O$ 16 g/L, $CuSO_4.5H_2O$ 3.2 g/L, $MnSO_4.H_2O$ 1.4 g/L, $H_3BO_3$ 0.8 g/L; 2 ml/L 10% Tween 80; 22.5 g/L ProFlo cottonseed flour (Traders protein, Memphis, Tenn.); 0.72 g/L $CaCO_3$. After two days growth at 28° C. and 140 rpm, 10% of the Proflo culture was transferred to a 250 ml shake flask containing 30 ml of Lactose Defined Media. The composition of the Lactose defined Media was as follows 5 g/L $(NH_4)_2SO_4$; 33 g/L 1,4-Piperazinebis(propanesulfonic acid) buffer; 9 g/L casamino acids; 4.5 g/L KH$_2$PO$_4$; 1.0 g/L MgSO$_4$.7H$_2$O; 5 ml/L Mazu DF60-P antifoam (Mazur Chemicals, IL); 1000× trace element solution; pH 5.5; 40 ml/L of 40% (v/v) lactose solution was added to the medium after sterilization. The Lactose Defined medium shake flasks were incubated at 28° C., 140 rpm for 4-5 days.

Samples of the culture supernatant were mixed with an appropriate volume of 2× sample loading buffer with reducing agent. Mycelium was removed by centrifugation and the supernatant was analyzed for total protein (BCA Protein Assay Kit, Pierce Cat. No. 23225).

GA activity was measured using the p-nitrophenyl-alpha-D-glucopyranoside (pNPG) assay with pNPG as a substrate (Sigma N-1377). In this assay the ability of glucoamylase to catalyze the hydrolysis of p-nitrophenyl-alpha-D-glucopyranoside (pNPG) to glucose and p-nitrophenol is measured. At an alkaline pH, the nitrophenol forms a yellow color that is proportional to glucoamylase activity and is monitored at 405 nm and compared against an enzyme standard measured as a GAU (Elder, M. T. and Montgomery R. S., Glucoamylase activity in industrial enzyme preparations using colorimetric enzymatic method, Journal of AOAC International, vol. 78(2), 1995). One GAU is defined as the amount of enzyme that will produce 1 gm of reducing sugar calculated as glucose per hour from a soluble starch substrate (4% ds) at pH 4.2 and 60° C.

The protein profile was determined by PAGE electrophoresis on NuPAGE® Novex 10% Bis-Tris Gel with MES SDS Running Buffer (Invitrogen, Carlsbad, Calif., USA).

Example 8

Small Scale Applications Testing of Selected Variants on Soluble Starch

*Trichoderma reesei* host strains expressing the single variants a) V314H, b) S211R, c) Q172F and d) Q208N were grown in fed-batch 14L fermentors at 34° C., pH 3.5 in nutrient media including glucose (Cerelose DE99), KH$_2$PO$_4$, MgSO$_4$.7H$_2$O, (NH$_4$)$_2$SO$_4$, CaCl$_2$.2H$_2$O, trace elements and Mazu anti-foam (DF6000K). Upon glucose depletion growth temperature and pH were shifted to 28° C. and 4.0, respectively. Cell material was removed by filtration and culture supernatants were collected and concentrated to contain greater than 90% glucoamylase as total protein.

Figure 6A:
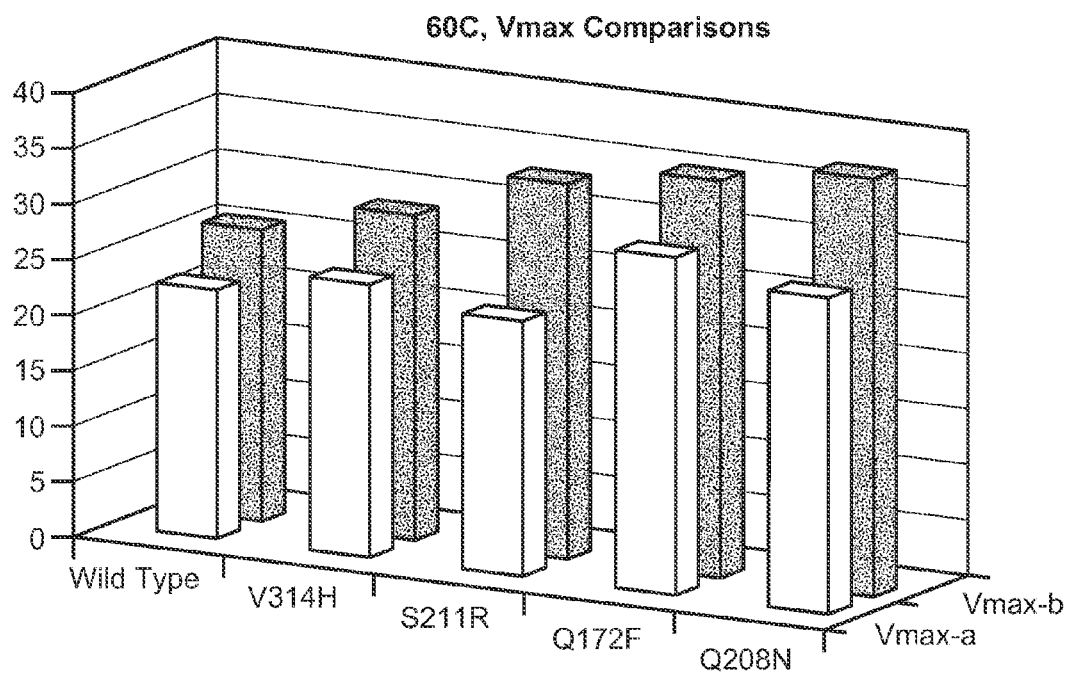
FIG. 6 depicts the $V_{max}$ (µM glucose/sec) comparison between the parent (wild-type) TrGA and variants, V314, S211R, Q172F, and Q208N at 60° C. and 32° C. as further discussed in Example 8.
Figure 6B:
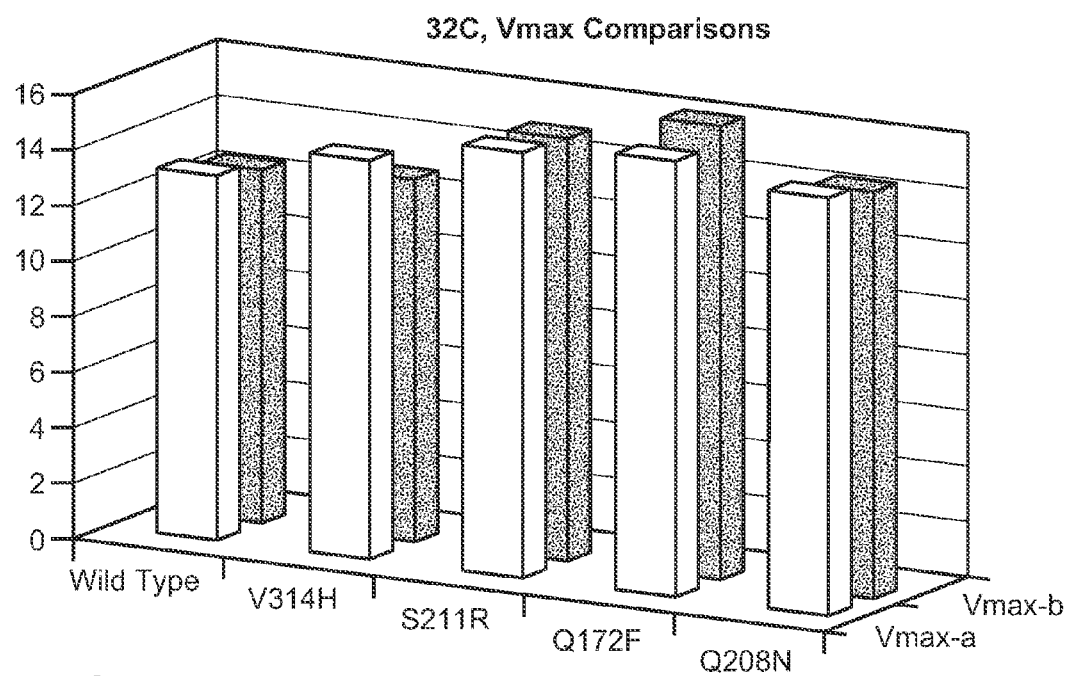

Various kinetic properties were determined for glucose production on soluble potato starch at pH 4.3 at 32° C. and at 60° C. and compared to the wild-type TrGA. Each of the four variants demonstrated increased V$_{max}$ (µM glucose/sec) values as compared to the wild type (TrGA) indicating elevated catalytic rates (k$_{cat}$ (sec$^{-1}$)). FIG. 6 illustrates the V$_{max}$ of two replicates for each temperature tested.

Example 9

Method to Determine the Performance on EOM Production of Variants

Validation of the screening was performed on the variants that were identified as having a higher performance index as compared to the parent TrGA (see Table 7/8) using a novel small scale Ethanol application test. Twenty-four variants derived from site evaluation and combinatorial (Table 9) libraries were selected and transformed directly into *T. reesei* for expression and testing on larger scale. The variants were tested for thermal unfolding using Differential Scanning calorimetry (DSC analysis described herein below) and performance using a novel secondary small-scale ethanol application assay. The method consisted of two steps: 1) injection of variants onto an anion exchange column to accurately determine the protein concentration; and 2) titration of variants with three different TrGA concentrations (0.3-0.15-0.075 g/28 g ds) in order to calculate their performance on ethanol production relative to the wild type molecule.

TABLE 9

List of combinatorial variants

| variant | mutation |
|---------|----------|
| LR8 | Q172F/Q208N |
| LR6 | Q172F/Q208N/V314H |
| LR12 | Q172F/S211R |
| SW3-1 | D24E/I43R/D44N/F175H/V181L/V314H/T353R |
| SW3-2 | D24L/I43F/D44N/F175H/V181L/V314H/T353R |
| ET4-1 | D24L/Q208Q/I292V/G294A/K297A/Y310R |
| ET4-2 | D24W/Q208F/I292V/G294Q/K297A/Y310R |
| ET5-1 | V181L/E243A/I292N/K297N/N317N/Y395Q |
| ET5-2 | V181L/E243R/I292F/K297A/N317N/Y395Q |
| ET7-1 | D24Y/V181L/Q208C/G294A/T353R/N375N/N409W |
| ET7-2 | D24L/V181L/Q208C/G294A/T353R/N375Q/N409W |
| ET8-1 | D24E/V181K/E243Y/I292V/G294Q/N409K |
| ET8-2 | D24E/V181F/E243R/I292N/G294I/N409W |
| ET9-1 | I043R/E243R/I292F/G294A/K297A |
| ET9-2 | I043R/E243R/I292L/G294A/K297M |

Protein Purification and Determination

A crude enzyme preparation was purified using an AKTA explorer 100 FPLC system (Amersham Biosciences, Piscataway, N.J.). β-Cyclodextrin was (Sigma-Aldrich, Zwijndrecht, The Netherlands; 85.608-8) coupled to epoxy-activated Sepharose beads (GE Healthcare, Diegem, Belgium; 17-0480-01). The column was used to capture glucoamylases from the enzyme preparation. Enzyme was eluted from the beads using 25 mM iris buffer pH 7.5 or 50 mM sodium acetate buffer pH 4.3 containing 10 mM α-cyclodextrin (Sigma, 28705). Purified samples were analyzed by SDS-PAGE, To accurately determine the protein concentration of the variants an FPLC based protein determination method was developed. The protein concentration of the purified marker TrGA molecule was first determined using a standard Bradford protocol (Bio-Rad cat#500-0205). Subsequently, purified samples were injected onto a ResourceQ_1 ml column (GE Healthcare) and enzyme was eluted with 25 mM Tris pH buffer containing 500 mM NaCl. Peak area was determined and the protein concentration was calculated relative to the peak area of the TrGA standard with known concentration.

Small Scale EtOH Application

Table 10 summarizes the production of ethanol and sugars (DP1, DP2, DP>3) by different combinatorial variants. A sample of corn mash liquefact obtained and diluted to 26% DS using thin stillage. The pH of the slurry was adjusted to pH 4.3 using 4N sulphuric acid. A 100 g aliquot of mash was placed into a 32° C. water bath and allowed to equilibrate. After 100 µl 400 ppm urea addition, 1 ml purified variant TrGA enzyme sample (150 µg/rd) or purified TrGA (300, 150, 75 µg/ml) was added to each corn mash sample. Finally, 333 µl of 30 minutes hydrated 15 g in 45 ml DI water solution of Red Star Red yeast (Lesaffre yeast Corp. Milwaukee, Wis.) was added to each sample. Samples were taken at 5, 21, 28, 48 and 52 hours and analyzed by HPLC using an Aminex HPX-87H column 9 (Bio-Rad).

Ethanol and Carbohydrate Determinations

A 2 ml eppendorf centrifuge tube was filled with fermentor beer and cooled on ice for 10 minutes. The sample was centrifuged for 3 minutes at 14.000×g and 500 µl of the supernatant was transferred to a test tube containing 50 µl of kill solution (1.1 N sulfuric acid) and allowed to stand for 5 minutes. 5.0 ml of water was added to the test tube and then filtered into a 0.22 µm filter plate (multiscreen, Millipore, Amsterdam, the Netherlands) and run on HPLC. Column Temperature: 60° C.; mobile phase: 0.01 N sulfuric acid; flow rate 0.6 ml/min; detector: RI; injection volume: 20 µl. The column separates molecules based on charge and molecular weight; DP1 (monosaccharides); DP2 (disaccharides); DP3 (trisaccharides); DP>3 (oligosaccharides sugars having a degree of polymerization greater than 3); succinic acid; lactic acid; glycerol; methanol; ethanol.

DSC Analysis

The melting temperature of purified enzyme samples (0.2-0.4 mg/ml) was determined using Differential Scanning calorimetry (DSC).

TABLE 10

Production of ethanol and saccharides

|  | hours | DP > 3 (m/v) % | DP2 (m/v) % | DP1 (m/v) % | ethanol (v/v) % |
|---|---|---|---|---|---|
| TrGA (0.3 mg) | 5.5 | 3.46 | 2.70 | 0.91 | 1.02 |
|  | 21.5 | 3.40 | 0.50 | 0.06 | 6.80 |
|  | 28.5 | 1.68 | 1.46 | 0.07 | 8.13 |
|  | 46 | 0.04 | 0.71 | 0.06 | 10.21 |
|  | 52.5 | 0.04 | 0.45 | 0.03 | 10.96 |
| TrGA (0.150 mg) | 5.5 | 3.40 | 2.43 | 0.15 | 1.00 |
|  | 21.5 | 3.78 | 0.21 | 0.03 | 4.23 |
|  | 28.5 | 3.86 | 0.20 | 0.03 | 5.07 |
|  | 46 | 2.73 | 0.52 | 0.06 | 7.86 |
|  | 52.5 | 1.70 | 0.87 | 0.04 | 7.92 |
| TrGA (0.075 mg) | 5.5 | 3.43 | 2.16 | −0.01 | 0.94 |
|  | 21.5 | 3.54 | 0.20 | 0.03 | 3.10 |
|  | 28.5 | 3.43 | 0.18 | 0.03 | 3.14 |
|  | 46 | 3.93 | 0.18 | 0.05 | 4.65 |
|  | 52.5 | 4.01 | 0.18 | 0.03 | 4.79 |
| ET7-1 | 5.5 | 3.45 | 2.53 | 0.21 | 1.00 |
|  | 21.5 | 3.94 | 0.22 | 0.04 | 4.77 |
|  | 28.5 | 3.89 | 0.23 | 0.04 | 5.58 |
|  | 46 | 1.58 | 1.22 | 0.06 | 8.64 |
|  | 52.5 | 0.62 | 1.50 | 0.04 | 9.14 |
| LR8 | 5.5 | 3.43 | 2.50 | 0.17 | 1.00 |
|  | 21.5 | 3.96 | 0.22 | 0.04 | 4.79 |
|  | 28.5 | 3.86 | 0.21 | 0.04 | 6.21 |
|  | 46 | 1.27 | 1.11 | 0.07 | 9.17 |
|  | 52.5 | 0.45 | 1.24 | 0.04 | 8.73 |
| LR12 | 5.5 | 3.47 | 2.51 | 0.16 | 1.05 |
|  | 21.5 | 3.86 | 0.22 | 0.04 | 4.44 |
|  | 28.5 | 3.94 | 0.22 | 0.04 | 5.30 |
|  | 46 | 2.09 | 1.08 | 0.07 | 8.56 |
|  | 52.5 | 0.99 | 1.52 | 0.04 | 9.16 |
| LR6 | 5.5 | 3.37 | 2.44 | 0.18 | 0.96 |
|  | 21.5 | 3.88 | 0.21 | 0.04 | 4.44 |
|  | 28.5 | 3.90 | 0.20 | 0.04 | 5.10 |
|  | 46 | 2.44 | 0.64 | 0.08 | 8.59 |
|  | 52.5 | 1.27 | 1.01 | 0.04 | 8.97 |
| ET8-1 | 5.5 | 3.46 | 2.53 | 0.22 | 0.99 |
|  | 21.5 | 3.99 | 0.21 | 0.04 | 4.86 |
|  | 28.5 | 3.90 | 0.21 | 0.04 | 5.76 |
|  | 46 | 1.29 | 1.11 | 0.08 | 8.94 |
|  | 52.5 | 0.47 | 1.25 | 0.04 | 9.56 |
| ET7-2 | 5.5 | 3.57 | 2.46 | 0.17 | 1.02 |
|  | 21.5 | 4.26 | 0.21 | 0.03 | 4.21 |
|  | 28.5 | 4.37 | 0.20 | 0.04 | 5.14 |
|  | 46 | 3.87 | 0.27 | 0.05 | 7.21 |
|  | 52.5 | 3.27 | 0.33 | 0.03 | 8.07 |

Table 11 represents the final ethanol yields and the performance of the variants at 0.15 mg dosage. The performance was calculated by interpolation of the 0.3 mg and 0.15 mg values of the TrGA by the values of the variants.

TABLE 11

Ethanol Yields

| variant | EtOH % (v/v) | performance relative to TrGA |
|---|---|---|
| TrGA 0.3 mg | 10.21 |  |
| TrGA 0.15 mg | 7.86 | 1.00 |
| TrGA 0.075 mg | 4.65 |  |
| ET7-1 | 8.64 | 1.33 |
| LR8 | 9.17 | 1.56 |
| LR12 | 8.56 | 1.30 |
| LR6 | 8.59 | 1.31 |
| ET8-1 | 8.94 | 1.46 |
| ET7-2 | 7.21 | 0.72 |

All combinatorial variants except ET7-2 performed better than TrGA wild type. LR8 performed the best with a 1.56 improved performance.

Table 12 gives an overview of all single site and combinatorial variants tested using the small-scale ethanol application assay. Variants that are shaded in Table 12 had a better performance than TrGA and also had a higher thermal unfolding temperature ($dT_m$).

TABLE 12

Performance and thermal unfolding of variants relative to TrGA

| Variant | X TrGA | dTm |
|---|---|---|
| LR8 | 1.56 | 0.30 |
| ET8-1 | 1.46 | 1.60 |
| ET7-1 | 1.33 | 0.90 |
| LR6 | 1.31 | 0.73 |
| LR12 | 1.30 | −0.13 |
| ET5-2 | 1.29 | −0.31 |
| ET4-2 | 1.27 | 0.71 |
| Y213C | 1.27 | 0.06 |
| ET4-1 | 1.21 | −2.64 |
| SW3-1 | 1.21 | 0.29 |
| Q172F | 1.18 | −0.01 |
| V314H | 1.17 | −0.44 |
| G294I | 1.16 | −0.22 |
| S211R | 1.12 | −0.44 |
| Q208N | 1.08 | −0.22 |
| ET9-1 | 1.04 | −1.33 |
| K297A | 1.03 | −1.11 |
| SW3-2 | 1.00 | 0.88 |
| TrGA | 1.00 | 0.00 |
| G294Q | 0.99 | −0.86 |
| ET8/2 | 0.93 | −0.01 |
| P94N | 0.76 | −5.17 |
| ET5-1 | 0.76 | −3.28 |
| ET7-2 | 0.72 | −3.59 |
| S214L/C222F | 0.70 | −3.98 |

The results showed that Chromatography (FPLC) was a useful tool to accurately determine the protein concentration. The results also showed that titration of variants with three TrGA concentrations was a valuable method to determine the performance of variants on small scale. Seven variants performed better than TrGA wild type (see Table 12) and also had a higher thermal unfolding temperature and the variants that did not perform as well as TrGA also had a lower $T_m$.

Example 10

Specific Activity Determination of a Selected Set of Combinatorial and Single Site Variants and Substrate Specificity of LR8

The specific activity of a set of the combinatorial variants and several single site variants that were used to construct combinatorial variants was analyzed (Table 13). LR8 (PI 1.56 determined with small scale application assay) as further studied with respect to substrate specificity. This was done by setting up an MTP assay to determine the glucose production rates of GA variants and to determine substrate specificity of the LR8 variant. The MTP assay was found to discriminate between variants and all variants except ET7-1 showed higher rates than the wild-type (wt) *Trichoderma reesei* glucoamylase. Further, several variants (LR8/ET8/Q172F) performed 20-30% better than TrGA. LR8 performed better on soluble corn starch and two different samples of corn mash liquefact compared to wild-type.

Substrates used in the following experiments were soluble corn starch stock solution prepared as follows: 8 g soluble corn starch (Sigma # S4180) was dissolved in 100 ml milliQ water and heated in a microwave for 1 minute. The dispersion was boiled for 5 minutes and after cooling the volume was adjusted to 100 ml. 4% soluble corn starch was prepared by diluting the stock solution 1:1 with 100 mM NaAc buffer pH 4. In one experiment, a corn liquefact substrate (NE) was prepared using a moisture analyzer to measure % ds, then substrate was diluted 7.5× with 50 mM NaAc to finally obtain 4% ds. The substrate was centrifuged for 5' at 2000×g and the supernatant was filtered with a 0.22 μm filter. In another experiment, a corn liquefact substrate (BSE) was prepared in the same way, except that the substrate was diluted 10× before centrifugation.

The enzyme was diluted using the Stock solution of 150 μg enzyme/ml (3 μg/180 μl reaction mixture). Solutions were further diluted with 50 mM NaAc pH 4.0 as follows: 300 ng (10×), 200 ng, 150 ng, 100 ng, 75 ng, 50 ng, 25 ng, 10 ng/180 μl reaction mixture The assay was performed as follows: 40 μl 50 mM NaAc pH 4.0, 120 μl 4% soluble corn starch, and 20 μl enzyme were added to each well. Samples were incubated for 2 hr at 32° C. 900 rpm and terminated on ice after addition of 90 μl 800 mM glycine-NaOH buffer pH 10 for 5 min. The plate was centrifuged for 5 min at 2000 rpm at 15° C. To a fresh plate, 85 μl milliQ water and 100 μl hexokinase cocktail (II test glucose (HK) kit, Instrumental Laboratory #182507-40) and 20 μl supernatant were added. For a glucose (0-1 mg/ml) calibration line 20 μl glucose stock was added instead. Plates were incubated for 10 min at room temperature in the dark followed by absorption measurement at 340 nm using the Spectramax.

TABLE 13

| | performance relative to wt | | | | | | | |
|---|---|---|---|---|---|---|---|---|
| | 300 | 200 | 150 | 100 | 75 | 50 | 25 | 10 ng GA |
| graph1 | | | | | | | | |
| TrGA | 1.00 | 1.00 | 1.00 | 1.00 | 1.00 | 1.00 | 1.00 | 1.00 |
| ET7-1 | 0.94 | 0.98 | 0.91 | 0.92 | 0.63 | 0.38 | 3.50 | 0.53 |
| LR8 | 0.93 | 1.00 | 1.22 | 0.91 | 0.64 | 0.06 | −0.89 | −3.99 |
| LR12 | 0.94 | 0.99 | 1.17 | 0.83 | 0.66 | −0.15 | −0.99 | 0.62 |
| LR6 | 0.94 | 1.01 | 1.16 | 0.99 | 0.55 | 0.17 | −1.67 | −4.36 |
| ET8-1 | 0.87 | 0.95 | 1.29 | 1.02 | 0.62 | −0.05 | −1.64 | −3.42 |
| ET7-2 | 0.94 | 1.00 | 1.24 | 0.93 | 0.50 | 0.22 | −0.62 | −1.40 |
| graph2 | | | | | | | | |
| V314H | 0.95 | 0.97 | 1.24 | 0.91 | 0.78 | 0.54 | 0.74 | 1.89 |
| G294Q | 0.98 | 0.99 | 1.03 | 1.21 | 1.10 | 0.19 | −0.34 | −1.12 |
| S211R | 0.97 | 0.99 | 1.21 | 1.05 | 0.94 | 0.27 | −1.32 | 0.53 |
| Q208N | 0.97 | 1.01 | 1.13 | 0.95 | 0.90 | −0.05 | −1.01 | −2.81 |
| Q172F | 0.99 | 1.04 | 1.31 | 1.23 | 1.32 | 0.38 | −1.59 | −2.20 |
| G294I | 0.91 | 0.96 | 1.07 | 1.25 | 0.80 | 0.09 | −1.20 | −3.66 |

TABLE 13-continued

| | performance relative to wt | | | | | | | |
|---|---|---|---|---|---|---|---|---|
| | 300 | 200 | 150 | 100 | 75 | 50 | 25 | 10 ng GA |
| P94N | 0.98 | 1.00 | 1.24 | 1.09 | 1.05 | 0.29 | 6.29 | −3.80 |
| TrGA | 1.00 | 1.00 | 1.00 | 1.00 | 1.00 | 1.00 | 1.00 | 1.00 |

Figure 7:
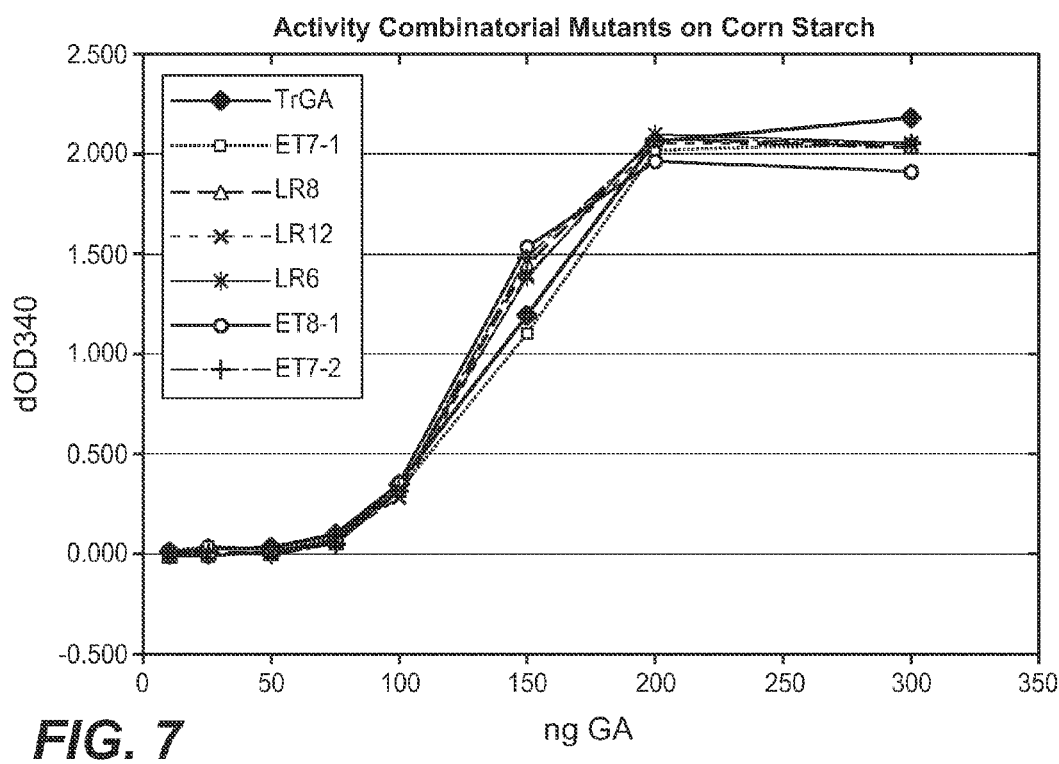
FIG. 7 depicts the activity of combinatorial variants on a starch substrate. Combinatorial variants described herein include ET7-1 (D24Y/V181L/Q208C/G294A/T353R/ N375N/N409W), LR8 (Q172F/Q208N), LR12 (Q172F/ S211R), LR6 (Q172F/Q208N/V314H), ET8-1 (D24E/ V181K/E243Y/I292V/G294Q/N409K), and ET7-2 (Q24L/ V181L/Q208C/G294A/T353R/N375Q/N409W). Activity is represented in units of absorption at 340 nm as a function of ng of indicated glucoamylase variants.
Figure 8:
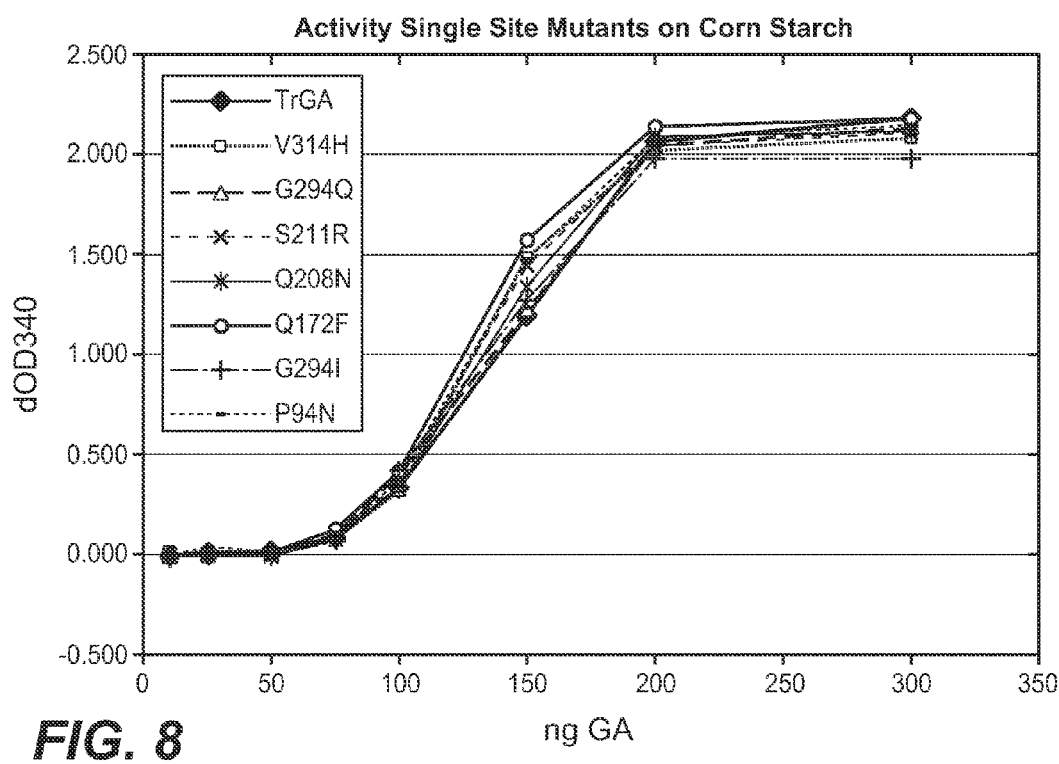
FIG. 8 depicts the activity of single site variants on a cornstarch substrate. Single site variants described herein include V314H, G294Q, S211R, Q208N, G294I, and P94N. Activity is represented in units of absorption at 340 nm as a function of ng of indicated glucoamylase variants.

The results of the assay to determine the glucose production rates of by GA variants are shown in FIGS. 7 and 8. In these figures, the relative performance to TrGA was calculated per amount of enzyme added. Conclusions were drawn from the linear region of the graph at 150 ng of enzyme. The results in FIGS. 7, 8 and Table 13 showed that LR8, ET8, ET7-2, S211R, Q172F and P94N performed better than wild-type over the linear range.

Figure 9:
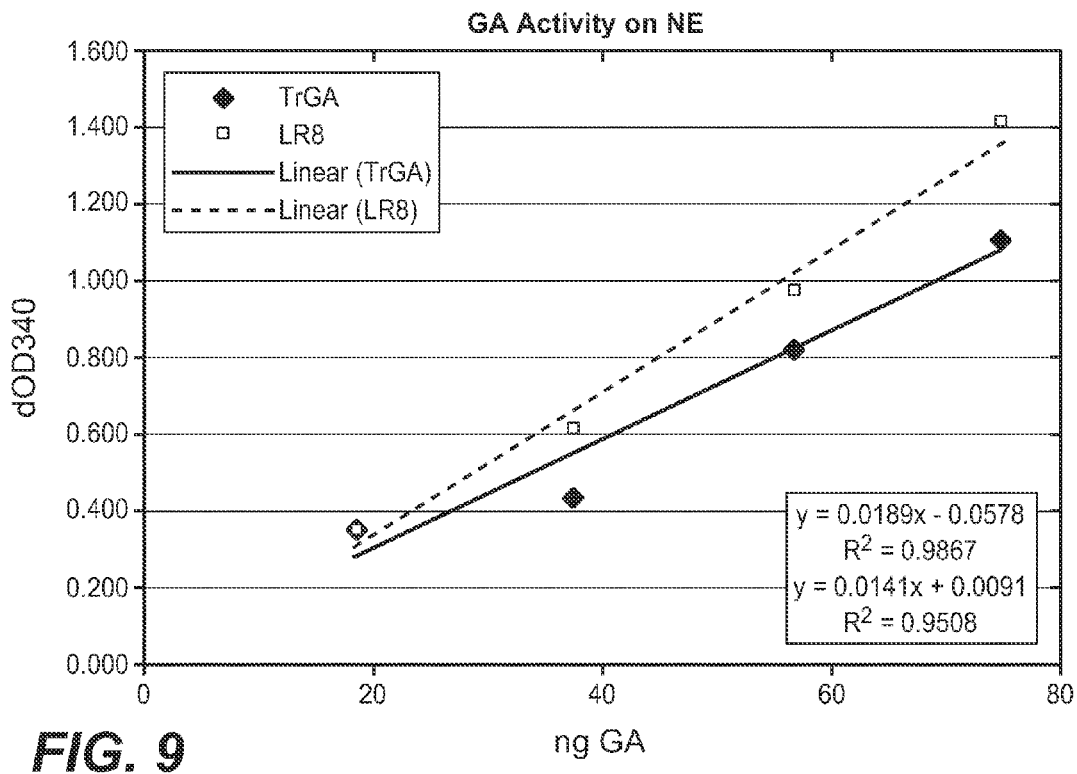
FIG. 9 depicts the glucoamylase activity of TrGA and the TrGA variant LR8 (Q172F/Q208N) on a sample of corn mash liquefact (NE).
Figure 10:
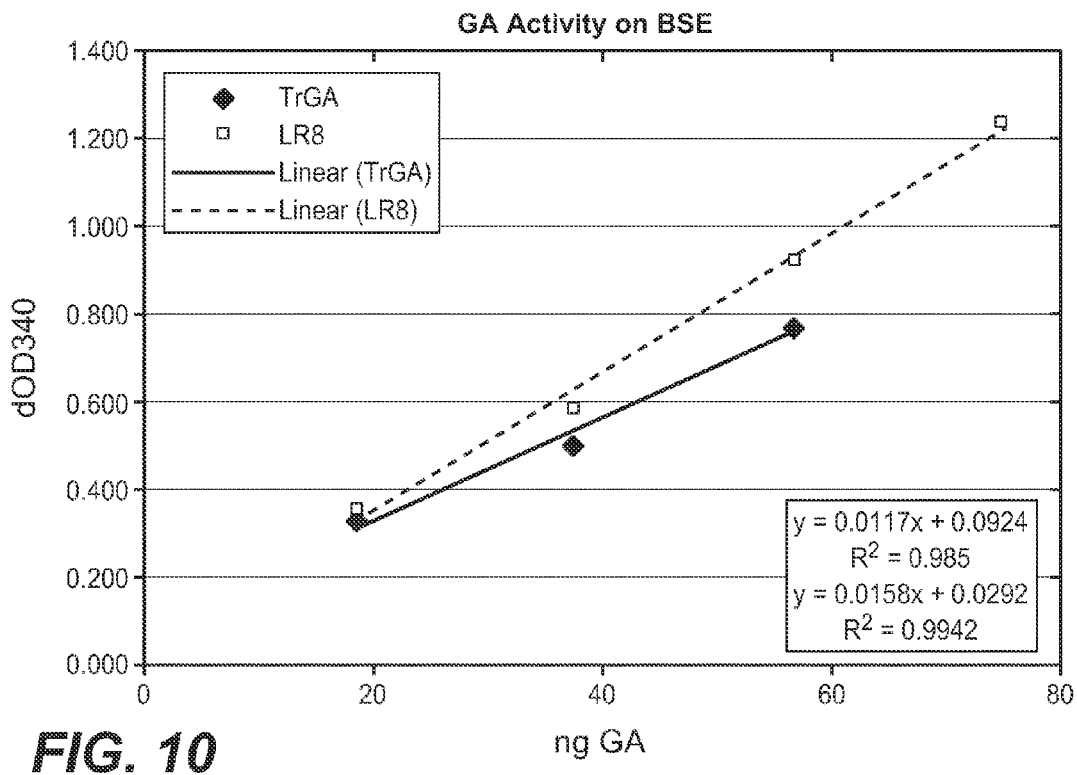
FIG. 10 depicts the activity profile of TrGA and the TrGA variant LR8 (Q172F/Q208N) on a sample of corn mash liquefact (BSE).
Figure 11:
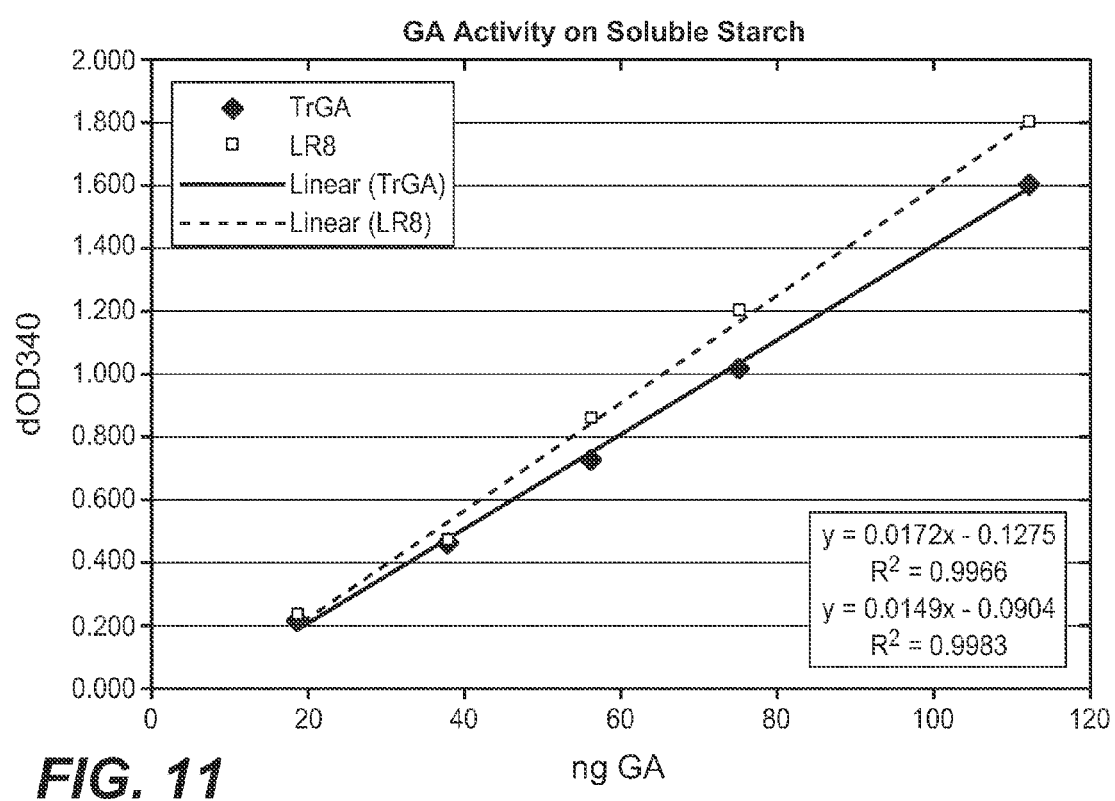
FIG. 11 depicts the activity profile of TrGA and the TrGA variant LR8 (Q172F/Q208N) on a sample soluble cornstarch substrate.

To determine the substrate specificity of LR8, the performance of LR8 and TrGA wild-type was tested on substrates (soluble corn starch, and the two corn mash substrates produced in Example 10) used in screening and application. When analyzed by HPLC, the substrates showed a difference in degree of polymerization (DP) pattern (see FIGS. 9-11). In NE and BSE DP1->=DP4 is present while soluble corn starch consist of at least four or more glucose molecules. On all substrates LR8 performed better than wild-type (see FIGS. 9, 10 and 11).

Example 11

Figure 14A:
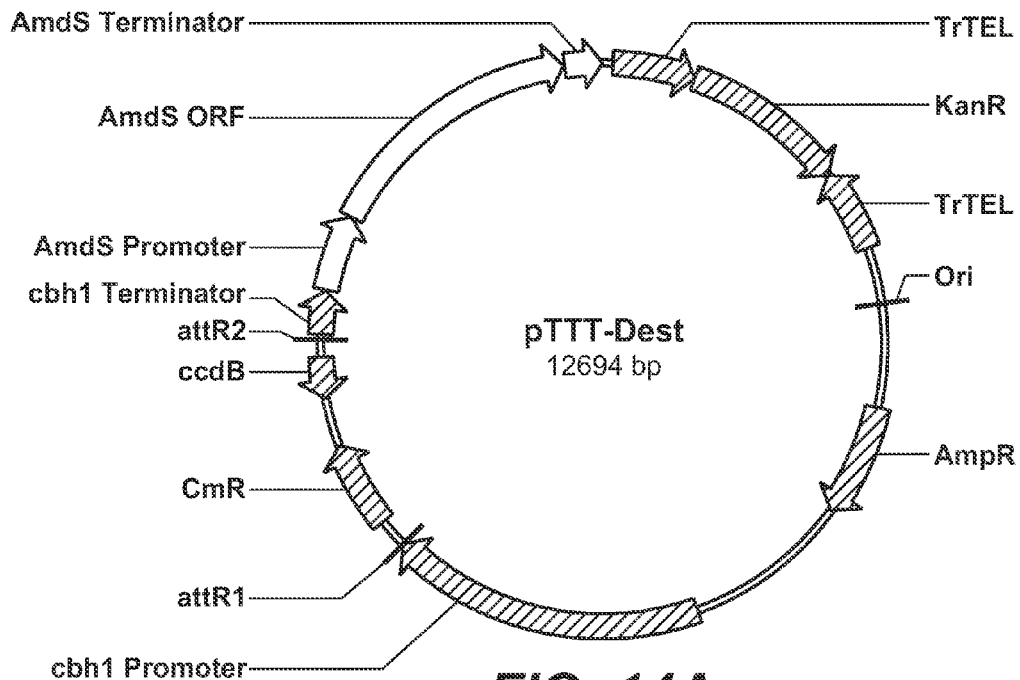
FIG. 14A depicts the plasmid pTTT-Dest.
Figure 14B:
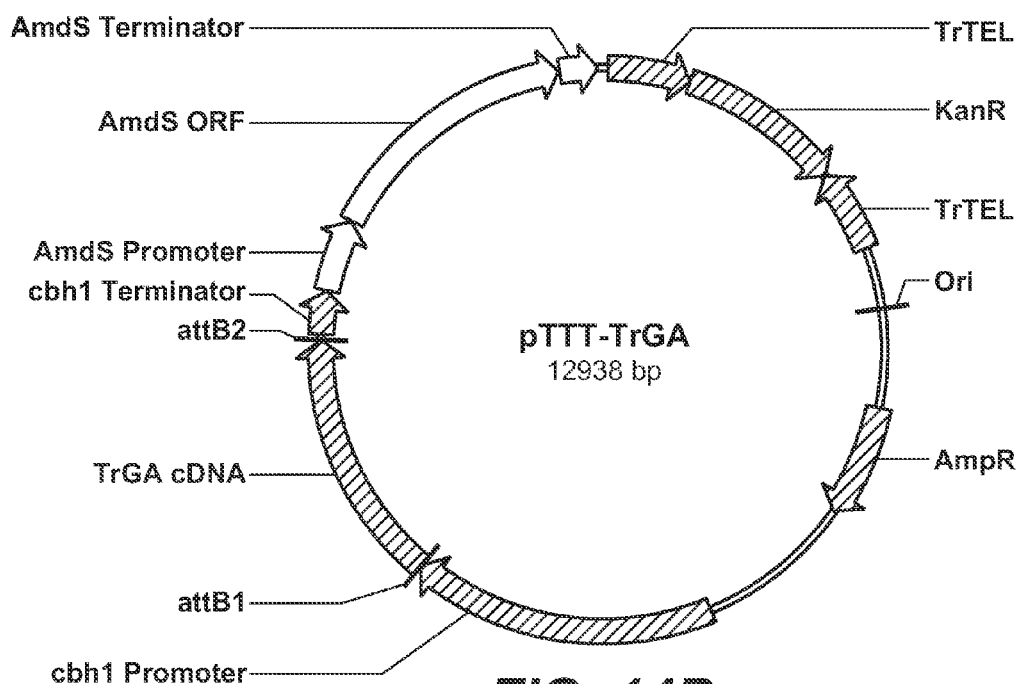
FIG. 14B depicts the plasmid pTTT-TrGA(B).

Screening and Characterization of Variants Expressed in *Trichoderma reesei* Using TrGA Site Evaluation Libraries (SELs) in the pTTT Vector Additional TrGA variants, particularly variants with substitutions within the SBD, were created and screened directly in *Trichoderma reesei*. Similar to Example 1, another ten TrGA site saturated mutagenesis (SSM) libraries were constructed using the pDONR-TrGA entry vector as a template and primers listed in Table 14. The sites include: N61, G73, L417, T430, A431, E503, Q511, A535, A539, and N563. Among these sites, E503, Q511, A535, A539, and N563 are located within the starch binding domain of the TrGA. Subsequently, the recombination was performed with the pTTT-Dest vector (FIG. 14) using the LR CLONASE™ II enzyme mix according to the protocol supplied by Invitrogen. The recombination products were transformed into *E. coli* Max efficiency DH5α (Invitrogeu and plated on 2×TY medium [Bacto Tryptone (Difco) 16 g/L, Bacto Yeast Extract (Difco) 10 g/t, NaCL 5 g/L] supplemented with 100 μg/mL ampicillin. After overnight incubation at 37° C., 96 single colonies of each library were picked from 2×TY agar plates with 100 μg/ml ampicillin and grown for 24 hrs at 37° C. in a MTP containing 200 μL 2×TY medium with 100 μg/ml ampicillin. Cultures were used for sequence analyses (ABI3100 sequence analyzer, Applied Biosystems). Each library contained from 15 to 19 different TrGA variants in the final expression vector. These variants were individually transformed into *T. reesei*.

TABLE 14

Primers used to generate additional TrGA SSM libraries

| AA-position | F/R | DNA sequence 5' to 3' |
|---|---|---|
| 61 | F | AGATAGCGCTCTTGTCTTCAAGNNSCTCATCGACCGC |
| 61 | R | CTTGAAGACAAGAGCGCTATC |
| 73 | F | CTTCACCGAAACGTACGATGCGNNSCTGCAGCGCCGC |
| 73 | R | CGCATCGTACGTTTCGGTGAA |
| 417 | F | CAGCGGCACTCCGCTGTCTGCGNNSCACCTGACGTGGT |
| 417 | R | CGCAGACAGCGGAGTGCCGCT |
| 430 | F | GTACGCCTCGTTCTTGACAGCCNNSGCCCGTCGGGCT |
| 430 | R | GGCTGTCAAGAACGAGGCGTA |
| 431 | F | CGCCTCGTTCTTGACAGCCACGNNSCGTCGGGCTGGC |
| 431 | R | CGTGGCTGTCAAGAACGAGGC |
| 503 | R | CTCCGTGGCCGTCACCTTCCACNNSCTCGTGTCGACACA |
| 503 | R | GTGGAAGGTGACGGCCACGGA |
| 511 | F | GCTCGTGTCGACACAGTTTGGCNNSACGGTCAAGGTG |
| 511 | R | GCCAAACTGTGTCGACACGAG |
| 535 | F | GAGCGCCGCCGTGGCTCTGGACNNSGTCAACTATGCCGATA |
| 535 | R | GTCCAGAGCCACGGCGGCGCTCGTGCT |
| 539 | F | GGCTCTGGACGCCGTCAACTATNNSGATAACCACCCCCTGT |
| 539 | R | ATAGTTGACGGCGTCCAGAGCCACGGC |
| 563 | F | CGTCGTGGAGTACAAGTACATCNNSGTGGGCCAAGATGGCTCC |
| 563 | R | GATGTACTTGTACTCCACGACGTCTCC |

The SELs were transformed into *T. reesei* using the PEG-protoplast method (see, e.g., Pentillä et al. (1987) *Gene* 61: 155-164). The *T. reesei* host is a strain derived from RL-P37 (IA52) and having four gene deletions (Δcbh1, Δcbh2, Δegl1, Δegl2; i.e., "quad-deleted;" see U.S. Pat. No. 5,847,276, WO 92/06184, and WO 05/001036). Transformation mixtures containing up to 600 ng of DNA and 1–5×10$^5$ protoplasts in a total volume of 25 μl were treated with 200 ml of 25% PEG solution, diluted with 2 volumes of 1.2 M sorbitol solution, mixed with 3% selective top agarose MM with acetamide and poured onto 2% selective agarose with acetamide either in 24 well microliter plates. The plates were incubated at 28° C. for 5 to 8 days. Spores from the total population of transformants regenerated on each individual well were harvested from the plates using a solution of 0.85% NaCl, 0.015% Tween 80. Spore suspensions were used to inoculate fermentations in 96 well MTP. In the case of 24 well MTPs, an additional plating step on a fresh 24 well MTP with selective acetamide MM was introduced in order to enrich the spore number.

The transformants were fermented in MTPs and the culture supernatants containing the expressed protein variants were used for assays. In brief, MTPs containing 200 μl of LD-GSM medium were inoculated in quadruplicate with spore suspensions of *T. reesei* transformants expressing TrGA variants (more than 10$^4$ spores per well). The plates were incubated at 28° C. with 230 rpm shaking and 80% humidity for 6 days. Culture supernatants were harvested by vacuum filtration. The supernatants were used in different assay for screening of variants with improved properties.

Variants exhibiting a performance index of more than 1.0 for thermal stability, specific activity, and both thermal stability and specific activity are shown in Tables 15-17.

TABLE 15

Thermal stability screening of additional TrGA variants

| Variants | PI of thermal stability | Variants | PI of thermal stability |
|---|---|---|---|
| N061V | 1.06 | E503A | 1.43 |
| G073F | 1.44 | E503C | 1.39 |
| G073M | 1.01 | E503S | 1.02 |
| G073N | 1.10 | E503T | 1.04 |
| G073W | 1.36 | E503V | 1.68 |
| L417I | 1.04 | Q511A | 1.11 |
| L417K | 1.20 | Q511D | 1.12 |
| L417M | 1.05 | Q511H | 1.33 |
| L417Q | 1.04 | Q511N | 1.14 |
| L417R | 1.20 | Q511S | 1.15 |
| L417V | 1.07 | A535D | 1.12 |
| L417Y | 1.01 | A535K | 1.24 |
| T430A | 1.05 | A535N | 1.37 |
| T430E | 1.02 | A535P | 1.59 |
| T430F | 1.06 | A535R | 1.26 |
| T430H | 1.10 | A539E | 1.32 |
| T430I | 1.04 | A539H | 1.17 |
| T430K | 1.08 | A539M | 1.05 |
| T430M | 1.17 | A539R | 1.36 |
| T430N | 1.13 | A539S | 1.30 |
| T430Q | 1.05 | N563A | 1.14 |
| T430R | 1.13 | N563C | 1.49 |

TABLE 15-continued

Thermal stability screening of additional TrGA variants

| Variants | PI of thermal stability | Variants | PI of thermal stability |
|---|---|---|---|
| T430S | 1.17 | N563E | 1.44 |
| T430V | 1.05 | N563I | 1.65 |
| A431I | 1.03 | N563K | 1.77 |
| A431N | 1.03 | N563L | 1.60 |
| A431P | 1.08 | N563Q | 1.29 |
| A431R | 1.08 | N563T | 1.31 |
| A431V | 1.03 | N563V | 1.53 |

TABLE 16

Specific activity screening of additional TrGA variants.

| Variants | PI of specific activity | Variants | PI of specific activity |
|---|---|---|---|
| N061D | 1.05 | A431I | 1.20 |
| N061I | 1.21 | A431L | 1.21 |
| N061L | 1.18 | A431M | 1.12 |
| N061Q | 1.08 | A431Q | 1.22 |
| N061V | 1.11 | A431R | 1.11 |
| N061W | 1.02 | A431S | 1.09 |
| G073C | 1.02 | A431W | 1.04 |
| G073L | 1.07 | A431Y | 1.13 |
| G073W | 1.03 | E503C | 1.05 |
| L417A | 1.12 | E503D | 1.06 |
| L417D | 1.19 | E503H | 1.01 |
| L417E | 1.10 | E503S | 1.10 |
| L417F | 1.08 | E503W | 1.04 |
| L417G | 1.19 | Q511C | 1.07 |
| L417I | 1.10 | Q511G | 1.06 |
| L417K | 1.02 | Q511H | 1.05 |
| L417Q | 1.04 | Q511I | 1.10 |
| L417R | 1.30 | Q511K | 1.09 |
| L417S | 1.05 | Q511T | 1.04 |
| L417T | 1.10 | Q511V | 1.04 |
| L417V | 1.21 | A535E | 1.19 |
| L417W | 1.05 | A535F | 1.06 |
| L417Y | 1.10 | A535G | 1.02 |
| T430A | 1.19 | A535K | 1.07 |
| T430E | 1.15 | A535L | 1.02 |
| T430F | 1.09 | A535N | 1.04 |
| T430G | 1.16 | A535P | 1.14 |
| T430H | 1.15 | A535R | 1.22 |
| T430I | 1.06 | A535S | 1.06 |
| T430K | 1.24 | A535T | 1.04 |
| T430M | 1.16 | A535V | 1.04 |
| T430N | 1.07 | A535W | 1.09 |
| T430Q | 1.15 | A535Y | 1.13 |
| T430R | 1.04 | A539E | 1.08 |
| T430V | 1.09 | A539M | 1.03 |
| A431C | 1.04 | A539S | 1.02 |
| A431E | 1.08 | A539W | 1.06 |
| A431H | 1.11 | A539R | 1.22 |

TABLE 17

Additional TrGA variants displaying both increased thermal stability and specific activity

| Variants | PI of specific activity | PI of thermal stability | Variants | PI of specific activity | PI of thermal stability |
|---|---|---|---|---|---|
| N061V | 1.11 | 1.06 | T430Q | 1.15 | 1.05 |
| G073W | 1.03 | 1.36 | T430R | 1.04 | 1.13 |
| L417I | 1.10 | 1.04 | T430V | 1.09 | 1.05 |
| L417K | 1.02 | 1.20 | A431I | 1.20 | 1.03 |
| L417Q | 1.04 | 1.04 | A431R | 1.11 | 1.08 |
| L417R | 1.30 | 1.20 | E503C | 1.05 | 1.39 |
| L417V | 1.21 | 1.07 | E503S | 1.10 | 1.02 |
| L417Y | 1.10 | 1.01 | Q511H | 1.05 | 1.33 |
| T430A | 1.19 | 1.05 | A535K | 1.07 | 1.24 |
| T430E | 1.15 | 1.02 | A535N | 1.04 | 1.37 |
| T430F | 1.09 | 1.06 | A535P | 1.14 | 1.59 |
| T430H | 1.15 | 1.10 | A535R | 1.22 | 1.26 |
| T430I | 1.06 | 1.04 | A539E | 1.08 | 1.32 |
| T430K | 1.24 | 1.08 | A539M | 1.03 | 1.05 |
| T430M | 1.16 | 1.17 | A539R | 1.22 | 1.36 |
| T430N | 1.07 | 1.13 | A539S | 1.02 | 1.30 |

Example 12

Characterization of a Selected Set of Single Site and Combinatorial Variants

Based on the results of Examples 4-6 and 11, a selected set of combinatorial variants, and single site variants were further characterized for their alter properties. The selected set includes single site and combinatorial variants with substitution(s) at: I43, D44, N61, G73, G294, L417, T430, A431, E503, Q511, A535, A539, and for N563. Variants were purified from large-scale fermentation, and PIs of thermal stability and specific activities were determined. Specifically, specific activities were determined using different substrates, including DP7, cornstarch, and liquefact. The results are shown in Table 18 and 19.

TABLE 18

PIs of a selected set of single site variants, each of which is from a 500 ml fermentation

| Variants | P.I. DP7-FPLC | P.I. CornStarch-FPLC | P.I. Thermal Stability | P.I. Liquefact-FPLC |
|---|---|---|---|---|
| N61I | 1.16 | 1.35 | 1.00 | 1.66 |
| A431L | 1.15 | 1.38 | 1.18 | 1.51 |
| L417V | 1.18 | 1.32 | 1.02 | 1.40 |
| A431Q | 1.06 | 1.20 | 0.92 | 1.24 |
| G294C | 1.01 | 0.84 | 0.94 | 1.23 |
| N563K | 1.07 | 1.12 | 1.97 | 1.15 |
| Q511H | 1.05 | 1.09 | 1.52 | 1.13 |
| T430M | 1.05 | 1.15 | 0.89 | 1.09 |
| E503A | 1.08 | 1.16 | 1.40 | 1.09 |
| I43Q | 1.11 | 1.24 | 0.94 | 1.08 |
| A539R | 1.15 | 1.37 | 1.43 | 1.08 |
| I43R | 1.03 | 1.07 | 1.41 | 1.07 |
| L417R | 1.23 | 1.27 | 1.51 | 1.04 |
| T430A | 1.13 | 1.35 | 1.23 | 1.04 |
| G73F | 1.06 | 1.06 | 1.45 | 1.03 |
| D44R | 0.97 | 1.06 | 1.46 | 0.98 |
| N563I | 1.09 | 1.22 | 2.06 | 0.92 |
| D44C | 0.80 | 0.82 | 0.96 | 0.91 |
| E503V | 1.17 | 1.07 | 1.66 | 0.88 |
| A535R | 1.09 | 1.44 | 1.47 | 0.85 |

TABLE 19

PIs of a selected set of combinatorial variants

| Ferm. | Variant | Substitutions | P.I. DP7-FPLC | P.I. Corn Starch-FPLC | P.I. Thermal Stability | P.I. Liquefact-FPLC |
|---|---|---|---|---|---|---|
| 100 ml | C4 | G73F/T430A/E503V/Q511H | 1.05 | 1.06 | 2.57 | 1.01 |
| 100 ml | C9 | D44C/G73F/L417R/N563K | 0.95 | 1.00 | 2.57 | 1.22 |
| 100 ml | C11 | D44C/G473F/N563K | 0.83 | 1.04 | 2.42 | |
| 500 ml | ALL5 | I43R/L417V/E503A/Q511H/A539R | 1.22 | 1.48 | 2.37 | 1.87 |
| 100 ml | C15 | D44C/L417R/N563K | 0.95 | 1.09 | 2.30 | 0.99 |
| 100 ml | C8 | D44C/G73F/N563K | 0.87 | 1.05 | 2.28 | |
| 500 ml | C5 | D44C/G73F/N563K | 0.90 | 0.71 | 2.16 | 0.97 |
| 500 ml | TS1 | I43R/T430A/E503V/A535R/N563K | | | 2.13 | |
| 500 ml | C7 | D44C/G73F/E503V/Q511H | 0.90 | 0.79 | 2.10 | 0.89 |
| 500 ml | ALL1 | I43Q/D44C/L417V/E503A/Q511H/A539R | 1.00 | 1.27 | 1.95 | 1.59 |
| 500 ml | CS4 | L417V/T430A/Q511H/A539R/N563I | 1.21 | 1.53 | 1.95 | 1.73 |
| 100 ml | C2 | I43R/G73F/T430A | 1.09 | 1.25 | 1.91 | 1.18 |
| 500 ml | RB7 | I43Q/T430A/Q511H/L417V/A539R | 1.11 | 1.36 | 1.85 | 2.17 |
| 500 ml | C1 | G73F/T430A/Q511H | 1.20 | 1.07 | 1.84 | 0.96 |
| 500 ml | ALL2 | I43Q/L417V/E503A/Q511H/A539R | 1.16 | 1.52 | 1.84 | 1.96 |
| 500 ml | ALL6 | I43R/N61I/L417V/E503A/Q511H/A539R | 1.06 | 1.53 | 1.84 | 2.24 |
| 500 ml | ALL8 | I43R/N61I/L417R/E503A/Q511H/A539R | 1.10 | 1.53 | 1.84 | 2.11 |
| 500 ml | RB20 | I43Q/Q511H/A539R/T430M/N61I/L417V | 1.01 | 1.55 | 1.79 | 1.95 |
| 500 ml | ALL4 | I43Q/N61I/L417V/E503A/Q511H/A539R | 1.08 | 1.52 | 1.79 | 1.73 |
| 500 ml | CS3 | L417V/T430A/Q511H/A535R/N563I | 0.98 | 1.40 | 1.69 | 1.78 |
| 500 ml | RB9 | I43Q/T430A/Q511H/A431L/E503A | 0.93 | 1.39 | 1.69 | 1.55 |
| 500 ml | RB17 | I43Q/Q511H/A539R/E503A | 1.12 | 1.38 | 1.68 | 1.40 |
| 500 ml | ALL7 | I43R/L417R/E503A/A539R | 1.04 | 1.54 | 1.67 | 1.62 |
| 500 ml | TS4 | I43R/T430A/E503A/Q511H/N563K | 0.98 | 1.33 | 1.66 | 1.33 |
| 500 ml | RB18 | I43Q/Q511H/A539R/T430M | 1.06 | 1.44 | 1.64 | 1.40 |
| 100 ml | C12 | I43R/T430A/ | 1.15 | 1.35 | 1.60 | 1.26 |
| 500 ml | RB16 | I43Q/Q511H/A539R/N61I | 1.11 | 1.43 | 1.60 | 1.34 |
| 500 ml | TS5 | D44R/T430A/Q511H/A535R | 0.89 | 1.22 | 1.59 | 1.21 |
| 500 ml | RB8 | I43Q/T430A/Q511H/A431L/A539R | 1.02 | 1.38 | 1.59 | 2.18 |
| 500 ml | RB11 | I43Q/T430A/Q511H/L417V/A539R/A431L | 1.05 | 1.36 | 1.58 | 2.03 |
| 500 ml | CS1 | L417V/T430A/A431L/Q511H/A535R/A539R/N563I | 1.08 | 1.71 | 1.56 | 2.35 |
| 500 ml | LQ5 | L417R/A431L/Q511H | 0.95 | 1.21 | 1.56 | 1.88 |
| 500 ml | CS2 | L417V/T430A/A431Q/Q511H/A535R/A539R/N563I | 1.07 | 1.71 | 1.56 | 2.32 |
| 500 ml | TS2 | D44R/E503A/Q511H/N563I | 0.90 | 1.14 | 1.53 | 1.23 |
| 500 ml | RB15 | I43Q/Q511H/A539R | 1.19 | 1.42 | 1.52 | 1.69 |
| 500 ml | RB13 | I43Q/Q511H/L417V | 1.06 | 1.38 | 1.50 | 1.50 |
| 500 ml | RB5 | I43Q/T430A/Q511H/A539R | 0.99 | 1.45 | 1.47 | 1.59 |
| 500 ml | RB4 | I43Q/T430A/Q511H/E503A | 1.07 | 1.29 | 1.47 | 1.50 |
| 500 ml | RB19 | I43Q/Q511H/A539R/T430M/N61I | 1.00 | 1.50 | 1.47 | 1.88 |
| 500 ml | ALL3 | I43Q/D44C/N61I/L417V/E503A/Q511H/A539R | 0.82 | 1.30 | 1.43 | 1.64 |
| 500 ml | LQ4 | G294C/L417R/A431Q/Q511H | 1.02 | 1.19 | 1.43 | 1.65 |
| 500 ml | RB2 | I43Q/T430A/Q511H/L417V | 1.09 | 1.38 | 1.42 | 1.87 |
| 500 ml | TS3 | E503A/N563I/ | 0.94 | 1.17 | 1.39 | 1.04 |
| 500 ml | RB12 | I43Q/Q511H/N61I | 0.96 | 1.25 | 1.37 | 1.56 |
| 500 ml | RB14 | I43Q/Q511H/A431L | 1.01 | 1.31 | 1.37 | 1.55 |
| 500 ml | LQ6 | L417V/A431Q/Q511H | 0.94 | 1.33 | 1.35 | 2.05 |
| 100 ml | C14 | I43Q/T430A/Q511H | 1.09 | 1.34 | 1.33 | 1.46 |
| 500 ml | LQ3 | G294C/L417V/A431L/Q511H | 0.80 | 1.21 | 1.29 | 2.07 |
| 500 ml | RB3 | I43Q/T430A/Q511H/A431L | 1.20 | 1.25 | 1.29 | 1.70 |
| 500 ml | RB10 | I43Q/T430A/Q511H/N61I/A539R/A431L | 0.87 | 1.47 | 1.29 | 1.73 |
| 500 ml | RB1 | I43Q/T430A/Q511H/N61I | 1.19 | 1.15 | 1.27 | 1.47 |
| 100 ml | C13 | I43Q/T430A/ | 1.07 | 1.29 | 1.10 | 1.45 |
| 500 ml | LQ1 | G294C/L417R/A431L | 0.90 | 1.08 | 1.04 | 1.77 |
| 500 ml | LQ2 | G294C/L417V/A431Q | 0.80 | 1.08 | 1.02 | 2.08 |
| 500 ml | RB6 | I43Q/T430A/Q511H/N61I/A539R | | | 0.94 | |

Example 11

Crystal Structure of TrGA

The complete three dimensional structure of *Trichoderma reesei* (*Hypocrea jecorina*) glucoamylase (TrGA) was determined at 1.9 Å resolution. Table 20 shows the coordinates for the *Trichoderma* glucoamylase crystal structure. TrGA was crystallized in an intact form containing 599 residues and all post-translational modifications that would normally occur in the natural host. The crystal structure was produced and analyzed as follows:

For protein expression and purification, the gene encoding *H. jecorina* GA was cloned and expressed according to the protocols described in the U.S. Pat. No. 7,413,887.

The TrGA protein material used for all crystallization experiments was initially purified in one step by anion exchange chromatography as follows: concentrated culture supernatants of expressed TrGA, consisting of 180 mg/ml total protein, were prepared by diluting sample 1:10 in a 25 mM Tris-HCl, pH 8.0 buffer. A HiPrep 16/10 Q Sepharose FF column (GE Helthcare) was employed for the anion exchange purification. The HiPrep column was equilibrated with 4 column volumes (CV) starting buffer (25 mM Tris-HCl, pH 8.0) followed by application of 10 ml of the diluted protein sample. An 8 CV linear gradient of 0 to 140 mM NaCl in the running buffer (25 mM Tris-HCl, pH 8.0) was applied to elute bound protein. Bound TrGA eluted from the HiPrep Q sepharose column at a salt concentration of approximately 80 mM NaCl. Fractions containing pure TrGA protein were pooled and concentrated to 50 mg/ml using a 25 ml Vivaspin centrifugal concentration tube (Viva Science) with a molecular weight cutoff (MWCO) of 10 kD. Purified and concentrated TrGA material was buffer exchanged using a DG-10 desalting column (Bio-Rad) equilibrated with 50 mM sodium acetate buffer, pH 4.3. Protein concentrations were determined by measuring the absorbance at 280 nm. The initially purified and concentrated TrGA protein stock was thereafter stored at −20° C.

Two additional purification steps, on additional anion exchange purification, and a size exclusion purification, were introduced to enhance the crystability of the TrGA protein material. These two additional purification steps were performed as follows. In the first anion exchange purification step a 10 ml MonoQ column (GE Helthcare) was employed. A Sample of 1 ml of the initially purified and frozen TrGA material (50 mg protein) was thawed and the butler was changed to 20 mM Tris-HCl, pH 8.0, by repeated dilution of the sample to 6 ml in the new buffer, followed by a concentration of the sample again to 0.5 ml using a 6 ml 5 kD MWCO concentration tube. The TrGA sample was diluted after the last concentration step in distilled water until a conductivity of the protein sample was reached that corresponded to the conductivity of the starting buffer of the anion purification, i.e. 25 mM Tris-HCl, pH 8.0. The MonoQ column was first equilibrated with 4 column volumes (CV) starting buffer, followed by application of the diluted protein sample to the column. Bound protein was eluted from the MonoQ column by two different gradients. In the first a 4 CV linear pH gradient was applied where the pH of the starting buffer was decreased from 8.0 to 6.0. In the second gradient an 8 CV long salt gradient was applied in which the salt concentration was increased from 0 to 350 mM NaCl in the running buffer (25 mM Tris-HCl, pH 6.0). Bound TrGA was found to elute from the column during the second salt gradient at an approximate NaCl concentration of 150 mM. Fractions containing TrGA were pooled and concentrated to 2 ml using a 6 ml 5 kD MWCO Vivaspin concentration tube. The concentrated TrGA sample was thereafter applied to a Superdex 200 16/60 size exclusion column (GE Helthcare) equilibrated with 4 CV of 20 mM, Tris-Cl, pH 8.0, and 50 mM NaCl, which also was used as running buffer. Fractions from the main elution peak after the size exclusion purification were pooled and concentrated to an approximate protein concentration of 7.5 mg/ml using a 6 ml 5 kD MWCO Vivaspin concentration tube.

For protein crystallization, the protein sample that was used to find the initial TrGA crystallization conditions was a sample of the TrGA material that was purified once by anion exchange purification and thereafter stored at −20° C., The TrGA protein sample was thawed and diluted with 50 mM sodium acetate buffer, pH 4.3, to approximately 12 mg/ml, prior to the initial crystallization experiments. The orthorhombic X-ray dataset, was used to solve the TrGA structure by molecular replacement (MR), and the high-resolution orthorhombic dataset, used for the final orthorhombic space group TrGA structure model. The orthorhombic TrGA crystals were found to grow in solution consisting of 25% PEG 3350, 0.20M ammonium acetate, 0.10M Bis-Tris pH 5.5 (reservoir solution), using the vapor-diffusion method with hanging drops (McPherson 1982), at 20° C. Crystallization drops were prepared by mixing equal amounts of protein solution (12 mg/ml) and reservoir solution to a final volume of 10 µl. The TrGA crystals were found to belong to the orthorhombic space group P212121 with approximate cell dimensions: a=52.2 Å, b=99.2 Å, c=121.2 Å, and have a calculated $V_m$ of 2.3 (Matthews 1968) with one molecules in the asymmetric unit.

For X-ray data collection, the two orthorhombic TrGA datasets were collected from single crystals mounted in sealed capillary tubes, at room temperature. The initial lo-resolution orthorhombic TrGA X-ray dataset, used to solve the structure by molecular replacement methods (MR), was collected on a home X-ray source, an MSC/Rigaku (Molecular Structures Corp., The Woodlands, Tex.) Raxis IV++ image plate detector with focusing mirrors using Cu Kα radiation from a Rigaku RU200 rotating anode generator. This dataset was processed, scaled, and averaged using the d*trek software provided by MSC/Rigaku. The C centered monoclinic dataset was collected from a single frozen TrGA crystal at 100K, equilibrated in a cryo-protective agent comprised of 25% PEG 3350, 15% Glycerol 50 mM $CaCl_2$ and 0.1 M Bis-Tris pH 5.5 as cryoprotectant, mounted in rayon-fiber loops, and plunge frozen in liquid nitrogen prior to transportation to the synchrotron. The high-resolution orthorhombic (1.9 Å) data set and the C centric monoclinic dataset (1.8 Å) were both collected at a synchrotron source, beam line 911:5 at MAX LAB in Lund, Sweden. Both datasets that were collected at a synchrotron source were processed with MOSFLM, and scaled with program SCALA included in the CCP4 program package (Collaborative Computational Project Number 4 1994). All subsequent data processing was performed using the CCP4 program package (Collaborative Computational Project Number 4 1994), unless otherwise stated. A set of 5% of the reflections from each data set was set aside and used for monitoring the R-free (Brünger, A (1992) *Nature,* 355:472-475).

The TrGA structure was initially solved by MR with the automatic replacement program MOLREP (Collaborative Computational Project Number 4 1994), included in the CCP4 program package, using the initial lo-resolution orthorhombic dataset, and using the coordinates of *Aspergillus awamori* GA (AaGA) variant X100 (pdb entry 1GLM (Aleshin et al. (1994) J. Mol. Biol. 238: 575-591) as search model. The *A. awamori* GA search model was edited to remove all glycosylation moieties attached to the protein molecule as N- and O-glycosylations, and all solvent molecules before carrying out the MR experiments. All reflections between 36.8 and 2.8 Å resolution, from the initial lo resolution TrGA dataset, was used for the MR solution. The MR program found a single rotation function solution, with a maxima of 11.1σ above background, the next highest maxima was 3.8σ above the background. The translation function solution gave an R-factor of 48.7% and had a contrast factor of 17.4. The MR solution was refined for 10 cycles of restrained least squares refinement using the program Refmac 5.0 (Murshudov et al (1997) *Acta Crystallogr. D*53: 240-255). This lowered the crystallographic R-factor to 31.1% while the R-free value dropped from 42.2% to 41.1%.

The refined MR solution model was used to calculate an initial density map from the lo-resolution orthorhombic TrGA dataset. Electron density for a disulfide bridge between residues 19 and 26 of TrGA, a disulfide bridge not present in the *A. awamori* variant X100 structure model, could readily be identified in this electron density map. This was taken as an indication that the electron density map was of sufficient quality to be used to build a structure model of TrGA from its amino acid sequence. The initial TrGA structure model, based on the lo-resolution dataset, was refined with alternating cycles of model building using Coot (Emsley and Cowtan, (2004) *Acta Crystallogr. D boil Crystallogr.* 60: 2126-2132), and maximum likelihood refinement using Refmac 5.0.

The resolution of the initial TrGA structure model was extended to the resolution of the high-resolution orthorhombic dataset (1.9 Å) by refining the initial TrGA structure model against the high-resolution dataset for 10 cycles of restrained refinement using the program Refmac 5.0. Most water molecules in the structure models were located automatically by using the water picking protocols in the refinement programs, and then manually selected or discarded by inspection by eye. Alt structural comparisons were made with either Coot (Emsley and Cowtan (2004) supra) or O (Jones et al. (1991) *Acta Crystallogr.* A47: 110-119), and figures were prepared with PyMOL (Delano W. L. (2002) The PyMOL Molecular Graphics System. Palo Alto, Calif., USA; Delano Scientific).

From these results, it can be seen that the TrGA catalytic core segment followed the same $(\alpha/\alpha)_6$-barrel topology described by Aleshin et al. 1992 for the AaGA, consisting of a double barrel of alpha helices with the C-terminal of the outer helix leading into the N-terminus of an inner helix. It was possible to identify key differences in the electron density such as the disulfide bridge between residues 19 and 26 and an insertion (residues 257-260) relative to AaGA. The segment comprising 80-100 also underwent extensive model rebuilding. One major glycosylation site was identified at Asn 171, which had up to four glycoside moieties attached. A similar glycosylation site was identified in AaGA. Additionally, the catalytic core containing three cis-peptides between residues 22-23, 44-45 and 122-123 were conserved between TrGA and AaGA. Overall there was an rms variation of 0.535 Å between 409 out of 453 Cα atoms when comparing the coordinates of the catalytic cores of TrGA and AaGA.

Example 14

Homology Between TrGA and AaGA

The crystal structure of the TrGA identified in Example 13, was superposed on the previously identified crystal structure of the *Aspergillus awamori* GA (AaGA). The AaGA crystal structure was obtained from the protein database (PDB) and the form of AaGA that was crystallized was the form containing only a catalytic domain. The structure of the *Trichoderma reesei* glucoamylase with all three regions intact was determined to 1.8 Angstrom resolution herein (see Table 15 and Example 12). Using the coordinates (see Table 20) the structure was aligned with the coordinates of the catalytic domain from *Aspergillus awamori* strain X100 that was determined previously (Aleshin, A. E., Hoffman, C., Firsov, L. M., and Honzatko, R. B. 1994 Refined crystal structures of glucoamylase from *Aspergillus awamori* var. X100. *J Mol Biol* 238: 575-591 and the PDB). As seen in FIGS. 12 and 13 the structure of the catalytic domain overlapped very closely and allowed the identification of equivalent residues based on this structural superposition.

Based on this analysis, sites were identified that could be mutated in TrGA and result in increased stability and/or specific activity. These sites include 108, 124, 175 and 316 at the active site. Also identified were specific pairwise variants Y47W/Y315F and Y47F/Y315W, Other sites identified were I43, D44, P45, D46, R122, R125, V181, E242, Y310, D313, V314, N317, R408, and N409. Because of the high structural homology it is expected that beneficial variants found at sites in TrGA would have similar consequences in *Aspergillus awamori* and other homologous glucoamylases.

Various modifications and variations of the described methods and system of the disclosure will be apparent to those skilled in the art without departing from the scope and spirit of the disclosure. Although the disclosure has been described in connection with specific representative embodiments, it should be understood that the subject matters as claimed should not be unduly limited to such specific embodiments. Indeed, various modifications of the described modes for carrying out the disclosure that are obvious to those skilled in the art are intended to be within the scope of the following claims.

TABLE 20

| CRYST1 | | 52.185 | | 99.232 | 121.240 | 90.00 | 90.00 | 90.00 | | |
|---|---|---|---|---|---|---|---|---|---|---|
| ORIGX1 | | | 1.000000 | 0.000000 | 0.000000 | | 0.00000 | | | |
| ORIGX2 | | | 0.000000 | 1.000000 | 0.000000 | | 0.00000 | | | |
| ORIGX3 | | | 0.000000 | 0.000000 | 1.000000 | | 0.00000 | | | |
| SCALE1 | | | 0.019163 | −0.000001 | −0.000001 | | 0.00000 | | | |
| SCALE2 | | | 0.000000 | 0.010077 | 0.000000 | | 0.00000 | | | |
| SCALE3 | | | 0.000000 | 0.000000 | 0.008248 | | 0.00000 | | | |
| ATOM | 1 | N | SER | A | 1 | −30.485 | 30.567 | −21.185 | 1.00 | 37.11 |
| ATOM | 2 | CA | SER | A | 1 | −30.568 | 29.350 | −20.326 | 1.00 | 37.00 |
| ATOM | 3 | CB | SER | A | 1 | −31.953 | 28.707 | −20.424 | 1.00 | 37.27 |
| ATOM | 4 | OG | SER | A | 1 | −32.137 | 28.089 | −21.695 | 1.00 | 40.11 |
| ATOM | 5 | C | SER | A | 1 | −29.519 | 28.345 | −20.772 | 1.00 | 35.91 |
| ATOM | 6 | O | SER | A | 1 | −29.043 | 28.415 | −21.911 | 1.00 | 35.46 |
| ATOM | 7 | N | VAL | A | 2 | −29.170 | 27.425 | −19.867 | 1.00 | 34.51 |
| ATOM | 8 | CA | VAL | A | 2 | −28.302 | 26.293 | −20.179 | 1.00 | 33.56 |
| ATOM | 9 | CB | VAL | A | 2 | −28.142 | 25.339 | −18.955 | 1.00 | 33.84 |
| ATOM | 10 | CG1 | VAL | A | 2 | −27.349 | 24.103 | −19.316 | 1.00 | 34.20 |
| ATOM | 11 | CG2 | VAL | A | 2 | −27.468 | 26.057 | −17.827 | 1.00 | 34.79 |
| ATOM | 12 | C | VAL | A | 2 | −28.846 | 25.506 | −21.363 | 1.00 | 32.48 |
| ATOM | 13 | O | VAL | A | 2 | −28.086 | 25.109 | −22.245 | 1.00 | 31.10 |
| ATOM | 14 | N | ASP | A | 3 | −30.160 | 25.286 | −21.381 | 1.00 | 31.43 |
| ATOM | 15 | CA | ASP | A | 3 | −30.791 | 24.530 | −22.457 | 1.00 | 31.38 |
| ATOM | 16 | CB | ASP | A | 3 | −32.283 | 24.323 | −22.190 | 1.00 | 32.17 |
| ATOM | 17 | CG | ASP | A | 3 | −32.522 | 23.492 | −20.943 | 1.00 | 35.28 |
| ATOM | 18 | OD1 | ASP | A | 3 | −32.413 | 22.251 | −21.028 | 1.00 | 36.80 |
| ATOM | 19 | OD2 | ASP | A | 3 | −32.786 | 24.092 | −19.870 | 1.00 | 40.63 |
| ATOM | 20 | C | ASP | A | 3 | −30.556 | 25.153 | −23.818 | 1.00 | 30.59 |

TABLE 20-continued

| ATOM | 21 | O | ASP | A | 3 | −30.282 | 24.446 | −24.778 | 1.00 | 30.19 |
|---|---|---|---|---|---|---|---|---|---|---|
| ATOM | 22 | N | ASP | A | 4 | −30.644 | 26.477 | −23.875 | 1.00 | 29.89 |
| ATOM | 23 | CA | ASP | A | 4 | −30.369 | 27.244 | −25.083 | 1.00 | 29.99 |
| ATOM | 24 | CB | ASP | A | 4 | −30.601 | 28.731 | −24.822 | 1.00 | 31.12 |
| ATOM | 25 | CG | ASP | A | 4 | −32.088 | 29.121 | −24.785 | 1.00 | 34.16 |
| ATOM | 26 | OD1 | ASP | A | 4 | −32.991 | 28.260 | −24.925 | 1.00 | 36.06 |
| ATOM | 27 | OD2 | ASP | A | 4 | −32.340 | 30.332 | −24.608 | 1.00 | 39.96 |
| ATOM | 28 | C | ASP | A | 4 | −28.925 | 27.049 | −25.579 | 1.00 | 28.65 |
| ATOM | 29 | O | ASP | A | 4 | −28.697 | 26.881 | −26.770 | 1.00 | 28.51 |
| ATOM | 30 | N | PHE | A | 5 | −27.961 | 27.096 | −24.660 | 1.00 | 26.74 |
| ATOM | 31 | CA | PHE | A | 5 | −26.553 | 26.860 | −24.994 | 1.00 | 25.21 |
| ATOM | 32 | CB | PHE | A | 5 | −25.666 | 27.110 | −23.764 | 1.00 | 25.59 |
| ATOM | 33 | CG | PHE | A | 5 | −24.244 | 26.646 | −23.931 | 1.00 | 26.03 |
| ATOM | 34 | CD1 | PHE | A | 5 | −23.395 | 27.259 | −24.854 | 1.00 | 27.29 |
| ATOM | 35 | CE1 | PHE | A | 5 | −22.063 | 26.823 | −25.009 | 1.00 | 27.33 |
| ATOM | 36 | CZ | PHE | A | 5 | −21.593 | 25.783 | −24.228 | 1.00 | 26.77 |
| ATOM | 37 | CE2 | PHE | A | 5 | −22.425 | 25.181 | −23.286 | 1.00 | 28.42 |
| ATOM | 38 | CD2 | PHE | A | 5 | −23.749 | 25.617 | −23.144 | 1.00 | 28.42 |
| ATOM | 39 | C | PHE | A | 5 | −26.352 | 25.438 | −25.539 | 1.00 | 24.23 |
| ATOM | 40 | O | PHE | A | 5 | −25.659 | 25.244 | −26.544 | 1.00 | 23.56 |
| ATOM | 41 | N | ILE | A | 6 | −26.974 | 24.458 | −24.892 | 1.00 | 22.71 |
| ATOM | 42 | CA | ILE | A | 6 | −26.835 | 23.065 | −25.312 | 1.00 | 22.36 |
| ATOM | 43 | CB | ILE | A | 6 | −27.491 | 22.106 | −24.299 | 1.00 | 21.86 |
| ATOM | 44 | CG1 | ILE | A | 6 | −26.744 | 22.181 | −22.956 | 1.00 | 22.27 |
| ATOM | 45 | CD1 | ILE | A | 6 | −27.384 | 21.347 | −21.834 | 1.00 | 22.36 |
| ATOM | 46 | CG2 | ILE | A | 6 | −27.571 | 20.669 | −24.848 | 1.00 | 21.69 |
| ATOM | 47 | C | ILE | A | 6 | −27.388 | 22.855 | −26.723 | 1.00 | 22.84 |
| ATOM | 48 | O | ILE | A | 6 | −26.753 | 22.216 | −27.573 | 1.00 | 21.76 |
| ATOM | 49 | N | SER | A | 7 | −28.556 | 23.420 | −26.996 | 1.00 | 23.10 |
| ATOM | 50 | CA | SER | A | 7 | −29.146 | 23.175 | −28.309 | 1.00 | 23.90 |
| ATOM | 51 | CB | SER | A | 7 | −30.627 | 23.570 | −28.320 | 1.00 | 25.04 |
| ATOM | 52 | OG | SER | A | 7 | −30.717 | 24.982 | −28.282 | 1.00 | 30.08 |
| ATOM | 53 | C | SER | A | 7 | −28.340 | 23.874 | −29.422 | 1.00 | 22.78 |
| ATOM | 54 | O | SER | A | 7 | −28.186 | 23.337 | −30.508 | 1.00 | 22.94 |
| ATOM | 55 | N | THR | A | 8 | −27.800 | 25.053 | −29.140 | 1.00 | 22.50 |
| ATOM | 56 | CA | THR | A | 8 | −26.984 | 25.780 | −30.115 | 1.00 | 23.05 |
| ATOM | 57 | CB | THR | A | 8 | −26.834 | 27.247 | −29.698 | 1.00 | 23.65 |
| ATOM | 58 | OG1 | THR | A | 8 | −28.138 | 27.839 | −29.700 | 1.00 | 27.60 |
| ATOM | 59 | CG2 | THR | A | 8 | −25.939 | 28.018 | −30.660 | 1.00 | 26.76 |
| ATOM | 60 | C | THR | A | 8 | −25.601 | 25.159 | −30.307 | 1.00 | 21.46 |
| ATOM | 61 | O | THR | A | 8 | −25.109 | 25.051 | −31.437 | 1.00 | 21.38 |
| ATOM | 62 | N | GLU | A | 9 | −24.978 | 24.768 | −29.200 | 1.00 | 19.11 |
| ATOM | 63 | CA | GLU | A | 9 | −23.596 | 24.269 | −29.243 | 1.00 | 18.01 |
| ATOM | 64 | CB | GLU | A | 9 | −22.959 | 24.334 | −27.847 | 1.00 | 17.76 |
| ATOM | 65 | CG | GLU | A | 9 | −21.449 | 23.945 | −27.794 | 1.00 | 17.71 |
| ATOM | 66 | CD | GLU | A | 9 | −20.536 | 24.892 | −28.609 | 1.00 | 20.86 |
| ATOM | 67 | OE1 | GLU | A | 9 | −20.949 | 26.010 | −28.971 | 1.00 | 19.89 |
| ATOM | 68 | OE2 | GLU | A | 9 | −19.389 | 24.500 | −28.909 | 1.00 | 19.22 |
| ATOM | 69 | C | GLU | A | 9 | −23.462 | 22.846 | −29.784 | 1.00 | 17.77 |
| ATOM | 70 | O | GLU | A | 9 | −22.423 | 22.505 | −30.368 | 1.00 | 18.05 |
| ATOM | 71 | N | THR | A | 10 | −24.485 | 22.020 | −29.593 | 1.00 | 15.87 |
| ATOM | 72 | CA | THR | A | 10 | −24.404 | 20.609 | −29.958 | 1.00 | 17.31 |
| ATOM | 73 | CB | THR | A | 10 | −25.677 | 19.823 | −29.525 | 1.00 | 17.46 |
| ATOM | 74 | OG1 | THR | A | 10 | −25.768 | 19.860 | −28.090 | 1.00 | 17.46 |
| ATOM | 75 | CG2 | THR | A | 10 | −25.616 | 18.374 | −30.037 | 1.00 | 18.42 |
| ATOM | 76 | C | THR | A | 10 | −24.026 | 20.346 | −31.430 | 1.00 | 17.40 |
| ATOM | 77 | O | THR | A | 10 | −23.073 | 19.615 | −31.682 | 1.00 | 17.22 |
| ATOM | 78 | N | PRO | A | 11 | −24.764 | 20.934 | −32.412 | 1.00 | 18.30 |
| ATOM | 79 | CA | PRO | A | 11 | −24.346 | 20.649 | −33.798 | 1.00 | 18.11 |
| ATOM | 80 | CB | PRO | A | 11 | −25.440 | 21.317 | −34.662 | 1.00 | 18.57 |
| ATOM | 81 | CG | PRO | A | 11 | −26.094 | 22.310 | −33.771 | 1.00 | 19.16 |
| ATOM | 82 | CD | PRO | A | 11 | −25.975 | 21.779 | −32.361 | 1.00 | 18.54 |
| ATOM | 83 | C | PRO | A | 11 | −22.963 | 21.231 | −34.142 | 1.00 | 17.81 |
| ATOM | 84 | O | PRO | A | 11 | −22.241 | 20.655 | −34.964 | 1.00 | 17.74 |
| ATOM | 85 | N | ILE | A | 12 | −22.601 | 22.353 | −33.520 | 1.00 | 16.85 |
| ATOM | 86 | CA | ILE | A | 12 | −21.279 | 22.936 | −33.731 | 1.00 | 16.66 |
| ATOM | 87 | CB | ILE | A | 12 | −21.161 | 24.319 | −33.112 | 1.00 | 17.25 |
| ATOM | 88 | CG1 | ILE | A | 12 | −22.194 | 25.267 | −33.751 | 1.00 | 19.25 |
| ATOM | 89 | CD1 | ILE | A | 12 | −22.289 | 26.635 | −33.101 | 1.00 | 21.45 |
| ATOM | 90 | CG2 | ILE | A | 12 | −19.714 | 24.855 | −33.270 | 1.00 | 18.75 |
| ATOM | 91 | C | ILE | A | 12 | −20.170 | 22.023 | −33.178 | 1.00 | 16.30 |
| ATOM | 92 | O | ILE | A | 12 | −19.155 | 21.798 | −33.848 | 1.00 | 14.64 |
| ATOM | 93 | N | ALA | A | 13 | −20.360 | 21.527 | −31.951 | 1.00 | 15.28 |
| ATOM | 94 | CA | ALA | A | 13 | −19.375 | 20.627 | −31.304 | 1.00 | 15.19 |
| ATOM | 95 | CB | ALA | A | 13 | −19.788 | 20.332 | −29.883 | 1.00 | 15.31 |
| ATOM | 96 | C | ALA | A | 13 | −19.204 | 19.326 | −32.092 | 1.00 | 15.37 |
| ATOM | 97 | O | ALA | A | 13 | −18.083 | 18.834 | −32.297 | 1.00 | 13.56 |
| ATOM | 98 | N | LEU | A | 14 | −20.320 | 18.743 | −32.531 | 1.00 | 15.13 |
| ATOM | 99 | CA | LEU | A | 14 | −20.225 | 17.503 | −33.285 | 1.00 | 16.06 |
| ATOM | 100 | CB | LEU | A | 14 | −21.630 | 16.921 | −33.510 | 1.00 | 17.33 |

TABLE 20-continued

| | | | | | | | | | |
|---|---|---|---|---|---|---|---|---|---|
| ATOM | 101 | CG | LEU | A | 14 | −21.689 | 15.563 | −34.212 | 1.00 | 20.02 |
| ATOM | 102 | CD1 | LEU | A | 14 | −20.946 | 14.460 | −33.471 | 1.00 | 23.09 |
| ATOM | 103 | CD2 | LEU | A | 14 | −23.150 | 15.225 | −34.390 | 1.00 | 21.86 |
| ATOM | 104 | C | LEU | A | 14 | −19.506 | 17.749 | −34.623 | 1.00 | 15.61 |
| ATOM | 105 | O | LEU | A | 14 | −18.651 | 16.947 | −35.039 | 1.00 | 14.82 |
| ATOM | 106 | N | ASN | A | 15 | −19.853 | 18.852 | −35.285 | 1.00 | 15.30 |
| ATOM | 107 | CA | ASN | A | 15 | −19.236 | 19.228 | −36.567 | 1.00 | 16.34 |
| ATOM | 108 | CB | ASN | A | 15 | −19.848 | 20.545 | −37.073 | 1.00 | 16.07 |
| ATOM | 109 | CG | ASN | A | 15 | −19.232 | 21.010 | −38.388 | 1.00 | 18.31 |
| ATOM | 110 | OD1 | ASN | A | 15 | −19.565 | 20.487 | −39.431 | 1.00 | 17.60 |
| ATOM | 111 | ND2 | ASN | A | 15 | −18.312 | 21.987 | −38.325 | 1.00 | 21.40 |
| ATOM | 112 | C | ASN | A | 15 | −17.736 | 19.450 | −36.405 | 1.00 | 15.35 |
| ATOM | 113 | O | ASN | A | 15 | −16.926 | 18.954 | −37.198 | 1.00 | 15.29 |
| ATOM | 114 | N | ASN | A | 16 | −17.385 | 20.180 | −35.355 | 1.00 | 14.82 |
| ATOM | 115 | CA | ASN | A | 16 | −15.992 | 20.555 | −35.144 | 1.00 | 15.27 |
| ATOM | 116 | CB | ASN | A | 16 | −15.872 | 21.693 | −34.148 | 1.00 | 15.41 |
| ATOM | 117 | CG | ASN | A | 16 | −16.276 | 23.023 | −34.737 | 1.00 | 16.53 |
| ATOM | 118 | OD1 | ASN | A | 16 | −16.517 | 23.136 | −35.954 | 1.00 | 18.08 |
| ATOM | 119 | ND2 | ASN | A | 16 | −16.326 | 24.050 | −33.896 | 1.00 | 16.35 |
| ATOM | 120 | C | ASN | A | 16 | −15.159 | 19.362 | −34.723 | 1.00 | 14.91 |
| ATOM | 121 | O | ASN | A | 16 | −13.975 | 19.261 | −35.099 | 1.00 | 15.34 |
| ATOM | 122 | N | LEU | A | 17 | −15.771 | 18.460 | −33.956 | 1.00 | 14.29 |
| ATOM | 123 | CA | LEU | A | 17 | −15.114 | 17.191 | −33.610 | 1.00 | 13.90 |
| ATOM | 124 | CB | LEU | A | 17 | −16.003 | 16.346 | −32.672 | 1.00 | 13.94 |
| ATOM | 125 | CG | LEU | A | 17 | −15.351 | 15.065 | −32.133 | 1.00 | 16.81 |
| ATOM | 126 | CD1 | LEU | A | 17 | −15.933 | 14.708 | −30.779 | 1.00 | 20.06 |
| ATOM | 127 | CD2 | LEU | A | 17 | −15.484 | 13.880 | −33.097 | 1.00 | 19.31 |
| ATOM | 128 | C | LEU | A | 17 | −14.763 | 16.409 | −34.880 | 1.00 | 14.06 |
| ATOM | 129 | O | LEU | A | 17 | −13.613 | 15.957 | −35.073 | 1.00 | 12.69 |
| ATOM | 130 | N | LEU | A | 18 | −15.774 | 16.215 | −35.730 | 1.00 | 13.19 |
| ATOM | 131 | CA | LEU | A | 18 | −15.589 | 15.441 | −36.957 | 1.00 | 14.25 |
| ATOM | 132 | CB | LEU | A | 18 | −16.952 | 15.027 | −37.545 | 1.00 | 13.56 |
| ATOM | 133 | CG | LEU | A | 18 | −17.717 | 14.013 | −36.684 | 1.00 | 16.49 |
| ATOM | 134 | CD1 | LEU | A | 18 | −19.171 | 13.874 | −37.165 | 1.00 | 16.33 |
| ATOM | 135 | CD2 | LEU | A | 18 | −17.020 | 12.647 | −36.655 | 1.00 | 18.51 |
| ATOM | 136 | C | LEU | A | 18 | −14.703 | 16.132 | −38.007 | 1.00 | 13.49 |
| ATOM | 137 | O | LEU | A | 18 | −14.083 | 15.435 | −38.820 | 1.00 | 14.69 |
| ATOM | 138 | N | CYS | A | 19 | −14.613 | 17.462 | −37.964 | 1.00 | 13.01 |
| ATOM | 139 | CA | CYS | A | 19 | −13.629 | 18.223 | −38.760 | 1.00 | 13.22 |
| ATOM | 140 | CB | CYS | A | 19 | −13.796 | 19.738 | −38.556 | 1.00 | 14.20 |
| ATOM | 141 | SG | CYS | A | 19 | −15.125 | 20.407 | −39.642 | 1.00 | 16.22 |
| ATOM | 142 | C | CYS | A | 19 | −12.182 | 17.808 | −38.450 | 1.00 | 13.86 |
| ATOM | 143 | O | CYS | A | 19 | −11.278 | 18.043 | −39.259 | 1.00 | 13.42 |
| ATOM | 144 | N | ASN | A | 20 | −11.968 | 17.219 | −37.272 | 1.00 | 13.21 |
| ATOM | 145 | CA | ASN | A | 20 | −10.594 | 16.850 | −36.830 | 1.00 | 13.62 |
| ATOM | 146 | CB | ASN | A | 20 | −10.394 | 17.184 | −35.324 | 1.00 | 13.52 |
| ATOM | 147 | CG | ASN | A | 20 | −10.242 | 18.687 | −35.055 | 1.00 | 16.17 |
| ATOM | 148 | OD1 | ASN | A | 20 | −10.035 | 19.119 | −33.897 | 1.00 | 17.34 |
| ATOM | 149 | ND2 | ASN | A | 20 | −10.343 | 19.486 | −36.090 | 1.00 | 11.87 |
| ATOM | 150 | C | ASN | A | 20 | −10.262 | 15.381 | −37.116 | 1.00 | 13.99 |
| ATOM | 151 | O | ASN | A | 20 | −9.238 | 14.857 | −36.646 | 1.00 | 14.28 |
| ATOM | 152 | N | VAL | A | 21 | −11.123 | 14.705 | −37.875 | 1.00 | 13.41 |
| ATOM | 153 | CA | VAL | A | 21 | −10.923 | 13.287 | −38.167 | 1.00 | 14.20 |
| ATOM | 154 | CB | VAL | A | 21 | −12.177 | 12.448 | −37.827 | 1.00 | 14.30 |
| ATOM | 155 | CG1 | VAL | A | 21 | −11.953 | 10.971 | −38.189 | 1.00 | 15.30 |
| ATOM | 156 | CG2 | VAL | A | 21 | −12.517 | 12.553 | −36.312 | 1.00 | 14.17 |
| ATOM | 157 | C | VAL | A | 21 | −10.551 | 13.136 | −39.644 | 1.00 | 14.35 |
| ATOM | 158 | O | VAL | A | 21 | −11.255 | 13.642 | −40.491 | 1.00 | 15.68 |
| ATOM | 159 | N | GLY | A | 22 | −9.461 | 12.449 | −39.953 | 1.00 | 15.67 |
| ATOM | 160 | CA | GLY | A | 22 | −9.061 | 12.300 | −41.377 | 1.00 | 15.70 |
| ATOM | 161 | C | GLY | A | 22 | −9.843 | 11.182 | −42.060 | 1.00 | 17.34 |
| ATOM | 162 | O | GLY | A | 22 | −10.453 | 10.358 | −41.397 | 1.00 | 17.15 |
| ATOM | 163 | N | PRO | A | 23 | −9.806 | 11.117 | −43.404 | 1.00 | 18.42 |
| ATOM | 164 | CA | PRO | A | 23 | −9.009 | 11.946 | −44.278 | 1.00 | 18.20 |
| ATOM | 165 | CB | PRO | A | 23 | −8.716 | 10.990 | −45.446 | 1.00 | 18.64 |
| ATOM | 166 | CG | PRO | A | 23 | −9.983 | 10.171 | −45.560 | 1.00 | 18.81 |
| ATOM | 167 | CD | PRO | A | 23 | −10.568 | 10.092 | −44.153 | 1.00 | 18.59 |
| ATOM | 168 | C | PRO | A | 23 | −9.761 | 13.182 | −44.753 | 1.00 | 19.05 |
| ATOM | 169 | O | PRO | A | 23 | −9.183 | 14.055 | −45.426 | 1.00 | 19.36 |
| ATOM | 170 | N | ASP | A | 24 | −11.034 | 13.288 | −44.385 | 1.00 | 18.76 |
| ATOM | 171 | CA | ASP | A | 24 | −11.878 | 14.305 | −44.996 | 1.00 | 19.39 |
| ATOM | 172 | CB | ASP | A | 24 | −13.015 | 13.636 | −45.781 | 1.00 | 20.87 |
| ATOM | 173 | CG | ASP | A | 24 | −13.920 | 12.784 | −44.913 | 1.00 | 24.34 |
| ATOM | 174 | OD1 | ASP | A | 24 | −13.502 | 12.291 | −43.839 | 1.00 | 27.70 |
| ATOM | 175 | OD2 | ASP | A | 24 | −15.079 | 12.580 | −45.330 | 1.00 | 28.83 |
| ATOM | 176 | C | ASP | A | 24 | −12.452 | 15.372 | −44.061 | 1.00 | 18.08 |
| ATOM | 177 | O | ASP | A | 24 | −13.208 | 16.245 | −44.509 | 1.00 | 17.78 |
| ATOM | 178 | N | GLY | A | 25 | −12.100 | 15.331 | −42.775 | 1.00 | 16.65 |
| ATOM | 179 | CA | GLY | A | 25 | −12.634 | 16.343 | −41.852 | 1.00 | 16.02 |
| ATOM | 180 | C | GLY | A | 25 | −12.152 | 17.718 | −42.292 | 1.00 | 15.70 |

TABLE 20-continued

| | | | | | | | | | |
|---|---|---|---|---|---|---|---|---|---|
| ATOM | 181 | O | GLY | A | 25 | −11.033 | 17.849 | −42.811 | 1.00 | 16.22 |
| ATOM | 182 | N | CYS | A | 26 | −12.979 | 18.752 | −42.086 | 1.00 | 15.10 |
| ATOM | 183 | CA | CYS | A | 26 | −12.698 | 20.078 | −42.637 | 1.00 | 15.46 |
| ATOM | 184 | CB | CYS | A | 26 | −13.899 | 21.037 | −42.475 | 1.00 | 15.47 |
| ATOM | 185 | SG | CYS | A | 26 | −14.147 | 21.739 | −40.786 | 1.00 | 16.91 |
| ATOM | 186 | C | CYS | A | 26 | −11.407 | 20.731 | −42.116 | 1.00 | 15.65 |
| ATOM | 187 | O | CYS | A | 26 | −10.896 | 21.643 | −42.763 | 1.00 | 15.80 |
| ATOM | 188 | N | ARG | A | 27 | −10.879 | 20.259 | −40.973 | 1.00 | 15.02 |
| ATOM | 189 | CA | ARG | A | 27 | −9.615 | 20.808 | −40.443 | 1.00 | 14.56 |
| ATOM | 190 | CB | ARG | A | 27 | −9.819 | 21.480 | −39.066 | 1.00 | 15.00 |
| ATOM | 191 | CG | ARG | A | 27 | −10.695 | 22.728 | −39.164 | 1.00 | 15.15 |
| ATOM | 192 | CD | ARG | A | 27 | −10.826 | 23.551 | −37.888 | 1.00 | 14.30 |
| ATOM | 193 | NE | ARG | A | 27 | −11.874 | 24.566 | −38.080 | 1.00 | 15.05 |
| ATOM | 194 | CZ | ARG | A | 27 | −13.160 | 24.420 | −37.761 | 1.00 | 17.96 |
| ATOM | 195 | NH1 | ARG | A | 27 | −13.623 | 23.293 | −37.211 | 1.00 | 17.37 |
| ATOM | 196 | NH2 | ARG | A | 27 | −14.009 | 25.415 | −38.025 | 1.00 | 19.55 |
| ATOM | 197 | C | ARG | A | 27 | −8.489 | 19.776 | −40.394 | 1.00 | 15.49 |
| ATOM | 198 | O | ARG | A | 27 | −7.389 | 20.079 | −39.888 | 1.00 | 15.40 |
| ATOM | 199 | N | ALA | A | 28 | −8.768 | 18.577 | −40.910 | 1.00 | 15.17 |
| ATOM | 200 | CA | ALA | A | 28 | −7.805 | 17.484 | −40.988 | 1.00 | 16.06 |
| ATOM | 201 | CB | ALA | A | 28 | −8.163 | 16.374 | −39.975 | 1.00 | 15.52 |
| ATOM | 202 | C | ALA | A | 28 | −7.744 | 16.913 | −42.394 | 1.00 | 16.96 |
| ATOM | 203 | O | ALA | A | 28 | −7.453 | 15.730 | −42.581 | 1.00 | 17.60 |
| ATOM | 204 | N | PHE | A | 29 | −8.028 | 17.756 | −43.380 | 1.00 | 17.45 |
| ATOM | 205 | CA | PHE | A | 29 | −8.188 | 17.272 | −44.744 | 1.00 | 18.68 |
| ATOM | 206 | CB | PHE | A | 29 | −8.728 | 18.376 | −45.636 | 1.00 | 19.45 |
| ATOM | 207 | CG | PHE | A | 29 | −9.299 | 17.864 | −46.919 | 1.00 | 20.86 |
| ATOM | 208 | CD1 | PHE | A | 29 | −8.515 | 17.827 | −48.071 | 1.00 | 23.76 |
| ATOM | 209 | CE1 | PHE | A | 29 | −9.042 | 17.343 | −49.267 | 1.00 | 25.46 |
| ATOM | 210 | CZ | PHE | A | 29 | −10.357 | 16.889 | −49.318 | 1.00 | 22.85 |
| ATOM | 211 | CE2 | PHE | A | 29 | −11.151 | 16.924 | −48.180 | 1.00 | 24.78 |
| ATOM | 212 | CD2 | PHE | A | 29 | −10.611 | 17.408 | −46.973 | 1.00 | 22.71 |
| ATOM | 213 | C | PHE | A | 29 | −6.853 | 16.783 | −45.296 | 1.00 | 19.10 |
| ATOM | 214 | O | PHE | A | 29 | −5.862 | 17.501 | −45.224 | 1.00 | 19.40 |
| ATOM | 215 | N | GLY | A | 30 | −6.830 | 15.558 | −45.816 | 1.00 | 18.73 |
| ATOM | 216 | CA | GLY | A | 30 | −5.603 | 15.008 | −46.398 | 1.00 | 19.00 |
| ATOM | 217 | C | GLY | A | 30 | −4.717 | 14.307 | −45.399 | 1.00 | 19.69 |
| ATOM | 218 | O | GLY | A | 30 | −3.657 | 13.809 | −45.768 | 1.00 | 19.61 |
| ATOM | 219 | N | THR | A | 31 | −5.133 | 14.255 | −44.123 | 1.00 | 18.86 |
| ATOM | 220 | CA | THR | A | 31 | −4.450 | 13.384 | −43.165 | 1.00 | 19.14 |
| ATOM | 221 | CB | THR | A | 31 | −4.846 | 13.689 | −41.689 | 1.00 | 18.79 |
| ATOM | 222 | OG1 | THR | A | 31 | −6.265 | 13.579 | −41.559 | 1.00 | 18.61 |
| ATOM | 223 | CG2 | THR | A | 31 | −4.410 | 15.106 | −41.262 | 1.00 | 16.47 |
| ATOM | 224 | C | THR | A | 31 | −4.812 | 11.925 | −43.498 | 1.00 | 19.11 |
| ATOM | 225 | O | THR | A | 31 | −5.713 | 11.661 | −44.313 | 1.00 | 19.69 |
| ATOM | 226 | N | SER | A | 32 | −4.107 | 10.982 | −42.881 | 1.00 | 19.74 |
| ATOM | 227 | CA | SER | A | 32 | −4.367 | 9.554 | −43.094 | 1.00 | 20.00 |
| ATOM | 228 | CB | SER | A | 32 | −3.411 | 8.722 | −42.248 | 1.00 | 20.73 |
| ATOM | 229 | OG | SER | A | 32 | −2.064 | 8.973 | −42.612 | 1.00 | 21.56 |
| ATOM | 230 | C | SER | A | 32 | −5.806 | 9.217 | −42.704 | 1.00 | 20.57 |
| ATOM | 231 | O | SER | A | 32 | −6.334 | 9.778 | −41.732 | 1.00 | 20.70 |
| ATOM | 232 | N | ALA | A | 33 | −6.443 | 8.319 | −43.452 | 1.00 | 19.94 |
| ATOM | 233 | CA | ALA | A | 33 | −7.768 | 7.823 | −43.068 | 1.00 | 19.61 |
| ATOM | 234 | CB | ALA | A | 33 | −8.232 | 6.729 | −44.035 | 1.00 | 19.31 |
| ATOM | 235 | C | ALA | A | 33 | −7.764 | 7.285 | −41.637 | 1.00 | 19.10 |
| ATOM | 236 | O | ALA | A | 33 | −6.906 | 6.482 | −41.264 | 1.00 | 19.49 |
| ATOM | 237 | N | GLY | A | 34 | −8.742 | 7.719 | −40.856 | 1.00 | 17.74 |
| ATOM | 238 | CA | GLY | A | 34 | −8.878 | 7.282 | −39.473 | 1.00 | 18.31 |
| ATOM | 239 | C | GLY | A | 34 | −7.988 | 8.020 | −38.473 | 1.00 | 18.48 |
| ATOM | 240 | O | GLY | A | 34 | −8.050 | 7.739 | −37.271 | 1.00 | 19.07 |
| ATOM | 241 | N | ALA | A | 35 | −7.173 | 8.959 | −38.937 | 1.00 | 17.05 |
| ATOM | 242 | CA | ALA | A | 35 | −6.329 | 9.723 | −38.000 | 1.00 | 17.17 |
| ATOM | 243 | CB | ALA | A | 35 | −5.167 | 10.376 | −38.730 | 1.00 | 17.10 |
| ATOM | 244 | C | ALA | A | 35 | −7.173 | 10.784 | −37.271 | 1.00 | 16.55 |
| ATOM | 245 | O | ALA | A | 35 | −8.174 | 11.271 | −37.808 | 1.00 | 17.35 |
| ATOM | 246 | N | VAL | A | 36 | −6.793 | 11.130 | −36.051 | 1.00 | 15.39 |
| ATOM | 247 | CA | VAL | A | 36 | −7.490 | 12.198 | −35.328 | 1.00 | 14.41 |
| ATOM | 248 | CB | VAL | A | 36 | −8.142 | 11.687 | −34.031 | 1.00 | 15.02 |
| ATOM | 249 | CG1 | VAL | A | 36 | −8.903 | 12.828 | −33.349 | 1.00 | 16.72 |
| ATOM | 250 | CG2 | VAL | A | 36 | −9.081 | 10.520 | −34.336 | 1.00 | 16.45 |
| ATOM | 251 | C | VAL | A | 36 | −6.407 | 13.201 | −34.944 | 1.00 | 14.36 |
| ATOM | 252 | O | VAL | A | 36 | −5.421 | 12.816 | −34.311 | 1.00 | 14.44 |
| ATOM | 253 | N | ILE | A | 37 | −6.566 | 14.454 | −35.331 | 1.00 | 13.68 |
| ATOM | 254 | CA | ILE | A | 37 | −5.614 | 15.470 | −34.893 | 1.00 | 13.67 |
| ATOM | 255 | CB | ILE | A | 37 | −5.528 | 16.687 | −35.849 | 1.00 | 13.66 |
| ATOM | 256 | CG1 | ILE | A | 37 | −6.847 | 17.486 | −35.901 | 1.00 | 14.31 |
| ATOM | 257 | CD1 | ILE | A | 37 | −6.773 | 18.712 | −36.864 | 1.00 | 14.21 |
| ATOM | 258 | CG2 | ILE | A | 37 | −5.158 | 16.214 | −37.260 | 1.00 | 14.62 |
| ATOM | 259 | C | ILE | A | 37 | −6.041 | 15.908 | −33.505 | 1.00 | 13.27 |
| ATOM | 260 | O | ILE | A | 37 | −7.235 | 16.011 | −33.224 | 1.00 | 12.99 |

TABLE 20-continued

| | | | | | | | | | |
|---|---|---|---|---|---|---|---|---|---|
| ATOM | 261 | N | ALA | A | 38 | −5.081 | 16.159 | −32.630 | 1.00 | 13.03 |
| ATOM | 262 | CA | ALA | A | 38 | −5.445 | 16.697 | −31.333 | 1.00 | 12.81 |
| ATOM | 263 | CB | ALA | A | 38 | −4.235 | 16.680 | −30.377 | 1.00 | 12.73 |
| ATOM | 264 | C | ALA | A | 38 | −6.046 | 18.122 | −31.497 | 1.00 | 12.45 |
| ATOM | 265 | O | ALA | A | 38 | −6.939 | 18.503 | −30.775 | 1.00 | 12.23 |
| ATOM | 266 | N | SER | A | 39 | −5.555 | 18.870 | −32.482 | 1.00 | 12.90 |
| ATOM | 267 | CA | SER | A | 39 | −5.973 | 20.246 | −32.769 | 1.00 | 12.85 |
| ATOM | 268 | CB | SER | A | 39 | −5.512 | 21.211 | −31.657 | 1.00 | 12.63 |
| ATOM | 269 | OG | SER | A | 39 | −5.312 | 22.563 | −32.108 | 1.00 | 12.57 |
| ATOM | 270 | C | SER | A | 39 | −5.281 | 20.593 | −34.090 | 1.00 | 13.33 |
| ATOM | 271 | O | SER | A | 39 | −4.215 | 20.043 | −34.376 | 1.00 | 13.48 |
| ATOM | 272 | N | PRO | A | 40 | −5.880 | 21.500 | −34.885 | 1.00 | 13.12 |
| ATOM | 273 | CA | PRO | A | 40 | −5.248 | 21.999 | −36.108 | 1.00 | 13.76 |
| ATOM | 274 | CB | PRO | A | 40 | −6.407 | 22.689 | −36.860 | 1.00 | 14.41 |
| ATOM | 275 | CG | PRO | A | 40 | −7.386 | 23.045 | −35.797 | 1.00 | 14.32 |
| ATOM | 276 | CD | PRO | A | 40 | −7.223 | 22.081 | −34.665 | 1.00 | 13.18 |
| ATOM | 277 | C | PRO | A | 40 | −4.126 | 23.010 | −35.860 | 1.00 | 14.27 |
| ATOM | 278 | O | PRO | A | 40 | −3.474 | 23.420 | −36.824 | 1.00 | 14.43 |
| ATOM | 279 | N | SER | A | 41 | −3.864 | 23.381 | −34.599 | 1.00 | 13.42 |
| ATOM | 280 | CA | SER | A | 41 | −2.799 | 24.336 | −34.318 | 1.00 | 14.56 |
| ATOM | 281 | CB | SER | A | 41 | −2.788 | 24.817 | −32.840 | 1.00 | 14.40 |
| ATOM | 282 | OG | SER | A | 41 | −3.962 | 25.574 | −32.534 | 1.00 | 16.91 |
| ATOM | 283 | C | SER | A | 41 | −1.446 | 23.713 | −34.676 | 1.00 | 14.51 |
| ATOM | 284 | O | SER | A | 41 | −1.123 | 22.626 | −34.218 | 1.00 | 13.96 |
| ATOM | 285 | N | THR | A | 42 | −0.650 | 24.433 | −35.470 | 1.00 | 15.63 |
| ATOM | 286 | CA | THR | A | 42 | 0.652 | 23.924 | −35.919 | 1.00 | 16.17 |
| ATOM | 287 | CB | THR | A | 42 | 0.750 | 23.997 | −37.458 | 1.00 | 17.02 |
| ATOM | 288 | OG1 | THR | A | 42 | 0.267 | 25.283 | −37.890 | 1.00 | 17.03 |
| ATOM | 289 | CG2 | THR | A | 42 | −0.110 | 22.906 | −38.078 | 1.00 | 16.03 |
| ATOM | 290 | C | THR | A | 42 | 1.814 | 24.732 | −35.322 | 1.00 | 17.44 |
| ATOM | 291 | O | THR | A | 42 | 2.967 | 24.297 | −35.382 | 1.00 | 17.10 |
| ATOM | 292 | N | ILE | A | 43 | 1.509 | 25.913 | −34.787 | 1.00 | 18.37 |
| ATOM | 293 | CA | ILE | A | 43 | 2.510 | 26.786 | −34.171 | 1.00 | 20.62 |
| ATOM | 294 | CB | ILE | A | 43 | 2.923 | 27.952 | −35.114 | 1.00 | 20.73 |
| ATOM | 295 | CG1 | ILE | A | 43 | 3.550 | 27.428 | −36.411 | 1.00 | 21.88 |
| ATOM | 296 | CD1 | ILE | A | 43 | 3.788 | 28.507 | −37.508 | 1.00 | 22.99 |
| ATOM | 297 | CG2 | ILE | A | 43 | 3.895 | 28.910 | −34.409 | 1.00 | 21.41 |
| ATOM | 298 | C | ILE | A | 43 | 1.908 | 27.395 | −32.935 | 1.00 | 21.00 |
| ATOM | 299 | O | ILE | A | 43 | 0.796 | 27.921 | −32.995 | 1.00 | 21.76 |
| ATOM | 300 | N | ASP | A | 44 | 2.683 | 27.470 | −31.874 | 1.00 | 21.61 |
| ATOM | 301 | CA | ASP | A | 44 | 2.237 | 27.975 | −30.572 | 1.00 | 23.04 |
| ATOM | 302 | CB | ASP | A | 44 | 2.408 | 29.506 | −30.492 | 1.00 | 24.75 |
| ATOM | 303 | CG | ASP | A | 44 | 2.170 | 30.064 | −29.098 | 1.00 | 31.28 |
| ATOM | 304 | OD1 | ASP | A | 44 | 2.362 | 29.340 | −28.094 | 1.00 | 37.92 |
| ATOM | 305 | OD2 | ASP | A | 44 | 1.766 | 31.260 | −28.997 | 1.00 | 40.00 |
| ATOM | 306 | C | ASP | A | 44 | 0.782 | 27.608 | −30.196 | 1.00 | 21.65 |
| ATOM | 307 | O | ASP | A | 44 | −0.046 | 28.502 | −29.981 | 1.00 | 22.69 |
| ATOM | 308 | N | PRO | A | 45 | 0.441 | 26.449 | −29.805 | 1.00 | 19.86 |
| ATOM | 309 | CA | PRO | A | 45 | 1.356 | 25.320 | −29.775 | 1.00 | 18.66 |
| ATOM | 310 | CB | PRO | A | 45 | 0.883 | 24.549 | −28.549 | 1.00 | 18.40 |
| ATOM | 311 | CG | PRO | A | 45 | −0.653 | 24.763 | −28.586 | 1.00 | 18.13 |
| ATOM | 312 | CD | PRO | A | 45 | −0.899 | 26.066 | −29.318 | 1.00 | 20.04 |
| ATOM | 313 | C | PRO | A | 45 | 1.253 | 24.454 | −31.026 | 1.00 | 17.74 |
| ATOM | 314 | O | PRO | A | 45 | 0.368 | 24.652 | −31.858 | 1.00 | 17.36 |
| ATOM | 315 | N | ASP | A | 46 | 2.178 | 23.512 | −31.160 | 1.00 | 15.95 |
| ATOM | 316 | CA | ASP | A | 46 | 2.124 | 22.573 | −32.275 | 1.00 | 14.75 |
| ATOM | 317 | CB | ASP | A | 46 | 3.551 | 22.255 | −32.738 | 1.00 | 14.59 |
| ATOM | 318 | CG | ASP | A | 46 | 3.601 | 21.161 | −33.818 | 1.00 | 16.17 |
| ATOM | 319 | OD1 | ASP | A | 46 | 2.543 | 20.787 | −34.389 | 1.00 | 15.61 |
| ATOM | 320 | OD2 | ASP | A | 46 | 4.712 | 20.641 | −34.054 | 1.00 | 20.18 |
| ATOM | 321 | C | ASP | A | 46 | 1.436 | 21.303 | −31.748 | 1.00 | 13.83 |
| ATOM | 322 | O | ASP | A | 46 | 2.081 | 20.489 | −31.089 | 1.00 | 13.59 |
| ATOM | 323 | N | TYR | A | 47 | 0.126 | 21.165 | −31.992 | 1.00 | 11.86 |
| ATOM | 324 | CA | TYR | A | 47 | −0.621 | 19.975 | −31.580 | 1.00 | 12.11 |
| ATOM | 325 | CB | TYR | A | 47 | −1.895 | 20.387 | −30.854 | 1.00 | 11.69 |
| ATOM | 326 | CG | TYR | A | 47 | −1.773 | 20.722 | −29.377 | 1.00 | 12.59 |
| ATOM | 327 | CD1 | TYR | A | 47 | −0.589 | 21.236 | −28.827 | 1.00 | 13.54 |
| ATOM | 328 | CE1 | TYR | A | 47 | −0.524 | 21.586 | −27.462 | 1.00 | 12.81 |
| ATOM | 329 | CZ | TYR | A | 47 | −1.652 | 21.407 | −26.673 | 1.00 | 13.40 |
| ATOM | 330 | OH | TYR | A | 47 | −1.620 | 21.755 | −25.354 | 1.00 | 13.08 |
| ATOM | 331 | CE2 | TYR | A | 47 | −2.825 | 20.887 | −27.208 | 1.00 | 12.02 |
| ATOM | 332 | CD2 | TYR | A | 47 | −2.876 | 20.540 | −28.532 | 1.00 | 12.76 |
| ATOM | 333 | C | TYR | A | 47 | −0.994 | 19.090 | −32.772 | 1.00 | 11.46 |
| ATOM | 334 | O | TYR | A | 47 | −1.885 | 18.239 | −32.692 | 1.00 | 11.66 |
| ATOM | 335 | N | TYR | A | 48 | −0.316 | 19.301 | −33.893 | 1.00 | 12.26 |
| ATOM | 336 | CA | TYR | A | 48 | −0.697 | 18.639 | −35.132 | 1.00 | 12.80 |
| ATOM | 337 | CB | TYR | A | 48 | −0.323 | 19.509 | −36.348 | 1.00 | 12.75 |
| ATOM | 338 | CG | TYR | A | 48 | −1.134 | 19.146 | −37.569 | 1.00 | 13.21 |
| ATOM | 339 | CD1 | TYR | A | 48 | −2.492 | 19.482 | −37.652 | 1.00 | 14.46 |
| ATOM | 340 | CE1 | TYR | A | 48 | −3.254 | 19.124 | −38.767 | 1.00 | 15.86 |

TABLE 20-continued

| ATOM | 341 | CZ | TYR | A | 48 | −2.643 | 18.453 | −39.823 | 1.00 | 14.62 |
| --- | --- | --- | --- | --- | --- | --- | --- | --- | --- | --- |
| ATOM | 342 | OH | TYR | A | 48 | −3.390 | 18.106 | −40.936 | 1.00 | 16.20 |
| ATOM | 343 | CE2 | TYR | A | 48 | −1.295 | 18.086 | −39.756 | 1.00 | 15.86 |
| ATOM | 344 | CD2 | TYR | A | 48 | −0.543 | 18.456 | −38.638 | 1.00 | 13.44 |
| ATOM | 345 | C | TYR | A | 48 | −0.072 | 17.245 | −35.187 | 1.00 | 13.47 |
| ATOM | 346 | O | TYR | A | 48 | 0.877 | 16.986 | −35.940 | 1.00 | 13.95 |
| ATOM | 347 | N | TYR | A | 49 | −0.592 | 16.360 | −34.338 | 1.00 | 13.13 |
| ATOM | 348 | CA | TYR | A | 49 | −0.131 | 14.987 | −34.171 | 1.00 | 13.51 |
| ATOM | 349 | CB | TYR | A | 49 | 0.887 | 14.842 | −33.009 | 1.00 | 13.11 |
| ATOM | 350 | CG | TYR | A | 49 | 2.133 | 15.662 | −33.216 | 1.00 | 13.90 |
| ATOM | 351 | CD1 | TYR | A | 49 | 3.193 | 15.174 | −33.996 | 1.00 | 13.54 |
| ATOM | 352 | CE1 | TYR | A | 49 | 4.354 | 15.964 | −34.216 | 1.00 | 13.41 |
| ATOM | 353 | CZ | TYR | A | 49 | 4.419 | 17.225 | −33.665 | 1.00 | 14.69 |
| ATOM | 354 | OH | TYR | A | 49 | 5.511 | 18.016 | −33.883 | 1.00 | 17.21 |
| ATOM | 355 | CE2 | TYR | A | 49 | 3.365 | 17.737 | −32.906 | 1.00 | 13.49 |
| ATOM | 356 | CD2 | TYR | A | 49 | 2.227 | 16.952 | −32.698 | 1.00 | 13.78 |
| ATOM | 357 | C | TYR | A | 49 | −1.349 | 14.181 | −33.783 | 1.00 | 13.93 |
| ATOM | 358 | O | TYR | A | 49 | −2.390 | 14.759 | −33.406 | 1.00 | 13.00 |
| ATOM | 359 | N | MET | A | 50 | −1.203 | 12.857 | −33.839 | 1.00 | 13.66 |
| ATOM | 360 | CA | MET | A | 50 | −2.241 | 11.940 | −33.365 | 1.00 | 14.56 |
| ATOM | 361 | CB | MET | A | 50 | −2.447 | 10.822 | −34.381 | 1.00 | 15.21 |
| ATOM | 362 | CG | MET | A | 50 | −3.532 | 9.811 | −33.947 | 1.00 | 15.64 |
| ATOM | 363 | SD | MET | A | 50 | −3.996 | 8.804 | −35.361 | 1.00 | 19.52 |
| ATOM | 364 | CE | MET | A | 50 | −5.204 | 7.742 | −34.566 | 1.00 | 17.12 |
| ATOM | 365 | C | MET | A | 50 | −1.797 | 11.323 | −32.060 | 1.00 | 14.38 |
| ATOM | 366 | O | MET | A | 50 | −0.806 | 10.583 | −32.024 | 1.00 | 13.80 |
| ATOM | 367 | N | TRP | A | 51 | −2.528 | 11.608 | −30.984 | 1.00 | 13.47 |
| ATOM | 368 | CA | TRP | A | 51 | −2.265 | 10.965 | −29.720 | 1.00 | 13.13 |
| ATOM | 369 | CB | TRP | A | 51 | −2.598 | 11.930 | −28.585 | 1.00 | 12.85 |
| ATOM | 370 | CG | TRP | A | 51 | −1.478 | 12.809 | −28.116 | 1.00 | 13.64 |
| ATOM | 371 | CD1 | TRP | A | 51 | −0.671 | 12.604 | −27.011 | 1.00 | 13.49 |
| ATOM | 372 | NE1 | TRP | A | 51 | 0.211 | 13.657 | −26.864 | 1.00 | 12.36 |
| ATOM | 373 | CE2 | TRP | A | 51 | −0.023 | 14.573 | −27.858 | 1.00 | 11.83 |
| ATOM | 374 | CD2 | TRP | A | 51 | −1.076 | 14.065 | −28.674 | 1.00 | 13.12 |
| ATOM | 375 | CE3 | TRP | A | 51 | −1.506 | 14.825 | −29.772 | 1.00 | 11.07 |
| ATOM | 376 | CZ3 | TRP | A | 51 | −0.859 | 16.061 | −30.035 | 1.00 | 12.87 |
| ATOM | 377 | CH2 | TRP | A | 51 | 0.193 | 16.522 | −29.218 | 1.00 | 13.24 |
| ATOM | 378 | CZ2 | TRP | A | 51 | 0.618 | 15.806 | −28.127 | 1.00 | 12.61 |
| ATOM | 379 | C | TRP | A | 51 | −3.136 | 9.732 | −29.575 | 1.00 | 13.35 |
| ATOM | 380 | O | TRP | A | 51 | −4.322 | 9.769 | −29.907 | 1.00 | 12.89 |
| ATOM | 381 | N | THR | A | 52 | −2.576 | 8.652 | −29.024 | 1.00 | 13.20 |
| ATOM | 382 | CA | THR | A | 52 | −3.386 | 7.462 | −28.753 | 1.00 | 13.02 |
| ATOM | 383 | CB | THR | A | 52 | −2.520 | 6.300 | −28.235 | 1.00 | 13.66 |
| ATOM | 384 | OG1 | THR | A | 52 | −1.553 | 5.999 | −29.246 | 1.00 | 15.07 |
| ATOM | 385 | CG2 | THR | A | 52 | −3.341 | 5.026 | −27.952 | 1.00 | 12.21 |
| ATOM | 386 | C | THR | A | 52 | −4.533 | 7.807 | −27.800 | 1.00 | 12.48 |
| ATOM | 387 | O | THR | A | 52 | −5.670 | 7.402 | −28.034 | 1.00 | 12.78 |
| ATOM | 388 | N | ARG | A | 53 | −4.224 | 8.556 | −26.747 | 1.00 | 12.03 |
| ATOM | 389 | CA | ARG | A | 53 | −5.238 | 8.868 | −25.737 | 1.00 | 11.89 |
| ATOM | 390 | CB | ARG | A | 53 | −4.607 | 9.570 | −24.545 | 1.00 | 11.46 |
| ATOM | 391 | CG | ARG | A | 53 | −5.611 | 10.330 | −23.618 | 1.00 | 13.19 |
| ATOM | 392 | CD | ARG | A | 53 | −4.896 | 10.881 | −22.375 | 1.00 | 11.14 |
| ATOM | 393 | NE | ARG | A | 53 | −3.793 | 11.694 | −22.819 | 1.00 | 12.52 |
| ATOM | 394 | CZ | ARG | A | 53 | −2.509 | 11.330 | −22.769 | 1.00 | 13.67 |
| ATOM | 395 | NH1 | ARG | A | 53 | −2.148 | 10.182 | −22.180 | 1.00 | 13.97 |
| ATOM | 396 | NH2 | ARG | A | 53 | −1.590 | 12.151 | −23.270 | 1.00 | 13.05 |
| ATOM | 397 | C | ARG | A | 53 | −6.395 | 9.709 | −26.319 | 1.00 | 12.45 |
| ATOM | 398 | O | ARG | A | 53 | −7.558 | 9.289 | −26.244 | 1.00 | 11.74 |
| ATOM | 399 | N | ASP | A | 54 | −6.090 | 10.885 | −26.874 | 1.00 | 11.73 |
| ATOM | 400 | CA | ASP | A | 54 | −7.169 | 11.747 | −27.385 | 1.00 | 11.90 |
| ATOM | 401 | CB | ASP | A | 54 | −6.638 | 13.018 | −28.053 | 1.00 | 12.25 |
| ATOM | 402 | CG | ASP | A | 54 | −5.794 | 13.879 | −27.120 | 1.00 | 13.97 |
| ATOM | 403 | OD1 | ASP | A | 54 | −4.983 | 13.332 | −26.354 | 1.00 | 13.57 |
| ATOM | 404 | OD2 | ASP | A | 54 | −5.910 | 15.110 | −27.215 | 1.00 | 13.88 |
| ATOM | 405 | C | ASP | A | 54 | −8.002 | 11.005 | −28.420 | 1.00 | 12.00 |
| ATOM | 406 | O | ASP | A | 54 | −9.236 | 11.138 | −28.454 | 1.00 | 10.97 |
| ATOM | 407 | N | SER | A | 55 | −7.334 | 10.250 | −29.297 | 1.00 | 11.19 |
| ATOM | 408 | CA | SER | A | 55 | −8.034 | 9.544 | −30.388 | 1.00 | 12.36 |
| ATOM | 409 | CB | SER | A | 55 | −7.017 | 8.901 | −31.340 | 1.00 | 13.05 |
| ATOM | 410 | OG | SER | A | 55 | −6.171 | 9.930 | −31.882 | 1.00 | 14.23 |
| ATOM | 411 | C | SER | A | 55 | −8.996 | 8.489 | −29.838 | 1.00 | 12.57 |
| ATOM | 412 | O | SER | A | 55 | −10.130 | 8.348 | −30.327 | 1.00 | 12.76 |
| ATOM | 413 | N | ALA | A | 56 | −8.556 | 7.764 | −28.819 | 1.00 | 12.60 |
| ATOM | 414 | CA | ALA | A | 56 | −9.373 | 6.718 | −28.218 | 1.00 | 13.25 |
| ATOM | 415 | CB | ALA | A | 56 | −8.517 | 5.830 | −27.329 | 1.00 | 12.73 |
| ATOM | 416 | C | ALA | A | 56 | −10.551 | 7.301 | −27.415 | 1.00 | 13.85 |
| ATOM | 417 | O | ALA | A | 56 | −11.640 | 6.723 | −27.409 | 1.00 | 14.51 |
| ATOM | 418 | N | LEU | A | 57 | −10.328 | 8.420 | −26.723 | 1.00 | 14.23 |
| ATOM | 419 | CA | LEU | A | 57 | −11.417 | 9.059 | −25.954 | 1.00 | 13.95 |
| ATOM | 420 | CB | LEU | A | 57 | −10.891 | 10.186 | −25.060 | 1.00 | 14.45 |

TABLE 20-continued

| | | | | | | | | | |
|---|---|---|---|---|---|---|---|---|---|
| ATOM | 421 | CG | LEU | A | 57 | −10.088 | 9.751 | −23.834 | 1.00 | 14.89 |
| ATOM | 422 | CD1 | LEU | A | 57 | −9.507 | 11.013 | −23.161 | 1.00 | 16.19 |
| ATOM | 423 | CD2 | LEU | A | 57 | −10.919 | 8.911 | −22.867 | 1.00 | 16.02 |
| ATOM | 424 | C | LEU | A | 57 | −12.483 | 9.609 | −26.886 | 1.00 | 13.92 |
| ATOM | 425 | O | LEU | A | 57 | −13.685 | 9.488 | −26.627 | 1.00 | 13.70 |
| ATOM | 426 | N | VAL | A | 58 | −12.027 | 10.199 | −27.975 | 1.00 | 13.15 |
| ATOM | 427 | CA | VAL | A | 58 | −12.920 | 10.751 | −28.989 | 1.00 | 15.20 |
| ATOM | 428 | CB | VAL | A | 58 | −12.133 | 11.605 | −30.031 | 1.00 | 14.52 |
| ATOM | 429 | CG1 | VAL | A | 58 | −12.970 | 11.861 | −31.302 | 1.00 | 17.86 |
| ATOM | 430 | CG2 | VAL | A | 58 | −11.704 | 12.954 | −29.393 | 1.00 | 15.79 |
| ATOM | 431 | C | VAL | A | 58 | −13.704 | 9.624 | −29.655 | 1.00 | 15.20 |
| ATOM | 432 | O | VAL | A | 58 | −14.930 | 9.718 | −29.784 | 1.00 | 15.30 |
| ATOM | 433 | N | PHE | A | 59 | −13.026 | 8.553 | −30.058 | 1.00 | 15.02 |
| ATOM | 434 | CA | PHE | A | 59 | −13.766 | 7.477 | −30.713 | 1.00 | 15.23 |
| ATOM | 435 | CB | PHE | A | 59 | −12.882 | 6.601 | −31.582 | 1.00 | 15.78 |
| ATOM | 436 | CG | PHE | A | 59 | −12.859 | 7.058 | −33.003 | 1.00 | 15.10 |
| ATOM | 437 | CD1 | PHE | A | 59 | −11.872 | 7.927 | −33.444 | 1.00 | 16.45 |
| ATOM | 438 | CE1 | PHE | A | 59 | −11.861 | 8.401 | −34.768 | 1.00 | 19.37 |
| ATOM | 439 | CZ | PHE | A | 59 | −12.876 | 8.026 | −35.644 | 1.00 | 16.44 |
| ATOM | 440 | CE2 | PHE | A | 59 | −13.901 | 7.165 | −35.186 | 1.00 | 16.90 |
| ATOM | 441 | CD2 | PHE | A | 59 | −13.895 | 6.709 | −33.882 | 1.00 | 16.17 |
| ATOM | 442 | C | PHE | A | 59 | −14.674 | 6.681 | −29.785 | 1.00 | 15.69 |
| ATOM | 443 | O | PHE | A | 59 | −15.699 | 6.175 | −30.220 | 1.00 | 15.46 |
| ATOM | 444 | N | LYS | A | 60 | −14.321 | 6.586 | −28.510 | 1.00 | 15.65 |
| ATOM | 445 | CA | LYS | A | 60 | −15.257 | 5.994 | −27.552 | 1.00 | 16.61 |
| ATOM | 446 | CB | LYS | A | 60 | −14.661 | 5.954 | −26.144 | 1.00 | 16.44 |
| ATOM | 447 | CG | LYS | A | 60 | −15.626 | 5.363 | −25.059 | 1.00 | 17.65 |
| ATOM | 448 | CD | LYS | A | 60 | −16.174 | 3.992 | −25.433 | 1.00 | 18.35 |
| ATOM | 449 | CE | LYS | A | 60 | −16.738 | 3.234 | −24.199 | 1.00 | 19.79 |
| ATOM | 450 | NZ | LYS | A | 60 | −17.819 | 3.976 | −23.512 | 1.00 | 18.40 |
| ATOM | 451 | C | LYS | A | 60 | −16.577 | 6.779 | −27.579 | 1.00 | 16.72 |
| ATOM | 452 | O | LYS | A | 60 | −17.663 | 6.182 | −27.681 | 1.00 | 17.08 |
| ATOM | 453 | N | ASN | A | 61 | −16.487 | 8.101 | −27.508 | 1.00 | 16.77 |
| ATOM | 454 | CA | ASN | A | 61 | −17.680 | 8.948 | −27.628 | 1.00 | 18.06 |
| ATOM | 455 | CB | ASN | A | 61 | −17.278 | 10.424 | −27.573 | 1.00 | 19.41 |
| ATOM | 456 | CG | ASN | A | 61 | −18.465 | 11.375 | −27.643 | 1.00 | 22.93 |
| ATOM | 457 | OD1 | ASN | A | 61 | −19.585 | 11.057 | −27.231 | 1.00 | 30.05 |
| ATOM | 458 | ND2 | ASN | A | 61 | −18.206 | 12.568 | −28.130 | 1.00 | 29.54 |
| ATOM | 459 | C | ASN | A | 61 | −18.480 | 8.659 | −28.907 | 1.00 | 17.28 |
| ATOM | 460 | O | ASN | A | 61 | −19.697 | 8.475 | −28.852 | 1.00 | 18.11 |
| ATOM | 461 | N | LEU | A | 62 | −17.799 | 8.647 | −30.056 | 1.00 | 16.54 |
| ATOM | 462 | CA | LEU | A | 62 | −18.460 | 8.379 | −31.334 | 1.00 | 16.19 |
| ATOM | 463 | CB | LEU | A | 62 | −17.479 | 8.572 | −32.499 | 1.00 | 16.85 |
| ATOM | 464 | CG | LEU | A | 62 | −17.047 | 10.027 | −32.697 | 1.00 | 18.47 |
| ATOM | 465 | CD1 | LEU | A | 62 | −16.118 | 10.153 | −33.916 | 1.00 | 20.38 |
| ATOM | 466 | CD2 | LEU | A | 62 | −18.263 | 10.925 | −32.837 | 1.00 | 19.93 |
| ATOM | 467 | C | LEU | A | 62 | −19.089 | 6.991 | −31.371 | 1.00 | 16.01 |
| ATOM | 468 | O | LEU | A | 62 | −20.225 | 6.833 | −31.842 | 1.00 | 15.98 |
| ATOM | 469 | N | ILE | A | 63 | −18.387 | 5.998 | −30.831 | 1.00 | 15.67 |
| ATOM | 470 | CA | ILE | A | 63 | −18.910 | 4.628 | −30.810 | 1.00 | 15.86 |
| ATOM | 471 | CB | ILE | A | 63 | −17.803 | 3.610 | −30.372 | 1.00 | 15.88 |
| ATOM | 472 | CG1 | ILE | A | 63 | −16.756 | 3.466 | −31.478 | 1.00 | 14.98 |
| ATOM | 473 | CD1 | ILE | A | 63 | −15.375 | 2.976 | −30.966 | 1.00 | 15.62 |
| ATOM | 474 | CG2 | ILE | A | 63 | −18.398 | 2.251 | −30.016 | 1.00 | 15.96 |
| ATOM | 475 | C | ILE | A | 63 | −20.156 | 4.538 | −29.920 | 1.00 | 16.39 |
| ATOM | 476 | O | ILE | A | 63 | −21.137 | 3.854 | −30.272 | 1.00 | 16.90 |
| ATOM | 477 | N | ASP | A | 64 | −20.129 | 5.242 | −28.796 | 1.00 | 16.51 |
| ATOM | 478 | CA | ASP | A | 64 | −21.299 | 5.324 | −27.922 | 1.00 | 17.76 |
| ATOM | 479 | CB | ASP | A | 64 | −20.953 | 6.022 | −26.594 | 1.00 | 17.81 |
| ATOM | 480 | CG | ASP | A | 64 | −20.089 | 5.164 | −25.682 | 1.00 | 17.84 |
| ATOM | 481 | OD1 | ASP | A | 64 | −19.883 | 3.944 | −25.963 | 1.00 | 18.57 |
| ATOM | 482 | OD2 | ASP | A | 64 | −19.595 | 5.699 | −24.659 | 1.00 | 20.95 |
| ATOM | 483 | C | ASP | A | 64 | −22.492 | 5.982 | −28.617 | 1.00 | 18.64 |
| ATOM | 484 | O | ASP | A | 64 | −23.617 | 5.493 | −28.507 | 1.00 | 20.85 |
| ATOM | 485 | N | ARG | A | 65 | −22.262 | 7.070 | −29.348 | 1.00 | 19.57 |
| ATOM | 486 | CA | ARG | A | 65 | −23.341 | 7.750 | −30.097 | 1.00 | 20.59 |
| ATOM | 487 | CB | ARG | A | 65 | −22.823 | 9.046 | −30.733 | 1.00 | 20.62 |
| ATOM | 488 | CG | ARG | A | 65 | −22.465 | 10.083 | −29.693 | 1.00 | 25.00 |
| ATOM | 489 | CD | ARG | A | 65 | −22.010 | 11.385 | −30.324 | 1.00 | 28.44 |
| ATOM | 490 | NE | ARG | A | 65 | −23.106 | 12.071 | −30.990 | 1.00 | 31.14 |
| ATOM | 491 | CZ | ARG | A | 65 | −23.968 | 12.878 | −30.373 | 1.00 | 32.75 |
| ATOM | 492 | NH1 | ARG | A | 65 | −23.873 | 13.095 | −29.060 | 1.00 | 32.10 |
| ATOM | 493 | NH2 | ARG | A | 65 | −24.928 | 13.459 | −31.080 | 1.00 | 32.31 |
| ATOM | 494 | C | ARG | A | 65 | −23.907 | 6.841 | −31.184 | 1.00 | 20.83 |
| ATOM | 495 | O | ARG | A | 65 | −25.129 | 6.711 | −31.357 | 1.00 | 20.48 |
| ATOM | 496 | N | PHE | A | 66 | −22.998 | 6.213 | −31.910 | 1.00 | 20.52 |
| ATOM | 497 | CA | PHE | A | 66 | −23.340 | 5.271 | −32.966 | 1.00 | 21.42 |
| ATOM | 498 | CB | PHE | A | 66 | −22.046 | 4.778 | −33.604 | 1.00 | 21.97 |
| ATOM | 499 | CG | PHE | A | 66 | −22.224 | 3.603 | −34.520 | 1.00 | 21.97 |
| ATOM | 500 | CD1 | PHE | A | 66 | −22.601 | 3.791 | −35.844 | 1.00 | 23.23 |

TABLE 20-continued

| | | | | | | | | | |
|---|---|---|---|---|---|---|---|---|---|
| ATOM | 501 | CE1 | PHE | A | 66 | −22.768 | 2.690 | −36.699 | 1.00 | 22.87 |
| ATOM | 502 | CZ | PHE | A | 66 | −22.552 | 1.409 | −36.221 | 1.00 | 22.60 |
| ATOM | 503 | CE2 | PHE | A | 66 | −22.165 | 1.216 | −34.895 | 1.00 | 23.74 |
| ATOM | 504 | CD2 | PHE | A | 66 | −22.006 | 2.309 | −34.054 | 1.00 | 23.07 |
| ATOM | 505 | C | PHE | A | 66 | −24.152 | 4.084 | −32.415 | 1.00 | 21.98 |
| ATOM | 506 | O | PHE | A | 66 | −25.040 | 3.551 | −33.099 | 1.00 | 21.80 |
| ATOM | 507 | N | THR | A | 67 | −23.831 | 3.654 | −31.195 | 1.00 | 22.48 |
| ATOM | 508 | CA | THR | A | 67 | −24.546 | 2.537 | −30.576 | 1.00 | 23.79 |
| ATOM | 509 | CB | THR | A | 67 | −23.809 | 1.999 | −29.333 | 1.00 | 23.68 |
| ATOM | 510 | OG1 | THR | A | 67 | −22.551 | 1.439 | −29.745 | 1.00 | 23.93 |
| ATOM | 511 | CG2 | THR | A | 67 | −24.613 | 0.881 | −28.653 | 1.00 | 23.90 |
| ATOM | 512 | C | THR | A | 67 | −25.992 | 2.925 | −30.258 | 1.00 | 24.77 |
| ATOM | 513 | O | THR | A | 67 | −26.893 | 2.090 | −30.349 | 1.00 | 25.31 |
| ATOM | 514 | N | GLU | A | 68 | −26.207 | 4.189 | −29.916 | 1.00 | 25.62 |
| ATOM | 515 | CA | GLU | A | 68 | −27.540 | 4.688 | −29.616 | 1.00 | 27.41 |
| ATOM | 516 | CB | GLU | A | 68 | −27.466 | 6.038 | −28.894 | 1.00 | 28.13 |
| ATOM | 517 | CG | GLU | A | 68 | −26.997 | 5.951 | −27.446 | 1.00 | 32.86 |
| ATOM | 518 | CD | GLU | A | 68 | −28.095 | 5.487 | −26.468 | 1.00 | 38.33 |
| ATOM | 519 | OE1 | GLU | A | 68 | −29.241 | 5.982 | −26.542 | 1.00 | 40.42 |
| ATOM | 520 | OE2 | GLU | A | 68 | −27.799 | 4.633 | −25.607 | 1.00 | 42.48 |
| ATOM | 521 | C | GLU | A | 68 | −28.418 | 4.784 | −30.873 | 1.00 | 27.86 |
| ATOM | 522 | O | GLU | A | 68 | −29.602 | 4.429 | −30.845 | 1.00 | 28.00 |
| ATOM | 523 | N | THR | A | 69 | −27.833 | 5.260 | −31.968 | 1.00 | 27.32 |
| ATOM | 524 | CA | THR | A | 69 | −28.540 | 5.373 | −33.241 | 1.00 | 27.32 |
| ATOM | 525 | CB | THR | A | 69 | −29.113 | 6.792 | −33.451 | 1.00 | 27.49 |
| ATOM | 526 | OG1 | THR | A | 69 | −29.922 | 7.153 | −32.334 | 1.00 | 30.86 |
| ATOM | 527 | CG2 | THR | A | 69 | −29.945 | 6.843 | −34.719 | 1.00 | 29.06 |
| ATOM | 528 | C | THR | A | 69 | −27.563 | 5.133 | −34.359 | 1.00 | 26.07 |
| ATOM | 529 | O | THR | A | 69 | −26.619 | 5.905 | −34.523 | 1.00 | 25.25 |
| ATOM | 530 | N | TYR | A | 70 | −27.790 | 4.064 | −35.123 | 1.00 | 25.65 |
| ATOM | 531 | CA | TYR | A | 70 | −26.948 | 3.738 | −36.267 | 1.00 | 25.36 |
| ATOM | 532 | CB | TYR | A | 70 | −27.480 | 2.504 | −37.013 | 1.00 | 25.26 |
| ATOM | 533 | CG | TYR | A | 70 | −26.638 | 2.104 | −38.217 | 1.00 | 25.62 |
| ATOM | 534 | CD1 | TYR | A | 70 | −26.949 | 2.567 | −39.498 | 1.00 | 25.62 |
| ATOM | 535 | CE1 | TYR | A | 70 | −26.190 | 2.201 | −40.611 | 1.00 | 26.48 |
| ATOM | 536 | CZ | TYR | A | 70 | −25.099 | 1.360 | −40.437 | 1.00 | 25.36 |
| ATOM | 537 | OH | TYR | A | 70 | −24.354 | 0.995 | −41.520 | 1.00 | 24.80 |
| ATOM | 538 | CE2 | TYR | A | 70 | −24.770 | 0.883 | −39.175 | 1.00 | 25.59 |
| ATOM | 539 | CD2 | TYR | A | 70 | −25.538 | 1.259 | −38.071 | 1.00 | 25.36 |
| ATOM | 540 | C | TYR | A | 70 | −26.816 | 4.909 | −37.230 | 1.00 | 25.38 |
| ATOM | 541 | O | TYR | A | 70 | −27.802 | 5.573 | −37.583 | 1.00 | 24.87 |
| ATOM | 542 | N | ASP | A | 71 | −25.575 | 5.127 | −37.666 | 1.00 | 25.16 |
| ATOM | 543 | CA | ASP | A | 71 | −25.188 | 6.210 | −38.550 | 1.00 | 25.40 |
| ATOM | 544 | CB | ASP | A | 71 | −24.668 | 7.404 | −37.724 | 1.00 | 25.60 |
| ATOM | 545 | CG | ASP | A | 71 | −24.361 | 8.642 | −38.573 | 1.00 | 26.17 |
| ATOM | 546 | OD1 | ASP | A | 71 | −23.801 | 8.526 | −39.681 | 1.00 | 25.82 |
| ATOM | 547 | OD2 | ASP | A | 71 | −24.675 | 9.755 | −38.108 | 1.00 | 27.85 |
| ATOM | 548 | C | ASP | A | 71 | −24.061 | 5.619 | −39.386 | 1.00 | 25.64 |
| ATOM | 549 | O | ASP | A | 71 | −22.956 | 5.377 | −38.875 | 1.00 | 24.82 |
| ATOM | 550 | N | ALA | A | 72 | −24.347 | 5.379 | −40.665 | 1.00 | 24.95 |
| ATOM | 551 | CA | ALA | A | 72 | −23.380 | 4.764 | −41.586 | 1.00 | 24.24 |
| ATOM | 552 | CB | ALA | A | 72 | −24.047 | 4.434 | −42.921 | 1.00 | 24.35 |
| ATOM | 553 | C | ALA | A | 72 | −22.152 | 5.657 | −41.812 | 1.00 | 24.04 |
| ATOM | 554 | O | ALA | A | 72 | −21.054 | 5.159 | −42.086 | 1.00 | 23.21 |
| ATOM | 555 | N | GLY | A | 73 | −22.356 | 6.970 | −41.695 | 1.00 | 23.63 |
| ATOM | 556 | CA | GLY | A | 73 | −21.265 | 7.938 | −41.761 | 1.00 | 24.20 |
| ATOM | 557 | C | GLY | A | 73 | −20.285 | 7.809 | −40.596 | 1.00 | 23.85 |
| ATOM | 558 | O | GLY | A | 73 | −19.067 | 7.927 | −40.806 | 1.00 | 24.81 |
| ATOM | 559 | N | LEU | A | 74 | −20.798 | 7.588 | −39.376 | 1.00 | 22.78 |
| ATOM | 560 | CA | LEU | A | 74 | −19.927 | 7.347 | −38.232 | 1.00 | 22.21 |
| ATOM | 561 | CB | LEU | A | 74 | −20.662 | 7.449 | −36.879 | 1.00 | 22.58 |
| ATOM | 562 | CG | LEU | A | 74 | −21.132 | 8.846 | −36.434 | 1.00 | 24.06 |
| ATOM | 563 | CD1 | LEU | A | 74 | −21.732 | 8.793 | −35.019 | 1.00 | 22.31 |
| ATOM | 564 | CD2 | LEU | A | 74 | −20.002 | 9.869 | −36.503 | 1.00 | 26.04 |
| ATOM | 565 | C | LEU | A | 74 | −19.256 | 5.999 | −38.370 | 1.00 | 21.94 |
| ATOM | 566 | O | LEU | A | 74 | −18.060 | 5.872 | −38.098 | 1.00 | 20.62 |
| ATOM | 567 | N | GLN | A | 75 | −20.019 | 4.988 | −38.814 | 1.00 | 21.47 |
| ATOM | 568 | CA | GLN | A | 75 | −19.451 | 3.654 | −38.989 | 1.00 | 21.07 |
| ATOM | 569 | CB | GLN | A | 75 | −20.469 | 2.709 | −39.619 | 1.00 | 21.44 |
| ATOM | 570 | CG | GLN | A | 75 | −20.002 | 1.280 | −39.594 | 1.00 | 23.11 |
| ATOM | 571 | CD | GLN | A | 75 | −21.101 | 0.312 | −39.945 | 1.00 | 24.74 |
| ATOM | 572 | OE1 | GLN | A | 75 | −21.273 | −0.719 | −39.290 | 1.00 | 26.57 |
| ATOM | 573 | NE2 | GLN | A | 75 | −21.872 | 0.654 | −40.950 | 1.00 | 23.71 |
| ATOM | 574 | C | GLN | A | 75 | −18.219 | 3.704 | −39.889 | 1.00 | 21.05 |
| ATOM | 575 | O | GLN | A | 75 | −17.229 | 3.046 | −39.611 | 1.00 | 21.10 |
| ATOM | 576 | N | ARG | A | 76 | −18.294 | 4.466 | −40.975 | 1.00 | 20.73 |
| ATOM | 577 | CA | ARG | A | 76 | −17.184 | 4.551 | −41.910 | 1.00 | 21.56 |
| ATOM | 578 | CB | ARG | A | 76 | −17.544 | 5.460 | −43.101 | 1.00 | 22.06 |
| ATOM | 579 | CG | ARG | A | 76 | −16.452 | 5.627 | −44.168 | 1.00 | 24.00 |
| ATOM | 580 | CD | ARG | A | 76 | −15.586 | 6.895 | −43.934 | 1.00 | 27.60 |

TABLE 20-continued

| | | | | | | | | | |
|---|---|---|---|---|---|---|---|---|---|
| ATOM | 581 | NE | ARG | A | 76 | −16.275 | 8.150 | −44.280 | 1.00 | 30.93 |
| ATOM | 582 | CZ | ARG | A | 76 | −15.778 | 9.378 | −44.082 | 1.00 | 32.20 |
| ATOM | 583 | NH1 | ARG | A | 76 | −14.572 | 9.556 | −43.535 | 1.00 | 30.72 |
| ATOM | 584 | NH2 | ARG | A | 76 | −16.491 | 10.443 | −44.437 | 1.00 | 32.29 |
| ATOM | 585 | C | ARG | A | 76 | −15.942 | 5.063 | −41.162 | 1.00 | 20.85 |
| ATOM | 586 | O | ARG | A | 76 | −14.858 | 4.514 | −41.296 | 1.00 | 20.93 |
| ATOM | 587 | N | ARG | A | 77 | −16.116 | 6.119 | −40.378 | 1.00 | 20.17 |
| ATOM | 588 | CA | ARG | A | 77 | −14.990 | 6.723 | −39.631 | 1.00 | 19.61 |
| ATOM | 589 | CB | ARG | A | 77 | −15.419 | 8.058 | −39.009 | 1.00 | 19.11 |
| ATOM | 590 | CG | ARG | A | 77 | −15.719 | 9.106 | −40.075 | 1.00 | 20.18 |
| ATOM | 591 | CD | ARG | A | 77 | −16.379 | 10.299 | −39.459 | 1.00 | 22.42 |
| ATOM | 592 | NE | ARG | A | 77 | −16.489 | 11.411 | −40.396 | 1.00 | 24.06 |
| ATOM | 593 | CZ | ARG | A | 77 | −17.501 | 11.592 | −41.243 | 1.00 | 27.81 |
| ATOM | 594 | NH1 | ARG | A | 77 | −18.508 | 10.714 | −41.303 | 1.00 | 28.01 |
| ATOM | 595 | NH2 | ARG | A | 77 | −17.509 | 12.658 | −42.033 | 1.00 | 27.19 |
| ATOM | 596 | C | ARG | A | 77 | −14.425 | 5.789 | −38.570 | 1.00 | 18.77 |
| ATOM | 597 | O | ARG | A | 77 | −13.197 | 5.685 | −38.411 | 1.00 | 18.64 |
| ATOM | 598 | N | ILE | A | 78 | −15.320 | 5.117 | −37.852 | 1.00 | 17.79 |
| ATOM | 599 | CA | ILE | A | 78 | −14.931 | 4.125 | −36.857 | 1.00 | 18.13 |
| ATOM | 600 | CB | ILE | A | 78 | −16.165 | 3.514 | −36.151 | 1.00 | 17.88 |
| ATOM | 601 | CG1 | ILE | A | 78 | −16.862 | 4.564 | −35.282 | 1.00 | 18.78 |
| ATOM | 602 | CD1 | ILE | A | 78 | −18.274 | 4.154 | −34.879 | 1.00 | 19.16 |
| ATOM | 603 | CG2 | ILE | A | 78 | −15.772 | 2.279 | −35.308 | 1.00 | 18.15 |
| ATOM | 604 | C | ILE | A | 78 | −14.105 | 3.012 | −37.491 | 1.00 | 18.09 |
| ATOM | 605 | O | ILE | A | 78 | −13.088 | 2.612 | −36.949 | 1.00 | 17.42 |
| ATOM | 606 | N | GLU | A | 79 | −14.565 | 2.495 | −38.631 | 1.00 | 18.82 |
| ATOM | 607 | CA | GLU | A | 79 | −13.826 | 1.446 | −39.341 | 1.00 | 20.22 |
| ATOM | 608 | CB | GLU | A | 79 | −14.587 | 1.017 | −40.609 | 1.00 | 20.36 |
| ATOM | 609 | CG | GLU | A | 79 | −15.811 | 0.136 | −40.312 | 1.00 | 22.29 |
| ATOM | 610 | CD | GLU | A | 79 | −16.633 | −0.206 | −41.565 | 1.00 | 22.92 |
| ATOM | 611 | OE1 | GLU | A | 79 | −16.345 | 0.328 | −42.670 | 1.00 | 26.99 |
| ATOM | 612 | OE2 | GLU | A | 79 | −17.579 | −1.012 | −41.425 | 1.00 | 25.69 |
| ATOM | 613 | C | GLU | A | 79 | −12.418 | 1.918 | −39.704 | 1.00 | 18.80 |
| ATOM | 614 | O | GLU | A | 79 | −11.450 | 1.191 | −39.507 | 1.00 | 19.44 |
| ATOM | 615 | N | GLN | A | 80 | −12.301 | 3.147 | −40.211 | 1.00 | 18.84 |
| ATOM | 616 | CA | GLN | A | 80 | −10.998 | 3.661 | −40.636 | 1.00 | 17.90 |
| ATOM | 617 | CB | GLN | A | 80 | −11.149 | 4.921 | −41.482 | 1.00 | 18.92 |
| ATOM | 618 | CG | GLN | A | 80 | −11.794 | 4.593 | −42.844 | 1.00 | 21.99 |
| ATOM | 619 | CD | GLN | A | 80 | −12.040 | 5.799 | −43.707 | 1.00 | 27.48 |
| ATOM | 620 | OE1 | GLN | A | 80 | −12.265 | 6.898 | −43.223 | 1.00 | 30.45 |
| ATOM | 621 | NE2 | GLN | A | 80 | −12.037 | 5.586 | −45.013 | 1.00 | 32.63 |
| ATOM | 622 | C | GLN | A | 80 | −10.059 | 3.892 | −39.456 | 1.00 | 17.64 |
| ATOM | 623 | O | GLN | A | 80 | −8.862 | 3.612 | −39.535 | 1.00 | 17.21 |
| ATOM | 624 | N | TYR | A | 81 | −10.607 | 4.408 | −38.365 | 1.00 | 17.29 |
| ATOM | 625 | CA | TYR | A | 81 | −9.839 | 4.552 | −37.122 | 1.00 | 17.64 |
| ATOM | 626 | CB | TYR | A | 81 | −10.750 | 5.139 | −36.023 | 1.00 | 17.24 |
| ATOM | 627 | CG | TYR | A | 81 | −10.188 | 4.973 | −34.621 | 1.00 | 17.79 |
| ATOM | 628 | CD1 | TYR | A | 81 | −9.085 | 5.728 | −34.184 | 1.00 | 16.36 |
| ATOM | 629 | CE1 | TYR | A | 81 | −8.561 | 5.568 | −32.882 | 1.00 | 17.45 |
| ATOM | 630 | CZ | TYR | A | 81 | −9.146 | 4.646 | −32.009 | 1.00 | 16.35 |
| ATOM | 631 | OH | TYR | A | 81 | −8.654 | 4.457 | −30.724 | 1.00 | 17.06 |
| ATOM | 632 | CE2 | TYR | A | 81 | −10.238 | 3.890 | −32.423 | 1.00 | 17.51 |
| ATOM | 633 | CD2 | TYR | A | 81 | −10.754 | 4.055 | −33.729 | 1.00 | 17.00 |
| ATOM | 634 | C | TYR | A | 81 | −9.271 | 3.197 | −36.686 | 1.00 | 18.04 |
| ATOM | 635 | O | TYR | A | 81 | −8.098 | 3.083 | −36.321 | 1.00 | 17.85 |
| ATOM | 636 | N | ILE | A | 82 | −10.096 | 2.159 | −36.746 | 1.00 | 17.99 |
| ATOM | 637 | CA | ILE | A | 82 | −9.661 | 0.839 | −36.295 | 1.00 | 19.35 |
| ATOM | 638 | CB | ILE | A | 82 | −10.844 | −0.166 | −36.187 | 1.00 | 18.93 |
| ATOM | 639 | CG1 | ILE | A | 82 | −11.753 | 0.233 | −35.017 | 1.00 | 19.40 |
| ATOM | 640 | CD1 | ILE | A | 82 | −13.093 | −0.565 | −34.896 | 1.00 | 20.46 |
| ATOM | 641 | CG2 | ILE | A | 82 | −10.301 | −1.587 | −35.984 | 1.00 | 20.61 |
| ATOM | 642 | C | ILE | A | 82 | −8.547 | 0.292 | −37.194 | 1.00 | 19.92 |
| ATOM | 643 | O | ILE | A | 82 | −7.543 | −0.239 | −36.708 | 1.00 | 20.26 |
| ATOM | 644 | N | THR | A | 83 | −8.713 | 0.432 | −38.503 | 1.00 | 20.05 |
| ATOM | 645 | CA | THR | A | 83 | −7.709 | −0.100 | −39.406 | 1.00 | 21.11 |
| ATOM | 646 | CB | THR | A | 83 | −8.241 | −0.297 | −40.845 | 1.00 | 21.63 |
| ATOM | 647 | OG1 | THR | A | 83 | −8.830 | 0.902 | −41.306 | 1.00 | 25.88 |
| ATOM | 648 | CG2 | THR | A | 83 | −9.330 | −1.347 | −40.851 | 1.00 | 21.56 |
| ATOM | 649 | C | THR | A | 83 | −6.410 | 0.690 | −39.337 | 1.00 | 20.59 |
| ATOM | 650 | O | THR | A | 83 | −5.338 | 0.105 | −39.511 | 1.00 | 20.72 |
| ATOM | 651 | N | ALA | A | 84 | −6.494 | 1.997 | −39.050 | 1.00 | 19.51 |
| ATOM | 652 | CA | ALA | A | 84 | −5.292 | 2.809 | −38.777 | 1.00 | 19.37 |
| ATOM | 653 | CB | ALA | A | 84 | −5.652 | 4.290 | −38.507 | 1.00 | 19.42 |
| ATOM | 654 | C | ALA | A | 84 | −4.436 | 2.231 | −37.643 | 1.00 | 19.32 |
| ATOM | 655 | O | ALA | A | 84 | −3.208 | 2.370 | −37.649 | 1.00 | 19.47 |
| ATOM | 656 | N | GLN | A | 85 | −5.063 | 1.535 | −36.695 | 1.00 | 19.34 |
| ATOM | 657 | CA | GLN | A | 85 | −4.325 | 0.998 | −35.544 | 1.00 | 18.78 |
| ATOM | 658 | CB | GLN | A | 85 | −5.266 | 0.609 | −34.396 | 1.00 | 19.29 |
| ATOM | 659 | CG | GLN | A | 85 | −6.260 | 1.735 | −34.007 | 1.00 | 17.98 |
| ATOM | 660 | CD | GLN | A | 85 | −5.593 | 3.098 | −33.830 | 1.00 | 17.20 |

TABLE 20-continued

| | | | | | | | | | |
|---|---|---|---|---|---|---|---|---|---|
| ATOM | 661 | OE1 | GLN | A | 85 | −6.021 | 4.095 | −34.418 | 1.00 | 20.82 |
| ATOM | 662 | NE2 | GLN | A | 85 | −4.540 | 3.143 | −33.034 | 1.00 | 13.47 |
| ATOM | 663 | C | GLN | A | 85 | −3.447 | −0.178 | −35.932 | 1.00 | 19.08 |
| ATOM | 664 | O | GLN | A | 85 | −2.478 | −0.473 | −35.251 | 1.00 | 17.94 |
| ATOM | 665 | N | VAL | A | 86 | −3.808 | −0.838 | −37.032 | 1.00 | 19.32 |
| ATOM | 666 | CA | VAL | A | 86 | −2.999 | −1.928 | −37.588 | 1.00 | 20.79 |
| ATOM | 667 | CB | VAL | A | 86 | −3.670 | −2.581 | −38.823 | 1.00 | 21.18 |
| ATOM | 668 | CG1 | VAL | A | 86 | −2.712 | −3.615 | −39.454 | 1.00 | 22.66 |
| ATOM | 669 | CG2 | VAL | A | 86 | −4.980 | −3.250 | −38.400 | 1.00 | 21.47 |
| ATOM | 670 | C | VAL | A | 86 | −1.617 | −1.381 | −37.940 | 1.00 | 20.63 |
| ATOM | 671 | O | VAL | A | 86 | −0.602 | −1.930 | −37.520 | 1.00 | 21.41 |
| ATOM | 672 | N | THR | A | 87 | −1.604 | −0.251 | −38.641 | 1.00 | 20.67 |
| ATOM | 673 | CA | THR | A | 87 | −0.361 | 0.419 | −39.015 | 1.00 | 21.10 |
| ATOM | 674 | CB | THR | A | 87 | −0.659 | 1.583 | −39.986 | 1.00 | 21.59 |
| ATOM | 675 | OG1 | THR | A | 87 | −1.176 | 1.033 | −41.202 | 1.00 | 23.63 |
| ATOM | 676 | CG2 | THR | A | 87 | 0.585 | 2.370 | −40.305 | 1.00 | 22.02 |
| ATOM | 677 | C | THR | A | 87 | 0.412 | 0.881 | −37.795 | 1.00 | 20.28 |
| ATOM | 678 | O | THR | A | 87 | 1.620 | 0.641 | −37.679 | 1.00 | 20.22 |
| ATOM | 679 | N | LEU | A | 88 | −0.280 | 1.543 | −36.874 | 1.00 | 19.11 |
| ATOM | 680 | CA | LEU | A | 88 | 0.367 | 2.097 | −35.697 | 1.00 | 18.71 |
| ATOM | 681 | CB | LEU | A | 88 | −0.585 | 3.015 | −34.903 | 1.00 | 18.08 |
| ATOM | 682 | CG | LEU | A | 88 | −1.016 | 4.294 | −35.596 | 1.00 | 18.50 |
| ATOM | 683 | CD1 | LEU | A | 88 | −2.038 | 5.058 | −34.706 | 1.00 | 19.12 |
| ATOM | 684 | CD2 | LEU | A | 88 | 0.206 | 5.193 | −35.937 | 1.00 | 19.81 |
| ATOM | 685 | C | LEU | A | 88 | 0.976 | 1.057 | −34.780 | 1.00 | 18.33 |
| ATOM | 686 | O | LEU | A | 88 | 2.101 | 1.244 | −34.336 | 1.00 | 18.76 |
| ATOM | 687 | N | GLN | A | 89 | 0.255 | −0.029 | −34.492 | 1.00 | 18.75 |
| ATOM | 688 | CA | GLN | A | 89 | 0.809 | −1.085 | −33.623 | 1.00 | 19.67 |
| ATOM | 689 | CB | GLN | A | 89 | −0.199 | −2.201 | −33.373 | 1.00 | 19.69 |
| ATOM | 690 | CG | GLN | A | 89 | −1.397 | −1.775 | −32.564 | 1.00 | 19.25 |
| ATOM | 691 | CD | GLN | A | 89 | −2.140 | −2.951 | −32.004 | 1.00 | 20.83 |
| ATOM | 692 | OE1 | GLN | A | 89 | −2.121 | −4.037 | −32.580 | 1.00 | 19.26 |
| ATOM | 693 | NE2 | GLN | A | 89 | −2.802 | −2.751 | −30.861 | 1.00 | 19.61 |
| ATOM | 694 | C | GLN | A | 89 | 2.097 | −1.683 | −34.203 | 1.00 | 20.68 |
| ATOM | 695 | O | GLN | A | 89 | 3.013 | −2.026 | −33.461 | 1.00 | 21.21 |
| ATOM | 696 | N | GLY | A | 90 | 2.164 | −1.778 | −35.524 | 1.00 | 21.75 |
| ATOM | 697 | CA | GLY | A | 90 | 3.330 | −2.374 | −36.173 | 1.00 | 23.35 |
| ATOM | 698 | C | GLY | A | 90 | 4.604 | −1.552 | −36.096 | 1.00 | 24.79 |
| ATOM | 699 | O | GLY | A | 90 | 5.699 | −2.104 | −36.299 | 1.00 | 25.52 |
| ATOM | 700 | N | ASN | A | 91 | 4.477 | −0.252 | −35.796 | 1.00 | 25.17 |
| ATOM | 701 | CA | ASN | A | 91 | 5.596 | 0.714 | −35.870 | 1.00 | 26.14 |
| ATOM | 702 | CB | ASN | A | 91 | 5.108 | 2.161 | −35.653 | 1.00 | 26.83 |
| ATOM | 703 | CG | ASN | A | 91 | 4.615 | 2.849 | −36.919 | 1.00 | 29.67 |
| ATOM | 704 | OD1 | ASN | A | 91 | 4.869 | 2.414 | −38.051 | 1.00 | 34.53 |
| ATOM | 705 | ND2 | ASN | A | 91 | 3.927 | 3.981 | −36.724 | 1.00 | 32.76 |
| ATOM | 706 | C | ASN | A | 91 | 6.656 | 0.489 | −34.820 | 1.00 | 25.67 |
| ATOM | 707 | O | ASN | A | 91 | 6.346 | 0.385 | −33.644 | 1.00 | 25.70 |
| ATOM | 708 | N | SER | A | 92 | 7.918 | 0.472 | −35.227 | 1.00 | 25.32 |
| ATOM | 709 | CA | SER | A | 92 | 8.990 | 0.668 | −34.257 | 1.00 | 25.27 |
| ATOM | 710 | CB | SER | A | 92 | 10.314 | 0.107 | −34.775 | 1.00 | 26.03 |
| ATOM | 711 | OG | SER | A | 92 | 10.212 | −1.305 | −34.803 | 1.00 | 30.67 |
| ATOM | 712 | C | SER | A | 92 | 9.103 | 2.171 | −34.003 | 1.00 | 23.80 |
| ATOM | 713 | O | SER | A | 92 | 9.055 | 2.979 | −34.942 | 1.00 | 24.56 |
| ATOM | 714 | N | ASN | A | 93 | 9.246 | 2.544 | −32.743 | 1.00 | 22.30 |
| ATOM | 715 | CA | ASN | A | 93 | 9.236 | 3.953 | −32.383 | 1.00 | 21.23 |
| ATOM | 716 | CB | ASN | A | 93 | 7.769 | 4.423 | −32.201 | 1.00 | 21.41 |
| ATOM | 717 | CG | ASN | A | 93 | 7.075 | 3.704 | −31.051 | 1.00 | 19.23 |
| ATOM | 718 | OD1 | ASN | A | 93 | 7.564 | 3.736 | −29.927 | 1.00 | 17.81 |
| ATOM | 719 | ND2 | ASN | A | 93 | 5.974 | 3.024 | −31.335 | 1.00 | 19.43 |
| ATOM | 720 | C | ASN | A | 93 | 10.103 | 4.149 | −31.150 | 1.00 | 20.39 |
| ATOM | 721 | O | ASN | A | 93 | 10.625 | 3.154 | −30.607 | 1.00 | 19.46 |
| ATOM | 722 | N | PRO | A | 94 | 10.337 | 5.410 | −30.732 | 1.00 | 19.95 |
| ATOM | 723 | CA | PRO | A | 94 | 11.228 | 5.604 | −29.574 | 1.00 | 19.89 |
| ATOM | 724 | CB | PRO | A | 94 | 11.235 | 7.131 | −29.385 | 1.00 | 19.51 |
| ATOM | 725 | CG | PRO | A | 94 | 10.988 | 7.653 | −30.753 | 1.00 | 19.96 |
| ATOM | 726 | CD | PRO | A | 94 | 9.952 | 6.717 | −31.325 | 1.00 | 19.99 |
| ATOM | 727 | C | PRO | A | 94 | 10.870 | 4.898 | −28.263 | 1.00 | 20.64 |
| ATOM | 728 | O | PRO | A | 94 | 11.756 | 4.727 | −27.430 | 1.00 | 20.54 |
| ATOM | 729 | N | SER | A | 95 | 9.610 | 4.485 | −28.073 | 1.00 | 20.36 |
| ATOM | 730 | CA | SER | A | 95 | 9.264 | 3.674 | −26.902 | 1.00 | 21.00 |
| ATOM | 731 | CB | SER | A | 95 | 7.770 | 3.736 | −26.587 | 1.00 | 20.05 |
| ATOM | 732 | OG | SER | A | 95 | 7.413 | 5.036 | −26.147 | 1.00 | 19.97 |
| ATOM | 733 | C | SER | A | 95 | 9.679 | 2.204 | −27.066 | 1.00 | 21.73 |
| ATOM | 734 | O | SER | A | 95 | 9.809 | 1.499 | −26.072 | 1.00 | 22.10 |
| ATOM | 735 | N | GLY | A | 96 | 9.853 | 1.748 | −28.306 | 1.00 | 21.90 |
| ATOM | 736 | CA | GLY | A | 96 | 10.229 | 0.350 | −28.562 | 1.00 | 23.56 |
| ATOM | 737 | C | GLY | A | 96 | 9.506 | −0.196 | −29.774 | 1.00 | 24.14 |
| ATOM | 738 | O | GLY | A | 96 | 9.121 | 0.557 | −30.664 | 1.00 | 24.24 |
| ATOM | 739 | N | SER | A | 97 | 9.315 | −1.510 | −29.828 | 1.00 | 25.24 |
| ATOM | 740 | CA | SER | A | 97 | 8.703 | −2.116 | −31.000 | 1.00 | 25.77 |

TABLE 20-continued

| | | | | | | | | | |
|---|---|---|---|---|---|---|---|---|---|
| ATOM | 741 | CB | SER | A | 97 | 9.751 | −2.874 | −31.834 | 1.00 | 27.15 |
| ATOM | 742 | OG | SER | A | 97 | 10.120 | −4.086 | −31.189 | 1.00 | 30.57 |
| ATOM | 743 | C | SER | A | 97 | 7.590 | −3.042 | −30.571 | 1.00 | 25.27 |
| ATOM | 744 | O | SER | A | 97 | 7.346 | −3.199 | −29.376 | 1.00 | 24.85 |
| ATOM | 745 | N | LEU | A | 98 | 6.930 | −3.655 | −31.543 | 1.00 | 24.82 |
| ATOM | 746 | CA | LEU | A | 98 | 5.826 | −4.559 | −31.252 | 1.00 | 25.88 |
| ATOM | 747 | CB | LEU | A | 98 | 4.982 | −4.813 | −32.504 | 1.00 | 25.31 |
| ATOM | 748 | CG | LEU | A | 98 | 3.714 | −5.673 | −32.420 | 1.00 | 25.89 |
| ATOM | 749 | CD1 | LEU | A | 98 | 2.745 | −5.169 | −31.337 | 1.00 | 25.58 |
| ATOM | 750 | CD2 | LEU | A | 98 | 3.006 | −5.724 | −33.778 | 1.00 | 26.27 |
| ATOM | 751 | C | LEU | A | 98 | 6.310 | −5.866 | −30.604 | 1.00 | 26.75 |
| ATOM | 752 | O | LEU | A | 98 | 5.607 | −6.438 | −29.762 | 1.00 | 27.41 |
| ATOM | 753 | N | ALA | A | 99 | 7.528 | −6.290 | −30.950 | 1.00 | 27.23 |
| ATOM | 754 | CA | ALA | A | 99 | 8.074 | −7.590 | −30.533 | 1.00 | 27.89 |
| ATOM | 755 | CB | ALA | A | 99 | 9.566 | −7.700 | −30.935 | 1.00 | 27.68 |
| ATOM | 756 | C | ALA | A | 99 | 7.893 | −7.911 | −29.053 | 1.00 | 27.86 |
| ATOM | 757 | O | ALA | A | 99 | 7.450 | −9.007 | −28.711 | 1.00 | 28.77 |
| ATOM | 758 | N | ASP | A | 100 | 8.241 | −6.966 | −28.181 | 1.00 | 27.75 |
| ATOM | 759 | CA | ASP | A | 100 | 8.030 | −7.137 | −26.741 | 1.00 | 27.20 |
| ATOM | 760 | CB | ASP | A | 100 | 9.328 | −6.937 | −25.966 | 1.00 | 27.10 |
| ATOM | 761 | CG | ASP | A | 100 | 9.845 | −5.525 | −26.038 | 1.00 | 30.19 |
| ATOM | 762 | OD1 | ASP | A | 100 | 10.891 | −5.281 | −25.419 | 1.00 | 32.28 |
| ATOM | 763 | OD2 | ASP | A | 100 | 9.225 | −4.654 | −26.694 | 1.00 | 30.36 |
| ATOM | 764 | C | ASP | A | 100 | 6.905 | −6.256 | −26.173 | 1.00 | 25.74 |
| ATOM | 765 | O | ASP | A | 100 | 6.761 | −6.108 | −24.956 | 1.00 | 26.33 |
| ATOM | 766 | N | GLY | A | 101 | 6.118 | −5.683 | −27.075 | 1.00 | 24.93 |
| ATOM | 767 | CA | GLY | A | 101 | 4.982 | −4.853 | −26.707 | 1.00 | 23.22 |
| ATOM | 768 | C | GLY | A | 101 | 5.326 | −3.418 | −26.342 | 1.00 | 22.68 |
| ATOM | 769 | O | GLY | A | 101 | 4.419 | −2.580 | −26.287 | 1.00 | 21.48 |
| ATOM | 770 | N | SER | A | 102 | 6.609 | −3.117 | −26.126 | 1.00 | 21.53 |
| ATOM | 771 | CA | SER | A | 102 | 6.996 | −1.815 | −25.563 | 1.00 | 21.49 |
| ATOM | 772 | CB | SER | A | 102 | 8.483 | −1.739 | −25.199 | 1.00 | 22.07 |
| ATOM | 773 | OG | SER | A | 102 | 9.283 | −1.958 | −26.345 | 1.00 | 21.77 |
| ATOM | 774 | C | SER | A | 102 | 6.604 | −0.643 | −26.449 | 1.00 | 20.66 |
| ATOM | 775 | O | SER | A | 102 | 6.279 | 0.403 | −25.925 | 1.00 | 20.67 |
| ATOM | 776 | N | GLY | A | 103 | 6.636 | −0.819 | −27.771 | 1.00 | 19.97 |
| ATOM | 777 | CA | GLY | A | 103 | 6.257 | 0.255 | −28.707 | 1.00 | 19.46 |
| ATOM | 778 | C | GLY | A | 103 | 4.824 | 0.777 | −28.539 | 1.00 | 18.94 |
| ATOM | 779 | O | GLY | A | 103 | 4.525 | 1.903 | −28.945 | 1.00 | 18.13 |
| ATOM | 780 | N | LEU | A | 104 | 3.939 | −0.043 | −27.956 | 1.00 | 18.13 |
| ATOM | 781 | CA | LEU | A | 104 | 2.517 | 0.326 | −27.818 | 1.00 | 16.92 |
| ATOM | 782 | CB | LEU | A | 104 | 1.672 | −0.924 | −27.447 | 1.00 | 17.28 |
| ATOM | 783 | CG | LEU | A | 104 | 1.715 | −2.104 | −28.430 | 1.00 | 16.76 |
| ATOM | 784 | CD1 | LEU | A | 104 | 1.072 | −3.356 | −27.836 | 1.00 | 21.62 |
| ATOM | 785 | CD2 | LEU | A | 104 | 1.069 | −1.751 | −29.761 | 1.00 | 19.06 |
| ATOM | 786 | C | LEU | A | 104 | 2.283 | 1.464 | −26.798 | 1.00 | 16.57 |
| ATOM | 787 | O | LEU | A | 104 | 1.202 | 2.092 | −26.807 | 1.00 | 16.79 |
| ATOM | 788 | N | GLY | A | 105 | 3.279 | 1.713 | −25.936 | 1.00 | 14.86 |
| ATOM | 789 | CA | GLY | A | 105 | 3.255 | 2.802 | −24.938 | 1.00 | 15.94 |
| ATOM | 790 | C | GLY | A | 105 | 3.558 | 4.199 | −25.482 | 1.00 | 15.05 |
| ATOM | 791 | O | GLY | A | 105 | 3.481 | 5.179 | −24.755 | 1.00 | 15.93 |
| ATOM | 792 | N | GLU | A | 106 | 3.869 | 4.292 | −26.780 | 1.00 | 14.63 |
| ATOM | 793 | CA | GLU | A | 106 | 4.236 | 5.548 | −27.416 | 1.00 | 14.49 |
| ATOM | 794 | CB | GLU | A | 106 | 4.728 | 5.250 | −28.847 | 1.00 | 13.83 |
| ATOM | 795 | CG | GLU | A | 106 | 5.215 | 6.470 | −29.678 | 1.00 | 16.14 |
| ATOM | 796 | CD | GLU | A | 106 | 6.479 | 7.155 | −29.139 | 1.00 | 18.44 |
| ATOM | 797 | OE1 | GLU | A | 106 | 6.978 | 6.817 | −28.044 | 1.00 | 21.44 |
| ATOM | 798 | OE2 | GLU | A | 106 | 6.972 | 8.083 | −29.817 | 1.00 | 21.04 |
| ATOM | 799 | C | GLU | A | 106 | 3.012 | 6.484 | −27.413 | 1.00 | 14.32 |
| ATOM | 800 | O | GLU | A | 106 | 1.928 | 6.074 | −27.828 | 1.00 | 15.51 |
| ATOM | 801 | N | PRO | A | 107 | 3.164 | 7.706 | −26.890 | 1.00 | 15.21 |
| ATOM | 802 | CA | PRO | A | 107 | 2.025 | 8.645 | −26.772 | 1.00 | 14.90 |
| ATOM | 803 | CB | PRO | A | 107 | 2.598 | 9.809 | −25.951 | 1.00 | 15.27 |
| ATOM | 804 | CG | PRO | A | 107 | 3.833 | 9.290 | −25.310 | 1.00 | 17.25 |
| ATOM | 805 | CD | PRO | A | 107 | 4.385 | 8.238 | −26.243 | 1.00 | 14.35 |
| ATOM | 806 | C | PRO | A | 107 | 1.468 | 9.219 | −28.066 | 1.00 | 14.48 |
| ATOM | 807 | O | PRO | A | 107 | 0.263 | 9.371 | −28.172 | 1.00 | 13.94 |
| ATOM | 808 | N | LYS | A | 108 | 2.320 | 9.567 | −29.027 | 1.00 | 14.24 |
| ATOM | 809 | CA | LYS | A | 108 | 1.837 | 10.309 | −30.204 | 1.00 | 14.51 |
| ATOM | 810 | CB | LYS | A | 108 | 1.853 | 11.828 | −29.960 | 1.00 | 14.26 |
| ATOM | 811 | CG | LYS | A | 108 | 3.225 | 12.524 | −30.029 | 1.00 | 13.88 |
| ATOM | 812 | CD | LYS | A | 108 | 3.102 | 14.033 | −29.775 | 1.00 | 15.15 |
| ATOM | 813 | CE | LYS | A | 108 | 4.299 | 14.820 | −30.283 | 1.00 | 17.08 |
| ATOM | 814 | NZ | LYS | A | 108 | 4.341 | 16.279 | −29.836 | 1.00 | 15.57 |
| ATOM | 815 | C | LYS | A | 108 | 2.608 | 9.953 | −31.454 | 1.00 | 14.69 |
| ATOM | 816 | O | LYS | A | 108 | 3.734 | 9.442 | −31.377 | 1.00 | 14.67 |
| ATOM | 817 | N | PHE | A | 109 | 1.976 | 10.203 | −32.594 | 1.00 | 14.54 |
| ATOM | 818 | CA | PHE | A | 109 | 2.530 | 9.860 | −33.902 | 1.00 | 15.20 |
| ATOM | 819 | CB | PHE | A | 109 | 1.839 | 8.594 | −34.451 | 1.00 | 15.67 |
| ATOM | 820 | CG | PHE | A | 109 | 1.973 | 7.407 | −33.553 | 1.00 | 16.81 |

TABLE 20-continued

| | | | | | | | | | |
|---|---|---|---|---|---|---|---|---|---|
| ATOM | 821 | CD1 | PHE | A | 109 | 1.081 | 7.219 | −32.490 | 1.00 | 17.93 |
| ATOM | 822 | CE1 | PHE | A | 109 | 1.205 | 6.117 | −31.649 | 1.00 | 21.93 |
| ATOM | 823 | CZ | PHE | A | 109 | 2.241 | 5.210 | −31.834 | 1.00 | 19.06 |
| ATOM | 824 | CE2 | PHE | A | 109 | 3.141 | 5.384 | −32.883 | 1.00 | 20.27 |
| ATOM | 825 | CD2 | PHE | A | 109 | 3.003 | 6.492 | −33.737 | 1.00 | 19.44 |
| ATOM | 826 | C | PHE | A | 109 | 2.301 | 10.992 | −34.881 | 1.00 | 15.19 |
| ATOM | 827 | O | PHE | A | 109 | 1.450 | 11.861 | −34.655 | 1.00 | 14.41 |
| ATOM | 828 | N | GLU | A | 110 | 3.039 | 10.971 | −35.993 | 1.00 | 15.14 |
| ATOM | 829 | CA | GLU | A | 110 | 2.756 | 11.905 | −37.077 | 1.00 | 15.24 |
| ATOM | 830 | CB | GLU | A | 110 | 3.905 | 11.933 | −38.103 | 1.00 | 15.00 |
| ATOM | 831 | CG | GLU | A | 110 | 5.302 | 12.204 | −37.493 | 1.00 | 16.29 |
| ATOM | 832 | CD | GLU | A | 110 | 5.554 | 13.673 | −37.174 | 1.00 | 17.52 |
| ATOM | 833 | OE1 | GLU | A | 110 | 4.708 | 14.544 | −37.504 | 1.00 | 17.65 |
| ATOM | 834 | OE2 | GLU | A | 110 | 6.619 | 13.963 | −36.587 | 1.00 | 18.74 |
| ATOM | 835 | C | GLU | A | 110 | 1.462 | 11.476 | −37.762 | 1.00 | 15.32 |
| ATOM | 836 | O | GLU | A | 110 | 1.093 | 10.278 | −37.753 | 1.00 | 15.26 |
| ATOM | 837 | N | LEU | A | 111 | 0.776 | 12.445 | −38.360 | 1.00 | 15.59 |
| ATOM | 838 | CA | LEU | A | 111 | −0.522 | 12.186 | −39.009 | 1.00 | 16.33 |
| ATOM | 839 | CB | LEU | A | 111 | −1.265 | 13.510 | −39.163 | 1.00 | 16.57 |
| ATOM | 840 | CG | LEU | A | 111 | −1.770 | 13.908 | −37.756 | 1.00 | 18.11 |
| ATOM | 841 | CD1 | LEU | A | 111 | −1.819 | 15.405 | −37.574 | 1.00 | 21.43 |
| ATOM | 842 | CD2 | LEU | A | 111 | −3.151 | 13.204 | −37.506 | 1.00 | 18.74 |
| ATOM | 843 | C | LEU | A | 111 | −0.409 | 11.436 | −40.350 | 1.00 | 17.37 |
| ATOM | 844 | O | LEU | A | 111 | −1.426 | 11.023 | −40.944 | 1.00 | 17.23 |
| ATOM | 845 | N | THR | A | 112 | 0.833 | 11.258 | −40.815 | 1.00 | 17.42 |
| ATOM | 846 | CA | THR | A | 112 | 1.144 | 10.301 | −41.887 | 1.00 | 17.92 |
| ATOM | 847 | CB | THR | A | 112 | 2.512 | 10.619 | −42.499 | 1.00 | 17.98 |
| ATOM | 848 | OG1 | THR | A | 112 | 3.476 | 10.702 | −41.445 | 1.00 | 18.32 |
| ATOM | 849 | CG2 | THR | A | 112 | 2.486 | 11.945 | −43.228 | 1.00 | 19.47 |
| ATOM | 850 | C | THR | A | 112 | 1.215 | 8.846 | −41.356 | 1.00 | 18.90 |
| ATOM | 851 | O | THR | A | 112 | 1.535 | 7.917 | −42.117 | 1.00 | 17.68 |
| ATOM | 852 | N | LEU | A | 113 | 0.944 | 8.664 | −40.055 | 1.00 | 18.48 |
| ATOM | 853 | CA | LEU | A | 113 | 1.041 | 7.379 | −39.348 | 1.00 | 19.78 |
| ATOM | 854 | CB | LEU | A | 113 | 0.061 | 6.319 | −39.904 | 1.00 | 19.45 |
| ATOM | 855 | CG | LEU | A | 113 | −1.411 | 6.699 | −40.074 | 1.00 | 21.71 |
| ATOM | 856 | CD1 | LEU | A | 113 | −2.194 | 5.470 | −40.477 | 1.00 | 23.46 |
| ATOM | 857 | CD2 | LEU | A | 113 | −2.005 | 7.323 | −38.800 | 1.00 | 21.59 |
| ATOM | 858 | C | LEU | A | 113 | 2.481 | 6.866 | −39.338 | 1.00 | 20.43 |
| ATOM | 859 | O | LEU | A | 113 | 2.737 | 5.704 | −39.653 | 1.00 | 20.96 |
| ATOM | 860 | N | LYS | A | 114 | 3.406 | 7.769 | −39.024 | 1.00 | 20.07 |
| ATOM | 861 | CA | LYS | A | 114 | 4.826 | 7.460 | −38.863 | 1.00 | 20.25 |
| ATOM | 862 | CB | LYS | A | 114 | 5.662 | 8.209 | −39.899 | 1.00 | 20.95 |
| ATOM | 863 | CG | LYS | A | 114 | 5.432 | 7.725 | −41.314 | 1.00 | 25.23 |
| ATOM | 864 | CD | LYS | A | 114 | 6.636 | 8.059 | −42.184 | 1.00 | 33.76 |
| ATOM | 865 | CE | LYS | A | 114 | 6.551 | 7.360 | −43.537 | 1.00 | 38.31 |
| ATOM | 866 | NZ | LYS | A | 114 | 5.285 | 7.711 | −44.251 | 1.00 | 41.29 |
| ATOM | 867 | C | LYS | A | 114 | 5.252 | 7.874 | −37.471 | 1.00 | 19.64 |
| ATOM | 868 | O | LYS | A | 114 | 4.576 | 8.708 | −36.845 | 1.00 | 19.39 |
| ATOM | 869 | N | PRO | A | 115 | 6.376 | 7.318 | −36.973 | 1.00 | 19.06 |
| ATOM | 870 | CA | PRO | A | 115 | 6.750 | 7.626 | −35.601 | 1.00 | 18.72 |
| ATOM | 871 | CB | PRO | A | 115 | 7.963 | 6.712 | −35.326 | 1.00 | 19.82 |
| ATOM | 872 | CG | PRO | A | 115 | 8.101 | 5.814 | −36.500 | 1.00 | 20.93 |
| ATOM | 873 | CD | PRO | A | 115 | 7.339 | 6.412 | −37.639 | 1.00 | 19.08 |
| ATOM | 874 | C | PRO | A | 115 | 7.156 | 9.093 | −35.434 | 1.00 | 18.70 |
| ATOM | 875 | O | PRO | A | 115 | 7.694 | 9.724 | −36.375 | 1.00 | 17.25 |
| ATOM | 876 | N | PHE | A | 116 | 6.844 | 9.628 | −34.256 | 1.00 | 18.55 |
| ATOM | 877 | CA | PHE | A | 116 | 7.342 | 10.918 | −33.805 | 1.00 | 18.27 |
| ATOM | 878 | CB | PHE | A | 116 | 6.359 | 11.566 | −32.809 | 1.00 | 18.41 |
| ATOM | 879 | CG | PHE | A | 116 | 6.908 | 12.804 | −32.151 | 1.00 | 17.33 |
| ATOM | 880 | CD1 | PHE | A | 116 | 6.942 | 14.014 | −32.847 | 1.00 | 16.98 |
| ATOM | 881 | CE1 | PHE | A | 116 | 7.457 | 15.173 | −32.254 | 1.00 | 16.22 |
| ATOM | 882 | CZ | PHE | A | 116 | 7.950 | 15.138 | −30.935 | 1.00 | 15.88 |
| ATOM | 883 | CE2 | PHE | A | 116 | 7.902 | 13.917 | −30.216 | 1.00 | 16.74 |
| ATOM | 884 | CD2 | PHE | A | 116 | 7.380 | 12.767 | −30.825 | 1.00 | 16.05 |
| ATOM | 885 | C | PHE | A | 116 | 8.701 | 10.695 | −33.141 | 1.00 | 19.14 |
| ATOM | 886 | O | PHE | A | 116 | 8.808 | 9.987 | −32.134 | 1.00 | 19.66 |
| ATOM | 887 | N | THR | A | 117 | 9.746 | 11.299 | −33.713 | 1.00 | 19.53 |
| ATOM | 888 | CA | THR | A | 117 | 11.116 | 11.020 | −33.315 | 1.00 | 20.15 |
| ATOM | 889 | CB | THR | A | 117 | 12.042 | 10.999 | −34.567 | 1.00 | 20.83 |
| ATOM | 890 | OG1 | THR | A | 117 | 11.988 | 12.277 | −35.222 | 1.00 | 22.59 |
| ATOM | 891 | CG2 | THR | A | 117 | 11.576 | 9.895 | −35.557 | 1.00 | 21.40 |
| ATOM | 892 | C | THR | A | 117 | 11.685 | 11.969 | −32.263 | 1.00 | 20.34 |
| ATOM | 893 | O | THR | A | 117 | 12.813 | 11.768 | −31.774 | 1.00 | 21.13 |
| ATOM | 894 | N | GLY | A | 118 | 10.943 | 13.017 | −31.914 | 1.00 | 19.25 |
| ATOM | 895 | CA | GLY | A | 118 | 11.451 | 14.018 | −30.974 | 1.00 | 19.41 |
| ATOM | 896 | C | GLY | A | 118 | 11.431 | 13.498 | −29.541 | 1.00 | 19.75 |
| ATOM | 897 | O | GLY | A | 118 | 10.913 | 12.397 | −29.281 | 1.00 | 19.99 |
| ATOM | 898 | N | ASN | A | 119 | 11.998 | 14.279 | −28.622 | 1.00 | 19.56 |
| ATOM | 899 | CA | ASN | A | 119 | 11.958 | 13.954 | −27.198 | 1.00 | 20.41 |
| ATOM | 900 | CB | ASN | A | 119 | 12.961 | 14.801 | −26.419 | 1.00 | 21.50 |

TABLE 20-continued

| | | | | | | | | | |
|---|---|---|---|---|---|---|---|---|---|
| ATOM | 901 | CG | ASN | A | 119 | 14.377 | 14.612 | −26.930 | 1.00 | 25.14 |
| ATOM | 902 | OD1 | ASN | A | 119 | 14.779 | 13.500 | −27.294 | 1.00 | 30.77 |
| ATOM | 903 | ND2 | ASN | A | 119 | 15.131 | 15.693 | −26.987 | 1.00 | 31.23 |
| ATOM | 904 | C | ASN | A | 119 | 10.550 | 14.194 | −26.696 | 1.00 | 20.06 |
| ATOM | 905 | O | ASN | A | 119 | 9.881 | 15.089 | −27.167 | 1.00 | 19.00 |
| ATOM | 906 | N | TRP | A | 120 | 10.084 | 13.348 | −25.787 | 1.00 | 19.74 |
| ATOM | 907 | CA | TRP | A | 120 | 8.707 | 13.466 | −25.316 | 1.00 | 19.03 |
| ATOM | 908 | CB | TRP | A | 120 | 7.717 | 12.917 | −26.359 | 1.00 | 18.71 |
| ATOM | 909 | CG | TRP | A | 120 | 6.351 | 13.522 | −26.162 | 1.00 | 19.76 |
| ATOM | 910 | CD1 | TRP | A | 120 | 5.239 | 12.901 | −25.673 | 1.00 | 19.81 |
| ATOM | 911 | NE1 | TRP | A | 120 | 4.186 | 13.799 | −25.593 | 1.00 | 19.49 |
| ATOM | 912 | CE2 | TRP | A | 120 | 4.612 | 15.021 | −26.042 | 1.00 | 19.44 |
| ATOM | 913 | CD2 | TRP | A | 120 | 5.975 | 14.886 | −26.410 | 1.00 | 19.35 |
| ATOM | 914 | CE3 | TRP | A | 120 | 6.657 | 16.014 | −26.895 | 1.00 | 18.94 |
| ATOM | 915 | CZ3 | TRP | A | 120 | 5.959 | 17.220 | −27.010 | 1.00 | 20.22 |
| ATOM | 916 | CH2 | TRP | A | 120 | 4.602 | 17.315 | −26.628 | 1.00 | 20.15 |
| ATOM | 917 | CZ2 | TRP | A | 120 | 3.918 | 16.233 | −26.160 | 1.00 | 18.83 |
| ATOM | 918 | C | TRP | A | 120 | 8.602 | 12.685 | −24.001 | 1.00 | 18.80 |
| ATOM | 919 | O | TRP | A | 120 | 9.454 | 11.833 | −23.722 | 1.00 | 18.83 |
| ATOM | 920 | N | GLY | A | 121 | 7.593 | 12.990 | −23.189 | 1.00 | 17.91 |
| ATOM | 921 | CA | GLY | A | 121 | 7.314 | 12.189 | −21.988 | 1.00 | 17.64 |
| ATOM | 922 | C | GLY | A | 121 | 6.721 | 10.834 | −22.362 | 1.00 | 18.93 |
| ATOM | 923 | O | GLY | A | 121 | 5.499 | 10.704 | −22.487 | 1.00 | 18.99 |
| ATOM | 924 | N | ARG | A | 122 | 7.589 | 9.828 | −22.536 | 1.00 | 17.95 |
| ATOM | 925 | CA | ARG | A | 122 | 7.195 | 8.483 | −22.958 | 1.00 | 17.86 |
| ATOM | 926 | CB | ARG | A | 122 | 7.686 | 8.193 | −24.394 | 1.00 | 17.37 |
| ATOM | 927 | CG | ARG | A | 122 | 9.181 | 8.529 | −24.626 | 1.00 | 19.53 |
| ATOM | 928 | CD | ARG | A | 122 | 9.689 | 7.987 | −25.969 | 1.00 | 17.88 |
| ATOM | 929 | NE | ARG | A | 122 | 9.012 | 8.549 | −27.159 | 1.00 | 18.08 |
| ATOM | 930 | CZ | ARG | A | 122 | 9.425 | 9.645 | −27.807 | 1.00 | 18.06 |
| ATOM | 931 | NH1 | ARG | A | 122 | 10.477 | 10.326 | −27.366 | 1.00 | 16.88 |
| ATOM | 932 | NH2 | ARG | A | 122 | 8.784 | 10.074 | −28.892 | 1.00 | 17.35 |
| ATOM | 933 | C | ARG | A | 122 | 7.799 | 7.450 | −21.976 | 1.00 | 17.48 |
| ATOM | 934 | O | ARG | A | 122 | 8.848 | 7.697 | −21.396 | 1.00 | 17.69 |
| ATOM | 935 | N | PRO | A | 123 | 7.142 | 6.298 | −21.781 | 1.00 | 17.14 |
| ATOM | 936 | CA | PRO | A | 123 | 5.886 | 5.916 | −22.382 | 1.00 | 16.01 |
| ATOM | 937 | CB | PRO | A | 123 | 5.908 | 4.385 | −22.266 | 1.00 | 16.51 |
| ATOM | 938 | CG | PRO | A | 123 | 6.585 | 4.144 | −20.969 | 1.00 | 16.30 |
| ATOM | 939 | CD | PRO | A | 123 | 7.658 | 5.238 | −20.873 | 1.00 | 16.95 |
| ATOM | 940 | C | PRO | A | 123 | 4.716 | 6.494 | −21.581 | 1.00 | 15.29 |
| ATOM | 941 | O | PRO | A | 123 | 4.926 | 7.057 | −20.521 | 1.00 | 15.07 |
| ATOM | 942 | N | GLN | A | 124 | 3.504 | 6.362 | −22.120 | 1.00 | 14.60 |
| ATOM | 943 | CA | GLN | A | 124 | 2.289 | 6.675 | −21.386 | 1.00 | 14.40 |
| ATOM | 944 | CB | GLN | A | 124 | 1.602 | 7.889 | −22.001 | 1.00 | 14.71 |
| ATOM | 945 | CG | GLN | A | 124 | 2.442 | 9.186 | −21.711 | 1.00 | 11.93 |
| ATOM | 946 | CD | GLN | A | 124 | 1.993 | 10.407 | −22.472 | 1.00 | 15.67 |
| ATOM | 947 | OE1 | GLN | A | 124 | 2.807 | 11.310 | −22.758 | 1.00 | 15.75 |
| ATOM | 948 | NE2 | GLN | A | 124 | 0.718 | 10.450 | −22.822 | 1.00 | 9.85 |
| ATOM | 949 | C | GLN | A | 124 | 1.441 | 5.421 | −21.511 | 1.00 | 14.28 |
| ATOM | 950 | O | GLN | A | 124 | 0.988 | 5.095 | −22.604 | 1.00 | 14.63 |
| ATOM | 951 | N | ARG | A | 125 | 1.241 | 4.731 | −20.390 | 1.00 | 13.50 |
| ATOM | 952 | CA | ARG | A | 125 | 0.700 | 3.382 | −20.398 | 1.00 | 13.96 |
| ATOM | 953 | CB | ARG | A | 125 | 1.331 | 2.567 | −19.256 | 1.00 | 14.28 |
| ATOM | 954 | CG | ARG | A | 125 | 2.864 | 2.703 | −19.249 | 1.00 | 15.16 |
| ATOM | 955 | CD | ARG | A | 125 | 3.503 | 1.577 | −18.439 | 1.00 | 18.07 |
| ATOM | 956 | NE | ARG | A | 125 | 4.924 | 1.827 | −18.132 | 1.00 | 17.46 |
| ATOM | 957 | CZ | ARG | A | 125 | 5.944 | 1.334 | −18.833 | 1.00 | 19.43 |
| ATOM | 958 | NH1 | ARG | A | 125 | 5.728 | 0.601 | −19.925 | 1.00 | 20.02 |
| ATOM | 959 | NH2 | ARG | A | 125 | 7.197 | 1.596 | −18.453 | 1.00 | 18.94 |
| ATOM | 960 | C | ARG | A | 125 | −0.829 | 3.335 | −20.359 | 1.00 | 14.48 |
| ATOM | 961 | O | ARG | A | 125 | −1.424 | 2.262 | −20.343 | 1.00 | 14.40 |
| ATOM | 962 | N | ASP | A | 126 | −1.462 | 4.509 | −20.374 | 1.00 | 14.03 |
| ATOM | 963 | CA | ASP | A | 126 | −2.919 | 4.568 | −20.542 | 1.00 | 13.39 |
| ATOM | 964 | CB | ASP | A | 126 | −3.488 | 5.922 | −20.067 | 1.00 | 13.17 |
| ATOM | 965 | CG | ASP | A | 126 | −2.926 | 7.092 | −20.845 | 1.00 | 14.17 |
| ATOM | 966 | OD1 | ASP | A | 126 | −1.713 | 7.108 | −21.143 | 1.00 | 12.29 |
| ATOM | 967 | OD2 | ASP | A | 126 | −3.705 | 8.003 | −21.187 | 1.00 | 16.69 |
| ATOM | 968 | C | ASP | A | 126 | −3.350 | 4.306 | −21.974 | 1.00 | 13.60 |
| ATOM | 969 | O | ASP | A | 126 | −4.452 | 3.806 | −22.189 | 1.00 | 13.56 |
| ATOM | 970 | N | GLY | A | 127 | −2.491 | 4.634 | −22.948 | 1.00 | 12.78 |
| ATOM | 971 | CA | GLY | A | 127 | −2.886 | 4.558 | −24.358 | 1.00 | 13.20 |
| ATOM | 972 | C | GLY | A | 127 | −3.473 | 3.213 | −24.794 | 1.00 | 12.77 |
| ATOM | 973 | O | GLY | A | 127 | −4.579 | 3.150 | −25.327 | 1.00 | 12.56 |
| ATOM | 974 | N | PRO | A | 128 | −2.720 | 2.120 | −24.613 | 1.00 | 13.94 |
| ATOM | 975 | CA | PRO | A | 128 | −3.262 | 0.810 | −24.978 | 1.00 | 12.97 |
| ATOM | 976 | CB | PRO | A | 128 | −2.135 | −0.162 | −24.552 | 1.00 | 14.15 |
| ATOM | 977 | CG | PRO | A | 128 | −0.907 | 0.656 | −24.721 | 1.00 | 14.39 |
| ATOM | 978 | CD | PRO | A | 128 | −1.323 | 2.010 | −24.150 | 1.00 | 13.67 |
| ATOM | 979 | C | PRO | A | 128 | −4.571 | 0.455 | −24.255 | 1.00 | 13.30 |
| ATOM | 980 | O | PRO | A | 128 | −5.433 | −0.161 | −24.869 | 1.00 | 13.72 |

TABLE 20-continued

| | | | | | | | | | |
|---|---|---|---|---|---|---|---|---|---|
| ATOM | 981 | N | ALA | A | 129 | −4.718 | 0.852 | −22.985 | 1.00 | 12.95 |
| ATOM | 982 | CA | ALA | A | 129 | −5.963 | 0.611 | −22.258 | 1.00 | 13.49 |
| ATOM | 983 | CB | ALA | A | 129 | −5.806 | 1.016 | −20.808 | 1.00 | 13.00 |
| ATOM | 984 | C | ALA | A | 129 | −7.162 | 1.329 | −22.923 | 1.00 | 13.43 |
| ATOM | 985 | O | ALA | A | 129 | −8.217 | 0.721 | −23.159 | 1.00 | 13.26 |
| ATOM | 986 | N | LEU | A | 130 | −6.998 | 2.619 | −23.221 | 1.00 | 12.51 |
| ATOM | 987 | CA | LEU | A | 130 | −8.068 | 3.409 | −23.813 | 1.00 | 12.69 |
| ATOM | 988 | CB | LEU | A | 130 | −7.678 | 4.903 | −23.806 | 1.00 | 12.56 |
| ATOM | 989 | CG | LEU | A | 130 | −7.458 | 5.555 | −22.426 | 1.00 | 14.76 |
| ATOM | 990 | CD1 | LEU | A | 130 | −6.959 | 6.991 | −22.643 | 1.00 | 15.23 |
| ATOM | 991 | CD2 | LEU | A | 130 | −8.776 | 5.544 | −21.651 | 1.00 | 15.30 |
| ATOM | 992 | C | LEU | A | 130 | −8.410 | 2.934 | −25.228 | 1.00 | 12.78 |
| ATOM | 993 | O | LEU | A | 130 | −9.571 | 2.863 | −25.607 | 1.00 | 12.83 |
| ATOM | 994 | N | ARG | A | 131 | −7.386 | 2.601 | −26.015 | 1.00 | 13.70 |
| ATOM | 995 | CA | ARG | A | 131 | −7.630 | 2.070 | −27.351 | 1.00 | 14.52 |
| ATOM | 996 | CB | ARG | A | 131 | −6.316 | 1.925 | −28.135 | 1.00 | 14.04 |
| ATOM | 997 | CG | ARG | A | 131 | −6.550 | 1.438 | −29.566 | 1.00 | 15.60 |
| ATOM | 998 | CD | ARG | A | 131 | −5.278 | 1.522 | −30.428 | 1.00 | 15.59 |
| ATOM | 999 | NE | ARG | A | 131 | −4.118 | 0.915 | −29.779 | 1.00 | 16.77 |
| ATOM | 1000 | CZ | ARG | A | 131 | −2.860 | 1.205 | −30.098 | 1.00 | 16.26 |
| ATOM | 1001 | NH1 | ARG | A | 131 | −2.610 | 2.104 | −31.054 | 1.00 | 16.37 |
| ATOM | 1002 | NH2 | ARG | A | 131 | −1.856 | 0.618 | −29.448 | 1.00 | 15.96 |
| ATOM | 1003 | C | ARG | A | 131 | −8.408 | 0.729 | −27.283 | 1.00 | 14.44 |
| ATOM | 1004 | O | ARG | A | 131 | −9.350 | 0.533 | −28.050 | 1.00 | 15.71 |
| ATOM | 1005 | N | ALA | A | 132 | −8.025 | −0.164 | −26.364 | 1.00 | 14.50 |
| ATOM | 1006 | CA | ALA | A | 132 | −8.738 | −1.456 | −26.195 | 1.00 | 15.06 |
| ATOM | 1007 | CB | ALA | A | 132 | −8.069 | −2.348 | −25.112 | 1.00 | 15.02 |
| ATOM | 1008 | C | ALA | A | 132 | −10.194 | −1.197 | −25.846 | 1.00 | 15.43 |
| ATOM | 1009 | O | ALA | A | 132 | −11.101 | −1.808 | −26.416 | 1.00 | 15.57 |
| ATOM | 1010 | N | ILE | A | 133 | −10.418 | −0.270 | −24.915 | 1.00 | 15.70 |
| ATOM | 1011 | CA | ILE | A | 133 | −11.777 | 0.049 | −24.491 | 1.00 | 14.44 |
| ATOM | 1012 | CB | ILE | A | 133 | −11.775 | 1.056 | −23.335 | 1.00 | 14.07 |
| ATOM | 1013 | CG1 | ILE | A | 133 | −11.268 | 0.387 | −22.046 | 1.00 | 15.40 |
| ATOM | 1014 | CD1 | ILE | A | 133 | −10.751 | 1.388 | −21.017 | 1.00 | 16.66 |
| ATOM | 1015 | CG2 | ILE | A | 133 | −13.176 | 1.702 | −23.101 | 1.00 | 13.98 |
| ATOM | 1016 | C | ILE | A | 133 | −12.633 | 0.517 | −25.679 | 1.00 | 14.36 |
| ATOM | 1017 | O | ILE | A | 133 | −13.781 | 0.102 | −25.807 | 1.00 | 14.69 |
| ATOM | 1018 | N | ALA | A | 134 | −12.079 | 1.362 | −26.545 | 1.00 | 13.69 |
| ATOM | 1019 | CA | ALA | A | 134 | −12.819 | 1.832 | −27.720 | 1.00 | 13.81 |
| ATOM | 1020 | CB | ALA | A | 134 | −12.019 | 2.949 | −28.452 | 1.00 | 13.99 |
| ATOM | 1021 | C | ALA | A | 134 | −13.140 | 0.662 | −28.657 | 1.00 | 14.62 |
| ATOM | 1022 | O | ALA | A | 134 | −14.279 | 0.473 | −29.087 | 1.00 | 14.90 |
| ATOM | 1023 | N | LEU | A | 135 | −12.133 | −0.155 | −28.947 | 1.00 | 14.66 |
| ATOM | 1024 | CA | LEU | A | 135 | −12.328 | −1.251 | −29.901 | 1.00 | 15.75 |
| ATOM | 1025 | CB | LEU | A | 135 | −10.984 | −1.875 | −30.311 | 1.00 | 15.75 |
| ATOM | 1026 | CG | LEU | A | 135 | −10.348 | −1.231 | −31.557 | 1.00 | 16.40 |
| ATOM | 1027 | CD1 | LEU | A | 135 | −10.257 | 0.308 | −31.471 | 1.00 | 18.56 |
| ATOM | 1028 | CD2 | LEU | A | 135 | −8.980 | −1.852 | −31.804 | 1.00 | 17.85 |
| ATOM | 1029 | C | LEU | A | 135 | −13.277 | −2.306 | −29.340 | 1.00 | 15.13 |
| ATOM | 1030 | O | LEU | A | 135 | −14.079 | −2.845 | −30.087 | 1.00 | 15.84 |
| ATOM | 1031 | N | ILE | A | 136 | −13.192 | −2.573 | −28.039 | 1.00 | 15.22 |
| ATOM | 1032 | CA | ILE | A | 136 | −14.153 | −3.473 | −27.377 | 1.00 | 15.71 |
| ATOM | 1033 | CB | ILE | A | 136 | −13.734 | −3.829 | −25.918 | 1.00 | 15.92 |
| ATOM | 1034 | CG1 | ILE | A | 136 | −12.408 | −4.598 | −25.904 | 1.00 | 15.39 |
| ATOM | 1035 | CD1 | ILE | A | 136 | −11.742 | −4.679 | −24.497 | 1.00 | 15.63 |
| ATOM | 1036 | CG2 | ILE | A | 136 | −14.842 | −4.611 | −25.204 | 1.00 | 16.20 |
| ATOM | 1037 | C | ILE | A | 136 | −15.565 | −2.902 | −27.457 | 1.00 | 17.10 |
| ATOM | 1038 | O | ILE | A | 136 | −16.531 | −3.631 | −27.728 | 1.00 | 17.48 |
| ATOM | 1039 | N | GLY | A | 137 | −15.685 | −1.581 | −27.297 | 1.00 | 16.46 |
| ATOM | 1040 | CA | GLY | A | 137 | −16.979 | −0.902 | −27.484 | 1.00 | 16.59 |
| ATOM | 1041 | C | GLY | A | 137 | −17.600 | −1.206 | −28.833 | 1.00 | 17.13 |
| ATOM | 1042 | O | GLY | A | 137 | −18.778 | −1.605 | −28.920 | 1.00 | 16.92 |
| ATOM | 1043 | N | TYR | A | 138 | −16.817 | −1.056 | −29.898 | 1.00 | 16.61 |
| ATOM | 1044 | CA | TYR | A | 138 | −17.353 | −1.349 | −31.224 | 1.00 | 17.93 |
| ATOM | 1045 | CB | TYR | A | 138 | −16.446 | −0.838 | −32.341 | 1.00 | 17.46 |
| ATOM | 1046 | CG | TYR | A | 138 | −17.112 | −0.897 | −33.693 | 1.00 | 18.28 |
| ATOM | 1047 | CD1 | TYR | A | 138 | −18.350 | −0.268 | −33.914 | 1.00 | 18.85 |
| ATOM | 1048 | CE1 | TYR | A | 138 | −18.966 | −0.314 | −35.153 | 1.00 | 21.29 |
| ATOM | 1049 | CZ | TYR | A | 138 | −18.358 | −1.001 | −36.207 | 1.00 | 20.99 |
| ATOM | 1050 | OH | TYR | A | 138 | −18.994 | −1.055 | −37.433 | 1.00 | 20.06 |
| ATOM | 1051 | CE2 | TYR | A | 138 | −17.133 | −1.636 | −36.026 | 1.00 | 19.88 |
| ATOM | 1052 | CD2 | TYR | A | 138 | −16.512 | −1.583 | −34.766 | 1.00 | 18.25 |
| ATOM | 1053 | C | TYR | A | 138 | −17.643 | −2.844 | −31.406 | 1.00 | 18.67 |
| ATOM | 1054 | O | TYR | A | 138 | −18.654 | −3.207 | −32.037 | 1.00 | 20.06 |
| ATOM | 1055 | N | SER | A | 139 | −16.766 | −3.686 | −30.864 | 1.00 | 19.48 |
| ATOM | 1056 | CA | SER | A | 139 | −16.942 | −5.146 | −30.900 | 1.00 | 21.02 |
| ATOM | 1057 | CB | SER | A | 139 | −15.808 | −5.829 | −30.129 | 1.00 | 21.09 |
| ATOM | 1058 | OG | SER | A | 139 | −14.581 | −5.598 | −30.789 | 1.00 | 21.49 |
| ATOM | 1059 | C | SER | A | 139 | −18.298 | −5.557 | −30.325 | 1.00 | 22.24 |
| ATOM | 1060 | O | SER | A | 139 | −19.002 | −6.392 | −30.907 | 1.00 | 23.64 |

TABLE 20-continued

| | | | | | | | | | |
|---|---|---|---|---|---|---|---|---|---|
| ATOM | 1061 | N | LYS | A | 140 | −18.669 | −4.976 | −29.188 | 1.00 | 22.77 |
| ATOM | 1062 | CA | LYS | A | 140 | −19.987 | −5.225 | −28.595 | 1.00 | 24.29 |
| ATOM | 1063 | CB | LYS | A | 140 | −20.218 | −4.343 | −27.370 | 1.00 | 24.29 |
| ATOM | 1064 | CG | LYS | A | 140 | −19.384 | −4.695 | −26.170 | 1.00 | 26.62 |
| ATOM | 1065 | CD | LYS | A | 140 | −19.696 | −3.693 | −25.060 | 1.00 | 28.24 |
| ATOM | 1066 | CE | LYS | A | 140 | −18.589 | −3.635 | −24.056 | 1.00 | 28.19 |
| ATOM | 1067 | NZ | LYS | A | 140 | −18.940 | −2.725 | −22.954 | 1.00 | 26.78 |
| ATOM | 1068 | C | LYS | A | 140 | −21.126 | −5.001 | −29.584 | 1.00 | 24.17 |
| ATOM | 1069 | O | LYS | A | 140 | −22.053 | −5.823 | −29.670 | 1.00 | 24.94 |
| ATOM | 1070 | N | TRP | A | 141 | −21.062 | −3.898 | −30.321 | 1.00 | 23.60 |
| ATOM | 1071 | CA | TRP | A | 141 | −22.054 | −3.613 | −31.338 | 1.00 | 24.29 |
| ATOM | 1072 | CB | TRP | A | 141 | −21.847 | −2.226 | −31.953 | 1.00 | 24.36 |
| ATOM | 1073 | CG | TRP | A | 141 | −22.973 | −1.833 | −32.874 | 1.00 | 24.25 |
| ATOM | 1074 | CD1 | TRP | A | 141 | −24.113 | −1.170 | −32.531 | 1.00 | 25.06 |
| ATOM | 1075 | NE1 | TRP | A | 141 | −24.921 | −1.016 | −33.638 | 1.00 | 25.22 |
| ATOM | 1076 | CE2 | TRP | A | 141 | −24.302 | −1.575 | −34.722 | 1.00 | 24.07 |
| ATOM | 1077 | CD2 | TRP | A | 141 | −23.078 | −2.115 | −34.276 | 1.00 | 24.80 |
| ATOM | 1078 | CE3 | TRP | A | 141 | −22.248 | −2.766 | −35.203 | 1.00 | 25.40 |
| ATOM | 1079 | CZ3 | TRP | A | 141 | −22.669 | −2.858 | −36.532 | 1.00 | 25.72 |
| ATOM | 1080 | CH2 | TRP | A | 141 | −23.891 | −2.304 | −36.940 | 1.00 | 24.95 |
| ATOM | 1081 | CZ2 | TRP | A | 141 | −24.721 | −1.666 | −36.051 | 1.00 | 25.14 |
| ATOM | 1082 | C | TRP | A | 141 | −22.078 | −4.666 | −32.448 | 1.00 | 24.47 |
| ATOM | 1083 | O | TRP | A | 141 | −23.155 | −5.152 | −32.831 | 1.00 | 24.52 |
| ATOM | 1084 | N | LEU | A | 142 | −20.904 | −4.991 | −32.985 | 1.00 | 24.39 |
| ATOM | 1085 | CA | LEU | A | 142 | −20.806 | −6.024 | −34.010 | 1.00 | 25.05 |
| ATOM | 1086 | CB | LEU | A | 142 | −19.361 | −6.199 | −34.473 | 1.00 | 24.56 |
| ATOM | 1087 | CG | LEU | A | 142 | −18.754 | −5.023 | −35.252 | 1.00 | 24.44 |
| ATOM | 1088 | CD1 | LEU | A | 142 | −17.274 | −5.304 | −35.441 | 1.00 | 23.72 |
| ATOM | 1089 | CD2 | LEU | A | 142 | −19.424 | −4.793 | −36.624 | 1.00 | 25.76 |
| ATOM | 1090 | C | LEU | A | 142 | −21.406 | −7.364 | −33.556 | 1.00 | 25.97 |
| ATOM | 1091 | O | LEU | A | 142 | −22.195 | −7.966 | −34.283 | 1.00 | 26.49 |
| ATOM | 1092 | N | ILE | A | 143 | −21.045 | −7.814 | −32.359 | 1.00 | 27.04 |
| ATOM | 1093 | CA | ILE | A | 143 | −21.596 | −9.040 | −31.792 | 1.00 | 28.46 |
| ATOM | 1094 | CB | ILE | A | 143 | −20.959 | −9.362 | −30.425 | 1.00 | 28.30 |
| ATOM | 1095 | CG1 | ILE | A | 143 | −19.474 | −9.722 | −30.609 | 1.00 | 27.97 |
| ATOM | 1096 | CD1 | ILE | A | 143 | −18.707 | −9.814 | −29.301 | 1.00 | 29.85 |
| ATOM | 1097 | CG2 | ILE | A | 143 | −21.720 | −10.494 | −29.717 | 1.00 | 29.57 |
| ATOM | 1098 | C | ILE | A | 143 | −23.124 | −8.992 | −31.682 | 1.00 | 29.52 |
| ATOM | 1099 | O | ILE | A | 143 | −23.813 | −9.928 | −32.118 | 1.00 | 30.10 |
| ATOM | 1100 | N | ASN | A | 144 | −23.655 | −7.916 | −31.111 | 1.00 | 30.37 |
| ATOM | 1101 | CA | ASN | A | 144 | −25.109 | −7.768 | −30.988 | 1.00 | 32.18 |
| ATOM | 1102 | CB | ASN | A | 144 | −25.479 | −6.522 | −30.186 | 1.00 | 32.73 |
| ATOM | 1103 | CG | ASN | A | 144 | −26.960 | −6.489 | −29.792 | 1.00 | 36.88 |
| ATOM | 1104 | OD1 | ASN | A | 144 | −27.444 | −7.350 | −29.041 | 1.00 | 42.25 |
| ATOM | 1105 | ND2 | ASN | A | 144 | −27.685 | −5.488 | −30.291 | 1.00 | 40.10 |
| ATOM | 1106 | C | ASN | A | 144 | −25.820 | −7.760 | −32.341 | 1.00 | 32.17 |
| ATOM | 1107 | O | ASN | A | 144 | −27.012 | −8.029 | −32.411 | 1.00 | 32.73 |
| ATOM | 1108 | N | ASN | A | 145 | −25.094 | −7.460 | −33.411 | 1.00 | 32.19 |
| ATOM | 1109 | CA | ASN | A | 145 | −25.705 | −7.403 | −34.726 | 1.00 | 32.78 |
| ATOM | 1110 | CB | ASN | A | 145 | −25.526 | −6.014 | −35.331 | 1.00 | 33.16 |
| ATOM | 1111 | CG | ASN | A | 145 | −26.397 | −4.986 | −34.639 | 1.00 | 34.32 |
| ATOM | 1112 | OD1 | ASN | A | 145 | −27.576 | −4.841 | −34.969 | 1.00 | 37.42 |
| ATOM | 1113 | ND2 | ASN | A | 145 | −25.834 | −4.289 | −33.647 | 1.00 | 34.31 |
| ATOM | 1114 | C | ASN | A | 145 | −25.285 | −8.533 | −35.671 | 1.00 | 33.13 |
| ATOM | 1115 | O | ASN | A | 145 | −25.412 | −8.415 | −36.902 | 1.00 | 33.03 |
| ATOM | 1116 | N | ASN | A | 146 | −24.789 | −9.618 | −35.065 | 1.00 | 33.43 |
| ATOM | 1117 | CA | ASN | A | 146 | −24.475 | −10.885 | −35.736 | 1.00 | 34.14 |
| ATOM | 1118 | CB | ASN | A | 146 | −25.710 | −11.459 | −36.461 | 1.00 | 34.85 |
| ATOM | 1119 | CG | ASN | A | 146 | −26.994 | −11.280 | −35.657 | 1.00 | 37.41 |
| ATOM | 1120 | OD1 | ASN | A | 146 | −27.033 | −11.543 | −34.450 | 1.00 | 41.43 |
| ATOM | 1121 | ND2 | ASN | A | 146 | −28.047 | −10.814 | −36.321 | 1.00 | 41.54 |
| ATOM | 1122 | C | ASN | A | 146 | −23.266 | −10.795 | −36.652 | 1.00 | 33.92 |
| ATOM | 1123 | O | ASN | A | 146 | −23.216 | −11.419 | −37.724 | 1.00 | 33.76 |
| ATOM | 1124 | N | TYR | A | 147 | −22.280 | −10.013 | −36.221 | 1.00 | 32.92 |
| ATOM | 1125 | CA | TYR | A | 147 | −21.049 | −9.870 | −36.974 | 1.00 | 32.90 |
| ATOM | 1126 | CB | TYR | A | 147 | −20.859 | −8.423 | −37.451 | 1.00 | 33.31 |
| ATOM | 1127 | CG | TYR | A | 147 | −21.966 | −7.893 | −38.339 | 1.00 | 33.29 |
| ATOM | 1128 | CD1 | TYR | A | 147 | −22.168 | −8.410 | −39.621 | 1.00 | 34.11 |
| ATOM | 1129 | CE1 | TYR | A | 147 | −23.177 | −7.924 | −40.438 | 1.00 | 34.19 |
| ATOM | 1130 | CZ | TYR | A | 147 | −23.986 | −6.888 | −39.983 | 1.00 | 34.10 |
| ATOM | 1131 | OH | TYR | A | 147 | −24.987 | −6.399 | −40.794 | 1.00 | 35.08 |
| ATOM | 1132 | CE2 | TYR | A | 147 | −23.798 | −6.345 | −38.722 | 1.00 | 32.48 |
| ATOM | 1133 | CD2 | TYR | A | 147 | −22.792 | −6.852 | −37.906 | 1.00 | 32.03 |
| ATOM | 1134 | C | TYR | A | 147 | −19.857 | −10.297 | −36.138 | 1.00 | 32.74 |
| ATOM | 1135 | O | TYR | A | 147 | −18.795 | −9.710 | −36.242 | 1.00 | 32.03 |
| ATOM | 1136 | N | GLN | A | 148 | −20.037 | −11.325 | −35.312 | 1.00 | 33.44 |
| ATOM | 1137 | CA | GLN | A | 148 | −18.977 | −11.807 | −34.427 | 1.00 | 34.39 |
| ATOM | 1138 | CB | GLN | A | 148 | −19.483 | −12.971 | −33.573 | 1.00 | 34.76 |
| ATOM | 1139 | CG | GLN | A | 148 | −18.523 | −13.445 | −32.481 | 1.00 | 35.56 |
| ATOM | 1140 | CD | GLN | A | 148 | −19.216 | −14.273 | −31.401 | 1.00 | 36.59 |

TABLE 20-continued

| ATOM | 1141 | OE1 | GLN | A | 148 | −20.296 | −13.913 | −30.916 | 1.00 | 41.20 |
|---|---|---|---|---|---|---|---|---|---|---|
| ATOM | 1142 | NE2 | GLN | A | 148 | −18.589 | −15.380 | −31.008 | 1.00 | 38.65 |
| ATOM | 1143 | C | GLN | A | 148 | −17.690 | −12.196 | −35.176 | 1.00 | 34.46 |
| ATOM | 1144 | O | GLN | A | 148 | −16.582 | −12.002 | −34.654 | 1.00 | 34.20 |
| ATOM | 1145 | N | PHE | A | 149 | −17.841 | −12.735 | −36.391 | 1.00 | 34.19 |
| ATOM | 1146 | CA | PHE | A | 149 | −16.696 | −13.131 | −37.217 | 1.00 | 34.10 |
| ATOM | 1147 | CB | PHE | A | 149 | −17.140 | −13.804 | −38.534 | 1.00 | 35.60 |
| ATOM | 1148 | CG | PHE | A | 149 | −18.346 | −13.168 | −39.193 | 1.00 | 38.70 |
| ATOM | 1149 | CD1 | PHE | A | 149 | −19.388 | −13.976 | −39.676 | 1.00 | 42.72 |
| ATOM | 1150 | CE1 | PHE | A | 149 | −20.518 | −13.417 | −40.295 | 1.00 | 43.69 |
| ATOM | 1151 | CZ | PHE | A | 149 | −20.615 | −12.019 | −40.437 | 1.00 | 43.12 |
| ATOM | 1152 | CE2 | PHE | A | 149 | −19.567 | −11.188 | −39.953 | 1.00 | 43.20 |
| ATOM | 1153 | CD2 | PHE | A | 149 | −18.451 | −11.772 | −39.341 | 1.00 | 42.33 |
| ATOM | 1154 | C | PHE | A | 149 | −15.746 | −11.960 | −37.517 | 1.00 | 32.49 |
| ATOM | 1155 | O | PHE | A | 149 | −14.528 | −12.132 | −37.548 | 1.00 | 32.23 |
| ATOM | 1156 | N | THR | A | 150 | −16.327 | −10.789 | −37.751 | 1.00 | 30.95 |
| ATOM | 1157 | CA | THR | A | 150 | −15.570 | −9.568 | −38.040 | 1.00 | 29.68 |
| ATOM | 1158 | CB | THR | A | 150 | −16.512 | −8.424 | −38.445 | 1.00 | 29.97 |
| ATOM | 1159 | OG1 | THR | A | 150 | −17.162 | −8.768 | −39.673 | 1.00 | 30.58 |
| ATOM | 1160 | CG2 | THR | A | 150 | −15.758 | −7.096 | −38.637 | 1.00 | 29.18 |
| ATOM | 1161 | C | THR | A | 150 | −14.727 | −9.203 | −36.822 | 1.00 | 28.54 |
| ATOM | 1162 | O | THR | A | 150 | −13.566 | −8.827 | −36.965 | 1.00 | 28.38 |
| ATOM | 1163 | N | VAL | A | 151 | −15.310 | −9.354 | −35.636 | 1.00 | 27.23 |
| ATOM | 1164 | CA | VAL | A | 151 | −14.597 | −9.146 | −34.374 | 1.00 | 26.78 |
| ATOM | 1165 | CB | VAL | A | 151 | −15.529 | −9.352 | −33.148 | 1.00 | 26.25 |
| ATOM | 1166 | CG1 | VAL | A | 151 | −14.752 | −9.213 | −31.832 | 1.00 | 26.50 |
| ATOM | 1167 | CG2 | VAL | A | 151 | −16.690 | −8.361 | −33.178 | 1.00 | 24.41 |
| ATOM | 1168 | C | VAL | A | 151 | −13.384 | −10.080 | −34.305 | 1.00 | 27.61 |
| ATOM | 1169 | O | VAL | A | 151 | −12.246 | −9.638 | −34.106 | 1.00 | 26.67 |
| ATOM | 1170 | N | SER | A | 152 | −13.625 | −11.375 | −34.505 | 1.00 | 28.53 |
| ATOM | 1171 | CA | SER | A | 152 | −12.551 | −12.369 | −34.470 | 1.00 | 30.01 |
| ATOM | 1172 | CB | SER | A | 152 | −13.102 | −13.759 | −34.773 | 1.00 | 30.18 |
| ATOM | 1173 | OG | SER | A | 152 | −13.612 | −14.300 | −33.586 | 1.00 | 32.28 |
| ATOM | 1174 | C | SER | A | 152 | −11.419 | −12.091 | −35.430 | 1.00 | 30.23 |
| ATOM | 1175 | O | SER | A | 152 | −10.250 | −12.250 | −35.090 | 1.00 | 30.95 |
| ATOM | 1176 | N | ASN | A | 153 | −11.762 | −11.705 | −36.641 | 1.00 | 31.46 |
| ATOM | 1177 | CA | ASN | A | 153 | −10.753 | −11.624 | −37.674 | 1.00 | 32.41 |
| ATOM | 1178 | CB | ASN | A | 153 | −11.333 | −12.118 | −38.997 | 1.00 | 33.62 |
| ATOM | 1179 | CG | ASN | A | 153 | −11.791 | −13.584 | −38.902 | 1.00 | 36.13 |
| ATOM | 1180 | OD1 | ASN | A | 153 | −12.931 | −13.918 | −39.231 | 1.00 | 40.99 |
| ATOM | 1181 | ND2 | ASN | A | 153 | −10.917 | −14.444 | −38.383 | 1.00 | 37.61 |
| ATOM | 1182 | C | ASN | A | 153 | −10.060 | −10.272 | −37.787 | 1.00 | 32.10 |
| ATOM | 1183 | O | ASN | A | 153 | −8.850 | −10.213 | −38.020 | 1.00 | 32.79 |
| ATOM | 1184 | N | VAL | A | 154 | −10.810 | −9.193 | −37.577 | 1.00 | 30.55 |
| ATOM | 1185 | CA | VAL | A | 154 | −10.251 | −7.854 | −37.750 | 1.00 | 28.93 |
| ATOM | 1186 | CB | VAL | A | 154 | −11.217 | −6.925 | −38.537 | 1.00 | 29.03 |
| ATOM | 1187 | CG1 | VAL | A | 154 | −10.565 | −5.577 | −38.827 | 1.00 | 29.23 |
| ATOM | 1188 | CG2 | VAL | A | 154 | −11.654 | −7.585 | −39.860 | 1.00 | 29.87 |
| ATOM | 1189 | C | VAL | A | 154 | −9.824 | −7.211 | −36.414 | 1.00 | 27.28 |
| ATOM | 1190 | O | VAL | A | 154 | −8.722 | −6.678 | −36.306 | 1.00 | 26.96 |
| ATOM | 1191 | N | ILE | A | 155 | −10.685 | −7.288 | −35.403 | 1.00 | 25.13 |
| ATOM | 1192 | CA | ILE | A | 155 | −10.525 | −6.459 | −34.197 | 1.00 | 23.05 |
| ATOM | 1193 | CB | ILE | A | 155 | −11.900 | −5.972 | −33.670 | 1.00 | 23.10 |
| ATOM | 1194 | CG1 | ILE | A | 155 | −12.596 | −5.128 | −34.741 | 1.00 | 22.49 |
| ATOM | 1195 | CD1 | ILE | A | 155 | −14.006 | −4.680 | −34.375 | 1.00 | 22.72 |
| ATOM | 1196 | CG2 | ILE | A | 155 | −11.731 | −5.144 | −32.399 | 1.00 | 23.05 |
| ATOM | 1197 | C | ILE | A | 155 | −9.710 | −7.136 | −33.092 | 1.00 | 22.44 |
| ATOM | 1198 | O | ILE | A | 155 | −8.789 | −6.537 | −32.533 | 1.00 | 21.14 |
| ATOM | 1199 | N | TRP | A | 156 | −10.006 | −8.409 | −32.822 | 1.00 | 21.48 |
| ATOM | 1200 | CA | TRP | A | 156 | −9.392 | −9.099 | −31.696 | 1.00 | 21.75 |
| ATOM | 1201 | CB | TRP | A | 156 | −9.958 | −10.520 | −31.511 | 1.00 | 22.50 |
| ATOM | 1202 | CG | TRP | A | 156 | −9.298 | −11.245 | −30.371 | 1.00 | 23.43 |
| ATOM | 1203 | CD1 | TRP | A | 156 | −8.420 | −12.298 | −30.461 | 1.00 | 24.92 |
| ATOM | 1204 | NE1 | TRP | A | 156 | −8.011 | −12.680 | −29.198 | 1.00 | 24.85 |
| ATOM | 1205 | CE2 | TRP | A | 156 | −8.600 | −11.863 | −28.269 | 1.00 | 26.38 |
| ATOM | 1206 | CD2 | TRP | A | 156 | −9.416 | −10.941 | −28.970 | 1.00 | 25.03 |
| ATOM | 1207 | CE3 | TRP | A | 156 | −10.139 | −9.983 | −28.236 | 1.00 | 25.01 |
| ATOM | 1208 | CZ3 | TRP | A | 156 | −10.024 | −9.982 | −26.844 | 1.00 | 24.30 |
| ATOM | 1209 | CH2 | TRP | A | 156 | −9.206 | −10.910 | −26.185 | 1.00 | 23.97 |
| ATOM | 1210 | CZ2 | TRP | A | 156 | −8.495 | −11.861 | −26.875 | 1.00 | 24.60 |
| ATOM | 1211 | C | TRP | A | 156 | −7.845 | −9.109 | −31.699 | 1.00 | 21.52 |
| ATOM | 1212 | O | TRP | A | 156 | −7.235 | −8.945 | −30.648 | 1.00 | 21.78 |
| ATOM | 1213 | N | PRO | A | 157 | −7.209 | −9.303 | −32.870 | 1.00 | 21.66 |
| ATOM | 1214 | CA | PRO | A | 157 | −5.726 | −9.258 | −32.878 | 1.00 | 21.40 |
| ATOM | 1215 | CB | PRO | A | 157 | −5.378 | −9.459 | −34.360 | 1.00 | 21.26 |
| ATOM | 1216 | CG | PRO | A | 157 | −6.583 | −10.172 | −34.955 | 1.00 | 22.82 |
| ATOM | 1217 | CD | PRO | A | 157 | −7.762 | −9.596 | −34.207 | 1.00 | 21.45 |
| ATOM | 1218 | C | PRO | A | 157 | −5.162 | −7.898 | −32.410 | 1.00 | 21.30 |
| ATOM | 1219 | O | PRO | A | 157 | −4.092 | −7.837 | −31.795 | 1.00 | 21.11 |
| ATOM | 1220 | N | ILE | A | 158 | −5.881 | −6.821 | −32.724 | 1.00 | 20.52 |

TABLE 20-continued

| ATOM | 1221 | CA | ILE | A | 158 | −5.457 | −5.467 | −32.318 | 1.00 | 19.93 |
|------|------|-----|-----|---|-----|--------|--------|---------|------|-------|
| ATOM | 1222 | CB | ILE | A | 158 | −6.273 | −4.348 | −33.034 | 1.00 | 19.73 |
| ATOM | 1223 | CG1 | ILE | A | 158 | −6.261 | −4.527 | −34.559 | 1.00 | 21.25 |
| ATOM | 1224 | CD1 | ILE | A | 158 | −7.229 | −3.640 | −35.351 | 1.00 | 20.03 |
| ATOM | 1225 | CG2 | ILE | A | 158 | −5.686 | −2.971 | −32.670 | 1.00 | 20.16 |
| ATOM | 1226 | C | ILE | A | 158 | −5.632 | −5.366 | −30.816 | 1.00 | 19.58 |
| ATOM | 1227 | O | ILE | A | 158 | −4.701 | −5.023 | −30.081 | 1.00 | 19.04 |
| ATOM | 1228 | N | VAL | A | 159 | −6.840 | −5.704 | −30.359 | 1.00 | 19.39 |
| ATOM | 1229 | CA | VAL | A | 159 | −7.201 | −5.624 | −28.953 | 1.00 | 19.15 |
| ATOM | 1230 | CB | VAL | A | 159 | −8.687 | −6.026 | −28.744 | 1.00 | 19.06 |
| ATOM | 1231 | CG1 | VAL | A | 159 | −9.046 | −6.028 | −27.253 | 1.00 | 20.39 |
| ATOM | 1232 | CG2 | VAL | A | 159 | −9.604 | −5.090 | −29.511 | 1.00 | 20.08 |
| ATOM | 1233 | C | VAL | A | 159 | −6.280 | −6.501 | −28.105 | 1.00 | 19.39 |
| ATOM | 1234 | O | VAL | A | 159 | −5.794 | −6.089 | −27.036 | 1.00 | 18.63 |
| ATOM | 1235 | N | ARG | A | 160 | −6.022 | −7.721 | −28.585 | 1.00 | 18.93 |
| ATOM | 1236 | CA | ARG | A | 160 | −5.171 | −8.633 | −27.833 | 1.00 | 19.64 |
| ATOM | 1237 | CB | ARG | A | 160 | −5.078 | −10.005 | −28.513 | 1.00 | 19.17 |
| ATOM | 1238 | CG | ARG | A | 160 | −4.064 | −10.942 | −27.872 | 1.00 | 21.41 |
| ATOM | 1239 | CD | ARG | A | 160 | −3.978 | −12.278 | −28.637 | 1.00 | 23.47 |
| ATOM | 1240 | NE | ARG | A | 160 | −3.542 | −12.066 | −30.021 | 1.00 | 29.25 |
| ATOM | 1241 | CZ | ARG | A | 160 | −3.963 | −12.771 | −31.074 | 1.00 | 33.46 |
| ATOM | 1242 | NH1 | ARG | A | 160 | −4.839 | −13.764 | −30.929 | 1.00 | 36.48 |
| ATOM | 1243 | NH2 | ARG | A | 160 | −3.501 | −12.489 | −32.289 | 1.00 | 34.33 |
| ATOM | 1244 | C | ARG | A | 160 | −3.785 | −8.058 | −27.580 | 1.00 | 18.24 |
| ATOM | 1245 | O | ARG | A | 160 | −3.262 | −8.233 | −26.517 | 1.00 | 18.13 |
| ATOM | 1246 | N | ASN | A | 161 | −3.182 | −7.371 | −28.551 | 1.00 | 18.57 |
| ATOM | 1247 | CA | ASN | A | 161 | −1.875 | −6.717 | −28.289 | 1.00 | 18.40 |
| ATOM | 1248 | CB | ASN | A | 161 | −1.344 | −6.052 | −29.561 | 1.00 | 18.82 |
| ATOM | 1249 | CG | ASN | A | 161 | −0.772 | −7.055 | −30.549 | 1.00 | 20.68 |
| ATOM | 1250 | OD1 | ASN | A | 161 | −0.240 | −8.097 | −30.149 | 1.00 | 22.60 |
| ATOM | 1251 | ND2 | ASN | A | 161 | −0.883 | −6.751 | −31.837 | 1.00 | 19.81 |
| ATOM | 1252 | C | ASN | A | 161 | −1.946 | −5.656 | −27.182 | 1.00 | 18.36 |
| ATOM | 1253 | O | ASN | A | 161 | −1.078 | −5.581 | −26.313 | 1.00 | 17.42 |
| ATOM | 1254 | N | ASP | A | 162 | −2.982 | −4.816 | −27.233 | 1.00 | 17.86 |
| ATOM | 1255 | CA | ASP | A | 162 | −3.163 | −3.782 | −26.194 | 1.00 | 16.85 |
| ATOM | 1256 | CB | ASP | A | 162 | −4.293 | −2.821 | −26.586 | 1.00 | 16.71 |
| ATOM | 1257 | CG | ASP | A | 162 | −3.851 | −1.791 | −27.623 | 1.00 | 17.46 |
| ATOM | 1258 | OD1 | ASP | A | 162 | −2.648 | −1.440 | −27.681 | 1.00 | 16.98 |
| ATOM | 1259 | OD2 | ASP | A | 162 | −4.719 | −1.333 | −28.388 | 1.00 | 18.89 |
| ATOM | 1260 | C | ASP | A | 162 | −3.421 | −4.354 | −24.799 | 1.00 | 16.51 |
| ATOM | 1261 | O | ASP | A | 162 | −2.846 | −3.897 | −23.822 | 1.00 | 15.71 |
| ATOM | 1262 | N | LEU | A | 163 | −4.278 | −5.371 | −24.715 | 1.00 | 16.83 |
| ATOM | 1263 | CA | LEU | A | 163 | −4.532 | −6.071 | −23.459 | 1.00 | 16.55 |
| ATOM | 1264 | CB | LEU | A | 163 | −5.661 | −7.088 | −23.637 | 1.00 | 16.96 |
| ATOM | 1265 | CG | LEU | A | 163 | −7.030 | −6.506 | −23.975 | 1.00 | 19.29 |
| ATOM | 1266 | CD1 | LEU | A | 163 | −8.007 | −7.663 | −24.227 | 1.00 | 19.71 |
| ATOM | 1267 | CD2 | LEU | A | 163 | −7.484 | −5.631 | −22.818 | 1.00 | 21.19 |
| ATOM | 1268 | C | LEU | A | 163 | −3.279 | −6.750 | −22.883 | 1.00 | 16.19 |
| ATOM | 1269 | O | LEU | A | 163 | −3.035 | −6.690 | −21.688 | 1.00 | 15.47 |
| ATOM | 1270 | N | ASN | A | 164 | −2.495 | −7.401 | −23.748 | 1.00 | 16.85 |
| ATOM | 1271 | CA | ASN | A | 164 | −1.251 | −8.040 | −23.305 | 1.00 | 16.44 |
| ATOM | 1272 | CB | ASN | A | 164 | −0.602 | −8.836 | −24.450 | 1.00 | 17.06 |
| ATOM | 1273 | CG | ASN | A | 164 | −1.333 | −10.153 | −24.718 | 1.00 | 19.63 |
| ATOM | 1274 | OD1 | ASN | A | 164 | −2.274 | −10.513 | −23.982 | 1.00 | 20.97 |
| ATOM | 1275 | ND2 | ASN | A | 164 | −0.903 | −10.881 | −25.756 | 1.00 | 19.79 |
| ATOM | 1276 | C | ASN | A | 164 | −0.301 | −7.022 | −22.761 | 1.00 | 16.80 |
| ATOM | 1277 | O | ASN | A | 164 | 0.349 | −7.261 | −21.751 | 1.00 | 15.97 |
| ATOM | 1278 | N | TYR | A | 165 | −0.250 | −5.860 | −23.415 | 1.00 | 16.45 |
| ATOM | 1279 | CA | TYR | A | 165 | 0.573 | −4.744 | −22.930 | 1.00 | 16.15 |
| ATOM | 1280 | CB | TYR | A | 165 | 0.420 | −3.508 | −23.844 | 1.00 | 16.63 |
| ATOM | 1281 | CG | TYR | A | 165 | 1.286 | −2.356 | −23.391 | 1.00 | 16.41 |
| ATOM | 1282 | CD1 | TYR | A | 165 | 0.838 | −1.459 | −22.404 | 1.00 | 17.94 |
| ATOM | 1283 | CE1 | TYR | A | 165 | 1.651 | −0.402 | −21.958 | 1.00 | 17.84 |
| ATOM | 1284 | CZ | TYR | A | 165 | 2.916 | −0.223 | −22.517 | 1.00 | 18.36 |
| ATOM | 1285 | OH | TYR | A | 165 | 3.699 | 0.841 | −22.091 | 1.00 | 16.54 |
| ATOM | 1286 | CE2 | TYR | A | 165 | 3.383 | −1.105 | −23.502 | 1.00 | 16.73 |
| ATOM | 1287 | CD2 | TYR | A | 165 | 2.552 | −2.157 | −23.942 | 1.00 | 16.01 |
| ATOM | 1288 | C | TYR | A | 165 | 0.198 | −4.366 | −21.503 | 1.00 | 16.26 |
| ATOM | 1289 | O | TYR | A | 165 | 1.073 | −4.218 | −20.650 | 1.00 | 15.43 |
| ATOM | 1290 | N | VAL | A | 166 | −1.104 | −4.177 | −21.258 | 1.00 | 16.75 |
| ATOM | 1291 | CA | VAL | A | 166 | −1.600 | −3.786 | −19.933 | 1.00 | 17.39 |
| ATOM | 1292 | CB | VAL | A | 166 | −3.124 | −3.479 | −19.986 | 1.00 | 17.57 |
| ATOM | 1293 | CG1 | VAL | A | 166 | −3.712 | −3.197 | −18.582 | 1.00 | 19.25 |
| ATOM | 1294 | CG2 | VAL | A | 166 | −3.363 | −2.272 | −20.909 | 1.00 | 16.49 |
| ATOM | 1295 | C | VAL | A | 166 | −1.258 | −4.829 | −18.865 | 1.00 | 17.83 |
| ATOM | 1296 | O | VAL | A | 166 | −0.741 | −4.483 | −17.792 | 1.00 | 18.00 |
| ATOM | 1297 | N | ALA | A | 167 | −1.520 | −6.099 | −19.188 | 1.00 | 18.26 |
| ATOM | 1298 | CA | ALA | A | 167 | −1.233 | −7.218 | −18.285 | 1.00 | 18.92 |
| ATOM | 1299 | CB | ALA | A | 167 | −1.716 | −8.532 | −18.899 | 1.00 | 18.25 |
| ATOM | 1300 | C | ALA | A | 167 | 0.251 | −7.325 | −17.956 | 1.00 | 19.08 |

TABLE 20-continued

| ATOM | 1301 | O   | ALA | A | 167 | 0.611  | −7.757 | −16.854 | 1.00 | 20.02 |
|------|------|-----|-----|---|-----|--------|--------|---------|------|-------|
| ATOM | 1302 | N   | GLN | A | 168 | 1.097  | −6.955 | −18.920 | 1.00 | 19.13 |
| ATOM | 1303 | CA  | GLN | A | 168 | 2.558  | −7.022 | −18.749 | 1.00 | 19.21 |
| ATOM | 1304 | CB  | GLN | A | 168 | 3.218  | −7.201 | −20.115 | 1.00 | 19.08 |
| ATOM | 1305 | CG  | GLN | A | 168 | 4.739  | −7.373 | −20.053 | 1.00 | 20.55 |
| ATOM | 1306 | CD  | GLN | A | 168 | 5.337  | −7.891 | −21.355 | 1.00 | 20.26 |
| ATOM | 1307 | OE1 | GLN | A | 168 | 4.634  | −8.378 | −22.238 | 1.00 | 22.69 |
| ATOM | 1308 | NE2 | GLN | A | 168 | 6.643  | −7.772 | −21.476 | 1.00 | 23.10 |
| ATOM | 1309 | C   | GLN | A | 168 | 3.182  | −5.807 | −18.048 | 1.00 | 19.60 |
| ATOM | 1310 | O   | GLN | A | 168 | 4.104  | −5.942 | −17.205 | 1.00 | 18.87 |
| ATOM | 1311 | N   | TYR | A | 169 | 2.709  | −4.609 | −18.404 | 1.00 | 19.23 |
| ATOM | 1312 | CA  | TYR | A | 169 | 3.399  | −3.377 | −18.011 | 1.00 | 19.45 |
| ATOM | 1313 | CB  | TYR | A | 169 | 3.760  | −2.560 | −19.266 | 1.00 | 20.43 |
| ATOM | 1314 | CG  | TYR | A | 169 | 4.773  | −3.203 | −20.203 | 1.00 | 21.30 |
| ATOM | 1315 | CD1 | TYR | A | 169 | 6.125  | −3.243 | −19.872 | 1.00 | 23.63 |
| ATOM | 1316 | CE1 | TYR | A | 169 | 7.065  | −3.822 | −20.723 | 1.00 | 24.59 |
| ATOM | 1317 | CZ  | TYR | A | 169 | 6.651  | −4.359 | −21.926 | 1.00 | 23.11 |
| ATOM | 1318 | OH  | TYR | A | 169 | 7.580  | −4.924 | −22.779 | 1.00 | 25.26 |
| ATOM | 1319 | CE2 | TYR | A | 169 | 5.309  | −4.330 | −22.288 | 1.00 | 22.49 |
| ATOM | 1320 | CD2 | TYR | A | 169 | 4.375  | −3.754 | −21.422 | 1.00 | 20.87 |
| ATOM | 1321 | C   | TYR | A | 169 | 2.675  | −2.449 | −17.015 | 1.00 | 19.49 |
| ATOM | 1322 | O   | TYR | A | 169 | 3.205  | −1.386 | −16.691 | 1.00 | 19.69 |
| ATOM | 1323 | N   | TRP | A | 170 | 1.508  | −2.850 | −16.498 | 1.00 | 18.91 |
| ATOM | 1324 | CA  | TRP | A | 170 | 0.735  | −1.981 | −15.588 | 1.00 | 19.29 |
| ATOM | 1325 | CB  | TRP | A | 170 | −0.610 | −2.626 | −15.208 | 1.00 | 18.85 |
| ATOM | 1326 | CG  | TRP | A | 170 | −0.489 | −3.743 | −14.215 | 1.00 | 21.04 |
| ATOM | 1327 | CD1 | TRP | A | 170 | −0.342 | −5.083 | −14.489 | 1.00 | 20.67 |
| ATOM | 1328 | NE1 | TRP | A | 170 | −0.259 | −5.793 | −13.317 | 1.00 | 22.09 |
| ATOM | 1329 | CE2 | TRP | A | 170 | −0.336 | −4.928 | −12.258 | 1.00 | 19.19 |
| ATOM | 1330 | CD2 | TRP | A | 170 | −0.481 | −3.621 | −12.789 | 1.00 | 20.35 |
| ATOM | 1331 | CE3 | TRP | A | 170 | −0.582 | −2.530 | −11.905 | 1.00 | 19.61 |
| ATOM | 1332 | CZ3 | TRP | A | 170 | −0.546 | −2.769 | −10.542 | 1.00 | 22.33 |
| ATOM | 1333 | CH2 | TRP | A | 170 | −0.404 | −4.090 | −10.038 | 1.00 | 21.08 |
| ATOM | 1334 | CZ2 | TRP | A | 170 | −0.297 | −5.179 | −10.884 | 1.00 | 20.76 |
| ATOM | 1335 | C   | TRP | A | 170 | 1.526  | −1.592 | −14.336 | 1.00 | 19.20 |
| ATOM | 1336 | O   | TRP | A | 170 | 1.395  | −0.475 | −13.808 | 1.00 | 19.24 |
| ATOM | 1337 | N   | ASN | A | 171 | 2.371  | −2.504 | −13.858 | 1.00 | 19.13 |
| ATOM | 1338 | CA  | ASN | A | 171 | 3.054  | −2.280 | −12.596 | 1.00 | 20.12 |
| ATOM | 1339 | CB  | ASN | A | 171 | 3.178  | −3.603 | −11.820 | 1.00 | 20.59 |
| ATOM | 1340 | CG  | ASN | A | 171 | 3.646  | −3.419 | −10.392 | 1.00 | 22.31 |
| ATOM | 1341 | OD1 | ASN | A | 171 | 4.531  | −4.155 | −9.938  | 1.00 | 23.68 |
| ATOM | 1342 | ND2 | ASN | A | 171 | 3.081  | −2.435 | −9.684  | 1.00 | 18.77 |
| ATOM | 1343 | C   | ASN | A | 171 | 4.392  | −1.557 | −12.797 | 1.00 | 20.93 |
| ATOM | 1344 | O   | ASN | A | 171 | 5.333  | −1.724 | −12.022 | 1.00 | 20.35 |
| ATOM | 1345 | N   | GLN | A | 172 | 4.449  | −0.712 | −13.826 | 1.00 | 20.64 |
| ATOM | 1346 | CA  | GLN | A | 172 | 5.644  | 0.061  | −14.156 | 1.00 | 22.31 |
| ATOM | 1347 | CB  | GLN | A | 172 | 6.262  | −0.452 | −15.469 | 1.00 | 22.04 |
| ATOM | 1348 | CG  | GLN | A | 172 | 6.784  | −1.895 | −15.312 | 1.00 | 25.79 |
| ATOM | 1349 | CD  | GLN | A | 172 | 7.536  | −2.450 | −16.515 | 1.00 | 27.61 |
| ATOM | 1350 | OE1 | GLN | A | 172 | 8.276  | −1.735 | −17.214 | 1.00 | 35.65 |
| ATOM | 1351 | NE2 | GLN | A | 172 | 7.367  | −3.755 | −16.752 | 1.00 | 33.80 |
| ATOM | 1352 | C   | GLN | A | 172 | 5.287  | 1.539  | −14.268 | 1.00 | 21.36 |
| ATOM | 1353 | O   | GLN | A | 172 | 4.175  | 1.867  | −14.704 | 1.00 | 21.04 |
| ATOM | 1354 | N   | THR | A | 173 | 6.209  | 2.417  | −13.871 | 1.00 | 19.73 |
| ATOM | 1355 | CA  | THR | A | 173 | 5.948  | 3.871  | −13.928 | 1.00 | 20.07 |
| ATOM | 1356 | CB  | THR | A | 173 | 7.001  | 4.703  | −13.168 | 1.00 | 19.48 |
| ATOM | 1357 | OG1 | THR | A | 173 | 8.300  | 4.427  | −13.707 | 1.00 | 21.56 |
| ATOM | 1358 | CG2 | THR | A | 173 | 6.988  | 4.375  | −11.690 | 1.00 | 20.86 |
| ATOM | 1359 | C   | THR | A | 173 | 5.913  | 4.347  | −15.375 | 1.00 | 18.53 |
| ATOM | 1360 | O   | THR | A | 173 | 6.395  | 3.665  | −16.292 | 1.00 | 18.48 |
| ATOM | 1361 | N   | GLY | A | 174 | 5.345  | 5.528  | −15.582 | 1.00 | 18.38 |
| ATOM | 1362 | CA  | GLY | A | 174 | 5.363  | 6.149  | −16.903 | 1.00 | 17.13 |
| ATOM | 1363 | C   | GLY | A | 174 | 4.760  | 7.522  | −16.736 | 1.00 | 16.77 |
| ATOM | 1364 | O   | GLY | A | 174 | 4.462  | 7.939  | −15.605 | 1.00 | 16.87 |
| ATOM | 1365 | N   | PHE | A | 175 | 4.571  | 8.223  | −17.849 | 1.00 | 14.68 |
| ATOM | 1366 | CA  | PHE | A | 175 | 4.004  | 9.577  | −17.776 | 1.00 | 14.68 |
| ATOM | 1367 | CB  | PHE | A | 175 | 4.522  | 10.432 | −18.948 | 1.00 | 15.16 |
| ATOM | 1368 | CG  | PHE | A | 175 | 5.943  | 10.847 | −18.756 | 1.00 | 15.28 |
| ATOM | 1369 | CD1 | PHE | A | 175 | 6.981  | 10.000 | −19.144 | 1.00 | 18.04 |
| ATOM | 1370 | CE1 | PHE | A | 175 | 8.313  | 10.359 | −18.915 | 1.00 | 19.53 |
| ATOM | 1371 | CZ  | PHE | A | 175 | 8.609  | 11.582 | −18.278 | 1.00 | 19.12 |
| ATOM | 1372 | CE2 | PHE | A | 175 | 7.571  | 12.429 | −17.876 | 1.00 | 18.63 |
| ATOM | 1373 | CD2 | PHE | A | 175 | 6.247  | 12.054 | −18.113 | 1.00 | 17.67 |
| ATOM | 1374 | C   | PHE | A | 175 | 2.483  | 9.584  | −17.655 | 1.00 | 14.11 |
| ATOM | 1375 | O   | PHE | A | 175 | 1.799  | 8.683  | −18.175 | 1.00 | 14.32 |
| ATOM | 1376 | N   | ASP | A | 176 | 1.972  | 10.591 | −16.938 | 1.00 | 14.79 |
| ATOM | 1377 | CA  | ASP | A | 176 | 0.541  | 10.764 | −16.713 | 1.00 | 14.45 |
| ATOM | 1378 | CB  | ASP | A | 176 | 0.297  | 11.661 | −15.506 | 1.00 | 13.51 |
| ATOM | 1379 | CG  | ASP | A | 176 | 0.685  | 13.126 | −15.760 | 1.00 | 14.99 |
| ATOM | 1380 | OD1 | ASP | A | 176 | 1.774  | 13.399 | −16.329 | 1.00 | 14.32 |

TABLE 20-continued

| | | | | | | | | | |
|---|---|---|---|---|---|---|---|---|---|
| ATOM | 1381 | OD2 | ASP | A | 176 | −0.112 | 14.012 | −15.376 | 1.00 | 15.08 |
| ATOM | 1382 | C | ASP | A | 176 | −0.143 | 11.343 | −17.962 | 1.00 | 14.21 |
| ATOM | 1383 | O | ASP | A | 176 | 0.525 | 11.641 | −18.963 | 1.00 | 14.31 |
| ATOM | 1384 | N | LEU | A | 177 | −1.467 | 11.511 | −17.891 | 1.00 | 13.30 |
| ATOM | 1385 | CA | LEU | A | 177 | −2.235 | 11.981 | −19.048 | 1.00 | 13.44 |
| ATOM | 1386 | CB | LEU | A | 177 | −3.752 | 11.839 | −18.832 | 1.00 | 13.71 |
| ATOM | 1387 | CG | LEU | A | 177 | −4.483 | 12.896 | −18.012 | 1.00 | 14.11 |
| ATOM | 1388 | CD1 | LEU | A | 177 | −5.996 | 12.647 | −18.061 | 1.00 | 13.65 |
| ATOM | 1389 | CD2 | LEU | A | 177 | −4.007 | 12.922 | −16.553 | 1.00 | 14.74 |
| ATOM | 1390 | C | LEU | A | 177 | −1.884 | 13.424 | −19.452 | 1.00 | 13.51 |
| ATOM | 1391 | O | LEU | A | 177 | −2.131 | 13.813 | −20.600 | 1.00 | 13.74 |
| ATOM | 1392 | N | TRP | A | 178 | −1.319 | 14.206 | −18.521 | 1.00 | 12.53 |
| ATOM | 1393 | CA | TRP | A | 178 | −0.804 | 15.553 | −18.855 | 1.00 | 12.95 |
| ATOM | 1394 | CB | TRP | A | 178 | −0.890 | 16.507 | −17.660 | 1.00 | 12.67 |
| ATOM | 1395 | CG | TRP | A | 178 | −2.247 | 16.549 | −17.005 | 1.00 | 13.10 |
| ATOM | 1396 | CD1 | TRP | A | 178 | −2.504 | 16.508 | −15.662 | 1.00 | 13.10 |
| ATOM | 1397 | NE1 | TRP | A | 178 | −3.856 | 16.568 | −15.440 | 1.00 | 12.14 |
| ATOM | 1398 | CE2 | TRP | A | 178 | −4.501 | 16.646 | −16.646 | 1.00 | 13.00 |
| ATOM | 1399 | CD2 | TRP | A | 178 | −3.516 | 16.641 | −17.657 | 1.00 | 12.53 |
| ATOM | 1400 | CE3 | TRP | A | 178 | −3.919 | 16.715 | −19.002 | 1.00 | 12.38 |
| ATOM | 1401 | CZ3 | TRP | A | 178 | −5.309 | 16.813 | −19.290 | 1.00 | 13.91 |
| ATOM | 1402 | CH2 | TRP | A | 178 | −6.262 | 16.804 | −18.257 | 1.00 | 13.52 |
| ATOM | 1403 | CZ2 | TRP | A | 178 | −5.883 | 16.718 | −16.930 | 1.00 | 13.97 |
| ATOM | 1404 | C | TRP | A | 178 | 0.632 | 15.565 | −19.400 | 1.00 | 13.35 |
| ATOM | 1405 | O | TRP | A | 178 | 1.147 | 16.641 | −19.756 | 1.00 | 13.76 |
| ATOM | 1406 | N | GLU | A | 179 | 1.255 | 14.387 | −19.447 | 1.00 | 13.33 |
| ATOM | 1407 | CA | GLU | A | 179 | 2.532 | 14.151 | −20.117 | 1.00 | 13.32 |
| ATOM | 1408 | CB | GLU | A | 179 | 2.503 | 14.632 | −21.582 | 1.00 | 12.64 |
| ATOM | 1409 | CG | GLU | A | 179 | 1.165 | 14.344 | −22.280 | 1.00 | 13.03 |
| ATOM | 1410 | CD | GLU | A | 179 | 1.274 | 14.434 | −23.785 | 1.00 | 14.68 |
| ATOM | 1411 | OE1 | GLU | A | 179 | 0.895 | 15.478 | −24.340 | 1.00 | 15.98 |
| ATOM | 1412 | OE2 | GLU | A | 179 | 1.730 | 13.457 | −24.405 | 1.00 | 15.44 |
| ATOM | 1413 | C | GLU | A | 179 | 3.667 | 14.853 | −19.374 | 1.00 | 15.00 |
| ATOM | 1414 | O | GLU | A | 179 | 4.626 | 15.292 | −20.004 | 1.00 | 14.90 |
| ATOM | 1415 | N | GLU | A | 180 | 3.561 | 14.932 | −18.048 | 1.00 | 14.78 |
| ATOM | 1416 | CA | GLU | A | 180 | 4.476 | 15.745 | −17.246 | 1.00 | 16.76 |
| ATOM | 1417 | CB | GLU | A | 180 | 3.719 | 16.928 | −16.630 | 1.00 | 16.95 |
| ATOM | 1418 | CG | GLU | A | 180 | 3.282 | 17.972 | −17.654 | 1.00 | 18.69 |
| ATOM | 1419 | CD | GLU | A | 180 | 2.240 | 18.969 | −17.122 | 1.00 | 19.72 |
| ATOM | 1420 | OE1 | GLU | A | 180 | 1.587 | 18.715 | −16.077 | 1.00 | 19.00 |
| ATOM | 1421 | OE2 | GLU | A | 180 | 2.076 | 20.020 | −17.793 | 1.00 | 24.62 |
| ATOM | 1422 | C | GLU | A | 180 | 5.124 | 14.954 | −16.104 | 1.00 | 16.50 |
| ATOM | 1423 | O | GLU | A | 180 | 6.265 | 15.202 | −15.750 | 1.00 | 17.36 |
| ATOM | 1424 | N | VAL | A | 181 | 4.364 | 14.056 | −15.488 | 1.00 | 16.77 |
| ATOM | 1425 | CA | VAL | A | 181 | 4.775 | 13.426 | −14.218 | 1.00 | 16.87 |
| ATOM | 1426 | CB | VAL | A | 181 | 3.672 | 13.555 | −13.130 | 1.00 | 16.78 |
| ATOM | 1427 | CG1 | VAL | A | 181 | 4.030 | 12.732 | −11.893 | 1.00 | 18.56 |
| ATOM | 1428 | CG2 | VAL | A | 181 | 3.490 | 15.008 | −12.726 | 1.00 | 17.21 |
| ATOM | 1429 | C | VAL | A | 181 | 5.057 | 11.953 | −14.451 | 1.00 | 17.22 |
| ATOM | 1430 | O | VAL | A | 181 | 4.177 | 11.205 | −14.825 | 1.00 | 16.93 |
| ATOM | 1431 | N | ASN | A | 182 | 6.290 | 11.532 | −14.201 | 1.00 | 18.39 |
| ATOM | 1432 | CA | ASN | A | 182 | 6.674 | 10.123 | −14.394 | 1.00 | 18.57 |
| ATOM | 1433 | CB | ASN | A | 182 | 8.136 | 10.079 | −14.845 | 1.00 | 19.77 |
| ATOM | 1434 | CG | ASN | A | 182 | 8.665 | 8.669 | −15.056 | 1.00 | 23.96 |
| ATOM | 1435 | OD1 | ASN | A | 182 | 9.881 | 8.470 | −15.058 | 1.00 | 33.20 |
| ATOM | 1436 | ND2 | ASN | A | 182 | 7.794 | 7.706 | −15.258 | 1.00 | 23.63 |
| ATOM | 1437 | C | ASN | A | 182 | 6.440 | 9.375 | −13.073 | 1.00 | 18.31 |
| ATOM | 1438 | O | ASN | A | 182 | 7.132 | 9.621 | −12.087 | 1.00 | 18.80 |
| ATOM | 1439 | N | GLY | A | 183 | 5.436 | 8.508 | −13.034 | 1.00 | 16.83 |
| ATOM | 1440 | CA | GLY | A | 183 | 5.091 | 7.828 | −11.790 | 1.00 | 15.98 |
| ATOM | 1441 | C | GLY | A | 183 | 3.989 | 6.837 | −12.033 | 1.00 | 15.59 |
| ATOM | 1442 | O | GLY | A | 183 | 3.937 | 6.228 | −13.117 | 1.00 | 15.30 |
| ATOM | 1443 | N | SER | A | 184 | 3.119 | 6.670 | −11.035 | 1.00 | 14.95 |
| ATOM | 1444 | CA | SER | A | 184 | 1.927 | 5.823 | −11.151 | 1.00 | 15.45 |
| ATOM | 1445 | CB | SER | A | 184 | 1.844 | 4.792 | −10.017 | 1.00 | 15.76 |
| ATOM | 1446 | OG | SER | A | 184 | 2.998 | 3.935 | −10.027 | 1.00 | 17.33 |
| ATOM | 1447 | C | SER | A | 184 | 0.731 | 6.758 | −11.073 | 1.00 | 15.14 |
| ATOM | 1448 | O | SER | A | 184 | 0.646 | 7.546 | −10.148 | 1.00 | 15.83 |
| ATOM | 1449 | N | SER | A | 185 | −0.151 | 6.706 | −12.066 | 1.00 | 14.73 |
| ATOM | 1450 | CA | SER | A | 185 | −1.169 | 7.755 | −12.190 | 1.00 | 13.87 |
| ATOM | 1451 | CB | SER | A | 185 | −0.991 | 8.535 | −13.515 | 1.00 | 14.73 |
| ATOM | 1452 | OG | SER | A | 185 | −1.793 | 9.721 | −13.544 | 1.00 | 14.93 |
| ATOM | 1453 | C | SER | A | 185 | −2.551 | 7.140 | −12.127 | 1.00 | 13.49 |
| ATOM | 1454 | O | SER | A | 185 | −2.834 | 6.134 | −12.792 | 1.00 | 13.35 |
| ATOM | 1455 | N | PHE | A | 186 | −3.427 | 7.782 | −11.354 | 1.00 | 13.72 |
| ATOM | 1456 | CA | PHE | A | 186 | −4.764 | 7.275 | −11.092 | 1.00 | 13.43 |
| ATOM | 1457 | CB | PHE | A | 186 | −5.511 | 8.319 | −10.260 | 1.00 | 13.58 |
| ATOM | 1458 | CG | PHE | A | 186 | −6.807 | 7.839 | −9.662 | 1.00 | 13.52 |
| ATOM | 1459 | CD1 | PHE | A | 186 | −6.819 | 6.873 | −8.655 | 1.00 | 16.11 |
| ATOM | 1460 | CE1 | PHE | A | 186 | −8.004 | 6.489 | −8.036 | 1.00 | 17.80 |

TABLE 20-continued

| ATOM | 1461 | CZ | PHE | A | 186 | −9.214 | 7.062 | −8.442 | 1.00 | 16.18 |
|------|------|-----|-----|---|-----|--------|-------|--------|------|-------|
| ATOM | 1462 | CE2 | PHE | A | 186 | −9.211 | 8.051 | −9.432 | 1.00 | 15.77 |
| ATOM | 1463 | CD2 | PHE | A | 186 | −8.003 | 8.435 | −10.030 | 1.00 | 14.62 |
| ATOM | 1464 | C | PHE | A | 186 | −5.552 | 6.946 | −12.372 | 1.00 | 13.57 |
| ATOM | 1465 | O | PHE | A | 186 | −6.053 | 5.839 | −12.524 | 1.00 | 13.36 |
| ATOM | 1466 | N | PHE | A | 187 | −5.693 | 7.927 | −13.267 | 1.00 | 12.53 |
| ATOM | 1467 | CA | PHE | A | 187 | −6.416 | 7.762 | −14.527 | 1.00 | 12.84 |
| ATOM | 1468 | CB | PHE | A | 187 | −6.284 | 9.056 | −15.356 | 1.00 | 11.69 |
| ATOM | 1469 | CG | PHE | A | 187 | −6.949 | 9.016 | −16.711 | 1.00 | 13.25 |
| ATOM | 1470 | CD1 | PHE | A | 187 | −8.284 | 9.338 | −16.855 | 1.00 | 12.86 |
| ATOM | 1471 | CE1 | PHE | A | 187 | −8.893 | 9.342 | −18.102 | 1.00 | 14.12 |
| ATOM | 1472 | CZ | PHE | A | 187 | −8.139 | 9.041 | −19.236 | 1.00 | 14.05 |
| ATOM | 1473 | CE2 | PHE | A | 187 | −6.806 | 8.721 | −19.111 | 1.00 | 14.30 |
| ATOM | 1474 | CD2 | PHE | A | 187 | −6.206 | 8.711 | −17.857 | 1.00 | 15.10 |
| ATOM | 1475 | C | PHE | A | 187 | −5.887 | 6.563 | −15.318 | 1.00 | 12.69 |
| ATOM | 1476 | O | PHE | A | 187 | −6.666 | 5.837 | −15.932 | 1.00 | 14.00 |
| ATOM | 1477 | N | THR | A | 188 | −4.571 | 6.357 | −15.294 | 1.00 | 12.97 |
| ATOM | 1478 | CA | THR | A | 188 | −3.938 | 5.302 | −16.084 | 1.00 | 13.65 |
| ATOM | 1479 | CB | THR | A | 188 | −2.411 | 5.541 | −16.104 | 1.00 | 13.69 |
| ATOM | 1480 | OG1 | THR | A | 188 | −2.158 | 6.789 | −16.753 | 1.00 | 15.37 |
| ATOM | 1481 | CG2 | THR | A | 188 | −1.648 | 4.432 | −16.833 | 1.00 | 13.24 |
| ATOM | 1482 | C | THR | A | 188 | −4.284 | 3.929 | −15.478 | 1.00 | 14.12 |
| ATOM | 1483 | O | THR | A | 188 | −4.766 | 3.039 | −16.173 | 1.00 | 14.40 |
| ATOM | 1484 | N | VAL | A | 189 | −4.066 | 3.798 | −14.173 | 1.00 | 13.34 |
| ATOM | 1485 | CA | VAL | A | 189 | −4.348 | 2.543 | −13.446 | 1.00 | 14.76 |
| ATOM | 1486 | CB | VAL | A | 189 | −3.893 | 2.612 | −11.958 | 1.00 | 14.90 |
| ATOM | 1487 | CG1 | VAL | A | 189 | −4.331 | 1.334 | −11.186 | 1.00 | 16.95 |
| ATOM | 1488 | CG2 | VAL | A | 189 | −2.374 | 2.799 | −11.865 | 1.00 | 15.31 |
| ATOM | 1489 | C | VAL | A | 189 | −5.836 | 2.167 | −13.560 | 1.00 | 14.48 |
| ATOM | 1490 | O | VAL | A | 189 | −6.159 | 1.024 | −13.853 | 1.00 | 14.65 |
| ATOM | 1491 | N | ALA | A | 190 | −6.732 | 3.146 | −13.372 | 1.00 | 13.77 |
| ATOM | 1492 | CA | ALA | A | 190 | −8.171 | 2.858 | −13.351 | 1.00 | 13.46 |
| ATOM | 1493 | CB | ALA | A | 190 | −8.996 | 4.128 | −12.922 | 1.00 | 12.74 |
| ATOM | 1494 | C | ALA | A | 190 | −8.614 | 2.388 | −14.706 | 1.00 | 13.27 |
| ATOM | 1495 | O | ALA | A | 190 | −9.432 | 1.479 | −14.815 | 1.00 | 13.24 |
| ATOM | 1496 | N | ASN | A | 191 | −8.093 | 3.017 | −15.760 | 1.00 | 12.50 |
| ATOM | 1497 | CA | ASN | A | 191 | −8.438 | 2.598 | −17.127 | 1.00 | 13.01 |
| ATOM | 1498 | CB | ASN | A | 191 | −8.122 | 3.707 | −18.137 | 1.00 | 12.65 |
| ATOM | 1499 | CG | ASN | A | 191 | −9.191 | 4.781 | −18.118 | 1.00 | 14.08 |
| ATOM | 1500 | OD1 | ASN | A | 191 | −10.319 | 4.541 | −18.554 | 1.00 | 16.39 |
| ATOM | 1501 | ND2 | ASN | A | 191 | −8.857 | 5.955 | −17.583 | 1.00 | 17.21 |
| ATOM | 1502 | C | ASN | A | 191 | −7.815 | 1.259 | −17.521 | 1.00 | 13.93 |
| ATOM | 1503 | O | ASN | A | 191 | −8.412 | 0.490 | −18.270 | 1.00 | 13.87 |
| ATOM | 1504 | N | GLN | A | 192 | −6.636 | 0.995 | −16.980 | 1.00 | 14.06 |
| ATOM | 1505 | CA | GLN | A | 192 | −5.988 | −0.311 | −17.139 | 1.00 | 14.96 |
| ATOM | 1506 | CB | GLN | A | 192 | −4.575 | −0.274 | −16.552 | 1.00 | 14.33 |
| ATOM | 1507 | CG | GLN | A | 192 | −3.555 | 0.435 | −17.500 | 1.00 | 13.64 |
| ATOM | 1508 | CD | GLN | A | 192 | −2.206 | 0.635 | −16.857 | 1.00 | 15.33 |
| ATOM | 1509 | OE1 | GLN | A | 192 | −2.074 | 0.568 | −15.646 | 1.00 | 15.48 |
| ATOM | 1510 | NE2 | GLN | A | 192 | −1.182 | 0.925 | −17.682 | 1.00 | 16.10 |
| ATOM | 1511 | C | GLN | A | 192 | −6.855 | −1.411 | −16.519 | 1.00 | 15.11 |
| ATOM | 1512 | O | GLN | A | 192 | −7.076 | −2.457 | −17.141 | 1.00 | 16.04 |
| ATOM | 1513 | N | HIS | A | 193 | −7.398 | −1.140 | −15.329 | 1.00 | 15.81 |
| ATOM | 1514 | CA | HIS | A | 193 | −8.314 | −2.069 | −14.668 | 1.00 | 16.01 |
| ATOM | 1515 | CB | HIS | A | 193 | −8.746 | −1.586 | −13.281 | 1.00 | 16.72 |
| ATOM | 1516 | CG | HIS | A | 193 | −9.806 | −2.454 | −12.669 | 1.00 | 17.39 |
| ATOM | 1517 | ND1 | HIS | A | 193 | −11.113 | −2.039 | −12.505 | 1.00 | 18.05 |
| ATOM | 1518 | CE1 | HIS | A | 193 | −11.821 | −3.028 | −11.983 | 1.00 | 18.70 |
| ATOM | 1519 | NE2 | HIS | A | 193 | −11.023 | −4.071 | −11.814 | 1.00 | 17.20 |
| ATOM | 1520 | CD2 | HIS | A | 193 | −9.758 | −3.739 | −12.242 | 1.00 | 18.04 |
| ATOM | 1521 | C | HIS | A | 193 | −9.536 | −2.343 | −15.521 | 1.00 | 15.85 |
| ATOM | 1522 | O | HIS | A | 193 | −9.898 | −3.501 | −15.732 | 1.00 | 15.70 |
| ATOM | 1523 | N | ARG | A | 194 | −10.185 | −1.285 | −15.995 | 1.00 | 15.27 |
| ATOM | 1524 | CA | ARG | A | 194 | −11.349 | −1.437 | −16.852 | 1.00 | 15.29 |
| ATOM | 1525 | CB | ARG | A | 194 | −11.922 | −0.073 | −17.234 | 1.00 | 14.30 |
| ATOM | 1526 | CG | ARG | A | 194 | −13.029 | −0.212 | −18.239 | 1.00 | 14.46 |
| ATOM | 1527 | CD | ARG | A | 194 | −13.614 | 1.102 | −18.723 | 1.00 | 15.43 |
| ATOM | 1528 | NE | ARG | A | 194 | −14.589 | 0.780 | −19.767 | 1.00 | 15.58 |
| ATOM | 1529 | CZ | ARG | A | 194 | −15.624 | 1.539 | −20.125 | 1.00 | 17.92 |
| ATOM | 1530 | NH1 | ARG | A | 194 | −15.815 | 2.744 | −19.576 | 1.00 | 14.60 |
| ATOM | 1531 | NH2 | ARG | A | 194 | −16.451 | 1.095 | −21.060 | 1.00 | 16.15 |
| ATOM | 1532 | C | ARG | A | 194 | −11.047 | −2.258 | −18.111 | 1.00 | 15.74 |
| ATOM | 1533 | O | ARG | A | 194 | −11.842 | −3.120 | −18.504 | 1.00 | 15.56 |
| ATOM | 1534 | N | ALA | A | 195 | −9.918 | −1.967 | −18.758 | 1.00 | 15.60 |
| ATOM | 1535 | CA | ALA | A | 195 | −9.562 | −2.638 | −20.004 | 1.00 | 15.90 |
| ATOM | 1536 | CB | ALA | A | 195 | −8.254 | −2.042 | −20.591 | 1.00 | 15.40 |
| ATOM | 1537 | C | ALA | A | 195 | −9.436 | −4.150 | −19.798 | 1.00 | 15.65 |
| ATOM | 1538 | O | ALA | A | 195 | −9.959 | −4.929 | −20.610 | 1.00 | 16.79 |
| ATOM | 1539 | N | LEU | A | 196 | −8.763 | −4.550 | −18.721 | 1.00 | 16.36 |
| ATOM | 1540 | CA | LEU | A | 196 | −8.552 | −5.976 | −18.423 | 1.00 | 17.02 |

TABLE 20-continued

| | | | | | | | | | |
|---|---|---|---|---|---|---|---|---|---|
| ATOM | 1541 | CB | LEU | A | 196 | −7.625 | −6.126 | −17.235 | 1.00 | 16.96 |
| ATOM | 1542 | CG | LEU | A | 196 | −6.167 | −5.744 | −17.532 | 1.00 | 16.96 |
| ATOM | 1543 | CD1 | LEU | A | 196 | −5.375 | −5.857 | −16.252 | 1.00 | 18.93 |
| ATOM | 1544 | CD2 | LEU | A | 196 | −5.590 | −6.636 | −18.630 | 1.00 | 20.38 |
| ATOM | 1545 | C | LEU | A | 196 | −9.877 | −6.685 | −18.167 | 1.00 | 17.92 |
| ATOM | 1546 | O | LEU | A | 196 | −10.102 | −7.795 | −18.643 | 1.00 | 18.98 |
| ATOM | 1547 | N | VAL | A | 197 | −10.779 | −6.014 | −17.454 | 1.00 | 18.51 |
| ATOM | 1548 | CA | VAL | A | 197 | −12.112 | −6.560 | −17.181 | 1.00 | 18.81 |
| ATOM | 1549 | CB | VAL | A | 197 | −12.875 | −5.702 | −16.130 | 1.00 | 18.26 |
| ATOM | 1550 | CG1 | VAL | A | 197 | −14.340 | −6.173 | −15.994 | 1.00 | 21.18 |
| ATOM | 1551 | CG2 | VAL | A | 197 | −12.149 | −5.784 | −14.778 | 1.00 | 19.79 |
| ATOM | 1552 | C | VAL | A | 197 | −12.924 | −6.779 | −18.462 | 1.00 | 19.05 |
| ATOM | 1553 | O | VAL | A | 197 | −13.456 | −7.884 | −18.693 | 1.00 | 18.62 |
| ATOM | 1554 | N | GLU | A | 198 | −13.010 | −5.752 | −19.308 | 1.00 | 18.43 |
| ATOM | 1555 | CA | GLU | A | 198 | −13.747 | −5.873 | −20.556 | 1.00 | 19.38 |
| ATOM | 1556 | CB | GLU | A | 198 | −13.849 | −4.517 | −21.241 | 1.00 | 19.38 |
| ATOM | 1557 | CG | GLU | A | 198 | −14.609 | −3.530 | −20.417 | 1.00 | 20.22 |
| ATOM | 1558 | CD | GLU | A | 198 | −15.334 | −2.537 | −21.298 | 1.00 | 22.66 |
| ATOM | 1559 | OE1 | GLU | A | 198 | −16.313 | −2.940 | −21.940 | 1.00 | 22.16 |
| ATOM | 1560 | OE2 | GLU | A | 198 | −14.924 | −1.369 | −21.342 | 1.00 | 22.92 |
| ATOM | 1561 | C | GLU | A | 198 | −13.094 | −6.861 | −21.509 | 1.00 | 19.78 |
| ATOM | 1562 | O | GLU | A | 198 | −13.780 | −7.506 | −22.303 | 1.00 | 20.29 |
| ATOM | 1563 | N | GLY | A | 199 | −11.770 | −6.944 | −21.435 | 1.00 | 19.78 |
| ATOM | 1564 | CA | GLY | A | 199 | −10.998 | −7.823 | −22.314 | 1.00 | 20.88 |
| ATOM | 1565 | C | GLY | A | 199 | −11.288 | −9.285 | −21.986 | 1.00 | 21.53 |
| ATOM | 1566 | O | GLY | A | 199 | −11.546 | −10.083 | −22.879 | 1.00 | 22.36 |
| ATOM | 1567 | N | ALA | A | 200 | −11.256 | −9.615 | −20.702 | 1.00 | 21.79 |
| ATOM | 1568 | CA | ALA | A | 200 | −11.605 | −10.956 | −20.234 | 1.00 | 22.44 |
| ATOM | 1569 | CB | ALA | A | 200 | −11.463 | −11.038 | −18.728 | 1.00 | 22.21 |
| ATOM | 1570 | C | ALA | A | 200 | −13.016 | −11.329 | −20.696 | 1.00 | 22.54 |
| ATOM | 1571 | O | ALA | A | 200 | −13.237 | −12.419 | −21.214 | 1.00 | 22.25 |
| ATOM | 1572 | N | THR | A | 201 | −13.965 | −10.403 | −20.573 | 1.00 | 22.56 |
| ATOM | 1573 | CA | THR | A | 201 | −15.345 | −10.671 | −20.989 | 1.00 | 22.77 |
| ATOM | 1574 | CB | THR | A | 201 | −16.302 | −9.527 | −20.551 | 1.00 | 22.83 |
| ATOM | 1575 | OG1 | THR | A | 201 | −16.219 | −9.387 | −19.134 | 1.00 | 24.92 |
| ATOM | 1576 | CG2 | THR | A | 201 | −17.756 | −9.819 | −20.929 | 1.00 | 23.76 |
| ATOM | 1577 | C | THR | A | 201 | −15.435 | −10.905 | −22.485 | 1.00 | 22.78 |
| ATOM | 1578 | O | THR | A | 201 | −16.099 | −11.851 | −22.925 | 1.00 | 22.95 |
| ATOM | 1579 | N | LEU | A | 202 | −14.760 | −10.069 | −23.275 | 1.00 | 21.78 |
| ATOM | 1580 | CA | LEU | A | 202 | −14.805 | −10.236 | −24.717 | 1.00 | 22.62 |
| ATOM | 1581 | CB | LEU | A | 202 | −14.149 | −9.055 | −25.434 | 1.00 | 22.14 |
| ATOM | 1582 | CG | LEU | A | 202 | −14.142 | −9.107 | −26.964 | 1.00 | 23.10 |
| ATOM | 1583 | CD1 | LEU | A | 202 | −15.544 | −9.198 | −27.564 | 1.00 | 24.20 |
| ATOM | 1584 | CD2 | LEU | A | 202 | −13.346 | −7.938 | −27.570 | 1.00 | 22.53 |
| ATOM | 1585 | C | LEU | A | 202 | −14.139 | −11.552 | −25.151 | 1.00 | 23.15 |
| ATOM | 1586 | O | LEU | A | 202 | −14.649 | −12.245 | −26.036 | 1.00 | 22.90 |
| ATOM | 1587 | N | ALA | A | 203 | −13.019 | −11.883 | −24.510 | 1.00 | 23.38 |
| ATOM | 1588 | CA | ALA | A | 203 | −12.300 | −13.129 | −24.787 | 1.00 | 24.07 |
| ATOM | 1589 | CB | ALA | A | 203 | −11.076 | −13.229 | −23.913 | 1.00 | 23.57 |
| ATOM | 1590 | C | ALA | A | 203 | −13.211 | −14.354 | −24.569 | 1.00 | 24.38 |
| ATOM | 1591 | O | ALA | A | 203 | −13.264 | −15.244 | −25.411 | 1.00 | 25.21 |
| ATOM | 1592 | N | ALA | A | 204 | −13.920 | −14.363 | −23.447 | 1.00 | 25.20 |
| ATOM | 1593 | CA | ALA | A | 204 | −14.849 | −15.442 | −23.093 | 1.00 | 26.63 |
| ATOM | 1594 | CB | ALA | A | 204 | −15.450 | −15.186 | −21.727 | 1.00 | 26.12 |
| ATOM | 1595 | C | ALA | A | 204 | −15.939 | −15.583 | −24.150 | 1.00 | 27.48 |
| ATOM | 1596 | O | ALA | A | 204 | −16.267 | −16.687 | −24.564 | 1.00 | 28.39 |
| ATOM | 1597 | N | THR | A | 205 | −16.494 | −14.461 | −24.593 | 1.00 | 27.71 |
| ATOM | 1598 | CA | THR | A | 205 | −17.497 | −14.470 | −25.652 | 1.00 | 28.39 |
| ATOM | 1599 | CB | THR | A | 205 | −18.088 | −13.051 | −25.855 | 1.00 | 28.42 |
| ATOM | 1600 | OG1 | THR | A | 205 | −18.669 | −12.631 | −24.622 | 1.00 | 29.32 |
| ATOM | 1601 | CG2 | THR | A | 205 | −19.150 | −13.051 | −26.932 | 1.00 | 27.32 |
| ATOM | 1602 | C | THR | A | 205 | −16.968 | −15.004 | −26.981 | 1.00 | 28.72 |
| ATOM | 1603 | O | THR | A | 205 | −17.697 | −15.690 | −27.719 | 1.00 | 29.06 |
| ATOM | 1604 | N | LEU | A | 206 | −15.712 | −14.698 | −27.288 | 1.00 | 28.58 |
| ATOM | 1605 | CA | LEU | A | 206 | −15.122 | −15.122 | −28.539 | 1.00 | 29.40 |
| ATOM | 1606 | CB | LEU | A | 206 | −14.034 | −14.144 | −29.001 | 1.00 | 29.40 |
| ATOM | 1607 | CG | LEU | A | 206 | −14.438 | −12.694 | −29.322 | 1.00 | 29.97 |
| ATOM | 1608 | CD1 | LEU | A | 206 | −13.212 | −11.899 | −29.755 | 1.00 | 30.30 |
| ATOM | 1609 | CD2 | LEU | A | 206 | −15.561 | −12.629 | −30.375 | 1.00 | 29.58 |
| ATOM | 1610 | C | LEU | A | 206 | −14.540 | −16.538 | −28.489 | 1.00 | 29.55 |
| ATOM | 1611 | O | LEU | A | 206 | −14.118 | −17.054 | −29.521 | 1.00 | 30.16 |
| ATOM | 1612 | N | GLY | A | 207 | −14.500 | −17.145 | −27.307 | 1.00 | 30.30 |
| ATOM | 1613 | CA | GLY | A | 207 | −13.786 | −18.419 | −27.122 | 1.00 | 30.91 |
| ATOM | 1614 | C | GLY | A | 207 | −12.294 | −18.274 | −27.375 | 1.00 | 31.55 |
| ATOM | 1615 | O | GLY | A | 207 | −11.654 | −19.173 | −27.935 | 1.00 | 31.31 |
| ATOM | 1616 | N | GLN | A | 208 | −11.746 | −17.115 | −26.989 | 1.00 | 31.08 |
| ATOM | 1617 | CA | GLN | A | 208 | −10.311 | −16.877 | −27.031 | 1.00 | 31.10 |
| ATOM | 1618 | CB | GLN | A | 208 | −9.999 | −15.540 | −27.703 | 1.00 | 31.08 |
| ATOM | 1619 | CG | GLN | A | 208 | −10.451 | −15.455 | −29.142 | 1.00 | 33.86 |
| ATOM | 1620 | CD | GLN | A | 208 | −9.469 | −16.059 | −30.126 | 1.00 | 38.19 |

TABLE 20-continued

| | | | | | | | | |
|---|---|---|---|---|---|---|---|---|
| ATOM | 1621 | OE1 | GLN | A | 208 | −9.686 | −15.999 | −31.335 | 1.00 | 41.96 |
| ATOM | 1622 | NE2 | GLN | A | 208 | −8.386 | −16.633 | −29.626 | 1.00 | 38.96 |
| ATOM | 1623 | C | GLN | A | 208 | −9.765 | −16.909 | −25.611 | 1.00 | 30.45 |
| ATOM | 1624 | O | GLN | A | 208 | −10.516 | −17.048 | −24.658 | 1.00 | 30.63 |
| ATOM | 1625 | N | SER | A | 209 | −8.451 | −16.816 | −25.469 | 1.00 | 29.96 |
| ATOM | 1626 | CA | SER | A | 209 | −7.841 | −16.898 | −24.160 | 1.00 | 30.04 |
| ATOM | 1627 | CB | SER | A | 209 | −6.382 | −17.343 | −24.297 | 1.00 | 30.04 |
| ATOM | 1628 | OG | SER | A | 209 | −5.763 | −17.371 | −23.030 | 1.00 | 32.75 |
| ATOM | 1629 | C | SER | A | 209 | −7.948 | −15.564 | −23.409 | 1.00 | 29.53 |
| ATOM | 1630 | O | SER | A | 209 | −7.493 | −14.532 | −23.908 | 1.00 | 29.85 |
| ATOM | 1631 | N | GLY | A | 210 | −8.545 | −15.594 | −22.216 | 1.00 | 28.41 |
| ATOM | 1632 | CA | GLY | A | 210 | −8.745 | −14.388 | −21.401 | 1.00 | 27.16 |
| ATOM | 1633 | C | GLY | A | 210 | −8.344 | −14.480 | −19.938 | 1.00 | 26.83 |
| ATOM | 1634 | O | GLY | A | 210 | −8.425 | −13.498 | −19.203 | 1.00 | 26.61 |
| ATOM | 1635 | N | SER | A | 211 | −7.888 | −15.648 | −19.497 | 1.00 | 25.85 |
| ATOM | 1636 | CA | SER | A | 211 | −7.651 | −15.867 | −18.067 | 1.00 | 25.26 |
| ATOM | 1637 | CB | SER | A | 211 | −7.401 | −17.353 | −17.783 | 1.00 | 25.87 |
| ATOM | 1638 | OG | SER | A | 211 | −6.315 | −17.789 | −18.573 | 1.00 | 26.62 |
| ATOM | 1639 | C | SER | A | 211 | −6.509 | −15.026 | −17.498 | 1.00 | 24.55 |
| ATOM | 1640 | O | SER | A | 211 | −6.542 | −14.676 | −16.311 | 1.00 | 24.46 |
| ATOM | 1641 | N | ALA | A | 212 | −5.505 | −14.712 | −18.323 | 1.00 | 23.56 |
| ATOM | 1642 | CA | ALA | A | 212 | −4.423 | −13.816 | −17.906 | 1.00 | 23.42 |
| ATOM | 1643 | CB | ALA | A | 212 | −3.417 | −13.622 | −19.031 | 1.00 | 23.66 |
| ATOM | 1644 | C | ALA | A | 212 | −4.999 | −12.450 | −17.496 | 1.00 | 23.54 |
| ATOM | 1645 | O | ALA | A | 212 | −4.566 | −11.848 | −16.513 | 1.00 | 24.00 |
| ATOM | 1646 | N | TYR | A | 213 | −5.970 | −11.979 | −18.271 | 1.00 | 22.79 |
| ATOM | 1647 | CA | TYR | A | 213 | −6.594 | −10.676 | −18.017 | 1.00 | 22.18 |
| ATOM | 1648 | CB | TYR | A | 213 | −7.453 | −10.241 | −19.193 | 1.00 | 21.74 |
| ATOM | 1649 | CG | TYR | A | 213 | −6.761 | −10.345 | −20.515 | 1.00 | 20.05 |
| ATOM | 1650 | CD1 | TYR | A | 213 | −7.461 | −10.761 | −21.637 | 1.00 | 20.58 |
| ATOM | 1651 | CE1 | TYR | A | 213 | −6.854 | −10.854 | −22.868 | 1.00 | 21.95 |
| ATOM | 1652 | CZ | TYR | A | 213 | −5.503 | −10.545 | −22.988 | 1.00 | 20.62 |
| ATOM | 1653 | OH | TYR | A | 213 | −4.930 | −10.668 | −24.220 | 1.00 | 21.72 |
| ATOM | 1654 | CE2 | TYR | A | 213 | −4.758 | −10.149 | −21.888 | 1.00 | 19.76 |
| ATOM | 1655 | CD2 | TYR | A | 213 | −5.400 | −10.038 | −20.647 | 1.00 | 20.61 |
| ATOM | 1656 | C | TYR | A | 213 | −7.423 | −10.710 | −16.758 | 1.00 | 23.06 |
| ATOM | 1657 | O | TYR | A | 213 | −7.320 | −9.804 | −15.939 | 1.00 | 22.56 |
| ATOM | 1658 | N | SER | A | 214 | −8.226 | −11.767 | −16.578 | 1.00 | 23.15 |
| ATOM | 1659 | CA | SER | A | 214 | −9.064 | −11.832 | −15.392 | 1.00 | 23.90 |
| ATOM | 1660 | CB | SER | A | 214 | −10.244 | −12.798 | −15.580 | 1.00 | 24.54 |
| ATOM | 1661 | OG | SER | A | 214 | −9.776 | −14.085 | −15.939 | 1.00 | 27.95 |
| ATOM | 1662 | C | SER | A | 214 | −8.259 | −12.122 | −14.122 | 1.00 | 23.64 |
| ATOM | 1663 | O | SER | A | 214 | −8.676 | −11.762 | −13.026 | 1.00 | 23.43 |
| ATOM | 1664 | N | SER | A | 215 | −7.095 | −12.743 | −14.248 | 1.00 | 23.82 |
| ATOM | 1665 | CA | SER | A | 215 | −6.295 | −12.970 | −13.050 | 1.00 | 24.66 |
| ATOM | 1666 | CB | SER | A | 215 | −5.390 | −14.205 | −13.200 | 1.00 | 25.70 |
| ATOM | 1667 | OG | SER | A | 215 | −4.267 | −13.914 | −14.004 | 1.00 | 29.15 |
| ATOM | 1668 | C | SER | A | 215 | −5.491 | −11.739 | −12.610 | 1.00 | 23.98 |
| ATOM | 1669 | O | SER | A | 215 | −5.217 | −11.561 | −11.421 | 1.00 | 24.09 |
| ATOM | 1670 | N | VAL | A | 216 | −5.115 | −10.894 | −13.566 | 1.00 | 22.89 |
| ATOM | 1671 | CA | VAL | A | 216 | −4.347 | −9.679 | −13.272 | 1.00 | 22.50 |
| ATOM | 1672 | CB | VAL | A | 216 | −3.442 | −9.296 | −14.493 | 1.00 | 22.52 |
| ATOM | 1673 | CG1 | VAL | A | 216 | −2.855 | −7.888 | −14.369 | 1.00 | 24.11 |
| ATOM | 1674 | CG2 | VAL | A | 216 | −2.296 | −10.317 | −14.652 | 1.00 | 22.49 |
| ATOM | 1675 | C | VAL | A | 216 | −5.256 | −8.520 | −12.801 | 1.00 | 21.88 |
| ATOM | 1676 | O | VAL | A | 216 | −4.869 | −7.745 | −11.936 | 1.00 | 21.84 |
| ATOM | 1677 | N | ALA | A | 217 | −6.475 | −8.440 | −13.332 | 1.00 | 21.86 |
| ATOM | 1678 | CA | ALA | A | 217 | −7.374 | −7.303 | −13.050 | 1.00 | 21.59 |
| ATOM | 1679 | CB | ALA | A | 217 | −8.721 | −7.479 | −13.760 | 1.00 | 21.26 |
| ATOM | 1680 | C | ALA | A | 217 | −7.571 | −6.968 | −11.558 | 1.00 | 21.55 |
| ATOM | 1681 | O | ALA | A | 217 | −7.447 | −5.804 | −11.165 | 1.00 | 21.20 |
| ATOM | 1682 | N | PRO | A | 218 | −7.842 | −7.988 | −10.701 | 1.00 | 21.95 |
| ATOM | 1683 | CA | PRO | A | 218 | −8.030 | −7.700 | −9.282 | 1.00 | 21.59 |
| ATOM | 1684 | CB | PRO | A | 218 | −8.283 | −9.104 | −8.670 | 1.00 | 22.29 |
| ATOM | 1685 | CG | PRO | A | 218 | −8.789 | −9.905 | −9.789 | 1.00 | 22.61 |
| ATOM | 1686 | CD | PRO | A | 218 | −7.966 | −9.435 | −10.963 | 1.00 | 22.11 |
| ATOM | 1687 | C | PRO | A | 218 | −6.798 | −7.065 | −8.634 | 1.00 | 21.27 |
| ATOM | 1688 | O | PRO | A | 218 | −6.928 | −6.299 | −7.680 | 1.00 | 20.92 |
| ATOM | 1689 | N | GLN | A | 219 | −5.608 | −7.386 | −9.141 | 1.00 | 21.17 |
| ATOM | 1690 | CA | GLN | A | 219 | −4.378 | −6.786 | −8.609 | 1.00 | 21.51 |
| ATOM | 1691 | CB | GLN | A | 219 | −3.149 | −7.569 | −9.084 | 1.00 | 22.72 |
| ATOM | 1692 | CG | GLN | A | 219 | −3.113 | −8.985 | −8.516 | 1.00 | 24.90 |
| ATOM | 1693 | CD | GLN | A | 219 | −3.323 | −8.982 | −7.015 | 1.00 | 29.57 |
| ATOM | 1694 | OE1 | GLN | A | 219 | −2.715 | −8.188 | −6.288 | 1.00 | 31.58 |
| ATOM | 1695 | NE2 | GLN | A | 219 | −4.207 | −9.843 | −6.545 | 1.00 | 33.22 |
| ATOM | 1696 | C | GLN | A | 219 | −4.240 | −5.301 | −8.996 | 1.00 | 21.04 |
| ATOM | 1697 | O | GLN | A | 219 | −3.687 | −4.490 | −8.229 | 1.00 | 21.07 |
| ATOM | 1698 | N | VAL | A | 220 | −4.728 | −4.973 | −10.187 | 1.00 | 20.00 |
| ATOM | 1699 | CA | VAL | A | 220 | −4.746 | −3.577 | −10.630 | 1.00 | 19.34 |
| ATOM | 1700 | CB | VAL | A | 220 | −5.098 | −3.456 | −12.128 | 1.00 | 19.63 |

TABLE 20-continued

| | | | | | | | | | |
|---|---|---|---|---|---|---|---|---|---|
| ATOM | 1701 | CG1 | VAL | A | 220 | −4.991 | −2.000 | −12.581 | 1.00 | 19.15 |
| ATOM | 1702 | CG2 | VAL | A | 220 | −4.162 | −4.342 | −12.974 | 1.00 | 17.97 |
| ATOM | 1703 | C | VAL | A | 220 | −5.730 | −2.809 | −9.737 | 1.00 | 19.65 |
| ATOM | 1704 | O | VAL | A | 220 | −5.419 | −1.728 | −9.257 | 1.00 | 18.97 |
| ATOM | 1705 | N | LEU | A | 221 | −6.903 | −3.391 | −9.490 | 1.00 | 20.12 |
| ATOM | 1706 | CA | LEU | A | 221 | −7.895 | −2.776 | −8.620 | 1.00 | 20.83 |
| ATOM | 1707 | CB | LEU | A | 221 | −9.180 | −3.602 | −8.599 | 1.00 | 20.48 |
| ATOM | 1708 | CG | LEU | A | 221 | −10.336 | −2.991 | −7.790 | 1.00 | 22.48 |
| ATOM | 1709 | CD1 | LEU | A | 221 | −10.857 | −1.726 | −8.458 | 1.00 | 22.33 |
| ATOM | 1710 | CD2 | LEU | A | 221 | −11.430 | −4.011 | −7.637 | 1.00 | 22.51 |
| ATOM | 1711 | C | LEU | A | 221 | −7.360 | −2.591 | −7.192 | 1.00 | 21.44 |
| ATOM | 1712 | O | LEU | A | 221 | −7.617 | −1.578 | −6.539 | 1.00 | 20.45 |
| ATOM | 1713 | N | CYS | A | 222 | −6.600 | −3.572 | −6.718 | 1.00 | 22.60 |
| ATOM | 1714 | CA | CYS | A | 222 | −5.957 | −3.477 | −5.415 | 1.00 | 22.10 |
| ATOM | 1715 | CB | CYS | A | 222 | −5.159 | −4.749 | −5.125 | 1.00 | 23.41 |
| ATOM | 1716 | SG | CYS | A | 222 | −4.975 | −5.000 | −3.356 | 1.00 | 28.49 |
| ATOM | 1717 | C | CYS | A | 222 | −5.035 | −2.270 | −5.317 | 1.00 | 21.22 |
| ATOM | 1718 | O | CYS | A | 222 | −5.060 | −1.531 | −4.331 | 1.00 | 21.24 |
| ATOM | 1719 | N | PHE | A | 223 | −4.210 | −2.070 | −6.347 | 1.00 | 20.11 |
| ATOM | 1720 | CA | PHE | A | 223 | −3.287 | −0.955 | −6.368 | 1.00 | 19.03 |
| ATOM | 1721 | CB | PHE | A | 223 | −2.334 | −1.108 | −7.558 | 1.00 | 19.15 |
| ATOM | 1722 | CG | PHE | A | 223 | −1.297 | −0.011 | −7.669 | 1.00 | 19.23 |
| ATOM | 1723 | CD1 | PHE | A | 223 | −0.576 | 0.410 | −6.558 | 1.00 | 19.90 |
| ATOM | 1724 | CE1 | PHE | A | 223 | 0.380 | 1.417 | −6.661 | 1.00 | 20.91 |
| ATOM | 1725 | CZ | PHE | A | 223 | 0.645 | 2.017 | −7.902 | 1.00 | 21.07 |
| ATOM | 1726 | CE2 | PHE | A | 223 | −0.061 | 1.598 | −9.024 | 1.00 | 18.81 |
| ATOM | 1727 | CD2 | PHE | A | 223 | −1.022 | 0.581 | −8.909 | 1.00 | 18.23 |
| ATOM | 1728 | C | PHE | A | 223 | −4.032 | 0.397 | −6.423 | 1.00 | 18.38 |
| ATOM | 1729 | O | PHE | A | 223 | −3.597 | 1.376 | −5.818 | 1.00 | 18.27 |
| ATOM | 1730 | N | LEU | A | 224 | −5.148 | 0.428 | −7.142 | 1.00 | 18.45 |
| ATOM | 1731 | CA | LEU | A | 224 | −5.957 | 1.665 | −7.277 | 1.00 | 18.42 |
| ATOM | 1732 | CB | LEU | A | 224 | −7.208 | 1.403 | −8.127 | 1.00 | 17.70 |
| ATOM | 1733 | CG | LEU | A | 224 | −7.990 | 2.645 | −8.610 | 1.00 | 19.73 |
| ATOM | 1734 | CD1 | LEU | A | 224 | −7.133 | 3.427 | −9.584 | 1.00 | 20.37 |
| ATOM | 1735 | CD2 | LEU | A | 224 | −9.302 | 2.228 | −9.264 | 1.00 | 18.64 |
| ATOM | 1736 | C | LEU | A | 224 | −6.385 | 2.226 | −5.917 | 1.00 | 18.87 |
| ATOM | 1737 | O | LEU | A | 224 | −6.553 | 3.438 | −5.757 | 1.00 | 18.45 |
| ATOM | 1738 | N | GLN | A | 225 | −6.578 | 1.336 | −4.944 | 1.00 | 19.17 |
| ATOM | 1739 | CA | GLN | A | 225 | −6.984 | 1.743 | −3.585 | 1.00 | 20.00 |
| ATOM | 1740 | CB | GLN | A | 225 | −7.340 | 0.511 | −2.725 | 1.00 | 20.26 |
| ATOM | 1741 | CG | GLN | A | 225 | −8.295 | −0.463 | −3.409 | 1.00 | 21.22 |
| ATOM | 1742 | CD | GLN | A | 225 | −9.519 | 0.225 | −3.993 | 1.00 | 22.53 |
| ATOM | 1743 | OE1 | GLN | A | 225 | −10.280 | 0.870 | −3.262 | 1.00 | 23.09 |
| ATOM | 1744 | NE2 | GLN | A | 225 | −9.718 | 0.092 | −5.302 | 1.00 | 19.33 |
| ATOM | 1745 | C | GLN | A | 225 | −5.944 | 2.599 | −2.871 | 1.00 | 20.19 |
| ATOM | 1746 | O | GLN | A | 225 | −6.299 | 3.399 | −2.009 | 1.00 | 20.64 |
| ATOM | 1747 | N | ARG | A | 226 | −4.678 | 2.450 | −3.253 | 1.00 | 20.51 |
| ATOM | 1748 | CA | ARG | A | 226 | −3.564 | 3.144 | −2.608 | 1.00 | 21.40 |
| ATOM | 1749 | CB | ARG | A | 226 | −2.219 | 2.505 | −2.990 | 1.00 | 22.72 |
| ATOM | 1750 | CG | ARG | A | 226 | −2.081 | 1.010 | −2.683 | 1.00 | 26.14 |
| ATOM | 1751 | CD | ARG | A | 226 | −1.806 | 0.741 | −1.204 | 1.00 | 32.16 |
| ATOM | 1752 | NE | ARG | A | 226 | −3.035 | 0.843 | −0.432 | 1.00 | 37.77 |
| ATOM | 1753 | CZ | ARG | A | 226 | −3.997 | −0.079 | −0.413 | 1.00 | 41.09 |
| ATOM | 1754 | NH1 | ARG | A | 226 | −5.093 | 0.120 | 0.322 | 1.00 | 42.17 |
| ATOM | 1755 | NH2 | ARG | A | 226 | −3.874 | −1.196 | −1.127 | 1.00 | 42.78 |
| ATOM | 1756 | C | ARG | A | 226 | −3.499 | 4.645 | −2.915 | 1.00 | 21.23 |
| ATOM | 1757 | O | ARG | A | 226 | −2.723 | 5.358 | −2.288 | 1.00 | 20.95 |
| ATOM | 1758 | N | PHE | A | 227 | −4.298 | 5.123 | −3.869 | 1.00 | 20.28 |
| ATOM | 1759 | CA | PHE | A | 227 | −4.280 | 6.545 | −4.250 | 1.00 | 19.67 |
| ATOM | 1760 | CB | PHE | A | 227 | −4.777 | 6.704 | −5.693 | 1.00 | 19.40 |
| ATOM | 1761 | CG | PHE | A | 227 | −3.814 | 6.195 | −6.744 | 1.00 | 18.28 |
| ATOM | 1762 | CD1 | PHE | A | 227 | −3.733 | 4.831 | −7.040 | 1.00 | 18.14 |
| ATOM | 1763 | CE1 | PHE | A | 227 | −2.855 | 4.355 | −8.046 | 1.00 | 18.24 |
| ATOM | 1764 | CZ | PHE | A | 227 | −2.034 | 5.264 | −8.748 | 1.00 | 16.75 |
| ATOM | 1765 | CE2 | PHE | A | 227 | −2.113 | 6.641 | −8.456 | 1.00 | 18.79 |
| ATOM | 1766 | CD2 | PHE | A | 227 | −3.005 | 7.091 | −7.452 | 1.00 | 17.51 |
| ATOM | 1767 | C | PHE | A | 227 | −5.126 | 7.435 | −3.343 | 1.00 | 20.55 |
| ATOM | 1768 | O | PHE | A | 227 | −4.967 | 8.659 | −3.334 | 1.00 | 20.38 |
| ATOM | 1769 | N | TRP | A | 228 | −6.032 | 6.820 | −2.583 | 1.00 | 20.72 |
| ATOM | 1770 | CA | TRP | A | 228 | −6.924 | 7.545 | −1.671 | 1.00 | 20.71 |
| ATOM | 1771 | CB | TRP | A | 228 | −8.036 | 6.596 | −1.211 | 1.00 | 20.41 |
| ATOM | 1772 | CG | TRP | A | 228 | −9.030 | 7.228 | −0.283 | 1.00 | 20.59 |
| ATOM | 1773 | CD1 | TRP | A | 228 | −9.243 | 6.915 | 1.040 | 1.00 | 21.81 |
| ATOM | 1774 | NE1 | TRP | A | 228 | −10.255 | 7.722 | 1.557 | 1.00 | 22.69 |
| ATOM | 1775 | CE2 | TRP | A | 228 | −10.712 | 8.553 | 0.565 | 1.00 | 20.71 |
| ATOM | 1776 | CD2 | TRP | A | 228 | −9.958 | 8.280 | −0.607 | 1.00 | 18.88 |
| ATOM | 1777 | CE3 | TRP | A | 228 | −10.225 | 9.014 | −1.772 | 1.00 | 18.79 |
| ATOM | 1778 | CZ3 | TRP | A | 228 | −11.209 | 9.986 | −1.734 | 1.00 | 20.13 |
| ATOM | 1779 | CH2 | TRP | A | 228 | −11.937 | 10.242 | −0.552 | 1.00 | 21.18 |
| ATOM | 1780 | CZ2 | TRP | A | 228 | −11.710 | 9.537 | 0.601 | 1.00 | 21.65 |

TABLE 20-continued

| | | | | | | | | | |
|---|---|---|---|---|---|---|---|---|---|
| ATOM | 1781 | C | TRP | A | 228 | −6.193 | 8.120 | −0.463 | 1.00 | 21.38 |
| ATOM | 1782 | O | TRP | A | 228 | −5.479 | 7.394 | 0.236 | 1.00 | 21.50 |
| ATOM | 1783 | N | VAL | A | 229 | −6.379 | 9.416 | −0.209 | 1.00 | 21.95 |
| ATOM | 1784 | CA | VAL | A | 229 | −5.844 | 10.065 | 0.983 | 1.00 | 22.99 |
| ATOM | 1785 | CB | VAL | A | 229 | −5.205 | 11.436 | 0.654 | 1.00 | 22.81 |
| ATOM | 1786 | CG1 | VAL | A | 229 | −4.490 | 12.026 | 1.871 | 1.00 | 23.48 |
| ATOM | 1787 | CG2 | VAL | A | 229 | −4.226 | 11.292 | −0.493 | 1.00 | 23.28 |
| ATOM | 1788 | C | VAL | A | 229 | −6.984 | 10.206 | 2.000 | 1.00 | 24.08 |
| ATOM | 1789 | O | VAL | A | 229 | −7.803 | 11.119 | 1.899 | 1.00 | 23.70 |
| ATOM | 1790 | N | SER | A | 230 | −7.044 | 9.298 | 2.974 | 1.00 | 25.37 |
| ATOM | 1791 | CA | SER | A | 230 | −8.193 | 9.290 | 3.905 | 1.00 | 27.59 |
| ATOM | 1792 | CB | SER | A | 230 | −8.254 | 8.000 | 4.728 | 1.00 | 27.67 |
| ATOM | 1793 | OG | SER | A | 230 | −7.029 | 7.805 | 5.402 | 1.00 | 31.30 |
| ATOM | 1794 | C | SER | A | 230 | −8.241 | 10.513 | 4.820 | 1.00 | 27.93 |
| ATOM | 1795 | O | SER | A | 230 | −9.321 | 10.983 | 5.174 | 1.00 | 28.91 |
| ATOM | 1796 | N | SER | A | 231 | −7.088 | 11.059 | 5.165 | 1.00 | 28.76 |
| ATOM | 1797 | CA | SER | A | 231 | −7.059 | 12.237 | 6.030 | 1.00 | 29.72 |
| ATOM | 1798 | CB | SER | A | 231 | −5.671 | 12.461 | 6.639 | 1.00 | 30.39 |
| ATOM | 1799 | OG | SER | A | 231 | −4.703 | 12.713 | 5.635 | 1.00 | 34.43 |
| ATOM | 1800 | C | SER | A | 231 | −7.566 | 13.491 | 5.323 | 1.00 | 29.39 |
| ATOM | 1801 | O | SER | A | 231 | −8.154 | 14.364 | 5.966 | 1.00 | 30.97 |
| ATOM | 1802 | N | GLY | A | 232 | −7.373 | 13.579 | 4.005 | 1.00 | 27.59 |
| ATOM | 1803 | CA | GLY | A | 232 | −7.867 | 14.728 | 3.247 | 1.00 | 25.22 |
| ATOM | 1804 | C | GLY | A | 232 | −9.181 | 14.518 | 2.493 | 1.00 | 23.25 |
| ATOM | 1805 | O | GLY | A | 232 | −9.810 | 15.487 | 2.077 | 1.00 | 23.19 |
| ATOM | 1806 | N | GLY | A | 233 | −9.589 | 13.265 | 2.320 | 1.00 | 20.97 |
| ATOM | 1807 | CA | GLY | A | 233 | −10.809 | 12.937 | 1.578 | 1.00 | 19.35 |
| ATOM | 1808 | C | GLY | A | 233 | −10.673 | 13.226 | 0.094 | 1.00 | 18.83 |
| ATOM | 1809 | O | GLY | A | 233 | −11.636 | 13.655 | −0.561 | 1.00 | 19.20 |
| ATOM | 1810 | N | TYR | A | 234 | −9.487 | 12.977 | −0.463 | 1.00 | 17.56 |
| ATOM | 1811 | CA | TYR | A | 234 | −9.309 | 13.155 | −1.915 | 1.00 | 17.17 |
| ATOM | 1812 | CB | TYR | A | 234 | −8.851 | 14.584 | −2.232 | 1.00 | 18.33 |
| ATOM | 1813 | CG | TYR | A | 234 | −7.441 | 14.876 | −1.758 | 1.00 | 20.39 |
| ATOM | 1814 | CD1 | TYR | A | 234 | −7.203 | 15.340 | −0.454 | 1.00 | 20.72 |
| ATOM | 1815 | CE1 | TYR | A | 234 | −5.905 | 15.594 | −0.018 | 1.00 | 24.11 |
| ATOM | 1816 | CZ | TYR | A | 234 | −4.840 | 15.399 | −0.897 | 1.00 | 23.78 |
| ATOM | 1817 | OH | TYR | A | 234 | −3.556 | 15.663 | −0.483 | 1.00 | 26.50 |
| ATOM | 1818 | CE2 | TYR | A | 234 | −5.055 | 14.956 | −2.187 | 1.00 | 24.07 |
| ATOM | 1819 | CD2 | TYR | A | 234 | −6.353 | 14.699 | −2.611 | 1.00 | 20.58 |
| ATOM | 1820 | C | TYR | A | 234 | −8.318 | 12.141 | −2.482 | 1.00 | 16.60 |
| ATOM | 1821 | O | TYR | A | 234 | −7.615 | 11.465 | −1.735 | 1.00 | 16.29 |
| ATOM | 1822 | N | VAL | A | 235 | −8.260 | 12.059 | −3.805 | 1.00 | 15.36 |
| ATOM | 1823 | CA | VAL | A | 235 | −7.325 | 11.164 | −4.472 | 1.00 | 15.62 |
| ATOM | 1824 | CB | VAL | A | 235 | −7.948 | 10.638 | −5.798 | 1.00 | 15.96 |
| ATOM | 1825 | CG1 | VAL | A | 235 | −6.889 | 9.893 | −6.645 | 1.00 | 17.31 |
| ATOM | 1826 | CG2 | VAL | A | 235 | −9.134 | 9.723 | −5.506 | 1.00 | 15.87 |
| ATOM | 1827 | C | VAL | A | 235 | −6.011 | 11.904 | −4.742 | 1.00 | 15.54 |
| ATOM | 1828 | O | VAL | A | 235 | −6.006 | 12.998 | −5.320 | 1.00 | 15.39 |
| ATOM | 1829 | N | ASP | A | 236 | −4.886 | 11.316 | −4.325 | 1.00 | 15.24 |
| ATOM | 1830 | CA | ASP | A | 236 | −3.580 | 11.837 | −4.705 | 1.00 | 15.22 |
| ATOM | 1831 | CB | ASP | A | 236 | −2.533 | 11.431 | −3.652 | 1.00 | 16.45 |
| ATOM | 1832 | CG | ASP | A | 236 | −1.145 | 11.922 | −3.970 | 1.00 | 18.62 |
| ATOM | 1833 | OD1 | ASP | A | 236 | −0.937 | 12.617 | −4.992 | 1.00 | 17.17 |
| ATOM | 1834 | OD2 | ASP | A | 236 | −0.223 | 11.568 | −3.182 | 1.00 | 22.79 |
| ATOM | 1835 | C | ASP | A | 236 | −3.303 | 11.256 | −6.098 | 1.00 | 15.06 |
| ATOM | 1836 | O | ASP | A | 236 | −3.088 | 10.040 | −6.261 | 1.00 | 15.39 |
| ATOM | 1837 | N | SER | A | 237 | −3.384 | 12.104 | −7.125 | 1.00 | 14.24 |
| ATOM | 1838 | CA | SER | A | 237 | −3.518 | 11.587 | −8.503 | 1.00 | 14.09 |
| ATOM | 1839 | CB | SER | A | 237 | −4.000 | 12.697 | −9.446 | 1.00 | 13.76 |
| ATOM | 1840 | OG | SER | A | 237 | −5.312 | 13.094 | −9.070 | 1.00 | 14.52 |
| ATOM | 1841 | C | SER | A | 237 | −2.277 | 10.883 | −9.053 | 1.00 | 14.22 |
| ATOM | 1842 | O | SER | A | 237 | −2.376 | 10.067 | −9.965 | 1.00 | 13.80 |
| ATOM | 1843 | N | ASN | A | 238 | −1.099 | 11.219 | −8.521 | 1.00 | 14.70 |
| ATOM | 1844 | CA | ASN | A | 238 | 0.116 | 10.547 | −8.952 | 1.00 | 15.28 |
| ATOM | 1845 | CB | ASN | A | 238 | 0.968 | 11.439 | −9.856 | 1.00 | 14.84 |
| ATOM | 1846 | CG | ASN | A | 238 | 0.277 | 11.742 | −11.176 | 1.00 | 17.08 |
| ATOM | 1847 | OD1 | ASN | A | 238 | 0.244 | 10.901 | −12.072 | 1.00 | 16.61 |
| ATOM | 1848 | ND2 | ASN | A | 238 | −0.308 | 12.932 | −11.278 | 1.00 | 16.63 |
| ATOM | 1849 | C | ASN | A | 238 | 0.912 | 10.150 | −7.736 | 1.00 | 16.07 |
| ATOM | 1850 | O | ASN | A | 238 | 1.169 | 10.988 | −6.890 | 1.00 | 15.88 |
| ATOM | 1851 | N | ILE | A | 239 | 1.280 | 8.875 | −7.659 | 1.00 | 16.09 |
| ATOM | 1852 | CA | ILE | A | 239 | 2.125 | 8.410 | −6.567 | 1.00 | 18.07 |
| ATOM | 1853 | CB | ILE | A | 239 | 1.340 | 7.452 | −5.600 | 1.00 | 17.66 |
| ATOM | 1854 | CG1 | ILE | A | 239 | 0.893 | 6.180 | −6.336 | 1.00 | 18.85 |
| ATOM | 1855 | CD1 | ILE | A | 239 | 0.184 | 5.109 | −5.437 | 1.00 | 19.02 |
| ATOM | 1856 | CG2 | ILE | A | 239 | 0.116 | 8.194 | −4.974 | 1.00 | 16.96 |
| ATOM | 1857 | C | ILE | A | 239 | 3.381 | 7.760 | −7.169 | 1.00 | 19.32 |
| ATOM | 1858 | O | ILE | A | 239 | 3.571 | 7.797 | −8.392 | 1.00 | 19.19 |
| ATOM | 1859 | N | ASN | A | 240 | 4.242 | 7.170 | −6.329 | 1.00 | 20.56 |
| ATOM | 1860 | CA | ASN | A | 240 | 5.517 | 6.617 | −6.823 | 1.00 | 22.24 |

TABLE 20-continued

| | | | | | | | | | |
|---|---|---|---|---|---|---|---|---|---|
| ATOM | 1861 | CB | ASN | A | 240 | 5.275 | 5.385 | −7.717 | 1.00 | 21.93 |
| ATOM | 1862 | CG | ASN | A | 240 | 4.874 | 4.153 | −6.926 | 1.00 | 24.19 |
| ATOM | 1863 | OD1 | ASN | A | 240 | 5.269 | 3.995 | −5.772 | 1.00 | 25.98 |
| ATOM | 1864 | ND2 | ASN | A | 240 | 4.083 | 3.278 | −7.538 | 1.00 | 22.26 |
| ATOM | 1865 | C | ASN | A | 240 | 6.334 | 7.677 | −7.571 | 1.00 | 23.27 |
| ATOM | 1866 | O | ASN | A | 240 | 7.000 | 7.381 | −8.562 | 1.00 | 23.15 |
| ATOM | 1867 | N | THR | A | 241 | 6.261 | 8.919 | −7.096 | 1.00 | 25.02 |
| ATOM | 1868 | CA | THR | A | 241 | 6.939 | 10.038 | −7.729 | 1.00 | 28.12 |
| ATOM | 1869 | CB | THR | A | 241 | 6.044 | 10.720 | −8.817 | 1.00 | 28.09 |
| ATOM | 1870 | OG1 | THR | A | 241 | 6.741 | 11.836 | −9.369 | 1.00 | 28.75 |
| ATOM | 1871 | CG2 | THR | A | 241 | 4.727 | 11.208 | −8.231 | 1.00 | 28.30 |
| ATOM | 1872 | C | THR | A | 241 | 7.302 | 11.065 | −6.674 | 1.00 | 29.96 |
| ATOM | 1873 | O | THR | A | 241 | 6.749 | 11.037 | −5.589 | 1.00 | 30.58 |
| ATOM | 1874 | N | ASN | A | 242 | 8.209 | 11.984 | −6.991 | 1.00 | 33.17 |
| ATOM | 1875 | CA | ASN | A | 242 | 8.585 | 13.019 | −6.024 | 1.00 | 36.07 |
| ATOM | 1876 | CB | ASN | A | 242 | 10.059 | 12.880 | −5.616 | 1.00 | 37.13 |
| ATOM | 1877 | CG | ASN | A | 242 | 10.324 | 11.631 | −4.771 | 1.00 | 40.96 |
| ATOM | 1878 | OD1 | ASN | A | 242 | 9.509 | 11.235 | −3.921 | 1.00 | 45.33 |
| ATOM | 1879 | ND2 | ASN | A | 242 | 11.477 | 11.007 | −4.998 | 1.00 | 44.43 |
| ATOM | 1880 | C | ASN | A | 242 | 8.321 | 14.427 | −6.528 | 1.00 | 37.00 |
| ATOM | 1881 | O | ASN | A | 242 | 9.091 | 15.346 | −6.245 | 1.00 | 37.94 |
| ATOM | 1882 | N | GLU | A | 243 | 7.210 | 14.602 | −7.233 | 1.00 | 37.54 |
| ATOM | 1883 | CA | GLU | A | 243 | 6.895 | 15.869 | −7.907 | 1.00 | 38.05 |
| ATOM | 1884 | CB | GLU | A | 243 | 5.775 | 15.638 | −8.925 | 1.00 | 38.77 |
| ATOM | 1885 | CG | GLU | A | 243 | 5.650 | 16.732 | −9.977 | 1.00 | 42.65 |
| ATOM | 1886 | CD | GLU | A | 243 | 6.959 | 16.985 | −10.709 | 1.00 | 47.49 |
| ATOM | 1887 | OE1 | GLU | A | 243 | 7.424 | 16.084 | −11.453 | 1.00 | 49.14 |
| ATOM | 1888 | OE2 | GLU | A | 243 | 7.520 | 18.090 | −10.532 | 1.00 | 50.15 |
| ATOM | 1889 | C | GLU | A | 243 | 6.559 | 17.088 | −7.015 | 1.00 | 37.15 |
| ATOM | 1890 | O | GLU | A | 243 | 6.645 | 18.240 | −7.469 | 1.00 | 38.39 |
| ATOM | 1891 | N | GLY | A | 244 | 6.174 | 16.873 | −5.766 | 1.00 | 35.69 |
| ATOM | 1892 | CA | GLY | A | 244 | 5.858 | 18.019 | −4.911 | 1.00 | 33.51 |
| ATOM | 1893 | C | GLY | A | 244 | 4.609 | 18.775 | −5.369 | 1.00 | 31.80 |
| ATOM | 1894 | O | GLY | A | 244 | 4.634 | 19.999 | −5.535 | 1.00 | 33.32 |
| ATOM | 1895 | N | ARG | A | 245 | 3.529 | 18.036 | −5.612 | 1.00 | 27.92 |
| ATOM | 1896 | CA | ARG | A | 245 | 2.200 | 18.618 | −5.781 | 1.00 | 24.21 |
| ATOM | 1897 | CB | ARG | A | 245 | 1.638 | 18.224 | −7.130 | 1.00 | 24.30 |
| ATOM | 1898 | CG | ARG | A | 245 | 2.410 | 18.842 | −8.275 | 1.00 | 24.62 |
| ATOM | 1899 | CD | ARG | A | 245 | 1.625 | 18.681 | −9.532 | 1.00 | 22.11 |
| ATOM | 1900 | NE | ARG | A | 245 | 2.462 | 18.829 | −10.713 | 1.00 | 21.13 |
| ATOM | 1901 | CZ | ARG | A | 245 | 2.114 | 18.302 | −11.878 | 1.00 | 21.50 |
| ATOM | 1902 | NH1 | ARG | A | 245 | 0.982 | 17.621 | −11.945 | 1.00 | 18.57 |
| ATOM | 1903 | NH2 | ARG | A | 245 | 2.883 | 18.443 | −12.951 | 1.00 | 20.83 |
| ATOM | 1904 | C | ARG | A | 245 | 1.295 | 18.040 | −4.718 | 1.00 | 21.84 |
| ATOM | 1905 | O | ARG | A | 245 | 1.624 | 17.021 | −4.128 | 1.00 | 20.65 |
| ATOM | 1906 | N | THR | A | 246 | 0.140 | 18.652 | −4.483 | 1.00 | 19.15 |
| ATOM | 1907 | CA | THR | A | 246 | −0.824 | 18.058 | −3.540 | 1.00 | 17.46 |
| ATOM | 1908 | CB | THR | A | 246 | −1.989 | 18.997 | −3.238 | 1.00 | 17.87 |
| ATOM | 1909 | OG1 | THR | A | 246 | −2.752 | 19.155 | −4.440 | 1.00 | 15.85 |
| ATOM | 1910 | CG2 | THR | A | 246 | −1.495 | 20.370 | −2.730 | 1.00 | 17.50 |
| ATOM | 1911 | C | THR | A | 246 | −1.426 | 16.769 | −4.103 | 1.00 | 17.25 |
| ATOM | 1912 | O | THR | A | 246 | −1.884 | 15.914 | −3.351 | 1.00 | 17.57 |
| ATOM | 1913 | N | GLY | A | 247 | −1.482 | 16.646 | −5.430 | 1.00 | 15.60 |
| ATOM | 1914 | CA | GLY | A | 247 | −2.148 | 15.492 | −6.054 | 1.00 | 15.02 |
| ATOM | 1915 | C | GLY | A | 247 | −3.609 | 15.761 | −6.396 | 1.00 | 14.69 |
| ATOM | 1916 | O | GLY | A | 247 | −4.260 | 14.939 | −7.059 | 1.00 | 14.45 |
| ATOM | 1917 | N | LYS | A | 248 | −4.137 | 16.890 | −5.928 | 1.00 | 13.43 |
| ATOM | 1918 | CA | LYS | A | 248 | −5.508 | 17.286 | −6.259 | 1.00 | 13.00 |
| ATOM | 1919 | CB | LYS | A | 248 | −5.969 | 18.453 | −5.396 | 1.00 | 12.32 |
| ATOM | 1920 | CG | LYS | A | 248 | −5.965 | 18.179 | −3.881 | 1.00 | 13.12 |
| ATOM | 1921 | CD | LYS | A | 248 | −6.133 | 19.493 | −3.102 | 1.00 | 14.08 |
| ATOM | 1922 | CE | LYS | A | 248 | −5.985 | 19.253 | −1.584 | 1.00 | 17.84 |
| ATOM | 1923 | NZ | LYS | A | 248 | −6.335 | 20.492 | −0.835 | 1.00 | 16.74 |
| ATOM | 1924 | C | LYS | A | 248 | −5.490 | 17.713 | −7.736 | 1.00 | 12.73 |
| ATOM | 1925 | O | LYS | A | 248 | −4.866 | 18.707 | −8.104 | 1.00 | 12.75 |
| ATOM | 1926 | N | ASP | A | 249 | −6.185 | 16.964 | −8.580 | 1.00 | 11.92 |
| ATOM | 1927 | CA | ASP | A | 249 | −5.958 | 17.098 | −10.024 | 1.00 | 11.16 |
| ATOM | 1928 | CB | ASP | A | 249 | −4.761 | 16.199 | −10.385 | 1.00 | 10.83 |
| ATOM | 1929 | CG | ASP | A | 249 | −4.268 | 16.349 | −11.831 | 1.00 | 12.54 |
| ATOM | 1930 | OD1 | ASP | A | 249 | −5.078 | 16.422 | −12.785 | 1.00 | 11.42 |
| ATOM | 1931 | OD2 | ASP | A | 249 | −3.025 | 16.342 | −12.001 | 1.00 | 13.30 |
| ATOM | 1932 | C | ASP | A | 249 | −7.232 | 16.577 | −10.662 | 1.00 | 11.38 |
| ATOM | 1933 | O | ASP | A | 249 | −7.774 | 15.542 | −10.236 | 1.00 | 10.86 |
| ATOM | 1934 | N | VAL | A | 250 | −7.700 | 17.265 | −11.703 | 1.00 | 11.28 |
| ATOM | 1935 | CA | VAL | A | 250 | −8.885 | 16.793 | −12.438 | 1.00 | 11.59 |
| ATOM | 1936 | CB | VAL | A | 250 | −9.366 | 17.859 | −13.493 | 1.00 | 12.49 |
| ATOM | 1937 | CG1 | VAL | A | 250 | −8.480 | 17.815 | −14.728 | 1.00 | 13.03 |
| ATOM | 1938 | CG2 | VAL | A | 250 | −10.859 | 17.654 | −13.852 | 1.00 | 13.75 |
| ATOM | 1939 | C | VAL | A | 250 | −8.711 | 15.386 | −13.064 | 1.00 | 11.77 |
| ATOM | 1940 | O | VAL | A | 250 | −9.698 | 14.750 | −13.467 | 1.00 | 11.71 |

TABLE 20-continued

| | | | | | | | | |
|---|---|---|---|---|---|---|---|---|
| ATOM | 1941 | N | ASN | A | 251 | −7.461 | 14.925 | −13.168 | 1.00 | 10.73 |
| ATOM | 1942 | CA | ASN | A | 251 | −7.131 | 13.491 | −13.378 | 1.00 | 11.20 |
| ATOM | 1943 | CB | ASN | A | 251 | −5.699 | 13.265 | −12.813 | 1.00 | 10.94 |
| ATOM | 1944 | CG | ASN | A | 251 | −5.221 | 11.810 | −12.892 | 1.00 | 11.58 |
| ATOM | 1945 | OD1 | ASN | A | 251 | −5.986 | 10.864 | −12.672 | 1.00 | 12.47 |
| ATOM | 1946 | ND2 | ASN | A | 251 | −3.898 | 11.639 | −13.164 | 1.00 | 14.40 |
| ATOM | 1947 | C | ASN | A | 251 | −8.151 | 12.560 | −12.706 | 1.00 | 10.99 |
| ATOM | 1948 | O | ASN | A | 251 | −8.755 | 11.706 | −13.355 | 1.00 | 11.49 |
| ATOM | 1949 | N | SER | A | 252 | −8.407 | 12.774 | −11.417 | 1.00 | 11.45 |
| ATOM | 1950 | CA | SER | A | 252 | −9.293 | 11.876 | −10.634 | 1.00 | 11.79 |
| ATOM | 1951 | CB | SER | A | 252 | −9.062 | 12.155 | −9.149 | 1.00 | 13.31 |
| ATOM | 1952 | OG | SER | A | 252 | −9.338 | 13.524 | −8.882 | 1.00 | 13.41 |
| ATOM | 1953 | C | SER | A | 252 | −10.784 | 12.002 | −10.996 | 1.00 | 11.39 |
| ATOM | 1954 | O | SER | A | 252 | −11.532 | 11.023 | −10.964 | 1.00 | 12.69 |
| ATOM | 1955 | N | VAL | A | 253 | −11.199 | 13.203 | −11.383 | 1.00 | 10.56 |
| ATOM | 1956 | CA | VAL | A | 253 | −12.582 | 13.459 | −11.821 | 1.00 | 10.70 |
| ATOM | 1957 | CB | VAL | A | 253 | −12.884 | 15.004 | −11.856 | 1.00 | 11.02 |
| ATOM | 1958 | CG1 | VAL | A | 253 | −14.335 | 15.262 | −12.345 | 1.00 | 11.24 |
| ATOM | 1959 | CG2 | VAL | A | 253 | −12.711 | 15.585 | −10.449 | 1.00 | 10.91 |
| ATOM | 1960 | C | VAL | A | 253 | −12.810 | 12.827 | −13.187 | 1.00 | 11.38 |
| ATOM | 1961 | O | VAL | A | 253 | −13.824 | 12.143 | −13.407 | 1.00 | 11.69 |
| ATOM | 1962 | N | LEU | A | 254 | −11.866 | 13.059 | −14.108 | 1.00 | 11.32 |
| ATOM | 1963 | CA | LEU | A | 254 | −11.891 | 12.393 | −15.417 | 1.00 | 12.12 |
| ATOM | 1964 | CB | LEU | A | 254 | −10.635 | 12.759 | −16.238 | 1.00 | 11.95 |
| ATOM | 1965 | CG | LEU | A | 254 | −10.634 | 14.202 | −16.763 | 1.00 | 12.23 |
| ATOM | 1966 | CD1 | LEU | A | 254 | −9.266 | 14.564 | −17.330 | 1.00 | 12.77 |
| ATOM | 1967 | CD2 | LEU | A | 254 | −11.714 | 14.371 | −17.845 | 1.00 | 15.26 |
| ATOM | 1968 | C | LEU | A | 254 | −11.963 | 10.872 | −15.271 | 1.00 | 12.22 |
| ATOM | 1969 | O | LEU | A | 254 | −12.675 | 10.201 | −16.024 | 1.00 | 12.01 |
| ATOM | 1970 | N | THR | A | 255 | −11.208 | 10.338 | −14.315 | 1.00 | 11.58 |
| ATOM | 1971 | CA | THR | A | 255 | −11.219 | 8.913 | −14.042 | 1.00 | 12.53 |
| ATOM | 1972 | CB | THR | A | 255 | −10.267 | 8.552 | −12.890 | 1.00 | 12.83 |
| ATOM | 1973 | OG1 | THR | A | 255 | −8.935 | 8.933 | −13.240 | 1.00 | 13.00 |
| ATOM | 1974 | CG2 | THR | A | 255 | −10.300 | 7.035 | −12.634 | 1.00 | 15.06 |
| ATOM | 1975 | C | THR | A | 255 | −12.632 | 8.448 | −13.705 | 1.00 | 13.12 |
| ATOM | 1976 | O | THR | A | 255 | −13.131 | 7.467 | −14.285 | 1.00 | 13.49 |
| ATOM | 1977 | N | SER | A | 256 | −13.289 | 9.158 | −12.790 | 1.00 | 13.46 |
| ATOM | 1978 | CA | SER | A | 256 | −14.641 | 8.781 | −12.343 | 1.00 | 12.85 |
| ATOM | 1979 | CB | SER | A | 256 | −15.152 | 9.760 | −11.282 | 1.00 | 13.40 |
| ATOM | 1980 | OG | SER | A | 256 | −16.332 | 9.252 | −10.674 | 1.00 | 16.69 |
| ATOM | 1981 | C | SER | A | 256 | −15.610 | 8.705 | −13.518 | 1.00 | 13.13 |
| ATOM | 1982 | O | SER | A | 256 | −16.360 | 7.711 | −13.654 | 1.00 | 13.10 |
| ATOM | 1983 | N | ILE | A | 257 | −15.594 | 9.728 | −14.377 | 1.00 | 12.32 |
| ATOM | 1984 | CA | ILE | A | 257 | −16.523 | 9.784 | −15.513 | 1.00 | 12.32 |
| ATOM | 1985 | CB | ILE | A | 257 | −16.747 | 11.215 | −16.072 | 1.00 | 11.55 |
| ATOM | 1986 | CG1 | ILE | A | 257 | −15.482 | 11.773 | −16.764 | 1.00 | 11.38 |
| ATOM | 1987 | CD1 | ILE | A | 257 | −15.699 | 13.143 | −17.441 | 1.00 | 13.23 |
| ATOM | 1988 | CG2 | ILE | A | 257 | −17.257 | 12.166 | −14.942 | 1.00 | 13.70 |
| ATOM | 1989 | C | ILE | A | 257 | −16.220 | 8.795 | −16.653 | 1.00 | 12.79 |
| ATOM | 1990 | O | ILE | A | 257 | −17.150 | 8.319 | −17.338 | 1.00 | 13.25 |
| ATOM | 1991 | N | HIS | A | 258 | −14.941 | 8.487 | −16.855 | 1.00 | 12.71 |
| ATOM | 1992 | CA | HIS | A | 258 | −14.565 | 7.566 | −17.931 | 1.00 | 13.41 |
| ATOM | 1993 | CB | HIS | A | 258 | −13.194 | 7.947 | −18.498 | 1.00 | 12.06 |
| ATOM | 1994 | CG | HIS | A | 258 | −13.268 | 9.175 | −19.341 | 1.00 | 13.92 |
| ATOM | 1995 | ND1 | HIS | A | 258 | −13.942 | 9.196 | −20.547 | 1.00 | 16.01 |
| ATOM | 1996 | CE1 | HIS | A | 258 | −13.891 | 10.421 | −21.047 | 1.00 | 18.57 |
| ATOM | 1997 | NE2 | HIS | A | 258 | −13.256 | 11.199 | −20.189 | 1.00 | 14.08 |
| ATOM | 1998 | CD2 | HIS | A | 258 | −12.861 | 10.449 | −19.108 | 1.00 | 13.51 |
| ATOM | 1999 | C | HIS | A | 258 | −14.649 | 6.091 | −17.565 | 1.00 | 14.12 |
| ATOM | 2000 | O | HIS | A | 258 | −14.645 | 5.239 | −18.454 | 1.00 | 14.90 |
| ATOM | 2001 | N | THR | A | 259 | −14.752 | 5.801 | −16.274 | 1.00 | 13.93 |
| ATOM | 2002 | CA | THR | A | 259 | −15.034 | 4.420 | −15.807 | 1.00 | 14.91 |
| ATOM | 2003 | CB | THR | A | 259 | −13.933 | 3.856 | −14.899 | 1.00 | 14.46 |
| ATOM | 2004 | OG1 | THR | A | 259 | −13.788 | 4.647 | −13.705 | 1.00 | 15.66 |
| ATOM | 2005 | CG2 | THR | A | 259 | −12.589 | 3.802 | −15.677 | 1.00 | 15.81 |
| ATOM | 2006 | C | THR | A | 259 | −16.433 | 4.248 | −15.173 | 1.00 | 14.21 |
| ATOM | 2007 | O | THR | A | 259 | −16.709 | 3.235 | −14.546 | 1.00 | 14.95 |
| ATOM | 2008 | N | PHE | A | 260 | −17.290 | 5.238 | −15.367 | 1.00 | 14.76 |
| ATOM | 2009 | CA | PHE | A | 260 | −18.691 | 5.194 | −14.926 | 1.00 | 15.13 |
| ATOM | 2010 | CB | PHE | A | 260 | −19.377 | 6.492 | −15.379 | 1.00 | 15.81 |
| ATOM | 2011 | CG | PHE | A | 260 | −20.886 | 6.508 | −15.228 | 1.00 | 15.47 |
| ATOM | 2012 | CD1 | PHE | A | 260 | −21.505 | 6.188 | −14.015 | 1.00 | 17.59 |
| ATOM | 2013 | CE1 | PHE | A | 260 | −22.903 | 6.259 | −13.898 | 1.00 | 19.11 |
| ATOM | 2014 | CZ | PHE | A | 260 | −23.682 | 6.653 | −14.991 | 1.00 | 17.18 |
| ATOM | 2015 | CE2 | PHE | A | 260 | −23.082 | 6.994 | −16.178 | 1.00 | 18.04 |
| ATOM | 2016 | CD2 | PHE | A | 260 | −21.679 | 6.917 | −16.296 | 1.00 | 17.22 |
| ATOM | 2017 | C | PHE | A | 260 | −19.436 | 3.977 | −15.475 | 1.00 | 15.55 |
| ATOM | 2018 | O | PHE | A | 260 | −19.426 | 3.725 | −16.684 | 1.00 | 15.81 |
| ATOM | 2019 | N | ASP | A | 261 | −20.093 | 3.235 | −14.586 | 1.00 | 15.51 |
| ATOM | 2020 | CA | ASP | A | 261 | −21.008 | 2.176 | −15.006 | 1.00 | 16.05 |

TABLE 20-continued

| ATOM | 2021 | CB | ASP | A | 261 | −20.303 | 0.813 | −15.015 | 1.00 | 16.46 |
|---|---|---|---|---|---|---|---|---|---|---|
| ATOM | 2022 | CG | ASP | A | 261 | −21.205 | −0.321 | −15.490 | 1.00 | 17.60 |
| ATOM | 2023 | OD1 | ASP | A | 261 | −22.440 | −0.122 | −15.579 | 1.00 | 18.97 |
| ATOM | 2024 | OD2 | ASP | A | 261 | −20.656 | −1.404 | −15.810 | 1.00 | 18.29 |
| ATOM | 2025 | C | ASP | A | 261 | −22.117 | 2.185 | −13.972 | 1.00 | 16.30 |
| ATOM | 2026 | O | ASP | A | 261 | −21.882 | 1.809 | −12.840 | 1.00 | 15.53 |
| ATOM | 2027 | N | PRO | A | 262 | −23.320 | 2.610 | −14.374 | 1.00 | 18.21 |
| ATOM | 2028 | CA | PRO | A | 262 | −24.438 | 2.716 | −13.412 | 1.00 | 20.39 |
| ATOM | 2029 | CB | PRO | A | 262 | −25.589 | 3.308 | −14.247 | 1.00 | 20.43 |
| ATOM | 2030 | CG | PRO | A | 262 | −25.235 | 3.044 | −15.669 | 1.00 | 20.06 |
| ATOM | 2031 | CD | PRO | A | 262 | −23.709 | 2.994 | −15.734 | 1.00 | 17.40 |
| ATOM | 2032 | C | PRO | A | 262 | −24.815 | 1.382 | −12.753 | 1.00 | 22.31 |
| ATOM | 2033 | O | PRO | A | 262 | −25.356 | 1.374 | −11.622 | 1.00 | 22.24 |
| ATOM | 2034 | N | ASN | A | 263 | −24.508 | 0.267 | −13.421 | 1.00 | 22.99 |
| ATOM | 2035 | CA | ASN | A | 263 | −24.750 | −1.048 | −12.838 | 1.00 | 25.42 |
| ATOM | 2036 | CB | ASN | A | 263 | −24.574 | −2.149 | −13.890 | 1.00 | 26.62 |
| ATOM | 2037 | CG | ASN | A | 263 | −25.680 | −2.128 | −14.948 | 1.00 | 30.74 |
| ATOM | 2038 | OD1 | ASN | A | 263 | −26.688 | −1.419 | −14.814 | 1.00 | 35.92 |
| ATOM | 2039 | ND2 | ASN | A | 263 | −25.490 | −2.906 | −16.007 | 1.00 | 35.87 |
| ATOM | 2040 | C | ASN | A | 263 | −23.894 | −1.316 | −11.598 | 1.00 | 25.45 |
| ATOM | 2041 | O | ASN | A | 263 | −24.210 | −2.190 | −10.795 | 1.00 | 26.56 |
| ATOM | 2042 | N | LEU | A | 264 | −22.835 | −0.529 | −11.413 | 1.00 | 24.54 |
| ATOM | 2043 | CA | LEU | A | 264 | −22.022 | −0.616 | −10.213 | 1.00 | 24.27 |
| ATOM | 2044 | CB | LEU | A | 264 | −20.549 | −0.287 | −10.520 | 1.00 | 24.43 |
| ATOM | 2045 | CG | LEU | A | 264 | −19.752 | −1.346 | −11.288 | 1.00 | 25.38 |
| ATOM | 2046 | CD1 | LEU | A | 264 | −18.375 | −0.809 | −11.659 | 1.00 | 26.05 |
| ATOM | 2047 | CD2 | LEU | A | 264 | −19.619 | −2.672 | −10.523 | 1.00 | 26.24 |
| ATOM | 2048 | C | LEU | A | 264 | −22.542 | 0.273 | −9.066 | 1.00 | 23.47 |
| ATOM | 2049 | O | LEU | A | 264 | −21.956 | 0.292 | −7.988 | 1.00 | 23.97 |
| ATOM | 2050 | N | GLY | A | 265 | −23.631 | 1.000 | −9.292 | 1.00 | 23.32 |
| ATOM | 2051 | CA | GLY | A | 265 | −24.218 | 1.840 | −8.237 | 1.00 | 22.74 |
| ATOM | 2052 | C | GLY | A | 265 | −23.204 | 2.843 | −7.729 | 1.00 | 21.84 |
| ATOM | 2053 | O | GLY | A | 265 | −22.416 | 3.373 | −8.510 | 1.00 | 22.83 |
| ATOM | 2054 | N | CYS | A | 266 | −23.175 | 3.086 | −6.424 | 1.00 | 21.37 |
| ATOM | 2055 | CA | CYS | A | 266 | −22.233 | 4.073 | −5.883 | 1.00 | 21.00 |
| ATOM | 2056 | CB | CYS | A | 266 | −22.947 | 5.049 | −4.936 | 1.00 | 20.86 |
| ATOM | 2057 | SG | CYS | A | 266 | −24.347 | 5.912 | −5.711 | 1.00 | 20.96 |
| ATOM | 2058 | C | CYS | A | 266 | −20.992 | 3.427 | −5.275 | 1.00 | 20.98 |
| ATOM | 2059 | O | CYS | A | 266 | −20.513 | 3.814 | −4.203 | 1.00 | 21.01 |
| ATOM | 2060 | N | ASP | A | 267 | −20.462 | 2.443 | −6.002 | 1.00 | 20.39 |
| ATOM | 2061 | CA | ASP | A | 267 | −19.303 | 1.686 | −5.577 | 1.00 | 20.67 |
| ATOM | 2062 | CB | ASP | A | 267 | −18.961 | 0.621 | −6.618 | 1.00 | 20.84 |
| ATOM | 2063 | CG | ASP | A | 267 | −17.666 | −0.101 | −6.288 | 1.00 | 24.28 |
| ATOM | 2064 | OD1 | ASP | A | 267 | −16.852 | −0.322 | −7.200 | 1.00 | 25.84 |
| ATOM | 2065 | OD2 | ASP | A | 267 | −17.455 | −0.407 | −5.098 | 1.00 | 27.46 |
| ATOM | 2066 | C | ASP | A | 267 | −18.072 | 2.567 | −5.391 | 1.00 | 19.78 |
| ATOM | 2067 | O | ASP | A | 267 | −17.593 | 3.161 | −6.353 | 1.00 | 18.61 |
| ATOM | 2068 | N | ALA | A | 268 | −17.544 | 2.621 | −4.174 | 1.00 | 18.35 |
| ATOM | 2069 | CA | ALA | A | 268 | −16.315 | 3.395 | −3.944 | 1.00 | 19.35 |
| ATOM | 2070 | CB | ALA | A | 268 | −16.207 | 3.868 | −2.472 | 1.00 | 19.46 |
| ATOM | 2071 | C | ALA | A | 268 | −15.017 | 2.701 | −4.415 | 1.00 | 19.46 |
| ATOM | 2072 | O | ALA | A | 268 | −14.009 | 3.371 | −4.665 | 1.00 | 19.42 |
| ATOM | 2073 | N | GLY | A | 269 | −15.029 | 1.370 | −4.534 | 1.00 | 19.01 |
| ATOM | 2074 | CA | GLY | A | 269 | −13.826 | 0.644 | −4.936 | 1.00 | 19.17 |
| ATOM | 2075 | C | GLY | A | 269 | −13.370 | 1.032 | −6.343 | 1.00 | 18.75 |
| ATOM | 2076 | O | GLY | A | 269 | −12.175 | 1.134 | −6.624 | 1.00 | 19.54 |
| ATOM | 2077 | N | THR | A | 270 | −14.330 | 1.257 | −7.230 | 1.00 | 17.92 |
| ATOM | 2078 | CA | THR | A | 270 | −14.016 | 1.662 | −8.594 | 1.00 | 18.35 |
| ATOM | 2079 | CB | THR | A | 270 | −14.852 | 0.882 | −9.616 | 1.00 | 18.43 |
| ATOM | 2080 | OG1 | THR | A | 270 | −16.246 | 1.085 | −9.350 | 1.00 | 18.51 |
| ATOM | 2081 | CG2 | THR | A | 270 | −14.529 | −0.626 | −9.555 | 1.00 | 19.75 |
| ATOM | 2082 | C | THR | A | 270 | −14.261 | 3.172 | −8.771 | 1.00 | 18.25 |
| ATOM | 2083 | O | THR | A | 270 | −14.326 | 3.674 | −9.904 | 1.00 | 17.88 |
| ATOM | 2084 | N | PHE | A | 271 | −14.434 | 3.880 | −7.650 | 1.00 | 17.17 |
| ATOM | 2085 | CA | PHE | A | 271 | −14.531 | 5.359 | −7.656 | 1.00 | 17.38 |
| ATOM | 2086 | CB | PHE | A | 271 | −13.183 | 5.965 | −8.121 | 1.00 | 17.67 |
| ATOM | 2087 | CG | PHE | A | 271 | −12.946 | 7.376 | −7.673 | 1.00 | 21.97 |
| ATOM | 2088 | CD1 | PHE | A | 271 | −12.656 | 7.653 | −6.337 | 1.00 | 24.90 |
| ATOM | 2089 | CE1 | PHE | A | 271 | −12.447 | 8.981 | −5.923 | 1.00 | 24.46 |
| ATOM | 2090 | CZ | PHE | A | 271 | −12.474 | 10.043 | −6.863 | 1.00 | 23.20 |
| ATOM | 2091 | CE2 | PHE | A | 271 | −12.733 | 9.783 | −8.196 | 1.00 | 21.92 |
| ATOM | 2092 | CD2 | PHE | A | 271 | −12.956 | 8.436 | −8.599 | 1.00 | 24.30 |
| ATOM | 2093 | C | PHE | A | 271 | −15.677 | 5.856 | −8.551 | 1.00 | 16.63 |
| ATOM | 2094 | O | PHE | A | 271 | −15.479 | 6.764 | −9.358 | 1.00 | 15.93 |
| ATOM | 2095 | N | GLN | A | 272 | −16.861 | 5.249 | −8.439 | 1.00 | 15.21 |
| ATOM | 2096 | CA | GLN | A | 272 | −18.011 | 5.673 | −9.251 | 1.00 | 14.97 |
| ATOM | 2097 | CB | GLN | A | 272 | −19.227 | 4.755 | −9.013 | 1.00 | 14.93 |
| ATOM | 2098 | CG | GLN | A | 272 | −19.021 | 3.355 | −9.615 | 1.00 | 16.30 |
| ATOM | 2099 | CD | GLN | A | 272 | −18.755 | 3.413 | −11.102 | 1.00 | 15.81 |
| ATOM | 2100 | OE1 | GLN | A | 272 | −19.575 | 3.909 | −11.883 | 1.00 | 16.97 |

TABLE 20-continued

| | | | | | | | | | |
|---|---|---|---|---|---|---|---|---|---|
| ATOM | 2101 | NE2 | GLN | A | 272 | −17.617 | 2.861 | −11.512 | 1.00 | 18.50 |
| ATOM | 2102 | C | GLN | A | 272 | −18.402 | 7.118 | −8.929 | 1.00 | 14.73 |
| ATOM | 2103 | O | GLN | A | 272 | −18.194 | 7.555 | −7.800 | 1.00 | 15.60 |
| ATOM | 2104 | N | PRO | A | 273 | −18.955 | 7.859 | −9.914 | 1.00 | 14.45 |
| ATOM | 2105 | CA | PRO | A | 273 | −19.342 | 9.255 | −9.682 | 1.00 | 14.57 |
| ATOM | 2106 | CB | PRO | A | 273 | −20.157 | 9.597 | −10.927 | 1.00 | 14.64 |
| ATOM | 2107 | CG | PRO | A | 273 | −19.443 | 8.767 | −12.031 | 1.00 | 14.70 |
| ATOM | 2108 | CD | PRO | A | 273 | −19.156 | 7.458 | −11.326 | 1.00 | 14.10 |
| ATOM | 2109 | C | PRO | A | 273 | −20.162 | 9.542 | −8.407 | 1.00 | 15.22 |
| ATOM | 2110 | O | PRO | A | 273 | −19.910 | 10.562 | −7.752 | 1.00 | 15.03 |
| ATOM | 2111 | N | CYS | A | 274 | −21.130 | 8.682 | −8.075 | 1.00 | 15.76 |
| ATOM | 2112 | CA | CYS | A | 274 | −21.926 | 8.913 | −6.853 | 1.00 | 16.22 |
| ATOM | 2113 | CB | CYS | A | 274 | −23.389 | 8.489 | −7.039 | 1.00 | 16.57 |
| ATOM | 2114 | SG | CYS | A | 274 | −23.611 | 6.769 | −7.423 | 1.00 | 17.39 |
| ATOM | 2115 | C | CYS | A | 274 | −21.331 | 8.281 | −5.605 | 1.00 | 16.64 |
| ATOM | 2116 | O | CYS | A | 274 | −21.958 | 8.329 | −4.529 | 1.00 | 16.55 |
| ATOM | 2117 | N | SER | A | 275 | −20.137 | 7.681 | −5.715 | 1.00 | 15.61 |
| ATOM | 2118 | CA | SER | A | 275 | −19.476 | 7.117 | −4.528 | 1.00 | 15.81 |
| ATOM | 2119 | CB | SER | A | 275 | −18.244 | 6.253 | −4.877 | 1.00 | 15.06 |
| ATOM | 2120 | OG | SER | A | 275 | −17.144 | 7.041 | −5.315 | 1.00 | 14.92 |
| ATOM | 2121 | C | SER | A | 275 | −19.097 | 8.232 | −3.545 | 1.00 | 16.06 |
| ATOM | 2122 | O | SER | A | 275 | −18.818 | 9.366 | −3.949 | 1.00 | 14.39 |
| ATOM | 2123 | N | ASP | A | 276 | −19.103 | 7.919 | −2.248 | 1.00 | 16.42 |
| ATOM | 2124 | CA | ASP | A | 276 | −18.731 | 8.935 | −1.271 | 1.00 | 16.52 |
| ATOM | 2125 | CB | ASP | A | 276 | −19.020 | 8.511 | 0.189 | 1.00 | 16.27 |
| ATOM | 2126 | CG | ASP | A | 276 | −18.244 | 7.281 | 0.656 | 1.00 | 19.14 |
| ATOM | 2127 | OD1 | ASP | A | 276 | −18.371 | 7.001 | 1.873 | 1.00 | 19.62 |
| ATOM | 2128 | OD2 | ASP | A | 276 | −17.544 | 6.593 | −0.120 | 1.00 | 17.10 |
| ATOM | 2129 | C | ASP | A | 276 | −17.312 | 9.469 | −1.492 | 1.00 | 16.17 |
| ATOM | 2130 | O | ASP | A | 276 | −17.084 | 10.683 | −1.415 | 1.00 | 15.20 |
| ATOM | 2131 | N | LYS | A | 277 | −16.381 | 8.577 | −1.823 | 1.00 | 15.43 |
| ATOM | 2132 | CA | LYS | A | 277 | −14.994 | 8.982 | −2.115 | 1.00 | 15.34 |
| ATOM | 2133 | CB | LYS | A | 277 | −14.089 | 7.763 | −2.326 | 1.00 | 15.23 |
| ATOM | 2134 | CG | LYS | A | 277 | −13.924 | 6.905 | −1.059 | 1.00 | 17.01 |
| ATOM | 2135 | CD | LYS | A | 277 | −12.752 | 5.929 | −1.204 | 1.00 | 21.20 |
| ATOM | 2136 | CE | LYS | A | 277 | −12.662 | 5.017 | 0.015 | 1.00 | 22.94 |
| ATOM | 2137 | NZ | LYS | A | 277 | −11.533 | 4.067 | −0.165 | 1.00 | 29.19 |
| ATOM | 2138 | C | LYS | A | 277 | −14.900 | 9.915 | −3.324 | 1.00 | 14.30 |
| ATOM | 2139 | O | LYS | A | 277 | −14.152 | 10.887 | −3.288 | 1.00 | 14.70 |
| ATOM | 2140 | N | ALA | A | 278 | −15.644 | 9.620 | −4.393 | 1.00 | 14.45 |
| ATOM | 2141 | CA | ALA | A | 278 | −15.588 | 10.464 | −5.605 | 1.00 | 13.61 |
| ATOM | 2142 | CB | ALA | A | 278 | −16.250 | 9.775 | −6.783 | 1.00 | 13.30 |
| ATOM | 2143 | C | ALA | A | 278 | −16.210 | 11.827 | −5.357 | 1.00 | 13.50 |
| ATOM | 2144 | O | ALA | A | 278 | −15.730 | 12.840 | −5.864 | 1.00 | 13.02 |
| ATOM | 2145 | N | LEU | A | 279 | −17.283 | 11.855 | −4.565 | 1.00 | 13.22 |
| ATOM | 2146 | CA | LEU | A | 279 | −17.936 | 13.132 | −4.239 | 1.00 | 12.92 |
| ATOM | 2147 | CB | LEU | A | 279 | −19.323 | 12.893 | −3.625 | 1.00 | 13.21 |
| ATOM | 2148 | CG | LEU | A | 279 | −20.384 | 12.358 | −4.601 | 1.00 | 13.94 |
| ATOM | 2149 | CD1 | LEU | A | 279 | −21.707 | 11.969 | −3.887 | 1.00 | 17.68 |
| ATOM | 2150 | CD2 | LEU | A | 279 | −20.653 | 13.319 | −5.781 | 1.00 | 17.52 |
| ATOM | 2151 | C | LEU | A | 279 | −17.065 | 13.995 | −3.348 | 1.00 | 12.84 |
| ATOM | 2152 | O | LEU | A | 279 | −16.941 | 15.203 | −3.577 | 1.00 | 13.54 |
| ATOM | 2153 | N | SER | A | 280 | −16.463 | 13.390 | −2.315 | 1.00 | 12.45 |
| ATOM | 2154 | CA | SER | A | 280 | −15.502 | 14.106 | −1.459 | 1.00 | 13.53 |
| ATOM | 2155 | CB | SER | A | 280 | −14.951 | 13.168 | −0.364 | 1.00 | 13.65 |
| ATOM | 2156 | OG | SER | A | 280 | −14.008 | 13.863 | 0.468 | 1.00 | 15.07 |
| ATOM | 2157 | C | SER | A | 280 | −14.332 | 14.672 | −2.285 | 1.00 | 14.09 |
| ATOM | 2158 | O | SER | A | 280 | −13.925 | 15.856 | −2.130 | 1.00 | 13.43 |
| ATOM | 2159 | N | ASN | A | 281 | −13.795 | 13.830 | −3.166 | 1.00 | 13.27 |
| ATOM | 2160 | CA | ASN | A | 281 | −12.690 | 14.257 | −4.027 | 1.00 | 13.19 |
| ATOM | 2161 | CB | ASN | A | 281 | −12.239 | 13.078 | −4.888 | 1.00 | 12.05 |
| ATOM | 2162 | CG | ASN | A | 281 | −11.116 | 13.455 | −5.849 | 1.00 | 13.13 |
| ATOM | 2163 | OD1 | ASN | A | 281 | −9.989 | 13.637 | −5.446 | 1.00 | 13.26 |
| ATOM | 2164 | ND2 | ASN | A | 281 | −11.442 | 13.573 | −7.124 | 1.00 | 11.63 |
| ATOM | 2165 | C | ASN | A | 281 | −13.096 | 15.432 | −4.933 | 1.00 | 12.33 |
| ATOM | 2166 | O | ASN | A | 281 | −12.330 | 16.380 | −5.109 | 1.00 | 13.49 |
| ATOM | 2167 | N | LEU | A | 282 | −14.287 | 15.355 | −5.506 | 1.00 | 12.05 |
| ATOM | 2168 | CA | LEU | A | 282 | −14.760 | 16.422 | −6.376 | 1.00 | 13.21 |
| ATOM | 2169 | CB | LEU | A | 282 | −16.147 | 16.109 | −6.949 | 1.00 | 12.17 |
| ATOM | 2170 | CG | LEU | A | 282 | −16.791 | 17.216 | −7.820 | 1.00 | 14.57 |
| ATOM | 2171 | CD1 | LEU | A | 282 | −16.011 | 17.378 | −9.126 | 1.00 | 16.58 |
| ATOM | 2172 | CD2 | LEU | A | 282 | −18.241 | 16.863 | −8.170 | 1.00 | 15.68 |
| ATOM | 2173 | C | LEU | A | 282 | −14.739 | 17.754 | −5.638 | 1.00 | 12.69 |
| ATOM | 2174 | O | LEU | A | 282 | −14.201 | 18.735 | −6.153 | 1.00 | 13.45 |
| ATOM | 2175 | N | LYS | A | 283 | −15.283 | 17.791 | −4.415 | 1.00 | 12.75 |
| ATOM | 2176 | CA | LYS | A | 283 | −15.306 | 19.026 | −3.656 | 1.00 | 12.89 |
| ATOM | 2177 | CB | LYS | A | 283 | −16.079 | 18.860 | −2.334 | 1.00 | 12.90 |
| ATOM | 2178 | CG | LYS | A | 283 | −15.912 | 20.089 | −1.432 | 1.00 | 13.94 |
| ATOM | 2179 | CD | LYS | A | 283 | −16.909 | 20.076 | −0.252 | 1.00 | 14.67 |
| ATOM | 2180 | CE | LYS | A | 283 | −16.530 | 21.136 | 0.797 | 1.00 | 13.67 |

TABLE 20-continued

| | | | | | | | | | |
|---|---|---|---|---|---|---|---|---|---|
| ATOM | 2181 | NZ | LYS | A | 283 | −16.315 | 22.489 | 0.212 | 1.00 | 19.03 |
| ATOM | 2182 | C | LYS | A | 283 | −13.889 | 19.537 | −3.385 | 1.00 | 12.43 |
| ATOM | 2183 | O | LYS | A | 283 | −13.612 | 20.710 | −3.556 | 1.00 | 12.14 |
| ATOM | 2184 | N | VAL | A | 284 | −12.988 | 18.652 | −2.966 | 1.00 | 12.02 |
| ATOM | 2185 | CA | VAL | A | 284 | −11.624 | 19.055 | −2.633 | 1.00 | 12.77 |
| ATOM | 2186 | CB | VAL | A | 284 | −10.845 | 17.875 | −2.014 | 1.00 | 13.17 |
| ATOM | 2187 | CG1 | VAL | A | 284 | −9.320 | 18.169 | −1.936 | 1.00 | 13.21 |
| ATOM | 2188 | CG2 | VAL | A | 284 | −11.391 | 17.557 | −0.630 | 1.00 | 15.81 |
| ATOM | 2189 | C | VAL | A | 284 | −10.927 | 19.599 | −3.881 | 1.00 | 12.74 |
| ATOM | 2190 | O | VAL | A | 284 | −10.228 | 20.636 | −3.827 | 1.00 | 12.21 |
| ATOM | 2191 | N | VAL | A | 285 | −11.153 | 18.927 | −5.012 | 1.00 | 11.54 |
| ATOM | 2192 | CA | VAL | A | 285 | −10.560 | 19.389 | −6.287 | 1.00 | 12.35 |
| ATOM | 2193 | CB | VAL | A | 285 | −10.694 | 18.330 | −7.425 | 1.00 | 12.36 |
| ATOM | 2194 | CG1 | VAL | A | 285 | −10.316 | 18.944 | −8.813 | 1.00 | 12.25 |
| ATOM | 2195 | CG2 | VAL | A | 285 | −9.795 | 17.104 | −7.140 | 1.00 | 13.25 |
| ATOM | 2196 | C | VAL | A | 285 | −11.130 | 20.770 | −6.712 | 1.00 | 12.08 |
| ATOM | 2197 | O | VAL | A | 285 | −10.367 | 21.696 | −6.989 | 1.00 | 12.60 |
| ATOM | 2198 | N | VAL | A | 286 | −12.452 | 20.913 | −6.728 | 1.00 | 11.87 |
| ATOM | 2199 | CA | VAL | A | 286 | −13.089 | 22.196 | −7.074 | 1.00 | 12.87 |
| ATOM | 2200 | CB | VAL | A | 286 | −14.631 | 22.080 | −7.038 | 1.00 | 13.01 |
| ATOM | 2201 | CG1 | VAL | A | 286 | −15.300 | 23.468 | −7.140 | 1.00 | 14.31 |
| ATOM | 2202 | CG2 | VAL | A | 286 | −15.103 | 21.157 | −8.200 | 1.00 | 14.42 |
| ATOM | 2203 | C | VAL | A | 286 | −12.586 | 23.324 | −6.164 | 1.00 | 12.84 |
| ATOM | 2204 | O | VAL | A | 286 | −12.206 | 24.402 | −6.635 | 1.00 | 13.75 |
| ATOM | 2205 | N | ASP | A | 287 | −12.552 | 23.064 | −4.853 | 1.00 | 12.85 |
| ATOM | 2206 | CA | ASP | A | 287 | −12.116 | 24.059 | −3.870 | 1.00 | 13.90 |
| ATOM | 2207 | CB | ASP | A | 287 | −12.199 | 23.506 | −2.440 | 1.00 | 13.12 |
| ATOM | 2208 | CG | ASP | A | 287 | −13.637 | 23.441 | −1.924 | 1.00 | 16.00 |
| ATOM | 2209 | OD1 | ASP | A | 287 | −14.541 | 24.002 | −2.583 | 1.00 | 16.20 |
| ATOM | 2210 | OD2 | ASP | A | 287 | −13.857 | 22.835 | −0.858 | 1.00 | 16.76 |
| ATOM | 2211 | C | ASP | A | 287 | −10.727 | 24.564 | −4.136 | 1.00 | 14.28 |
| ATOM | 2212 | O | ASP | A | 287 | −10.425 | 25.722 | −3.841 | 1.00 | 15.53 |
| ATOM | 2213 | N | SER | A | 288 | −9.862 | 23.709 | −4.677 | 1.00 | 14.50 |
| ATOM | 2214 | CA | SER | A | 288 | −8.478 | 24.093 | −4.949 | 1.00 | 14.58 |
| ATOM | 2215 | CB | SER | A | 288 | −7.625 | 22.843 | −5.229 | 1.00 | 14.15 |
| ATOM | 2216 | OG | SER | A | 288 | −7.758 | 22.417 | −6.565 | 1.00 | 13.73 |
| ATOM | 2217 | C | SER | A | 288 | −8.326 | 25.186 | −6.038 | 1.00 | 14.61 |
| ATOM | 2218 | O | SER | A | 288 | −7.274 | 25.847 | −6.143 | 1.00 | 14.59 |
| ATOM | 2219 | N | PHE | A | 289 | −9.392 | 25.416 | −6.809 | 1.00 | 13.99 |
| ATOM | 2220 | CA | PHE | A | 289 | −9.419 | 26.447 | −7.831 | 1.00 | 14.09 |
| ATOM | 2221 | CB | PHE | A | 289 | −9.994 | 25.882 | −9.135 | 1.00 | 13.52 |
| ATOM | 2222 | CG | PHE | A | 289 | −9.169 | 24.807 | −9.704 | 1.00 | 11.38 |
| ATOM | 2223 | CD1 | PHE | A | 289 | −7.976 | 25.114 | −10.367 | 1.00 | 12.17 |
| ATOM | 2224 | CE1 | PHE | A | 289 | −7.184 | 24.095 | −10.905 | 1.00 | 13.93 |
| ATOM | 2225 | CZ | PHE | A | 289 | −7.572 | 22.783 | −10.771 | 1.00 | 13.96 |
| ATOM | 2226 | CE2 | PHE | A | 289 | −8.756 | 22.452 | −10.097 | 1.00 | 11.77 |
| ATOM | 2227 | CD2 | PHE | A | 289 | −9.555 | 23.472 | −9.571 | 1.00 | 11.08 |
| ATOM | 2228 | C | PHE | A | 289 | −10.219 | 27.698 | −7.491 | 1.00 | 14.73 |
| ATOM | 2229 | O | PHE | A | 289 | −10.092 | 28.713 | −8.189 | 1.00 | 14.71 |
| ATOM | 2230 | N | ARG | A | 290 | −11.054 | 27.621 | −6.464 | 1.00 | 15.09 |
| ATOM | 2231 | CA | ARG | A | 290 | −11.953 | 28.740 | −6.140 | 1.00 | 16.64 |
| ATOM | 2232 | CB | ARG | A | 290 | −12.842 | 28.401 | −4.936 | 1.00 | 15.99 |
| ATOM | 2233 | CG | ARG | A | 290 | −13.913 | 27.375 | −5.230 | 1.00 | 15.65 |
| ATOM | 2234 | CD | ARG | A | 290 | −14.821 | 27.163 | −4.012 | 1.00 | 16.79 |
| ATOM | 2235 | NE | ARG | A | 290 | −15.843 | 26.172 | −4.330 | 1.00 | 15.04 |
| ATOM | 2236 | CZ | ARG | A | 290 | −16.986 | 26.470 | −4.933 | 1.00 | 17.22 |
| ATOM | 2237 | NH1 | ARG | A | 290 | −17.248 | 27.734 | −5.243 | 1.00 | 15.41 |
| ATOM | 2238 | NH2 | ARG | A | 290 | −17.855 | 25.511 | −5.239 | 1.00 | 15.94 |
| ATOM | 2239 | C | ARG | A | 290 | −11.240 | 30.046 | −5.864 | 1.00 | 18.04 |
| ATOM | 2240 | O | ARG | A | 290 | −11.690 | 31.125 | −6.279 | 1.00 | 19.61 |
| ATOM | 2241 | N | SER | A | 291 | −10.150 | 29.984 | −5.128 | 1.00 | 19.44 |
| ATOM | 2242 | CA | SER | A | 291 | −9.571 | 31.246 | −4.667 | 1.00 | 21.57 |
| ATOM | 2243 | CB | SER | A | 291 | −9.146 | 31.101 | −3.212 | 1.00 | 22.18 |
| ATOM | 2244 | OG | SER | A | 291 | −7.998 | 30.284 | −3.144 | 1.00 | 28.35 |
| ATOM | 2245 | C | SER | A | 291 | −8.423 | 31.762 | −5.534 | 1.00 | 20.65 |
| ATOM | 2246 | O | SER | A | 291 | −7.865 | 32.851 | −5.272 | 1.00 | 22.43 |
| ATOM | 2247 | N | ILE | A | 292 | −8.066 | 31.019 | −6.576 | 1.00 | 19.16 |
| ATOM | 2248 | CA | ILE | A | 292 | −6.855 | 31.367 | −7.330 | 1.00 | 17.65 |
| ATOM | 2249 | CB | ILE | A | 292 | −5.805 | 30.185 | −7.408 | 1.00 | 18.07 |
| ATOM | 2250 | CG1 | ILE | A | 292 | −6.379 | 28.972 | −8.194 | 1.00 | 17.67 |
| ATOM | 2251 | CD1 | ILE | A | 292 | −5.315 | 27.924 | −8.649 | 1.00 | 17.27 |
| ATOM | 2252 | CG2 | ILE | A | 292 | −5.341 | 29.795 | −5.994 | 1.00 | 18.29 |
| ATOM | 2253 | C | ILE | A | 292 | −7.065 | 31.973 | −8.708 | 1.00 | 17.20 |
| ATOM | 2254 | O | ILE | A | 292 | −6.136 | 32.563 | −9.251 | 1.00 | 16.35 |
| ATOM | 2255 | N | TYR | A | 293 | −8.252 | 31.797 | −9.290 | 1.00 | 15.85 |
| ATOM | 2256 | CA | TYR | A | 293 | −8.509 | 32.304 | −10.648 | 1.00 | 15.83 |
| ATOM | 2257 | CB | TYR | A | 293 | −9.301 | 31.270 | −11.474 | 1.00 | 15.43 |
| ATOM | 2258 | CG | TYR | A | 293 | −8.571 | 30.014 | −11.886 | 1.00 | 15.10 |
| ATOM | 2259 | CD1 | TYR | A | 293 | −7.183 | 29.960 | −11.965 | 1.00 | 14.38 |
| ATOM | 2260 | CE1 | TYR | A | 293 | −6.540 | 28.795 | −12.395 | 1.00 | 14.38 |

TABLE 20-continued

| ATOM | 2261 | CZ | TYR | A | 293 | −7.306 | 27.685 | −12.743 | 1.00 | 14.90 |
| --- | --- | --- | --- | --- | --- | --- | --- | --- | --- | --- |
| ATOM | 2262 | OH | TYR | A | 293 | −6.700 | 26.522 | −13.158 | 1.00 | 15.55 |
| ATOM | 2263 | CE2 | TYR | A | 293 | −8.670 | 27.722 | −12.671 | 1.00 | 15.47 |
| ATOM | 2264 | CD2 | TYR | A | 293 | −9.298 | 28.875 | −12.255 | 1.00 | 13.91 |
| ATOM | 2265 | C | TYR | A | 293 | −9.351 | 33.581 | −10.591 | 1.00 | 15.69 |
| ATOM | 2266 | O | TYR | A | 293 | −10.404 | 33.594 | −9.942 | 1.00 | 15.47 |
| ATOM | 2267 | N | GLY | A | 294 | −8.892 | 34.629 | −11.276 | 1.00 | 14.83 |
| ATOM | 2268 | CA | GLY | A | 294 | −9.641 | 35.899 | −11.353 | 1.00 | 15.57 |
| ATOM | 2269 | C | GLY | A | 294 | −11.078 | 35.702 | −11.858 | 1.00 | 15.93 |
| ATOM | 2270 | O | GLY | A | 294 | −12.010 | 36.359 | −11.376 | 1.00 | 15.66 |
| ATOM | 2271 | N | VAL | A | 295 | −11.288 | 34.773 | −12.799 | 1.00 | 15.60 |
| ATOM | 2272 | CA | VAL | A | 295 | −12.651 | 34.520 | −13.270 | 1.00 | 16.24 |
| ATOM | 2273 | CB | VAL | A | 295 | −12.753 | 33.561 | −14.501 | 1.00 | 16.31 |
| ATOM | 2274 | CG1 | VAL | A | 295 | −12.170 | 34.195 | −15.740 | 1.00 | 16.26 |
| ATOM | 2275 | CG2 | VAL | A | 295 | −12.128 | 32.184 | −14.199 | 1.00 | 16.19 |
| ATOM | 2276 | C | VAL | A | 295 | −13.596 | 34.013 | −12.172 | 1.00 | 16.97 |
| ATOM | 2277 | O | VAL | A | 295 | −14.813 | 34.108 | −12.320 | 1.00 | 18.03 |
| ATOM | 2278 | N | ASN | A | 296 | −13.047 | 33.463 | −11.092 | 1.00 | 16.93 |
| ATOM | 2279 | CA | ASN | A | 296 | −13.878 | 32.920 | −10.020 | 1.00 | 17.69 |
| ATOM | 2280 | CB | ASN | A | 296 | −13.250 | 31.633 | −9.472 | 1.00 | 17.57 |
| ATOM | 2281 | CG | ASN | A | 296 | −13.296 | 30.493 | −10.482 | 1.00 | 16.44 |
| ATOM | 2282 | OD1 | ASN | A | 296 | −14.158 | 30.481 | −11.356 | 1.00 | 17.29 |
| ATOM | 2283 | ND2 | ASN | A | 296 | −12.401 | 29.513 | −10.336 | 1.00 | 15.99 |
| ATOM | 2284 | C | ASN | A | 296 | −14.187 | 33.915 | −8.896 | 1.00 | 19.30 |
| ATOM | 2285 | O | ASN | A | 296 | −14.945 | 33.601 | −7.979 | 1.00 | 19.07 |
| ATOM | 2286 | N | LYS | A | 297 | −13.617 | 35.116 | −9.007 | 1.00 | 20.37 |
| ATOM | 2287 | CA | LYS | A | 297 | −13.811 | 36.203 | −8.038 | 1.00 | 22.43 |
| ATOM | 2288 | CB | LYS | A | 297 | −13.209 | 37.502 | −8.584 | 1.00 | 22.90 |
| ATOM | 2289 | CG | LYS | A | 297 | −11.741 | 37.680 | −8.316 | 1.00 | 30.03 |
| ATOM | 2290 | CD | LYS | A | 297 | −11.401 | 39.189 | −8.309 | 1.00 | 35.34 |
| ATOM | 2291 | CE | LYS | A | 297 | −12.247 | 39.913 | −7.255 | 1.00 | 39.86 |
| ATOM | 2292 | NZ | LYS | A | 297 | −11.995 | 41.386 | −7.178 | 1.00 | 42.72 |
| ATOM | 2293 | C | LYS | A | 297 | −15.275 | 36.453 | −7.782 | 1.00 | 21.89 |
| ATOM | 2294 | O | LYS | A | 297 | −16.061 | 36.585 | −8.712 | 1.00 | 21.96 |
| ATOM | 2295 | N | GLY | A | 298 | −15.659 | 36.537 | −6.517 | 1.00 | 22.72 |
| ATOM | 2296 | CA | GLY | A | 298 | −17.050 | 36.869 | −6.219 | 1.00 | 22.99 |
| ATOM | 2297 | C | GLY | A | 298 | −18.043 | 35.720 | −6.278 | 1.00 | 23.54 |
| ATOM | 2298 | O | GLY | A | 298 | −19.180 | 35.885 | −5.855 | 1.00 | 25.04 |
| ATOM | 2299 | N | ILE | A | 299 | −17.647 | 34.546 | −6.784 | 1.00 | 22.16 |
| ATOM | 2300 | CA | ILE | A | 299 | −18.574 | 33.393 | −6.763 | 1.00 | 21.47 |
| ATOM | 2301 | CB | ILE | A | 299 | −18.251 | 32.350 | −7.884 | 1.00 | 21.22 |
| ATOM | 2302 | CG1 | ILE | A | 299 | −18.356 | 32.985 | −9.274 | 1.00 | 19.64 |
| ATOM | 2303 | CD1 | ILE | A | 299 | −17.740 | 32.095 | −10.415 | 1.00 | 19.76 |
| ATOM | 2304 | CG2 | ILE | A | 299 | −19.163 | 31.091 | −7.762 | 1.00 | 20.54 |
| ATOM | 2305 | C | ILE | A | 299 | −18.562 | 32.740 | −5.375 | 1.00 | 22.34 |
| ATOM | 2306 | O | ILE | A | 299 | −17.486 | 32.395 | −4.861 | 1.00 | 22.29 |
| ATOM | 2307 | N | PRO | A | 300 | −19.743 | 32.580 | −4.751 | 1.00 | 23.04 |
| ATOM | 2308 | CA | PRO | A | 300 | −19.791 | 32.018 | −3.392 | 1.00 | 23.60 |
| ATOM | 2309 | CB | PRO | A | 300 | −21.217 | 32.364 | −2.922 | 1.00 | 24.19 |
| ATOM | 2310 | CG | PRO | A | 300 | −22.015 | 32.437 | −4.178 | 1.00 | 23.80 |
| ATOM | 2311 | CD | PRO | A | 300 | −21.085 | 32.934 | −5.253 | 1.00 | 23.06 |
| ATOM | 2312 | C | PRO | A | 300 | −19.584 | 30.500 | −3.322 | 1.00 | 23.50 |
| ATOM | 2313 | O | PRO | A | 300 | −19.664 | 29.810 | −4.347 | 1.00 | 22.46 |
| ATOM | 2314 | N | ALA | A | 301 | −19.325 | 29.985 | −2.116 | 1.00 | 22.68 |
| ATOM | 2315 | CA | ALA | A | 301 | −19.380 | 28.549 | −1.905 | 1.00 | 22.89 |
| ATOM | 2316 | CB | ALA | A | 301 | −18.988 | 28.185 | −0.465 | 1.00 | 23.54 |
| ATOM | 2317 | C | ALA | A | 301 | −20.788 | 28.074 | −2.236 | 1.00 | 21.91 |
| ATOM | 2318 | O | ALA | A | 301 | −21.759 | 28.834 | −2.108 | 1.00 | 23.09 |
| ATOM | 2319 | N | GLY | A | 302 | −20.898 | 26.838 | −2.698 | 1.00 | 20.96 |
| ATOM | 2320 | CA | GLY | A | 302 | −22.173 | 26.272 | −3.115 | 1.00 | 19.69 |
| ATOM | 2321 | C | GLY | A | 302 | −22.565 | 26.637 | −4.537 | 1.00 | 19.78 |
| ATOM | 2322 | O | GLY | A | 302 | −23.661 | 26.283 | −4.991 | 1.00 | 19.32 |
| ATOM | 2323 | N | ALA | A | 303 | −21.686 | 27.355 | −5.235 | 1.00 | 17.97 |
| ATOM | 2324 | CA | ALA | A | 303 | −21.948 | 27.708 | −6.635 | 1.00 | 17.13 |
| ATOM | 2325 | CB | ALA | A | 303 | −22.168 | 29.212 | −6.812 | 1.00 | 16.73 |
| ATOM | 2326 | C | ALA | A | 303 | −20.784 | 27.245 | −7.481 | 1.00 | 16.19 |
| ATOM | 2327 | O | ALA | A | 303 | −19.647 | 27.171 | −7.004 | 1.00 | 16.23 |
| ATOM | 2328 | N | ALA | A | 304 | −21.067 | 26.956 | −8.746 | 1.00 | 15.66 |
| ATOM | 2329 | CA | ALA | A | 304 | −20.069 | 26.378 | −9.640 | 1.00 | 15.10 |
| ATOM | 2330 | CB | ALA | A | 304 | −20.750 | 25.795 | −10.860 | 1.00 | 15.80 |
| ATOM | 2331 | C | ALA | A | 304 | −19.002 | 27.394 | −10.044 | 1.00 | 14.74 |
| ATOM | 2332 | O | ALA | A | 304 | −19.270 | 28.587 | −10.121 | 1.00 | 14.27 |
| ATOM | 2333 | N | VAL | A | 305 | −17.783 | 26.914 | −10.300 | 1.00 | 14.18 |
| ATOM | 2334 | CA | VAL | A | 305 | −16.680 | 27.783 | −10.698 | 1.00 | 13.54 |
| ATOM | 2335 | CB | VAL | A | 305 | −15.656 | 27.971 | −9.543 | 1.00 | 13.42 |
| ATOM | 2336 | CG1 | VAL | A | 305 | −16.224 | 28.881 | −8.418 | 1.00 | 14.25 |
| ATOM | 2337 | CG2 | VAL | A | 305 | −15.218 | 26.597 | −8.966 | 1.00 | 14.99 |
| ATOM | 2338 | C | VAL | A | 305 | −15.952 | 27.141 | −11.873 | 1.00 | 13.34 |
| ATOM | 2339 | O | VAL | A | 305 | −16.121 | 25.944 | −12.126 | 1.00 | 12.46 |
| ATOM | 2340 | N | ALA | A | 306 | −15.130 | 27.921 | −12.562 | 1.00 | 13.38 |

TABLE 20-continued

| | | | | | | | | |
|---|---|---|---|---|---|---|---|---|
| ATOM | 2341 | CA | ALA | A | 306 | −14.233 | 27.376 | −13.573 | 1.00 | 14.37 |
| ATOM | 2342 | CB | ALA | A | 306 | −13.709 | 28.504 | −14.470 | 1.00 | 15.32 |
| ATOM | 2343 | C | ALA | A | 306 | −13.082 | 26.626 | −12.938 | 1.00 | 14.68 |
| ATOM | 2344 | O | ALA | A | 306 | −12.457 | 27.116 | −11.974 | 1.00 | 15.21 |
| ATOM | 2345 | N | ILE | A | 307 | −12.781 | 25.452 | −13.484 | 1.00 | 13.50 |
| ATOM | 2346 | CA | ILE | A | 307 | −11.667 | 24.668 | −12.975 | 1.00 | 13.67 |
| ATOM | 2347 | CB | ILE | A | 307 | −12.134 | 23.438 | −12.163 | 1.00 | 14.45 |
| ATOM | 2348 | CG1 | ILE | A | 307 | −12.756 | 22.386 | −13.072 | 1.00 | 15.37 |
| ATOM | 2349 | CD1 | ILE | A | 307 | −12.921 | 21.033 | −12.368 | 1.00 | 19.15 |
| ATOM | 2350 | CG2 | ILE | A | 307 | −13.119 | 23.848 | −11.005 | 1.00 | 15.52 |
| ATOM | 2351 | C | ILE | A | 307 | −10.646 | 24.290 | −14.059 | 1.00 | 12.52 |
| ATOM | 2352 | O | ILE | A | 307 | −10.974 | 24.232 | −15.264 | 1.00 | 12.22 |
| ATOM | 2353 | N | GLY | A | 308 | −9.405 | 24.095 | −13.604 | 1.00 | 11.71 |
| ATOM | 2354 | CA | GLY | A | 308 | −8.276 | 23.737 | −14.452 | 1.00 | 11.64 |
| ATOM | 2355 | C | GLY | A | 308 | −7.853 | 22.306 | −14.199 | 1.00 | 11.62 |
| ATOM | 2356 | O | GLY | A | 308 | −8.667 | 21.444 | −13.806 | 1.00 | 12.05 |
| ATOM | 2357 | N | ARG | A | 309 | −6.583 | 22.026 | −14.454 | 1.00 | 11.39 |
| ATOM | 2358 | CA | ARG | A | 309 | −6.091 | 20.661 | −14.337 | 1.00 | 11.23 |
| ATOM | 2359 | CB | ARG | A | 309 | −4.896 | 20.467 | −15.275 | 1.00 | 11.37 |
| ATOM | 2360 | CG | ARG | A | 309 | −5.220 | 20.697 | −16.791 | 1.00 | 11.29 |
| ATOM | 2361 | CD | ARG | A | 309 | −4.066 | 20.130 | −17.625 | 1.00 | 12.62 |
| ATOM | 2362 | NE | ARG | A | 309 | −2.845 | 20.919 | −17.425 | 1.00 | 12.15 |
| ATOM | 2363 | CZ | ARG | A | 309 | −1.701 | 20.665 | −18.047 | 1.00 | 15.00 |
| ATOM | 2364 | NH1 | ARG | A | 309 | −1.630 | 19.633 | −18.910 | 1.00 | 12.05 |
| ATOM | 2365 | NH2 | ARG | A | 309 | −0.624 | 21.395 | −17.778 | 1.00 | 13.85 |
| ATOM | 2366 | C | ARG | A | 309 | −5.654 | 20.425 | −12.888 | 1.00 | 11.83 |
| ATOM | 2367 | O | ARG | A | 309 | −6.093 | 19.481 | −12.221 | 1.00 | 11.38 |
| ATOM | 2368 | N | TYR | A | 310 | −4.806 | 21.322 | −12.399 | 1.00 | 11.88 |
| ATOM | 2369 | CA | TYR | A | 310 | −4.293 | 21.215 | −11.022 | 1.00 | 11.17 |
| ATOM | 2370 | CB | TYR | A | 310 | −3.225 | 20.082 | −10.878 | 1.00 | 12.49 |
| ATOM | 2371 | CG | TYR | A | 310 | −2.065 | 20.201 | −11.844 | 1.00 | 13.10 |
| ATOM | 2372 | CD1 | TYR | A | 310 | −2.128 | 19.622 | −13.138 | 1.00 | 12.57 |
| ATOM | 2373 | CE1 | TYR | A | 310 | −1.069 | 19.772 | −14.039 | 1.00 | 15.63 |
| ATOM | 2374 | CZ | TYR | A | 310 | 0.065 | 20.475 | −13.649 | 1.00 | 14.31 |
| ATOM | 2375 | OH | TYR | A | 310 | 1.119 | 20.611 | −14.529 | 1.00 | 14.42 |
| ATOM | 2376 | CE2 | TYR | A | 310 | 0.159 | 21.030 | −12.379 | 1.00 | 12.68 |
| ATOM | 2377 | CD2 | TYR | A | 310 | −0.909 | 20.906 | −11.485 | 1.00 | 14.04 |
| ATOM | 2378 | C | TYR | A | 310 | −3.779 | 22.596 | −10.644 | 1.00 | 12.74 |
| ATOM | 2379 | O | TYR | A | 310 | −3.333 | 23.356 | −11.505 | 1.00 | 12.44 |
| ATOM | 2380 | N | ALA | A | 311 | −3.872 | 22.945 | −9.362 | 1.00 | 11.99 |
| ATOM | 2381 | CA | ALA | A | 311 | −3.618 | 24.337 | −8.975 | 1.00 | 13.33 |
| ATOM | 2382 | CB | ALA | A | 311 | −4.084 | 24.589 | −7.508 | 1.00 | 12.88 |
| ATOM | 2383 | C | ALA | A | 311 | −2.157 | 24.768 | −9.197 | 1.00 | 13.50 |
| ATOM | 2384 | O | ALA | A | 311 | −1.906 | 25.951 | −9.468 | 1.00 | 14.52 |
| ATOM | 2385 | N | GLU | A | 312 | −1.216 | 23.823 | −9.140 | 1.00 | 13.52 |
| ATOM | 2386 | CA | GLU | A | 312 | 0.219 | 24.134 | −9.332 | 1.00 | 14.23 |
| ATOM | 2387 | CB | GLU | A | 312 | 1.111 | 23.020 | −8.790 | 1.00 | 15.44 |
| ATOM | 2388 | CG | GLU | A | 312 | 0.933 | 22.802 | −7.303 | 1.00 | 16.54 |
| ATOM | 2389 | CD | GLU | A | 312 | −0.130 | 21.762 | −6.950 | 1.00 | 18.91 |
| ATOM | 2390 | OE1 | GLU | A | 312 | −0.941 | 21.338 | −7.808 | 1.00 | 16.89 |
| ATOM | 2391 | OE2 | GLU | A | 312 | −0.150 | 21.345 | −5.778 | 1.00 | 18.72 |
| ATOM | 2392 | C | GLU | A | 312 | 0.591 | 24.380 | −10.796 | 1.00 | 14.80 |
| ATOM | 2393 | O | GLU | A | 312 | 1.741 | 24.736 | −11.100 | 1.00 | 14.98 |
| ATOM | 2394 | N | ASP | A | 313 | −0.374 | 24.197 | −11.697 | 1.00 | 13.37 |
| ATOM | 2395 | CA | ASP | A | 313 | −0.112 | 24.258 | −13.155 | 1.00 | 13.71 |
| ATOM | 2396 | CB | ASP | A | 313 | −1.457 | 24.079 | −13.888 | 1.00 | 12.88 |
| ATOM | 2397 | CG | ASP | A | 313 | −1.320 | 23.671 | −15.343 | 1.00 | 14.44 |
| ATOM | 2398 | OD1 | ASP | A | 313 | −0.197 | 23.597 | −15.900 | 1.00 | 13.19 |
| ATOM | 2399 | OD2 | ASP | A | 313 | −2.400 | 23.406 | −15.923 | 1.00 | 13.61 |
| ATOM | 2400 | C | ASP | A | 313 | 0.512 | 25.589 | −13.587 | 1.00 | 14.00 |
| ATOM | 2401 | O | ASP | A | 313 | 0.007 | 26.662 | −13.219 | 1.00 | 14.35 |
| ATOM | 2402 | N | VAL | A | 314 | 1.577 | 25.530 | −14.399 | 1.00 | 13.84 |
| ATOM | 2403 | CA | VAL | A | 314 | 2.145 | 26.747 | −14.988 | 1.00 | 15.19 |
| ATOM | 2404 | CB | VAL | A | 314 | 3.602 | 27.016 | −14.520 | 1.00 | 16.70 |
| ATOM | 2405 | CG1 | VAL | A | 314 | 3.638 | 27.295 | −13.009 | 1.00 | 17.94 |
| ATOM | 2406 | CG2 | VAL | A | 314 | 4.551 | 25.857 | −14.915 | 1.00 | 16.69 |
| ATOM | 2407 | C | VAL | A | 314 | 2.123 | 26.729 | −16.528 | 1.00 | 15.30 |
| ATOM | 2408 | O | VAL | A | 314 | 2.712 | 27.598 | −17.165 | 1.00 | 15.13 |
| ATOM | 2409 | N | TYR | A | 315 | 1.441 | 25.743 | −17.111 | 1.00 | 14.51 |
| ATOM | 2410 | CA | TYR | A | 315 | 1.351 | 25.634 | −18.580 | 1.00 | 15.65 |
| ATOM | 2411 | CB | TYR | A | 315 | 0.768 | 24.264 | −18.957 | 1.00 | 15.82 |
| ATOM | 2412 | CG | TYR | A | 315 | 0.694 | 23.988 | −20.457 | 1.00 | 16.29 |
| ATOM | 2413 | CD1 | TYR | A | 315 | 1.824 | 24.124 | −21.265 | 1.00 | 17.01 |
| ATOM | 2414 | CE1 | TYR | A | 315 | 1.778 | 23.859 | −22.634 | 1.00 | 18.92 |
| ATOM | 2415 | CZ | TYR | A | 315 | 0.588 | 23.421 | −23.208 | 1.00 | 16.14 |
| ATOM | 2416 | OH | TYR | A | 315 | 0.557 | 23.164 | −24.577 | 1.00 | 16.95 |
| ATOM | 2417 | CE2 | TYR | A | 315 | −0.552 | 23.261 | −22.423 | 1.00 | 15.41 |
| ATOM | 2418 | CD2 | TYR | A | 315 | −0.492 | 23.539 | −21.044 | 1.00 | 14.48 |
| ATOM | 2419 | C | TYR | A | 315 | 0.489 | 26.777 | −19.107 | 1.00 | 15.56 |
| ATOM | 2420 | O | TYR | A | 315 | −0.688 | 26.888 | −18.748 | 1.00 | 16.36 |

TABLE 20-continued

| | | | | | | | | | |
|---|---|---|---|---|---|---|---|---|---|
| ATOM | 2421 | N | TYR | A | 316 | 1.072 | 27.645 | −19.944 | 1.00 | 16.61 |
| ATOM | 2422 | CA | TYR | A | 316 | 0.404 | 28.890 | −20.380 | 1.00 | 17.53 |
| ATOM | 2423 | CB | TYR | A | 316 | −0.778 | 28.603 | −21.337 | 1.00 | 18.31 |
| ATOM | 2424 | CG | TYR | A | 316 | −0.329 | 28.321 | −22.742 | 1.00 | 19.74 |
| ATOM | 2425 | CD1 | TYR | A | 316 | −0.071 | 27.026 | −23.169 | 1.00 | 18.95 |
| ATOM | 2426 | CE1 | TYR | A | 316 | 0.353 | 26.757 | −24.466 | 1.00 | 18.69 |
| ATOM | 2427 | CZ | TYR | A | 316 | 0.551 | 27.812 | −25.342 | 1.00 | 21.77 |
| ATOM | 2428 | OH | TYR | A | 316 | 1.002 | 27.557 | −26.617 | 1.00 | 23.75 |
| ATOM | 2429 | CE2 | TYR | A | 316 | 0.329 | 29.125 | −24.932 | 1.00 | 22.39 |
| ATOM | 2430 | CD2 | TYR | A | 316 | −0.111 | 29.369 | −23.639 | 1.00 | 21.90 |
| ATOM | 2431 | C | TYR | A | 316 | −0.037 | 29.730 | −19.173 | 1.00 | 17.87 |
| ATOM | 2432 | O | TYR | A | 316 | −0.968 | 30.517 | −19.266 | 1.00 | 17.06 |
| ATOM | 2433 | N | ASN | A | 317 | 0.689 | 29.555 | −18.066 | 1.00 | 18.34 |
| ATOM | 2434 | CA | ASN | A | 317 | 0.483 | 30.231 | −16.766 | 1.00 | 19.27 |
| ATOM | 2435 | CB | ASN | A | 317 | 0.106 | 31.699 | −16.921 | 1.00 | 20.01 |
| ATOM | 2436 | CG | ASN | A | 317 | 1.171 | 32.489 | −17.624 | 1.00 | 24.51 |
| ATOM | 2437 | OD1 | ASN | A | 317 | 2.363 | 32.384 | −17.305 | 1.00 | 29.46 |
| ATOM | 2438 | ND2 | ASN | A | 317 | 0.756 | 33.269 | −18.603 | 1.00 | 29.08 |
| ATOM | 2439 | C | ASN | A | 317 | −0.506 | 29.551 | −15.842 | 1.00 | 18.28 |
| ATOM | 2440 | O | ASN | A | 317 | −0.706 | 30.001 | −14.719 | 1.00 | 19.05 |
| ATOM | 2441 | N | GLY | A | 318 | −1.114 | 28.459 | −16.300 | 1.00 | 17.74 |
| ATOM | 2442 | CA | GLY | A | 318 | −2.086 | 27.721 | −15.475 | 1.00 | 15.34 |
| ATOM | 2443 | C | GLY | A | 318 | −3.458 | 28.356 | −15.550 | 1.00 | 15.47 |
| ATOM | 2444 | O | GLY | A | 318 | −3.700 | 29.390 | −14.932 | 1.00 | 15.75 |
| ATOM | 2445 | N | ASN | A | 319 | −4.369 | 27.733 | −16.306 | 1.00 | 13.16 |
| ATOM | 2446 | CA | ASN | A | 319 | −5.672 | 28.305 | −16.557 | 1.00 | 12.74 |
| ATOM | 2447 | CB | ASN | A | 319 | −5.693 | 28.883 | −17.980 | 1.00 | 12.31 |
| ATOM | 2448 | CG | ASN | A | 319 | −4.676 | 29.979 | −18.187 | 1.00 | 13.01 |
| ATOM | 2449 | OD1 | ASN | A | 319 | −4.832 | 31.117 | −17.699 | 1.00 | 14.18 |
| ATOM | 2450 | ND2 | ASN | A | 319 | −3.640 | 29.665 | −18.942 | 1.00 | 11.49 |
| ATOM | 2451 | C | ASN | A | 319 | −6.799 | 27.271 | −16.442 | 1.00 | 12.27 |
| ATOM | 2452 | O | ASN | A | 319 | −6.545 | 26.071 | −16.456 | 1.00 | 12.28 |
| ATOM | 2453 | N | PRO | A | 320 | −8.054 | 27.732 | −16.334 | 1.00 | 12.96 |
| ATOM | 2454 | CA | PRO | A | 320 | −9.113 | 26.759 | −16.472 | 1.00 | 12.58 |
| ATOM | 2455 | CB | PRO | A | 320 | −10.395 | 27.579 | −16.324 | 1.00 | 13.28 |
| ATOM | 2456 | CG | PRO | A | 320 | −10.007 | 29.011 | −16.183 | 1.00 | 14.34 |
| ATOM | 2457 | CD | PRO | A | 320 | −8.537 | 29.090 | −15.991 | 1.00 | 12.66 |
| ATOM | 2458 | C | PRO | A | 320 | −9.101 | 26.090 | −17.851 | 1.00 | 12.18 |
| ATOM | 2459 | O | PRO | A | 320 | −8.643 | 26.698 | −18.820 | 1.00 | 11.99 |
| ATOM | 2460 | N | TRP | A | 321 | −9.589 | 24.852 | −17.912 | 1.00 | 11.79 |
| ATOM | 2461 | CA | TRP | A | 321 | −9.739 | 24.116 | −19.154 | 1.00 | 11.97 |
| ATOM | 2462 | CB | TRP | A | 321 | −8.988 | 22.775 | −19.063 | 1.00 | 11.15 |
| ATOM | 2463 | CG | TRP | A | 321 | −7.469 | 22.900 | −19.200 | 1.00 | 12.16 |
| ATOM | 2464 | CD1 | TRP | A | 321 | −6.658 | 23.837 | −18.627 | 1.00 | 13.28 |
| ATOM | 2465 | NE1 | TRP | A | 321 | −5.347 | 23.636 | −19.016 | 1.00 | 13.24 |
| ATOM | 2466 | CE2 | TRP | A | 321 | −5.290 | 22.538 | −19.831 | 1.00 | 13.51 |
| ATOM | 2467 | CD2 | TRP | A | 321 | −6.617 | 22.054 | −19.978 | 1.00 | 12.68 |
| ATOM | 2468 | CE3 | TRP | A | 321 | −6.846 | 20.938 | −20.787 | 1.00 | 14.41 |
| ATOM | 2469 | CZ3 | TRP | A | 321 | −5.741 | 20.323 | −21.428 | 1.00 | 13.49 |
| ATOM | 2470 | CH2 | TRP | A | 321 | −4.436 | 20.819 | −21.250 | 1.00 | 13.43 |
| ATOM | 2471 | CZ2 | TRP | A | 321 | −4.193 | 21.948 | −20.479 | 1.00 | 14.69 |
| ATOM | 2472 | C | TRP | A | 321 | −11.202 | 23.797 | −19.342 | 1.00 | 11.99 |
| ATOM | 2473 | O | TRP | A | 321 | −11.875 | 23.448 | −18.388 | 1.00 | 11.51 |
| ATOM | 2474 | N | TYR | A | 322 | −11.696 | 23.896 | −20.579 | 1.00 | 11.47 |
| ATOM | 2475 | CA | TYR | A | 322 | −13.088 | 23.511 | −20.841 | 1.00 | 11.31 |
| ATOM | 2476 | CB | TYR | A | 322 | −13.433 | 23.691 | −22.322 | 1.00 | 12.14 |
| ATOM | 2477 | CG | TYR | A | 322 | −13.352 | 25.130 | −22.793 | 1.00 | 12.81 |
| ATOM | 2478 | CD1 | TYR | A | 322 | −12.260 | 25.574 | −23.509 | 1.00 | 11.43 |
| ATOM | 2479 | CE1 | TYR | A | 322 | −12.173 | 26.914 | −23.965 | 1.00 | 12.91 |
| ATOM | 2480 | CZ | TYR | A | 322 | −13.216 | 27.802 | −23.697 | 1.00 | 14.27 |
| ATOM | 2481 | OH | TYR | A | 322 | −13.127 | 29.104 | −24.146 | 1.00 | 15.10 |
| ATOM | 2482 | CE2 | TYR | A | 322 | −14.324 | 27.373 | −22.982 | 1.00 | 13.40 |
| ATOM | 2483 | CD2 | TYR | A | 322 | −14.378 | 26.031 | −22.522 | 1.00 | 11.58 |
| ATOM | 2484 | C | TYR | A | 322 | −13.367 | 22.082 | −20.433 | 1.00 | 11.31 |
| ATOM | 2485 | O | TYR | A | 322 | −14.380 | 21.795 | −19.771 | 1.00 | 11.08 |
| ATOM | 2486 | N | LEU | A | 323 | −12.480 | 21.169 | −20.814 | 1.00 | 10.96 |
| ATOM | 2487 | CA | LEU | A | 323 | −12.770 | 19.750 | −20.561 | 1.00 | 11.04 |
| ATOM | 2488 | CB | LEU | A | 323 | −11.787 | 18.844 | −21.315 | 1.00 | 11.26 |
| ATOM | 2489 | CG | LEU | A | 323 | −10.314 | 18.876 | −20.903 | 1.00 | 10.53 |
| ATOM | 2490 | CD1 | LEU | A | 323 | −10.074 | 17.902 | −19.745 | 1.00 | 14.57 |
| ATOM | 2491 | CD2 | LEU | A | 323 | −9.474 | 18.437 | −22.112 | 1.00 | 13.19 |
| ATOM | 2492 | C | LEU | A | 323 | −12.778 | 19.449 | −19.048 | 1.00 | 11.68 |
| ATOM | 2493 | O | LEU | A | 323 | −13.444 | 18.510 | −18.602 | 1.00 | 12.06 |
| ATOM | 2494 | N | ALA | A | 324 | −12.036 | 20.239 | −18.268 | 1.00 | 9.86 |
| ATOM | 2495 | CA | ALA | A | 324 | −11.969 | 20.017 | −16.812 | 1.00 | 10.09 |
| ATOM | 2496 | CB | ALA | A | 324 | −10.746 | 20.767 | −16.234 | 1.00 | 9.76 |
| ATOM | 2497 | C | ALA | A | 324 | −13.272 | 20.518 | −16.178 | 1.00 | 10.17 |
| ATOM | 2498 | O | ALA | A | 324 | −13.866 | 19.840 | −15.325 | 1.00 | 10.29 |
| ATOM | 2499 | N | THR | A | 325 | −13.758 | 21.662 | −16.665 | 1.00 | 9.84 |
| ATOM | 2500 | CA | THR | A | 325 | −15.000 | 22.267 | −16.172 | 1.00 | 11.14 |

TABLE 20-continued

| | | | | | | | | | |
|---|---|---|---|---|---|---|---|---|---|
| ATOM | 2501 | CB | THR | A | 325 | −15.102 | 23.765 | −16.623 | 1.00 | 12.15 |
| ATOM | 2502 | OG1 | THR | A | 325 | −14.002 | 24.498 | −16.063 | 1.00 | 13.16 |
| ATOM | 2503 | CG2 | THR | A | 325 | −16.402 | 24.411 | −16.152 | 1.00 | 11.83 |
| ATOM | 2504 | C | THR | A | 325 | −16.218 | 21.413 | −16.570 | 1.00 | 11.50 |
| ATOM | 2505 | O | THR | A | 325 | −17.086 | 21.126 | −15.727 | 1.00 | 10.79 |
| ATOM | 2506 | N | PHE | A | 326 | −16.234 | 20.925 | −17.816 | 1.00 | 10.79 |
| ATOM | 2507 | CA | PHE | A | 326 | −17.272 | 19.959 | −18.240 | 1.00 | 12.12 |
| ATOM | 2508 | CB | PHE | A | 326 | −17.194 | 19.652 | −19.746 | 1.00 | 12.14 |
| ATOM | 2509 | CG | PHE | A | 326 | −17.518 | 20.851 | −20.640 | 1.00 | 13.71 |
| ATOM | 2510 | CD1 | PHE | A | 326 | −16.777 | 21.077 | −21.804 | 1.00 | 15.21 |
| ATOM | 2511 | CE1 | PHE | A | 326 | −17.043 | 22.188 | −22.635 | 1.00 | 14.99 |
| ATOM | 2512 | CZ | PHE | A | 326 | −18.072 | 23.066 | −22.311 | 1.00 | 16.33 |
| ATOM | 2513 | CE2 | PHE | A | 326 | −18.851 | 22.832 | −21.160 | 1.00 | 20.12 |
| ATOM | 2514 | CD2 | PHE | A | 326 | −18.561 | 21.717 | −20.331 | 1.00 | 16.63 |
| ATOM | 2515 | C | PHE | A | 326 | −17.216 | 18.643 | −17.464 | 1.00 | 11.56 |
| ATOM | 2516 | O | PHE | A | 326 | −18.263 | 18.069 | −17.180 | 1.00 | 11.74 |
| ATOM | 2517 | N | ALA | A | 327 | −16.014 | 18.174 | −17.103 | 1.00 | 11.35 |
| ATOM | 2518 | CA | ALA | A | 327 | −15.889 | 16.909 | −16.346 | 1.00 | 11.41 |
| ATOM | 2519 | CB | ALA | A | 327 | −14.397 | 16.538 | −16.158 | 1.00 | 11.95 |
| ATOM | 2520 | C | ALA | A | 327 | −16.612 | 16.964 | −14.965 | 1.00 | 12.04 |
| ATOM | 2521 | O | ALA | A | 327 | −17.260 | 15.985 | −14.561 | 1.00 | 12.69 |
| ATOM | 2522 | N | ALA | A | 328 | −16.505 | 18.097 | −14.266 | 1.00 | 12.13 |
| ATOM | 2523 | CA | ALA | A | 328 | −17.207 | 18.293 | −12.985 | 1.00 | 12.24 |
| ATOM | 2524 | CB | ALA | A | 328 | −16.871 | 19.662 | −12.369 | 1.00 | 12.48 |
| ATOM | 2525 | C | ALA | A | 328 | −18.707 | 18.157 | −13.177 | 1.00 | 12.90 |
| ATOM | 2526 | O | ALA | A | 328 | −19.378 | 17.454 | −12.411 | 1.00 | 13.60 |
| ATOM | 2527 | N | ALA | A | 329 | −19.239 | 18.814 | −14.202 | 1.00 | 12.55 |
| ATOM | 2528 | CA | ALA | A | 329 | −20.669 | 18.682 | −14.504 | 1.00 | 12.31 |
| ATOM | 2529 | CB | ALA | A | 329 | −21.027 | 19.551 | −15.692 | 1.00 | 12.87 |
| ATOM | 2530 | C | ALA | A | 329 | −21.035 | 17.226 | −14.788 | 1.00 | 12.71 |
| ATOM | 2531 | O | ALA | A | 329 | −22.016 | 16.700 | −14.266 | 1.00 | 12.32 |
| ATOM | 2532 | N | GLU | A | 330 | −20.231 | 16.572 | −15.629 | 1.00 | 12.54 |
| ATOM | 2533 | CA | GLU | A | 330 | −20.500 | 15.187 | −16.003 | 1.00 | 12.84 |
| ATOM | 2534 | CB | GLU | A | 330 | −19.519 | 14.718 | −17.100 | 1.00 | 12.55 |
| ATOM | 2535 | CG | GLU | A | 330 | −19.850 | 13.303 | −17.626 | 1.00 | 13.80 |
| ATOM | 2536 | CD | GLU | A | 330 | −19.108 | 12.953 | −18.917 | 1.00 | 13.54 |
| ATOM | 2537 | OE1 | GLU | A | 330 | −18.650 | 13.889 | −19.604 | 1.00 | 12.29 |
| ATOM | 2538 | OE2 | GLU | A | 330 | −18.998 | 11.739 | −19.209 | 1.00 | 14.52 |
| ATOM | 2539 | C | GLU | A | 330 | −20.523 | 14.231 | −14.809 | 1.00 | 12.94 |
| ATOM | 2540 | O | GLU | A | 330 | −21.400 | 13.346 | −14.726 | 1.00 | 12.90 |
| ATOM | 2541 | N | GLN | A | 331 | −19.598 | 14.402 | −13.866 | 1.00 | 12.03 |
| ATOM | 2542 | CA | GLN | A | 331 | −19.589 | 13.502 | −12.726 | 1.00 | 12.38 |
| ATOM | 2543 | CB | GLN | A | 331 | −18.415 | 13.795 | −11.797 | 1.00 | 12.24 |
| ATOM | 2544 | CG | GLN | A | 331 | −18.357 | 12.759 | −10.670 | 1.00 | 13.61 |
| ATOM | 2545 | CD | GLN | A | 331 | −17.327 | 13.072 | −9.608 | 1.00 | 15.82 |
| ATOM | 2546 | OE1 | GLN | A | 331 | −16.263 | 13.617 | −9.895 | 1.00 | 15.39 |
| ATOM | 2547 | NE2 | GLN | A | 331 | −17.628 | 12.702 | −8.372 | 1.00 | 13.76 |
| ATOM | 2548 | C | GLN | A | 331 | −20.912 | 13.643 | −11.969 | 1.00 | 12.33 |
| ATOM | 2549 | O | GLN | A | 331 | −21.512 | 12.659 | −11.556 | 1.00 | 12.45 |
| ATOM | 2550 | N | LEU | A | 332 | −21.377 | 14.873 | −11.844 | 1.00 | 12.57 |
| ATOM | 2551 | CA | LEU | A | 332 | −22.628 | 15.138 | −11.134 | 1.00 | 13.59 |
| ATOM | 2552 | CB | LEU | A | 332 | −22.747 | 16.631 | −10.868 | 1.00 | 13.17 |
| ATOM | 2553 | CG | LEU | A | 332 | −21.681 | 17.142 | −9.867 | 1.00 | 16.56 |
| ATOM | 2554 | CD1 | LEU | A | 332 | −21.718 | 18.678 | −9.801 | 1.00 | 18.10 |
| ATOM | 2555 | CD2 | LEU | A | 332 | −21.851 | 16.476 | −8.492 | 1.00 | 19.47 |
| ATOM | 2556 | C | LEU | A | 332 | −23.861 | 14.600 | −11.864 | 1.00 | 13.57 |
| ATOM | 2557 | O | LEU | A | 332 | −24.770 | 14.053 | −11.239 | 1.00 | 13.24 |
| ATOM | 2558 | N | TYR | A | 333 | −23.909 | 14.766 | −13.179 | 1.00 | 13.90 |
| ATOM | 2559 | CA | TYR | A | 333 | −24.988 | 14.131 | −13.972 | 1.00 | 14.37 |
| ATOM | 2560 | CB | TYR | A | 333 | −24.901 | 14.523 | −15.468 | 1.00 | 14.48 |
| ATOM | 2561 | CG | TYR | A | 333 | −25.056 | 16.001 | −15.721 | 1.00 | 13.91 |
| ATOM | 2562 | CD1 | TYR | A | 333 | −26.086 | 16.738 | −15.118 | 1.00 | 14.64 |
| ATOM | 2563 | CE1 | TYR | A | 333 | −26.208 | 18.117 | −15.350 | 1.00 | 15.65 |
| ATOM | 2564 | CZ | TYR | A | 333 | −25.315 | 18.758 | −16.196 | 1.00 | 16.47 |
| ATOM | 2565 | OH | TYR | A | 333 | −25.431 | 20.101 | −16.442 | 1.00 | 17.22 |
| ATOM | 2566 | CE2 | TYR | A | 333 | −24.310 | 18.050 | −16.836 | 1.00 | 16.59 |
| ATOM | 2567 | CD2 | TYR | A | 333 | −24.192 | 16.669 | −16.601 | 1.00 | 11.27 |
| ATOM | 2568 | C | TYR | A | 333 | −25.022 | 12.613 | −13.843 | 1.00 | 15.03 |
| ATOM | 2569 | O | TYR | A | 333 | −26.108 | 12.012 | −13.824 | 1.00 | 14.78 |
| ATOM | 2570 | N | ASP | A | 334 | −23.836 | 11.998 | −13.807 | 1.00 | 14.06 |
| ATOM | 2571 | CA | ASP | A | 334 | −23.714 | 10.555 | −13.602 | 1.00 | 14.83 |
| ATOM | 2572 | CB | ASP | A | 334 | −22.239 | 10.114 | −13.714 | 1.00 | 13.83 |
| ATOM | 2573 | CG | ASP | A | 334 | −21.708 | 10.149 | −15.136 | 1.00 | 15.84 |
| ATOM | 2574 | OD1 | ASP | A | 334 | −22.495 | 10.373 | −16.081 | 1.00 | 13.95 |
| ATOM | 2575 | OD2 | ASP | A | 334 | −20.470 | 9.943 | −15.313 | 1.00 | 15.50 |
| ATOM | 2576 | C | ASP | A | 334 | −24.254 | 10.163 | −12.224 | 1.00 | 15.21 |
| ATOM | 2577 | O | ASP | A | 334 | −24.941 | 9.132 | −12.080 | 1.00 | 15.93 |
| ATOM | 2578 | N | ALA | A | 335 | −23.933 | 10.969 | −11.213 | 1.00 | 15.09 |
| ATOM | 2579 | CA | ALA | A | 335 | −24.454 | 10.735 | −9.855 | 1.00 | 16.00 |
| ATOM | 2580 | CB | ALA | A | 335 | −23.809 | 11.719 | −8.864 | 1.00 | 15.13 |

TABLE 20-continued

| | | | | | | | | | |
|---|---|---|---|---|---|---|---|---|---|
| ATOM | 2581 | C | ALA | A | 335 | −25.980 | 10.823 | −9.803 | 1.00 | 16.10 |
| ATOM | 2582 | O | ALA | A | 335 | −26.643 | 9.916 | −9.245 | 1.00 | 16.77 |
| ATOM | 2583 | N | ILE | A | 336 | −26.530 | 11.879 | −10.398 | 1.00 | 16.35 |
| ATOM | 2584 | CA | ILE | A | 336 | −27.987 | 12.087 | −10.470 | 1.00 | 18.39 |
| ATOM | 2585 | CB | ILE | A | 336 | −28.332 | 13.422 | −11.162 | 1.00 | 18.85 |
| ATOM | 2586 | CG1 | ILE | A | 336 | −27.891 | 14.596 | −10.279 | 1.00 | 19.14 |
| ATOM | 2587 | CD1 | ILE | A | 336 | −27.879 | 15.904 | −10.986 | 1.00 | 22.50 |
| ATOM | 2588 | CG2 | ILE | A | 336 | −29.839 | 13.539 | −11.506 | 1.00 | 20.14 |
| ATOM | 2589 | C | ILE | A | 336 | −28.681 | 10.902 | −11.156 | 1.00 | 18.83 |
| ATOM | 2590 | O | ILE | A | 336 | −29.707 | 10.404 | −10.675 | 1.00 | 18.06 |
| ATOM | 2591 | N | TYR | A | 337 | −28.102 | 10.443 | −12.267 | 1.00 | 18.50 |
| ATOM | 2592 | CA | TYR | A | 337 | −28.642 | 9.287 | −12.970 | 1.00 | 18.99 |
| ATOM | 2593 | CB | TYR | A | 337 | −27.753 | 8.908 | −14.169 | 1.00 | 19.80 |
| ATOM | 2594 | CG | TYR | A | 337 | −28.328 | 7.737 | −14.954 | 1.00 | 20.76 |
| ATOM | 2595 | CD1 | TYR | A | 337 | −27.988 | 6.429 | −14.620 | 1.00 | 20.95 |
| ATOM | 2596 | CE1 | TYR | A | 337 | −28.511 | 5.345 | −15.322 | 1.00 | 22.94 |
| ATOM | 2597 | CZ | TYR | A | 337 | −29.382 | 5.559 | −16.356 | 1.00 | 22.19 |
| ATOM | 2598 | OH | TYR | A | 337 | −29.877 | 4.447 | −17.018 | 1.00 | 24.87 |
| ATOM | 2599 | CE2 | TYR | A | 337 | −29.752 | 6.845 | −16.721 | 1.00 | 22.31 |
| ATOM | 2600 | CD2 | TYR | A | 337 | −29.220 | 7.942 | −16.009 | 1.00 | 21.58 |
| ATOM | 2601 | C | TYR | A | 337 | −28.839 | 8.083 | −12.057 | 1.00 | 18.60 |
| ATOM | 2602 | O | TYR | A | 337 | −29.918 | 7.476 | −12.041 | 1.00 | 18.61 |
| ATOM | 2603 | N | VAL | A | 338 | −27.802 | 7.737 | −11.297 | 1.00 | 18.67 |
| ATOM | 2604 | CA | VAL | A | 338 | −27.837 | 6.573 | −10.406 | 1.00 | 18.90 |
| ATOM | 2605 | CB | VAL | A | 338 | −26.424 | 6.195 | −9.919 | 1.00 | 18.99 |
| ATOM | 2606 | CG1 | VAL | A | 338 | −26.462 | 5.121 | −8.820 | 1.00 | 19.71 |
| ATOM | 2607 | CG2 | VAL | A | 338 | −25.600 | 5.698 | −11.111 | 1.00 | 18.75 |
| ATOM | 2608 | C | VAL | A | 338 | −28.810 | 6.788 | −9.234 | 1.00 | 19.41 |
| ATOM | 2609 | O | VAL | A | 338 | −29.565 | 5.871 | −8.869 | 1.00 | 19.45 |
| ATOM | 2610 | N | TRP | A | 339 | −28.797 | 7.987 | −8.654 | 1.00 | 19.81 |
| ATOM | 2611 | CA | TRP | A | 339 | −29.743 | 8.290 | −7.559 | 1.00 | 20.46 |
| ATOM | 2612 | CB | TRP | A | 339 | −29.514 | 9.705 | −7.029 | 1.00 | 20.35 |
| ATOM | 2613 | CG | TRP | A | 339 | −28.222 | 9.830 | −6.329 | 1.00 | 18.64 |
| ATOM | 2614 | CD1 | TRP | A | 339 | −27.540 | 8.846 | −5.676 | 1.00 | 16.51 |
| ATOM | 2615 | NE1 | TRP | A | 339 | −26.391 | 9.359 | −5.126 | 1.00 | 17.81 |
| ATOM | 2616 | CE2 | TRP | A | 339 | −26.312 | 10.693 | −5.423 | 1.00 | 17.12 |
| ATOM | 2617 | CD2 | TRP | A | 339 | −27.452 | 11.025 | −6.183 | 1.00 | 17.64 |
| ATOM | 2618 | CE3 | TRP | A | 339 | −27.624 | 12.343 | −6.614 | 1.00 | 17.59 |
| ATOM | 2619 | CZ3 | TRP | A | 339 | −26.637 | 13.283 | −6.284 | 1.00 | 19.24 |
| ATOM | 2620 | CH2 | TRP | A | 339 | −25.510 | 12.912 | −5.520 | 1.00 | 18.24 |
| ATOM | 2621 | CZ2 | TRP | A | 339 | −25.320 | 11.626 | −5.103 | 1.00 | 18.45 |
| ATOM | 2622 | C | TRP | A | 339 | −31.201 | 8.108 | −7.997 | 1.00 | 21.83 |
| ATOM | 2623 | O | TRP | A | 339 | −31.981 | 7.478 | −7.274 | 1.00 | 22.01 |
| ATOM | 2624 | N | LYS | A | 340 | −31.549 | 8.646 | −9.168 | 1.00 | 22.85 |
| ATOM | 2625 | CA | LYS | A | 340 | −32.904 | 8.541 | −9.721 | 1.00 | 25.61 |
| ATOM | 2626 | CB | LYS | A | 340 | −33.066 | 9.411 | −10.967 | 1.00 | 25.52 |
| ATOM | 2627 | CG | LYS | A | 340 | −33.174 | 10.905 | −10.689 | 1.00 | 28.19 |
| ATOM | 2628 | CD | LYS | A | 340 | −33.227 | 11.692 | −11.991 | 1.00 | 34.04 |
| ATOM | 2629 | CE | LYS | A | 340 | −33.966 | 13.011 | −11.805 | 1.00 | 38.04 |
| ATOM | 2630 | NZ | LYS | A | 340 | −33.868 | 13.876 | −13.017 | 1.00 | 41.83 |
| ATOM | 2631 | C | LYS | A | 340 | −33.276 | 7.108 | −10.062 | 1.00 | 27.14 |
| ATOM | 2632 | O | LYS | A | 340 | −34.413 | 6.686 | −9.830 | 1.00 | 27.56 |
| ATOM | 2633 | N | LYS | A | 341 | −32.317 | 6.358 | −10.604 | 1.00 | 28.13 |
| ATOM | 2634 | CA | LYS | A | 341 | −32.552 | 4.975 | −11.018 | 1.00 | 30.18 |
| ATOM | 2635 | CB | LYS | A | 341 | −31.358 | 4.428 | −11.800 | 1.00 | 29.83 |
| ATOM | 2636 | CG | LYS | A | 341 | −31.688 | 3.173 | −12.624 | 1.00 | 33.04 |
| ATOM | 2637 | CD | LYS | A | 341 | −30.472 | 2.624 | −13.395 | 1.00 | 33.62 |
| ATOM | 2638 | CE | LYS | A | 341 | −29.652 | 1.592 | −12.588 | 1.00 | 38.22 |
| ATOM | 2639 | NZ | LYS | A | 341 | −28.691 | 2.188 | −11.573 | 1.00 | 40.88 |
| ATOM | 2640 | C | LYS | A | 341 | −32.816 | 4.081 | −9.817 | 1.00 | 30.19 |
| ATOM | 2641 | O | LYS | A | 341 | −33.744 | 3.260 | −9.837 | 1.00 | 30.15 |
| ATOM | 2642 | N | THR | A | 342 | −31.999 | 4.246 | −8.777 | 1.00 | 29.52 |
| ATOM | 2643 | CA | THR | A | 342 | −32.074 | 3.400 | −7.595 | 1.00 | 29.75 |
| ATOM | 2644 | CB | THR | A | 342 | −30.687 | 3.221 | −6.916 | 1.00 | 29.68 |
| ATOM | 2645 | OG1 | THR | A | 342 | −30.254 | 4.458 | −6.333 | 1.00 | 32.01 |
| ATOM | 2646 | CG2 | THR | A | 342 | −29.628 | 2.735 | −7.929 | 1.00 | 31.40 |
| ATOM | 2647 | C | THR | A | 342 | −33.129 | 3.901 | −6.596 | 1.00 | 29.01 |
| ATOM | 2648 | O | THR | A | 342 | −33.572 | 3.148 | −5.734 | 1.00 | 29.92 |
| ATOM | 2649 | N | GLY | A | 343 | −33.534 | 5.158 | −6.732 | 1.00 | 28.20 |
| ATOM | 2650 | CA | GLY | A | 343 | −34.537 | 5.782 | −5.862 | 1.00 | 28.30 |
| ATOM | 2651 | C | GLY | A | 343 | −34.068 | 6.045 | −4.438 | 1.00 | 27.91 |
| ATOM | 2652 | O | GLY | A | 343 | −34.887 | 6.133 | −3.519 | 1.00 | 28.16 |
| ATOM | 2653 | N | SER | A | 344 | −32.760 | 6.226 | −4.260 | 1.00 | 27.22 |
| ATOM | 2654 | CA | SER | A | 344 | −32.142 | 6.306 | −2.939 | 1.00 | 26.60 |
| ATOM | 2655 | CB | SER | A | 344 | −31.870 | 4.880 | −2.462 | 1.00 | 27.28 |
| ATOM | 2656 | OG | SER | A | 344 | −31.354 | 4.855 | −1.161 | 1.00 | 29.50 |
| ATOM | 2657 | C | SER | A | 344 | −30.823 | 7.107 | −2.979 | 1.00 | 26.02 |
| ATOM | 2658 | O | SER | A | 344 | −30.068 | 6.992 | −3.944 | 1.00 | 25.80 |
| ATOM | 2659 | N | ILE | A | 345 | −30.557 | 7.900 | −1.936 | 1.00 | 24.20 |
| ATOM | 2660 | CA | ILE | A | 345 | −29.295 | 8.641 | −1.770 | 1.00 | 23.04 |

TABLE 20-continued

| | | | | | | | | | |
|---|---|---|---|---|---|---|---|---|---|
| ATOM | 2661 | CB | ILE | A | 345 | −29.477 | 10.171 | −1.954 | 1.00 | 23.03 |
| ATOM | 2662 | CG1 | ILE | A | 345 | −30.021 | 10.474 | −3.340 | 1.00 | 22.44 |
| ATOM | 2663 | CD1 | ILE | A | 345 | −30.399 | 11.918 | −3.599 | 1.00 | 23.24 |
| ATOM | 2664 | CG2 | ILE | A | 345 | −28.138 | 10.918 | −1.670 | 1.00 | 22.00 |
| ATOM | 2665 | C | ILE | A | 345 | −28.726 | 8.415 | −0.378 | 1.00 | 23.13 |
| ATOM | 2666 | O | ILE | A | 345 | −29.392 | 8.684 | 0.623 | 1.00 | 23.57 |
| ATOM | 2667 | N | THR | A | 346 | −27.490 | 7.943 | −0.307 | 1.00 | 22.23 |
| ATOM | 2668 | CA | THR | A | 346 | −26.820 | 7.765 | 0.963 | 1.00 | 23.25 |
| ATOM | 2669 | CB | THR | A | 346 | −26.246 | 6.338 | 1.101 | 1.00 | 23.78 |
| ATOM | 2670 | OG1 | THR | A | 346 | −27.327 | 5.396 | 1.020 | 1.00 | 27.42 |
| ATOM | 2671 | CG2 | THR | A | 346 | −25.507 | 6.129 | 2.443 | 1.00 | 24.74 |
| ATOM | 2672 | C | THR | A | 346 | −25.753 | 8.849 | 1.138 | 1.00 | 23.03 |
| ATOM | 2673 | O | THR | A | 346 | −24.916 | 9.067 | 0.260 | 1.00 | 23.47 |
| ATOM | 2674 | N | VAL | A | 347 | −25.848 | 9.561 | 2.255 | 1.00 | 21.33 |
| ATOM | 2675 | CA | VAL | A | 347 | −24.845 | 10.537 | 2.674 | 1.00 | 20.11 |
| ATOM | 2676 | CB | VAL | A | 347 | −25.522 | 11.844 | 3.212 | 1.00 | 19.06 |
| ATOM | 2677 | CG1 | VAL | A | 347 | −24.489 | 12.834 | 3.700 | 1.00 | 19.66 |
| ATOM | 2678 | CG2 | VAL | A | 347 | −26.418 | 12.465 | 2.137 | 1.00 | 20.32 |
| ATOM | 2679 | C | VAL | A | 347 | −24.066 | 9.865 | 3.785 | 1.00 | 20.14 |
| ATOM | 2680 | O | VAL | A | 347 | −24.667 | 9.340 | 4.728 | 1.00 | 19.79 |
| ATOM | 2681 | N | THR | A | 348 | −22.734 | 9.878 | 3.671 | 1.00 | 19.85 |
| ATOM | 2682 | CA | THR | A | 348 | −21.851 | 9.274 | 4.660 | 1.00 | 19.92 |
| ATOM | 2683 | CB | THR | A | 348 | −20.965 | 8.185 | 4.018 | 1.00 | 19.82 |
| ATOM | 2684 | OG1 | THR | A | 348 | −19.921 | 8.815 | 3.277 | 1.00 | 20.35 |
| ATOM | 2685 | CG2 | THR | A | 348 | −21.785 | 7.278 | 3.092 | 1.00 | 21.67 |
| ATOM | 2686 | C | THR | A | 348 | −20.964 | 10.354 | 5.256 | 1.00 | 19.60 |
| ATOM | 2687 | O | THR | A | 348 | −20.961 | 11.484 | 4.760 | 1.00 | 19.51 |
| ATOM | 2688 | N | ALA | A | 349 | −20.191 | 10.006 | 6.292 | 1.00 | 19.18 |
| ATOM | 2689 | CA | ALA | A | 349 | −19.243 | 10.932 | 6.885 | 1.00 | 20.02 |
| ATOM | 2690 | CB | ALA | A | 349 | −18.494 | 10.275 | 8.044 | 1.00 | 20.61 |
| ATOM | 2691 | C | ALA | A | 349 | −18.240 | 11.466 | 5.842 | 1.00 | 19.79 |
| ATOM | 2692 | O | ALA | A | 349 | −17.756 | 12.601 | 5.947 | 1.00 | 20.15 |
| ATOM | 2693 | N | THR | A | 350 | −17.906 | 10.619 | 4.873 | 1.00 | 18.87 |
| ATOM | 2694 | CA | THR | A | 350 | −16.911 | 10.971 | 3.850 | 1.00 | 18.30 |
| ATOM | 2695 | CB | THR | A | 350 | −16.435 | 9.717 | 3.093 | 1.00 | 18.67 |
| ATOM | 2696 | OG1 | THR | A | 350 | −15.780 | 8.850 | 4.027 | 1.00 | 19.82 |
| ATOM | 2697 | CG2 | THR | A | 350 | −15.426 | 10.097 | 1.974 | 1.00 | 17.73 |
| ATOM | 2698 | C | THR | A | 350 | −17.463 | 12.003 | 2.871 | 1.00 | 17.30 |
| ATOM | 2699 | O | THR | A | 350 | −16.747 | 12.930 | 2.487 | 1.00 | 17.99 |
| ATOM | 2700 | N | SER | A | 351 | −18.716 | 11.847 | 2.467 | 1.00 | 16.16 |
| ATOM | 2701 | CA | SER | A | 351 | −19.316 | 12.803 | 1.517 | 1.00 | 15.78 |
| ATOM | 2702 | CB | SER | A | 351 | −20.214 | 12.076 | 0.512 | 1.00 | 15.85 |
| ATOM | 2703 | OG | SER | A | 351 | −21.280 | 11.412 | 1.156 | 1.00 | 17.14 |
| ATOM | 2704 | C | SER | A | 351 | −20.087 | 13.941 | 2.193 | 1.00 | 15.63 |
| ATOM | 2705 | O | SER | A | 351 | −20.736 | 14.743 | 1.524 | 1.00 | 13.62 |
| ATOM | 2706 | N | LEU | A | 352 | −20.048 | 14.006 | 3.527 | 1.00 | 15.09 |
| ATOM | 2707 | CA | LEU | A | 352 | −20.901 | 14.985 | 4.212 | 1.00 | 16.29 |
| ATOM | 2708 | CB | LEU | A | 352 | −20.759 | 14.851 | 5.736 | 1.00 | 16.64 |
| ATOM | 2709 | CG | LEU | A | 352 | −21.713 | 15.734 | 6.570 | 1.00 | 17.22 |
| ATOM | 2710 | CD1 | LEU | A | 352 | −23.138 | 15.281 | 6.418 | 1.00 | 19.06 |
| ATOM | 2711 | CD2 | LEU | A | 352 | −21.263 | 15.636 | 8.032 | 1.00 | 20.02 |
| ATOM | 2712 | C | LEU | A | 352 | −20.592 | 16.427 | 3.787 | 1.00 | 16.09 |
| ATOM | 2713 | O | LEU | A | 352 | −21.499 | 17.219 | 3.601 | 1.00 | 16.35 |
| ATOM | 2714 | N | ALA | A | 353 | −19.311 | 16.763 | 3.643 | 1.00 | 16.19 |
| ATOM | 2715 | CA | ALA | A | 353 | −18.933 | 18.148 | 3.354 | 1.00 | 15.74 |
| ATOM | 2716 | CB | ALA | A | 353 | −17.460 | 18.314 | 3.424 | 1.00 | 16.30 |
| ATOM | 2717 | C | ALA | A | 353 | −19.459 | 18.544 | 1.972 | 1.00 | 16.11 |
| ATOM | 2718 | O | ALA | A | 353 | −19.957 | 19.668 | 1.781 | 1.00 | 15.44 |
| ATOM | 2719 | N | PHE | A | 354 | −19.367 | 17.607 | 1.021 | 1.00 | 16.10 |
| ATOM | 2720 | CA | PHE | A | 354 | −19.885 | 17.849 | −0.325 | 1.00 | 15.25 |
| ATOM | 2721 | CB | PHE | A | 354 | −19.718 | 16.618 | −1.220 | 1.00 | 16.59 |
| ATOM | 2722 | CG | PHE | A | 354 | −20.497 | 16.707 | −2.500 | 1.00 | 15.45 |
| ATOM | 2723 | CD1 | PHE | A | 354 | −19.959 | 17.375 | −3.603 | 1.00 | 16.95 |
| ATOM | 2724 | CE1 | PHE | A | 354 | −20.664 | 17.489 | −4.793 | 1.00 | 17.06 |
| ATOM | 2725 | CZ | PHE | A | 354 | −21.956 | 16.953 | −4.888 | 1.00 | 16.75 |
| ATOM | 2726 | CE2 | PHE | A | 354 | −22.517 | 16.276 | −3.791 | 1.00 | 16.91 |
| ATOM | 2727 | CD2 | PHE | A | 354 | −21.778 | 16.160 | −2.594 | 1.00 | 17.48 |
| ATOM | 2728 | C | PHE | A | 354 | −21.374 | 18.188 | −0.226 | 1.00 | 15.56 |
| ATOM | 2729 | O | PHE | A | 354 | −21.815 | 19.183 | −0.797 | 1.00 | 15.08 |
| ATOM | 2730 | N | PHE | A | 355 | −22.140 | 17.347 | 0.474 | 1.00 | 14.54 |
| ATOM | 2731 | CA | PHE | A | 355 | −23.588 | 17.544 | 0.517 | 1.00 | 15.29 |
| ATOM | 2732 | CB | PHE | A | 355 | −24.295 | 16.319 | 1.078 | 1.00 | 15.61 |
| ATOM | 2733 | CG | PHE | A | 355 | −24.386 | 15.176 | 0.112 | 1.00 | 15.51 |
| ATOM | 2734 | CD1 | PHE | A | 355 | −25.306 | 15.205 | −0.945 | 1.00 | 14.91 |
| ATOM | 2735 | CE1 | PHE | A | 355 | −25.404 | 14.131 | −1.832 | 1.00 | 16.52 |
| ATOM | 2736 | CZ | PHE | A | 355 | −24.567 | 13.033 | −1.676 | 1.00 | 16.12 |
| ATOM | 2737 | CE2 | PHE | A | 355 | −23.648 | 12.994 | −0.628 | 1.00 | 15.62 |
| ATOM | 2738 | CD2 | PHE | A | 355 | −23.562 | 14.071 | 0.255 | 1.00 | 13.62 |
| ATOM | 2739 | C | PHE | A | 355 | −23.988 | 18.789 | 1.303 | 1.00 | 15.19 |
| ATOM | 2740 | O | PHE | A | 355 | −24.920 | 19.477 | 0.902 | 1.00 | 15.69 |

TABLE 20-continued

| | | | | | | | | | |
|---|---|---|---|---|---|---|---|---|---|
| ATOM | 2741 | N | GLN | A | 356 | −23.283 | 19.084 | 2.398 | 1.00 | 15.78 |
| ATOM | 2742 | CA | GLN | A | 356 | −23.679 | 20.216 | 3.257 | 1.00 | 16.16 |
| ATOM | 2743 | CB | GLN | A | 356 | −22.987 | 20.165 | 4.627 | 1.00 | 16.84 |
| ATOM | 2744 | CG | GLN | A | 356 | −23.564 | 19.115 | 5.579 | 1.00 | 17.13 |
| ATOM | 2745 | CD | GLN | A | 356 | −22.907 | 19.170 | 6.973 | 1.00 | 18.06 |
| ATOM | 2746 | OE1 | GLN | A | 356 | −21.808 | 19.707 | 7.138 | 1.00 | 20.29 |
| ATOM | 2747 | NE2 | GLN | A | 356 | −23.569 | 18.589 | 7.965 | 1.00 | 20.95 |
| ATOM | 2748 | C | GLN | A | 356 | −23.444 | 21.546 | 2.584 | 1.00 | 16.08 |
| ATOM | 2749 | O | GLN | A | 356 | −24.142 | 22.507 | 2.868 | 1.00 | 15.59 |
| ATOM | 2750 | N | GLU | A | 357 | −22.482 | 21.599 | 1.661 | 1.00 | 16.07 |
| ATOM | 2751 | CA | GLU | A | 357 | −22.261 | 22.808 | 0.884 | 1.00 | 16.41 |
| ATOM | 2752 | CB | GLU | A | 357 | −20.994 | 22.683 | 0.005 | 1.00 | 16.33 |
| ATOM | 2753 | CG | GLU | A | 357 | −20.671 | 23.942 | −0.770 | 1.00 | 15.64 |
| ATOM | 2754 | CD | GLU | A | 357 | −19.326 | 23.894 | −1.516 | 1.00 | 17.67 |
| ATOM | 2755 | OE1 | GLU | A | 357 | −18.931 | 24.947 | −2.066 | 1.00 | 19.03 |
| ATOM | 2756 | OE2 | GLU | A | 357 | −18.685 | 22.822 | −1.575 | 1.00 | 14.75 |
| ATOM | 2757 | C | GLU | A | 357 | −23.492 | 23.105 | 0.019 | 1.00 | 15.84 |
| ATOM | 2758 | O | GLU | A | 357 | −23.786 | 24.237 | −0.224 | 1.00 | 18.07 |
| ATOM | 2759 | N | LEU | A | 358 | −24.213 | 22.084 | −0.420 | 1.00 | 14.72 |
| ATOM | 2760 | CA | LEU | A | 358 | −25.364 | 22.251 | −1.310 | 1.00 | 15.75 |
| ATOM | 2761 | CB | LEU | A | 358 | −25.368 | 21.147 | −2.369 | 1.00 | 16.49 |
| ATOM | 2762 | CG | LEU | A | 358 | −24.057 | 21.100 | −3.168 | 1.00 | 16.81 |
| ATOM | 2763 | CD1 | LEU | A | 358 | −24.087 | 19.977 | −4.182 | 1.00 | 19.73 |
| ATOM | 2764 | CD2 | LEU | A | 358 | −23.775 | 22.465 | −3.846 | 1.00 | 19.34 |
| ATOM | 2765 | C | LEU | A | 358 | −26.708 | 22.251 | −0.582 | 1.00 | 15.36 |
| ATOM | 2766 | O | LEU | A | 358 | −27.656 | 22.911 | −1.028 | 1.00 | 14.78 |
| ATOM | 2767 | N | VAL | A | 359 | −26.786 | 21.511 | 0.520 | 1.00 | 15.34 |
| ATOM | 2768 | CA | VAL | A | 359 | −28.001 | 21.404 | 1.321 | 1.00 | 15.00 |
| ATOM | 2769 | CB | VAL | A | 359 | −28.691 | 20.006 | 1.154 | 1.00 | 15.90 |
| ATOM | 2770 | CG1 | VAL | A | 359 | −29.999 | 19.917 | 1.962 | 1.00 | 15.16 |
| ATOM | 2771 | CG2 | VAL | A | 359 | −28.967 | 19.685 | −0.348 | 1.00 | 16.26 |
| ATOM | 2772 | C | VAL | A | 359 | −27.531 | 21.624 | 2.775 | 1.00 | 14.72 |
| ATOM | 2773 | O | VAL | A | 359 | −27.192 | 20.653 | 3.500 | 1.00 | 14.22 |
| ATOM | 2774 | N | PRO | A | 360 | −27.467 | 22.893 | 3.193 | 1.00 | 14.98 |
| ATOM | 2775 | CA | PRO | A | 360 | −26.937 | 23.179 | 4.539 | 1.00 | 15.45 |
| ATOM | 2776 | CB | PRO | A | 360 | −27.150 | 24.700 | 4.700 | 1.00 | 15.45 |
| ATOM | 2777 | CG | PRO | A | 360 | −27.188 | 25.219 | 3.274 | 1.00 | 16.15 |
| ATOM | 2778 | CD | PRO | A | 360 | −27.854 | 24.127 | 2.471 | 1.00 | 14.54 |
| ATOM | 2779 | C | PRO | A | 360 | −27.692 | 22.385 | 5.611 | 1.00 | 15.31 |
| ATOM | 2780 | O | PRO | A | 360 | −28.918 | 22.262 | 5.555 | 1.00 | 15.07 |
| ATOM | 2781 | N | GLY | A | 361 | −26.936 | 21.842 | 6.560 | 1.00 | 15.94 |
| ATOM | 2782 | CA | GLY | A | 361 | −27.512 | 21.143 | 7.709 | 1.00 | 16.53 |
| ATOM | 2783 | C | GLY | A | 361 | −27.870 | 19.680 | 7.488 | 1.00 | 17.03 |
| ATOM | 2784 | O | GLY | A | 361 | −28.268 | 18.997 | 8.429 | 1.00 | 17.68 |
| ATOM | 2785 | N | VAL | A | 362 | −27.762 | 19.176 | 6.261 | 1.00 | 16.13 |
| ATOM | 2786 | CA | VAL | A | 362 | −28.163 | 17.769 | 6.037 | 1.00 | 16.72 |
| ATOM | 2787 | CB | VAL | A | 362 | −28.217 | 17.416 | 4.525 | 1.00 | 16.47 |
| ATOM | 2788 | CG1 | VAL | A | 362 | −26.808 | 17.311 | 3.947 | 1.00 | 16.75 |
| ATOM | 2789 | CG2 | VAL | A | 362 | −29.054 | 16.142 | 4.280 | 1.00 | 17.21 |
| ATOM | 2790 | C | VAL | A | 362 | −27.208 | 16.849 | 6.811 | 1.00 | 17.24 |
| ATOM | 2791 | O | VAL | A | 362 | −26.044 | 17.187 | 7.006 | 1.00 | 17.07 |
| ATOM | 2792 | N | THR | A | 363 | −27.695 | 15.703 | 7.274 | 1.00 | 18.15 |
| ATOM | 2793 | CA | THR | A | 363 | −26.821 | 14.789 | 8.025 | 1.00 | 19.86 |
| ATOM | 2794 | CB | THR | A | 363 | −27.388 | 14.459 | 9.405 | 1.00 | 20.59 |
| ATOM | 2795 | OG1 | THR | A | 363 | −28.634 | 13.776 | 9.217 | 1.00 | 22.85 |
| ATOM | 2796 | CG2 | THR | A | 363 | −27.610 | 15.742 | 10.182 | 1.00 | 22.71 |
| ATOM | 2797 | C | THR | A | 363 | −26.660 | 13.476 | 7.310 | 1.00 | 19.18 |
| ATOM | 2798 | O | THR | A | 363 | −27.398 | 13.184 | 6.371 | 1.00 | 18.87 |
| ATOM | 2799 | N | ALA | A | 364 | −25.697 | 12.679 | 7.769 | 1.00 | 19.67 |
| ATOM | 2800 | CA | ALA | A | 364 | −25.495 | 11.342 | 7.222 | 1.00 | 20.19 |
| ATOM | 2801 | CB | ALA | A | 364 | −24.361 | 10.637 | 7.930 | 1.00 | 20.38 |
| ATOM | 2802 | C | ALA | A | 364 | −26.783 | 10.541 | 7.343 | 1.00 | 21.17 |
| ATOM | 2803 | O | ALA | A | 364 | −27.551 | 10.720 | 8.293 | 1.00 | 21.92 |
| ATOM | 2804 | N | GLY | A | 365 | −27.041 | 9.687 | 6.360 | 1.00 | 21.67 |
| ATOM | 2805 | CA | GLY | A | 365 | −28.207 | 8.823 | 6.371 | 1.00 | 22.35 |
| ATOM | 2806 | C | GLY | A | 365 | −28.584 | 8.415 | 4.968 | 1.00 | 23.66 |
| ATOM | 2807 | O | GLY | A | 365 | −27.924 | 8.804 | 3.991 | 1.00 | 23.66 |
| ATOM | 2808 | N | THR | A | 366 | −29.639 | 7.615 | 4.862 | 1.00 | 23.70 |
| ATOM | 2809 | CA | THR | A | 366 | −30.148 | 7.183 | 3.582 | 1.00 | 24.56 |
| ATOM | 2810 | CB | THR | A | 366 | −30.188 | 5.644 | 3.491 | 1.00 | 25.67 |
| ATOM | 2811 | OG1 | THR | A | 366 | −28.849 | 5.143 | 3.649 | 1.00 | 27.09 |
| ATOM | 2812 | CG2 | THR | A | 366 | −30.715 | 5.216 | 2.159 | 1.00 | 25.47 |
| ATOM | 2813 | C | THR | A | 366 | −31.520 | 7.769 | 3.344 | 1.00 | 25.15 |
| ATOM | 2814 | O | THR | A | 366 | −32.427 | 7.612 | 4.177 | 1.00 | 25.01 |
| ATOM | 2815 | N | TYR | A | 367 | −31.668 | 8.447 | 2.210 | 1.00 | 24.20 |
| ATOM | 2816 | CA | TYR | A | 367 | −32.900 | 9.146 | 1.883 | 1.00 | 24.30 |
| ATOM | 2817 | CB | TYR | A | 367 | −32.616 | 10.648 | 1.701 | 1.00 | 23.51 |
| ATOM | 2818 | CG | TYR | A | 367 | −31.924 | 11.238 | 2.907 | 1.00 | 22.68 |
| ATOM | 2819 | CD1 | TYR | A | 367 | −32.639 | 11.506 | 4.078 | 1.00 | 21.99 |
| ATOM | 2820 | CE1 | TYR | A | 367 | −32.012 | 12.019 | 5.199 | 1.00 | 20.27 |

TABLE 20-continued

| | | | | | | | | | |
|---|---|---|---|---|---|---|---|---|---|
| ATOM | 2821 | CZ | TYR | A | 367 | −30.650 | 12.263 | 5.176 | 1.00 | 22.67 |
| ATOM | 2822 | OH | TYR | A | 367 | −30.036 | 12.789 | 6.287 | 1.00 | 21.24 |
| ATOM | 2823 | CE2 | TYR | A | 367 | −29.897 | 11.994 | 4.023 | 1.00 | 20.71 |
| ATOM | 2824 | CD2 | TYR | A | 367 | −30.541 | 11.479 | 2.904 | 1.00 | 20.37 |
| ATOM | 2825 | C | TYR | A | 367 | −33.531 | 8.542 | 0.641 | 1.00 | 25.39 |
| ATOM | 2826 | O | TYR | A | 367 | −32.900 | 8.456 | −0.415 | 1.00 | 24.86 |
| ATOM | 2827 | N | SER | A | 368 | −34.782 | 8.109 | 0.758 | 1.00 | 25.82 |
| ATOM | 2828 | CA | SER | A | 368 | −35.416 | 7.454 | −0.374 | 1.00 | 27.29 |
| ATOM | 2829 | CB | SER | A | 368 | −36.339 | 6.332 | 0.107 | 1.00 | 27.90 |
| ATOM | 2830 | OG | SER | A | 368 | −37.519 | 6.895 | 0.634 | 1.00 | 30.69 |
| ATOM | 2831 | C | SER | A | 368 | −36.171 | 8.466 | −1.218 | 1.00 | 27.68 |
| ATOM | 2832 | O | SER | A | 368 | −36.361 | 9.612 | −0.805 | 1.00 | 26.96 |
| ATOM | 2833 | N | SER | A | 369 | −36.629 | 8.025 | −2.388 | 1.00 | 28.98 |
| ATOM | 2834 | CA | SER | A | 369 | −37.260 | 8.908 | −3.367 | 1.00 | 30.52 |
| ATOM | 2835 | CB | SER | A | 369 | −37.520 | 8.167 | −4.681 | 1.00 | 30.90 |
| ATOM | 2836 | OG | SER | A | 369 | −38.269 | 6.983 | −4.452 | 1.00 | 32.57 |
| ATOM | 2837 | C | SER | A | 369 | −38.536 | 9.583 | −2.871 | 1.00 | 31.50 |
| ATOM | 2838 | O | SER | A | 369 | −38.954 | 10.572 | −3.442 | 1.00 | 32.33 |
| ATOM | 2839 | N | SER | A | 370 | −39.150 | 9.067 | −1.809 | 1.00 | 32.18 |
| ATOM | 2840 | CA | SER | A | 370 | −40.365 | 9.712 | −1.279 | 1.00 | 32.96 |
| ATOM | 2841 | CB | SER | A | 370 | −41.313 | 8.692 | −0.624 | 1.00 | 33.18 |
| ATOM | 2842 | OG | SER | A | 370 | −40.610 | 7.847 | 0.273 | 1.00 | 34.18 |
| ATOM | 2843 | C | SER | A | 370 | −40.049 | 10.864 | −0.323 | 1.00 | 32.37 |
| ATOM | 2844 | O | SER | A | 370 | −40.901 | 11.729 | −0.078 | 1.00 | 33.26 |
| ATOM | 2845 | N | SER | A | 371 | −38.825 | 10.893 | 0.197 | 1.00 | 31.13 |
| ATOM | 2846 | CA | SER | A | 371 | −38.443 | 11.911 | 1.174 | 1.00 | 30.04 |
| ATOM | 2847 | CB | SER | A | 371 | −37.180 | 11.487 | 1.912 | 1.00 | 29.83 |
| ATOM | 2848 | OG | SER | A | 371 | −36.046 | 11.714 | 1.100 | 1.00 | 30.43 |
| ATOM | 2849 | C | SER | A | 371 | −38.247 | 13.295 | 0.553 | 1.00 | 29.13 |
| ATOM | 2850 | O | SER | A | 371 | −37.795 | 13.424 | −0.589 | 1.00 | 28.84 |
| ATOM | 2851 | N | SER | A | 372 | −38.571 | 14.340 | 1.312 | 1.00 | 27.84 |
| ATOM | 2852 | CA | SER | A | 372 | −38.300 | 15.689 | 0.845 | 1.00 | 27.18 |
| ATOM | 2853 | CB | SER | A | 372 | −38.896 | 16.737 | 1.789 | 1.00 | 27.36 |
| ATOM | 2854 | OG | SER | A | 372 | −38.331 | 16.609 | 3.080 | 1.00 | 28.50 |
| ATOM | 2855 | C | SER | A | 372 | −36.783 | 15.902 | 0.680 | 1.00 | 25.79 |
| ATOM | 2856 | O | SER | A | 372 | −36.358 | 16.690 | −0.173 | 1.00 | 26.29 |
| ATOM | 2857 | N | THR | A | 373 | −35.979 | 15.193 | 1.479 | 1.00 | 24.06 |
| ATOM | 2858 | CA | THR | A | 373 | −34.517 | 15.337 | 1.448 | 1.00 | 22.51 |
| ATOM | 2859 | CB | THR | A | 373 | −33.833 | 14.501 | 2.545 | 1.00 | 22.26 |
| ATOM | 2860 | OG1 | THR | A | 373 | −34.543 | 14.636 | 3.788 | 1.00 | 23.04 |
| ATOM | 2861 | CG2 | THR | A | 373 | −32.370 | 14.926 | 2.734 | 1.00 | 21.06 |
| ATOM | 2862 | C | THR | A | 373 | −33.984 | 14.906 | 0.076 | 1.00 | 21.61 |
| ATOM | 2863 | O | THR | A | 373 | −33.134 | 15.578 | −0.513 | 1.00 | 19.74 |
| ATOM | 2864 | N | PHE | A | 374 | −34.493 | 13.777 | −0.413 | 1.00 | 21.13 |
| ATOM | 2865 | CA | PHE | A | 374 | −34.137 | 13.280 | −1.749 | 1.00 | 22.10 |
| ATOM | 2866 | CB | PHE | A | 374 | −34.950 | 12.023 | −2.051 | 1.00 | 22.12 |
| ATOM | 2867 | CG | PHE | A | 374 | −34.624 | 11.380 | −3.366 | 1.00 | 22.90 |
| ATOM | 2868 | CD1 | PHE | A | 374 | −33.677 | 10.368 | −3.432 | 1.00 | 23.83 |
| ATOM | 2869 | CE1 | PHE | A | 374 | −33.381 | 9.749 | −4.649 | 1.00 | 22.56 |
| ATOM | 2870 | CZ | PHE | A | 374 | −34.041 | 10.162 | −5.802 | 1.00 | 23.24 |
| ATOM | 2871 | CE2 | PHE | A | 374 | −34.985 | 11.161 | −5.752 | 1.00 | 23.36 |
| ATOM | 2872 | CD2 | PHE | A | 374 | −35.280 | 11.769 | −4.523 | 1.00 | 23.73 |
| ATOM | 2873 | C | PHE | A | 374 | −34.343 | 14.349 | −2.818 | 1.00 | 22.24 |
| ATOM | 2874 | O | PHE | A | 374 | −33.413 | 14.681 | −3.548 | 1.00 | 22.63 |
| ATOM | 2875 | N | THR | A | 375 | −35.549 | 14.923 | −2.880 | 1.00 | 22.72 |
| ATOM | 2876 | CA | THR | A | 375 | −35.890 | 15.963 | −3.852 | 1.00 | 23.34 |
| ATOM | 2877 | CB | THR | A | 375 | −37.364 | 16.398 | −3.683 | 1.00 | 23.63 |
| ATOM | 2878 | OG1 | THR | A | 375 | −38.193 | 15.244 | −3.809 | 1.00 | 27.83 |
| ATOM | 2879 | CG2 | THR | A | 375 | −37.768 | 17.413 | −4.749 | 1.00 | 27.05 |
| ATOM | 2880 | C | THR | A | 375 | −35.003 | 17.203 | −3.746 | 1.00 | 22.66 |
| ATOM | 2881 | O | THR | A | 375 | −34.603 | 17.766 | −4.756 | 1.00 | 21.43 |
| ATOM | 2882 | N | ASN | A | 376 | −34.744 | 17.632 | −2.508 | 1.00 | 20.80 |
| ATOM | 2883 | CA | ASN | A | 376 | −33.880 | 18.766 | −2.207 | 1.00 | 21.33 |
| ATOM | 2884 | CB | ASN | A | 376 | −33.856 | 18.975 | −0.688 | 1.00 | 21.98 |
| ATOM | 2885 | CG | ASN | A | 376 | −33.343 | 20.354 | −0.278 | 1.00 | 27.01 |
| ATOM | 2886 | OD1 | ASN | A | 376 | −32.582 | 21.011 | −1.004 | 1.00 | 31.72 |
| ATOM | 2887 | ND2 | ASN | A | 376 | −33.748 | 20.793 | 0.913 | 1.00 | 30.14 |
| ATOM | 2888 | C | ASN | A | 376 | −32.465 | 18.527 | −2.733 | 1.00 | 19.80 |
| ATOM | 2889 | O | ASN | A | 376 | −31.898 | 19.389 | −3.415 | 1.00 | 19.75 |
| ATOM | 2890 | N | ILE | A | 377 | −31.915 | 17.354 | −2.431 | 1.00 | 19.00 |
| ATOM | 2891 | CA | ILE | A | 377 | −30.586 | 16.983 | −2.916 | 1.00 | 18.66 |
| ATOM | 2892 | CB | ILE | A | 377 | −30.081 | 15.651 | −2.319 | 1.00 | 18.56 |
| ATOM | 2893 | CG1 | ILE | A | 377 | −29.834 | 15.813 | −0.800 | 1.00 | 18.42 |
| ATOM | 2894 | CD1 | ILE | A | 377 | −29.634 | 14.481 | −0.028 | 1.00 | 19.35 |
| ATOM | 2895 | CG2 | ILE | A | 377 | −28.787 | 15.233 | −3.025 | 1.00 | 18.07 |
| ATOM | 2896 | C | ILE | A | 377 | −30.546 | 16.964 | −4.451 | 1.00 | 18.87 |
| ATOM | 2897 | O | ILE | A | 377 | −29.655 | 17.575 | −5.058 | 1.00 | 18.47 |
| ATOM | 2898 | N | ILE | A | 378 | −31.513 | 16.293 | −5.068 | 1.00 | 18.45 |
| ATOM | 2899 | CA | ILE | A | 378 | −31.556 | 16.216 | −6.539 | 1.00 | 19.78 |
| ATOM | 2900 | CB | ILE | A | 378 | −32.738 | 15.359 | −7.085 | 1.00 | 20.45 |

TABLE 20-continued

| ATOM | 2901 | CG1 | ILE | A | 378 | −32.593 | 13.891 | −6.650 | 1.00 | 22.32 |
|---|---|---|---|---|---|---|---|---|---|---|
| ATOM | 2902 | CD1 | ILE | A | 378 | −31.414 | 13.145 | −7.270 | 1.00 | 24.68 |
| ATOM | 2903 | CG2 | ILE | A | 378 | −32.829 | 15.472 | −8.646 | 1.00 | 21.27 |
| ATOM | 2904 | C | ILE | A | 378 | −31.561 | 17.588 | −7.177 | 1.00 | 19.82 |
| ATOM | 2905 | O | ILE | A | 378 | −30.760 | 17.849 | −8.101 | 1.00 | 19.62 |
| ATOM | 2906 | N | ASN | A | 379 | −32.441 | 18.470 | −6.689 | 1.00 | 18.68 |
| ATOM | 2907 | CA | ASN | A | 379 | −32.531 | 19.820 | −7.224 | 1.00 | 19.13 |
| ATOM | 2908 | CB | ASN | A | 379 | −33.738 | 20.578 | −6.658 | 1.00 | 20.08 |
| ATOM | 2909 | CG | ASN | A | 379 | −35.066 | 19.956 | −7.087 | 1.00 | 25.11 |
| ATOM | 2910 | OD1 | ASN | A | 379 | −35.121 | 19.173 | −8.044 | 1.00 | 29.37 |
| ATOM | 2911 | ND2 | ASN | A | 379 | −36.144 | 20.289 | −6.369 | 1.00 | 29.08 |
| ATOM | 2912 | C | ASN | A | 379 | −31.241 | 20.604 | −7.040 | 1.00 | 17.96 |
| ATOM | 2913 | O | ASN | A | 379 | −30.774 | 21.273 | −7.981 | 1.00 | 17.85 |
| ATOM | 2914 | N | ALA | A | 380 | −30.662 | 20.497 | −5.841 | 1.00 | 15.93 |
| ATOM | 2915 | CA | ALA | A | 380 | −29.458 | 21.241 | −5.509 | 1.00 | 16.08 |
| ATOM | 2916 | CB | ALA | A | 380 | −29.120 | 21.061 | −4.033 | 1.00 | 16.14 |
| ATOM | 2917 | C | ALA | A | 380 | −28.299 | 20.783 | −6.389 | 1.00 | 15.64 |
| ATOM | 2918 | O | ALA | A | 380 | −27.566 | 21.607 | −6.938 | 1.00 | 16.56 |
| ATOM | 2919 | N | VAL | A | 381 | −28.153 | 19.471 | −6.519 | 1.00 | 15.22 |
| ATOM | 2920 | CA | VAL | A | 381 | −27.039 | 18.912 | −7.302 | 1.00 | 15.77 |
| ATOM | 2921 | CB | VAL | A | 381 | −26.823 | 17.403 | −6.999 | 1.00 | 15.61 |
| ATOM | 2922 | CG1 | VAL | A | 381 | −25.747 | 16.777 | −7.940 | 1.00 | 14.83 |
| ATOM | 2923 | CG2 | VAL | A | 381 | −26.386 | 17.234 | −5.551 | 1.00 | 14.84 |
| ATOM | 2924 | C | VAL | A | 381 | −27.243 | 19.211 | −8.794 | 1.00 | 16.08 |
| ATOM | 2925 | O | VAL | A | 381 | −26.281 | 19.508 | −9.505 | 1.00 | 16.62 |
| ATOM | 2926 | N | SER | A | 382 | −28.482 | 19.112 | −9.278 | 1.00 | 16.66 |
| ATOM | 2927 | CA | SER | A | 382 | −28.772 | 19.453 | −10.690 | 1.00 | 18.67 |
| ATOM | 2928 | CB | SER | A | 382 | −30.246 | 19.212 | −11.043 | 1.00 | 18.26 |
| ATOM | 2929 | OG | SER | A | 382 | −30.538 | 17.855 | −10.893 | 1.00 | 24.56 |
| ATOM | 2930 | C | SER | A | 382 | −28.434 | 20.894 | −11.005 | 1.00 | 18.10 |
| ATOM | 2931 | O | SER | A | 382 | −27.815 | 21.183 | −12.027 | 1.00 | 18.05 |
| ATOM | 2932 | N | THR | A | 383 | −28.853 | 21.810 | −10.132 | 1.00 | 17.66 |
| ATOM | 2933 | CA | THR | A | 383 | −28.521 | 23.216 | −10.298 | 1.00 | 17.72 |
| ATOM | 2934 | CB | THR | A | 383 | −29.199 | 24.063 | −9.180 | 1.00 | 18.48 |
| ATOM | 2935 | OG1 | THR | A | 383 | −30.606 | 23.985 | −9.373 | 1.00 | 19.72 |
| ATOM | 2936 | CG2 | THR | A | 383 | −28.771 | 25.550 | −9.227 | 1.00 | 19.59 |
| ATOM | 2937 | C | THR | A | 383 | −27.017 | 23.470 | −10.314 | 1.00 | 17.09 |
| ATOM | 2938 | O | THR | A | 383 | −26.524 | 24.286 | −11.109 | 1.00 | 17.00 |
| ATOM | 2939 | N | TYR | A | 384 | −26.299 | 22.774 | −9.435 | 1.00 | 15.62 |
| ATOM | 2940 | CA | TYR | A | 384 | −24.858 | 22.925 | −9.312 | 1.00 | 15.37 |
| ATOM | 2941 | CB | TYR | A | 384 | −24.397 | 22.164 | −8.068 | 1.00 | 15.00 |
| ATOM | 2942 | CG | TYR | A | 384 | −22.958 | 22.345 | −7.630 | 1.00 | 15.08 |
| ATOM | 2943 | CD1 | TYR | A | 384 | −22.361 | 23.601 | −7.578 | 1.00 | 15.83 |
| ATOM | 2944 | CE1 | TYR | A | 384 | −21.049 | 23.752 | −7.131 | 1.00 | 16.33 |
| ATOM | 2945 | CZ | TYR | A | 384 | −20.321 | 22.623 | −6.737 | 1.00 | 16.13 |
| ATOM | 2946 | OH | TYR | A | 384 | −19.018 | 22.738 | −6.302 | 1.00 | 16.22 |
| ATOM | 2947 | CE2 | TYR | A | 384 | −20.890 | 21.386 | −6.778 | 1.00 | 13.72 |
| ATOM | 2948 | CD2 | TYR | A | 384 | −22.203 | 21.242 | −7.232 | 1.00 | 14.72 |
| ATOM | 2949 | C | TYR | A | 384 | −24.186 | 22.396 | −10.590 | 1.00 | 15.13 |
| ATOM | 2950 | O | TYR | A | 384 | −23.319 | 23.065 | −11.173 | 1.00 | 14.43 |
| ATOM | 2951 | N | ALA | A | 385 | −24.605 | 21.213 | −11.033 | 1.00 | 15.02 |
| ATOM | 2952 | CA | ALA | A | 385 | −24.045 | 20.639 | −12.263 | 1.00 | 15.60 |
| ATOM | 2953 | CB | ALA | A | 385 | −24.634 | 19.295 | −12.503 | 1.00 | 15.85 |
| ATOM | 2954 | C | ALA | A | 385 | −24.249 | 21.564 | −13.477 | 1.00 | 16.15 |
| ATOM | 2955 | O | ALA | A | 385 | −23.292 | 21.857 | −14.211 | 1.00 | 15.49 |
| ATOM | 2956 | N | ASP | A | 386 | −25.483 | 22.055 | −13.660 | 1.00 | 15.57 |
| ATOM | 2957 | CA | ASP | A | 386 | −25.782 | 23.058 | −14.694 | 1.00 | 16.09 |
| ATOM | 2958 | CB | ASP | A | 386 | −27.279 | 23.433 | −14.687 | 1.00 | 15.88 |
| ATOM | 2959 | CG | ASP | A | 386 | −28.158 | 22.379 | −15.349 | 1.00 | 18.85 |
| ATOM | 2960 | OD1 | ASP | A | 386 | −27.672 | 21.307 | −15.766 | 1.00 | 18.94 |
| ATOM | 2961 | OD2 | ASP | A | 386 | −29.365 | 22.624 | −15.461 | 1.00 | 23.88 |
| ATOM | 2962 | C | ASP | A | 386 | −24.938 | 24.322 | −14.526 | 1.00 | 15.81 |
| ATOM | 2963 | O | ASP | A | 386 | −24.594 | 24.998 | −15.501 | 1.00 | 16.29 |
| ATOM | 2964 | N | GLY | A | 387 | −24.591 | 24.640 | −13.290 | 1.00 | 15.76 |
| ATOM | 2965 | CA | GLY | A | 387 | −23.735 | 25.787 | −13.038 | 1.00 | 14.35 |
| ATOM | 2966 | C | GLY | A | 387 | −22.354 | 25.654 | −13.663 | 1.00 | 14.35 |
| ATOM | 2967 | O | GLY | A | 387 | −21.791 | 26.644 | −14.129 | 1.00 | 13.79 |
| ATOM | 2968 | N | PHE | A | 388 | −21.771 | 24.453 | −13.624 | 1.00 | 14.30 |
| ATOM | 2969 | CA | PHE | A | 388 | −20.479 | 24.217 | −14.312 | 1.00 | 14.69 |
| ATOM | 2970 | CB | PHE | A | 388 | −19.912 | 22.824 | −13.987 | 1.00 | 14.42 |
| ATOM | 2971 | CG | PHE | A | 388 | −19.359 | 22.730 | −12.584 | 1.00 | 13.79 |
| ATOM | 2972 | CD1 | PHE | A | 388 | −18.139 | 23.335 | −12.269 | 1.00 | 14.50 |
| ATOM | 2973 | CE1 | PHE | A | 388 | −17.621 | 23.261 | −10.947 | 1.00 | 16.38 |
| ATOM | 2974 | CZ | PHE | A | 388 | −18.377 | 22.627 | −9.951 | 1.00 | 14.77 |
| ATOM | 2975 | CE2 | PHE | A | 388 | −19.604 | 22.045 | −10.265 | 1.00 | 16.35 |
| ATOM | 2976 | CD2 | PHE | A | 388 | −20.088 | 22.100 | −11.578 | 1.00 | 14.00 |
| ATOM | 2977 | C | PHE | A | 388 | −20.601 | 24.428 | −15.821 | 1.00 | 15.31 |
| ATOM | 2978 | O | PHE | A | 388 | −19.740 | 25.078 | −16.440 | 1.00 | 15.55 |
| ATOM | 2979 | N | LEU | A | 389 | −21.669 | 23.913 | −16.415 | 1.00 | 16.52 |
| ATOM | 2980 | CA | LEU | A | 389 | −21.889 | 24.159 | −17.856 | 1.00 | 17.84 |

TABLE 20-continued

| | | | | | | | | | |
|---|---|---|---|---|---|---|---|---|---|
| ATOM | 2981 | CB | LEU | A | 389 | −23.137 | 23.431 | −18.382 | 1.00 | 17.83 |
| ATOM | 2982 | CG | LEU | A | 389 | −23.172 | 21.911 | −18.427 | 1.00 | 22.75 |
| ATOM | 2983 | CD1 | LEU | A | 389 | −24.247 | 21.418 | −19.401 | 1.00 | 22.55 |
| ATOM | 2984 | CD2 | LEU | A | 389 | −21.805 | 21.333 | −18.806 | 1.00 | 24.63 |
| ATOM | 2985 | C | LEU | A | 389 | −22.013 | 25.634 | −18.136 | 1.00 | 18.32 |
| ATOM | 2986 | O | LEU | A | 389 | −21.409 | 26.138 | −19.091 | 1.00 | 19.50 |
| ATOM | 2987 | N | SER | A | 390 | −22.775 | 26.341 | −17.295 | 1.00 | 18.55 |
| ATOM | 2988 | CA | SER | A | 390 | −23.021 | 27.767 | −17.469 | 1.00 | 19.33 |
| ATOM | 2989 | CB | SER | A | 390 | −24.090 | 28.246 | −16.491 | 1.00 | 19.89 |
| ATOM | 2990 | OG | SER | A | 390 | −25.325 | 27.693 | −16.891 | 1.00 | 24.07 |
| ATOM | 2991 | C | SER | A | 390 | −21.763 | 28.603 | −17.323 | 1.00 | 19.51 |
| ATOM | 2992 | O | SER | A | 390 | −21.575 | 29.585 | −18.055 | 1.00 | 19.69 |
| ATOM | 2993 | N | GLU | A | 391 | −20.893 | 28.200 | −16.399 | 1.00 | 18.87 |
| ATOM | 2994 | CA | GLU | A | 391 | −19.633 | 28.879 | −16.220 | 1.00 | 19.59 |
| ATOM | 2995 | CB | GLU | A | 391 | −18.901 | 28.393 | −14.952 | 1.00 | 20.02 |
| ATOM | 2996 | CG | GLU | A | 391 | −19.528 | 28.924 | −13.668 | 1.00 | 23.54 |
| ATOM | 2997 | CD | GLU | A | 391 | −19.590 | 30.448 | −13.634 | 1.00 | 26.61 |
| ATOM | 2998 | OE1 | GLU | A | 391 | −18.609 | 31.102 | −14.023 | 1.00 | 28.42 |
| ATOM | 2999 | OE2 | GLU | A | 391 | −20.637 | 30.994 | −13.227 | 1.00 | 29.52 |
| ATOM | 3000 | C | GLU | A | 391 | −18.738 | 28.729 | −17.457 | 1.00 | 19.12 |
| ATOM | 3001 | O | GLU | A | 391 | −18.123 | 29.709 | −17.906 | 1.00 | 19.40 |
| ATOM | 3002 | N | ALA | A | 392 | −18.654 | 27.516 | −17.991 | 1.00 | 18.81 |
| ATOM | 3003 | CA | ALA | A | 392 | −17.861 | 27.304 | −19.201 | 1.00 | 19.72 |
| ATOM | 3004 | CB | ALA | A | 392 | −17.758 | 25.815 | −19.526 | 1.00 | 19.45 |
| ATOM | 3005 | C | ALA | A | 392 | −18.478 | 28.098 | −20.363 | 1.00 | 19.59 |
| ATOM | 3006 | O | ALA | A | 392 | −17.764 | 28.724 | −21.157 | 1.00 | 18.65 |
| ATOM | 3007 | N | ALA | A | 393 | −19.808 | 28.117 | −20.425 | 1.00 | 20.40 |
| ATOM | 3008 | CA | ALA | A | 393 | −20.526 | 28.820 | −21.507 | 1.00 | 21.27 |
| ATOM | 3009 | CB | ALA | A | 393 | −22.035 | 28.524 | −21.421 | 1.00 | 21.83 |
| ATOM | 3010 | C | ALA | A | 393 | −20.266 | 30.334 | −21.574 | 1.00 | 21.79 |
| ATOM | 3011 | O | ALA | A | 393 | −20.283 | 30.920 | −22.664 | 1.00 | 21.96 |
| ATOM | 3012 | N | LYS | A | 394 | −19.976 | 30.971 | −20.435 | 1.00 | 21.37 |
| ATOM | 3013 | CA | LYS | A | 394 | −19.626 | 32.383 | −20.447 | 1.00 | 22.02 |
| ATOM | 3014 | CB | LYS | A | 394 | −19.289 | 32.916 | −19.043 | 1.00 | 23.11 |
| ATOM | 3015 | CG | LYS | A | 394 | −20.411 | 32.980 | −18.044 | 1.00 | 25.98 |
| ATOM | 3016 | CD | LYS | A | 394 | −19.782 | 33.341 | −16.700 | 1.00 | 28.89 |
| ATOM | 3017 | CE | LYS | A | 394 | −20.793 | 33.314 | −15.576 | 1.00 | 34.05 |
| ATOM | 3018 | NZ | LYS | A | 394 | −20.097 | 33.674 | −14.290 | 1.00 | 33.96 |
| ATOM | 3019 | C | LYS | A | 394 | −18.403 | 32.626 | −21.310 | 1.00 | 21.55 |
| ATOM | 3020 | O | LYS | A | 394 | −18.188 | 33.742 | −21.771 | 1.00 | 22.41 |
| ATOM | 3021 | N | TYR | A | 395 | −17.570 | 31.604 | −21.488 | 1.00 | 19.98 |
| ATOM | 3022 | CA | TYR | A | 395 | −16.287 | 31.824 | −22.132 | 1.00 | 19.46 |
| ATOM | 3023 | CB | TYR | A | 395 | −15.137 | 31.464 | −21.185 | 1.00 | 20.82 |
| ATOM | 3024 | CG | TYR | A | 395 | −15.291 | 32.165 | −19.872 | 1.00 | 22.04 |
| ATOM | 3025 | CD1 | TYR | A | 395 | −15.644 | 31.450 | −18.716 | 1.00 | 23.21 |
| ATOM | 3026 | CE1 | TYR | A | 395 | −15.806 | 32.097 | −17.508 | 1.00 | 23.70 |
| ATOM | 3027 | CZ | TYR | A | 395 | −15.661 | 33.473 | −17.460 | 1.00 | 23.93 |
| ATOM | 3028 | OH | TYR | A | 395 | −15.828 | 34.143 | −16.272 | 1.00 | 26.14 |
| ATOM | 3029 | CE2 | TYR | A | 395 | −15.327 | 34.202 | −18.593 | 1.00 | 24.38 |
| ATOM | 3030 | CD2 | TYR | A | 395 | −15.157 | 33.548 | −19.791 | 1.00 | 22.37 |
| ATOM | 3031 | C | TYR | A | 395 | −16.157 | 31.119 | −23.451 | 1.00 | 19.22 |
| ATOM | 3032 | O | TYR | A | 395 | −15.045 | 30.940 | −23.941 | 1.00 | 18.70 |
| ATOM | 3033 | N | VAL | A | 396 | −17.299 | 30.718 | −24.018 | 1.00 | 18.16 |
| ATOM | 3034 | CA | VAL | A | 396 | −17.331 | 30.135 | −25.352 | 1.00 | 19.03 |
| ATOM | 3035 | CB | VAL | A | 396 | −18.396 | 29.025 | −25.458 | 1.00 | 18.18 |
| ATOM | 3036 | CG1 | VAL | A | 396 | −18.469 | 28.465 | −26.898 | 1.00 | 18.63 |
| ATOM | 3037 | CG2 | VAL | A | 396 | −18.094 | 27.915 | −24.452 | 1.00 | 18.97 |
| ATOM | 3038 | C | VAL | A | 396 | −17.654 | 31.288 | −26.308 | 1.00 | 19.65 |
| ATOM | 3039 | O | VAL | A | 396 | −18.644 | 31.986 | −26.098 | 1.00 | 19.66 |
| ATOM | 3040 | N | PRO | A | 397 | −16.810 | 31.507 | −27.328 | 1.00 | 20.41 |
| ATOM | 3041 | CA | PRO | A | 397 | −17.016 | 32.626 | −28.256 | 1.00 | 20.82 |
| ATOM | 3042 | CB | PRO | A | 397 | −15.794 | 32.561 | −29.175 | 1.00 | 21.47 |
| ATOM | 3043 | CG | PRO | A | 397 | −14.819 | 31.725 | −28.475 | 1.00 | 21.69 |
| ATOM | 3044 | CD | PRO | A | 397 | −15.598 | 30.741 | −27.661 | 1.00 | 19.70 |
| ATOM | 3045 | C | PRO | A | 397 | −18.280 | 32.434 | −29.073 | 1.00 | 21.11 |
| ATOM | 3046 | O | PRO | A | 397 | −18.844 | 31.339 | −29.088 | 1.00 | 19.88 |
| ATOM | 3047 | N | ALA | A | 398 | −18.713 | 33.492 | −29.765 | 1.00 | 21.26 |
| ATOM | 3048 | CA | ALA | A | 398 | −19.951 | 33.424 | −30.559 | 1.00 | 21.44 |
| ATOM | 3049 | CB | ALA | A | 398 | −20.227 | 34.766 | −31.230 | 1.00 | 22.38 |
| ATOM | 3050 | C | ALA | A | 398 | −19.971 | 32.297 | −31.587 | 1.00 | 21.30 |
| ATOM | 3051 | O | ALA | A | 398 | −21.038 | 31.769 | −31.901 | 1.00 | 22.15 |
| ATOM | 3052 | N | ASP | A | 399 | −18.804 | 31.896 | −32.102 | 1.00 | 20.30 |
| ATOM | 3053 | CA | ASP | A | 399 | −18.780 | 30.858 | −33.133 | 1.00 | 19.40 |
| ATOM | 3054 | CB | ASP | A | 399 | −17.587 | 31.032 | −34.071 | 1.00 | 19.42 |
| ATOM | 3055 | CG | ASP | A | 399 | −16.233 | 30.835 | −33.381 | 1.00 | 21.84 |
| ATOM | 3056 | OD1 | ASP | A | 399 | −16.146 | 30.569 | −32.159 | 1.00 | 20.91 |
| ATOM | 3057 | OD2 | ASP | A | 399 | −15.229 | 30.950 | −34.104 | 1.00 | 24.62 |
| ATOM | 3058 | C | ASP | A | 399 | −18.834 | 29.435 | −32.579 | 1.00 | 18.14 |
| ATOM | 3059 | O | ASP | A | 399 | −18.802 | 28.465 | −33.350 | 1.00 | 16.78 |
| ATOM | 3060 | N | GLY | A | 400 | −18.891 | 29.322 | −31.245 | 1.00 | 16.82 |

TABLE 20-continued

| | | | | | | | | | |
|---|---|---|---|---|---|---|---|---|---|
| ATOM | 3061 | CA | GLY | A | 400 | −18.996 | 28.015 | −30.607 | 1.00 | 15.41 |
| ATOM | 3062 | C | GLY | A | 400 | −17.693 | 27.229 | −30.556 | 1.00 | 15.07 |
| ATOM | 3063 | O | GLY | A | 400 | −17.704 | 26.041 | −30.203 | 1.00 | 15.23 |
| ATOM | 3064 | N | SER | A | 401 | −16.572 | 27.861 | −30.882 | 1.00 | 14.21 |
| ATOM | 3065 | CA | SER | A | 401 | −15.312 | 27.119 | −30.893 | 1.00 | 14.76 |
| ATOM | 3066 | CB | SER | A | 401 | −14.241 | 27.840 | −31.718 | 1.00 | 14.71 |
| ATOM | 3067 | OG | SER | A | 401 | −14.059 | 29.160 | −31.257 | 1.00 | 16.86 |
| ATOM | 3068 | C | SER | A | 401 | −14.815 | 26.866 | −29.448 | 1.00 | 14.38 |
| ATOM | 3069 | O | SER | A | 401 | −14.992 | 27.717 | −28.562 | 1.00 | 14.58 |
| ATOM | 3070 | N | LEU | A | 402 | −14.169 | 25.720 | −29.249 | 1.00 | 13.54 |
| ATOM | 3071 | CA | LEU | A | 402 | −13.603 | 25.364 | −27.968 | 1.00 | 13.21 |
| ATOM | 3072 | CB | LEU | A | 402 | −14.271 | 24.080 | −27.450 | 1.00 | 13.42 |
| ATOM | 3073 | CG | LEU | A | 402 | −15.776 | 24.192 | −27.162 | 1.00 | 14.06 |
| ATOM | 3074 | CD1 | LEU | A | 402 | −16.289 | 22.834 | −26.668 | 1.00 | 13.87 |
| ATOM | 3075 | CD2 | LEU | A | 402 | −15.997 | 25.264 | −26.109 | 1.00 | 17.00 |
| ATOM | 3076 | C | LEU | A | 402 | −12.111 | 25.143 | −28.109 | 1.00 | 12.99 |
| ATOM | 3077 | O | LEU | A | 402 | −11.695 | 24.166 | −28.707 | 1.00 | 13.19 |
| ATOM | 3078 | N | ALA | A | 403 | −11.320 | 26.070 | −27.578 | 1.00 | 13.02 |
| ATOM | 3079 | CA | ALA | A | 403 | −9.884 | 25.870 | −27.454 | 1.00 | 12.06 |
| ATOM | 3080 | CB | ALA | A | 403 | −9.194 | 27.226 | −27.220 | 1.00 | 11.77 |
| ATOM | 3081 | C | ALA | A | 403 | −9.591 | 24.907 | −26.300 | 1.00 | 12.81 |
| ATOM | 3082 | O | ALA | A | 403 | −10.508 | 24.315 | −25.714 | 1.00 | 12.36 |
| ATOM | 3083 | N | GLU | A | 404 | −8.308 | 24.772 | −25.959 | 1.00 | 11.39 |
| ATOM | 3084 | CA | GLU | A | 404 | −7.918 | 23.922 | −24.855 | 1.00 | 11.47 |
| ATOM | 3085 | CB | GLU | A | 404 | −6.412 | 23.689 | −24.931 | 1.00 | 11.02 |
| ATOM | 3086 | CG | GLU | A | 404 | −5.865 | 22.723 | −23.873 | 1.00 | 11.30 |
| ATOM | 3087 | CD | GLU | A | 404 | −4.363 | 22.669 | −23.954 | 1.00 | 12.25 |
| ATOM | 3088 | OE1 | GLU | A | 404 | −3.729 | 23.692 | −23.622 | 1.00 | 12.06 |
| ATOM | 3089 | OE2 | GLU | A | 404 | −3.818 | 21.624 | −24.390 | 1.00 | 12.60 |
| ATOM | 3090 | C | GLU | A | 404 | −8.246 | 24.635 | −23.538 | 1.00 | 11.77 |
| ATOM | 3091 | O | GLU | A | 404 | −8.755 | 24.006 | −22.590 | 1.00 | 11.08 |
| ATOM | 3092 | N | GLN | A | 405 | −7.890 | 25.924 | −23.453 | 1.00 | 12.07 |
| ATOM | 3093 | CA | GLN | A | 405 | −7.952 | 26.655 | −22.196 | 1.00 | 13.33 |
| ATOM | 3094 | CB | GLN | A | 405 | −6.539 | 26.986 | −21.678 | 1.00 | 13.24 |
| ATOM | 3095 | CG | GLN | A | 405 | −5.625 | 25.821 | −21.553 | 1.00 | 15.96 |
| ATOM | 3096 | CD | GLN | A | 405 | −4.229 | 26.213 | −21.051 | 1.00 | 14.97 |
| ATOM | 3097 | OE1 | GLN | A | 405 | −4.068 | 27.130 | −20.236 | 1.00 | 15.09 |
| ATOM | 3098 | NE2 | GLN | A | 405 | −3.236 | 25.475 | −21.496 | 1.00 | 15.87 |
| ATOM | 3099 | C | GLN | A | 405 | −8.687 | 27.985 | −22.356 | 1.00 | 13.51 |
| ATOM | 3100 | O | GLN | A | 405 | −8.870 | 28.475 | −23.489 | 1.00 | 13.74 |
| ATOM | 3101 | N | PHE | A | 406 | −9.041 | 28.587 | −21.226 | 1.00 | 12.60 |
| ATOM | 3102 | CA | PHE | A | 406 | −9.516 | 29.990 | −21.207 | 1.00 | 13.82 |
| ATOM | 3103 | CB | PHE | A | 406 | −11.058 | 30.104 | −21.232 | 1.00 | 13.56 |
| ATOM | 3104 | CG | PHE | A | 406 | −11.800 | 29.385 | −20.123 | 1.00 | 15.20 |
| ATOM | 3105 | CD1 | PHE | A | 406 | −12.155 | 28.026 | −20.242 | 1.00 | 16.33 |
| ATOM | 3106 | CE1 | PHE | A | 406 | −12.879 | 27.370 | −19.239 | 1.00 | 16.80 |
| ATOM | 3107 | CZ | PHE | A | 406 | −13.340 | 28.094 | −18.114 | 1.00 | 16.74 |
| ATOM | 3108 | CE2 | PHE | A | 406 | −13.020 | 29.453 | −17.993 | 1.00 | 15.37 |
| ATOM | 3109 | CD2 | PHE | A | 406 | −12.260 | 30.101 | −19.000 | 1.00 | 17.56 |
| ATOM | 3110 | C | PHE | A | 406 | −8.836 | 30.737 | −20.078 | 1.00 | 13.80 |
| ATOM | 3111 | O | PHE | A | 406 | −8.587 | 30.151 | −19.018 | 1.00 | 14.02 |
| ATOM | 3112 | N | ASP | A | 407 | −8.481 | 31.997 | −20.321 | 1.00 | 14.98 |
| ATOM | 3113 | CA | ASP | A | 407 | −7.547 | 32.726 | −19.438 | 1.00 | 15.04 |
| ATOM | 3114 | CB | ASP | A | 407 | −7.237 | 34.115 | −20.032 | 1.00 | 15.99 |
| ATOM | 3115 | CG | ASP | A | 407 | −6.159 | 34.829 | −19.293 | 1.00 | 18.17 |
| ATOM | 3116 | OD1 | ASP | A | 407 | −6.474 | 35.508 | −18.293 | 1.00 | 20.41 |
| ATOM | 3117 | OD2 | ASP | A | 407 | −4.993 | 34.683 | −19.685 | 1.00 | 20.75 |
| ATOM | 3118 | C | ASP | A | 407 | −8.100 | 32.829 | −18.005 | 1.00 | 14.54 |
| ATOM | 3119 | O | ASP | A | 407 | −9.257 | 33.185 | −17.800 | 1.00 | 15.12 |
| ATOM | 3120 | N | ARG | A | 408 | −7.248 | 32.548 | −17.018 | 1.00 | 14.63 |
| ATOM | 3121 | CA | ARG | A | 408 | −7.644 | 32.530 | −15.609 | 1.00 | 15.33 |
| ATOM | 3122 | CB | ARG | A | 408 | −6.453 | 32.095 | −14.753 | 1.00 | 15.32 |
| ATOM | 3123 | CG | ARG | A | 408 | −5.236 | 33.062 | −14.828 | 1.00 | 14.48 |
| ATOM | 3124 | CD | ARG | A | 408 | −4.009 | 32.479 | −14.122 | 1.00 | 16.22 |
| ATOM | 3125 | NE | ARG | A | 408 | −4.237 | 32.248 | −12.695 | 1.00 | 15.55 |
| ATOM | 3126 | CZ | ARG | A | 408 | −3.613 | 31.323 | −11.961 | 1.00 | 18.66 |
| ATOM | 3127 | NH1 | ARG | A | 408 | −3.878 | 31.231 | −10.658 | 1.00 | 17.51 |
| ATOM | 3128 | NH2 | ARG | A | 408 | −2.717 | 30.499 | −12.511 | 1.00 | 17.12 |
| ATOM | 3129 | C | ARG | A | 408 | −8.167 | 33.886 | −15.108 | 1.00 | 16.66 |
| ATOM | 3130 | O | ARG | A | 408 | −8.898 | 33.943 | −14.110 | 1.00 | 16.82 |
| ATOM | 3131 | N | ASN | A | 409 | −7.781 | 34.964 | −15.790 | 1.00 | 18.00 |
| ATOM | 3132 | CA | ASN | A | 409 | −8.252 | 36.316 | −15.421 | 1.00 | 20.06 |
| ATOM | 3133 | CB | ASN | A | 409 | −7.069 | 37.275 | −15.355 | 1.00 | 20.32 |
| ATOM | 3134 | CG | ASN | A | 409 | −6.119 | 36.937 | −14.224 | 1.00 | 21.65 |
| ATOM | 3135 | OD1 | ASN | A | 409 | −6.549 | 36.678 | −13.111 | 1.00 | 24.42 |
| ATOM | 3136 | ND2 | ASN | A | 409 | −4.830 | 36.914 | −14.516 | 1.00 | 23.96 |
| ATOM | 3137 | C | ASN | A | 409 | −9.320 | 36.903 | −16.336 | 1.00 | 21.43 |
| ATOM | 3138 | O | ASN | A | 409 | −10.272 | 37.524 | −15.857 | 1.00 | 22.03 |
| ATOM | 3139 | N | SER | A | 410 | −9.152 | 36.724 | −17.646 | 1.00 | 22.25 |
| ATOM | 3140 | CA | SER | A | 410 | −10.007 | 37.410 | −18.624 | 1.00 | 22.76 |

TABLE 20-continued

| | | | | | | | | | |
|---|---|---|---|---|---|---|---|---|---|
| ATOM | 3141 | CB | SER | A | 410 | −9.146 | 38.159 | −19.636 | 1.00 | 23.45 |
| ATOM | 3142 | OG | SER | A | 410 | −8.470 | 37.260 | −20.495 | 1.00 | 23.38 |
| ATOM | 3143 | C | SER | A | 410 | −10.971 | 36.472 | −19.343 | 1.00 | 22.82 |
| ATOM | 3144 | O | SER | A | 410 | −11.898 | 36.925 | −20.010 | 1.00 | 23.59 |
| ATOM | 3145 | N | GLY | A | 411 | −10.758 | 35.161 | −19.238 | 1.00 | 21.64 |
| ATOM | 3146 | CA | GLY | A | 411 | −11.668 | 34.221 | −19.877 | 1.00 | 20.39 |
| ATOM | 3147 | C | GLY | A | 411 | −11.476 | 34.087 | −21.379 | 1.00 | 19.99 |
| ATOM | 3148 | O | GLY | A | 411 | −12.223 | 33.368 | −22.029 | 1.00 | 20.85 |
| ATOM | 3149 | N | THR | A | 412 | −10.478 | 34.750 | −21.941 | 1.00 | 19.04 |
| ATOM | 3150 | CA | THR | A | 412 | −10.268 | 34.658 | −23.383 | 1.00 | 20.25 |
| ATOM | 3151 | CB | THR | A | 412 | −9.447 | 35.853 | −23.922 | 1.00 | 21.81 |
| ATOM | 3152 | OG1 | THR | A | 412 | −8.187 | 35.900 | −23.257 | 1.00 | 26.24 |
| ATOM | 3153 | CG2 | THR | A | 412 | −10.160 | 37.163 | −23.631 | 1.00 | 23.82 |
| ATOM | 3154 | C | THR | A | 412 | −9.615 | 33.294 | −23.732 | 1.00 | 19.17 |
| ATOM | 3155 | O | THR | A | 412 | −8.786 | 32.796 | −22.970 | 1.00 | 17.70 |
| ATOM | 3156 | N | PRO | A | 413 | −9.996 | 32.688 | −24.874 | 1.00 | 18.84 |
| ATOM | 3157 | CA | PRO | A | 413 | −9.466 | 31.348 | −25.234 | 1.00 | 18.32 |
| ATOM | 3158 | CB | PRO | A | 413 | −10.220 | 31.002 | −26.525 | 1.00 | 18.75 |
| ATOM | 3159 | CG | PRO | A | 413 | −11.513 | 31.928 | −26.451 | 1.00 | 19.42 |
| ATOM | 3160 | CD | PRO | A | 413 | −10.943 | 33.195 | −25.891 | 1.00 | 19.40 |
| ATOM | 3161 | C | PRO | A | 413 | −7.959 | 31.399 | −25.464 | 1.00 | 18.87 |
| ATOM | 3162 | O | PRO | A | 413 | −7.436 | 32.406 | −25.955 | 1.00 | 18.20 |
| ATOM | 3163 | N | LEU | A | 414 | −7.253 | 30.353 | −25.051 | 1.00 | 18.44 |
| ATOM | 3164 | CA | LEU | A | 414 | −5.822 | 30.275 | −25.305 | 1.00 | 18.90 |
| ATOM | 3165 | CB | LEU | A | 414 | −4.992 | 30.974 | −24.208 | 1.00 | 21.66 |
| ATOM | 3166 | CG | LEU | A | 414 | −5.019 | 30.574 | −22.754 | 1.00 | 24.35 |
| ATOM | 3167 | CD1 | LEU | A | 414 | −4.134 | 31.484 | −21.892 | 1.00 | 27.42 |
| ATOM | 3168 | CD2 | LEU | A | 414 | −6.406 | 30.669 | −22.224 | 1.00 | 30.77 |
| ATOM | 3169 | C | LEU | A | 414 | −5.362 | 28.854 | −25.518 | 1.00 | 17.24 |
| ATOM | 3170 | O | LEU | A | 414 | −6.138 | 27.913 | −25.406 | 1.00 | 15.97 |
| ATOM | 3171 | N | SER | A | 415 | −4.091 | 28.733 | −25.865 | 1.00 | 15.34 |
| ATOM | 3172 | CA | SER | A | 415 | −3.473 | 27.481 | −26.257 | 1.00 | 15.28 |
| ATOM | 3173 | CB | SER | A | 415 | −3.434 | 26.468 | −25.101 | 1.00 | 14.94 |
| ATOM | 3174 | OG | SER | A | 415 | −2.632 | 25.355 | −25.445 | 1.00 | 14.00 |
| ATOM | 3175 | C | SER | A | 415 | −4.141 | 26.932 | −27.528 | 1.00 | 15.13 |
| ATOM | 3176 | O | SER | A | 415 | −4.665 | 27.718 | −28.334 | 1.00 | 14.92 |
| ATOM | 3177 | N | ALA | A | 416 | −4.097 | 25.618 | −27.714 | 1.00 | 14.27 |
| ATOM | 3178 | CA | ALA | A | 416 | −4.540 | 24.977 | −28.976 | 1.00 | 14.25 |
| ATOM | 3179 | CB | ALA | A | 416 | −4.380 | 23.486 | −28.889 | 1.00 | 13.68 |
| ATOM | 3180 | C | ALA | A | 416 | −5.981 | 25.314 | −29.315 | 1.00 | 14.33 |
| ATOM | 3181 | O | ALA | A | 416 | −6.854 | 25.216 | −28.459 | 1.00 | 14.09 |
| ATOM | 3182 | N | LEU | A | 417 | −6.223 | 25.680 | −30.567 | 1.00 | 13.34 |
| ATOM | 3183 | CA | LEU | A | 417 | −7.584 | 25.985 | −31.006 | 1.00 | 14.22 |
| ATOM | 3184 | CB | LEU | A | 417 | −7.536 | 26.931 | −32.194 | 1.00 | 16.32 |
| ATOM | 3185 | CG | LEU | A | 417 | −6.841 | 28.283 | −31.942 | 1.00 | 18.75 |
| ATOM | 3186 | CD1 | LEU | A | 417 | −7.005 | 29.127 | −33.163 | 1.00 | 23.81 |
| ATOM | 3187 | CD2 | LEU | A | 417 | −7.419 | 28.991 | −30.712 | 1.00 | 21.76 |
| ATOM | 3188 | C | LEU | A | 417 | −8.279 | 24.687 | −31.413 | 1.00 | 13.18 |
| ATOM | 3189 | O | LEU | A | 417 | −7.610 | 23.712 | −31.775 | 1.00 | 13.19 |
| ATOM | 3190 | N | HIS | A | 418 | −9.609 | 24.658 | −31.311 | 1.00 | 12.26 |
| ATOM | 3191 | CA | HIS | A | 418 | −10.399 | 23.496 | −31.764 | 1.00 | 11.77 |
| ATOM | 3192 | CB | HIS | A | 418 | −10.487 | 23.454 | −33.303 | 1.00 | 13.41 |
| ATOM | 3193 | CG | HIS | A | 418 | −11.294 | 24.566 | −33.898 | 1.00 | 14.68 |
| ATOM | 3194 | ND1 | HIS | A | 418 | −12.646 | 24.717 | −33.660 | 1.00 | 16.00 |
| ATOM | 3195 | CE1 | HIS | A | 418 | −13.095 | 25.762 | −34.341 | 1.00 | 17.83 |
| ATOM | 3196 | NE2 | HIS | A | 418 | −12.085 | 26.290 | −35.015 | 1.00 | 17.38 |
| ATOM | 3197 | CD2 | HIS | A | 418 | −10.948 | 25.557 | −34.763 | 1.00 | 17.65 |
| ATOM | 3198 | C | HIS | A | 418 | −9.826 | 22.187 | −31.206 | 1.00 | 12.24 |
| ATOM | 3199 | O | HIS | A | 418 | −9.540 | 21.250 | −31.947 | 1.00 | 12.10 |
| ATOM | 3200 | N | LEU | A | 419 | −9.656 | 22.116 | −29.880 | 1.00 | 10.99 |
| ATOM | 3201 | CA | LEU | A | 419 | −9.152 | 20.881 | −29.301 | 1.00 | 10.46 |
| ATOM | 3202 | CB | LEU | A | 419 | −8.742 | 21.069 | −27.826 | 1.00 | 10.91 |
| ATOM | 3203 | CG | LEU | A | 419 | −7.983 | 19.883 | −27.220 | 1.00 | 10.16 |
| ATOM | 3204 | CD1 | LEU | A | 419 | −6.524 | 19.944 | −27.669 | 1.00 | 11.45 |
| ATOM | 3205 | CD2 | LEU | A | 419 | −8.080 | 19.960 | −25.657 | 1.00 | 10.73 |
| ATOM | 3206 | C | LEU | A | 419 | −10.215 | 19.812 | −29.398 | 1.00 | 10.49 |
| ATOM | 3207 | O | LEU | A | 419 | −11.312 | 19.973 | −28.863 | 1.00 | 10.67 |
| ATOM | 3208 | N | THR | A | 420 | −9.860 | 18.686 | −30.021 | 1.00 | 10.22 |
| ATOM | 3209 | CA | THR | A | 420 | −10.833 | 17.629 | −30.296 | 1.00 | 10.90 |
| ATOM | 3210 | CB | THR | A | 420 | −10.201 | 16.460 | −31.096 | 1.00 | 11.55 |
| ATOM | 3211 | OG1 | THR | A | 420 | −9.357 | 16.999 | −32.115 | 1.00 | 12.00 |
| ATOM | 3212 | CG2 | THR | A | 420 | −11.310 | 15.625 | −31.786 | 1.00 | 12.52 |
| ATOM | 3213 | C | THR | A | 420 | −11.426 | 17.135 | −28.995 | 1.00 | 11.43 |
| ATOM | 3214 | O | THR | A | 420 | −12.648 | 16.903 | −28.891 | 1.00 | 11.83 |
| ATOM | 3215 | N | TRP | A | 421 | −10.569 | 16.987 | −27.980 | 1.00 | 9.79 |
| ATOM | 3216 | CA | TRP | A | 421 | −11.052 | 16.511 | −26.688 | 1.00 | 11.67 |
| ATOM | 3217 | CB | TRP | A | 421 | −9.839 | 16.184 | −25.803 | 1.00 | 12.06 |
| ATOM | 3218 | CG | TRP | A | 421 | −10.075 | 15.476 | −24.508 | 1.00 | 11.94 |
| ATOM | 3219 | CD1 | TRP | A | 421 | −11.274 | 15.202 | −23.881 | 1.00 | 14.46 |
| ATOM | 3220 | NE1 | TRP | A | 421 | −11.044 | 14.590 | −22.663 | 1.00 | 14.38 |

TABLE 20-continued

| | | | | | | | | | |
|---|---|---|---|---|---|---|---|---|---|
| ATOM | 3221 | CE2 | TRP | A | 421 | −9.691 | 14.497 | −22.468 | 1.00 | 13.52 |
| ATOM | 3222 | CD2 | TRP | A | 421 | −9.053 | 15.039 | −23.616 | 1.00 | 13.01 |
| ATOM | 3223 | CE3 | TRP | A | 421 | −7.652 | 15.045 | −23.680 | 1.00 | 15.38 |
| ATOM | 3224 | CZ3 | TRP | A | 421 | −6.932 | 14.503 | −22.605 | 1.00 | 16.10 |
| ATOM | 3225 | CH2 | TRP | A | 421 | −7.603 | 13.973 | −21.475 | 1.00 | 14.87 |
| ATOM | 3226 | CZ2 | TRP | A | 421 | −8.973 | 13.945 | −21.398 | 1.00 | 14.27 |
| ATOM | 3227 | C | TRP | A | 421 | −12.035 | 17.514 | −26.032 | 1.00 | 10.89 |
| ATOM | 3228 | O | TRP | A | 421 | −12.966 | 17.092 | −25.357 | 1.00 | 10.96 |
| ATOM | 3229 | N | SER | A | 422 | −11.844 | 18.822 | −26.211 | 1.00 | 10.49 |
| ATOM | 3230 | CA | SER | A | 422 | −12.833 | 19.794 | −25.696 | 1.00 | 11.13 |
| ATOM | 3231 | CB | SER | A | 422 | −12.459 | 21.243 | −26.049 | 1.00 | 10.97 |
| ATOM | 3232 | OG | SER | A | 422 | −11.302 | 21.682 | −25.338 | 1.00 | 13.73 |
| ATOM | 3233 | C | SER | A | 422 | −14.229 | 19.496 | −26.257 | 1.00 | 11.40 |
| ATOM | 3234 | O | SER | A | 422 | −15.204 | 19.468 | −25.530 | 1.00 | 12.11 |
| ATOM | 3235 | N | TYR | A | 423 | −14.320 | 19.281 | −27.563 | 1.00 | 11.29 |
| ATOM | 3236 | CA | TYR | A | 423 | −15.617 | 18.990 | −28.170 | 1.00 | 11.29 |
| ATOM | 3237 | CB | TYR | A | 423 | −15.502 | 19.020 | −29.717 | 1.00 | 11.85 |
| ATOM | 3238 | CG | TYR | A | 423 | −15.132 | 20.389 | −30.274 | 1.00 | 12.18 |
| ATOM | 3239 | CD1 | TYR | A | 423 | −16.002 | 21.485 | −30.145 | 1.00 | 10.35 |
| ATOM | 3240 | CE1 | TYR | A | 423 | −15.668 | 22.741 | −30.643 | 1.00 | 11.83 |
| ATOM | 3241 | CZ | TYR | A | 423 | −14.468 | 22.912 | −31.316 | 1.00 | 12.29 |
| ATOM | 3242 | OH | TYR | A | 423 | −14.157 | 24.145 | −31.783 | 1.00 | 13.08 |
| ATOM | 3243 | CE2 | TYR | A | 423 | −13.588 | 21.845 | −31.496 | 1.00 | 13.57 |
| ATOM | 3244 | CD2 | TYR | A | 423 | −13.942 | 20.572 | −30.991 | 1.00 | 12.74 |
| ATOM | 3245 | C | TYR | A | 423 | −16.217 | 17.673 | −27.658 | 1.00 | 12.12 |
| ATOM | 3246 | O | TYR | A | 423 | −17.430 | 17.622 | −27.323 | 1.00 | 12.13 |
| ATOM | 3247 | N | ALA | A | 424 | −15.385 | 16.623 | −27.539 | 1.00 | 10.99 |
| ATOM | 3248 | CA | ALA | A | 424 | −15.853 | 15.337 | −26.986 | 1.00 | 11.26 |
| ATOM | 3249 | CB | ALA | A | 424 | −14.717 | 14.294 | −26.952 | 1.00 | 11.73 |
| ATOM | 3250 | C | ALA | A | 424 | −16.411 | 15.535 | −25.588 | 1.00 | 10.93 |
| ATOM | 3251 | O | ALA | A | 424 | −17.465 | 14.974 | −25.246 | 1.00 | 11.68 |
| ATOM | 3252 | N | SER | A | 425 | −15.696 | 16.308 | −24.770 | 1.00 | 9.74 |
| ATOM | 3253 | CA | SER | A | 425 | −16.077 | 16.519 | −23.379 | 1.00 | 10.92 |
| ATOM | 3254 | CB | SER | A | 425 | −14.948 | 17.228 | −22.602 | 1.00 | 11.59 |
| ATOM | 3255 | OG | SER | A | 425 | −14.817 | 18.604 | −22.957 | 1.00 | 13.86 |
| ATOM | 3256 | C | SER | A | 425 | −17.402 | 17.291 | −23.219 | 1.00 | 11.65 |
| ATOM | 3257 | O | SER | A | 425 | −18.132 | 17.043 | −22.276 | 1.00 | 11.86 |
| ATOM | 3258 | N | PHE | A | 426 | −17.683 | 18.220 | −24.133 | 1.00 | 12.13 |
| ATOM | 3259 | CA | PHE | A | 426 | −18.983 | 18.891 | −24.154 | 1.00 | 12.95 |
| ATOM | 3260 | CB | PHE | A | 426 | −19.018 | 20.053 | −25.173 | 1.00 | 13.14 |
| ATOM | 3261 | CG | PHE | A | 426 | −20.410 | 20.575 | −25.391 | 1.00 | 15.93 |
| ATOM | 3262 | CD1 | PHE | A | 426 | −20.951 | 21.522 | −24.516 | 1.00 | 17.76 |
| ATOM | 3263 | CE1 | PHE | A | 426 | −22.279 | 21.980 | −24.688 | 1.00 | 17.49 |
| ATOM | 3264 | CZ | PHE | A | 426 | −23.064 | 21.455 | −25.716 | 1.00 | 17.22 |
| ATOM | 3265 | CE2 | PHE | A | 426 | −22.561 | 20.496 | −26.558 | 1.00 | 17.04 |
| ATOM | 3266 | CD2 | PHE | A | 426 | −21.225 | 20.045 | −26.396 | 1.00 | 17.29 |
| ATOM | 3267 | C | PHE | A | 426 | −20.079 | 17.878 | −24.502 | 1.00 | 13.31 |
| ATOM | 3268 | O | PHE | A | 426 | −21.120 | 17.827 | −23.850 | 1.00 | 13.38 |
| ATOM | 3269 | N | LEU | A | 427 | −19.834 | 17.077 | −25.539 | 1.00 | 13.23 |
| ATOM | 3270 | CA | LEU | A | 427 | −20.811 | 16.090 | −25.996 | 1.00 | 14.41 |
| ATOM | 3271 | CB | LEU | A | 427 | −20.339 | 15.410 | −27.291 | 1.00 | 14.32 |
| ATOM | 3272 | CG | LEU | A | 427 | −20.363 | 16.336 | −28.506 | 1.00 | 15.96 |
| ATOM | 3273 | CD1 | LEU | A | 427 | −19.661 | 15.639 | −29.689 | 1.00 | 18.66 |
| ATOM | 3274 | CD2 | LEU | A | 427 | −21.773 | 16.800 | −28.876 | 1.00 | 16.20 |
| ATOM | 3275 | C | LEU | A | 427 | −21.137 | 15.045 | −24.959 | 1.00 | 14.86 |
| ATOM | 3276 | O | LEU | A | 427 | −22.307 | 14.667 | −24.833 | 1.00 | 16.01 |
| ATOM | 3277 | N | THR | A | 428 | −20.130 | 14.551 | −24.235 | 1.00 | 13.81 |
| ATOM | 3278 | CA | THR | A | 428 | −20.397 | 13.544 | −23.196 | 1.00 | 13.67 |
| ATOM | 3279 | CB | THR | A | 428 | −19.134 | 12.732 | −22.745 | 1.00 | 12.87 |
| ATOM | 3280 | OG1 | THR | A | 428 | −18.127 | 13.597 | −22.185 | 1.00 | 12.33 |
| ATOM | 3281 | CG2 | THR | A | 428 | −18.533 | 11.902 | −23.923 | 1.00 | 13.77 |
| ATOM | 3282 | C | THR | A | 428 | −21.146 | 14.133 | −21.980 | 1.00 | 13.66 |
| ATOM | 3283 | O | THR | A | 428 | −22.102 | 13.517 | −21.478 | 1.00 | 15.09 |
| ATOM | 3284 | N | ALA | A | 429 | −20.738 | 15.312 | −21.524 | 1.00 | 13.72 |
| ATOM | 3285 | CA | ALA | A | 429 | −21.367 | 15.942 | −20.355 | 1.00 | 14.65 |
| ATOM | 3286 | CB | ALA | A | 429 | −20.704 | 17.295 | −20.036 | 1.00 | 14.11 |
| ATOM | 3287 | C | ALA | A | 429 | −22.852 | 16.158 | −20.643 | 1.00 | 15.47 |
| ATOM | 3288 | O | ALA | A | 429 | −23.704 | 15.908 | −19.783 | 1.00 | 15.97 |
| ATOM | 3289 | N | THR | A | 430 | −23.151 | 16.622 | −21.854 | 1.00 | 15.48 |
| ATOM | 3290 | CA | THR | A | 430 | −24.554 | 16.940 | −22.208 | 1.00 | 15.64 |
| ATOM | 3291 | CB | THR | A | 430 | −24.675 | 17.968 | −23.353 | 1.00 | 16.50 |
| ATOM | 3292 | OG1 | THR | A | 430 | −23.980 | 17.494 | −24.514 | 1.00 | 16.24 |
| ATOM | 3293 | CG2 | THR | A | 430 | −24.101 | 19.317 | −22.916 | 1.00 | 16.43 |
| ATOM | 3294 | C | THR | A | 430 | −25.401 | 15.690 | −22.463 | 1.00 | 15.41 |
| ATOM | 3295 | O | THR | A | 430 | −26.611 | 15.674 | −22.158 | 1.00 | 15.67 |
| ATOM | 3296 | N | ALA | A | 431 | −24.772 | 14.632 | −22.968 | 1.00 | 15.22 |
| ATOM | 3297 | CA | ALA | A | 431 | −25.437 | 13.311 | −23.049 | 1.00 | 16.26 |
| ATOM | 3298 | CB | ALA | A | 431 | −24.560 | 12.300 | −23.762 | 1.00 | 16.39 |
| ATOM | 3299 | C | ALA | A | 431 | −25.842 | 12.797 | −21.673 | 1.00 | 16.53 |
| ATOM | 3300 | O | ALA | A | 431 | −26.985 | 12.319 | −21.485 | 1.00 | 16.61 |

TABLE 20-continued

| | | | | | | | | | |
|---|---|---|---|---|---|---|---|---|---|
| ATOM | 3301 | N | ARG | A | 432 | −24.937 | 12.895 | −20.689 | 1.00 | 15.66 |
| ATOM | 3302 | CA | ARG | A | 432 | −25.256 | 12.410 | −19.342 | 1.00 | 15.64 |
| ATOM | 3303 | CB | ARG | A | 432 | −24.022 | 12.413 | −18.432 | 1.00 | 15.83 |
| ATOM | 3304 | CG | ARG | A | 432 | −22.862 | 11.574 | −18.994 | 1.00 | 14.85 |
| ATOM | 3305 | CD | ARG | A | 432 | −23.174 | 10.051 | −19.154 | 1.00 | 17.10 |
| ATOM | 3306 | NE | ARG | A | 432 | −21.958 | 9.472 | −19.708 | 1.00 | 18.67 |
| ATOM | 3307 | CZ | ARG | A | 432 | −21.766 | 9.225 | −21.003 | 1.00 | 20.81 |
| ATOM | 3308 | NH1 | ARG | A | 432 | −22.769 | 9.372 | −21.868 | 1.00 | 17.45 |
| ATOM | 3309 | NH2 | ARG | A | 432 | −20.576 | 8.781 | −21.427 | 1.00 | 19.90 |
| ATOM | 3310 | C | ARG | A | 432 | −26.375 | 13.235 | −18.719 | 1.00 | 16.42 |
| ATOM | 3311 | O | ARG | A | 432 | −27.256 | 12.685 | −18.030 | 1.00 | 17.47 |
| ATOM | 3312 | N | ARG | A | 433 | −26.371 | 14.535 | −18.996 | 1.00 | 16.54 |
| ATOM | 3313 | CA | ARG | A | 433 | −27.425 | 15.418 | −18.493 | 1.00 | 17.60 |
| ATOM | 3314 | CB | ARG | A | 433 | −27.204 | 16.852 | −18.960 | 1.00 | 16.74 |
| ATOM | 3315 | CG | ARG | A | 433 | −28.287 | 17.833 | −18.461 | 1.00 | 18.39 |
| ATOM | 3316 | CD | ARG | A | 433 | −27.931 | 19.239 | −18.866 | 1.00 | 20.79 |
| ATOM | 3317 | NE | ARG | A | 433 | −28.739 | 20.260 | −18.166 | 1.00 | 23.05 |
| ATOM | 3318 | CZ | ARG | A | 433 | −29.859 | 20.799 | −18.654 | 1.00 | 26.97 |
| ATOM | 3319 | NH1 | ARG | A | 433 | −30.333 | 20.404 | −19.837 | 1.00 | 24.94 |
| ATOM | 3320 | NH2 | ARG | A | 433 | −30.506 | 21.738 | −17.954 | 1.00 | 25.73 |
| ATOM | 3321 | C | ARG | A | 433 | −28.793 | 14.943 | −18.956 | 1.00 | 17.90 |
| ATOM | 3322 | O | ARG | A | 433 | −29.761 | 14.984 | −18.184 | 1.00 | 18.50 |
| ATOM | 3323 | N | ALA | A | 434 | −28.861 | 14.502 | −20.210 | 1.00 | 18.06 |
| ATOM | 3324 | CA | ALA | A | 434 | −30.103 | 13.993 | −20.806 | 1.00 | 19.10 |
| ATOM | 3325 | CB | ALA | A | 434 | −30.067 | 14.202 | −22.318 | 1.00 | 19.95 |
| ATOM | 3326 | C | ALA | A | 434 | −30.399 | 12.532 | −20.475 | 1.00 | 20.48 |
| ATOM | 3327 | O | ALA | A | 434 | −31.371 | 11.975 | −20.980 | 1.00 | 21.63 |
| ATOM | 3328 | N | GLY | A | 435 | −29.594 | 11.904 | −19.620 | 1.00 | 19.94 |
| ATOM | 3329 | CA | GLY | A | 435 | −29.865 | 10.531 | −19.182 | 1.00 | 21.09 |
| ATOM | 3330 | C | GLY | A | 435 | −29.415 | 9.475 | −20.188 | 1.00 | 21.57 |
| ATOM | 3331 | O | GLY | A | 435 | −29.847 | 8.304 | −20.130 | 1.00 | 21.64 |
| ATOM | 3332 | N | ILE | A | 436 | −28.529 | 9.873 | −21.100 | 1.00 | 20.44 |
| ATOM | 3333 | CA | ILE | A | 436 | −27.951 | 8.937 | −22.060 | 1.00 | 20.81 |
| ATOM | 3334 | CB | ILE | A | 436 | −27.753 | 9.601 | −23.447 | 1.00 | 20.75 |
| ATOM | 3335 | CG1 | ILE | A | 436 | −29.132 | 9.977 | −24.027 | 1.00 | 23.03 |
| ATOM | 3336 | CD1 | ILE | A | 436 | −29.103 | 11.031 | −25.128 | 1.00 | 26.34 |
| ATOM | 3337 | CG2 | ILE | A | 436 | −27.031 | 8.643 | −24.395 | 1.00 | 21.35 |
| ATOM | 3338 | C | ILE | A | 436 | −26.634 | 8.412 | −21.485 | 1.00 | 20.99 |
| ATOM | 3339 | O | ILE | A | 436 | −25.666 | 9.171 | −21.339 | 1.00 | 20.46 |
| ATOM | 3340 | N | VAL | A | 437 | −26.616 | 7.120 | −21.162 | 1.00 | 20.70 |
| ATOM | 3341 | CA | VAL | A | 437 | −25.465 | 6.479 | −20.517 | 1.00 | 21.39 |
| ATOM | 3342 | CB | VAL | A | 437 | −25.848 | 5.826 | −19.160 | 1.00 | 21.74 |
| ATOM | 3343 | CG1 | VAL | A | 437 | −26.340 | 6.911 | −18.205 | 1.00 | 22.12 |
| ATOM | 3344 | CG2 | VAL | A | 437 | −26.909 | 4.703 | −19.334 | 1.00 | 21.83 |
| ATOM | 3345 | C | VAL | A | 437 | −24.802 | 5.459 | −21.444 | 1.00 | 21.79 |
| ATOM | 3346 | O | VAL | A | 437 | −25.459 | 4.901 | −22.312 | 1.00 | 22.18 |
| ATOM | 3347 | N | PRO | A | 438 | −23.497 | 5.208 | −21.255 | 1.00 | 22.28 |
| ATOM | 3348 | CA | PRO | A | 438 | −22.837 | 4.291 | −22.181 | 1.00 | 22.83 |
| ATOM | 3349 | CB | PRO | A | 438 | −21.365 | 4.642 | −22.009 | 1.00 | 22.45 |
| ATOM | 3350 | CG | PRO | A | 438 | −21.248 | 5.054 | −20.578 | 1.00 | 23.88 |
| ATOM | 3351 | CD | PRO | A | 438 | −22.575 | 5.707 | −20.214 | 1.00 | 22.50 |
| ATOM | 3352 | C | PRO | A | 438 | −23.093 | 2.840 | −21.753 | 1.00 | 22.80 |
| ATOM | 3353 | O | PRO | A | 438 | −23.580 | 2.604 | −20.626 | 1.00 | 23.06 |
| ATOM | 3354 | N | PRO | A | 439 | −22.796 | 1.878 | −22.639 | 1.00 | 22.65 |
| ATOM | 3355 | CA | PRO | A | 439 | −22.911 | 0.452 | −22.283 | 1.00 | 22.08 |
| ATOM | 3356 | CB | PRO | A | 439 | −22.300 | −0.269 | −23.499 | 1.00 | 21.30 |
| ATOM | 3357 | CG | PRO | A | 439 | −22.526 | 0.664 | −24.618 | 1.00 | 22.81 |
| ATOM | 3358 | CD | PRO | A | 439 | −22.391 | 2.062 | −24.050 | 1.00 | 22.29 |
| ATOM | 3359 | C | PRO | A | 439 | −22.122 | 0.129 | −21.037 | 1.00 | 21.88 |
| ATOM | 3360 | O | PRO | A | 439 | −21.075 | 0.750 | −20.776 | 1.00 | 20.95 |
| ATOM | 3361 | N | SER | A | 440 | −22.628 | −0.818 | −20.253 | 1.00 | 22.34 |
| ATOM | 3362 | CA | SER | A | 440 | −21.932 | −1.273 | −19.060 | 1.00 | 23.42 |
| ATOM | 3363 | CB | SER | A | 440 | −22.818 | −2.195 | −18.224 | 1.00 | 24.01 |
| ATOM | 3364 | OG | SER | A | 440 | −23.805 | −1.412 | −17.566 | 1.00 | 26.78 |
| ATOM | 3365 | C | SER | A | 440 | −20.654 | −1.992 | −19.430 | 1.00 | 23.78 |
| ATOM | 3366 | O | SER | A | 440 | −20.540 | −2.554 | −20.522 | 1.00 | 23.97 |
| ATOM | 3367 | N | TRP | A | 441 | −19.681 | −1.929 | −18.536 | 1.00 | 24.15 |
| ATOM | 3368 | CA | TRP | A | 441 | −18.431 | −2.646 | −18.718 | 1.00 | 24.63 |
| ATOM | 3369 | CB | TRP | A | 441 | −17.255 | −1.679 | −18.819 | 1.00 | 22.62 |
| ATOM | 3370 | CG | TRP | A | 441 | −16.963 | −0.837 | −17.583 | 1.00 | 19.24 |
| ATOM | 3371 | CD1 | TRP | A | 441 | −17.409 | 0.432 | −17.339 | 1.00 | 16.95 |
| ATOM | 3372 | NE1 | TRP | A | 441 | −16.909 | 0.878 | −16.138 | 1.00 | 17.89 |
| ATOM | 3373 | CE2 | TRP | A | 441 | −16.111 | −0.098 | −15.595 | 1.00 | 17.88 |
| ATOM | 3374 | CD2 | TRP | A | 441 | −16.130 | −1.194 | −16.476 | 1.00 | 18.22 |
| ATOM | 3375 | CE3 | TRP | A | 441 | −15.377 | −2.338 | −16.149 | 1.00 | 19.64 |
| ATOM | 3376 | CZ3 | TRP | A | 441 | −14.658 | −2.355 | −14.961 | 1.00 | 18.61 |
| ATOM | 3377 | CH2 | TRP | A | 441 | −14.670 | −1.246 | −14.094 | 1.00 | 20.62 |
| ATOM | 3378 | CZ2 | TRP | A | 441 | −15.400 | −0.114 | −14.391 | 1.00 | 19.39 |
| ATOM | 3379 | C | TRP | A | 441 | −18.179 | −3.661 | −17.625 | 1.00 | 26.71 |
| ATOM | 3380 | O | TRP | A | 441 | −17.410 | −4.592 | −17.813 | 1.00 | 25.60 |

TABLE 20-continued

| | | | | | | | | |
|---|---|---|---|---|---|---|---|---|
| ATOM | 3381 | N | ALA | A | 442 | −18.798 | −3.471 | −16.468 | 1.00 | 29.78 |
| ATOM | 3382 | CA | ALA | A | 442 | −18.442 | −4.292 | −15.330 | 1.00 | 33.94 |
| ATOM | 3383 | CB | ALA | A | 442 | −18.347 | −3.447 | −14.082 | 1.00 | 33.18 |
| ATOM | 3384 | C | ALA | A | 442 | −19.447 | −5.412 | −15.136 | 1.00 | 37.28 |
| ATOM | 3385 | O | ALA | A | 442 | −20.383 | −5.561 | −15.915 | 1.00 | 38.51 |
| ATOM | 3386 | N | ASN | A | 443 | −19.201 | −6.222 | −14.116 | 1.00 | 41.45 |
| ATOM | 3387 | CA | ASN | A | 443 | −20.226 | −7.030 | −13.467 | 1.00 | 45.10 |
| ATOM | 3388 | CB | ASN | A | 443 | −20.135 | −8.490 | −13.914 | 1.00 | 45.75 |
| ATOM | 3389 | CG | ASN | A | 443 | −18.815 | −9.129 | −13.531 | 1.00 | 48.14 |
| ATOM | 3390 | OD1 | ASN | A | 443 | −18.620 | −9.524 | −12.380 | 1.00 | 50.51 |
| ATOM | 3391 | ND2 | ASN | A | 443 | −17.888 | −9.212 | −14.492 | 1.00 | 50.01 |
| ATOM | 3392 | C | ASN | A | 443 | −19.946 | −6.892 | −11.972 | 1.00 | 46.93 |
| ATOM | 3393 | O | ASN | A | 443 | −18.878 | −6.396 | −11.580 | 1.00 | 47.13 |
| ATOM | 3394 | N | SER | A | 444 | −20.873 | −7.343 | −11.135 | 1.00 | 49.21 |
| ATOM | 3395 | CA | SER | A | 444 | −20.719 | −7.201 | −9.684 | 1.00 | 51.08 |
| ATOM | 3396 | CB | SER | A | 444 | −21.713 | −8.096 | −8.936 | 1.00 | 51.21 |
| ATOM | 3397 | OG | SER | A | 444 | −21.738 | −7.735 | −7.563 | 1.00 | 52.90 |
| ATOM | 3398 | C | SER | A | 444 | −19.291 | −7.452 | −9.165 | 1.00 | 51.89 |
| ATOM | 3399 | O | SER | A | 444 | −18.743 | −6.610 | −8.433 | 1.00 | 52.46 |
| ATOM | 3400 | N | SER | A | 445 | −18.700 | −8.588 | −9.558 | 1.00 | 52.45 |
| ATOM | 3401 | CA | SER | A | 445 | −17.400 | −9.030 | −9.029 | 1.00 | 52.98 |
| ATOM | 3402 | CB | SER | A | 445 | −17.138 | −10.497 | −9.385 | 1.00 | 53.12 |
| ATOM | 3403 | OG | SER | A | 445 | −16.901 | −10.650 | −10.775 | 1.00 | 54.45 |
| ATOM | 3404 | C | SER | A | 445 | −16.202 | −8.159 | −9.449 | 1.00 | 52.99 |
| ATOM | 3405 | O | SER | A | 445 | −15.184 | −8.112 | −8.738 | 1.00 | 53.28 |
| ATOM | 3406 | N | ALA | A | 446 | −16.328 | −7.472 | −10.588 | 1.00 | 52.67 |
| ATOM | 3407 | CA | ALA | A | 446 | −15.301 | −6.536 | −11.063 | 1.00 | 52.20 |
| ATOM | 3408 | CB | ALA | A | 446 | −15.695 | −5.960 | −12.425 | 1.00 | 52.45 |
| ATOM | 3409 | C | ALA | A | 446 | −14.996 | −5.406 | −10.059 | 1.00 | 51.92 |
| ATOM | 3410 | O | ALA | A | 446 | −14.144 | −4.553 | −10.322 | 1.00 | 51.77 |
| ATOM | 3411 | N | SER | A | 447 | −15.696 | −5.413 | −8.919 | 1.00 | 51.23 |
| ATOM | 3412 | CA | SER | A | 447 | −15.471 | −4.453 | −7.827 | 1.00 | 50.73 |
| ATOM | 3413 | CB | SER | A | 447 | −16.769 | −3.706 | −7.495 | 1.00 | 50.70 |
| ATOM | 3414 | OG | SER | A | 447 | −17.765 | −4.605 | −7.021 | 1.00 | 50.91 |
| ATOM | 3415 | C | SER | A | 447 | −14.886 | −5.072 | −6.537 | 1.00 | 50.31 |
| ATOM | 3416 | O | SER | A | 447 | −14.604 | −4.345 | −5.580 | 1.00 | 50.16 |
| ATOM | 3417 | N | THR | A | 448 | −14.704 | −6.394 | −6.508 | 1.00 | 49.55 |
| ATOM | 3418 | CA | THR | A | 448 | −14.165 | −7.070 | −5.314 | 1.00 | 49.05 |
| ATOM | 3419 | CB | THR | A | 448 | −14.579 | −8.561 | −5.233 | 1.00 | 49.15 |
| ATOM | 3420 | OG1 | THR | A | 448 | −14.076 | −9.255 | −6.378 | 1.00 | 49.97 |
| ATOM | 3421 | CG2 | THR | A | 448 | −16.096 | −8.705 | −5.180 | 1.00 | 49.11 |
| ATOM | 3422 | C | THR | A | 448 | −12.641 | −6.958 | −5.215 | 1.00 | 48.34 |
| ATOM | 3423 | O | THR | A | 448 | −11.911 | −7.325 | −6.135 | 1.00 | 47.84 |
| ATOM | 3424 | N | ILE | A | 449 | −12.174 | −6.444 | −4.084 | 1.00 | 47.93 |
| ATOM | 3425 | CA | ILE | A | 449 | −10.760 | −6.150 | −3.891 | 1.00 | 47.42 |
| ATOM | 3426 | CB | ILE | A | 449 | −10.577 | −4.798 | −3.142 | 1.00 | 47.53 |
| ATOM | 3427 | CG1 | ILE | A | 449 | −11.346 | −3.680 | −3.863 | 1.00 | 46.60 |
| ATOM | 3428 | CD1 | ILE | A | 449 | −11.727 | −2.523 | −2.981 | 1.00 | 45.49 |
| ATOM | 3429 | CG2 | ILE | A | 449 | −9.097 | −4.438 | −2.999 | 1.00 | 46.84 |
| ATOM | 3430 | C | ILE | A | 449 | −10.104 | −7.299 | −3.124 | 1.00 | 47.45 |
| ATOM | 3431 | O | ILE | A | 449 | −10.606 | −7.688 | −2.067 | 1.00 | 47.66 |
| ATOM | 3432 | N | PRO | A | 450 | −8.993 | −7.857 | −3.663 | 1.00 | 47.28 |
| ATOM | 3433 | CA | PRO | A | 450 | −8.202 | −8.926 | −3.036 | 1.00 | 47.25 |
| ATOM | 3434 | CB | PRO | A | 450 | −6.982 | −9.040 | −3.946 | 1.00 | 47.03 |
| ATOM | 3435 | CG | PRO | A | 450 | −7.430 | −8.535 | −5.237 | 1.00 | 47.02 |
| ATOM | 3436 | CD | PRO | A | 450 | −8.431 | −7.470 | −4.969 | 1.00 | 47.07 |
| ATOM | 3437 | C | PRO | A | 450 | −7.731 | −8.562 | −1.639 | 1.00 | 47.48 |
| ATOM | 3438 | O | PRO | A | 450 | −7.608 | −7.377 | −1.322 | 1.00 | 47.43 |
| ATOM | 3439 | N | SER | A | 451 | −7.452 | −9.587 | −0.832 | 1.00 | 47.94 |
| ATOM | 3440 | CA | SER | A | 451 | −7.020 | −9.436 | 0.568 | 1.00 | 48.19 |
| ATOM | 3441 | CB | SER | A | 451 | −7.017 | −10.801 | 1.277 | 1.00 | 48.52 |
| ATOM | 3442 | OG | SER | A | 451 | −8.297 | −11.414 | 1.235 | 1.00 | 49.64 |
| ATOM | 3443 | C | SER | A | 451 | −5.641 | −8.799 | 0.701 | 1.00 | 47.83 |
| ATOM | 3444 | O | SER | A | 451 | −5.415 | −7.963 | 1.575 | 1.00 | 48.39 |
| ATOM | 3445 | N | THR | A | 452 | −4.715 | −9.212 | −0.158 | 1.00 | 47.14 |
| ATOM | 3446 | CA | THR | A | 452 | −3.379 | −8.613 | −0.211 | 1.00 | 46.42 |
| ATOM | 3447 | CB | THR | A | 452 | −2.323 | −9.540 | 0.434 | 1.00 | 46.66 |
| ATOM | 3448 | OG1 | THR | A | 452 | −2.518 | −10.887 | −0.032 | 1.00 | 48.38 |
| ATOM | 3449 | CG2 | THR | A | 452 | −2.446 | −9.514 | 1.962 | 1.00 | 47.77 |
| ATOM | 3450 | C | THR | A | 452 | −3.011 | −8.323 | −1.673 | 1.00 | 44.81 |
| ATOM | 3451 | O | THR | A | 452 | −3.348 | −9.107 | −2.558 | 1.00 | 44.97 |
| ATOM | 3452 | N | CYS | A | 453 | −2.363 | −7.187 | −1.931 | 1.00 | 43.37 |
| ATOM | 3453 | CA | CYS | A | 453 | −1.971 | −6.854 | −3.306 | 1.00 | 41.40 |
| ATOM | 3454 | CB | CYS | A | 453 | −1.918 | −5.339 | −3.574 | 1.00 | 41.01 |
| ATOM | 3455 | SG | CYS | A | 453 | −3.187 | −4.199 | −2.908 | 1.00 | 40.58 |
| ATOM | 3456 | C | CYS | A | 453 | −0.591 | −7.408 | −3.602 | 1.00 | 40.33 |
| ATOM | 3457 | O | CYS | A | 453 | 0.293 | −7.370 | −2.753 | 1.00 | 39.88 |
| ATOM | 3458 | N | SER | A | 454 | −0.405 | −7.911 | −4.812 | 1.00 | 39.25 |
| ATOM | 3459 | CA | SER | A | 454 | 0.937 | −8.142 | −5.336 | 1.00 | 38.68 |
| ATOM | 3460 | CB | SER | A | 454 | 1.222 | −9.638 | −5.484 | 1.00 | 38.56 |

TABLE 20-continued

| | | | | | | | | | |
|---|---|---|---|---|---|---|---|---|---|
| ATOM | 3461 | OG | SER | A | 454 | 0.276 | −10.251 | −6.349 | 1.00 | 40.44 |
| ATOM | 3462 | C | SER | A | 454 | 1.047 | −7.450 | −6.690 | 1.00 | 37.78 |
| ATOM | 3463 | O | SER | A | 454 | 0.030 | −7.187 | −7.347 | 1.00 | 36.71 |
| ATOM | 3464 | N | GLY | A | 455 | 2.275 | −7.175 | −7.111 | 1.00 | 37.06 |
| ATOM | 3465 | CA | GLY | A | 455 | 2.514 | −6.613 | −8.431 | 1.00 | 36.79 |
| ATOM | 3466 | C | GLY | A | 455 | 2.493 | −7.658 | −9.539 | 1.00 | 36.18 |
| ATOM | 3467 | O | GLY | A | 455 | 3.410 | −7.708 | −10.367 | 1.00 | 36.73 |
| ATOM | 3468 | N | ALA | A | 456 | 1.445 | −8.480 | −9.562 | 1.00 | 35.26 |
| ATOM | 3469 | CA | ALA | A | 456 | 1.321 | −9.584 | −10.512 | 1.00 | 34.46 |
| ATOM | 3470 | CB | ALA | A | 456 | 0.125 | −10.454 | −10.158 | 1.00 | 34.50 |
| ATOM | 3471 | C | ALA | A | 456 | 1.195 | −9.111 | −11.963 | 1.00 | 34.16 |
| ATOM | 3472 | O | ALA | A | 456 | 0.283 | −8.353 | −12.301 | 1.00 | 33.56 |
| ATOM | 3473 | N | SER | A | 457 | 2.097 | −9.588 | −12.817 | 1.00 | 33.11 |
| ATOM | 3474 | CA | SER | A | 457 | 2.013 | −9.302 | −14.241 | 1.00 | 32.60 |
| ATOM | 3475 | CB | SER | A | 457 | 3.022 | −8.219 | −14.635 | 1.00 | 32.50 |
| ATOM | 3476 | OG | SER | A | 457 | 4.352 | −8.691 | −14.519 | 1.00 | 33.28 |
| ATOM | 3477 | C | SER | A | 457 | 2.228 | −10.575 | −15.044 | 1.00 | 32.31 |
| ATOM | 3478 | O | SER | A | 457 | 2.641 | −11.605 | −14.494 | 1.00 | 32.32 |
| ATOM | 3479 | N | VAL | A | 458 | 1.908 | −10.511 | −16.330 | 1.00 | 31.12 |
| ATOM | 3480 | CA | VAL | A | 458 | 2.063 | −11.629 | −17.246 | 1.00 | 31.09 |
| ATOM | 3481 | CB | VAL | A | 458 | 0.682 | −12.199 | −17.659 | 1.00 | 31.00 |
| ATOM | 3482 | CG1 | VAL | A | 458 | 0.806 | −13.173 | −18.830 | 1.00 | 30.72 |
| ATOM | 3483 | CG2 | VAL | A | 458 | −0.014 | −12.847 | −16.459 | 1.00 | 31.08 |
| ATOM | 3484 | C | VAL | A | 458 | 2.817 | −11.144 | −18.480 | 1.00 | 30.88 |
| ATOM | 3485 | O | VAL | A | 458 | 2.401 | −10.177 | −19.126 | 1.00 | 29.70 |
| ATOM | 3486 | N | VAL | A | 459 | 3.924 | −11.811 | −18.805 | 1.00 | 30.81 |
| ATOM | 3487 | CA | VAL | A | 459 | 4.643 | −11.525 | −20.051 | 1.00 | 30.95 |
| ATOM | 3488 | CB | VAL | A | 459 | 6.046 | −12.172 | −20.071 | 1.00 | 31.34 |
| ATOM | 3489 | CG1 | VAL | A | 459 | 6.664 | −12.102 | −21.492 | 1.00 | 30.45 |
| ATOM | 3490 | CG2 | VAL | A | 459 | 6.947 | −11.522 | −19.030 | 1.00 | 32.03 |
| ATOM | 3491 | C | VAL | A | 459 | 3.805 | −12.032 | −21.227 | 1.00 | 31.37 |
| ATOM | 3492 | O | VAL | A | 459 | 3.443 | −13.214 | −21.288 | 1.00 | 31.84 |
| ATOM | 3493 | N | GLY | A | 460 | 3.480 | −11.137 | −22.154 | 1.00 | 30.71 |
| ATOM | 3494 | CA | GLY | A | 460 | 2.596 | −11.495 | −23.258 | 1.00 | 30.77 |
| ATOM | 3495 | C | GLY | A | 460 | 3.349 | −11.799 | −24.536 | 1.00 | 30.66 |
| ATOM | 3496 | O | GLY | A | 460 | 4.585 | −11.773 | −24.582 | 1.00 | 30.90 |
| ATOM | 3497 | N | SER | A | 461 | 2.606 | −12.094 | −25.584 | 1.00 | 30.44 |
| ATOM | 3498 | CA | SER | A | 461 | 3.219 | −12.227 | −26.877 | 1.00 | 31.06 |
| ATOM | 3499 | CB | SER | A | 461 | 3.301 | −13.695 | −27.308 | 1.00 | 31.44 |
| ATOM | 3500 | OG | SER | A | 461 | 2.018 | −14.278 | −27.419 | 1.00 | 34.77 |
| ATOM | 3501 | C | SER | A | 461 | 2.463 | −11.357 | −27.864 | 1.00 | 30.21 |
| ATOM | 3502 | O | SER | A | 461 | 1.246 | −11.156 | −27.736 | 1.00 | 30.87 |
| ATOM | 3503 | N | TYR | A | 462 | 3.192 | −10.822 | −28.836 | 1.00 | 28.84 |
| ATOM | 3504 | CA | TYR | A | 462 | 2.651 | −9.797 | −29.712 | 1.00 | 28.13 |
| ATOM | 3505 | CB | TYR | A | 462 | 3.365 | −8.471 | −29.426 | 1.00 | 26.74 |
| ATOM | 3506 | CG | TYR | A | 462 | 3.264 | −8.098 | −27.976 | 1.00 | 25.28 |
| ATOM | 3507 | CD1 | TYR | A | 462 | 2.184 | −7.335 | −27.508 | 1.00 | 23.75 |
| ATOM | 3508 | CE1 | TYR | A | 462 | 2.066 | −7.022 | −26.162 | 1.00 | 23.41 |
| ATOM | 3509 | CZ | TYR | A | 462 | 3.030 | −7.458 | −25.268 | 1.00 | 23.32 |
| ATOM | 3510 | OH | TYR | A | 462 | 2.907 | −7.155 | −23.941 | 1.00 | 23.50 |
| ATOM | 3511 | CE2 | TYR | A | 462 | 4.113 | −8.226 | −25.698 | 1.00 | 22.57 |
| ATOM | 3512 | CD2 | TYR | A | 462 | 4.223 | −8.537 | −27.050 | 1.00 | 24.71 |
| ATOM | 3513 | C | TYR | A | 462 | 2.844 | −10.191 | −31.152 | 1.00 | 28.83 |
| ATOM | 3514 | O | TYR | A | 462 | 3.898 | −10.697 | −31.529 | 1.00 | 29.33 |
| ATOM | 3515 | N | SER | A | 463 | 1.828 | −9.973 | −31.961 | 1.00 | 29.66 |
| ATOM | 3516 | CA | SER | A | 463 | 1.970 | −10.202 | −33.388 | 1.00 | 30.77 |
| ATOM | 3517 | CB | SER | A | 463 | 1.424 | −11.574 | −33.784 | 1.00 | 30.99 |
| ATOM | 3518 | OG | SER | A | 463 | 0.168 | −11.815 | −33.192 | 1.00 | 33.22 |
| ATOM | 3519 | C | SER | A | 463 | 1.311 | −9.082 | −34.170 | 1.00 | 31.28 |
| ATOM | 3520 | O | SER | A | 463 | 0.329 | −8.481 | −33.723 | 1.00 | 30.40 |
| ATOM | 3521 | N | ARG | A | 464 | 1.886 | −8.789 | −35.330 | 1.00 | 31.94 |
| ATOM | 3522 | CA | ARG | A | 464 | 1.377 | −7.775 | −36.225 | 1.00 | 32.97 |
| ATOM | 3523 | CB | ARG | A | 464 | 2.362 | −7.620 | −37.385 | 1.00 | 33.68 |
| ATOM | 3524 | CG | ARG | A | 464 | 2.353 | −6.274 | −38.061 | 1.00 | 36.94 |
| ATOM | 3525 | CD | ARG | A | 464 | 3.502 | −6.206 | −39.088 | 1.00 | 42.45 |
| ATOM | 3526 | NE | ARG | A | 464 | 4.794 | −6.065 | −38.415 | 1.00 | 45.53 |
| ATOM | 3527 | CZ | ARG | A | 464 | 5.416 | −4.903 | −38.227 | 1.00 | 47.50 |
| ATOM | 3528 | NH1 | ARG | A | 464 | 4.882 | −3.775 | −38.688 | 1.00 | 49.50 |
| ATOM | 3529 | NH2 | ARG | A | 464 | 6.580 | −4.863 | −37.592 | 1.00 | 48.59 |
| ATOM | 3530 | C | ARG | A | 464 | −0.017 | −8.171 | −36.741 | 1.00 | 33.03 |
| ATOM | 3531 | O | ARG | A | 464 | −0.166 | −9.228 | −37.358 | 1.00 | 33.00 |
| ATOM | 3532 | N | PRO | A | 465 | −1.053 | −7.333 | −36.479 | 1.00 | 32.72 |
| ATOM | 3533 | CA | PRO | A | 465 | −2.344 | −7.593 | −37.131 | 1.00 | 32.69 |
| ATOM | 3534 | CB | PRO | A | 465 | −3.274 | −6.504 | −36.558 | 1.00 | 32.50 |
| ATOM | 3535 | CG | PRO | A | 465 | −2.581 | −5.981 | −35.345 | 1.00 | 32.47 |
| ATOM | 3536 | CD | PRO | A | 465 | −1.102 | −6.134 | −35.618 | 1.00 | 32.83 |
| ATOM | 3537 | C | PRO | A | 465 | −2.189 | −7.421 | −38.642 | 1.00 | 33.30 |
| ATOM | 3538 | O | PRO | A | 465 | −1.332 | −6.661 | −39.097 | 1.00 | 33.20 |
| ATOM | 3539 | N | THR | A | 466 | −2.990 | −8.136 | −39.412 | 1.00 | 34.26 |
| ATOM | 3540 | CA | THR | A | 466 | −2.810 | −8.131 | −40.855 | 1.00 | 35.62 |

TABLE 20-continued

| ATOM | 3541 | CB | THR | A | 466 | −2.264 | −9.486 | −41.370 | 1.00 | 35.33 |
|---|---|---|---|---|---|---|---|---|---|---|
| ATOM | 3542 | OG1 | THR | A | 466 | −3.225 | −10.512 | −41.136 | 1.00 | 36.81 |
| ATOM | 3543 | CG2 | THR | A | 466 | −0.965 | −9.848 | −40.656 | 1.00 | 35.91 |
| ATOM | 3544 | C | THR | A | 466 | −4.076 | −7.711 | −41.600 | 1.00 | 36.15 |
| ATOM | 3545 | O | THR | A | 466 | −3.983 | −7.077 | −42.648 | 1.00 | 36.93 |
| ATOM | 3546 | N | ALA | A | 467 | −5.242 | −8.051 | −41.048 | 1.00 | 36.82 |
| ATOM | 3547 | CA | ALA | A | 467 | −6.540 | −7.648 | −41.609 | 1.00 | 37.30 |
| ATOM | 3548 | CB | ALA | A | 467 | −7.663 | −8.403 | −40.930 | 1.00 | 37.04 |
| ATOM | 3549 | C | ALA | A | 467 | −6.767 | −6.136 | −41.509 | 1.00 | 38.13 |
| ATOM | 3550 | O | ALA | A | 467 | −6.715 | −5.556 | −40.417 | 1.00 | 37.96 |
| ATOM | 3551 | N | THR | A | 468 | −7.011 | −5.502 | −42.653 | 1.00 | 38.66 |
| ATOM | 3552 | CA | THR | A | 468 | −7.146 | −4.050 | −42.702 | 1.00 | 39.18 |
| ATOM | 3553 | CB | THR | A | 468 | −5.970 | −3.406 | −43.428 | 1.00 | 39.43 |
| ATOM | 3554 | OG1 | THR | A | 468 | −5.955 | −3.879 | −44.778 | 1.00 | 40.06 |
| ATOM | 3555 | CG2 | THR | A | 468 | −4.637 | −3.717 | −42.734 | 1.00 | 39.67 |
| ATOM | 3556 | C | THR | A | 468 | −8.405 | −3.591 | −43.427 | 1.00 | 39.33 |
| ATOM | 3557 | O | THR | A | 468 | −8.468 | −2.451 | −43.890 | 1.00 | 39.79 |
| ATOM | 3558 | N | SER | A | 469 | −9.403 | −4.457 | −43.529 | 1.00 | 39.12 |
| ATOM | 3559 | CA | SER | A | 469 | −10.651 | −4.065 | −44.176 | 1.00 | 39.41 |
| ATOM | 3560 | CB | SER | A | 469 | −10.624 | −4.369 | −45.684 | 1.00 | 39.77 |
| ATOM | 3561 | OG | SER | A | 469 | −10.476 | −5.763 | −45.916 | 1.00 | 41.02 |
| ATOM | 3562 | C | SER | A | 469 | −11.850 | −4.732 | −43.537 | 1.00 | 38.54 |
| ATOM | 3563 | O | SER | A | 469 | −11.771 | −5.856 | −43.046 | 1.00 | 38.85 |
| ATOM | 3564 | N | PHE | A | 470 | −12.962 | −4.014 | −43.558 | 1.00 | 38.00 |
| ATOM | 3565 | CA | PHE | A | 470 | −14.216 | −4.507 | −43.031 | 1.00 | 37.29 |
| ATOM | 3566 | CB | PHE | A | 470 | −14.880 | −3.406 | −42.220 | 1.00 | 36.87 |
| ATOM | 3567 | CG | PHE | A | 470 | −14.277 | −3.212 | −40.865 | 1.00 | 35.43 |
| ATOM | 3568 | CD1 | PHE | A | 470 | −13.146 | −2.428 | −40.696 | 1.00 | 35.15 |
| ATOM | 3569 | CE1 | PHE | A | 470 | −12.589 | −2.252 | −39.437 | 1.00 | 33.73 |
| ATOM | 3570 | CZ | PHE | A | 470 | −13.159 | −2.852 | −38.332 | 1.00 | 35.04 |
| ATOM | 3571 | CE2 | PHE | A | 470 | −14.292 | −3.638 | −38.479 | 1.00 | 36.26 |
| ATOM | 3572 | CD2 | PHE | A | 470 | −14.844 | −3.816 | −39.751 | 1.00 | 35.71 |
| ATOM | 3573 | C | PHE | A | 470 | −15.128 | −4.923 | −44.181 | 1.00 | 37.34 |
| ATOM | 3574 | O | PHE | A | 470 | −15.059 | −4.337 | −45.258 | 1.00 | 37.21 |
| ATOM | 3575 | N | PRO | A | 471 | −15.987 | −5.931 | −43.959 | 1.00 | 37.46 |
| ATOM | 3576 | CA | PRO | A | 471 | −16.983 | −6.243 | −44.985 | 1.00 | 38.04 |
| ATOM | 3577 | CB | PRO | A | 471 | −17.790 | −7.383 | −44.361 | 1.00 | 37.60 |
| ATOM | 3578 | CG | PRO | A | 471 | −16.877 | −7.986 | −43.337 | 1.00 | 38.09 |
| ATOM | 3579 | CD | PRO | A | 471 | −16.093 | −6.828 | −42.795 | 1.00 | 37.31 |
| ATOM | 3580 | C | PRO | A | 471 | −17.879 | −5.033 | −45.231 | 1.00 | 38.96 |
| ATOM | 3581 | O | PRO | A | 471 | −18.108 | −4.245 | −44.306 | 1.00 | 38.78 |
| ATOM | 3582 | N | PRO | A | 472 | −18.378 | −4.869 | −46.471 | 1.00 | 39.78 |
| ATOM | 3583 | CA | PRO | A | 472 | −19.238 | −3.723 | −46.771 | 1.00 | 39.87 |
| ATOM | 3584 | CB | PRO | A | 472 | −19.378 | −3.780 | −48.293 | 1.00 | 40.09 |
| ATOM | 3585 | CG | PRO | A | 472 | −19.171 | −5.225 | −48.635 | 1.00 | 40.28 |
| ATOM | 3586 | CD | PRO | A | 472 | −18.171 | −5.740 | −47.649 | 1.00 | 40.02 |
| ATOM | 3587 | C | PRO | A | 472 | −20.604 | −3.864 | −46.114 | 1.00 | 39.75 |
| ATOM | 3588 | O | PRO | A | 472 | −21.017 | −4.980 | −45.798 | 1.00 | 40.10 |
| ATOM | 3589 | N | SER | A | 473 | −21.268 | −2.734 | −45.881 | 1.00 | 39.71 |
| ATOM | 3590 | CA | SER | A | 473 | −22.675 | −2.696 | −45.467 | 1.00 | 39.61 |
| ATOM | 3591 | CB | SER | A | 473 | −23.571 | −3.070 | −46.651 | 1.00 | 40.16 |
| ATOM | 3592 | OG | SER | A | 473 | −23.468 | −2.074 | −47.658 | 1.00 | 42.55 |
| ATOM | 3593 | C | SER | A | 473 | −23.043 | −3.509 | −44.221 | 1.00 | 38.94 |
| ATOM | 3594 | O | SER | A | 473 | −24.041 | −4.258 | −44.210 | 1.00 | 39.07 |
| ATOM | 3595 | N | GLN | A | 474 | −22.257 | −3.340 | −43.159 | 1.00 | 37.75 |
| ATOM | 3596 | CA | GLN | A | 474 | −22.558 | −3.993 | −41.888 | 1.00 | 36.60 |
| ATOM | 3597 | CB | GLN | A | 474 | −21.291 | −4.205 | −41.057 | 1.00 | 36.41 |
| ATOM | 3598 | CG | GLN | A | 474 | −20.331 | −5.169 | −41.732 | 1.00 | 36.24 |
| ATOM | 3599 | CD | GLN | A | 474 | −19.295 | −5.757 | −40.795 | 1.00 | 36.45 |
| ATOM | 3600 | OE1 | GLN | A | 474 | −18.478 | −5.040 | −40.211 | 1.00 | 35.30 |
| ATOM | 3601 | NE2 | GLN | A | 474 | −19.304 | −7.077 | −40.671 | 1.00 | 36.85 |
| ATOM | 3602 | C | GLN | A | 474 | −23.620 | −3.191 | −41.149 | 1.00 | 36.40 |
| ATOM | 3603 | O | GLN | A | 474 | −23.329 | −2.444 | −40.208 | 1.00 | 35.99 |
| ATOM | 3604 | N | THR | A | 475 | −24.859 | −3.350 | −41.616 | 1.00 | 35.59 |
| ATOM | 3605 | CA | THR | A | 475 | −26.012 | −2.595 | −41.148 | 1.00 | 35.20 |
| ATOM | 3606 | CB | THR | A | 475 | −27.051 | −2.478 | −42.287 | 1.00 | 35.73 |
| ATOM | 3607 | OG1 | THR | A | 475 | −27.120 | −3.737 | −42.959 | 1.00 | 36.85 |
| ATOM | 3608 | CG2 | THR | A | 475 | −26.642 | −1.418 | −43.310 | 1.00 | 34.51 |
| ATOM | 3609 | C | THR | A | 475 | −26.635 | −3.256 | −39.910 | 1.00 | 35.16 |
| ATOM | 3610 | O | THR | A | 475 | −26.363 | −4.420 | −39.622 | 1.00 | 34.47 |
| ATOM | 3611 | N | PRO | A | 476 | −27.453 | −2.510 | −39.148 | 1.00 | 35.36 |
| ATOM | 3612 | CA | PRO | A | 476 | −27.990 | −3.111 | −37.923 | 1.00 | 36.40 |
| ATOM | 3613 | CB | PRO | A | 476 | −28.567 | −1.910 | −37.167 | 1.00 | 36.04 |
| ATOM | 3614 | CG | PRO | A | 476 | −28.890 | −0.912 | −38.230 | 1.00 | 35.98 |
| ATOM | 3615 | CD | PRO | A | 476 | −27.907 | −1.119 | −39.339 | 1.00 | 35.70 |
| ATOM | 3616 | C | PRO | A | 476 | −29.085 | −4.171 | −38.158 | 1.00 | 37.45 |
| ATOM | 3617 | O | PRO | A | 476 | −29.654 | −4.244 | −39.254 | 1.00 | 36.95 |
| ATOM | 3618 | N | LYS | A | 477 | −29.342 | −4.984 | −37.133 | 1.00 | 39.01 |
| ATOM | 3619 | CA | LYS | A | 477 | −30.472 | −5.911 | −37.111 | 1.00 | 41.20 |
| ATOM | 3620 | CB | LYS | A | 477 | −30.541 | −6.641 | −35.774 | 1.00 | 41.46 |

TABLE 20-continued

| ATOM | 3621 | CG | LYS | A | 477 | −29.665 | −7.850 | −35.604 | 1.00 | 41.87 |
| ATOM | 3622 | CD | LYS | A | 477 | −29.939 | −8.517 | −34.237 | 1.00 | 42.36 |
| ATOM | 3623 | CE | LYS | A | 477 | −29.996 | −7.497 | −33.076 | 1.00 | 44.55 |
| ATOM | 3624 | NZ | LYS | A | 477 | −29.705 | −8.110 | −31.718 | 1.00 | 44.56 |
| ATOM | 3625 | C | LYS | A | 477 | −31.766 | −5.118 | −37.230 | 1.00 | 42.27 |
| ATOM | 3626 | O | LYS | A | 477 | −31.818 | −3.960 | −36.798 | 1.00 | 42.18 |
| ATOM | 3627 | N | PRO | A | 478 | −32.831 | −5.743 | −37.780 | 1.00 | 43.46 |
| ATOM | 3628 | CA | PRO | A | 478 | −34.150 | −5.106 | −37.669 | 1.00 | 44.02 |
| ATOM | 3629 | CB | PRO | A | 478 | −35.106 | −6.144 | −38.267 | 1.00 | 43.89 |
| ATOM | 3630 | CG | PRO | A | 478 | −34.255 | −7.033 | −39.105 | 1.00 | 44.08 |
| ATOM | 3631 | CD | PRO | A | 478 | −32.885 | −7.034 | −38.493 | 1.00 | 43.41 |
| ATOM | 3632 | C | PRO | A | 478 | −34.480 | −4.892 | −36.194 | 1.00 | 44.52 |
| ATOM | 3633 | O | PRO | A | 478 | −34.197 | −5.769 | −35.364 | 1.00 | 44.73 |
| ATOM | 3634 | N | GLY | A | 479 | −35.043 | −3.728 | −35.874 | 1.00 | 45.20 |
| ATOM | 3635 | CA | GLY | A | 479 | −35.421 | −3.395 | −34.494 | 1.00 | 45.90 |
| ATOM | 3636 | C | GLY | A | 479 | −34.386 | −2.601 | −33.711 | 1.00 | 46.37 |
| ATOM | 3637 | O | GLY | A | 479 | −34.576 | −2.331 | −32.520 | 1.00 | 46.98 |
| ATOM | 3638 | N | VAL | A | 480 | −33.282 | −2.244 | −34.367 | 1.00 | 46.28 |
| ATOM | 3639 | CA | VAL | A | 480 | −32.261 | −1.383 | −33.760 | 1.00 | 46.15 |
| ATOM | 3640 | CB | VAL | A | 480 | −30.820 | −1.863 | −34.121 | 1.00 | 46.20 |
| ATOM | 3641 | CG1 | VAL | A | 480 | −29.755 | −0.899 | −33.584 | 1.00 | 45.85 |
| ATOM | 3642 | CG2 | VAL | A | 480 | −30.569 | −3.281 | −33.603 | 1.00 | 46.25 |
| ATOM | 3643 | C | VAL | A | 480 | −32.498 | 0.046 | −34.260 | 1.00 | 45.93 |
| ATOM | 3644 | O | VAL | A | 480 | −32.673 | 0.240 | −35.465 | 1.00 | 46.15 |
| ATOM | 3645 | N | PRO | A | 481 | −32.534 | 1.049 | −33.344 | 1.00 | 45.70 |
| ATOM | 3646 | CA | PRO | A | 481 | −32.648 | 2.443 | −33.804 | 1.00 | 45.36 |
| ATOM | 3647 | CB | PRO | A | 481 | −32.388 | 3.266 | −32.542 | 1.00 | 45.39 |
| ATOM | 3648 | CG | PRO | A | 481 | −32.778 | 2.375 | −31.427 | 1.00 | 45.52 |
| ATOM | 3649 | CD | PRO | A | 481 | −32.481 | 0.962 | −31.873 | 1.00 | 45.83 |
| ATOM | 3650 | C | PRO | A | 481 | −31.609 | 2.762 | −34.877 | 1.00 | 45.08 |
| ATOM | 3651 | O | PRO | A | 481 | −30.405 | 2.555 | −34.681 | 1.00 | 44.45 |
| ATOM | 3652 | N | SER | A | 482 | −32.100 | 3.241 | −36.011 | 1.00 | 44.83 |
| ATOM | 3653 | CA | SER | A | 482 | −31.281 | 3.485 | −37.180 | 1.00 | 44.52 |
| ATOM | 3654 | CB | SER | A | 482 | −31.502 | 2.375 | −38.211 | 1.00 | 44.74 |
| ATOM | 3655 | OG | SER | A | 482 | −30.769 | 2.622 | −39.399 | 1.00 | 45.89 |
| ATOM | 3656 | C | SER | A | 482 | −31.661 | 4.836 | −37.765 | 1.00 | 43.84 |
| ATOM | 3657 | O | SER | A | 482 | −32.836 | 5.219 | −37.741 | 1.00 | 44.07 |
| ATOM | 3658 | N | GLY | A | 483 | −30.667 | 5.550 | −38.282 | 1.00 | 42.68 |
| ATOM | 3659 | CA | GLY | A | 483 | −30.872 | 6.872 | −38.853 | 1.00 | 41.64 |
| ATOM | 3660 | C | GLY | A | 483 | −30.085 | 7.095 | −40.130 | 1.00 | 41.05 |
| ATOM | 3661 | O | GLY | A | 483 | −29.430 | 6.179 | −40.647 | 1.00 | 41.09 |
| ATOM | 3662 | N | THR | A | 484 | −30.155 | 8.317 | −40.647 | 1.00 | 40.22 |
| ATOM | 3663 | CA | THR | A | 484 | −29.461 | 8.677 | −41.888 | 1.00 | 39.91 |
| ATOM | 3664 | CB | THR | A | 484 | −30.148 | 9.876 | −42.619 | 1.00 | 40.21 |
| ATOM | 3665 | OG1 | THR | A | 484 | −30.115 | 11.040 | −41.780 | 1.00 | 41.48 |
| ATOM | 3666 | CG2 | THR | A | 484 | −31.604 | 9.541 | −43.000 | 1.00 | 40.86 |
| ATOM | 3667 | C | THR | A | 484 | −27.995 | 9.033 | −41.603 | 1.00 | 38.43 |
| ATOM | 3668 | O | THR | A | 484 | −27.669 | 9.421 | −40.483 | 1.00 | 38.52 |
| ATOM | 3669 | N | PRO | A | 485 | −27.109 | 8.893 | −42.612 | 1.00 | 37.36 |
| ATOM | 3670 | CA | PRO | A | 485 | −25.695 | 9.226 | −42.413 | 1.00 | 36.29 |
| ATOM | 3671 | CB | PRO | A | 485 | −25.077 | 8.974 | −43.795 | 1.00 | 36.75 |
| ATOM | 3672 | CG | PRO | A | 485 | −25.997 | 7.985 | −44.442 | 1.00 | 37.04 |
| ATOM | 3673 | CD | PRO | A | 485 | −27.359 | 8.393 | −43.976 | 1.00 | 37.30 |
| ATOM | 3674 | C | PRO | A | 485 | −25.460 | 10.684 | −41.988 | 1.00 | 35.20 |
| ATOM | 3675 | O | PRO | A | 485 | −26.201 | 11.599 | −42.396 | 1.00 | 34.39 |
| ATOM | 3676 | N | TYR | A | 486 | −24.428 | 10.887 | −41.174 | 1.00 | 33.60 |
| ATOM | 3677 | CA | TYR | A | 486 | −24.025 | 12.233 | −40.782 | 1.00 | 32.74 |
| ATOM | 3678 | CB | TYR | A | 486 | −22.821 | 12.180 | −39.826 | 1.00 | 32.31 |
| ATOM | 3679 | CG | TYR | A | 486 | −22.348 | 13.564 | −39.452 | 1.00 | 32.79 |
| ATOM | 3680 | CD1 | TYR | A | 486 | −21.243 | 14.146 | −40.083 | 1.00 | 31.74 |
| ATOM | 3681 | CE1 | TYR | A | 486 | −20.827 | 15.430 | −39.742 | 1.00 | 30.85 |
| ATOM | 3682 | CZ | TYR | A | 486 | −21.527 | 16.141 | −38.778 | 1.00 | 31.99 |
| ATOM | 3683 | OH | TYR | A | 486 | −21.143 | 17.423 | −38.427 | 1.00 | 32.20 |
| ATOM | 3684 | CE2 | TYR | A | 486 | −22.629 | 15.588 | −38.160 | 1.00 | 31.88 |
| ATOM | 3685 | CD2 | TYR | A | 486 | −23.036 | 14.311 | −38.500 | 1.00 | 32.49 |
| ATOM | 3686 | C | TYR | A | 486 | −23.652 | 13.082 | −41.999 | 1.00 | 31.99 |
| ATOM | 3687 | O | TYR | A | 486 | −22.949 | 12.602 | −42.900 | 1.00 | 31.62 |
| ATOM | 3688 | N | THR | A | 487 | −24.106 | 14.336 | −42.004 | 1.00 | 31.14 |
| ATOM | 3689 | CA | THR | A | 487 | −23.676 | 15.336 | −42.986 | 1.00 | 31.43 |
| ATOM | 3690 | CB | THR | A | 487 | −24.879 | 15.785 | −43.869 | 1.00 | 31.94 |
| ATOM | 3691 | OG1 | THR | A | 487 | −25.321 | 14.665 | −44.644 | 1.00 | 35.19 |
| ATOM | 3692 | CG2 | THR | A | 487 | −24.489 | 16.904 | −44.810 | 1.00 | 32.95 |
| ATOM | 3693 | C | THR | A | 487 | −23.110 | 16.561 | −42.261 | 1.00 | 29.79 |
| ATOM | 3694 | O | THR | A | 487 | −23.761 | 17.078 | −41.363 | 1.00 | 29.20 |
| ATOM | 3695 | N | PRO | A | 488 | −21.901 | 17.027 | −42.644 | 1.00 | 29.20 |
| ATOM | 3696 | CA | PRO | A | 488 | −21.309 | 18.228 | −42.005 | 1.00 | 28.77 |
| ATOM | 3697 | CB | PRO | A | 488 | −19.988 | 18.435 | −42.763 | 1.00 | 28.75 |
| ATOM | 3698 | CG | PRO | A | 488 | −19.684 | 17.126 | −43.408 | 1.00 | 29.52 |
| ATOM | 3699 | CD | PRO | A | 488 | −21.010 | 16.448 | −43.667 | 1.00 | 29.41 |
| ATOM | 3700 | C | PRO | A | 488 | −22.175 | 19.463 | −42.194 | 1.00 | 28.44 |

TABLE 20-continued

| | | | | | | | | | |
|---|---|---|---|---|---|---|---|---|---|
| ATOM | 3701 | O | PRO | A | 488 | −23.003 | 19.499 | −43.116 | 1.00 | 28.51 |
| ATOM | 3702 | N | LEU | A | 489 | −21.971 | 20.469 | −41.345 | 1.00 | 27.28 |
| ATOM | 3703 | CA | LEU | A | 489 | −22.606 | 21.775 | −41.522 | 1.00 | 26.52 |
| ATOM | 3704 | CB | LEU | A | 489 | −22.269 | 22.708 | −40.365 | 1.00 | 27.19 |
| ATOM | 3705 | CG | LEU | A | 489 | −22.805 | 22.303 | −38.987 | 1.00 | 27.53 |
| ATOM | 3706 | CD1 | LEU | A | 489 | −22.233 | 23.242 | −37.929 | 1.00 | 26.81 |
| ATOM | 3707 | CD2 | LEU | A | 489 | −24.332 | 22.323 | −38.970 | 1.00 | 28.98 |
| ATOM | 3708 | C | LEU | A | 489 | −22.137 | 22.402 | −42.833 | 1.00 | 26.65 |
| ATOM | 3709 | O | LEU | A | 489 | −20.983 | 22.210 | −43.245 | 1.00 | 25.40 |
| ATOM | 3710 | N | PRO | A | 490 | −23.030 | 23.153 | −43.503 | 1.00 | 26.84 |
| ATOM | 3711 | CA | PRO | A | 490 | −22.636 | 23.745 | −44.786 | 1.00 | 26.44 |
| ATOM | 3712 | CB | PRO | A | 490 | −23.983 | 24.107 | −45.432 | 1.00 | 27.00 |
| ATOM | 3713 | CG | PRO | A | 490 | −24.900 | 24.341 | −44.289 | 1.00 | 27.68 |
| ATOM | 3714 | CD | PRO | A | 490 | −24.425 | 23.475 | −43.137 | 1.00 | 26.91 |
| ATOM | 3715 | C | PRO | A | 490 | −21.737 | 24.982 | −44.668 | 1.00 | 26.22 |
| ATOM | 3716 | O | PRO | A | 490 | −21.826 | 25.729 | −43.698 | 1.00 | 25.74 |
| ATOM | 3717 | N | CYS | A | 491 | −20.858 | 25.182 | −45.650 | 1.00 | 26.06 |
| ATOM | 3718 | CA | CYS | A | 491 | −20.079 | 26.412 | −45.754 | 1.00 | 26.88 |
| ATOM | 3719 | CB | CYS | A | 491 | −18.630 | 26.194 | −45.302 | 1.00 | 27.00 |
| ATOM | 3720 | SG | CYS | A | 491 | −18.450 | 25.196 | −43.819 | 1.00 | 27.23 |
| ATOM | 3721 | C | CYS | A | 491 | −20.032 | 26.822 | −47.217 | 1.00 | 27.27 |
| ATOM | 3722 | O | CYS | A | 491 | −20.369 | 26.026 | −48.083 | 1.00 | 27.34 |
| ATOM | 3723 | N | ALA | A | 492 | −19.577 | 28.045 | −47.484 | 1.00 | 28.05 |
| ATOM | 3724 | CA | ALA | A | 492 | −19.205 | 28.449 | −48.845 | 1.00 | 29.40 |
| ATOM | 3725 | CB | ALA | A | 492 | −18.837 | 29.928 | −48.866 | 1.00 | 29.49 |
| ATOM | 3726 | C | ALA | A | 492 | −18.023 | 27.599 | −49.320 | 1.00 | 30.37 |
| ATOM | 3727 | O | ALA | A | 492 | −17.310 | 26.998 | −48.497 | 1.00 | 30.36 |
| ATOM | 3728 | N | THR | A | 493 | −17.828 | 27.508 | −50.633 | 1.00 | 31.27 |
| ATOM | 3729 | CA | THR | A | 493 | −16.612 | 26.883 | −51.163 | 1.00 | 32.43 |
| ATOM | 3730 | CB | THR | A | 493 | −16.845 | 26.234 | −52.533 | 1.00 | 33.22 |
| ATOM | 3731 | OG1 | THR | A | 493 | −17.944 | 25.324 | −52.431 | 1.00 | 38.55 |
| ATOM | 3732 | CG2 | THR | A | 493 | −15.590 | 25.464 | −52.996 | 1.00 | 33.71 |
| ATOM | 3733 | C | THR | A | 493 | −15.596 | 28.006 | −51.254 | 1.00 | 31.35 |
| ATOM | 3734 | O | THR | A | 493 | −15.916 | 29.068 | −51.795 | 1.00 | 31.58 |
| ATOM | 3735 | N | PRO | A | 494 | −14.390 | 27.815 | −50.682 | 1.00 | 30.44 |
| ATOM | 3736 | CA | PRO | A | 494 | −13.464 | 28.947 | −50.696 | 1.00 | 30.01 |
| ATOM | 3737 | CB | PRO | A | 494 | −12.414 | 28.555 | −49.645 | 1.00 | 30.26 |
| ATOM | 3738 | CG | PRO | A | 494 | −12.416 | 27.077 | −49.658 | 1.00 | 30.56 |
| ATOM | 3739 | CD | PRO | A | 494 | −13.815 | 26.635 | −49.997 | 1.00 | 30.85 |
| ATOM | 3740 | C | PRO | A | 494 | −12.809 | 29.089 | −52.060 | 1.00 | 28.81 |
| ATOM | 3741 | O | PRO | A | 494 | −12.801 | 28.137 | −52.834 | 1.00 | 28.82 |
| ATOM | 3742 | N | THR | A | 495 | −12.260 | 30.258 | −52.352 | 1.00 | 28.43 |
| ATOM | 3743 | CA | THR | A | 495 | −11.551 | 30.419 | −53.623 | 1.00 | 28.44 |
| ATOM | 3744 | CB | THR | A | 495 | −11.885 | 31.748 | −54.319 | 1.00 | 28.68 |
| ATOM | 3745 | OG1 | THR | A | 495 | −11.449 | 32.839 | −53.500 | 1.00 | 30.39 |
| ATOM | 3746 | CG2 | THR | A | 495 | −13.383 | 31.858 | −54.564 | 1.00 | 29.85 |
| ATOM | 3747 | C | THR | A | 495 | −10.057 | 30.335 | −53.404 | 1.00 | 27.94 |
| ATOM | 3748 | O | THR | A | 495 | −9.289 | 30.159 | −54.352 | 1.00 | 27.63 |
| ATOM | 3749 | N | SER | A | 496 | −9.671 | 30.463 | −52.139 | 1.00 | 27.51 |
| ATOM | 3750 | CA | SER | A | 496 | −8.279 | 30.492 | −51.722 | 1.00 | 27.18 |
| ATOM | 3751 | CB | SER | A | 496 | −7.928 | 31.916 | −51.329 | 1.00 | 27.72 |
| ATOM | 3752 | OG | SER | A | 496 | −6.531 | 32.076 | −51.240 | 1.00 | 32.60 |
| ATOM | 3753 | C | SER | A | 496 | −8.134 | 29.583 | −50.501 | 1.00 | 25.85 |
| ATOM | 3754 | O | SER | A | 496 | −9.024 | 29.548 | −49.634 | 1.00 | 25.10 |
| ATOM | 3755 | N | VAL | A | 497 | −7.039 | 28.824 | −50.430 | 1.00 | 24.43 |
| ATOM | 3756 | CA | VAL | A | 497 | −6.801 | 28.032 | −49.209 | 1.00 | 22.17 |
| ATOM | 3757 | CB | VAL | A | 497 | −7.281 | 26.511 | −49.290 | 1.00 | 23.00 |
| ATOM | 3758 | CG1 | VAL | A | 497 | −6.224 | 25.445 | −48.881 | 1.00 | 22.48 |
| ATOM | 3759 | CG2 | VAL | A | 497 | −8.049 | 26.161 | −50.578 | 1.00 | 22.62 |
| ATOM | 3760 | C | VAL | A | 497 | −5.388 | 28.251 | −48.672 | 1.00 | 21.13 |
| ATOM | 3761 | O | VAL | A | 497 | −4.419 | 28.359 | −49.439 | 1.00 | 20.38 |
| ATOM | 3762 | N | ALA | A | 498 | −5.302 | 28.395 | −47.355 | 1.00 | 19.70 |
| ATOM | 3763 | CA | ALA | A | 498 | −4.020 | 28.576 | −46.702 | 1.00 | 18.92 |
| ATOM | 3764 | CB | ALA | A | 498 | −4.226 | 29.126 | −45.290 | 1.00 | 19.31 |
| ATOM | 3765 | C | ALA | A | 498 | −3.396 | 27.185 | −46.655 | 1.00 | 18.67 |
| ATOM | 3766 | O | ALA | A | 498 | −3.966 | 26.266 | −46.047 | 1.00 | 19.29 |
| ATOM | 3767 | N | VAL | A | 499 | −2.252 | 27.021 | −47.319 | 1.00 | 17.23 |
| ATOM | 3768 | CA | VAL | A | 499 | −1.551 | 25.735 | −47.361 | 1.00 | 16.09 |
| ATOM | 3769 | CB | VAL | A | 499 | −1.165 | 25.347 | −48.814 | 1.00 | 16.97 |
| ATOM | 3770 | CG1 | VAL | A | 499 | −0.403 | 23.984 | −48.863 | 1.00 | 16.08 |
| ATOM | 3771 | CG2 | VAL | A | 499 | −2.413 | 25.291 | −49.696 | 1.00 | 17.03 |
| ATOM | 3772 | C | VAL | A | 499 | −0.306 | 25.841 | −46.491 | 1.00 | 15.95 |
| ATOM | 3773 | O | VAL | A | 499 | 0.604 | 26.607 | −46.791 | 1.00 | 16.15 |
| ATOM | 3774 | N | THR | A | 500 | −0.279 | 25.085 | −45.404 | 1.00 | 15.16 |
| ATOM | 3775 | CA | THR | A | 500 | 0.863 | 25.116 | −44.505 | 1.00 | 14.85 |
| ATOM | 3776 | CB | THR | A | 500 | 0.415 | 24.916 | −43.035 | 1.00 | 14.76 |
| ATOM | 3777 | OG1 | THR | A | 500 | −0.403 | 26.022 | −42.635 | 1.00 | 16.00 |
| ATOM | 3778 | CG2 | THR | A | 500 | 1.639 | 24.856 | −42.136 | 1.00 | 15.39 |
| ATOM | 3779 | C | THR | A | 500 | 1.796 | 23.993 | −44.932 | 1.00 | 14.99 |
| ATOM | 3780 | O | THR | A | 500 | 1.480 | 22.804 | −44.792 | 1.00 | 14.81 |

TABLE 20-continued

| ATOM | 3781 | N | PHE | A | 501 | 2.941 | 24.370 | −45.481 | 1.00 | 14.71 |
| ATOM | 3782 | CA | PHE | A | 501 | 3.981 | 23.411 | −45.793 | 1.00 | 15.64 |
| ATOM | 3783 | CB | PHE | A | 501 | 4.943 | 23.964 | −46.832 | 1.00 | 15.86 |
| ATOM | 3784 | CG | PHE | A | 501 | 4.289 | 24.172 | −48.168 | 1.00 | 18.38 |
| ATOM | 3785 | CD1 | PHE | A | 501 | 3.676 | 25.388 | −48.469 | 1.00 | 19.85 |
| ATOM | 3786 | CE1 | PHE | A | 501 | 3.052 | 25.581 | −49.709 | 1.00 | 21.58 |
| ATOM | 3787 | CZ | PHE | A | 501 | 3.015 | 24.547 | −50.642 | 1.00 | 19.80 |
| ATOM | 3788 | CE2 | PHE | A | 501 | 3.607 | 23.324 | −50.356 | 1.00 | 21.69 |
| ATOM | 3789 | CD2 | PHE | A | 501 | 4.231 | 23.134 | −49.095 | 1.00 | 21.96 |
| ATOM | 3790 | C | PHE | A | 501 | 4.711 | 23.009 | −44.536 | 1.00 | 15.81 |
| ATOM | 3791 | O | PHE | A | 501 | 5.207 | 23.852 | −43.804 | 1.00 | 16.78 |
| ATOM | 3792 | N | HIS | A | 502 | 4.789 | 21.698 | −44.317 | 1.00 | 14.85 |
| ATOM | 3793 | CA | HIS | A | 502 | 5.239 | 21.175 | −43.027 | 1.00 | 14.17 |
| ATOM | 3794 | CB | HIS | A | 502 | 3.987 | 20.565 | −42.356 | 1.00 | 14.85 |
| ATOM | 3795 | CG | HIS | A | 502 | 4.221 | 19.875 | −41.054 | 1.00 | 13.69 |
| ATOM | 3796 | ND1 | HIS | A | 502 | 4.819 | 18.637 | −40.966 | 1.00 | 12.55 |
| ATOM | 3797 | CE1 | HIS | A | 502 | 4.816 | 18.241 | −39.702 | 1.00 | 15.76 |
| ATOM | 3798 | NE2 | HIS | A | 502 | 4.191 | 19.155 | −38.980 | 1.00 | 14.42 |
| ATOM | 3799 | CD2 | HIS | A | 502 | 3.797 | 20.183 | −39.804 | 1.00 | 14.92 |
| ATOM | 3800 | C | HIS | A | 502 | 6.317 | 20.161 | −43.412 | 1.00 | 14.16 |
| ATOM | 3801 | O | HIS | A | 502 | 6.013 | 19.043 | −43.824 | 1.00 | 13.85 |
| ATOM | 3802 | N | GLU | A | 503 | 7.577 | 20.590 | −43.352 | 1.00 | 13.63 |
| ATOM | 3803 | CA | GLU | A | 503 | 8.678 | 19.821 | −43.968 | 1.00 | 14.46 |
| ATOM | 3804 | CB | GLU | A | 503 | 9.434 | 20.712 | −44.996 | 1.00 | 14.22 |
| ATOM | 3805 | CG | GLU | A | 503 | 10.782 | 20.121 | −45.524 | 1.00 | 16.31 |
| ATOM | 3806 | CD | GLU | A | 503 | 10.620 | 18.973 | −46.539 | 1.00 | 21.32 |
| ATOM | 3807 | OE1 | GLU | A | 503 | 11.523 | 18.819 | −47.393 | 1.00 | 21.21 |
| ATOM | 3808 | OE2 | GLU | A | 503 | 9.609 | 18.230 | −46.510 | 1.00 | 20.10 |
| ATOM | 3809 | C | GLU | A | 503 | 9.657 | 19.322 | −42.917 | 1.00 | 14.22 |
| ATOM | 3810 | O | GLU | A | 503 | 10.175 | 20.121 | −42.131 | 1.00 | 15.31 |
| ATOM | 3811 | N | LEU | A | 504 | 9.960 | 18.027 | −42.927 | 1.00 | 14.92 |
| ATOM | 3812 | CA | LEU | A | 504 | 11.026 | 17.518 | −42.052 | 1.00 | 15.49 |
| ATOM | 3813 | CB | LEU | A | 504 | 10.658 | 16.147 | −41.489 | 1.00 | 16.33 |
| ATOM | 3814 | CG | LEU | A | 504 | 9.479 | 16.178 | −40.498 | 1.00 | 17.19 |
| ATOM | 3815 | CD1 | LEU | A | 504 | 8.922 | 14.753 | −40.320 | 1.00 | 19.08 |
| ATOM | 3816 | CD2 | LEU | A | 504 | 9.953 | 16.723 | −39.198 | 1.00 | 17.28 |
| ATOM | 3817 | C | LEU | A | 504 | 12.318 | 17.428 | −42.846 | 1.00 | 16.59 |
| ATOM | 3818 | O | LEU | A | 504 | 12.403 | 16.656 | −43.785 | 1.00 | 16.72 |
| ATOM | 3819 | N | VAL | A | 505 | 13.317 | 18.201 | −42.444 | 1.00 | 17.20 |
| ATOM | 3820 | CA | VAL | A | 505 | 14.592 | 18.235 | −43.154 | 1.00 | 19.16 |
| ATOM | 3821 | CB | VAL | A | 505 | 14.548 | 19.141 | −44.418 | 1.00 | 18.88 |
| ATOM | 3822 | CG1 | VAL | A | 505 | 14.028 | 20.539 | −44.090 | 1.00 | 19.28 |
| ATOM | 3823 | CG2 | VAL | A | 505 | 15.948 | 19.219 | −45.095 | 1.00 | 21.65 |
| ATOM | 3824 | C | VAL | A | 505 | 15.674 | 18.705 | −42.188 | 1.00 | 20.00 |
| ATOM | 3825 | O | VAL | A | 505 | 15.595 | 19.785 | −41.595 | 1.00 | 19.92 |
| ATOM | 3826 | N | SER | A | 506 | 16.685 | 17.868 | −42.011 | 1.00 | 21.73 |
| ATOM | 3827 | CA | SER | A | 506 | 17.761 | 18.216 | −41.104 | 1.00 | 23.33 |
| ATOM | 3828 | CB | SER | A | 506 | 18.570 | 16.974 | −40.771 | 1.00 | 23.74 |
| ATOM | 3829 | OG | SER | A | 506 | 19.583 | 17.320 | −39.847 | 1.00 | 28.30 |
| ATOM | 3830 | C | SER | A | 506 | 18.646 | 19.284 | −41.759 | 1.00 | 23.03 |
| ATOM | 3831 | O | SER | A | 506 | 19.070 | 19.139 | −42.908 | 1.00 | 23.20 |
| ATOM | 3832 | N | THR | A | 507 | 18.888 | 20.371 | −41.049 | 1.00 | 24.01 |
| ATOM | 3833 | CA | THR | A | 507 | 19.685 | 21.464 | −41.600 | 1.00 | 25.15 |
| ATOM | 3834 | CB | THR | A | 507 | 18.845 | 22.725 | −41.833 | 1.00 | 25.01 |
| ATOM | 3835 | OG1 | THR | A | 507 | 18.104 | 23.015 | −40.650 | 1.00 | 24.43 |
| ATOM | 3836 | CG2 | THR | A | 507 | 17.891 | 22.536 | −43.000 | 1.00 | 24.71 |
| ATOM | 3837 | C | THR | A | 507 | 20.795 | 21.812 | −40.623 | 1.00 | 27.09 |
| ATOM | 3838 | O | THR | A | 507 | 20.729 | 21.448 | −39.451 | 1.00 | 26.15 |
| ATOM | 3839 | N | GLN | A | 508 | 21.798 | 22.536 | −41.113 | 1.00 | 29.34 |
| ATOM | 3840 | CA | GLN | A | 508 | 22.912 | 22.986 | −40.272 | 1.00 | 32.54 |
| ATOM | 3841 | CB | GLN | A | 508 | 24.239 | 22.542 | −40.897 | 1.00 | 32.54 |
| ATOM | 3842 | CG | GLN | A | 508 | 24.369 | 21.010 | −40.972 | 1.00 | 34.32 |
| ATOM | 3843 | CD | GLN | A | 508 | 25.400 | 20.515 | −41.991 | 1.00 | 36.23 |
| ATOM | 3844 | OE1 | GLN | A | 508 | 26.283 | 19.700 | −41.660 | 1.00 | 41.79 |
| ATOM | 3845 | NE2 | GLN | A | 508 | 25.279 | 20.977 | −43.242 | 1.00 | 40.42 |
| ATOM | 3846 | C | GLN | A | 508 | 22.827 | 24.502 | −40.100 | 1.00 | 33.06 |
| ATOM | 3847 | O | GLN | A | 508 | 22.136 | 25.178 | −40.873 | 1.00 | 32.49 |
| ATOM | 3848 | N | PHE | A | 509 | 23.494 | 25.037 | −39.075 | 1.00 | 33.80 |
| ATOM | 3849 | CA | PHE | A | 509 | 23.432 | 26.476 | −38.782 | 1.00 | 35.03 |
| ATOM | 3850 | CB | PHE | A | 509 | 24.413 | 26.837 | −37.651 | 1.00 | 36.75 |
| ATOM | 3851 | CG | PHE | A | 509 | 24.481 | 28.315 | −37.340 | 1.00 | 39.07 |
| ATOM | 3852 | CD1 | PHE | A | 509 | 23.592 | 28.893 | −36.428 | 1.00 | 41.58 |
| ATOM | 3853 | CE1 | PHE | A | 509 | 23.642 | 30.265 | −36.140 | 1.00 | 42.61 |
| ATOM | 3854 | CZ | PHE | A | 509 | 24.603 | 31.073 | −36.766 | 1.00 | 41.78 |
| ATOM | 3855 | CE2 | PHE | A | 509 | 25.507 | 30.503 | −37.678 | 1.00 | 42.48 |
| ATOM | 3856 | CD2 | PHE | A | 509 | 25.441 | 29.127 | −37.955 | 1.00 | 41.46 |
| ATOM | 3857 | C | PHE | A | 509 | 23.712 | 27.311 | −40.040 | 1.00 | 34.58 |
| ATOM | 3858 | O | PHE | A | 509 | 24.614 | 26.990 | −40.815 | 1.00 | 34.58 |
| ATOM | 3859 | N | GLY | A | 510 | 22.912 | 28.355 | −40.256 | 1.00 | 33.85 |
| ATOM | 3860 | CA | GLY | A | 510 | 23.101 | 29.241 | −41.407 | 1.00 | 33.22 |

TABLE 20-continued

| | | | | | | | | | |
|---|---|---|---|---|---|---|---|---|---|
| ATOM | 3861 | C | GLY | A | 510 | 22.352 | 28.826 | −42.671 | 1.00 | 32.36 |
| ATOM | 3862 | O | GLY | A | 510 | 22.369 | 29.545 | −43.679 | 1.00 | 32.97 |
| ATOM | 3863 | N | GLN | A | 511 | 21.705 | 27.663 | −42.628 | 1.00 | 30.50 |
| ATOM | 3864 | CA | GLN | A | 511 | 20.885 | 27.217 | −43.745 | 1.00 | 29.02 |
| ATOM | 3865 | CB | GLN | A | 511 | 21.026 | 25.712 | −43.931 | 1.00 | 28.92 |
| ATOM | 3866 | CG | GLN | A | 511 | 22.436 | 25.276 | −44.349 | 1.00 | 29.91 |
| ATOM | 3867 | CD | GLN | A | 511 | 22.571 | 23.776 | −44.439 | 1.00 | 31.36 |
| ATOM | 3868 | OE1 | GLN | A | 511 | 21.760 | 23.036 | −43.879 | 1.00 | 31.69 |
| ATOM | 3869 | NE2 | GLN | A | 511 | 23.590 | 23.309 | −45.160 | 1.00 | 30.72 |
| ATOM | 3870 | C | GLN | A | 511 | 19.418 | 27.619 | −43.543 | 1.00 | 27.82 |
| ATOM | 3871 | O | GLN | A | 511 | 18.928 | 27.695 | −42.399 | 1.00 | 27.36 |
| ATOM | 3872 | N | THR | A | 512 | 18.727 | 27.895 | −44.650 | 1.00 | 25.92 |
| ATOM | 3873 | CA | THR | A | 512 | 17.305 | 28.271 | −44.613 | 1.00 | 24.51 |
| ATOM | 3874 | CB | THR | A | 512 | 17.126 | 29.763 | −44.994 | 1.00 | 24.95 |
| ATOM | 3875 | OG1 | THR | A | 512 | 17.769 | 30.580 | −44.004 | 1.00 | 27.43 |
| ATOM | 3876 | CG2 | THR | A | 512 | 15.653 | 30.151 | −45.069 | 1.00 | 25.94 |
| ATOM | 3877 | C | THR | A | 512 | 16.536 | 27.384 | −45.600 | 1.00 | 23.09 |
| ATOM | 3878 | O | THR | A | 512 | 16.994 | 27.152 | −46.717 | 1.00 | 22.75 |
| ATOM | 3879 | N | VAL | A | 513 | 15.376 | 26.877 | −45.200 | 1.00 | 20.62 |
| ATOM | 3880 | CA | VAL | A | 513 | 14.593 | 26.074 | −46.136 | 1.00 | 19.05 |
| ATOM | 3881 | CB | VAL | A | 513 | 13.946 | 24.855 | −45.428 | 1.00 | 19.18 |
| ATOM | 3882 | CG1 | VAL | A | 513 | 13.041 | 24.064 | −46.397 | 1.00 | 18.87 |
| ATOM | 3883 | CG2 | VAL | A | 513 | 15.042 | 23.938 | −44.895 | 1.00 | 20.56 |
| ATOM | 3884 | C | VAL | A | 513 | 13.536 | 26.979 | −46.748 | 1.00 | 17.98 |
| ATOM | 3885 | O | VAL | A | 513 | 12.910 | 27.768 | −46.029 | 1.00 | 16.65 |
| ATOM | 3886 | N | LYS | A | 514 | 13.346 | 26.857 | −48.063 | 1.00 | 17.91 |
| ATOM | 3887 | CA | LYS | A | 514 | 12.279 | 27.583 | −48.757 | 1.00 | 18.14 |
| ATOM | 3888 | CB | LYS | A | 514 | 12.845 | 28.712 | −49.638 | 1.00 | 17.66 |
| ATOM | 3889 | CG | LYS | A | 514 | 13.867 | 29.576 | −48.945 | 1.00 | 19.26 |
| ATOM | 3890 | CD | LYS | A | 514 | 14.197 | 30.839 | −49.765 | 1.00 | 21.27 |
| ATOM | 3891 | CE | LYS | A | 514 | 15.224 | 31.675 | −49.001 | 1.00 | 26.06 |
| ATOM | 3892 | NZ | LYS | A | 514 | 15.461 | 33.022 | −49.626 | 1.00 | 28.70 |
| ATOM | 3893 | C | LYS | A | 514 | 11.494 | 26.621 | −49.625 | 1.00 | 18.22 |
| ATOM | 3894 | O | LYS | A | 514 | 11.949 | 25.502 | −49.912 | 1.00 | 18.39 |
| ATOM | 3895 | N | VAL | A | 515 | 10.304 | 27.037 | −50.045 | 1.00 | 18.20 |
| ATOM | 3896 | CA | VAL | A | 515 | 9.546 | 26.212 | −50.980 | 1.00 | 19.00 |
| ATOM | 3897 | CB | VAL | A | 515 | 8.198 | 25.731 | −50.404 | 1.00 | 20.00 |
| ATOM | 3898 | CG1 | VAL | A | 515 | 7.403 | 26.904 | −49.879 | 1.00 | 21.01 |
| ATOM | 3899 | CG2 | VAL | A | 515 | 7.417 | 24.903 | −51.447 | 1.00 | 20.10 |
| ATOM | 3900 | C | VAL | A | 515 | 9.421 | 26.973 | −52.302 | 1.00 | 18.89 |
| ATOM | 3901 | O | VAL | A | 515 | 9.079 | 28.159 | −52.317 | 1.00 | 18.67 |
| ATOM | 3902 | N | ALA | A | 516 | 9.781 | 26.295 | −53.390 | 1.00 | 19.87 |
| ATOM | 3903 | CA | ALA | A | 516 | 9.796 | 26.898 | −54.732 | 1.00 | 20.38 |
| ATOM | 3904 | CB | ALA | A | 516 | 11.177 | 26.768 | −55.356 | 1.00 | 20.58 |
| ATOM | 3905 | C | ALA | A | 516 | 8.789 | 26.110 | −55.525 | 1.00 | 20.65 |
| ATOM | 3906 | O | ALA | A | 516 | 8.638 | 24.910 | −55.303 | 1.00 | 20.40 |
| ATOM | 3907 | N | GLY | A | 517 | 8.075 | 26.765 | −56.430 | 1.00 | 20.80 |
| ATOM | 3908 | CA | GLY | A | 517 | 7.092 | 26.039 | −57.214 | 1.00 | 22.32 |
| ATOM | 3909 | C | GLY | A | 517 | 6.536 | 26.853 | −58.352 | 1.00 | 22.86 |
| ATOM | 3910 | O | GLY | A | 517 | 6.902 | 28.024 | −58.527 | 1.00 | 22.58 |
| ATOM | 3911 | N | ASN | A | 518 | 5.642 | 26.233 | −59.116 | 1.00 | 24.66 |
| ATOM | 3912 | CA | ASN | A | 518 | 5.201 | 26.817 | −60.390 | 1.00 | 26.74 |
| ATOM | 3913 | CB | ASN | A | 518 | 4.670 | 25.754 | −61.354 | 1.00 | 26.97 |
| ATOM | 3914 | CG | ASN | A | 518 | 3.386 | 25.117 | −60.872 | 1.00 | 31.69 |
| ATOM | 3915 | OD1 | ASN | A | 518 | 3.004 | 25.226 | −59.677 | 1.00 | 28.89 |
| ATOM | 3916 | ND2 | ASN | A | 518 | 2.707 | 24.419 | −61.786 | 1.00 | 31.65 |
| ATOM | 3917 | C | ASN | A | 518 | 4.199 | 27.937 | −60.232 | 1.00 | 27.20 |
| ATOM | 3918 | O | ASN | A | 518 | 4.154 | 28.822 | −61.079 | 1.00 | 28.68 |
| ATOM | 3919 | N | ALA | A | 519 | 3.399 | 27.907 | −59.163 | 1.00 | 27.04 |
| ATOM | 3920 | CA | ALA | A | 519 | 2.424 | 28.978 | −58.898 | 1.00 | 26.47 |
| ATOM | 3921 | CB | ALA | A | 519 | 1.473 | 28.598 | −57.747 | 1.00 | 27.02 |
| ATOM | 3922 | C | ALA | A | 519 | 3.090 | 30.322 | −58.629 | 1.00 | 26.35 |
| ATOM | 3923 | O | ALA | A | 519 | 4.226 | 30.394 | −58.135 | 1.00 | 25.27 |
| ATOM | 3924 | N | ALA | A | 520 | 2.369 | 31.394 | −58.954 | 1.00 | 26.25 |
| ATOM | 3925 | CA | ALA | A | 520 | 2.887 | 32.741 | −58.784 | 1.00 | 26.77 |
| ATOM | 3926 | CB | ALA | A | 520 | 1.872 | 33.775 | −59.298 | 1.00 | 27.50 |
| ATOM | 3927 | C | ALA | A | 520 | 3.250 | 33.004 | −57.317 | 1.00 | 26.68 |
| ATOM | 3928 | O | ALA | A | 520 | 4.301 | 33.560 | −57.030 | 1.00 | 26.01 |
| ATOM | 3929 | N | ALA | A | 521 | 2.395 | 32.548 | −56.399 | 1.00 | 26.75 |
| ATOM | 3930 | CA | ALA | A | 521 | 2.628 | 32.712 | −54.963 | 1.00 | 26.82 |
| ATOM | 3931 | CB | ALA | A | 521 | 1.395 | 32.251 | −54.167 | 1.00 | 26.85 |
| ATOM | 3932 | C | ALA | A | 521 | 3.876 | 31.950 | −54.504 | 1.00 | 26.51 |
| ATOM | 3933 | O | ALA | A | 521 | 4.485 | 32.305 | −53.494 | 1.00 | 26.63 |
| ATOM | 3934 | N | LEU | A | 522 | 4.261 | 30.919 | −55.259 | 1.00 | 26.79 |
| ATOM | 3935 | CA | LEU | A | 522 | 5.452 | 30.113 | −54.932 | 1.00 | 26.50 |
| ATOM | 3936 | CB | LEU | A | 522 | 5.185 | 28.626 | −55.155 | 1.00 | 26.64 |
| ATOM | 3937 | CG | LEU | A | 522 | 4.224 | 27.946 | −54.169 | 1.00 | 26.58 |
| ATOM | 3938 | CD1 | LEU | A | 522 | 4.049 | 26.489 | −54.533 | 1.00 | 27.59 |
| ATOM | 3939 | CD2 | LEU | A | 522 | 4.718 | 28.092 | −52.730 | 1.00 | 28.08 |
| ATOM | 3940 | C | LEU | A | 522 | 6.696 | 30.559 | −55.709 | 1.00 | 26.54 |

TABLE 20-continued

| ATOM | 3941 | O | LEU | A | 522 | 7.779 | 29.987 | −55.547 | 1.00 | 25.56 |
| ATOM | 3942 | N | GLY | A | 523 | 6.518 | 31.575 | −56.552 | 1.00 | 26.25 |
| ATOM | 3943 | CA | GLY | A | 523 | 7.637 | 32.267 | −57.199 | 1.00 | 26.16 |
| ATOM | 3944 | C | GLY | A | 523 | 7.996 | 31.809 | −58.607 | 1.00 | 26.84 |
| ATOM | 3945 | O | GLY | A | 523 | 9.029 | 32.227 | −59.152 | 1.00 | 25.81 |
| ATOM | 3946 | N | ASN | A | 524 | 7.162 | 30.946 | −59.193 | 1.00 | 27.13 |
| ATOM | 3947 | CA | ASN | A | 524 | 7.413 | 30.419 | −60.539 | 1.00 | 27.74 |
| ATOM | 3948 | CB | ASN | A | 524 | 7.046 | 31.484 | −61.591 | 1.00 | 28.43 |
| ATOM | 3949 | CG | ASN | A | 524 | 7.123 | 30.960 | −63.015 | 1.00 | 30.79 |
| ATOM | 3950 | OD1 | ASN | A | 524 | 6.856 | 29.780 | −63.285 | 1.00 | 30.80 |
| ATOM | 3951 | ND2 | ASN | A | 524 | 7.515 | 31.838 | −63.936 | 1.00 | 33.61 |
| ATOM | 3952 | C | ASN | A | 524 | 8.845 | 29.857 | −60.710 | 1.00 | 28.44 |
| ATOM | 3953 | O | ASN | A | 524 | 9.531 | 30.104 | −61.720 | 1.00 | 27.82 |
| ATOM | 3954 | N | TRP | A | 525 | 9.280 | 29.111 | −59.693 | 1.00 | 27.99 |
| ATOM | 3955 | CA | TRP | A | 525 | 10.573 | 28.398 | −59.659 | 1.00 | 28.92 |
| ATOM | 3956 | CB | TRP | A | 525 | 10.787 | 27.507 | −60.896 | 1.00 | 28.31 |
| ATOM | 3957 | CG | TRP | A | 525 | 9.803 | 26.394 | −61.060 | 1.00 | 27.68 |
| ATOM | 3958 | CD1 | TRP | A | 525 | 8.902 | 26.247 | −62.078 | 1.00 | 27.96 |
| ATOM | 3959 | NE1 | TRP | A | 525 | 8.166 | 25.106 | −61.907 | 1.00 | 27.55 |
| ATOM | 3960 | CE2 | TRP | A | 525 | 8.589 | 24.471 | −60.762 | 1.00 | 30.58 |
| ATOM | 3961 | CD2 | TRP | A | 525 | 9.609 | 25.277 | −60.184 | 1.00 | 27.84 |
| ATOM | 3962 | CE3 | TRP | A | 525 | 10.230 | 24.842 | −59.001 | 1.00 | 26.50 |
| ATOM | 3963 | CZ3 | TRP | A | 525 | 9.787 | 23.655 | −58.411 | 1.00 | 27.55 |
| ATOM | 3964 | CH2 | TRP | A | 525 | 8.752 | 22.889 | −58.998 | 1.00 | 27.90 |
| ATOM | 3965 | CZ2 | TRP | A | 525 | 8.144 | 23.279 | −60.168 | 1.00 | 26.22 |
| ATOM | 3966 | C | TRP | A | 525 | 11.790 | 29.301 | −59.452 | 1.00 | 29.66 |
| ATOM | 3967 | O | TRP | A | 525 | 12.921 | 28.804 | −59.346 | 1.00 | 30.61 |
| ATOM | 3968 | N | SER | A | 526 | 11.570 | 30.613 | −59.380 | 1.00 | 30.33 |
| ATOM | 3969 | CA | SER | A | 526 | 12.645 | 31.536 | −59.004 | 1.00 | 31.13 |
| ATOM | 3970 | CB | SER | A | 526 | 12.213 | 32.993 | −59.187 | 1.00 | 31.02 |
| ATOM | 3971 | OG | SER | A | 526 | 13.166 | 33.838 | −58.562 | 1.00 | 33.69 |
| ATOM | 3972 | C | SER | A | 526 | 13.086 | 31.312 | −57.560 | 1.00 | 31.29 |
| ATOM | 3973 | O | SER | A | 526 | 12.271 | 31.381 | −56.627 | 1.00 | 31.21 |
| ATOM | 3974 | N | THR | A | 527 | 14.373 | 31.049 | −57.367 | 1.00 | 31.34 |
| ATOM | 3975 | CA | THR | A | 527 | 14.880 | 30.794 | −56.021 | 1.00 | 31.64 |
| ATOM | 3976 | CB | THR | A | 527 | 16.259 | 30.098 | −56.024 | 1.00 | 31.79 |
| ATOM | 3977 | OG1 | THR | A | 527 | 17.217 | 30.931 | −56.682 | 1.00 | 31.43 |
| ATOM | 3978 | CG2 | THR | A | 527 | 16.169 | 28.739 | −56.724 | 1.00 | 32.27 |
| ATOM | 3979 | C | THR | A | 527 | 14.911 | 32.045 | −55.152 | 1.00 | 31.99 |
| ATOM | 3980 | O | THR | A | 527 | 14.847 | 31.959 | −53.922 | 1.00 | 32.36 |
| ATOM | 3981 | N | SER | A | 528 | 14.986 | 33.209 | −55.787 | 1.00 | 31.79 |
| ATOM | 3982 | CA | SER | A | 528 | 14.928 | 34.463 | −55.054 | 1.00 | 32.02 |
| ATOM | 3983 | CB | SER | A | 528 | 15.517 | 35.615 | −55.885 | 1.00 | 32.70 |
| ATOM | 3984 | OG | SER | A | 528 | 14.712 | 35.882 | −57.031 | 1.00 | 34.94 |
| ATOM | 3985 | C | SER | A | 528 | 13.497 | 34.784 | −54.579 | 1.00 | 31.23 |
| ATOM | 3986 | O | SER | A | 528 | 13.330 | 35.435 | −53.550 | 1.00 | 32.02 |
| ATOM | 3987 | N | ALA | A | 529 | 12.479 | 34.314 | −55.306 | 1.00 | 29.33 |
| ATOM | 3988 | CA | ALA | A | 529 | 11.093 | 34.506 | −54.893 | 1.00 | 27.60 |
| ATOM | 3989 | CB | ALA | A | 529 | 10.211 | 34.864 | −56.086 | 1.00 | 27.34 |
| ATOM | 3990 | C | ALA | A | 529 | 10.482 | 33.328 | −54.112 | 1.00 | 26.40 |
| ATOM | 3991 | O | ALA | A | 529 | 9.311 | 33.382 | −53.754 | 1.00 | 26.54 |
| ATOM | 3992 | N | ALA | A | 530 | 11.268 | 32.286 | −53.842 | 1.00 | 25.12 |
| ATOM | 3993 | CA | ALA | A | 530 | 10.777 | 31.114 | −53.096 | 1.00 | 24.19 |
| ATOM | 3994 | CB | ALA | A | 530 | 11.855 | 30.063 | −52.991 | 1.00 | 23.88 |
| ATOM | 3995 | C | ALA | A | 530 | 10.336 | 31.555 | −51.706 | 1.00 | 23.55 |
| ATOM | 3996 | O | ALA | A | 530 | 10.848 | 32.540 | −51.182 | 1.00 | 23.61 |
| ATOM | 3997 | N | VAL | A | 531 | 9.396 | 30.833 | −51.110 | 1.00 | 22.18 |
| ATOM | 3998 | CA | VAL | A | 531 | 8.851 | 31.248 | −49.821 | 1.00 | 22.62 |
| ATOM | 3999 | CB | VAL | A | 531 | 7.380 | 30.821 | −49.677 | 1.00 | 22.81 |
| ATOM | 4000 | CG1 | VAL | A | 531 | 6.815 | 31.335 | −48.346 | 1.00 | 25.06 |
| ATOM | 4001 | CG2 | VAL | A | 531 | 6.551 | 31.353 | −50.886 | 1.00 | 25.38 |
| ATOM | 4002 | C | VAL | A | 531 | 9.659 | 30.646 | −48.674 | 1.00 | 21.29 |
| ATOM | 4003 | O | VAL | A | 531 | 9.768 | 29.425 | −48.564 | 1.00 | 20.72 |
| ATOM | 4004 | N | ALA | A | 532 | 10.215 | 31.493 | −47.819 | 1.00 | 20.86 |
| ATOM | 4005 | CA | ALA | A | 532 | 11.008 | 30.999 | −46.698 | 1.00 | 20.26 |
| ATOM | 4006 | CB | ALA | A | 532 | 11.850 | 32.128 | −46.084 | 1.00 | 21.02 |
| ATOM | 4007 | C | ALA | A | 532 | 10.093 | 30.356 | −45.646 | 1.00 | 20.51 |
| ATOM | 4008 | O | ALA | A | 532 | 9.019 | 30.884 | −45.337 | 1.00 | 20.05 |
| ATOM | 4009 | N | LEU | A | 533 | 10.514 | 29.200 | −45.129 | 1.00 | 19.00 |
| ATOM | 4010 | CA | LEU | A | 533 | 9.855 | 28.565 | −43.999 | 1.00 | 18.65 |
| ATOM | 4011 | CB | LEU | A | 533 | 9.901 | 27.029 | −44.148 | 1.00 | 18.14 |
| ATOM | 4012 | CG | LEU | A | 533 | 9.395 | 26.450 | −45.483 | 1.00 | 19.25 |
| ATOM | 4013 | CD1 | LEU | A | 533 | 9.385 | 24.923 | −45.427 | 1.00 | 21.28 |
| ATOM | 4014 | CD2 | LEU | A | 533 | 8.030 | 26.980 | −45.894 | 1.00 | 18.58 |
| ATOM | 4015 | C | LEU | A | 533 | 10.541 | 29.014 | −42.702 | 1.00 | 18.95 |
| ATOM | 4016 | O | LEU | A | 533 | 11.622 | 29.648 | −42.744 | 1.00 | 18.94 |
| ATOM | 4017 | N | ASP | A | 534 | 9.905 | 28.715 | −41.570 | 1.00 | 18.56 |
| ATOM | 4018 | CA | ASP | A | 534 | 10.381 | 29.096 | −40.238 | 1.00 | 18.36 |
| ATOM | 4019 | CB | ASP | A | 534 | 9.220 | 29.634 | −39.374 | 1.00 | 19.76 |
| ATOM | 4020 | CG | ASP | A | 534 | 8.757 | 30.992 | −39.798 | 1.00 | 23.55 |

TABLE 20-continued

| | | | | | | | | | |
|---|---|---|---|---|---|---|---|---|---|
| ATOM | 4021 | OD1 | ASP | A | 534 | 7.548 | 31.264 | −39.659 | 1.00 | 26.14 |
| ATOM | 4022 | OD2 | ASP | A | 534 | 9.600 | 31.774 | −40.283 | 1.00 | 27.39 |
| ATOM | 4023 | C | ASP | A | 534 | 10.877 | 27.867 | −39.504 | 1.00 | 17.68 |
| ATOM | 4024 | O | ASP | A | 534 | 10.310 | 26.780 | −39.667 | 1.00 | 16.10 |
| ATOM | 4025 | N | ALA | A | 535 | 11.883 | 28.057 | −38.654 | 1.00 | 17.05 |
| ATOM | 4026 | CA | ALA | A | 535 | 12.405 | 26.950 | −37.835 | 1.00 | 17.76 |
| ATOM | 4027 | CB | ALA | A | 535 | 13.926 | 26.952 | −37.832 | 1.00 | 17.96 |
| ATOM | 4028 | C | ALA | A | 535 | 11.872 | 27.027 | −36.403 | 1.00 | 17.82 |
| ATOM | 4029 | O | ALA | A | 535 | 12.482 | 26.490 | −35.474 | 1.00 | 18.36 |
| ATOM | 4030 | N | VAL | A | 536 | 10.745 | 27.706 | −36.225 | 1.00 | 17.68 |
| ATOM | 4031 | CA | VAL | A | 536 | 10.138 | 27.861 | −34.898 | 1.00 | 18.65 |
| ATOM | 4032 | CB | VAL | A | 536 | 8.824 | 28.719 | −34.975 | 1.00 | 18.66 |
| ATOM | 4033 | CG1 | VAL | A | 536 | 7.805 | 28.123 | −35.971 | 1.00 | 19.98 |
| ATOM | 4034 | CG2 | VAL | A | 536 | 8.208 | 28.962 | −33.570 | 1.00 | 20.19 |
| ATOM | 4035 | C | VAL | A | 536 | 9.938 | 26.514 | −34.155 | 1.00 | 18.51 |
| ATOM | 4036 | O | VAL | A | 536 | 10.124 | 26.437 | −32.923 | 1.00 | 19.61 |
| ATOM | 4037 | N | ASN | A | 537 | 9.570 | 25.468 | −34.883 | 1.00 | 18.59 |
| ATOM | 4038 | CA | ASN | A | 537 | 9.344 | 24.154 | −34.261 | 1.00 | 19.07 |
| ATOM | 4039 | CB | ASN | A | 537 | 8.074 | 23.498 | −34.816 | 1.00 | 19.28 |
| ATOM | 4040 | CG | ASN | A | 537 | 6.800 | 24.252 | −34.448 | 1.00 | 21.02 |
| ATOM | 4041 | OD1 | ASN | A | 537 | 6.742 | 24.940 | −33.435 | 1.00 | 24.12 |
| ATOM | 4042 | ND2 | ASN | A | 537 | 5.762 | 24.089 | −35.265 | 1.00 | 20.99 |
| ATOM | 4043 | C | ASN | A | 537 | 10.518 | 23.182 | −34.445 | 1.00 | 19.15 |
| ATOM | 4044 | O | ASN | A | 537 | 10.394 | 21.971 | −34.196 | 1.00 | 18.60 |
| ATOM | 4045 | N | TYR | A | 538 | 11.653 | 23.699 | −34.897 | 1.00 | 19.05 |
| ATOM | 4046 | CA | TYR | A | 538 | 12.767 | 22.830 | −35.234 | 1.00 | 20.32 |
| ATOM | 4047 | CB | TYR | A | 538 | 13.816 | 23.618 | −36.026 | 1.00 | 20.37 |
| ATOM | 4048 | CG | TYR | A | 538 | 14.916 | 22.747 | −36.588 | 1.00 | 20.37 |
| ATOM | 4049 | CD1 | TYR | A | 538 | 14.822 | 22.238 | −37.886 | 1.00 | 20.39 |
| ATOM | 4050 | CE1 | TYR | A | 538 | 15.853 | 21.436 | −38.437 | 1.00 | 20.49 |
| ATOM | 4051 | CZ | TYR | A | 538 | 16.961 | 21.137 | −37.670 | 1.00 | 20.65 |
| ATOM | 4052 | OH | TYR | A | 538 | 17.946 | 20.341 | −38.218 | 1.00 | 21.53 |
| ATOM | 4053 | CE2 | TYR | A | 538 | 17.066 | 21.602 | −36.361 | 1.00 | 22.05 |
| ATOM | 4054 | CD2 | TYR | A | 538 | 16.043 | 22.418 | −35.825 | 1.00 | 21.95 |
| ATOM | 4055 | C | TYR | A | 538 | 13.436 | 22.209 | −33.981 | 1.00 | 21.29 |
| ATOM | 4056 | O | TYR | A | 538 | 13.733 | 22.919 | −33.036 | 1.00 | 21.89 |
| ATOM | 4057 | N | ALA | A | 539 | 13.695 | 20.902 | −34.014 | 1.00 | 22.15 |
| ATOM | 4058 | CA | ALA | A | 539 | 14.646 | 20.258 | −33.083 | 1.00 | 23.67 |
| ATOM | 4059 | CB | ALA | A | 539 | 13.909 | 19.536 | −31.976 | 1.00 | 23.94 |
| ATOM | 4060 | C | ALA | A | 539 | 15.545 | 19.289 | −33.849 | 1.00 | 24.35 |
| ATOM | 4061 | O | ALA | A | 539 | 15.117 | 18.698 | −34.833 | 1.00 | 23.63 |
| ATOM | 4062 | N | ASP | A | 540 | 16.793 | 19.118 | −33.405 | 1.00 | 25.69 |
| ATOM | 4063 | CA | ASP | A | 540 | 17.722 | 18.196 | −34.099 | 1.00 | 27.42 |
| ATOM | 4064 | CB | ASP | A | 540 | 19.044 | 18.051 | −33.339 | 1.00 | 28.62 |
| ATOM | 4065 | CG | ASP | A | 540 | 19.724 | 19.368 | −33.140 | 1.00 | 33.80 |
| ATOM | 4066 | OD1 | ASP | A | 540 | 19.875 | 20.115 | −34.147 | 1.00 | 36.83 |
| ATOM | 4067 | OD2 | ASP | A | 540 | 20.080 | 19.663 | −31.970 | 1.00 | 40.32 |
| ATOM | 4068 | C | ASP | A | 540 | 17.150 | 16.818 | −34.400 | 1.00 | 26.63 |
| ATOM | 4069 | O | ASP | A | 540 | 17.386 | 16.277 | −35.485 | 1.00 | 27.28 |
| ATOM | 4070 | N | ASN | A | 541 | 16.403 | 16.247 | −33.458 | 1.00 | 25.08 |
| ATOM | 4071 | CA | ASN | A | 541 | 15.827 | 14.922 | −33.687 | 1.00 | 24.03 |
| ATOM | 4072 | CB | ASN | A | 541 | 15.988 | 14.032 | −32.441 | 1.00 | 25.14 |
| ATOM | 4073 | CG | ASN | A | 541 | 15.337 | 14.623 | −31.191 | 1.00 | 27.81 |
| ATOM | 4074 | OD1 | ASN | A | 541 | 15.366 | 14.001 | −30.118 | 1.00 | 31.57 |
| ATOM | 4075 | ND2 | ASN | A | 541 | 14.771 | 15.824 | −31.306 | 1.00 | 28.81 |
| ATOM | 4076 | C | ASN | A | 541 | 14.349 | 14.991 | −34.118 | 1.00 | 22.46 |
| ATOM | 4077 | O | ASN | A | 541 | 13.660 | 13.979 | −34.172 | 1.00 | 22.35 |
| ATOM | 4078 | N | HIS | A | 542 | 13.871 | 16.197 | −34.403 | 1.00 | 19.85 |
| ATOM | 4079 | CA | HIS | A | 542 | 12.580 | 16.354 | −35.083 | 1.00 | 18.22 |
| ATOM | 4080 | CB | HIS | A | 542 | 11.426 | 16.392 | −34.062 | 1.00 | 16.89 |
| ATOM | 4081 | CG | HIS | A | 542 | 10.071 | 16.341 | −34.699 | 1.00 | 17.32 |
| ATOM | 4082 | ND1 | HIS | A | 542 | 9.211 | 17.417 | −34.711 | 1.00 | 16.28 |
| ATOM | 4083 | CE1 | HIS | A | 542 | 8.111 | 17.088 | −35.371 | 1.00 | 14.64 |
| ATOM | 4084 | NE2 | HIS | A | 542 | 8.217 | 15.834 | −35.765 | 1.00 | 15.41 |
| ATOM | 4085 | CD2 | HIS | A | 542 | 9.435 | 15.340 | −35.358 | 1.00 | 15.14 |
| ATOM | 4086 | C | HIS | A | 542 | 12.662 | 17.650 | −35.902 | 1.00 | 17.48 |
| ATOM | 4087 | O | HIS | A | 542 | 12.198 | 18.698 | −35.446 | 1.00 | 17.79 |
| ATOM | 4088 | N | PRO | A | 543 | 13.324 | 17.584 | −37.083 | 1.00 | 17.00 |
| ATOM | 4089 | CA | PRO | A | 543 | 13.797 | 18.752 | −37.832 | 1.00 | 17.09 |
| ATOM | 4090 | CB | PRO | A | 543 | 14.948 | 18.164 | −38.677 | 1.00 | 16.57 |
| ATOM | 4091 | CG | PRO | A | 543 | 14.472 | 16.759 | −38.994 | 1.00 | 18.22 |
| ATOM | 4092 | CD | PRO | A | 543 | 13.676 | 16.321 | −37.764 | 1.00 | 17.39 |
| ATOM | 4093 | C | PRO | A | 543 | 12.718 | 19.435 | −38.691 | 1.00 | 16.46 |
| ATOM | 4094 | O | PRO | A | 543 | 12.811 | 19.497 | −39.922 | 1.00 | 17.09 |
| ATOM | 4095 | N | LEU | A | 544 | 11.726 | 19.987 | −38.009 | 1.00 | 15.36 |
| ATOM | 4096 | CA | LEU | A | 544 | 10.534 | 20.535 | −38.636 | 1.00 | 15.10 |
| ATOM | 4097 | CB | LEU | A | 544 | 9.341 | 20.376 | −37.672 | 1.00 | 15.29 |
| ATOM | 4098 | CG | LEU | A | 544 | 7.968 | 20.927 | −38.134 | 1.00 | 16.53 |
| ATOM | 4099 | CD1 | LEU | A | 544 | 7.524 | 20.364 | −39.494 | 1.00 | 15.92 |
| ATOM | 4100 | CD2 | LEU | A | 544 | 6.900 | 20.700 | −37.062 | 1.00 | 14.59 |

TABLE 20-continued

| ATOM | 4101 | C | LEU | A | 544 | 10.694 | 22.018 | −39.025 | 1.00 | 15.09 |
| ATOM | 4102 | O | LEU | A | 544 | 11.037 | 22.851 | −38.197 | 1.00 | 15.34 |
| ATOM | 4103 | N | TRP | A | 545 | 10.456 | 22.298 | −40.303 | 1.00 | 15.03 |
| ATOM | 4104 | CA | TRP | A | 545 | 10.327 | 23.637 | −40.843 | 1.00 | 15.36 |
| ATOM | 4105 | CB | TRP | A | 545 | 11.288 | 23.790 | −42.023 | 1.00 | 15.40 |
| ATOM | 4106 | CG | TRP | A | 545 | 12.758 | 23.921 | −41.663 | 1.00 | 15.62 |
| ATOM | 4107 | CD1 | TRP | A | 545 | 13.653 | 22.903 | −41.384 | 1.00 | 16.85 |
| ATOM | 4108 | NE1 | TRP | A | 545 | 14.906 | 23.437 | −41.129 | 1.00 | 18.69 |
| ATOM | 4109 | CE2 | TRP | A | 545 | 14.837 | 24.803 | −41.246 | 1.00 | 17.78 |
| ATOM | 4110 | CD2 | TRP | A | 545 | 13.498 | 25.140 | −41.584 | 1.00 | 17.01 |
| ATOM | 4111 | CE3 | TRP | A | 545 | 13.163 | 26.488 | −41.777 | 1.00 | 17.17 |
| ATOM | 4112 | CZ3 | TRP | A | 545 | 14.165 | 27.456 | −41.637 | 1.00 | 18.29 |
| ATOM | 4113 | CH2 | TRP | A | 545 | 15.483 | 27.085 | −41.295 | 1.00 | 17.22 |
| ATOM | 4114 | CZ2 | TRP | A | 545 | 15.835 | 25.767 | −41.111 | 1.00 | 19.09 |
| ATOM | 4115 | C | TRP | A | 545 | 8.907 | 23.832 | −41.359 | 1.00 | 15.14 |
| ATOM | 4116 | O | TRP | A | 545 | 8.327 | 22.933 | −41.986 | 1.00 | 14.45 |
| ATOM | 4117 | N | ILE | A | 546 | 8.362 | 25.025 | −41.149 | 1.00 | 15.19 |
| ATOM | 4118 | CA | ILE | A | 546 | 6.938 | 25.244 | −41.428 | 1.00 | 16.51 |
| ATOM | 4119 | CB | ILE | A | 546 | 6.107 | 24.988 | −40.130 | 1.00 | 17.39 |
| ATOM | 4120 | CG1 | ILE | A | 546 | 4.615 | 24.852 | −40.420 | 1.00 | 20.44 |
| ATOM | 4121 | CD1 | ILE | A | 546 | 3.882 | 23.992 | −39.392 | 1.00 | 23.59 |
| ATOM | 4122 | CG2 | ILE | A | 546 | 6.391 | 26.064 | −39.050 | 1.00 | 17.70 |
| ATOM | 4123 | C | ILE | A | 546 | 6.674 | 26.635 | −42.006 | 1.00 | 16.75 |
| ATOM | 4124 | O | ILE | A | 546 | 7.352 | 27.593 | −41.647 | 1.00 | 15.81 |
| ATOM | 4125 | N | ALA | A | 547 | 5.716 | 26.743 | −42.925 | 1.00 | 16.88 |
| ATOM | 4126 | CA | ALA | A | 547 | 5.197 | 28.057 | −43.279 | 1.00 | 17.94 |
| ATOM | 4127 | CB | ALA | A | 547 | 6.222 | 28.893 | −43.931 | 1.00 | 21.49 |
| ATOM | 4128 | C | ALA | A | 547 | 4.009 | 27.919 | −44.167 | 1.00 | 18.29 |
| ATOM | 4129 | O | ALA | A | 547 | 3.727 | 26.828 | −44.655 | 1.00 | 18.52 |
| ATOM | 4130 | N | THR | A | 548 | 3.316 | 29.031 | −44.362 | 1.00 | 17.99 |
| ATOM | 4131 | CA | THR | A | 548 | 1.970 | 29.017 | −44.919 | 1.00 | 18.72 |
| ATOM | 4132 | CB | THR | A | 548 | 0.929 | 29.419 | −43.855 | 1.00 | 18.65 |
| ATOM | 4133 | OG1 | THR | A | 548 | 1.000 | 28.500 | −42.751 | 1.00 | 19.46 |
| ATOM | 4134 | CG2 | THR | A | 548 | −0.491 | 29.379 | −44.438 | 1.00 | 18.79 |
| ATOM | 4135 | C | THR | A | 548 | 1.865 | 29.960 | −46.104 | 1.00 | 19.60 |
| ATOM | 4136 | O | THR | A | 548 | 2.347 | 31.090 | −46.040 | 1.00 | 19.83 |
| ATOM | 4137 | N | VAL | A | 549 | 1.227 | 29.485 | −47.164 | 1.00 | 20.41 |
| ATOM | 4138 | CA | VAL | A | 549 | 1.048 | 30.280 | −48.389 | 1.00 | 22.36 |
| ATOM | 4139 | CB | VAL | A | 549 | 1.944 | 29.722 | −49.537 | 1.00 | 22.77 |
| ATOM | 4140 | CG1 | VAL | A | 549 | 1.717 | 30.491 | −50.845 | 1.00 | 25.80 |
| ATOM | 4141 | CG2 | VAL | A | 549 | 3.429 | 29.781 | −49.148 | 1.00 | 24.78 |
| ATOM | 4142 | C | VAL | A | 549 | −0.399 | 30.119 | −48.800 | 1.00 | 22.21 |
| ATOM | 4143 | O | VAL | A | 549 | −0.943 | 29.018 | −48.719 | 1.00 | 21.56 |
| ATOM | 4144 | N | ASN | A | 550 | −1.028 | 31.211 | −49.240 | 1.00 | 22.80 |
| ATOM | 4145 | CA | ASN | A | 550 | −2.356 | 31.107 | −49.831 | 1.00 | 23.95 |
| ATOM | 4146 | CB | ASN | A | 550 | −3.114 | 32.411 | −49.649 | 1.00 | 24.39 |
| ATOM | 4147 | CG | ASN | A | 550 | −3.367 | 32.706 | −48.201 | 1.00 | 27.42 |
| ATOM | 4148 | OD1 | ASN | A | 550 | −3.811 | 31.838 | −47.462 | 1.00 | 28.69 |
| ATOM | 4149 | ND2 | ASN | A | 550 | −3.041 | 33.911 | −47.771 | 1.00 | 31.89 |
| ATOM | 4150 | C | ASN | A | 550 | −2.278 | 30.733 | −51.294 | 1.00 | 23.98 |
| ATOM | 4151 | O | ASN | A | 550 | −1.598 | 31.400 | −52.065 | 1.00 | 24.73 |
| ATOM | 4152 | N | LEU | A | 551 | −2.973 | 29.667 | −51.662 | 1.00 | 24.24 |
| ATOM | 4153 | CA | LEU | A | 551 | −3.016 | 29.180 | −53.020 | 1.00 | 24.78 |
| ATOM | 4154 | CB | LEU | A | 551 | −2.348 | 27.797 | −53.135 | 1.00 | 25.00 |
| ATOM | 4155 | CG | LEU | A | 551 | −0.858 | 27.721 | −52.787 | 1.00 | 25.19 |
| ATOM | 4156 | CD1 | LEU | A | 551 | −0.356 | 26.284 | −52.803 | 1.00 | 27.45 |
| ATOM | 4157 | CD2 | LEU | A | 551 | −0.018 | 28.613 | −53.718 | 1.00 | 26.73 |
| ATOM | 4158 | C | LEU | A | 551 | −4.471 | 29.104 | −53.488 | 1.00 | 25.46 |
| ATOM | 4159 | O | LEU | A | 551 | −5.393 | 29.018 | −52.675 | 1.00 | 24.27 |
| ATOM | 4160 | N | GLU | A | 552 | −4.661 | 29.148 | −54.804 | 1.00 | 26.15 |
| ATOM | 4161 | CA | GLU | A | 552 | −6.004 | 29.165 | −55.366 | 1.00 | 28.20 |
| ATOM | 4162 | CB | GLU | A | 552 | −5.955 | 29.639 | −56.823 | 1.00 | 28.30 |
| ATOM | 4163 | CG | GLU | A | 552 | −7.326 | 29.739 | −57.494 | 1.00 | 32.28 |
| ATOM | 4164 | CD | GLU | A | 552 | −7.250 | 30.281 | −58.926 | 1.00 | 33.44 |
| ATOM | 4165 | OE1 | GLU | A | 552 | −8.110 | 31.126 | −59.274 | 1.00 | 41.80 |
| ATOM | 4166 | OE2 | GLU | A | 552 | −6.340 | 29.873 | −59.695 | 1.00 | 39.14 |
| ATOM | 4167 | C | GLU | A | 552 | −6.610 | 27.768 | −55.253 | 1.00 | 26.97 |
| ATOM | 4168 | O | GLU | A | 552 | −5.979 | 26.783 | −55.622 | 1.00 | 26.49 |
| ATOM | 4169 | N | ALA | A | 553 | −7.822 | 27.684 | −54.723 | 1.00 | 27.21 |
| ATOM | 4170 | CA | ALA | A | 553 | −8.502 | 26.399 | −54.603 | 1.00 | 27.89 |
| ATOM | 4171 | CB | ALA | A | 553 | −9.876 | 26.574 | −53.953 | 1.00 | 28.37 |
| ATOM | 4172 | C | ALA | A | 553 | −8.637 | 25.773 | −55.979 | 1.00 | 28.57 |
| ATOM | 4173 | O | ALA | A | 553 | −8.900 | 26.477 | −56.952 | 1.00 | 28.83 |
| ATOM | 4174 | N | GLY | A | 554 | −8.438 | 24.465 | −56.064 | 1.00 | 28.44 |
| ATOM | 4175 | CA | GLY | A | 554 | −8.556 | 23.753 | −57.330 | 1.00 | 29.66 |
| ATOM | 4176 | C | GLY | A | 554 | −7.274 | 23.693 | −58.145 | 1.00 | 30.04 |
| ATOM | 4177 | O | GLY | A | 554 | −7.122 | 22.814 | −59.000 | 1.00 | 30.33 |
| ATOM | 4178 | N | ASP | A | 555 | −6.347 | 24.606 | −57.869 | 1.00 | 30.23 |
| ATOM | 4179 | CA | ASP | A | 555 | −5.098 | 24.716 | −58.630 | 1.00 | 30.61 |
| ATOM | 4180 | CB | ASP | A | 555 | −4.313 | 25.939 | −58.161 | 1.00 | 30.85 |

TABLE 20-continued

| | | | | | | | | | |
|---|---|---|---|---|---|---|---|---|---|
| ATOM | 4181 | CG | ASP | A | 555 | −3.382 | 26.503 | −59.236 | 1.00 | 34.49 |
| ATOM | 4182 | OD1 | ASP | A | 555 | −3.441 | 26.053 | −60.407 | 1.00 | 37.19 |
| ATOM | 4183 | OD2 | ASP | A | 555 | −2.572 | 27.408 | −58.901 | 1.00 | 36.59 |
| ATOM | 4184 | C | ASP | A | 555 | −4.238 | 23.467 | −58.486 | 1.00 | 30.14 |
| ATOM | 4185 | O | ASP | A | 555 | −4.156 | 22.882 | −57.419 | 1.00 | 30.07 |
| ATOM | 4186 | N | VAL | A | 556 | −3.602 | 23.046 | −59.572 | 1.00 | 29.55 |
| ATOM | 4187 | CA | VAL | A | 556 | −2.628 | 21.963 | −59.492 | 1.00 | 28.74 |
| ATOM | 4188 | CB | VAL | A | 556 | −2.732 | 20.987 | −60.680 | 1.00 | 29.35 |
| ATOM | 4189 | CG1 | VAL | A | 556 | −1.666 | 19.877 | −60.569 | 1.00 | 28.99 |
| ATOM | 4190 | CG2 | VAL | A | 556 | −4.125 | 20.365 | −60.720 | 1.00 | 30.44 |
| ATOM | 4191 | C | VAL | A | 556 | −1.261 | 22.623 | −59.448 | 1.00 | 28.04 |
| ATOM | 4192 | O | VAL | A | 556 | −0.869 | 23.336 | −60.384 | 1.00 | 27.25 |
| ATOM | 4193 | N | VAL | A | 557 | −0.544 | 22.389 | −58.352 | 1.00 | 26.81 |
| ATOM | 4194 | CA | VAL | A | 557 | 0.739 | 23.040 | −58.100 | 1.00 | 26.14 |
| ATOM | 4195 | CB | VAL | A | 557 | 0.690 | 23.859 | −56.759 | 1.00 | 26.71 |
| ATOM | 4196 | CG1 | VAL | A | 557 | 2.073 | 24.140 | −56.219 | 1.00 | 27.82 |
| ATOM | 4197 | CG2 | VAL | A | 557 | −0.088 | 25.175 | −56.952 | 1.00 | 27.34 |
| ATOM | 4198 | C | VAL | A | 557 | 1.856 | 21.999 | −58.092 | 1.00 | 25.64 |
| ATOM | 4199 | O | VAL | A | 557 | 1.646 | 20.845 | −57.693 | 1.00 | 25.24 |
| ATOM | 4200 | N | GLU | A | 558 | 3.035 | 22.409 | −58.553 | 1.00 | 24.16 |
| ATOM | 4201 | CA | GLU | A | 558 | 4.223 | 21.579 | −58.516 | 1.00 | 24.38 |
| ATOM | 4202 | CB | GLU | A | 558 | 4.737 | 21.296 | −59.933 | 1.00 | 24.86 |
| ATOM | 4203 | CG | GLU | A | 558 | 4.064 | 20.108 | −60.606 | 1.00 | 26.34 |
| ATOM | 4204 | CD | GLU | A | 558 | 4.670 | 19.790 | −61.962 | 1.00 | 27.68 |
| ATOM | 4205 | OE1 | GLU | A | 558 | 5.917 | 19.684 | −62.065 | 1.00 | 30.56 |
| ATOM | 4206 | OE2 | GLU | A | 558 | 3.883 | 19.638 | −62.915 | 1.00 | 32.45 |
| ATOM | 4207 | C | GLU | A | 558 | 5.262 | 22.337 | −57.730 | 1.00 | 22.54 |
| ATOM | 4208 | O | GLU | A | 558 | 5.389 | 23.550 | −57.883 | 1.00 | 22.93 |
| ATOM | 4209 | N | TYR | A | 559 | 5.992 | 21.640 | −56.867 | 1.00 | 21.45 |
| ATOM | 4210 | CA | TYR | A | 559 | 6.927 | 22.346 | −55.995 | 1.00 | 19.96 |
| ATOM | 4211 | CB | TYR | A | 559 | 6.188 | 22.972 | −54.784 | 1.00 | 19.42 |
| ATOM | 4212 | CG | TYR | A | 559 | 5.624 | 21.952 | −53.796 | 1.00 | 18.65 |
| ATOM | 4213 | CD1 | TYR | A | 559 | 6.383 | 21.524 | −52.703 | 1.00 | 18.64 |
| ATOM | 4214 | CE1 | TYR | A | 559 | 5.887 | 20.595 | −51.794 | 1.00 | 19.09 |
| ATOM | 4215 | CZ | TYR | A | 559 | 4.614 | 20.090 | −51.955 | 1.00 | 18.58 |
| ATOM | 4216 | OH | TYR | A | 559 | 4.135 | 19.160 | −51.056 | 1.00 | 20.55 |
| ATOM | 4217 | CE2 | TYR | A | 559 | 3.819 | 20.493 | −53.024 | 1.00 | 18.22 |
| ATOM | 4218 | CD2 | TYR | A | 559 | 4.335 | 21.438 | −53.946 | 1.00 | 18.82 |
| ATOM | 4219 | C | TYR | A | 559 | 8.066 | 21.445 | −55.541 | 1.00 | 20.13 |
| ATOM | 4220 | O | TYR | A | 559 | 8.008 | 20.215 | −55.679 | 1.00 | 20.26 |
| ATOM | 4221 | N | LYS | A | 560 | 9.098 | 22.079 | −54.995 | 1.00 | 19.51 |
| ATOM | 4222 | CA | LYS | A | 560 | 10.208 | 21.379 | −54.349 | 1.00 | 19.72 |
| ATOM | 4223 | CB | LYS | A | 560 | 11.410 | 21.175 | −55.282 | 1.00 | 19.66 |
| ATOM | 4224 | CG | LYS | A | 560 | 11.390 | 19.870 | −56.058 | 1.00 | 22.20 |
| ATOM | 4225 | CD | LYS | A | 560 | 12.767 | 19.633 | −56.714 | 1.00 | 24.46 |
| ATOM | 4226 | CE | LYS | A | 560 | 12.781 | 18.341 | −57.531 | 1.00 | 26.96 |
| ATOM | 4227 | NZ | LYS | A | 560 | 14.189 | 18.050 | −57.980 | 1.00 | 26.97 |
| ATOM | 4228 | C | LYS | A | 560 | 10.680 | 22.257 | −53.234 | 1.00 | 18.68 |
| ATOM | 4229 | O | LYS | A | 560 | 10.583 | 23.484 | −53.318 | 1.00 | 19.68 |
| ATOM | 4230 | N | TYR | A | 561 | 11.240 | 21.640 | −52.206 | 1.00 | 17.87 |
| ATOM | 4231 | CA | TYR | A | 561 | 11.927 | 22.420 | −51.187 | 1.00 | 17.82 |
| ATOM | 4232 | CB | TYR | A | 561 | 11.921 | 21.690 | −49.840 | 1.00 | 17.42 |
| ATOM | 4233 | CG | TYR | A | 561 | 10.518 | 21.449 | −49.346 | 1.00 | 16.12 |
| ATOM | 4234 | CD1 | TYR | A | 561 | 9.831 | 20.276 | −49.661 | 1.00 | 15.94 |
| ATOM | 4235 | CE1 | TYR | A | 561 | 8.511 | 20.062 | −49.199 | 1.00 | 15.79 |
| ATOM | 4236 | CZ | TYR | A | 561 | 7.897 | 21.050 | −48.456 | 1.00 | 15.89 |
| ATOM | 4237 | OH | TYR | A | 561 | 6.614 | 20.889 | −47.981 | 1.00 | 17.17 |
| ATOM | 4238 | CE2 | TYR | A | 561 | 8.557 | 22.224 | −48.164 | 1.00 | 16.19 |
| ATOM | 4239 | CD2 | TYR | A | 561 | 9.856 | 22.430 | −48.625 | 1.00 | 17.57 |
| ATOM | 4240 | C | TYR | A | 561 | 13.360 | 22.650 | −51.607 | 1.00 | 18.63 |
| ATOM | 4241 | O | TYR | A | 561 | 13.963 | 21.786 | −52.265 | 1.00 | 18.40 |
| ATOM | 4242 | N | ILE | A | 562 | 13.904 | 23.792 | −51.201 | 1.00 | 18.56 |
| ATOM | 4243 | CA | ILE | A | 562 | 15.322 | 24.085 | −51.434 | 1.00 | 20.18 |
| ATOM | 4244 | CB | ILE | A | 562 | 15.524 | 25.247 | −52.419 | 1.00 | 19.65 |
| ATOM | 4245 | CG1 | ILE | A | 562 | 14.837 | 26.520 | −51.896 | 1.00 | 21.64 |
| ATOM | 4246 | CD1 | ILE | A | 562 | 15.074 | 27.789 | −52.741 | 1.00 | 21.24 |
| ATOM | 4247 | CG2 | ILE | A | 562 | 15.017 | 24.829 | −53.797 | 1.00 | 20.44 |
| ATOM | 4248 | C | ILE | A | 562 | 15.971 | 24.446 | −50.128 | 1.00 | 20.56 |
| ATOM | 4249 | O | ILE | A | 562 | 15.316 | 24.956 | −49.229 | 1.00 | 19.84 |
| ATOM | 4250 | N | ASN | A | 563 | 17.254 | 24.134 | −50.029 | 1.00 | 21.41 |
| ATOM | 4251 | CA | ASN | A | 563 | 18.076 | 24.467 | −48.886 | 1.00 | 22.99 |
| ATOM | 4252 | CB | ASN | A | 563 | 18.833 | 23.209 | −48.435 | 1.00 | 22.69 |
| ATOM | 4253 | CG | ASN | A | 563 | 19.629 | 23.433 | −47.156 | 1.00 | 25.48 |
| ATOM | 4254 | OD1 | ASN | A | 563 | 20.203 | 24.492 | −46.965 | 1.00 | 28.81 |
| ATOM | 4255 | ND2 | ASN | A | 563 | 19.669 | 22.436 | −46.285 | 1.00 | 25.82 |
| ATOM | 4256 | C | ASN | A | 563 | 19.039 | 25.561 | −49.372 | 1.00 | 24.66 |
| ATOM | 4257 | O | ASN | A | 563 | 19.794 | 25.326 | −50.323 | 1.00 | 24.16 |
| ATOM | 4258 | N | VAL | A | 564 | 18.977 | 26.749 | −48.780 | 1.00 | 26.20 |
| ATOM | 4259 | CA | VAL | A | 564 | 19.877 | 27.837 | −49.206 | 1.00 | 28.74 |
| ATOM | 4260 | CB | VAL | A | 564 | 19.156 | 29.091 | −49.832 | 1.00 | 28.91 |

TABLE 20-continued

| ATOM | 4261 | CG1 | VAL | A | 564 | 19.461 | 30.408 | −49.087 | 1.00 | 31.10 |
| ATOM | 4262 | CG2 | VAL | A | 564 | 17.655 | 28.836 | −50.079 | 1.00 | 28.92 |
| ATOM | 4263 | C | VAL | A | 564 | 20.886 | 28.181 | −48.122 | 1.00 | 29.56 |
| ATOM | 4264 | O | VAL | A | 564 | 20.538 | 28.320 | −46.954 | 1.00 | 29.10 |
| ATOM | 4265 | N | GLY | A | 565 | 22.150 | 28.266 | −48.527 | 1.00 | 32.02 |
| ATOM | 4266 | CA | GLY | A | 565 | 23.252 | 28.423 | −47.577 | 1.00 | 34.92 |
| ATOM | 4267 | C | GLY | A | 565 | 23.539 | 29.876 | −47.248 | 1.00 | 37.47 |
| ATOM | 4268 | O | GLY | A | 565 | 22.969 | 30.788 | −47.871 | 1.00 | 37.66 |
| ATOM | 4269 | N | GLN | A | 566 | 24.419 | 30.098 | −46.267 | 1.00 | 39.85 |
| ATOM | 4270 | CA | GLN | A | 566 | 24.897 | 31.456 | −45.926 | 1.00 | 42.75 |
| ATOM | 4271 | CB | GLN | A | 566 | 26.054 | 31.398 | −44.918 | 1.00 | 42.83 |
| ATOM | 4272 | CG | GLN | A | 566 | 25.727 | 30.761 | −43.565 | 1.00 | 44.99 |
| ATOM | 4273 | CD | GLN | A | 566 | 26.940 | 30.689 | −42.626 | 1.00 | 44.88 |
| ATOM | 4274 | OE1 | GLN | A | 566 | 27.972 | 30.089 | −42.958 | 1.00 | 47.67 |
| ATOM | 4275 | NE2 | GLN | A | 566 | 26.810 | 31.293 | −41.441 | 1.00 | 47.62 |
| ATOM | 4276 | C | GLN | A | 566 | 25.373 | 32.195 | −47.181 | 1.00 | 43.30 |
| ATOM | 4277 | O | GLN | A | 566 | 25.052 | 33.365 | −47.389 | 1.00 | 44.01 |
| ATOM | 4278 | N | ASP | A | 567 | 26.118 | 31.479 | −48.023 | 1.00 | 44.30 |
| ATOM | 4279 | CA | ASP | A | 567 | 26.739 | 32.029 | −49.236 | 1.00 | 44.62 |
| ATOM | 4280 | CB | ASP | A | 567 | 27.916 | 31.139 | −49.650 | 1.00 | 45.13 |
| ATOM | 4281 | CG | ASP | A | 567 | 27.492 | 29.702 | −49.966 | 1.00 | 47.62 |
| ATOM | 4282 | OD1 | ASP | A | 567 | 26.421 | 29.255 | −49.485 | 1.00 | 48.73 |
| ATOM | 4283 | OD2 | ASP | A | 567 | 28.245 | 29.010 | −50.693 | 1.00 | 50.47 |
| ATOM | 4284 | C | ASP | A | 567 | 25.776 | 32.197 | −50.421 | 1.00 | 44.04 |
| ATOM | 4285 | O | ASP | A | 567 | 26.196 | 32.575 | −51.522 | 1.00 | 44.36 |
| ATOM | 4286 | N | GLY | A | 568 | 24.497 | 31.899 | −50.205 | 1.00 | 42.85 |
| ATOM | 4287 | CA | GLY | A | 568 | 23.488 | 32.045 | −51.247 | 1.00 | 41.38 |
| ATOM | 4288 | C | GLY | A | 568 | 23.359 | 30.851 | −52.177 | 1.00 | 40.41 |
| ATOM | 4289 | O | GLY | A | 568 | 22.496 | 30.854 | −53.054 | 1.00 | 40.62 |
| ATOM | 4290 | N | SER | A | 569 | 24.195 | 29.827 | −51.990 | 1.00 | 39.02 |
| ATOM | 4291 | CA | SER | A | 569 | 24.137 | 28.623 | −52.827 | 1.00 | 37.72 |
| ATOM | 4292 | CB | SER | A | 569 | 25.365 | 27.746 | −52.600 | 1.00 | 38.07 |
| ATOM | 4293 | OG | SER | A | 569 | 25.454 | 27.359 | −51.238 | 1.00 | 39.18 |
| ATOM | 4294 | C | SER | A | 569 | 22.868 | 27.819 | −52.540 | 1.00 | 36.72 |
| ATOM | 4295 | O | SER | A | 569 | 22.474 | 27.672 | −51.382 | 1.00 | 36.47 |
| ATOM | 4296 | N | VAL | A | 570 | 22.222 | 27.313 | −53.583 | 1.00 | 35.25 |
| ATOM | 4297 | CA | VAL | A | 570 | 20.988 | 26.558 | −53.365 | 1.00 | 34.26 |
| ATOM | 4298 | CB | VAL | A | 570 | 19.709 | 27.243 | −53.987 | 1.00 | 34.42 |
| ATOM | 4299 | CG1 | VAL | A | 570 | 18.992 | 26.358 | −55.020 | 1.00 | 35.11 |
| ATOM | 4300 | CG2 | VAL | A | 570 | 20.010 | 28.651 | −54.506 | 1.00 | 35.12 |
| ATOM | 4301 | C | VAL | A | 570 | 21.113 | 25.080 | −53.718 | 1.00 | 33.29 |
| ATOM | 4302 | O | VAL | A | 570 | 21.735 | 24.694 | −54.714 | 1.00 | 32.88 |
| ATOM | 4303 | N | THR | A | 571 | 20.515 | 24.261 | −52.864 | 1.00 | 31.66 |
| ATOM | 4304 | CA | THR | A | 571 | 20.480 | 22.825 | −53.021 | 1.00 | 30.87 |
| ATOM | 4305 | CB | THR | A | 571 | 21.016 | 22.146 | −51.752 | 1.00 | 30.96 |
| ATOM | 4306 | OG1 | THR | A | 571 | 22.311 | 22.686 | −51.442 | 1.00 | 33.18 |
| ATOM | 4307 | CG2 | THR | A | 571 | 21.117 | 20.637 | −51.935 | 1.00 | 30.95 |
| ATOM | 4308 | C | THR | A | 571 | 19.018 | 22.473 | −53.210 | 1.00 | 29.72 |
| ATOM | 4309 | O | THR | A | 571 | 18.186 | 22.832 | −52.373 | 1.00 | 28.84 |
| ATOM | 4310 | N | TRP | A | 572 | 18.697 | 21.846 | −54.337 | 1.00 | 29.01 |
| ATOM | 4311 | CA | TRP | A | 572 | 17.331 | 21.388 | −54.589 | 1.00 | 28.49 |
| ATOM | 4312 | CB | TRP | A | 572 | 17.004 | 21.367 | −56.086 | 1.00 | 28.99 |
| ATOM | 4313 | CG | TRP | A | 572 | 16.950 | 22.690 | −56.739 | 1.00 | 29.65 |
| ATOM | 4314 | CD1 | TRP | A | 572 | 18.014 | 23.419 | −57.217 | 1.00 | 30.67 |
| ATOM | 4315 | NE1 | TRP | A | 572 | 17.564 | 24.603 | −57.769 | 1.00 | 31.84 |
| ATOM | 4316 | CE2 | TRP | A | 572 | 16.196 | 24.655 | −57.668 | 1.00 | 30.45 |
| ATOM | 4317 | CD2 | TRP | A | 572 | 15.770 | 23.464 | −57.028 | 1.00 | 30.30 |
| ATOM | 4318 | CE3 | TRP | A | 572 | 14.398 | 23.274 | −56.791 | 1.00 | 29.43 |
| ATOM | 4319 | CZ3 | TRP | A | 572 | 13.502 | 24.266 | −57.205 | 1.00 | 30.24 |
| ATOM | 4320 | CH2 | TRP | A | 572 | 13.959 | 25.437 | −57.846 | 1.00 | 30.31 |
| ATOM | 4321 | CZ2 | TRP | A | 572 | 15.298 | 25.649 | −58.083 | 1.00 | 29.71 |
| ATOM | 4322 | C | TRP | A | 572 | 17.205 | 19.991 | −54.031 | 1.00 | 28.21 |
| ATOM | 4323 | O | TRP | A | 572 | 18.168 | 19.212 | −54.060 | 1.00 | 27.50 |
| ATOM | 4324 | N | GLU | A | 573 | 16.033 | 19.647 | −53.499 | 1.00 | 27.69 |
| ATOM | 4325 | CA | GLU | A | 573 | 15.819 | 18.251 | −53.123 | 1.00 | 27.17 |
| ATOM | 4326 | CB | GLU | A | 573 | 14.586 | 18.074 | −52.222 | 1.00 | 27.18 |
| ATOM | 4327 | CG | GLU | A | 573 | 13.287 | 18.406 | −52.901 | 1.00 | 26.04 |
| ATOM | 4328 | CD | GLU | A | 573 | 12.059 | 18.111 | −52.028 | 1.00 | 26.20 |
| ATOM | 4329 | OE1 | GLU | A | 573 | 12.112 | 17.224 | −51.141 | 1.00 | 25.84 |
| ATOM | 4330 | OE2 | GLU | A | 573 | 11.032 | 18.764 | −52.264 | 1.00 | 22.24 |
| ATOM | 4331 | C | GLU | A | 573 | 15.725 | 17.419 | −54.405 | 1.00 | 27.91 |
| ATOM | 4332 | O | GLU | A | 573 | 15.498 | 17.957 | −55.497 | 1.00 | 26.94 |
| ATOM | 4333 | N | SER | A | 574 | 15.907 | 16.108 | −54.267 | 1.00 | 28.48 |
| ATOM | 4334 | CA | SER | A | 574 | 15.880 | 15.201 | −55.410 | 1.00 | 29.59 |
| ATOM | 4335 | CB | SER | A | 574 | 16.296 | 13.805 | −54.975 | 1.00 | 29.73 |
| ATOM | 4336 | OG | SER | A | 574 | 17.609 | 13.875 | −54.449 | 1.00 | 32.74 |
| ATOM | 4337 | C | SER | A | 574 | 14.526 | 15.134 | −56.095 | 1.00 | 29.70 |
| ATOM | 4338 | O | SER | A | 574 | 13.500 | 15.482 | −55.513 | 1.00 | 29.12 |
| ATOM | 4339 | N | ASP | A | 575 | 14.544 | 14.669 | −57.339 | 1.00 | 29.54 |
| ATOM | 4340 | CA | ASP | A | 575 | 13.337 | 14.435 | −58.109 | 1.00 | 29.98 |

TABLE 20-continued

| | | | | | | | | | |
|---|---|---|---|---|---|---|---|---|---|
| ATOM | 4341 | CB | ASP | A | 575 | 13.705 | 14.000 | −59.534 | 1.00 | 30.69 |
| ATOM | 4342 | CG | ASP | A | 575 | 14.324 | 15.125 | −60.331 | 1.00 | 33.96 |
| ATOM | 4343 | OD1 | ASP | A | 575 | 14.056 | 16.299 | −59.997 | 1.00 | 36.25 |
| ATOM | 4344 | OD2 | ASP | A | 575 | 15.083 | 14.846 | −61.290 | 1.00 | 37.94 |
| ATOM | 4345 | C | ASP | A | 575 | 12.519 | 13.358 | −57.428 | 1.00 | 28.93 |
| ATOM | 4346 | O | ASP | A | 575 | 13.050 | 12.633 | −56.600 | 1.00 | 28.34 |
| ATOM | 4347 | N | PRO | A | 576 | 11.217 | 13.267 | −57.760 | 1.00 | 28.58 |
| ATOM | 4348 | CA | PRO | A | 576 | 10.469 | 14.173 | −58.650 | 1.00 | 27.92 |
| ATOM | 4349 | CB | PRO | A | 576 | 9.319 | 13.294 | −59.131 | 1.00 | 28.52 |
| ATOM | 4350 | CG | PRO | A | 576 | 9.053 | 12.378 | −57.954 | 1.00 | 28.29 |
| ATOM | 4351 | CD | PRO | A | 576 | 10.377 | 12.159 | −57.267 | 1.00 | 28.76 |
| ATOM | 4352 | C | PRO | A | 576 | 9.894 | 15.397 | −57.938 | 1.00 | 27.25 |
| ATOM | 4353 | O | PRO | A | 576 | 9.887 | 15.452 | −56.703 | 1.00 | 28.13 |
| ATOM | 4354 | N | ASN | A | 577 | 9.394 | 16.360 | −58.707 | 1.00 | 25.62 |
| ATOM | 4355 | CA | ASN | A | 577 | 8.612 | 17.449 | −58.129 | 1.00 | 24.83 |
| ATOM | 4356 | CB | ASN | A | 577 | 8.013 | 18.336 | −59.224 | 1.00 | 24.90 |
| ATOM | 4357 | CG | ASN | A | 577 | 9.055 | 19.184 | −59.913 | 1.00 | 25.61 |
| ATOM | 4358 | OD1 | ASN | A | 577 | 10.176 | 19.321 | −59.423 | 1.00 | 25.83 |
| ATOM | 4359 | ND2 | ASN | A | 577 | 8.693 | 19.756 | −61.060 | 1.00 | 25.07 |
| ATOM | 4360 | C | ASN | A | 577 | 7.466 | 16.868 | −57.322 | 1.00 | 24.22 |
| ATOM | 4361 | O | ASN | A | 577 | 6.949 | 15.798 | −57.672 | 1.00 | 23.69 |
| ATOM | 4362 | N | HIS | A | 578 | 7.057 | 17.562 | −56.259 | 1.00 | 23.20 |
| ATOM | 4363 | CA | HIS | A | 578 | 5.830 | 17.179 | −55.570 | 1.00 | 22.96 |
| ATOM | 4364 | CB | HIS | A | 578 | 5.734 | 17.844 | −54.200 | 1.00 | 22.09 |
| ATOM | 4365 | CG | HIS | A | 578 | 6.874 | 17.538 | −53.285 | 1.00 | 21.80 |
| ATOM | 4366 | ND1 | HIS | A | 578 | 6.809 | 16.558 | −52.318 | 1.00 | 21.62 |
| ATOM | 4367 | CE1 | HIS | A | 578 | 7.948 | 16.530 | −51.645 | 1.00 | 21.36 |
| ATOM | 4368 | NE2 | HIS | A | 578 | 8.743 | 17.465 | −52.133 | 1.00 | 20.16 |
| ATOM | 4369 | CD2 | HIS | A | 578 | 8.096 | 18.109 | −53.160 | 1.00 | 19.78 |
| ATOM | 4370 | C | HIS | A | 578 | 4.697 | 17.707 | −56.429 | 1.00 | 23.58 |
| ATOM | 4371 | O | HIS | A | 578 | 4.814 | 18.794 | −56.976 | 1.00 | 23.64 |
| ATOM | 4372 | N | THR | A | 579 | 3.603 | 16.955 | −56.534 | 1.00 | 23.98 |
| ATOM | 4373 | CA | THR | A | 579 | 2.426 | 17.448 | −57.254 | 1.00 | 25.34 |
| ATOM | 4374 | CB | THR | A | 579 | 2.092 | 16.568 | −58.477 | 1.00 | 26.08 |
| ATOM | 4375 | OG1 | THR | A | 579 | 3.162 | 16.672 | −59.429 | 1.00 | 29.14 |
| ATOM | 4376 | CG2 | THR | A | 579 | 0.749 | 16.979 | −59.126 | 1.00 | 26.14 |
| ATOM | 4377 | C | THR | A | 579 | 1.259 | 17.480 | −56.291 | 1.00 | 25.05 |
| ATOM | 4378 | O | THR | A | 579 | 0.977 | 16.487 | −55.629 | 1.00 | 25.73 |
| ATOM | 4379 | N | TYR | A | 580 | 0.591 | 18.619 | −56.213 | 1.00 | 25.23 |
| ATOM | 4380 | CA | TYR | A | 580 | −0.450 | 18.802 | −55.211 | 1.00 | 25.68 |
| ATOM | 4381 | CB | TYR | A | 580 | 0.098 | 19.556 | −53.976 | 1.00 | 25.88 |
| ATOM | 4382 | CG | TYR | A | 580 | −0.931 | 19.763 | −52.866 | 1.00 | 26.21 |
| ATOM | 4383 | CD1 | TYR | A | 580 | −1.284 | 21.048 | −52.429 | 1.00 | 26.22 |
| ATOM | 4384 | CE1 | TYR | A | 580 | −2.256 | 21.233 | −51.399 | 1.00 | 27.53 |
| ATOM | 4385 | CZ | TYR | A | 580 | −2.860 | 20.111 | −50.841 | 1.00 | 27.08 |
| ATOM | 4386 | OH | TYR | A | 580 | −3.806 | 20.207 | −49.844 | 1.00 | 27.88 |
| ATOM | 4387 | CE2 | TYR | A | 580 | −2.510 | 18.841 | −51.264 | 1.00 | 26.97 |
| ATOM | 4388 | CD2 | TYR | A | 580 | −1.562 | 18.671 | −52.276 | 1.00 | 26.29 |
| ATOM | 4389 | C | TYR | A | 580 | −1.634 | 19.523 | −55.828 | 1.00 | 25.65 |
| ATOM | 4390 | O | TYR | A | 580 | −1.490 | 20.596 | −56.403 | 1.00 | 25.29 |
| ATOM | 4391 | N | THR | A | 581 | −2.813 | 18.915 | −55.732 | 1.00 | 25.95 |
| ATOM | 4392 | CA | THR | A | 581 | −4.015 | 19.629 | −56.117 | 1.00 | 25.78 |
| ATOM | 4393 | CB | THR | A | 581 | −5.016 | 18.700 | −56.806 | 1.00 | 26.75 |
| ATOM | 4394 | OG1 | THR | A | 581 | −4.332 | 18.000 | −57.855 | 1.00 | 26.57 |
| ATOM | 4395 | CG2 | THR | A | 581 | −6.189 | 19.498 | −57.397 | 1.00 | 27.62 |
| ATOM | 4396 | C | THR | A | 581 | −4.627 | 20.285 | −54.874 | 1.00 | 25.36 |
| ATOM | 4397 | O | THR | A | 581 | −5.024 | 19.595 | −53.935 | 1.00 | 25.22 |
| ATOM | 4398 | N | VAL | A | 582 | −4.685 | 21.615 | −54.880 | 1.00 | 24.54 |
| ATOM | 4399 | CA | VAL | A | 582 | −5.255 | 22.382 | −53.777 | 1.00 | 24.15 |
| ATOM | 4400 | CB | VAL | A | 582 | −5.006 | 23.915 | −53.953 | 1.00 | 24.21 |
| ATOM | 4401 | CG1 | VAL | A | 582 | −5.472 | 24.700 | −52.744 | 1.00 | 23.87 |
| ATOM | 4402 | CG2 | VAL | A | 582 | −3.514 | 24.218 | −54.219 | 1.00 | 25.33 |
| ATOM | 4403 | C | VAL | A | 582 | −6.759 | 22.063 | −53.706 | 1.00 | 24.32 |
| ATOM | 4404 | O | VAL | A | 582 | −7.478 | 22.204 | −54.700 | 1.00 | 23.26 |
| ATOM | 4405 | N | PRO | A | 583 | −7.236 | 21.587 | −52.546 | 1.00 | 24.10 |
| ATOM | 4406 | CA | PRO | A | 583 | −8.665 | 21.230 | −52.476 | 1.00 | 24.34 |
| ATOM | 4407 | CB | PRO | A | 583 | −8.865 | 20.763 | −51.022 | 1.00 | 24.33 |
| ATOM | 4408 | CG | PRO | A | 583 | −7.516 | 20.538 | −50.468 | 1.00 | 25.16 |
| ATOM | 4409 | CD | PRO | A | 583 | −6.508 | 21.310 | −51.294 | 1.00 | 24.72 |
| ATOM | 4410 | C | PRO | A | 583 | −9.597 | 22.404 | −52.768 | 1.00 | 24.50 |
| ATOM | 4411 | O | PRO | A | 583 | −9.262 | 23.558 | −52.487 | 1.00 | 23.93 |
| ATOM | 4412 | N | ALA | A | 584 | −10.756 | 22.104 | −53.350 | 1.00 | 24.61 |
| ATOM | 4413 | CA | ALA | A | 584 | −11.817 | 23.084 | −53.477 | 1.00 | 24.77 |
| ATOM | 4414 | CB | ALA | A | 584 | −12.065 | 23.439 | −54.943 | 1.00 | 25.29 |
| ATOM | 4415 | C | ALA | A | 584 | −13.036 | 22.434 | −52.847 | 1.00 | 24.94 |
| ATOM | 4416 | O | ALA | A | 584 | −13.922 | 21.932 | −53.537 | 1.00 | 25.03 |
| ATOM | 4417 | N | VAL | A | 585 | −13.052 | 22.406 | −51.517 | 1.00 | 24.24 |
| ATOM | 4418 | CA | VAL | A | 585 | −14.075 | 21.673 | −50.776 | 1.00 | 23.75 |
| ATOM | 4419 | CB | VAL | A | 585 | −13.465 | 20.452 | −50.029 | 1.00 | 24.50 |
| ATOM | 4420 | CG1 | VAL | A | 585 | −14.515 | 19.770 | −49.151 | 1.00 | 24.48 |

TABLE 20-continued

| | | | | | | | | | |
|---|---|---|---|---|---|---|---|---|---|
| ATOM | 4421 | CG2 | VAL | A | 585 | −12.863 | 19.447 | −51.026 | 1.00 | 25.32 |
| ATOM | 4422 | C | VAL | A | 585 | −14.707 | 22.639 | −49.781 | 1.00 | 23.20 |
| ATOM | 4423 | O | VAL | A | 585 | −13.999 | 23.347 | −49.065 | 1.00 | 22.13 |
| ATOM | 4424 | N | ALA | A | 586 | −16.044 | 22.679 | −49.739 | 1.00 | 22.43 |
| ATOM | 4425 | CA | ALA | A | 586 | −16.749 | 23.546 | −48.804 | 1.00 | 21.79 |
| ATOM | 4426 | CB | ALA | A | 586 | −18.240 | 23.212 | −48.820 | 1.00 | 22.19 |
| ATOM | 4427 | C | ALA | A | 586 | −16.160 | 23.324 | −47.389 | 1.00 | 21.57 |
| ATOM | 4428 | O | ALA | A | 586 | −15.954 | 22.180 | −46.990 | 1.00 | 20.89 |
| ATOM | 4429 | N | CYS | A | 587 | −15.872 | 24.414 | −46.679 | 1.00 | 21.59 |
| ATOM | 4430 | CA | CYS | A | 587 | −15.388 | 24.379 | −45.268 | 1.00 | 21.68 |
| ATOM | 4431 | CB | CYS | A | 587 | −16.131 | 23.323 | −44.441 | 1.00 | 22.08 |
| ATOM | 4432 | SG | CYS | A | 587 | −17.952 | 23.374 | −44.507 | 1.00 | 23.60 |
| ATOM | 4433 | C | CYS | A | 587 | −13.886 | 24.129 | −45.094 | 1.00 | 21.27 |
| ATOM | 4434 | O | CYS | A | 587 | −13.386 | 24.225 | −43.980 | 1.00 | 21.08 |
| ATOM | 4435 | N | VAL | A | 588 | −13.178 | 23.780 | −46.170 | 1.00 | 20.53 |
| ATOM | 4436 | CA | VAL | A | 588 | −11.742 | 23.499 | −46.085 | 1.00 | 20.52 |
| ATOM | 4437 | CB | VAL | A | 588 | −11.351 | 22.268 | −46.958 | 1.00 | 20.47 |
| ATOM | 4438 | CG1 | VAL | A | 588 | −9.846 | 21.959 | −46.844 | 1.00 | 20.87 |
| ATOM | 4439 | CG2 | VAL | A | 588 | −12.163 | 21.042 | −46.549 | 1.00 | 20.51 |
| ATOM | 4440 | C | VAL | A | 588 | −10.949 | 24.731 | −46.504 | 1.00 | 20.59 |
| ATOM | 4441 | O | VAL | A | 588 | −10.699 | 24.950 | −47.705 | 1.00 | 21.88 |
| ATOM | 4442 | N | THR | A | 589 | −10.533 | 25.522 | −45.528 | 1.00 | 19.56 |
| ATOM | 4443 | CA | THR | A | 589 | −9.903 | 26.807 | −45.795 | 1.00 | 19.48 |
| ATOM | 4444 | CB | THR | A | 589 | −10.595 | 27.914 | −44.988 | 1.00 | 20.13 |
| ATOM | 4445 | OG1 | THR | A | 589 | −10.527 | 27.565 | −43.592 | 1.00 | 21.49 |
| ATOM | 4446 | CG2 | THR | A | 589 | −12.085 | 28.018 | −45.410 | 1.00 | 20.03 |
| ATOM | 4447 | C | THR | A | 589 | −8.424 | 26.819 | −45.427 | 1.00 | 19.42 |
| ATOM | 4448 | O | THR | A | 589 | −7.694 | 27.767 | −45.743 | 1.00 | 18.66 |
| ATOM | 4449 | N | GLN | A | 590 | −7.995 | 25.772 | −44.734 | 1.00 | 19.62 |
| ATOM | 4450 | CA | GLN | A | 590 | −6.606 | 25.629 | −44.317 | 1.00 | 20.20 |
| ATOM | 4451 | CB | GLN | A | 590 | −6.359 | 26.261 | −42.939 | 1.00 | 21.06 |
| ATOM | 4452 | CG | GLN | A | 590 | −4.950 | 25.956 | −42.410 | 1.00 | 27.00 |
| ATOM | 4453 | CD | GLN | A | 590 | −4.184 | 27.189 | −41.989 | 1.00 | 33.74 |
| ATOM | 4454 | OE1 | GLN | A | 590 | −4.771 | 28.196 | −41.611 | 1.00 | 37.22 |
| ATOM | 4455 | NE2 | GLN | A | 590 | −2.855 | 27.118 | −42.066 | 1.00 | 36.77 |
| ATOM | 4456 | C | GLN | A | 590 | −6.247 | 24.159 | −44.295 | 1.00 | 19.00 |
| ATOM | 4457 | O | GLN | A | 590 | −7.004 | 23.335 | −43.771 | 1.00 | 18.70 |
| ATOM | 4458 | N | VAL | A | 591 | −5.113 | 23.811 | −44.904 | 1.00 | 17.70 |
| ATOM | 4459 | CA | VAL | A | 591 | −4.682 | 22.404 | −44.940 | 1.00 | 17.15 |
| ATOM | 4460 | CB | VAL | A | 591 | −4.843 | 21.750 | −46.330 | 1.00 | 17.82 |
| ATOM | 4461 | CG1 | VAL | A | 591 | −6.316 | 21.701 | −46.744 | 1.00 | 18.11 |
| ATOM | 4462 | CG2 | VAL | A | 591 | −3.970 | 22.470 | −47.390 | 1.00 | 17.60 |
| ATOM | 4463 | C | VAL | A | 591 | −3.213 | 22.360 | −44.551 | 1.00 | 17.42 |
| ATOM | 4464 | O | VAL | A | 591 | −2.531 | 23.377 | −44.638 | 1.00 | 17.32 |
| ATOM | 4465 | N | VAL | A | 592 | −2.731 | 21.206 | −44.090 | 1.00 | 17.26 |
| ATOM | 4466 | CA | VAL | A | 592 | −1.291 | 21.092 | −43.887 | 1.00 | 17.03 |
| ATOM | 4467 | CB | VAL | A | 592 | −0.762 | 21.198 | −42.365 | 1.00 | 18.70 |
| ATOM | 4468 | CG1 | VAL | A | 592 | 0.335 | 20.217 | −41.930 | 1.00 | 18.75 |
| ATOM | 4469 | CG2 | VAL | A | 592 | −1.810 | 21.731 | −41.315 | 1.00 | 15.36 |
| ATOM | 4470 | C | VAL | A | 592 | −0.736 | 19.951 | −44.730 | 1.00 | 16.99 |
| ATOM | 4471 | O | VAL | A | 592 | −1.318 | 18.862 | −44.828 | 1.00 | 16.23 |
| ATOM | 4472 | N | LYS | A | 593 | 0.357 | 20.253 | −45.403 | 1.00 | 15.38 |
| ATOM | 4473 | CA | LYS | A | 593 | 0.953 | 19.302 | −46.293 | 1.00 | 16.27 |
| ATOM | 4474 | CB | LYS | A | 593 | 1.301 | 20.010 | −47.616 | 1.00 | 16.69 |
| ATOM | 4475 | CG | LYS | A | 593 | 1.835 | 19.096 | −48.694 | 1.00 | 20.55 |
| ATOM | 4476 | CD | LYS | A | 593 | 0.791 | 18.101 | −49.203 | 1.00 | 24.73 |
| ATOM | 4477 | CE | LYS | A | 593 | 1.330 | 17.311 | −50.409 | 1.00 | 27.26 |
| ATOM | 4478 | NZ | LYS | A | 593 | 2.395 | 16.299 | −50.074 | 1.00 | 28.37 |
| ATOM | 4479 | C | LYS | A | 593 | 2.209 | 18.783 | −45.588 | 1.00 | 16.01 |
| ATOM | 4480 | O | LYS | A | 593 | 3.175 | 19.525 | −45.427 | 1.00 | 15.12 |
| ATOM | 4481 | N | GLU | A | 594 | 2.195 | 17.519 | −45.175 | 1.00 | 15.82 |
| ATOM | 4482 | CA | GLU | A | 594 | 3.308 | 16.969 | −44.407 | 1.00 | 16.23 |
| ATOM | 4483 | CB | GLU | A | 594 | 2.798 | 16.017 | −43.317 | 1.00 | 16.26 |
| ATOM | 4484 | CG | GLU | A | 594 | 1.866 | 16.732 | −42.299 | 1.00 | 16.62 |
| ATOM | 4485 | CD | GLU | A | 594 | 1.727 | 15.949 | −40.991 | 1.00 | 18.94 |
| ATOM | 4486 | OE1 | GLU | A | 594 | 1.267 | 14.778 | −41.024 | 1.00 | 21.31 |
| ATOM | 4487 | OE2 | GLU | A | 594 | 2.107 | 16.507 | −39.940 | 1.00 | 16.43 |
| ATOM | 4488 | C | GLU | A | 594 | 4.286 | 16.245 | −45.323 | 1.00 | 17.34 |
| ATOM | 4489 | O | GLU | A | 594 | 3.973 | 15.177 | −45.852 | 1.00 | 17.78 |
| ATOM | 4490 | N | ASP | A | 595 | 5.463 | 16.833 | −45.487 | 1.00 | 17.05 |
| ATOM | 4491 | CA | ASP | A | 595 | 6.481 | 16.326 | −46.405 | 1.00 | 17.21 |
| ATOM | 4492 | CB | ASP | A | 595 | 6.823 | 17.379 | −47.475 | 1.00 | 16.63 |
| ATOM | 4493 | CG | ASP | A | 595 | 5.678 | 17.619 | −48.455 | 1.00 | 17.91 |
| ATOM | 4494 | OD1 | ASP | A | 595 | 5.023 | 16.631 | −48.857 | 1.00 | 20.73 |
| ATOM | 4495 | OD2 | ASP | A | 595 | 5.434 | 18.795 | −48.844 | 1.00 | 18.08 |
| ATOM | 4496 | C | ASP | A | 595 | 7.734 | 15.955 | −45.631 | 1.00 | 17.47 |
| ATOM | 4497 | O | ASP | A | 595 | 7.915 | 16.375 | −44.492 | 1.00 | 16.44 |
| ATOM | 4498 | N | THR | A | 596 | 8.598 | 15.162 | −46.277 | 1.00 | 18.11 |
| ATOM | 4499 | CA | THR | A | 596 | 9.917 | 14.835 | −45.747 | 1.00 | 18.85 |
| ATOM | 4500 | CB | THR | A | 596 | 9.991 | 13.390 | −45.188 | 1.00 | 19.58 |

TABLE 20-continued

| | | | | | | | | |
|---|---|---|---|---|---|---|---|---|
| ATOM | 4501 | OG1 | THR | A | 596 | 9.057 | 13.248 | −44.116 | 1.00 | 20.97 |
| ATOM | 4502 | CG2 | THR | A | 596 | 11.385 | 13.124 | −44.598 | 1.00 | 20.94 |
| ATOM | 4503 | C | THR | A | 596 | 10.895 | 14.978 | −46.914 | 1.00 | 19.34 |
| ATOM | 4504 | O | THR | A | 596 | 10.588 | 14.531 | −48.024 | 1.00 | 19.05 |
| ATOM | 4505 | N | TRP | A | 597 | 12.050 | 15.581 | −46.631 | 1.00 | 20.24 |
| ATOM | 4506 | CA | TRP | A | 597 | 13.074 | 15.921 | −47.633 | 1.00 | 21.94 |
| ATOM | 4507 | CB | TRP | A | 597 | 14.325 | 16.453 | −46.940 | 1.00 | 22.34 |
| ATOM | 4508 | CG | TRP | A | 597 | 15.445 | 16.854 | −47.882 | 1.00 | 23.75 |
| ATOM | 4509 | CD1 | TRP | A | 597 | 16.509 | 16.079 | −48.275 | 1.00 | 25.08 |
| ATOM | 4510 | NE1 | TRP | A | 597 | 17.327 | 16.801 | −49.138 | 1.00 | 24.85 |
| ATOM | 4511 | CE2 | TRP | A | 597 | 16.802 | 18.059 | −49.300 | 1.00 | 25.25 |
| ATOM | 4512 | CD2 | TRP | A | 597 | 15.611 | 18.128 | −48.527 | 1.00 | 24.09 |
| ATOM | 4513 | CE3 | TRP | A | 597 | 14.875 | 19.325 | −48.519 | 1.00 | 24.91 |
| ATOM | 4514 | CZ3 | TRP | A | 597 | 15.334 | 20.401 | −49.262 | 1.00 | 23.38 |
| ATOM | 4515 | CH2 | TRP | A | 597 | 16.520 | 20.299 | −50.028 | 1.00 | 25.14 |
| ATOM | 4516 | CZ2 | TRP | A | 597 | 17.265 | 19.137 | −50.053 | 1.00 | 22.49 |
| ATOM | 4517 | C | TRP | A | 597 | 13.424 | 14.708 | −48.473 | 1.00 | 23.42 |
| ATOM | 4518 | O | TRP | A | 597 | 13.675 | 13.635 | −47.939 | 1.00 | 22.37 |
| ATOM | 4519 | N | GLN | A | 598 | 13.409 | 14.904 | −49.788 | 1.00 | 25.26 |
| ATOM | 4520 | CA | GLN | A | 598 | 13.698 | 13.850 | −50.755 | 1.00 | 27.05 |
| ATOM | 4521 | CB | GLN | A | 598 | 12.936 | 14.124 | −52.052 | 1.00 | 26.51 |
| ATOM | 4522 | CG | GLN | A | 598 | 11.418 | 13.948 | −51.895 | 1.00 | 26.10 |
| ATOM | 4523 | CD | GLN | A | 598 | 10.642 | 14.209 | −53.156 | 1.00 | 26.76 |
| ATOM | 4524 | OE1 | GLN | A | 598 | 11.194 | 14.620 | −54.175 | 1.00 | 27.68 |
| ATOM | 4525 | NE2 | GLN | A | 598 | 9.340 | 13.990 | −53.095 | 1.00 | 25.96 |
| ATOM | 4526 | C | GLN | A | 598 | 15.204 | 13.787 | −50.977 | 1.00 | 29.21 |
| ATOM | 4527 | O | GLN | A | 598 | 15.794 | 14.694 | −51.574 | 1.00 | 28.61 |
| ATOM | 4528 | N | SER | A | 599 | 15.818 | 12.722 | −50.453 | 1.00 | 32.41 |
| ATOM | 4529 | CA | SER | A | 599 | 17.273 | 12.530 | −50.498 | 1.00 | 35.70 |
| ATOM | 4530 | CB | SER | A | 599 | 17.747 | 11.698 | −49.302 | 1.00 | 35.61 |
| ATOM | 4531 | OG | SER | A | 599 | 17.374 | 12.296 | −48.072 | 1.00 | 39.62 |
| ATOM | 4532 | C | SER | A | 599 | 17.703 | 11.831 | −51.785 | 1.00 | 36.66 |
| ATOM | 4533 | O | SER | A | 599 | 16.916 | 11.145 | −52.433 | 1.00 | 37.44 |
| ATOM | 4534 | OXT | SER | A | 599 | 18.863 | 11.922 | −52.194 | 1.00 | 38.18 |
| ATOM | 4535 | C1 | MAN | A | 601 | −3.602 | −3.018 | −46.412 | 1.00 | 102.64 |
| ATOM | 4536 | C2 | MAN | A | 601 | −4.584 | −2.109 | −47.156 | 1.00 | 102.73 |
| ATOM | 4537 | O2 | MAN | A | 601 | −3.951 | −1.548 | −48.288 | 1.00 | 102.91 |
| ATOM | 4538 | C3 | MAN | A | 601 | −5.867 | −2.845 | −47.570 | 1.00 | 102.38 |
| ATOM | 4539 | O3 | MAN | A | 601 | −6.544 | −2.112 | −48.566 | 1.00 | 102.32 |
| ATOM | 4540 | C4 | MAN | A | 601 | −5.640 | −4.269 | −48.082 | 1.00 | 102.18 |
| ATOM | 4541 | O4 | MAN | A | 601 | −6.860 | −4.967 | −47.984 | 1.00 | 101.76 |
| ATOM | 4542 | C5 | MAN | A | 601 | −4.561 | −5.018 | −47.298 | 1.00 | 102.40 |
| ATOM | 4543 | C6 | MAN | A | 601 | −4.172 | −6.307 | −48.010 | 1.00 | 102.48 |
| ATOM | 4544 | O6 | MAN | A | 601 | −3.156 | −6.957 | −47.280 | 1.00 | 102.80 |
| ATOM | 4545 | O5 | MAN | A | 601 | −3.400 | −4.222 | −47.131 | 1.00 | 102.71 |
| ATOM | 4546 | C1 | MAN | A | 602 | −29.428 | −4.974 | −42.477 | 1.00 | 77.32 |
| ATOM | 4547 | C2 | MAN | A | 602 | −28.973 | −6.434 | −42.405 | 1.00 | 77.44 |
| ATOM | 4548 | O2 | MAN | A | 602 | −30.120 | −7.253 | −42.347 | 1.00 | 77.72 |
| ATOM | 4549 | C3 | MAN | A | 602 | −28.044 | −6.835 | −43.565 | 1.00 | 77.20 |
| ATOM | 4550 | O3 | MAN | A | 602 | −27.940 | −8.239 | −43.664 | 1.00 | 76.96 |
| ATOM | 4551 | C4 | MAN | A | 602 | −28.487 | −6.260 | −44.909 | 1.00 | 77.22 |
| ATOM | 4552 | O4 | MAN | A | 602 | −27.471 | −6.474 | −45.862 | 1.00 | 76.90 |
| ATOM | 4553 | C5 | MAN | A | 602 | −28.766 | −4.766 | −44.768 | 1.00 | 77.47 |
| ATOM | 4554 | C6 | MAN | A | 602 | −29.185 | −4.115 | −46.081 | 1.00 | 77.84 |
| ATOM | 4555 | O6 | MAN | A | 602 | −28.163 | −3.228 | −46.483 | 1.00 | 78.24 |
| ATOM | 4556 | O5 | MAN | A | 602 | −29.768 | −4.562 | −43.790 | 1.00 | 77.46 |
| ATOM | 4557 | C1 | MAN | A | 603 | −18.689 | 25.235 | −53.677 | 1.00 | 47.04 |
| ATOM | 4558 | C2 | MAN | A | 603 | −20.074 | 24.872 | −53.114 | 1.00 | 51.09 |
| ATOM | 4559 | O2 | MAN | A | 603 | −21.044 | 25.065 | −54.120 | 1.00 | 52.42 |
| ATOM | 4560 | C3 | MAN | A | 603 | −20.141 | 23.420 | −52.620 | 1.00 | 51.78 |
| ATOM | 4561 | O3 | MAN | A | 603 | −21.465 | 23.079 | −52.262 | 1.00 | 53.36 |
| ATOM | 4562 | C4 | MAN | A | 603 | −19.602 | 22.466 | −53.686 | 1.00 | 51.72 |
| ATOM | 4563 | O4 | MAN | A | 603 | −19.615 | 21.142 | −53.209 | 1.00 | 51.94 |
| ATOM | 4564 | C5 | MAN | A | 603 | −18.179 | 22.911 | −54.021 | 1.00 | 51.66 |
| ATOM | 4565 | C6 | MAN | A | 603 | −17.421 | 21.906 | −54.892 | 1.00 | 53.80 |
| ATOM | 4566 | O6 | MAN | A | 603 | −17.915 | 21.885 | −56.214 | 1.00 | 55.49 |
| ATOM | 4567 | O5 | MAN | A | 603 | −18.217 | 24.223 | −54.581 | 1.00 | 49.62 |
| ATOM | 4568 | C1 | MAN | A | 605 | −4.678 | 15.117 | −57.896 | 1.00 | 58.79 |
| ATOM | 4569 | C2 | MAN | A | 605 | −3.360 | 15.555 | −58.538 | 1.00 | 58.65 |
| ATOM | 4570 | O2 | MAN | A | 605 | −2.564 | 14.412 | −58.722 | 1.00 | 59.38 |
| ATOM | 4571 | C3 | MAN | A | 605 | −3.570 | 16.269 | −59.878 | 1.00 | 58.70 |
| ATOM | 4572 | O3 | MAN | A | 605 | −2.523 | 15.985 | −60.778 | 1.00 | 59.27 |
| ATOM | 4573 | C4 | MAN | A | 605 | −4.915 | 15.892 | −60.491 | 1.00 | 58.73 |
| ATOM | 4574 | O4 | MAN | A | 605 | −5.084 | 16.538 | −61.730 | 1.00 | 59.62 |
| ATOM | 4575 | C5 | MAN | A | 605 | −6.054 | 16.284 | −59.547 | 1.00 | 58.90 |
| ATOM | 4576 | C6 | MAN | A | 605 | −7.370 | 15.612 | −59.932 | 1.00 | 58.75 |
| ATOM | 4577 | O6 | MAN | A | 605 | −7.255 | 14.219 | −59.738 | 1.00 | 59.42 |
| ATOM | 4578 | O5 | MAN | A | 605 | −5.730 | 16.034 | −58.173 | 1.00 | 58.30 |
| ATOM | 4579 | C1 | MAN | A | 606 | −10.273 | 28.688 | −42.727 | 1.00 | 25.90 |
| ATOM | 4580 | C2 | MAN | A | 606 | −9.839 | 27.944 | −41.452 | 1.00 | 28.64 |

TABLE 20-continued

| | | | | | | | | | |
|---|---|---|---|---|---|---|---|---|---|
| ATOM | 4581 | O2 | MAN | A | 606 | −9.245 | 28.909 | −40.620 | 1.00 | 28.84 |
| ATOM | 4582 | C3 | MAN | A | 606 | −10.999 | 27.249 | −40.710 | 1.00 | 29.65 |
| ATOM | 4583 | O3 | MAN | A | 606 | −10.568 | 26.763 | −39.441 | 1.00 | 28.85 |
| ATOM | 4584 | C4 | MAN | A | 606 | −12.203 | 28.177 | −40.551 | 1.00 | 30.36 |
| ATOM | 4585 | O4 | MAN | A | 606 | −13.330 | 27.463 | −40.084 | 1.00 | 30.29 |
| ATOM | 4586 | C5 | MAN | A | 606 | −12.553 | 28.769 | −41.914 | 1.00 | 30.72 |
| ATOM | 4587 | C6 | MAN | A | 606 | −13.730 | 29.731 | −41.778 | 1.00 | 33.97 |
| ATOM | 4588 | O6 | MAN | A | 606 | −13.624 | 30.732 | −42.762 | 1.00 | 36.82 |
| ATOM | 4589 | O5 | MAN | A | 606 | −11.434 | 29.464 | −42.435 | 1.00 | 28.12 |
| ATOM | 4590 | C1 | MAN | A | 607 | −31.396 | 1.963 | −40.521 | 1.00 | 50.29 |
| ATOM | 4591 | C2 | MAN | A | 607 | −30.220 | 1.790 | −41.485 | 1.00 | 52.65 |
| ATOM | 4592 | O2 | MAN | A | 607 | −30.541 | 0.785 | −42.419 | 1.00 | 54.93 |
| ATOM | 4593 | C3 | MAN | A | 607 | −29.845 | 3.092 | −42.208 | 1.00 | 52.48 |
| ATOM | 4594 | O3 | MAN | A | 607 | −28.932 | 2.836 | −43.251 | 1.00 | 53.01 |
| ATOM | 4595 | C4 | MAN | A | 607 | −31.068 | 3.818 | −42.766 | 1.00 | 52.78 |
| ATOM | 4596 | O4 | MAN | A | 607 | −30.672 | 5.070 | −43.297 | 1.00 | 52.92 |
| ATOM | 4597 | C5 | MAN | A | 607 | −32.103 | 3.985 | −41.652 | 1.00 | 52.23 |
| ATOM | 4598 | C6 | MAN | A | 607 | −33.331 | 4.749 | −42.153 | 1.00 | 52.96 |
| ATOM | 4599 | O6 | MAN | A | 607 | −34.520 | 4.076 | −41.791 | 1.00 | 52.95 |
| ATOM | 4600 | O5 | MAN | A | 607 | −32.451 | 2.702 | −41.127 | 1.00 | 51.79 |
| ATOM | 4601 | C1 | MAN | A | 608 | 3.870 | 15.416 | −59.489 | 1.00 | 37.21 |
| ATOM | 4602 | C2 | MAN | A | 608 | 5.134 | 15.938 | −60.168 | 1.00 | 40.45 |
| ATOM | 4603 | O2 | MAN | A | 608 | 6.091 | 14.903 | −60.120 | 1.00 | 38.47 |
| ATOM | 4604 | C3 | MAN | A | 608 | 4.872 | 16.381 | −61.608 | 1.00 | 42.66 |
| ATOM | 4605 | O3 | MAN | A | 608 | 6.071 | 16.726 | −62.263 | 1.00 | 44.20 |
| ATOM | 4606 | C4 | MAN | A | 608 | 4.122 | 15.321 | −62.401 | 1.00 | 44.80 |
| ATOM | 4607 | O4 | MAN | A | 608 | 3.708 | 15.907 | −63.612 | 1.00 | 47.73 |
| ATOM | 4608 | C5 | MAN | A | 608 | 2.893 | 14.887 | −61.597 | 1.00 | 44.80 |
| ATOM | 4609 | C6 | MAN | A | 608 | 2.042 | 13.861 | −62.342 | 1.00 | 47.55 |
| ATOM | 4610 | O6 | MAN | A | 608 | 1.085 | 14.582 | −63.104 | 1.00 | 49.87 |
| ATOM | 4611 | O5 | MAN | A | 608 | 3.262 | 14.423 | −60.302 | 1.00 | 42.18 |
| ATOM | 4612 | C1 | NAG | A | 611 | 3.450 | −2.354 | −8.282 | 1.00 | 23.44 |
| ATOM | 4613 | C2 | NAG | A | 611 | 3.474 | −0.875 | −7.878 | 1.00 | 24.51 |
| ATOM | 4614 | N2 | NAG | A | 611 | 4.425 | −0.077 | −8.630 | 1.00 | 21.95 |
| ATOM | 4615 | C7 | NAG | A | 611 | 4.123 | 0.454 | −9.818 | 1.00 | 22.94 |
| ATOM | 4616 | O7 | NAG | A | 611 | 3.030 | 0.322 | −10.367 | 1.00 | 20.93 |
| ATOM | 4617 | C8 | NAG | A | 611 | 5.216 | 1.232 | −10.481 | 1.00 | 21.54 |
| ATOM | 4618 | C3 | NAG | A | 611 | 3.741 | −0.713 | −6.380 | 1.00 | 25.60 |
| ATOM | 4619 | O3 | NAG | A | 611 | 3.676 | 0.655 | −6.047 | 1.00 | 24.91 |
| ATOM | 4620 | C4 | NAG | A | 611 | 2.741 | −1.528 | −5.554 | 1.00 | 25.70 |
| ATOM | 4621 | O4 | NAG | A | 611 | 3.196 | −1.598 | −4.227 | 1.00 | 28.27 |
| ATOM | 4622 | C5 | NAG | A | 611 | 2.648 | −2.952 | −6.086 | 1.00 | 26.18 |
| ATOM | 4623 | C6 | NAG | A | 611 | 1.524 | −3.738 | −5.397 | 1.00 | 26.64 |
| ATOM | 4624 | O6 | NAG | A | 611 | 0.278 | −3.081 | −5.497 | 1.00 | 25.38 |
| ATOM | 4625 | O5 | NAG | A | 611 | 2.437 | −2.975 | −7.488 | 1.00 | 24.34 |
| ATOM | 4626 | C1 | NAG | A | 612 | 2.499 | −0.713 | −3.326 | 1.00 | 32.04 |
| ATOM | 4627 | C2 | NAG | A | 612 | 2.710 | −1.192 | −1.879 | 1.00 | 35.81 |
| ATOM | 4628 | N2 | NAG | A | 612 | 2.254 | −2.556 | −1.666 | 1.00 | 37.89 |
| ATOM | 4629 | C7 | NAG | A | 612 | 3.072 | −3.605 | −1.753 | 1.00 | 39.19 |
| ATOM | 4630 | O7 | NAG | A | 612 | 4.277 | −3.517 | −2.031 | 1.00 | 40.58 |
| ATOM | 4631 | C8 | NAG | A | 612 | 2.439 | −4.947 | −1.507 | 1.00 | 38.98 |
| ATOM | 4632 | C3 | NAG | A | 612 | 2.012 | −0.256 | −0.899 | 1.00 | 37.96 |
| ATOM | 4633 | O3 | NAG | A | 612 | 2.352 | −0.666 | 0.403 | 1.00 | 41.23 |
| ATOM | 4634 | C4 | NAG | A | 612 | 2.491 | 1.176 | −1.129 | 1.00 | 37.63 |
| ATOM | 4635 | O4 | NAG | A | 612 | 1.789 | 2.053 | −0.278 | 1.00 | 40.85 |
| ATOM | 4636 | C5 | NAG | A | 612 | 2.294 | 1.565 | −2.604 | 1.00 | 35.10 |
| ATOM | 4637 | C6 | NAG | A | 612 | 2.785 | 2.982 | −2.903 | 1.00 | 31.93 |
| ATOM | 4638 | O6 | NAG | A | 612 | 4.188 | 2.994 | −3.008 | 0.58 | 32.70 |
| ATOM | 4639 | O5 | NAG | A | 612 | 2.974 | 0.625 | −3.425 | 1.00 | 31.95 |
| ATOM | 4640 | O8 | BTB | A | 620 | −1.213 | 18.638 | −21.639 | 1.00 | 23.78 |
| ATOM | 4641 | C8 | BTB | A | 620 | −1.255 | 19.440 | −22.838 | 1.00 | 17.50 |
| ATOM | 4642 | C7 | BTB | A | 620 | −2.257 | 18.851 | −23.831 | 1.00 | 15.39 |
| ATOM | 4643 | N | BTB | A | 620 | −1.808 | 17.505 | −24.294 | 1.00 | 13.88 |
| ATOM | 4644 | C5 | BTB | A | 620 | −1.274 | 17.600 | −25.684 | 1.00 | 12.99 |
| ATOM | 4645 | C6 | BTB | A | 620 | 0.017 | 18.399 | −25.786 | 1.00 | 14.67 |
| ATOM | 4646 | O6 | BTB | A | 620 | 0.949 | 18.004 | −24.768 | 1.00 | 16.93 |
| ATOM | 4647 | C2 | BTB | A | 620 | −2.926 | 16.495 | −24.191 | 1.00 | 13.33 |
| ATOM | 4648 | C4 | BTB | A | 620 | −4.238 | 16.972 | −24.835 | 1.00 | 13.45 |
| ATOM | 4649 | O4 | BTB | A | 620 | −4.167 | 17.018 | −26.265 | 1.00 | 14.77 |
| ATOM | 4650 | C3 | BTB | A | 620 | −3.213 | 16.295 | −22.703 | 1.00 | 13.18 |
| ATOM | 4651 | O3 | BTB | A | 620 | −1.984 | 15.920 | −22.059 | 1.00 | 12.74 |
| ATOM | 4652 | C1 | BTB | A | 620 | −2.501 | 15.161 | −24.845 | 1.00 | 13.57 |
| ATOM | 4653 | O1 | BTB | A | 620 | −3.463 | 14.138 | −24.525 | 1.00 | 13.07 |
| ATOM | 4654 | O | WAT | W | 1 | −7.741 | 16.530 | −28.587 | 1.00 | 12.90 |
| ATOM | 4655 | O | WAT | W | 2 | −1.955 | 18.721 | −7.814 | 1.00 | 11.77 |
| ATOM | 4656 | O | WAT | W | 3 | −17.101 | 16.033 | −19.836 | 1.00 | 15.26 |
| ATOM | 4657 | O | WAT | W | 4 | −1.389 | 7.464 | −24.070 | 1.00 | 15.86 |
| ATOM | 4658 | O | WAT | W | 5 | −8.070 | 20.758 | −43.462 | 1.00 | 19.56 |
| ATOM | 4659 | O | WAT | W | 6 | −12.959 | 28.534 | −26.860 | 1.00 | 16.12 |
| ATOM | 4660 | O | WAT | W | 7 | −0.502 | 31.488 | −57.004 | 1.00 | 33.06 |

TABLE 20-continued

| | | | | | | | | | |
|---|---|---|---|---|---|---|---|---|---|
| ATOM | 4661 | O | WAT | W | 8 | 2.095 | 5.710 | −17.808 | 1.00 | 18.68 |
| ATOM | 4662 | O | WAT | W | 9 | −7.601 | 14.567 | −6.827 | 1.00 | 14.97 |
| ATOM | 4663 | O | WAT | W | 10 | 24.863 | 23.325 | −37.431 | 1.00 | 32.31 |
| ATOM | 4664 | O | WAT | W | 11 | −22.569 | 7.289 | −10.357 | 1.00 | 17.52 |
| ATOM | 4665 | O | WAT | W | 12 | −18.987 | 1.758 | −22.078 | 1.00 | 23.03 |
| ATOM | 4666 | O | WAT | W | 13 | −3.226 | 16.264 | −54.338 | 1.00 | 32.98 |
| ATOM | 4667 | O | WAT | W | 14 | 6.141 | 16.546 | −42.196 | 1.00 | 16.00 |
| ATOM | 4668 | O | WAT | W | 15 | −10.356 | 21.827 | −22.675 | 1.00 | 13.52 |
| ATOM | 4669 | O | WAT | W | 16 | −3.130 | 25.355 | −17.925 | 1.00 | 14.01 |
| ATOM | 4670 | O | WAT | W | 17 | −11.823 | 29.479 | −29.411 | 1.00 | 17.50 |
| ATOM | 4671 | O | WAT | W | 18 | −14.383 | 15.964 | −19.553 | 1.00 | 13.02 |
| ATOM | 4672 | O | WAT | W | 19 | −1.180 | 16.935 | −10.101 | 1.00 | 18.86 |
| ATOM | 4673 | O | WAT | W | 20 | −31.133 | 23.501 | 4.462 | 1.00 | 16.66 |
| ATOM | 4674 | O | WAT | W | 21 | −4.819 | 24.193 | −15.023 | 1.00 | 14.31 |
| ATOM | 4675 | O | WAT | W | 22 | 1.709 | 22.276 | −4.126 | 1.00 | 21.96 |
| ATOM | 4676 | O | WAT | W | 23 | −5.339 | 21.386 | −7.463 | 1.00 | 15.78 |
| ATOM | 4677 | O | WAT | W | 24 | −17.232 | 15.476 | 1.374 | 1.00 | 17.64 |
| ATOM | 4678 | O | WAT | W | 25 | −11.449 | 4.860 | −24.929 | 1.00 | 17.45 |
| ATOM | 4679 | O | WAT | W | 26 | −17.555 | 17.679 | −39.815 | 1.00 | 23.23 |
| ATOM | 4680 | O | WAT | W | 27 | 10.075 | 17.015 | −49.295 | 1.00 | 24.05 |
| ATOM | 4681 | O | WAT | W | 28 | −16.018 | −0.740 | −24.205 | 1.00 | 18.07 |
| ATOM | 4682 | O | WAT | W | 29 | 9.446 | 24.991 | −37.612 | 1.00 | 19.20 |
| ATOM | 4683 | O | WAT | W | 30 | −4.165 | 26.137 | −12.642 | 1.00 | 18.33 |
| ATOM | 4684 | O | WAT | W | 31 | 2.771 | 22.947 | −14.916 | 1.00 | 25.80 |
| ATOM | 4685 | O | WAT | W | 32 | −12.297 | 21.394 | −35.680 | 1.00 | 14.89 |
| ATOM | 4686 | O | WAT | W | 33 | −24.061 | 13.570 | 10.081 | 1.00 | 24.96 |
| ATOM | 4687 | O | WAT | W | 34 | 10.032 | 29.725 | −56.684 | 1.00 | 26.97 |
| ATOM | 4688 | O | WAT | W | 35 | 0.231 | 4.133 | −28.595 | 1.00 | 17.67 |
| ATOM | 4689 | O | WAT | W | 36 | 0.335 | 2.173 | −30.650 | 1.00 | 18.32 |
| ATOM | 4690 | O | WAT | W | 37 | −10.199 | 24.315 | −42.717 | 1.00 | 22.38 |
| ATOM | 4691 | O | WAT | W | 38 | −14.151 | 12.872 | −8.204 | 1.00 | 16.16 |
| ATOM | 4692 | O | WAT | W | 39 | −2.710 | 9.564 | −16.092 | 1.00 | 14.10 |
| ATOM | 4693 | O | WAT | W | 40 | 5.954 | 7.990 | −32.401 | 1.00 | 16.59 |
| ATOM | 4694 | O | WAT | W | 41 | 0.294 | 5.561 | −25.249 | 1.00 | 17.87 |
| ATOM | 4695 | O | WAT | W | 42 | 2.102 | 15.148 | −37.718 | 1.00 | 14.64 |
| ATOM | 4696 | O | WAT | W | 43 | −19.351 | 1.384 | −26.295 | 1.00 | 20.27 |
| ATOM | 4697 | O | WAT | W | 44 | −19.623 | 9.533 | −17.751 | 1.00 | 14.67 |
| ATOM | 4698 | O | WAT | W | 45 | 3.117 | 18.767 | −36.336 | 1.00 | 12.66 |
| ATOM | 4699 | O | WAT | W | 46 | −15.016 | 16.950 | 0.662 | 1.00 | 20.14 |
| ATOM | 4700 | O | WAT | W | 47 | −22.261 | 4.600 | −10.993 | 1.00 | 16.38 |
| ATOM | 4701 | O | WAT | W | 48 | −12.926 | 5.474 | −22.680 | 1.00 | 19.85 |
| ATOM | 4702 | O | WAT | W | 49 | 5.564 | 17.071 | −37.018 | 1.00 | 16.82 |
| ATOM | 4703 | O | WAT | W | 50 | −19.848 | 20.552 | −2.718 | 1.00 | 19.38 |
| ATOM | 4704 | O | WAT | W | 51 | −15.859 | 17.744 | −41.901 | 1.00 | 19.69 |
| ATOM | 4705 | O | WAT | W | 52 | −16.430 | 25.522 | −1.123 | 1.00 | 19.97 |
| ATOM | 4706 | O | WAT | W | 53 | −15.978 | 5.366 | −12.193 | 1.00 | 26.02 |
| ATOM | 4707 | O | WAT | W | 54 | −1.637 | 9.365 | −26.035 | 1.00 | 14.42 |
| ATOM | 4708 | O | WAT | W | 55 | −10.759 | 27.212 | −30.898 | 1.00 | 17.28 |
| ATOM | 4709 | O | WAT | W | 56 | −11.509 | 0.756 | −13.101 | 1.00 | 20.70 |
| ATOM | 4710 | O | WAT | W | 57 | −16.950 | 15.108 | 4.727 | 1.00 | 23.86 |
| ATOM | 4711 | O | WAT | W | 58 | −25.368 | 26.009 | −7.106 | 1.00 | 25.08 |
| ATOM | 4712 | O | WAT | W | 59 | −16.870 | 22.937 | −3.651 | 1.00 | 17.56 |
| ATOM | 4713 | O | WAT | W | 60 | −14.388 | 13.258 | −40.897 | 1.00 | 27.90 |
| ATOM | 4714 | O | WAT | W | 61 | −1.509 | −4.779 | −6.723 | 1.00 | 31.01 |
| ATOM | 4715 | O | WAT | W | 62 | −1.973 | 27.723 | −11.521 | 1.00 | 21.99 |
| ATOM | 4716 | O | WAT | W | 63 | −1.159 | −10.623 | −29.592 | 1.00 | 36.68 |
| ATOM | 4717 | O | WAT | W | 64 | −1.943 | 16.930 | −42.957 | 1.00 | 21.57 |
| ATOM | 4718 | O | WAT | W | 65 | −1.507 | 25.238 | −40.032 | 1.00 | 31.36 |
| ATOM | 4719 | O | WAT | W | 66 | −4.023 | 5.499 | −31.787 | 1.00 | 20.03 |
| ATOM | 4720 | O | WAT | W | 67 | −13.383 | 13.873 | −21.065 | 1.00 | 12.01 |
| ATOM | 4721 | O | WAT | W | 68 | −15.098 | 10.726 | −24.467 | 1.00 | 24.34 |
| ATOM | 4722 | O | WAT | W | 69 | −2.122 | 13.975 | −13.435 | 1.00 | 12.51 |
| ATOM | 4723 | O | WAT | W | 70 | −4.807 | 19.360 | −43.270 | 1.00 | 20.93 |
| ATOM | 4724 | O | WAT | W | 71 | −26.028 | 26.143 | −33.768 | 1.00 | 28.78 |
| ATOM | 4725 | O | WAT | W | 72 | −19.347 | 21.638 | 3.482 | 1.00 | 19.92 |
| ATOM | 4726 | O | WAT | W | 73 | −27.299 | 24.219 | −6.045 | 1.00 | 20.97 |
| ATOM | 4727 | O | WAT | W | 74 | −21.114 | −0.343 | −28.050 | 1.00 | 22.38 |
| ATOM | 4728 | O | WAT | W | 75 | −5.818 | 34.483 | −11.645 | 1.00 | 20.61 |
| ATOM | 4729 | O | WAT | W | 76 | 6.048 | 1.098 | −23.393 | 1.00 | 16.77 |
| ATOM | 4730 | O | WAT | W | 77 | −3.946 | 23.711 | −39.552 | 1.00 | 25.07 |
| ATOM | 4731 | O | WAT | W | 78 | −18.572 | 21.631 | −41.884 | 1.00 | 25.98 |
| ATOM | 4732 | O | WAT | W | 79 | 5.239 | 26.273 | −31.646 | 1.00 | 27.95 |
| ATOM | 4733 | O | WAT | W | 80 | 0.054 | 15.597 | −45.905 | 1.00 | 28.45 |
| ATOM | 4734 | O | WAT | W | 81 | −3.130 | 21.534 | −5.652 | 1.00 | 20.95 |
| ATOM | 4735 | O | WAT | W | 82 | −12.534 | 4.331 | −20.095 | 1.00 | 17.49 |
| ATOM | 4736 | O | WAT | W | 83 | 0.785 | 16.541 | −14.558 | 1.00 | 14.65 |
| ATOM | 4737 | O | WAT | W | 84 | −5.197 | 12.827 | −31.553 | 1.00 | 14.10 |
| ATOM | 4738 | O | WAT | W | 85 | −16.738 | 26.994 | −34.463 | 1.00 | 23.74 |
| ATOM | 4739 | O | WAT | W | 86 | 3.596 | 22.076 | −36.828 | 1.00 | 22.68 |
| ATOM | 4740 | O | WAT | W | 87 | 5.170 | 14.460 | −40.572 | 1.00 | 26.56 |

TABLE 20-continued

| | | | | | | | | | |
|---|---|---|---|---|---|---|---|---|---|
| ATOM | 4741 | O | WAT | W | 88 | −12.322 | 21.050 | 0.328 | 1.00 | 30.36 |
| ATOM | 4742 | O | WAT | W | 89 | 7.426 | 14.327 | −48.857 | 1.00 | 26.44 |
| ATOM | 4743 | O | WAT | W | 90 | −13.702 | 19.025 | 1.863 | 1.00 | 28.28 |
| ATOM | 4744 | O | WAT | W | 91 | 8.794 | 2.010 | −23.444 | 1.00 | 34.69 |
| ATOM | 4745 | O | WAT | W | 92 | −6.185 | 5.529 | −30.210 | 1.00 | 17.03 |
| ATOM | 4746 | O | WAT | W | 93 | −18.081 | 20.709 | −4.839 | 1.00 | 17.61 |
| ATOM | 4747 | O | WAT | W | 94 | −15.469 | 13.082 | −22.717 | 1.00 | 15.55 |
| ATOM | 4748 | O | WAT | W | 95 | 13.101 | 16.811 | −29.771 | 1.00 | 29.16 |
| ATOM | 4749 | O | WAT | W | 96 | −25.944 | 7.031 | −2.628 | 1.00 | 27.42 |
| ATOM | 4750 | O | WAT | W | 97 | −4.552 | 34.207 | −7.388 | 1.00 | 22.19 |
| ATOM | 4751 | O | WAT | W | 98 | −2.231 | −9.858 | −32.291 | 1.00 | 26.28 |
| ATOM | 4752 | O | WAT | W | 99 | 5.314 | 10.271 | −28.762 | 1.00 | 29.39 |
| ATOM | 4753 | O | WAT | W | 100 | −15.379 | 27.478 | −46.620 | 1.00 | 37.77 |
| ATOM | 4754 | O | WAT | W | 101 | 26.815 | 24.874 | −36.295 | 1.00 | 31.11 |
| ATOM | 4755 | O | WAT | W | 102 | −18.489 | −0.112 | −24.256 | 1.00 | 23.63 |
| ATOM | 4756 | O | WAT | W | 103 | −23.763 | 26.890 | −9.454 | 1.00 | 20.50 |
| ATOM | 4757 | O | WAT | W | 104 | −10.933 | 23.904 | −50.315 | 1.00 | 25.63 |
| ATOM | 4758 | O | WAT | W | 105 | 5.864 | 12.071 | −41.668 | 1.00 | 29.27 |
| ATOM | 4759 | O | WAT | W | 106 | 2.526 | 9.409 | −13.116 | 1.00 | 20.75 |
| ATOM | 4760 | O | WAT | W | 107 | −11.557 | −6.653 | −10.981 | 1.00 | 30.68 |
| ATOM | 4761 | O | WAT | W | 108 | −14.882 | 7.238 | −22.254 | 1.00 | 24.81 |
| ATOM | 4762 | O | WAT | W | 109 | −5.331 | −13.390 | −25.293 | 1.00 | 35.63 |
| ATOM | 4763 | O | WAT | W | 110 | −8.068 | 24.248 | −40.534 | 1.00 | 39.14 |
| ATOM | 4764 | O | WAT | W | 111 | −0.779 | 14.419 | −43.060 | 1.00 | 24.01 |
| ATOM | 4765 | O | WAT | W | 112 | −22.279 | 12.054 | −26.750 | 1.00 | 32.13 |
| ATOM | 4766 | O | WAT | W | 113 | −26.829 | 1.352 | −33.787 | 1.00 | 26.97 |
| ATOM | 4767 | O | WAT | W | 114 | −14.120 | 14.116 | 3.214 | 1.00 | 36.89 |
| ATOM | 4768 | O | WAT | W | 115 | 0.582 | −9.914 | −21.103 | 1.00 | 23.30 |
| ATOM | 4769 | O | WAT | W | 116 | −24.305 | 22.723 | 6.995 | 1.00 | 21.67 |
| ATOM | 4770 | O | WAT | W | 117 | −28.275 | 12.468 | −15.419 | 1.00 | 21.87 |
| ATOM | 4771 | O | WAT | W | 118 | 3.699 | 27.669 | −20.781 | 1.00 | 34.08 |
| ATOM | 4772 | O | WAT | W | 119 | −30.428 | 26.452 | 3.757 | 1.00 | 24.51 |
| ATOM | 4773 | O | WAT | W | 120 | 19.168 | 26.858 | −59.022 | 1.00 | 33.45 |
| ATOM | 4774 | O | WAT | W | 121 | −8.803 | 21.729 | −1.693 | 1.00 | 18.30 |
| ATOM | 4775 | O | WAT | W | 122 | 2.863 | 1.621 | −31.755 | 1.00 | 19.96 |
| ATOM | 4776 | O | WAT | W | 123 | −2.357 | 28.930 | −56.725 | 1.00 | 35.51 |
| ATOM | 4777 | O | WAT | W | 124 | −16.780 | 5.504 | −21.523 | 1.00 | 31.34 |
| ATOM | 4778 | O | WAT | W | 125 | 6.216 | 18.141 | −30.592 | 1.00 | 20.87 |
| ATOM | 4779 | O | WAT | W | 126 | 11.789 | 32.722 | −38.773 | 1.00 | 40.41 |
| ATOM | 4780 | O | WAT | W | 127 | −5.001 | 7.195 | −45.656 | 1.00 | 35.03 |
| ATOM | 4781 | O | WAT | W | 128 | −18.743 | 1.608 | −1.861 | 1.00 | 32.49 |
| ATOM | 4782 | O | WAT | W | 129 | −25.089 | −1.945 | −20.935 | 1.00 | 35.17 |
| ATOM | 4783 | O | WAT | W | 130 | −7.097 | −2.177 | −28.928 | 1.00 | 30.93 |
| ATOM | 4784 | O | WAT | W | 131 | −12.591 | 2.907 | −11.929 | 1.00 | 18.60 |
| ATOM | 4785 | O | WAT | W | 132 | −17.913 | −2.374 | −39.429 | 1.00 | 29.36 |
| ATOM | 4786 | O | WAT | W | 133 | −6.507 | −7.038 | −37.710 | 1.00 | 37.27 |
| ATOM | 4787 | O | WAT | W | 134 | −0.628 | 7.596 | −18.660 | 1.00 | 20.01 |
| ATOM | 4788 | O | WAT | W | 135 | −11.683 | 28.527 | −37.016 | 1.00 | 36.45 |
| ATOM | 4789 | O | WAT | W | 136 | −3.169 | 33.267 | −18.049 | 1.00 | 24.89 |
| ATOM | 4790 | O | WAT | W | 137 | −16.742 | 8.938 | −23.161 | 1.00 | 26.79 |
| ATOM | 4791 | O | WAT | W | 138 | −28.456 | 17.726 | −22.449 | 1.00 | 32.61 |
| ATOM | 4792 | O | WAT | W | 139 | 25.559 | 27.237 | −45.392 | 1.00 | 43.21 |
| ATOM | 4793 | O | WAT | W | 140 | −26.925 | 5.789 | −41.722 | 1.00 | 26.97 |
| ATOM | 4794 | O | WAT | W | 141 | −16.907 | 20.013 | −43.283 | 1.00 | 29.68 |
| ATOM | 4795 | O | WAT | W | 142 | −20.029 | 5.119 | −1.799 | 1.00 | 24.76 |
| ATOM | 4796 | O | WAT | W | 143 | 8.706 | 1.050 | −13.115 | 1.00 | 32.81 |
| ATOM | 4797 | O | WAT | W | 144 | −4.353 | 22.506 | −1.252 | 1.00 | 24.86 |
| ATOM | 4798 | O | WAT | W | 145 | −29.660 | 14.750 | −15.295 | 1.00 | 32.62 |
| ATOM | 4799 | O | WAT | W | 146 | 2.173 | 2.240 | −12.124 | 1.00 | 26.38 |
| ATOM | 4800 | O | WAT | W | 147 | 4.174 | −4.659 | −14.794 | 1.00 | 25.20 |
| ATOM | 4801 | O | WAT | W | 148 | −10.913 | 29.083 | −33.130 | 1.00 | 27.78 |
| ATOM | 4802 | O | WAT | W | 149 | −21.448 | 30.157 | −10.670 | 1.00 | 25.07 |
| ATOM | 4803 | O | WAT | W | 150 | −23.296 | 18.641 | −36.646 | 1.00 | 27.11 |
| ATOM | 4804 | O | WAT | W | 151 | −19.426 | 8.262 | −24.240 | 1.00 | 25.11 |
| ATOM | 4805 | O | WAT | W | 152 | 4.729 | −0.512 | −31.679 | 1.00 | 23.50 |
| ATOM | 4806 | O | WAT | W | 153 | 9.247 | 19.703 | −33.306 | 1.00 | 23.44 |
| ATOM | 4807 | O | WAT | W | 154 | 6.024 | 15.401 | −22.768 | 1.00 | 27.11 |
| ATOM | 4808 | O | WAT | W | 155 | −16.077 | 30.180 | −4.530 | 1.00 | 23.52 |
| ATOM | 4809 | O | WAT | W | 156 | −0.038 | 14.751 | −8.812 | 1.00 | 25.64 |
| ATOM | 4810 | O | WAT | W | 157 | 2.962 | 18.631 | −29.190 | 1.00 | 18.13 |
| ATOM | 4811 | O | WAT | W | 158 | 8.793 | 12.371 | −36.745 | 1.00 | 23.77 |
| ATOM | 4812 | O | WAT | W | 159 | −22.406 | 9.468 | −0.415 | 1.00 | 21.66 |
| ATOM | 4813 | O | WAT | W | 160 | −10.961 | 33.685 | −7.076 | 1.00 | 25.30 |
| ATOM | 4814 | O | WAT | W | 161 | −8.504 | 27.891 | −3.964 | 1.00 | 33.88 |
| ATOM | 4815 | O | WAT | W | 162 | 6.836 | 20.663 | −32.439 | 1.00 | 24.97 |
| ATOM | 4816 | O | WAT | W | 163 | 4.292 | 23.232 | −29.206 | 1.00 | 32.74 |
| ATOM | 4817 | O | WAT | W | 164 | 2.350 | 3.656 | −15.645 | 1.00 | 23.29 |
| ATOM | 4818 | O | WAT | W | 165 | −17.377 | 10.190 | −20.605 | 1.00 | 25.21 |
| ATOM | 4819 | O | WAT | W | 166 | −23.426 | 24.714 | 4.551 | 1.00 | 26.12 |
| ATOM | 4820 | O | WAT | W | 167 | 0.338 | 1.730 | −14.995 | 1.00 | 31.29 |

TABLE 20-continued

| | | | | | | | | | |
|---|---|---|---|---|---|---|---|---|---|
| ATOM | 4821 | O | WAT | W | 168 | −3.303 | 17.836 | −46.350 | 1.00 | 28.34 |
| ATOM | 4822 | O | WAT | W | 169 | 1.465 | 6.514 | −14.840 | 1.00 | 22.81 |
| ATOM | 4823 | O | WAT | W | 170 | 2.409 | 11.466 | −4.481 | 1.00 | 29.82 |
| ATOM | 4824 | O | WAT | W | 171 | 0.998 | 19.313 | −20.348 | 1.00 | 31.57 |
| ATOM | 4825 | O | WAT | W | 172 | 7.556 | −3.076 | −34.213 | 1.00 | 31.62 |
| ATOM | 4826 | O | WAT | W | 173 | −25.163 | 1.132 | −18.852 | 1.00 | 33.45 |
| ATOM | 4827 | O | WAT | W | 174 | −25.606 | 17.471 | −26.509 | 1.00 | 27.89 |
| ATOM | 4828 | O | WAT | W | 175 | 5.952 | 32.621 | −65.955 | 1.00 | 42.20 |
| ATOM | 4829 | O | WAT | W | 176 | −27.397 | 26.421 | −12.489 | 1.00 | 29.06 |
| ATOM | 4830 | O | WAT | W | 177 | −17.506 | 35.918 | −29.284 | 1.00 | 36.40 |
| ATOM | 4831 | O | WAT | W | 178 | −18.298 | 7.055 | −19.628 | 1.00 | 30.04 |
| ATOM | 4832 | O | WAT | W | 179 | −24.383 | 14.811 | −26.605 | 1.00 | 29.51 |
| ATOM | 4833 | O | WAT | W | 180 | −1.204 | 27.462 | −35.328 | 1.00 | 29.93 |
| ATOM | 4834 | O | WAT | W | 181 | −14.112 | 33.822 | −23.916 | 1.00 | 34.66 |
| ATOM | 4835 | O | WAT | W | 182 | 2.887 | 26.714 | −9.619 | 1.00 | 34.18 |
| ATOM | 4836 | O | WAT | W | 183 | −16.062 | 4.698 | 1.046 | 1.00 | 32.44 |
| ATOM | 4837 | O | WAT | W | 184 | −13.340 | 36.111 | −4.359 | 1.00 | 39.14 |
| ATOM | 4838 | O | WAT | W | 185 | 9.661 | 34.457 | −47.977 | 1.00 | 37.66 |
| ATOM | 4839 | O | WAT | W | 186 | −8.465 | 24.284 | −1.237 | 1.00 | 33.71 |
| ATOM | 4840 | O | WAT | W | 187 | 16.971 | 15.520 | −43.951 | 1.00 | 42.49 |
| ATOM | 4841 | O | WAT | W | 188 | −12.038 | −14.614 | −20.299 | 1.00 | 34.37 |
| ATOM | 4842 | O | WAT | W | 189 | −5.887 | 22.387 | −40.784 | 1.00 | 33.70 |
| ATOM | 4843 | O | WAT | W | 190 | −3.962 | −18.100 | −17.720 | 1.00 | 31.33 |
| ATOM | 4844 | O | WAT | W | 191 | −30.888 | 11.643 | −15.288 | 1.00 | 36.84 |
| ATOM | 4845 | O | WAT | W | 192 | 11.576 | 13.142 | −37.752 | 1.00 | 32.89 |
| ATOM | 4846 | O | WAT | W | 193 | −7.856 | 3.348 | −41.927 | 1.00 | 34.02 |
| ATOM | 4847 | O | WAT | W | 194 | −20.849 | 7.518 | 7.652 | 1.00 | 32.37 |
| ATOM | 4848 | O | WAT | W | 195 | 16.954 | 13.938 | −58.514 | 1.00 | 42.65 |
| ATOM | 4849 | O | WAT | W | 196 | −31.884 | 7.593 | −13.893 | 1.00 | 37.54 |
| ATOM | 4850 | O | WAT | W | 197 | 4.560 | −14.190 | −17.137 | 1.00 | 36.09 |
| ATOM | 4851 | O | WAT | W | 198 | 1.116 | 27.617 | −39.051 | 1.00 | 37.08 |
| ATOM | 4852 | O | WAT | W | 199 | −1.019 | −12.134 | −21.800 | 1.00 | 36.12 |
| ATOM | 4853 | O | WAT | W | 200 | 8.350 | 0.111 | −21.198 | 1.00 | 36.56 |
| ATOM | 4854 | O | WAT | W | 201 | −2.691 | 31.235 | −26.910 | 1.00 | 32.08 |
| ATOM | 4855 | O | WAT | W | 202 | 13.222 | 30.530 | −38.626 | 1.00 | 36.46 |
| ATOM | 4856 | O | WAT | W | 203 | −11.218 | 19.535 | −54.549 | 1.00 | 35.12 |
| ATOM | 4857 | O | WAT | W | 204 | −5.623 | 10.865 | −46.910 | 1.00 | 35.48 |
| ATOM | 4858 | O | WAT | W | 205 | −18.073 | 1.743 | −43.946 | 1.00 | 40.62 |
| ATOM | 4859 | O | WAT | W | 206 | −32.195 | 23.231 | 2.102 | 1.00 | 34.73 |
| ATOM | 4860 | O | WAT | W | 207 | −24.204 | 8.994 | −2.941 | 1.00 | 30.29 |
| ATOM | 4861 | O | WAT | W | 208 | −4.771 | 18.292 | −48.610 | 1.00 | 31.87 |
| ATOM | 4862 | O | WAT | W | 209 | −17.156 | 23.843 | −40.674 | 1.00 | 35.73 |
| ATOM | 4863 | O | WAT | W | 210 | 8.319 | 13.422 | −13.297 | 1.00 | 37.43 |
| ATOM | 4864 | O | WAT | W | 211 | −25.962 | 8.559 | −33.791 | 1.00 | 33.46 |
| ATOM | 4865 | O | WAT | W | 212 | −36.129 | 8.276 | 3.147 | 1.00 | 40.24 |
| ATOM | 4866 | O | WAT | W | 213 | 20.833 | 21.074 | −56.185 | 1.00 | 39.11 |
| ATOM | 4867 | O | WAT | W | 214 | −17.726 | 14.087 | 8.330 | 1.00 | 39.10 |
| ATOM | 4868 | O | WAT | W | 215 | 8.944 | 8.011 | −10.493 | 1.00 | 41.24 |
| ATOM | 4869 | O | WAT | W | 216 | −16.566 | 35.858 | −11.282 | 1.00 | 38.90 |
| ATOM | 4870 | O | WAT | W | 217 | −20.560 | 11.198 | −43.128 | 1.00 | 34.83 |
| ATOM | 4871 | O | WAT | W | 218 | 3.261 | −0.833 | −39.177 | 1.00 | 32.67 |
| ATOM | 4872 | O | WAT | W | 219 | −22.370 | −13.152 | −34.412 | 1.00 | 59.42 |
| ATOM | 4873 | O | WAT | W | 220 | −24.775 | 6.925 | 5.968 | 1.00 | 34.28 |
| ATOM | 4874 | O | WAT | W | 221 | −20.357 | 21.098 | −45.702 | 1.00 | 36.83 |
| ATOM | 4875 | O | WAT | W | 222 | 2.502 | 28.932 | −40.686 | 1.00 | 36.85 |
| ATOM | 4876 | O | WAT | W | 223 | −17.630 | −5.533 | −21.334 | 1.00 | 35.08 |
| ATOM | 4877 | O | WAT | W | 224 | −19.358 | −1.912 | −43.190 | 1.00 | 35.83 |
| ATOM | 4878 | O | WAT | W | 225 | −14.632 | 25.995 | −42.094 | 1.00 | 41.12 |
| ATOM | 4879 | O | WAT | W | 226 | −28.967 | 5.606 | −22.103 | 1.00 | 45.63 |
| ATOM | 4880 | O | WAT | W | 227 | −4.326 | 9.934 | 5.097 | 1.00 | 44.46 |
| ATOM | 4881 | O | WAT | W | 228 | 3.983 | 22.711 | −17.336 | 1.00 | 46.21 |
| ATOM | 4882 | O | WAT | W | 229 | −17.238 | 16.931 | 6.949 | 1.00 | 42.44 |
| ATOM | 4883 | O | WAT | W | 230 | −25.871 | 18.809 | 10.364 | 1.00 | 36.15 |
| ATOM | 4884 | O | WAT | W | 231 | −23.524 | 31.294 | −19.082 | 1.00 | 35.99 |
| ATOM | 4885 | O | WAT | W | 232 | −5.261 | −9.321 | −38.277 | 1.00 | 43.42 |
| ATOM | 4886 | O | WAT | W | 233 | −22.757 | 28.188 | −29.173 | 1.00 | 39.56 |
| ATOM | 4887 | O | WAT | W | 234 | −25.699 | 26.238 | −0.299 | 1.00 | 40.26 |
| ATOM | 4888 | O | WAT | W | 235 | −21.884 | −4.007 | −22.294 | 1.00 | 38.01 |
| ATOM | 4889 | O | WAT | W | 236 | −6.696 | −17.346 | −27.753 | 1.00 | 39.83 |
| ATOM | 4890 | O | WAT | W | 237 | −18.052 | 5.515 | 3.888 | 1.00 | 37.82 |
| ATOM | 4891 | O | WAT | W | 238 | −6.073 | 35.708 | −9.057 | 1.00 | 36.25 |
| ATOM | 4892 | O | WAT | W | 239 | −8.876 | 2.984 | −44.368 | 1.00 | 45.85 |
| ATOM | 4893 | O | WAT | W | 240 | 9.232 | 31.613 | −65.496 | 1.00 | 45.82 |
| ATOM | 4894 | O | WAT | W | 241 | −28.246 | 26.806 | −0.118 | 1.00 | 36.45 |
| ATOM | 4895 | O | WAT | W | 242 | −27.793 | 14.675 | −45.312 | 1.00 | 52.10 |
| ATOM | 4896 | O | WAT | W | 243 | 7.463 | 14.079 | −55.045 | 1.00 | 36.97 |
| ATOM | 4897 | O | WAT | W | 244 | −28.572 | 4.769 | −1.130 | 1.00 | 36.20 |
| ATOM | 4898 | O | WAT | W | 245 | 8.221 | 12.936 | −50.870 | 1.00 | 38.81 |
| ATOM | 4899 | O | WAT | W | 246 | −23.302 | −2.082 | −27.191 | 1.00 | 32.98 |
| ATOM | 4900 | O | WAT | W | 247 | −13.035 | 8.248 | −46.620 | 1.00 | 51.73 |

TABLE 20-continued

| ATOM | 4901 | O | WAT | W | 248 | −11.869 | 31.852 | −50.157 | 1.00 | 56.13 |
|------|------|---|-----|---|-----|---------|--------|---------|------|-------|
| ATOM | 4902 | O | WAT | W | 249 | 0.898 | 13.920 | −6.521 | 1.00 | 27.38 |
| ATOM | 4903 | O | WAT | W | 250 | 20.427 | 30.852 | −45.446 | 1.00 | 35.54 |
| ATOM | 4904 | O | WAT | W | 251 | −1.397 | 12.400 | −44.617 | 1.00 | 39.33 |
| ATOM | 4905 | O | WAT | W | 252 | −27.354 | 24.696 | −3.162 | 1.00 | 35.38 |
| ATOM | 4906 | O | WAT | W | 253 | 17.587 | 20.557 | −31.069 | 1.00 | 41.51 |
| ATOM | 4907 | O | WAT | W | 254 | −7.936 | 35.055 | −7.354 | 1.00 | 39.02 |
| ATOM | 4908 | O | WAT | W | 255 | −22.469 | 7.215 | −2.044 | 1.00 | 38.25 |
| ATOM | 4909 | O | WAT | W | 256 | 2.038 | 15.474 | −52.963 | 1.00 | 50.04 |
| ATOM | 4910 | O | WAT | W | 257 | 10.889 | 10.184 | −21.700 | 1.00 | 44.84 |
| ATOM | 4911 | O | WAT | W | 258 | −11.714 | 10.583 | 4.136 | 1.00 | 42.70 |
| ATOM | 4912 | O | WAT | W | 259 | −14.719 | 6.574 | 2.959 | 1.00 | 43.18 |
| ATOM | 4913 | O | WAT | W | 260 | −16.694 | 25.390 | −37.688 | 1.00 | 36.77 |
| ATOM | 4914 | O | WAT | W | 261 | −9.212 | 13.388 | −48.363 | 1.00 | 38.05 |
| ATOM | 4915 | O | WAT | W | 264 | −0.611 | −1.965 | −3.253 | 1.00 | 37.95 |
| ATOM | 4916 | O | WAT | W | 265 | −16.380 | 30.998 | −14.262 | 1.00 | 32.44 |
| ATOM | 4917 | O | WAT | W | 266 | 9.420 | 16.012 | −61.368 | 1.00 | 35.22 |
| ATOM | 4918 | O | WAT | W | 267 | −4.976 | −15.180 | −21.223 | 1.00 | 45.50 |
| ATOM | 4919 | O | WAT | W | 268 | −16.631 | 33.287 | −14.201 | 1.00 | 34.50 |
| ATOM | 4920 | O | WAT | W | 269 | −16.883 | 34.052 | −32.249 | 1.00 | 36.88 |
| ATOM | 4921 | O | WAT | W | 270 | −8.293 | −16.006 | −14.535 | 1.00 | 34.80 |
| ATOM | 4922 | O | WAT | W | 273 | 0.240 | 4.589 | −13.868 | 1.00 | 32.34 |
| ATOM | 4923 | O | WAT | W | 275 | 3.657 | 14.447 | −55.516 | 1.00 | 43.54 |
| ATOM | 4924 | O | WAT | W | 276 | −17.602 | 20.784 | −51.471 | 1.00 | 38.88 |
| ATOM | 4925 | O | WAT | W | 277 | −10.479 | 31.683 | −30.513 | 1.00 | 40.35 |
| ATOM | 4926 | O | WAT | W | 278 | −10.974 | 4.308 | −5.745 | 1.00 | 40.30 |
| ATOM | 4927 | O | WAT | W | 280 | −4.336 | 36.908 | −17.666 | 1.00 | 34.01 |
| ATOM | 4928 | O | WAT | W | 281 | 6.720 | 33.970 | −53.572 | 1.00 | 38.81 |
| ATOM | 4929 | O | WAT | W | 282 | −30.457 | 23.527 | −0.621 | 1.00 | 34.61 |
| ATOM | 4930 | O | WAT | W | 283 | 16.969 | 17.394 | −30.816 | 1.00 | 55.74 |
| ATOM | 4931 | O | WAT | W | 284 | −24.391 | 5.834 | −24.909 | 1.00 | 37.92 |
| ATOM | 4932 | O | WAT | W | 285 | 4.567 | 9.814 | −4.438 | 1.00 | 44.83 |
| ATOM | 4933 | O | WAT | W | 286 | −24.370 | −7.328 | −27.875 | 1.00 | 56.18 |
| ATOM | 4934 | O | WAT | W | 287 | −21.605 | 11.887 | 9.715 | 1.00 | 43.15 |
| ATOM | 4935 | O | WAT | W | 288 | 8.603 | 0.412 | −37.887 | 1.00 | 40.47 |
| ATOM | 4936 | O | WAT | W | 290 | −20.056 | 21.495 | 6.073 | 1.00 | 41.68 |
| ATOM | 4937 | O | WAT | W | 291 | −3.221 | 28.158 | −33.448 | 1.00 | 44.24 |
| ATOM | 4938 | O | WAT | W | 292 | 9.171 | 9.103 | −38.735 | 1.00 | 34.30 |
| ATOM | 4939 | O | WAT | W | 293 | 2.894 | 22.763 | −25.829 | 1.00 | 38.57 |
| ATOM | 4940 | O | WAT | W | 294 | −29.901 | 19.604 | −14.929 | 1.00 | 37.66 |
| ATOM | 4941 | O | WAT | W | 296 | −4.579 | 30.229 | −29.110 | 1.00 | 40.57 |
| ATOM | 4942 | O | WAT | W | 297 | −23.821 | 11.441 | −33.187 | 1.00 | 42.81 |
| ATOM | 4943 | O | WAT | W | 298 | −26.753 | −3.087 | −31.243 | 1.00 | 39.08 |
| ATOM | 4944 | O | WAT | W | 300 | −10.820 | 35.024 | −53.050 | 1.00 | 55.39 |
| ATOM | 4945 | O | WAT | W | 302 | −1.992 | 7.169 | −31.692 | 1.00 | 39.12 |
| ATOM | 4946 | O | WAT | W | 303 | −15.282 | −19.000 | −23.770 | 1.00 | 34.62 |
| ATOM | 4947 | O | WAT | W | 304 | 12.106 | 10.568 | −25.112 | 1.00 | 39.04 |
| ATOM | 4948 | O | WAT | W | 305 | 2.585 | 2.766 | 1.880 | 1.00 | 53.88 |
| ATOM | 4949 | O | WAT | W | 306 | 3.680 | 21.122 | −19.818 | 1.00 | 46.35 |
| ATOM | 4950 | O | WAT | W | 307 | 22.759 | 24.721 | −48.099 | 1.00 | 40.35 |
| ATOM | 4951 | O | WAT | W | 309 | −17.062 | −6.726 | −19.202 | 1.00 | 41.54 |
| ATOM | 4952 | O | WAT | W | 311 | 12.594 | 1.109 | −31.461 | 1.00 | 47.85 |
| ATOM | 4953 | O | WAT | W | 312 | 23.347 | 25.060 | −50.638 | 1.00 | 49.64 |
| ATOM | 4954 | O | WAT | W | 314 | −18.291 | 4.422 | −19.151 | 1.00 | 39.17 |
| ATOM | 4955 | O | WAT | W | 315 | −11.815 | −7.807 | −8.676 | 1.00 | 37.74 |
| ATOM | 4956 | O | WAT | W | 316 | −25.147 | 1.885 | −4.649 | 1.00 | 44.72 |
| ATOM | 4957 | O | WAT | W | 317 | −36.473 | 13.592 | 5.315 | 1.00 | 44.38 |
| ATOM | 4958 | O | WAT | W | 318 | −17.587 | 20.023 | −46.231 | 1.00 | 48.30 |
| ATOM | 4959 | O | WAT | W | 319 | −16.081 | 29.024 | −54.668 | 1.00 | 39.40 |
| ATOM | 4960 | O | WAT | W | 320 | −14.210 | 32.143 | −5.494 | 1.00 | 42.73 |
| ATOM | 4961 | O | WAT | W | 321 | −15.274 | 28.830 | −38.916 | 1.00 | 46.47 |
| ATOM | 4962 | O | WAT | W | 322 | −32.792 | 22.221 | −3.433 | 1.00 | 41.52 |
| ATOM | 4963 | O | WAT | W | 323 | −32.475 | 16.905 | −12.401 | 1.00 | 46.29 |
| ATOM | 4964 | O | WAT | W | 325 | 15.341 | 22.212 | −60.490 | 1.00 | 34.67 |
| ATOM | 4965 | O | WAT | W | 326 | −12.668 | 8.518 | −41.723 | 1.00 | 36.26 |
| ATOM | 4966 | O | WAT | W | 327 | 4.709 | 20.490 | −10.568 | 1.00 | 38.04 |
| ATOM | 4967 | O | WAT | W | 328 | 13.937 | 10.625 | −29.312 | 1.00 | 38.32 |
| ATOM | 4968 | O | WAT | W | 329 | −21.964 | 9.615 | −24.896 | 1.00 | 40.43 |
| ATOM | 4969 | O | WAT | W | 330 | 19.325 | 25.925 | −40.199 | 1.00 | 51.36 |
| ATOM | 4970 | O | WAT | W | 331 | −19.010 | 8.073 | −45.255 | 1.00 | 46.06 |
| ATOM | 4971 | O | WAT | W | 332 | −25.024 | −2.892 | −29.306 | 1.00 | 41.74 |
| ATOM | 4972 | O | WAT | W | 333 | −16.593 | −7.067 | −23.297 | 1.00 | 38.54 |
| ATOM | 4973 | O | WAT | W | 334 | −17.517 | 24.078 | 2.157 | 1.00 | 45.82 |
| ATOM | 4974 | O | WAT | W | 335 | −19.123 | 31.941 | 0.010 | 1.00 | 38.91 |
| ATOM | 4975 | O | WAT | W | 337 | 10.677 | 21.901 | −62.740 | 1.00 | 44.31 |
| ATOM | 4976 | O | WAT | W | 338 | 4.510 | 15.230 | −51.810 | 1.00 | 42.12 |
| ATOM | 4977 | O | WAT | W | 339 | 13.979 | 14.161 | −43.380 | 1.00 | 46.42 |
| ATOM | 4978 | O | WAT | W | 341 | 5.979 | −11.625 | −28.739 | 1.00 | 43.09 |
| ATOM | 4979 | O | WAT | W | 342 | −19.453 | 13.347 | 10.394 | 1.00 | 42.44 |
| ATOM | 4980 | O | WAT | W | 343 | 7.085 | 23.050 | −30.796 | 1.00 | 34.94 |

TABLE 20-continued

| | | | | | | | | | |
|---|---|---|---|---|---|---|---|---|---|
| ATOM | 4981 | O | WAT | W | 345 | 6.471 | 24.087 | −63.943 | 1.00 | 45.16 |
| ATOM | 4982 | O | WAT | W | 347 | 3.734 | 22.842 | −12.031 | 1.00 | 43.85 |
| ATOM | 4983 | O | WAT | W | 348 | −17.739 | 7.564 | 5.723 | 1.00 | 43.77 |
| ATOM | 4984 | O | WAT | W | 351 | −22.014 | 31.372 | −24.708 | 1.00 | 42.69 |
| ATOM | 4985 | O | WAT | W | 352 | 25.016 | 25.103 | −46.967 | 1.00 | 40.51 |
| ATOM | 4986 | O | WAT | W | 353 | 7.969 | 32.464 | −67.637 | 1.00 | 57.78 |
| ATOM | 4987 | O | WAT | W | 354 | −27.444 | 5.101 | 5.861 | 1.00 | 48.31 |
| ATOM | 4988 | O | WAT | W | 356 | 8.012 | 11.087 | −40.867 | 1.00 | 47.51 |
| ATOM | 4989 | O | WAT | W | 357 | 4.974 | 29.116 | −17.433 | 1.00 | 43.72 |
| ATOM | 4990 | O | WAT | W | 358 | −0.457 | 9.488 | −45.288 | 1.00 | 45.63 |
| ATOM | 4991 | O | WAT | W | 360 | −3.090 | 36.536 | −12.138 | 1.00 | 46.29 |
| ATOM | 4992 | O | WAT | W | 361 | 20.072 | 19.772 | −36.896 | 1.00 | 38.73 |
| ATOM | 4993 | O | WAT | W | 363 | −26.217 | 15.345 | −28.735 | 1.00 | 49.07 |
| ATOM | 4994 | O | WAT | W | 365 | −25.308 | 0.100 | −48.602 | 1.00 | 60.01 |
| ATOM | 4995 | O | WAT | W | 367 | 19.369 | 29.586 | −58.438 | 1.00 | 48.19 |
| ATOM | 4996 | O | WAT | W | 369 | 12.808 | 11.144 | −54.427 | 1.00 | 48.48 |
| ATOM | 4997 | O | WAT | W | 370 | 9.410 | 2.674 | −16.115 | 1.00 | 44.59 |
| ATOM | 4998 | O | WAT | W | 372 | −10.249 | 38.564 | −13.215 | 1.00 | 48.60 |
| ATOM | 4999 | O | WAT | W | 373 | −24.151 | 16.211 | 10.617 | 1.00 | 42.16 |
| ATOM | 5000 | O | WAT | W | 375 | −6.459 | 31.697 | −48.106 | 1.00 | 46.03 |
| ATOM | 5001 | O | WAT | W | 376 | −11.605 | 27.116 | −1.562 | 1.00 | 44.58 |
| ATOM | 5002 | O | WAT | W | 377 | −4.703 | 24.150 | −62.673 | 1.00 | 48.70 |
| ATOM | 5003 | O | WAT | W | 379 | 6.889 | 0.036 | −7.530 | 1.00 | 45.35 |
| ATOM | 5004 | O | WAT | W | 381 | −13.601 | 32.742 | −32.002 | 1.00 | 51.37 |
| ATOM | 5005 | O | WAT | W | 383 | −28.077 | 5.243 | −4.688 | 1.00 | 37.46 |
| END | | | | | | | | | | |

What is claimed is:

1. A glucoamylase variant comprising amino acid substitutions at the positions corresponding to positions 417, 430, and 563 of SEQ ID NO: 2, or equivalent positions in a parent glucoamylase having at least 90% sequence identity to SEQ ID NO: 1 or 2, and
wherein the glucoamylase variant has at least 90% sequence identity with SEQ ID NO: 1 or 2 and glucoamylase activity.

2. The glucoamylase variant of claim 1, wherein the amino acid substitutions are L417V, T430A, and N563I.

3. The glucoamylase variant of claim 1, wherein the parent glucoamylase has a catalytic domain that has at least 90% sequence identity with the catalytic domain of SEQ ID NO: 1, 2, 3, 5, 6, 7, 8, or 9.

4. The glucoamylase variant of claim 1, wherein the parent glucoamylase has a starch binding domain that has at least 95% sequence identity with the starch binding domain of SEQ ID NO: 1 or 2.

5. The glucoamylase variant of claim 1, wherein the glucoamylase variant has at least 95% sequence identity with SEQ ID NO: 1 or 2.

6. The glucoamylase variant of claim 1, wherein the glucoamylase variant has at least 99.5% sequence identity with SEQ ID NO: 1 or 2.

7. The glucoamylase variant of claim 1, wherein the parent glucoamylase comprises SEQ ID NO: 1 or 2.

8. The glucoamylase variant of claim 1, wherein the parent glucoamylase consists of SEQ ID NO: 1 or 2.

9. The glucoamylase variant of claim 1, wherein the glucoamylase variant further comprises one or more additional amino acid substitutions at the positions corresponding to positions: 43, 44, 61, 73, 294, 431, 503, or 535 of SEQ ID NO: 2, or an equivalent position in the parent glucoamylase.

10. The glucoamylase variant of claim 9, wherein the amino acid substitutions are: I43Q/R, D44C/R, N61I, G73F, G294C, A431L/Q, E503A/V, or A535R of SEQ ID NO: 2, or an equivalent position in the parent glucoamylase.

11. The glucoamylase variant of claim 1, wherein the glucoamylase variant exhibits increased thermostability as compared to the parent glucoamylase.

12. The glucoamylase variant of claim 1, wherein the glucoamylase variant exhibits increased specific activity as compared to the parent glucoamylase.

13. The glucoamylase variant of claim 4, wherein increased specific activity of the glucoamylase variant is measured by using DP7, cornstarch, or liquefact as a substrate.

14. The glucoamylase variant of claim 1, wherein the glucoamylase variant exhibits both increased thermostability and increased specific activity as compared to the parent glucoamylase.

15. The glucoamylase variant of claim 1, wherein the parent glucoamylase is selected from a glucoamylase obtained from a *Trichoderma* spp., an *Aspergillus* spp., a *Humicola* spp., a *Penicillium* spp., a *Talaromycese* spp., or a *Schizosaccharmyces* spp.

16. The glucoamylase variant of claim 15, wherein the parent glucoamylase is obtained from a *Trichoderma* spp. or an *Aspergillus* spp.

17. An enzyme composition comprising the glucoamylase variant of claim 1.

18. A method of hydrolyzing starch comprising admixing the enzyme composition of claim 17 with starch for a time and under conditions sufficient to hydrolyze the starch.

19. A method of producing a high glucose syrup comprising contacting the enzyme composition of claim 17 with starch for a time and under conditions sufficient to produce a high glucose syrup.

* * * * *